(12) United States Patent
Hudson et al.

(10) Patent No.: US 10,870,652 B2
(45) Date of Patent: Dec. 22, 2020

(54) COMPOUNDS AND METHODS FOR MODULATING BRUTON'S TYROSINE KINASE

(71) Applicant: CORVUS PHARMACEUTICALS, INC., Burlingame, CA (US)

(72) Inventors: Ryan Hudson, San Jose, CA (US); Anne-Marie Beausoleil, San Mateo, CA (US); Richard A. Miller, Portola Valley, CA (US); Erik Verner, Belmont, CA (US)

(73) Assignee: CORVUS PHARMACEUTICALS, INC., Burlingame, CA (US)

( * ) Notice: Subject to any disclaimer, the term of this patent is extended or adjusted under 35 U.S.C. 154(b) by 78 days.

(21) Appl. No.: 16/083,409

(22) PCT Filed: Mar. 10, 2017

(86) PCT No.: PCT/US2017/021966
§ 371 (c)(1),
(2) Date: Sep. 7, 2018

(87) PCT Pub. No.: WO2017/156495
PCT Pub. Date: Sep. 14, 2017

(65) Prior Publication Data
US 2019/0106423 A1 Apr. 11, 2019

Related U.S. Application Data

(60) Provisional application No. 62/307,399, filed on Mar. 11, 2016, provisional application No. 62/342,004, filed on May 26, 2016.

(51) Int. Cl.
| | | |
|---|---|---|
| *C07D 487/04* | (2006.01) | |
| *C07D 471/04* | (2006.01) | |
| *A61P 37/02* | (2006.01) | |
| *A61P 29/00* | (2006.01) | |
| *A61P 35/00* | (2006.01) | |

(52) U.S. Cl.
CPC .......... *C07D 487/04* (2013.01); *A61P 29/00* (2018.01); *A61P 35/00* (2018.01); *A61P 37/02* (2018.01); *C07D 471/04* (2013.01)

(58) Field of Classification Search
CPC .. C07D 231/56; C07D 471/02; C07D 471/04; C07D 487/04; A61K 31/519
See application file for complete search history.

(56) References Cited

U.S. PATENT DOCUMENTS

| | | | |
|---|---|---|---|
| 8,940,750 B2 * | 1/2015 | Honigberg | A61K 31/519 514/262.1 |
| 8,957,080 B2 * | 2/2015 | Goldstein | A61K 31/519 514/262.1 |
| 2007/0213327 A1 | 9/2007 | Collier et al. | |
| 2016/0000792 A1 | 1/2016 | Buggy et al. | |
| 2018/0222904 A1 * | 8/2018 | Liao | C07D 473/34 |
| 2019/0062328 A1 * | 2/2019 | Liao | A61K 31/496 |

FOREIGN PATENT DOCUMENTS

| | | |
|---|---|---|
| WO | WO-00/057877 A1 | 10/2000 |
| WO | WO-2007/070398 A1 | 6/2007 |
| WO | WO-2011/099764 A2 | 8/2011 |
| WO | WO-2013/010136 A2 | 1/2013 |
| WO | WO-2017/066014 A1 | 4/2017 |

OTHER PUBLICATIONS

Pearce et al., Failure modes in anticancer drug discovery and development, Cancer Drug Design and Discovery Edited by Stephen Neidle, Chapter 18, pp. 424-435 (2008).*
Simone, Oncology: Introduction, Cecil Textbook of Medicine, 20th Edition, vol. 1, pp. 1004-101 O, 1995.*
Johnson et al., Relationships between drug activity in NCI preclinical in vitro and in vivo models and early clinical trials, British Journal of Cancer, 84(10):1424-1431, 2001.*
Gura et al., Systems for identifying new drugs are often faulty, Science, 278:1041-1042, 1997.*
Ten Hacken et al., Microenvironment dependency in Chronic Lymphocytic Leukemia: The basis for new targeted therapies, 11 pages, Pharmacology & Therapeutics 144, (2014) pp. 338-348.*
Acute Leukemia, Merck Manual (Online Edition) 6 pages, pp. 1-6 (2013).*
Dheen, S. T. et al. (2007). "Microglial Activation and its Implications in the Brain Diseases." Current Medicinal Chemistry, 14(11): 1189-1197.
European Search Report issued in European Patent Application No. EP17764260.0, dated Aug. 19, 2019 (Aug. 19, 2019), 7 pages.
Graeber, M.B. et al. (2011, e-published Aug. 30, 2011). "Role of microglia in CNS inflammation," FEBS Letters, 585(23):3798-3805.
International Search Report issued in International Patent Application No. PCT/US2017/21966, dated May 24, 2017. 3 pages.
Reus, G.Z. et al. (Aug. 6, 2015, e-published May 14, 2015). "The Role of Inflammation and Microglial Activation in the Pathophysiology of Psychiatric Disorders," Neuroscience, 300:141-54.

(Continued)

*Primary Examiner* — Deepak R Rao
(74) *Attorney, Agent, or Firm* — Mintz, Levin, Cohn, Ferris, Glovsky and Popeo, P.C.; Doris Lee

(57) ABSTRACT

Provided herein, inter alia, are compounds and methods for modulating Bruton's Tyrosine Kinase.

28 Claims, No Drawings

(56) References Cited

OTHER PUBLICATIONS

Written Opinion issued in International Patent Application No. PCT/US2017/21966, dated May 24, 2017. 10 pages.

Allchin, R.L. et al. (2019). "Structural and diffusion weighted MRI demonstrates responses to ibrutinib in a mouse model of follicular helper (Tfh) T-cell lymphoma," *PLoS ONE* 14(4): e0215765. 16 pages.

Decker, S. et al. (2019). "Optimized Xenograft Protocol for Chronic Lymphocytic Leukemia Results in High Engraftment Efficiency for All CLL Subgroups," *Int. J. Mol. Sci.* 20, 6277. 17 pages.

Muqbil, I. et al. (2019) "Pre-clinical anti-tumor activity of Bruton's Tyrosine Kinase inhibitor in Hodgkin's Lymphoma cellular and subcutaneous tumor model," *Heliyon.* 5(8):e02290. 7 pages.

Zou, Y. et al. (2016)."Structure-based discovery of novel 4,5,6-trisubstituted pyrimidines as potent covalent Bruton's tyrosine kinase inhibitors," *Bioorg. Med. Chem. Lett.*, 8 pages. http://dx.doi.org/10.1016/j.bmcl.2016.05.014.

\* cited by examiner

COMPOUNDS AND METHODS FOR MODULATING BRUTON'S TYROSINE KINASE

CROSS-REFERENCES TO RELATED APPLICATIONS

This application claims the benefit of International Application No. PCT/US2017/021966 filed Mar. 10, 2017, U.S. Provisional Application No. 62/307,399, filed Mar. 11, 2016, and U.S. Provisional Application No. 62/342,004, filed May 26, 2016, which are incorporated herein by reference in their entirety and for all purposes.

BACKGROUND

Bruton's Tyrosine Kinase (BTK) plays an important role in B cell development, differentiation, signalling, and maturation. BTK was originally identified as a disease gene for human X-linked agammaglobulinemia, but has further been implicated in inflammation (e.g., inflammatory skin conditions), autoimmune, allergic disease conditions, and cancers (e.g., B-cell cancers such as B-cell lymphoma and lymphblastic B-cell leukemia). Thus, there is a need in the art for BTK modulators. Disclosed herein, inter alia, are solutions to these and other problems in the art.

BRIEF SUMMARY OF THE INVENTION

Herein are provided, inter alia, compounds capable of modulating the level of activity of Bruton's Tyrosine Kinase (BTK) and methods of using the same.

In an aspect is provided a compound having the formula:

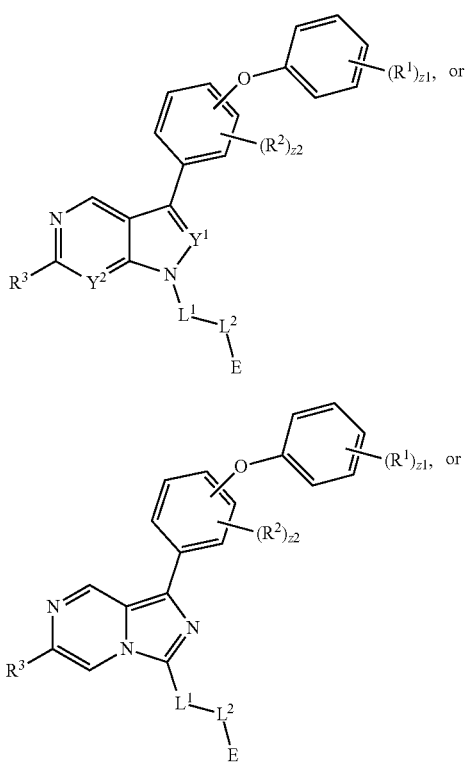

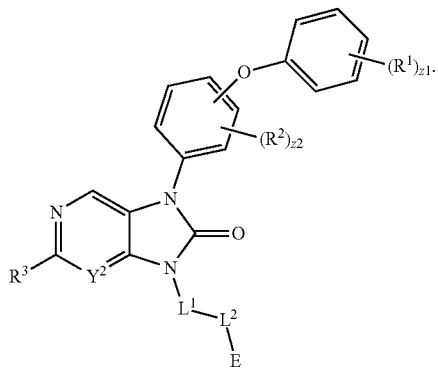

$R^1$ is independently halogen, $-CX_3$, $-CHX^1{}_2$, $-CH_2X^1$, $-OCX^1{}_3$, $-OCH_2X^1$, $-OCHX^1{}_2$, $-CN$, $-SO_{n1}R^{1D}$, $-SO_{v1}$ $NR^{1A}R^{1B}$, $-NHC(O)NR^{1A}R^{1B}$, $-N(O)_{m1}$, $-NR^{1A}R^{1B}$, $-C(O)R^{1C}$, $-C(O)-OR^{1C}$, $-C(O)NR^{1A}R^{1B}$, $-OR^{1D}$, $-NR^{1A}SO_2R^{1D}$, $-NR^{1A}C(O)R^{1C}$, $-NR^{1A}C(O)O$ $R^{1C}$, $-NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl. The symbol z1 is an integer from 0 to 5. $R^2$ is independently halogen, $-CX^2{}_3$, $-CHX^2{}_2$, $-CH_2X^2$, $-OCX^2{}_3$, $-OCH_2X^2$, $-OCHX^2{}_2$, $-CN$, $-SO_{n2}R^{2D}$, $-SO_{v2}$ $NR^{2A}R^{2B}$, $-NHC(O)NR^{2A}R^{2B}$, $-N(O)_{m2}$, $-NR^{2A}R^{2B}$, $-C(O)R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl. The symbol $z^2$ is an integer from 0 to 4. $R^3$ is hydrogen or $-NH_2$. The symbol $Y^1$ is N or $C(R^4)$. $R^4$ is hydrogen, halogen, $-CX^4{}_3$, $-CHX^4{}_2$, $-CH_2X^4$, $-OCX^4{}_3$, $-OCH_2X^4$, $-OCHX^4{}_2$, $-CN$, $-SO_{n4}R^{4D}$, $-SO_{v4}$ $NR^{4A}R^{4B}$, $-NHC(O)NR^{4A}R^{4B}$, $-N(O)_{m4}$, $-NR^{4A}R^{4B}$, $-C(O)R^{4C}$, $-C(O)-OR^{4C}$, $-C(O)NR^{4A}R^{4B}$, $-OR^{4D}$, $-NR^{4A}SO_2R^{4D}$, $-NR^{4A}C(O)R^{4C}$, $-NR^{4A}C(O)OR^{4C}$, $-NR^{4A}OR^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbol $Y^2$ is N or $C(R^5)$. $R^5$ is hydrogen, halogen, $-CX^5{}_3$, $-CHX^5{}_2$, $-CH_2X^5$, $-OCX^5{}_3$, $-OCH_2X^5$, $-OCHX^5{}_2$, $-CN$, $-SO_{n5}R^{5D}$, $-SO_{v5}$ $NR^{5A}R^{5B}$, $-NHC(O)NR^{5A}R^{5B}$, $-N(O)_{m5}$, $-NR^{5A}R^{5B}$, $-C(O)R^{5C}$, $-C(O)-OR^{5C}$, $-C(O)NR^{5A}R^{5B}$, $-OR^{5D}$, $-NR^{5A}SO_2R^{5D}$, $-NR^{5A}C(O)R^{5C}$, $-NR^{5A}C(O)OR^{5C}$, $-NR^{5A}OR^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $L^1$ is a bond, —S(O)$_2$—, —S(O)$_2$-Ph-, —NR$^6$—, —O—, —S—, —C(O)—, —C(O)NR$^6$—, —NR$^6$C(O)—, —NR$^6$C(O) NH—, —NHC(O)NR$^6$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. R$^6$ is hydrogen, halogen, —CX$^6_3$, —CHX$^6_2$, —CH$_2$X$^6$, —OCX$^6_3$, —OCH$_2$X$^6$, —OCHX$^6_2$, —CN, —SO$_{n6}$R$^{6D}$, —SO$_{v6}$ NR$^{6A}$R$^{6B}$, —NHC(O)NR$^{6A}$R$^{6B}$, —N(O)$_{m6}$, —NR$^{6A}$R$^{6B}$, —C(O)R$^{6C}$, —C(O)—OR$^{6C}$, —C(O)NR$^{6A}$R$^{6B}$, —OR$^{6D}$, —NR$^{6A}$SO$_2$R$^{6D}$, —NR$^{6A}$C(O) R$^{6C}$, —NR$^{6A}$C(O)OR$^{6C}$, —NR$^{6A}$OR$^{6C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. L$^2$ is a bond, —S(O)$_2$—, —S(O)$_2$-Ph-, —NR$^{7A}$—, —O—, —S—, —C(O)—, —C(O)NR$^{7A}$—, —NR$^7$C(O)—, —NR$^7$C(O) NH—, —NHC(O)NR—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. R$^7$ is hydrogen, halogen, —CX$^7_3$, —CHX$^7_2$, —CH$_2$X$^7$, —OCX$^7_3$, —OCH$_2$X$^7$, —OCHX$^7_2$, —CN, —SO$_{n7}$R$^{7D}$, —SO$_{v7}$ NR$^{7A}$R$^{7B}$, —NHC(O)NR$^{7A}$R$^{7B}$, —N(O)$_{m7}$, —NR$^{7A}$R$^{7B}$, —C(O)R$^{7C}$, —C(O)—OR$^{7C}$, —C(O)NR$^{7A}$R$^{7B}$, —OR$^{7D}$, —NR$^{7A}$SO$_2$R$^{7D}$, —NR$^{7A}$C(O) R$^{7C}$, —NR$^{7A}$C(O)OR$^{7C}$, —NR$^{7A}$OR$^{7C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. E is an electrophilic moiety. Each R$^{1A}$, R$^{1B}$, R$^{1C}$, R$^{1D}$, R$^{2A}$, R$^{2B}$, R$^{2C}$, R$^{2D}$, R$^{4A}$, R$^{4B}$, R$^{4C}$, R$^{4D}$, R$^{5A}$, R$^{5B}$, R$^{5C}$, R$^{5D}$, R$^{6A}$, R$^{6B}$, R$^{6C}$, R$^{6D}$, R$^{7A}$, R$^{7B}$, R$^{7C}$, and R$^{7D}$ is independently hydrogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{1A}$ and R$^{1B}$ substituents bonded to the same nitrogen atom may optionally be joined to form a substituted or unsubstituted heterocycloalkyl or substituted or unsubstituted heteroaryl. R$^{2A}$ and R$^{2B}$ substituents bonded to the same nitrogen atom may optionally be joined to form a substituted or unsubstituted heterocycloalkyl or substituted or unsubstituted heteroaryl. R$^{4A}$ and R$^{4B}$ substituents bonded to the same nitrogen atom may optionally be joined to form a substituted or unsubstituted heterocycloalkyl or substituted or unsubstituted heteroaryl. R$^{5A}$ and R$^{5B}$ substituents bonded to the same nitrogen atom may optionally be joined to form a substituted or unsubstituted heterocycloalkyl or substituted or unsubstituted heteroaryl. R$^{6A}$ and R$^{6B}$ substituents bonded to the same nitrogen atom may optionally be joined to form a substituted or unsubstituted heterocycloalkyl or substituted or unsubstituted heteroaryl. R$^{7A}$ and R$^{7B}$ substituents bonded to the same nitrogen atom may optionally be joined to form a substituted or unsubstituted heterocycloalkyl or unsubstituted heteroaryl. Each X, X$^1$, X$^2$, X$^4$, X$^5$, X$^6$, and X$^7$ is independently —F, —Cl, —Br, or —I. The symbols n1, n2, n4, n5, n6, and n7 are independently an integer from 0 to 4. The symbols m1, m2, m4, m5, m6, m7, v1, v2, v4, v5, v6, and v7 are independently an integer from 1 to 2.

In an aspect is provided a pharmaceutical composition including a compound described herein, or pharmaceutically acceptable salt thereof, and a pharmaceutically acceptable excipient.

In an aspect is provided a method of treating cancer including administering to a subject in need thereof an effective amount of a compound described herein.

In an aspect is provided a method of treating an inflammatory disease including administering to a subject in need thereof an effective amount of a compound described herein.

In an aspect is provided a method of treating a disease associated with Bruton's Tyrosine Kinase activity including administering to a subject in need thereof an effective amount of a compound described herein. In embodiments, the disease is associated with aberrant Bruton's Tyrosine Kinase activity.

In an aspect is provided a method of inhibiting Bruton's Tyrosine Kinase activity including contacting the Bruton's Tyrosine Kinase with a compound described herein.

In an aspect is provided a Bruton's tyrosine kinase protein covalently bonded to a compound described herein (e.g., Bruton's Tyrosine Kinase inhibitor, Bruton's Tyrosine Kinase antagonist, compound described herein, or a portion of a compound described herein).

In an aspect is provided a Bruton's Tyrosine Kinase protein (e.g., human BTK) covalently bonded to a Bruton's Tyrosine Kinase inhibitor (e.g., Bruton's Tyrosine Kinase antagonist, compound described herein, or a portion of a compound described herein).

DETAILED DESCRIPTION

I. Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene)

group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, or S), and wherein the nitrogen and sulfur atoms may optionally be oxidized, and the nitrogen heteroatom may optionally be quaternized. The heteroatom(s) (e.g., O, N, P, S, B, As, or Si) may be placed at any interior position of the heteroalkyl group or at the position at which the alkyl group is attached to the remainder of the molecule. Heteroalkyl is an uncyclized chain. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—O$CH_3$ and —$CH_2$—O—Si($CH_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P).

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. In embodiments, a cycloalkyl is a spirocyclic cycloalkyl, wherein the spirocyclic rings are cycloalkyl rings. In embodiments, a cycloalkyl is a fused ring cycloalkyl, wherein the fused rings are cycloalkyl rings. In embodiments, a cycloalkyl is a bridged ring cycloalkyl, wherein the bridged rings are cycloalkyl rings. In embodiments, a cycloalkyl is monocyclic. In embodiments, a cycloalkyl is two rings. In embodiments, a cycloalkyl is three rings. In embodiments, a cycloalkyl is four rings. In embodiments, a cycloalkyl is five rings. In embodiments, a cycloalkyl is polycyclic. In embodiments, a heterocycloalkyl is a spirocyclic heterocycloalkyl, wherein the spirocyclic rings are one or more heterocycloalkyl rings and optionally one or more cycloalkyl rings. In embodiments, a heterocycloalkyl is a fused ring heterocycloalkyl, wherein the fused rings are one or more heterocycloalkyl rings and optionally one or more cycloalkyl rings. In embodiments, a heterocycloalkyl is a bridged ring heterocycloalkyl, wherein the bridged rings are one or more heterocycloalkyl rings and optionally one or more cycloalkyl rings. In embodiments, the rings of a spirocyclic, fused ring, or bridged ring heterocycloalkyl are heterocyclic rings. In embodiments, a heterocycloalkyl is monocyclic. In embodiments, a heterocycloalkyl is two rings. In embodiments, a heterocycloalkyl is three rings. In embodiments, a heterocycloalkyl is four rings. In embodiments, a heterocycloalkyl is five rings. In embodiments, a heterocycloalkyl is polycyclic. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. In embodiments, a cycloalkylene or heterocycloalkylene is polycyclic. In embodiments, a heterocycloalkylene is a spirocyclic heterocycloalkylene, wherein the spirocyclic rings are one or more heterocycloalkyl rings and optionally one or more cycloalkyl rings.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocyclic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "⌇" denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

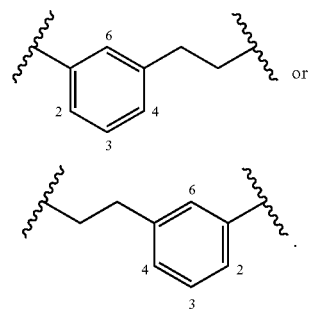

An alkylarylene moiety may be substituted (e.g. with a substituent group) on the alkylene moiety or the arylene linker (e.g. at carbons 2, 3, 4, or 6) with halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$CH$_3$— SO$_3$H, —OSO$_3$H, —SO$_2$NH$_2$, —NHNH$_2$, —ONH$_2$, —NHC(O)NHNH$_2$, substituted or unsubstituted C$_1$-C$_5$ alkyl or substituted or unsubstituted 2 to 5 membered heteroalkyl). In embodiments, the alkylarylene is unsubstituted.

Each of the above terms (e.g., "alkyl," "heteroalkyl," "cyclalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —NR'NR"R'", —ONR'R", —NR'C(O)NR"NR'''R'''', —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R''', and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R'''' group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —NR'NR"R"', —ONR'R", —NR'C(O)NR"NR"'R"", —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C(O)R", —NR'C(O)—OR", —NR'OR", in a number ranging from zero to the total number of open valences on the aromatic ring system; and where R', R", R"', and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R"', and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R"')$_d$—, where s and d are independently integers of from 0 to 3, and X' is —O—, —NR'—, —S—, —S(O)—, —S(O)$_2$—, or —S(O)$_2$NR'—. The substituents R, R', R", and R"' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:

(i) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, heteroaryl, substituted with at least one substituent selected from:

(a) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, heteroaryl, substituted with at least one substituent selected from: oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_2$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, FIGURES, or tables below.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those that are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present invention, whether radioactive or not, are encompassed within the scope of the present invention.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^1$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

A "covalent cysteine modifier moiety" as used herein refers to a substituent that is capable of reacting with the sulfhydryl functional group of a cysteine amino acid (e.g. cysteine 481 of the Bruton's Tyrosine Kinase protein (e.g., human BTK)) to form a covalent bond. Thus, the covalent cysteine modifier moiety is typically electrophilic.

A "detectable moiety" as used herein refers to a moiety that can be covalently or noncovalently attached to a compound or biomolecule that can be detected for instance, using techniques known in the art. In embodiments, the detectable moiety is covalently attached. The detectable moiety may provide for imaging of the attached compound or biomolecule. The detectable moiety may indicate the contacting between two compounds. Exemplary detectable moieties are fluorophores, antibodies, reactive dies, radiolabeled moieties, magnetic contrast agents, and quantum dots. Exemplary fluorophores include fluorescein, rhodamine, GFP, coumarin, FITC, Alexa fluor, Cy3, Cy5, BODIPY, and cyanine dyes. Exemplary radionuclides include Fluorine-18, Gallium-68, and Copper-64. Exemplary magnetic contrast agents include gadolinium, iron oxide and iron platinum, and manganese.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Prodrugs of the compounds described herein may be converted in vivo after administration. Additionally, prodrugs can be converted to the compounds of the present invention by chemical or biochemical methods in an ex vivo environment, such as, for example, when contacted with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

An "Bruton's Tyrosine Kinase inhibitor" or "BTK compound" or "BTK inhibitor" refers to a compound (e.g. compounds described herein) that reduces the activity of Bruton's Tyrosine Kinase when compared to a control, such as absence of the compound or a compound with known inactivity.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A polypeptide, or a cell is "recombinant" when it is artificial or engineered, or derived from or contains an artificial or engineered protein or nucleic acid (e.g. non-natural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

An amino acid residue in a protein "corresponds" to a given residue when it occupies the same essential structural position within the protein as the given residue. For example, a selected residue in a selected protein corresponds to Cys481 of human Bruton's Tyrosine Kinase when the selected residue occupies the same essential spatial or other structural relationship as Cys481 in human Bruton's Tyrosine Kinase. In some embodiments, where a selected protein is aligned for maximum homology with the human Bruton's Tyrosine Kinase protein, the position in the aligned selected protein aligning with Cys481 is said to correspond to Cys481. Instead of a primary sequence alignment, a three dimensional structural alignment can also be used, e.g., where the structure of the selected protein is aligned for maximum correspondence with the human Bruton's Tyrosine Kinase protein and the overall structures compared. In this case, an amino acid that occupies the same essential position as Cys481 in the structural model is said to correspond to the Cys481 residue.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

As defined herein, the term "activation", "activate", "activating" and the like in reference to a protein refers to conversion of a protein into a biologically active derivative from an initial inactive or deactivated state. The terms reference activation, or activating, sensitizing, or up-regulating signal transduction or enzymatic activity or the amount of a protein decreased in a disease.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In embodiments inhibition means negatively affecting (e.g. decreasing) the concentration or levels of the protein relative to the concentration or level of the protein in the absence of the inhibitor. In embodiments inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation). A "Bruton's Tyrosine Kinase inhibitor" and "BTK inhibitor" is a compound that negatively affects (e.g. decreases) the activity or function of Bruton's Tyrosine Kinase relative to the activity or function of Bruton's Tyrosine Kinase in the absence of the inhibitor (e.g., wherein the BTK inhibitor binds BTK).

The terms "Bruton's Tyrosine Kinase" and "BTK" refer to a protein (including homologs, isoforms, and functional fragments thereof) with Bruton's Tyrosine Kinase activity. The term includes any recombinant or naturally-occurring form of Bruton's Tyrosine Kinase or variants thereof that maintain Bruton's Tyrosine Kinase activity (e.g. within at least 30%, 40%, 50%, 60%, 70%, 80%, 90%, 95%, or 100% activity compared to wildtype Bruton's Tyrosine Kinase). In embodiments, the Bruton's Tyrosine Kinase protein encoded by the BTK gene has the amino acid sequence set forth in or corresponding to Entrez 695, UniProt Q06187, or RefSeq (protein) NP_000052. In embodiments, the Bruton's Tyrosine Kinase BTK gene has the nucleic acid sequence set forth in RefSeq (mRNA) NM_000061. In embodiments, the amino acid sequence or nucleic acid sequence is the sequence known at the time of filing of the present application. In embodiments, the sequence corresponds to GI:4557377. In embodiments, the sequence corresponds to NP_000052.1. In embodiments, the sequence corresponds to NM_000061.2. In embodiments, the sequence corresponds to GI: 213385292. In embodiments, the Bruton's Tyrosine Kinase is a human Bruton's Tyrosine Kinase, such as a human cancer causing Bruton's Tyrosine Kinase.

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The terms "disease" or "condition" refer to a state of being or health status of a patient or subject capable of being treated with the compounds or methods provided herein. The disease may be a cancer. The disease may be stroke. The disease may be an inflammatory disease. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma.

As used herein, the term "inflammatory disease" refers to a disease or condition characterized by aberrant inflammation (e.g. an increased level of inflammation compared to a control such as a healthy person not suffering from a disease). Examples of inflammatory diseases include autoimmune diseases, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, ischemia reperfusion injury, stroke, sarcoidosis, transplant rejection, interstitial cystitis, atherosclerosis, scleroderma, and atopic dermatitis.

As used herein, the term "cancer" refers to all types of cancer, neoplasm or malignant tumors found in mammals (e.g. humans), including leukemia, carcinomas and sarcomas. Exemplary cancers that may be treated with a compound or method provided herein include brain cancer, glioma, glioblastoma, neuroblastoma, prostate cancer, colorectal cancer, pancreatic cancer, cervical cancer, gastric cancer, ovarian cancer, lung cancer, and cancer of the head. Exemplary cancers that may be treated with a compound or method provided herein include cancer of the thyroid, endocrine system, brain, breast, cervix, colon, head & neck, liver, kidney, lung, non-small cell lung, melanoma, mesothelioma, ovary, sarcoma, stomach, uterus, Medulloblastoma, colorectal cancer, pancreatic cancer. Additional examples include, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abernethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma exulcere, carcinoma fibrosum, gelatinifomi carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

The terms "treating", or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

A "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal) compatible with the preparation. Parenteral administration includes, e.g., intravenous, intramuscular, intraarteriole, intradermal, subcutaneous, intraperitoneal, intraventricular, and intracranial. Other modes of delivery include, but are not limited to, the use of liposomal formulations, intravenous infusion, transdermal patches, etc.

"Co-administer" it is meant that a composition described herein is administered at the same time, just prior to, or just after the administration of one or more additional therapies. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered transdermally, by a topical route, or formulated as applicator sticks, solutions, suspensions, emulsions, gels, creams, ointments, pastes, jellies, paints, powders, and aerosols.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., spodoptera) and human cells. Cells may be useful when they are naturally nonadherent or have been treated not to adhere to surfaces, for example by trypsinization.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

The term "modulator" refers to a composition that increases or decreases the level of a target molecule or the function of a target molecule or the physical state of the target of the molecule. In some embodiments, an Bruton's Tyrosine Kinase associated disease modulator is a compound that reduces the severity of one or more symptoms of a disease associated with Bruton's Tyrosine Kinase (e.g. cancer, inflammatory disease). A Bruton's Tyrosine Kinase modulator is a compound that increases or decreases the activity or function or level of activity or level of function of Bruton's Tyrosine Kinase.

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

The term "associated" or "associated with" in the context of a substance or substance activity or function associated with a disease (e.g. a protein associated disease, a cancer associated with Bruton's Tyrosine Kinase activity, Bruton's Tyrosine Kinase associated cancer, Bruton's Tyrosine Kinase associated disease) means that the disease (e.g. cancer, inflammatory disease) is caused by (in whole or in part), or a symptom of the disease is caused by (in whole or inpart) the substance or substance activity or function. For example, a cancer associated with Bruton's Tyrosine Kinase activity or function may be a cancer that results (entirely or partially) from aberrant Bruton's Tyrosine Kinase function (e.g. enzyme activity, protein-protein interaction, signaling pathway) or a cancer wherein a particular symptom of the disease is caused (entirely or partially) by aberrant Bruton's Tyrosine Kinase activity or function. As used herein, what is described as being associated with a disease, if a causative agent, could be a target for treatment of the disease. For example, a cancer associated with Bruton's Tyrosine Kinase activity or function or a Bruton's Tyrosine Kinase associated cancer, may be treated with a Bruton's Tyrosine Kinase modulator or Bruton's Tyrosine Kinase inhibitor, in the instance where increased Bruton's Tyrosine Kinase activity or function (e.g. signaling pathway activity) causes the cancer. For example, an inflammatory disease associated with Bruton's Tyrosine Kinase activity or function or an Bruton's Tyrosine Kinase associated inflammatory disease, may be treated with an Bruton's Tyrosine Kinase modulator or Bruton's Tyrosine Kinase inhibitor, in the instance where increased Bruton's Tyrosine Kinase activity or function (e.g. signaling pathway activity) causes the disease.

The term "aberrant" as used herein refers to different from normal. When used to describe enzymatic activity or protein function, aberrant refers to activity or function that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propogated to other signaling pathway components. For example, binding of a Bruton's Tyrosine Kinase with a compound as described herein may reduce the level of a product of the Bruton's Tyrosine Kinase catalyzed reaction or thr level of a downstream derivative of the product or binding may reduce the interactions between the Bruton's Tyrosine Kinase enzyme or an Bruton's Tyrosine Kinase reaction product and downstream effectors or signaling pathway components, resulting in changes in cell growth, proliferation, or survival.

The term "electrophilic chemical moiety" is used in accordance with its plain ordinary chemical meaning and refers to a monovalent chemical group that is electrophilic.

II. Compounds

In an aspect is provided a compound having the formula:

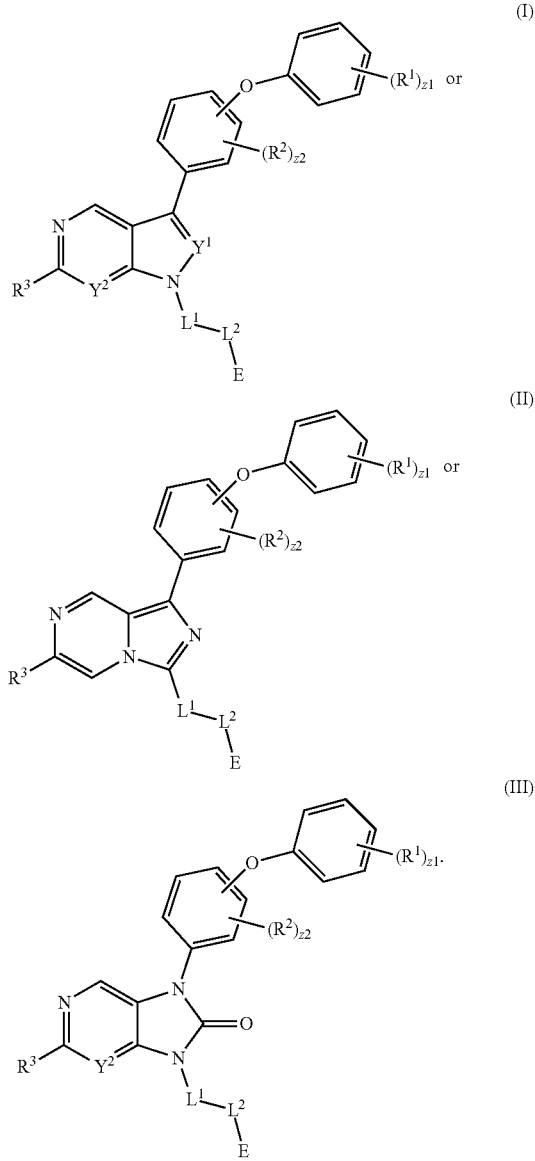

$R^1$ is independently halogen, $-CX^1_3$, $-CHX^1_2$, $-CH_2X^1$, $-OCX^1_3$, $-OCH_2X^1$, $-OCHX^1_2$, $-CN$, $-SO_{n1}R^{1D}$, $-SO_{v1}NR^{1A}R^{1B}$, $-NHC(O)NR^{1A}R^{1B}$, $-N(O)_{m1}$, $-NR^{1A}R^{1B}$, $-C(O)R^{1C}$, $-C(O)-OR^{1C}$, $-C(O)NR^{1A}R^{1B}$, $-OR^{1D}$, $-NR^{1A}SO_2R^{1D}$, $-NR^{1A}C(O)$ $R^{1C}$, $-NR^{1A}C(O)O$ $R^{1C}$, $-NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl. The symbol z1 is an integer from 0 to 5. $R^2$ is independently halogen, $-CX^2_3$, $-CHX^2_2$, $-CH_2X^2$, $-OCX^2_3$, $-OCH_2X^2$, $-OCHX^2_2$, —CN, —SO$_{n2}$R$^{2D}$, —SO$_{v2}$NR$^{2A}$R$^{2B}$, —NHC(O)NR$^{2A}$R$^{2B}$, —N(O)$_{m2}$, —NR$^{2A}$R$^{2B}$, —C(O)R$^{2C}$, —C(O)—OR$^{2C}$, —C(O)NR$^{2A}$R$^{2B}$, —OR$^{2D}$, —NR$^{2A}$SO$_2$R$^{2D}$, —NR$^{2A}$C(O)R$^{2C}$, —NR$^{2A}$C(O)OR$^{2C}$, —NR$^{2A}$OR$^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Two adjacent R$^2$ substituents may optionally be joined to form a substituted or unsubstituted cycloalkyl, substituted or unsubstituted heterocycloalkyl, substituted or unsubstituted aryl, or substituted or unsubstituted heteroaryl. The symbol z2 is an integer from 0 to 4. R$^3$ is hydrogen or —NH$_2$. The symbol Y$^1$ is N or C(R$^4$). R$^4$ is hydrogen, halogen, —CX$^{43}$, —CHX$^{42}$, —CH$_2$X$^4$, —OCX$^4_3$, —OCH$_2$X$^4$, —OCHX$^{42}$, —CN, —SO$_{n4}$R$^{4D}$, —SO$_4$NR$^{4A}$R$^{4B}$, —NHC(O)NR$^{4A}$R$^{4B}$, —N(O)$_{m4}$, —NR$^{4A}$R$^{4B}$, —C(O)R$^{4C}$, —C(O)—OR$^{4C}$, —C(O)NR$^{4A}$R$^{4B}$, —OR$^{4D}$, —NR$^{4A}$SO$_2$R$^{4D}$, —NR$^{4A}$C(O)R$^{4C}$, —NR$^{4A}$C(O)OR$^{4C}$, —NR$^{4A}$OR$^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbol Y$^2$ is N or C(R$^5$). R$^5$ is hydrogen, halogen, —CX$^5_3$, —CHX$^5_2$, —CH$_2$X$^5$, —OCX$^5_3$, —OCH$_2$X$^5$, —OCHX$^5_2$, —CN, —SO$_{n1}$R$^{5D}$, —S$_{v5}$NR$^{5A}$R$^{5B}$, —NHC(O)NR$^{5A}$R$^{5B}$, —N(O)$_{m5}$, —NR$^{5A}$R$^{5B}$, —C(O)R$^{5C}$, —C(O)—OR$^{5C}$, —C(O)NR$^{5A}$R$^{5B}$, —OR$^{5D}$, —NR$^{5A}$SO$_2$R$^{5D}$, —NR$^{5A}$C(O)R$^{5C}$, —NR$^{5A}$C(O)OR$^{5C}$, —NR$^{5A}$OR$^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. L$^1$ is a bond, —S(O)$_2$—, —S(O)$_2$-Ph-, —NR$^6$—, —O—, —S—, —C(O)—, —C(O)NR$^6$—, —NR$^6$C(O)—, —NRC(O)NH—, —NHC(O)NR$^6$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. R$^6$ is hydrogen, halogen, —CX$^6_3$, —CHX$^6_2$, —CH$_2$X$^6$, —OCX$^6_3$, —OCH$_2$X$^6$, —OCHX$^6_2$, —CN, —SO$_{n6}$R$^{6D}$, —SO$_{v6}$NR$^{6A}$R$^{6B}$, —NHC(O)NR$^{6A}$R$^{6B}$, —N(O)$_{m6}$, —NR$^{6A}$R$^{6B}$, —C(O)R$^{6C}$, —C(O)—OR$^{6C}$, —C(O)NR$^{6A}$R$^{6B}$, —OR$^{6D}$, —NR$^{6A}$SO$_2$R$^{6D}$, —NR$^{6A}$C(O)R$^{6C}$, —NR$^{6A}$C(O)O R$^{6C}$, —NR$^{6A}$OR$^{6C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. L$^2$ is a bond, —S(O)$_2$—, —S(O)$_2$-Ph-, —NR$^{7A}$—, —O—, —S—, —C(O)—, —C(O)NR$^{7A}$—, —NR$^7$C(O)—, —NR$^7$C(O)NH—, —NHC(O)NR—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. R$^7$ is hydrogen, halogen, —CX$^7_3$, —CHX$^7_2$, —CH$_2$X$^7$, —OCX$^7_3$, —OCH$_2$X$^7$, —OCHX$^7_2$, —CN, —SO$_{n7}$R$^{7D}$, —SO$_{v7}$NR$^{7A}$R$^{7B}$, —NHC(O)NR$^{7A}$R$^{7B}$, —N(O)$_{m7}$, —NR$^{7A}$R$^{7B}$, —C(O)R$^{7C}$, —C(O)—OR$^{7C}$, —C(O)NR$^{7A}$R$^{7B}$, —OR$^{7D}$, —NR$^{7A}$SO$_2$R$^{7D}$, —NR$^{7A}$C(O)R$^{7C}$, —NR$^{7A}$C(O)O R$^{7C}$, —NR$^{7A}$OR$^{7C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. E is an electrophilic moiety. Each R$^{1A}$, R$^{1B}$, R$^{1C}$, R$^{1D}$, R$^{2A}$, R$^{2B}$, R$^{2C}$, R$^{2D}$, R$^{4A}$, R$^{4B}$, R$^{4C}$, R$^{4D}$, R$^{5A}$, R$^{5B}$, R$^{5C}$, R$^{5D}$, R$^{6A}$, R$^{6B}$, R$^{6C}$, R$^{6D}$, R$^{7A}$, R$^{7B}$, R$^{7C}$, and R$^{7D}$ is independently hydrogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{1A}$ and R$^{1B}$ substituents bonded to the same nitrogen atom may optionally be joined to form a substituted or unsubstituted heterocycloalkyl or substituted or unsubstituted heteroaryl. R$^{2A}$ and R$^{2B}$ substituents bonded to the same nitrogen atom may optionally be joined to form a substituted or unsubstituted heterocycloalkyl or substituted or unsubstituted heteroaryl. R$^{4A}$ and R$^{4B}$ substituents bonded to the same nitrogen atom may optionally be joined to form a substituted or unsubstituted heterocycloalkyl or substituted or unsubstituted heteroaryl. R$^{5A}$ and R$^{5B}$ substituents bonded to the same nitrogen atom may optionally be joined to form a substituted or unsubstituted heterocycloalkyl or substituted or unsubstituted heteroaryl. R$^{6A}$ and R$^{6B}$ substituents bonded to the same nitrogen atom may optionally be joined to form a substituted or unsubstituted heterocycloalkyl or substituted or unsubstituted heteroaryl. R$^{7A}$ and R$^{7B}$ substituents bonded to the same nitrogen atom may optionally be joined to form a substituted or unsubstituted heterocycloalkyl or substituted or unsubstituted heteroaryl. Each X, X$^1$, X$^2$, X$^4$, X$^5$, X$^6$, and X$^7$ is independently —F, —Cl, —Br, or —I. The symbols n1, n2, n4, n5, n6, and n7 are independently an integer from 0 to 4. The symbols m1, m2, m4, m5, m6, m7, v1, v2, v4, v5, v6, and v7 are independently an integer from 1 to 2.

In embodiments, the compound has the formula

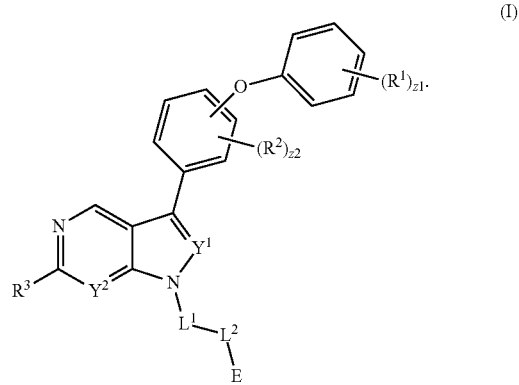

(I)

R$^1$, R$^2$, R$^3$, L$^1$, L$^2$, Y$^1$, Y$^2$, z1, z2, and E are as described herein.

In embodiments, the compound has the formula

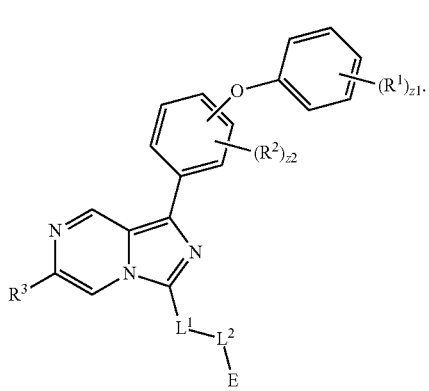
(II)

$R^1$, $R^2$, $R^3$, $L^1$, $L^2$, z1, z2, and E are as described herein.

In embodiments, the compound has the formula

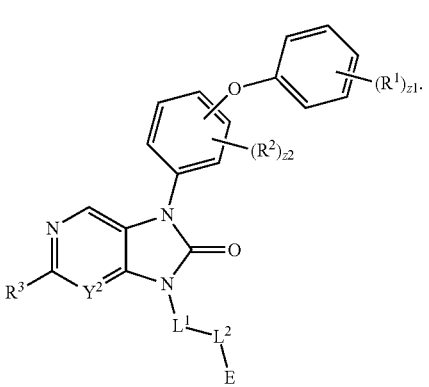
(III)

$R^1$, $R^2$, $R^3$, $L^1$, $L^2$, $Y^1$, $Y^2$, z1, z2, and E are as described herein.

In embodiments, the compound has the formula

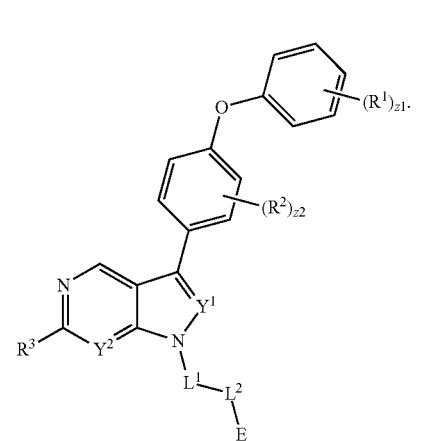
(IA)

$R^1$, $R^2$, $R^3$, $L^1$, $L^2$, $Y^1$, $Y^2$, z1, z2, and E are as described herein.

In embodiments, the compound has the formula

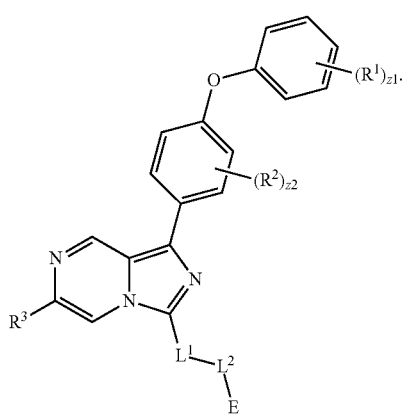
(IIA)

$R^1$, $R^2$, $R^3$, $L^1$, $L^2$, z1, z2, and E are as described herein.

In embodiments, the compound has the formula

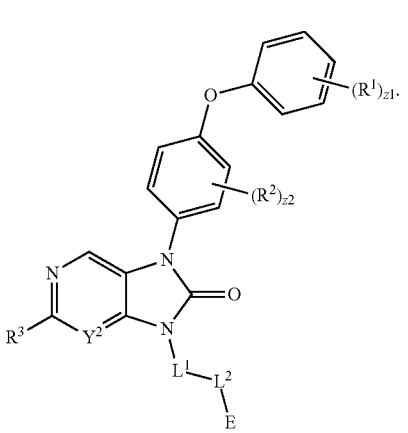
(IIIA)

$R^1$, $R^2$, $R^3$, $L^1$, $L^2$, $Y^2$, z1, z2, and E are as described herein.

In embodiments, the compound has the formula

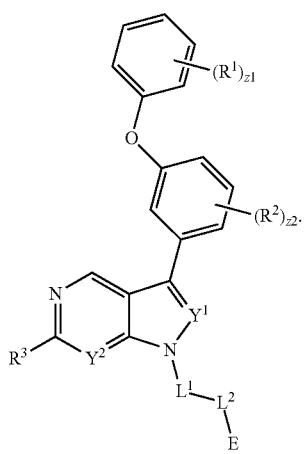
(IB)

$R^1$, $R^2$, $R^3$, $L^1$, $L^2$, $Y^1$, $Y^2$, z1, z2, and E are as described herein.

In embodiments, the compound has the formula

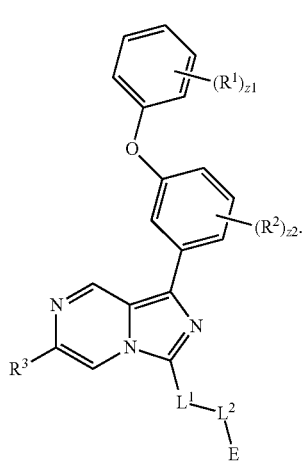

(IIB)

R¹, R², R³, L¹, L², z1, z2, and E are as described herein.
In embodiments, the compound has the formula

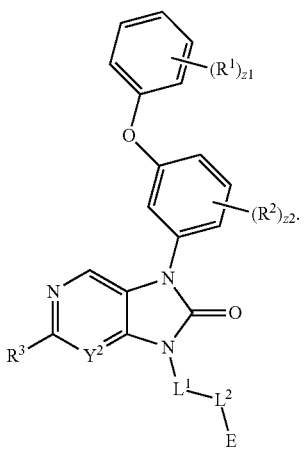

(IIIB)

R¹, R², R³, L¹, L², Y², z1, z2, and E are as described herein.
In embodiments, the compound has the formula

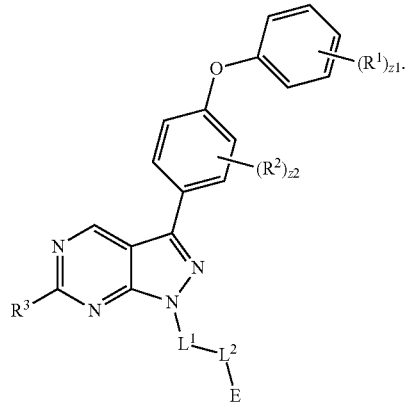

(IC)

R¹, R², R³, L¹, L², z1, z2, and E are as described herein.

In embodiments, the compound has the formula

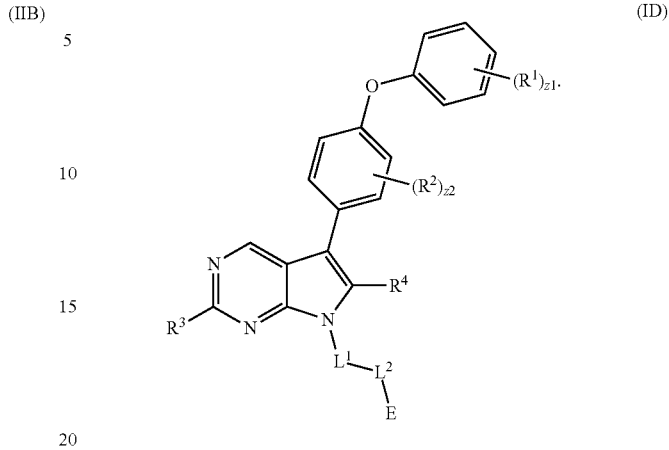

(ID)

R¹, R², R³, R⁴, L¹, L², z1, z2, and E are as described herein.
In embodiments, the compound has the formula

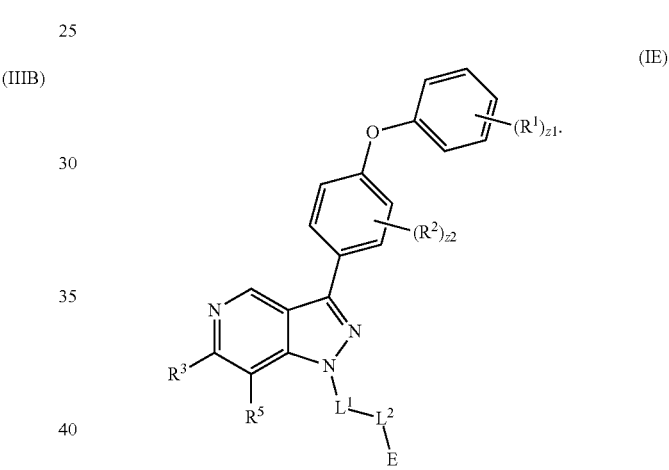

(IE)

R¹, R², R³, R, L¹, L², z1, z2, and E are as described herein.
In embodiments, the compound has the formula

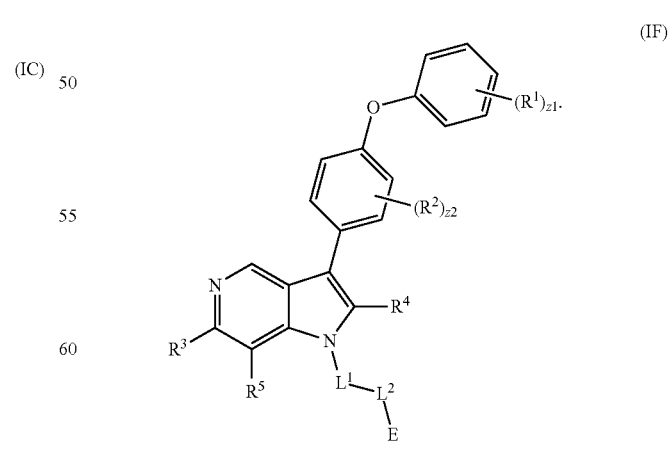

(IF)

R¹, R², R³, R⁴, R⁵, L¹, L², z1, z2, and E are as described herein.

In embodiments, the compound has the formula

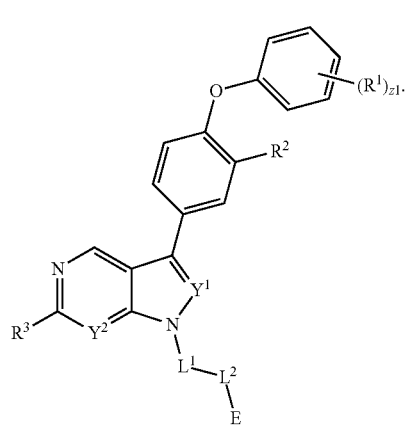

(IAi)

$R^1$, $R^2$, $R^3$, $L^1$, $L^2$, $Y^1$, $Y^2$, z1, and E are as described herein.

In embodiments, the compound has the formula

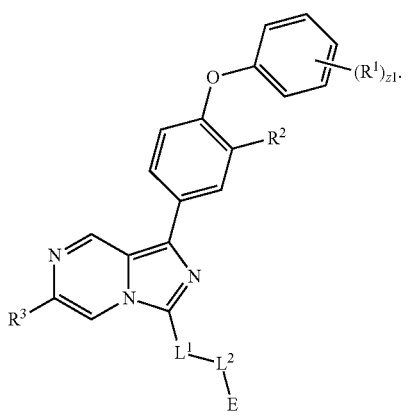

(IIAi)

$R^1$, $R^2$, $R^3$, $L^1$, $L^2$, z1, and E are as described herein.

In embodiments, the compound has the formula

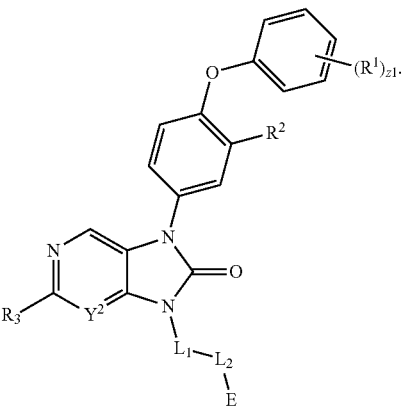

(IIIAi)

$R^1$, $R^2$, $R^3$, $L^1$, $L^2$, $Y^2$, z1, and E are as described herein.

In embodiments, the compound has the formula (IBi)

$R^1$, $R^2$, $R^3$, $L^1$, $L^2$, $Y^1$, $Y^2$, z1, and E are as described herein.

In embodiments, the compound has the formula (IIBi)

$R^1$, $R^2$, $R^3$, $L^1$, $L^2$, z1, and E are as described herein.

In embodiments, the compound has the formula

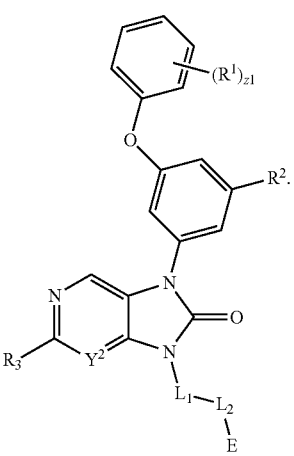

(IIIBi)

$R^1$, $R^2$, $R^3$, $L^1$, $L^2$, $Y^2$, z1, and E are as described herein.

In embodiments, the compound has the formula

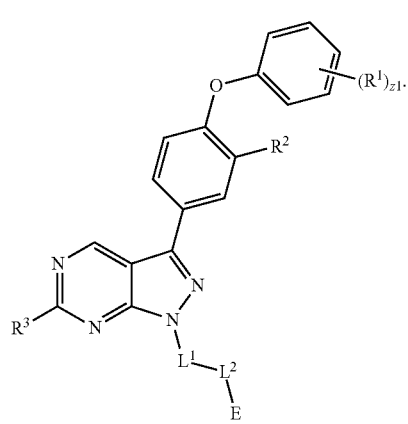
(ICi)

$R^1$, $R^2$, $R^3$, $L^1$, $L^2$, z1, and E are as described herein.

In embodiments, the compound has the formula

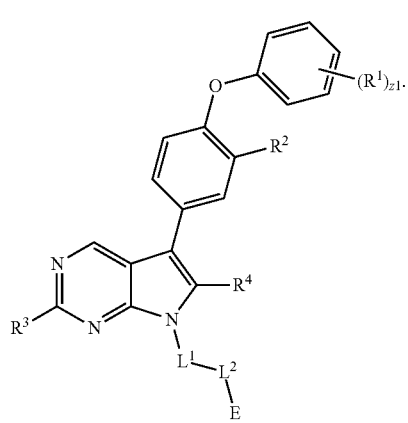
(IDi)

$R^1$, $R^2$, $R^3$, $R^4$, $L^1$, $L^2$, z1, and E are as described herein.

In embodiments, the compound has the formula

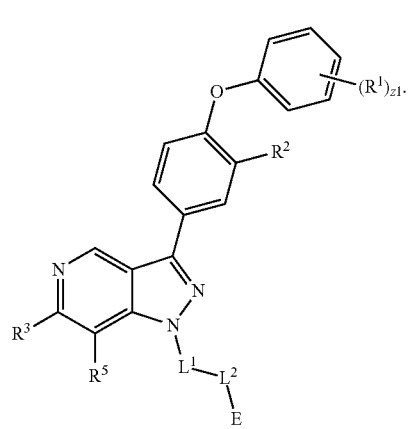
(IEi)

$R^1$, $R^2$, $R^3$, $R^5$, $L^1$, $L^2$, z1, and E are as described herein.

In embodiments, the compound has the formula

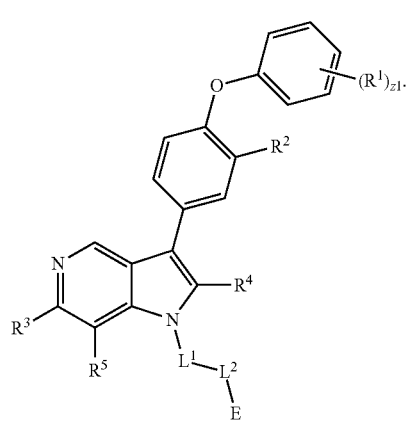
(IFi)

$R^1$, $R^2$, $R^3$, $R^4$, R, $L^1$, $L^2$, z1, and E are as described herein.

In embodiments, the compound has the formula

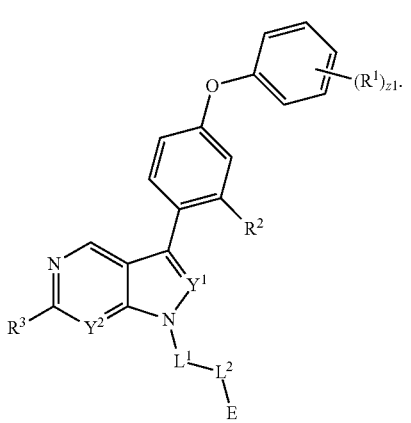
(IAii)

$R^1$, $R^2$, $R^3$, $L^1$, $L^2$, $Y^1$, $Y^2$, z1, and E are as described herein.

In embodiments, the compound has the formula

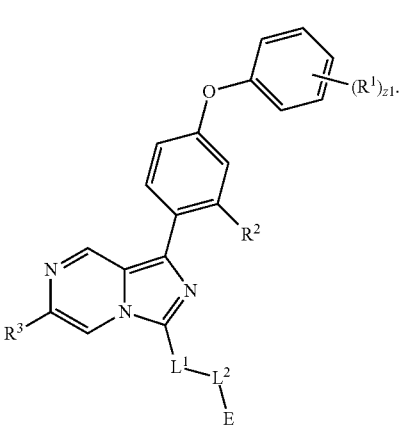
(IIAii)

$R^1$, $R^2$, $R^3$, $L^1$, $L^2$, z1, and E are as described herein.

In embodiments, the compound has the formula

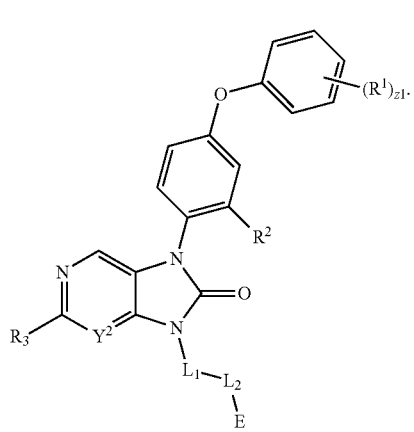

(IIIAii)

$R^1$, $R^2$, $R^3$, $L^1$, $L^2$, $Y^1$, z1, and E are as described herein.
In embodiments, the compound has the formula

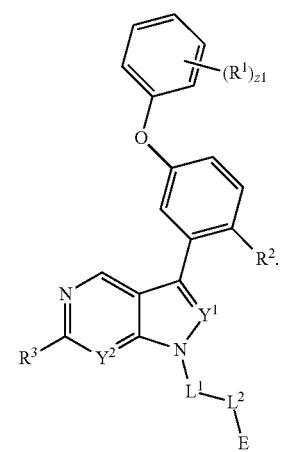

(IBii)

$R^1$, $R^2$, $R^3$, $L^1$, $L^2$, $Y^1$, $Y^2$, z1, and E are as described herein.
In embodiments, the compound has the formula

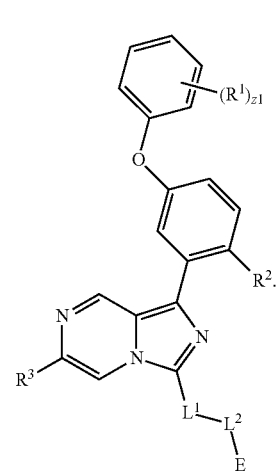

(IIBii)

$R^1$, $R^2$, $R^3$, $L^1$, $L^2$, z1, and E are as described herein.

In embodiments, the compound has the formula

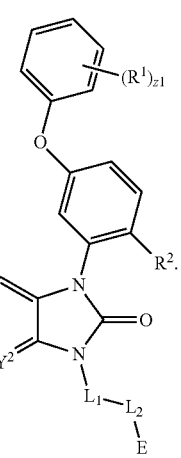

(IIIBii)

$R^1$, $R^2$, $R^3$, $L^1$, $L^2$, $Y^2$, z1, and E are as described herein.
In embodiments, the compound has the formula

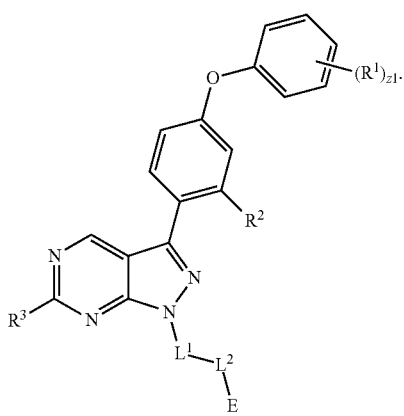

(ICii)

$R^1$, $R^2$, $R^3$, $L^1$, $L^2$, z1, and E are as described herein.
In embodiments, the compound has the formula

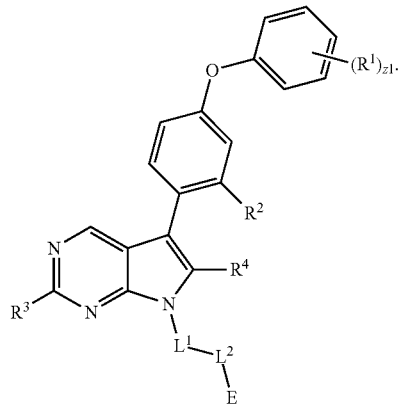

(IDii)

$R^1$, $R^2$, $R^3$, $R^4$, $L^1$, $L^2$, z1, and E are as described herein.

In embodiments, the compound has the formula

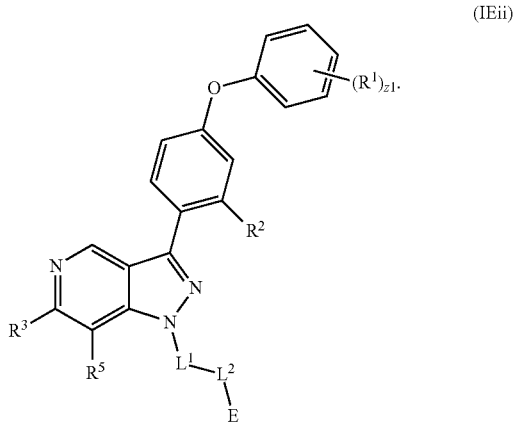

(IEii)

$R^1$, $R^2$, $R^3$, $R^5$, $L^1$, $L^2$, z1, and E are as described herein.

In embodiments, the compound has the formula

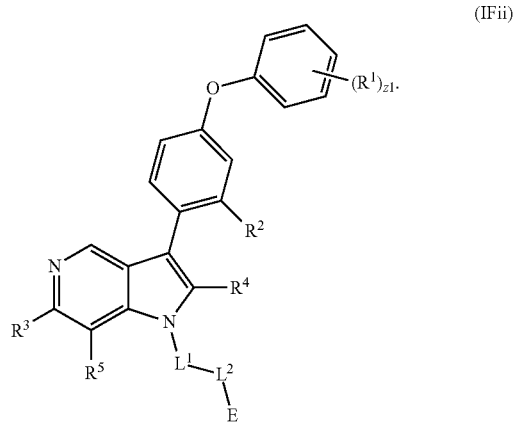

(IFii)

$R^1$, $R^2$, $R^3$, $R^4$, $R^5$, $L^1$, $L^2$, z1, and E are as described herein.

In embodiments, $R^1$ is independently halogen, —$CX^1_3$, —CN, —OH, —$NH_2$, —COOH, —$CONH_2$, —$NO_2$, —SH, —$OCX^1_3$, —$OCHX^1_2$, —$CHX^1_2$, —$CH_2X^1$, substituted or unsubstituted $C_1$-$C_8$ alkyl, or substituted or unsubstituted 2 to 8 membered heteroalkyl; two adjacent $R^1$ substituents may optionally be joined to form a substituted or unsubstituted $C_3$-$C_8$ cycloalkyl, substituted or unsubstituted 3 to 8 membered heterocycloalkyl, substituted or unsubstituted phenyl, or substituted or unsubstituted 5 to 6 membered heteroaryl. In embodiments, $R^1$ is independently halogen, —$CX^1_3$, —CN, unsubstituted $C_1$-$C_4$ alkyl, or unsubstituted 2 to 4 membered heteroalkyl. In embodiments, $R^1$ is independently halogen, —$CX_3$, —CN, unsubstituted methyl, unsubstituted ethyl, unsubstituted methoxy, or unsubstituted ethoxy. In embodiments, $R^1$ is independently unsubstituted methyl. In embodiments, $R^1$ is independently unsubstituted ethyl. In embodiments, $R^1$ is independently unsubstituted propyl. In embodiments, $R^1$ is independently unsubstituted n-propyl. In embodiments, $R^1$ is independently unsubstituted isopropyl. In embodiments, $R^1$ is independently unsubstituted butyl. In embodiments, $R^1$ is independently unsubstituted n-butyl. In embodiments, $R^1$ is independently unsubstituted isobutyl. In embodiments, $R^1$ is independently unsubstituted tert-butyl. In embodiments, $R^1$ is independently unsubstituted pentyl. In embodiments, $R^1$ is independently unsubstituted hexyl. In embodiments, $R^1$ is independently unsubstituted heptyl. In embodiments, $R^1$ is independently unsubstituted octyl. In embodiments, $R^1$ is independently —F. In embodiments, $R^1$ is independently —Cl. In embodiments, $R^1$ is independently —Br. In embodiments, $R^1$ is independently —I. In embodiments, $R^1$ is independently unsubstituted methoxy. In embodiments, $R^1$ is independently unsubstituted ethoxy. In embodiments, $R^1$ is independently —$CF_3$. In embodiments, $R^1$ is independently halogen. In embodiments, $R^1$ is independently —$CCl_3$.

In embodiments, $R^1$ is independently —$CX^1_3$. In embodiments, $R^1$ is independently —$CHX_2$. In embodiments, $R^1$ is independently —$CH_2X^1$. In embodiments, $R^1$ is independently —$OCX_3$. In embodiments, $R^1$ is independently —$OCH_2X^1$. In embodiments, $R^1$ is independently —$OCHX^{12}$. In embodiments, $R^1$ is independently —CN. In embodiments, R is independently —$SO_{n1}R^{1D}$. In embodiments, $R^1$ is independently —$SO_{v1}NR^{1A}R^{1B}$. In embodiments, $R^1$ is independently —$NHC(O)NR^{1A}R^{1B}$. In embodiments, $R^1$ is independently —$N(O)_{m1}$. In embodiments, $R^1$ is independently —$NR^{1A}R^{1B}$. In embodiments, $R^1$ is independently —$C(O)R^{1C}$. In embodiments, $R^1$ is independently —C(O)—$OR^{1C}$. In embodiments, $R^1$ is independently —$C(O)NR^{1A}R^{1B}$. In embodiments, $R^1$ is independently —$OR^{1D}$. In embodiments, $R^1$ is independently —$NR^{1A}SO_2R^{1D}$. In embodiments, $R^1$ is independently —$NR^{1A}C(O)R^{1C}$. In embodiments, $R^1$ is independently —$NR^{A}C(O)OR^{1C}$. In embodiments, $R^1$ is independently —$NR^{1A}OR^{1C}$. In embodiments, $R^1$ is independently —OH. In embodiments, $R^1$ is independently —$NH_2$. In embodiments, $R^1$ is independently —COOH. In embodiments, $R^1$ is independently —$CONH_2$. In embodiments, $R^1$ is independently —$NO_2$. In embodiments, $R^1$ is independently —SH.

In embodiments, $R^1$ is independently substituted or unsubstituted alkyl. In embodiments, $R^1$ is independently substituted or unsubstituted heteroalkyl. In embodiments, $R^1$ is independently substituted or unsubstituted cycloalkyl. In embodiments, $R^1$ is independently, substituted or unsubstituted heterocycloalkyl. In embodiments, $R^1$ is independently substituted or unsubstituted aryl. In embodiments, $R^1$ is independently substituted or unsubstituted heteroaryl. In embodiments, $R^1$ is independently substituted alkyl. In embodiments, $R^1$ is independently substituted heteroalkyl. In embodiments, $R^1$ is independently substituted cycloalkyl. In embodiments, $R^1$ is independently, substituted heterocycloalkyl. In embodiments, $R^1$ is independently substituted aryl. In embodiments, $R^1$ is independently substituted heteroaryl. In embodiments, $R^1$ is independently unsubstituted alkyl. In embodiments, $R^1$ is independently unsubstituted heteroalkyl. In embodiments, $R^1$ is independently unsubstituted cycloalkyl. In embodiments, $R^1$ is independently, unsubstituted heterocycloalkyl. In embodiments, $R^1$ is independently unsubstituted aryl. In embodiments, $R^1$ is independently unsubstituted heteroaryl. In embodiments, $R^1$ is independently substituted or unsubstituted $C_1$-$C_8$ alkyl. In embodiments, $R^1$ is independently substituted or unsubstituted 2 to 8 membered heteroalkyl. In embodiments, $R^1$ is independently substituted or unsubstituted $C_3$-$C_8$ cycloalkyl. In embodiments, $R^1$ is independently, substituted or unsubstituted 3 to 8 membered heterocycloalkyl. In embodiments, $R^1$ is independently substituted or unsubstituted $C_6$-$C_{10}$ aryl. In embodiments, $R^1$ is independently substituted or unsubstituted 5 to 10 membered heteroaryl. In embodiments, $R^1$ is independently substituted $C_1$-$C_8$ alkyl. In embodiments, $R^1$ is independently substituted 2 to 8 membered heteroalkyl. In embodiments, $R^1$ is independently substituted $C_3$-$C_8$ cycloalkyl. In embodiments, $R^1$ is independently, substituted 3 to 8 membered heterocycloalkyl. In embodiments, $R^1$ is independently substituted $C_6$-$C_{10}$ aryl. In embodiments, $R^1$ is independently substituted 5 to 10 membered heteroaryl. In embodiments, $R^1$ is independently unsubstituted $C_1$-$C_8$ alkyl. In embodiments, $R^1$ is independently unsubstituted 2 to 8 membered heteroalkyl. In embodiments, $R^1$ is independently unsubstituted $C_3$-$C_8$ cycloalkyl. In embodiments, $R^1$ is independently, unsubstituted 3 to 8 membered heterocycloalkyl. In embodiments, $R^1$ is independently unsubstituted $C_6$-$C_{10}$ aryl. In embodiments, $R^1$ is independently unsubstituted 5 to 10 membered heteroaryl. In embodiments, $R^1$ is independently substituted or unsubstituted $C_1$-$C_4$ alkyl. In embodiments, $R^1$ is independently substituted or unsubstituted 2 to 4 membered heteroalkyl. In embodiments, $R^1$ is independently substituted or unsubstituted $C_3$-$C_6$ cycloalkyl. In embodiments, $R^1$ is independently, substituted or unsubstituted 3 to 6 membered heterocycloalkyl. In embodiments, $R^1$ is independently substituted or unsubstituted phenyl. In embodiments, $R^1$ is independently substituted or unsubstituted 5 to 6 membered heteroaryl. In embodiments, $R^1$ is independently substituted $C_1$-$C_4$ alkyl. In embodiments, $R^1$ is independently substituted 2 to 4 membered heteroalkyl. In embodiments, $R^1$ is independently substituted $C_3$-$C_6$ cycloalkyl. In embodiments, $R^1$ is independently, substituted 3 to 6 membered heterocycloalkyl. In embodiments, $R^1$ is independently substituted phenyl. In embodiments, $R^1$ is independently substituted 5 to 6 membered heteroaryl. In embodiments, $R^1$ is independently unsubstituted $C_1$-$C_4$ alkyl. In embodiments, $R^1$ is independently unsubstituted 2 to 4 membered heteroalkyl. In embodiments, $R^1$ is independently unsubstituted $C_3$-$C_6$ cycloalkyl. In embodiments, $R^1$ is independently unsubstituted 3 to 6 membered heterocycloalkyl. In embodiments, $R^1$ is independently unsubstituted phenyl. In embodiments, $R^1$ is independently unsubstituted 5 to 6 membered heteroaryl.

In embodiments, two adjacent $R^1$ substituents may optionally be joined to form a substituted or unsubstituted cycloalkyl. In embodiments, two adjacent $R^1$ substituents may optionally be joined to forma substituted or unsubstituted heterocycloalkyl. In embodiments, two adjacent $R^1$ substituents may optionally be joined to form a substituted or unsubstituted aryl. In embodiments, two adjacent $R^1$ substituents may optionally be joined to form a substituted or unsubstituted heteroaryl. In embodiments, two adjacent $R^1$ substituents may optionally be joined to form a substituted cycloalkyl. In embodiments, two adjacent $R^1$ substituents may optionally be joined to forma substituted heterocycloalkyl. In embodiments, two adjacent $R^1$ substituents may optionally be joined to form a substituted aryl. In embodiments, two adjacent $R^1$ substituents may optionally be joined to form a substituted heteroaryl. In embodiments, two adjacent $R^1$ substituents may optionally be joined to form an unsubstituted cycloalkyl. In embodiments, two adjacent $R^1$ substituents may optionally be joined to form an unsubstituted heterocycloalkyl. In embodiments, two adjacent $R^1$ substituents may optionally be joined to form an unsubstituted aryl. In embodiments, two adjacent $R^1$ substituents may optionally be joined to form an unsubstituted heteroaryl. In embodiments, two adjacent $R^1$ substituents may optionally be joined to form a substituted or unsubstituted $C_3$-$C_8$ cycloalkyl. In embodiments, two adjacent $R^1$ substituents may optionally be joined to form a substituted or unsubstituted 3 to 8 membered heterocycloalkyl. In embodiments, two adjacent $R^1$ substituents may optionally be joined to form a substituted or unsubstituted $C_6$-$C_{10}$ aryl. In embodiments, two adjacent $R^1$ substituents may optionally be joined to form a substituted or unsubstituted 5 to 10 membered heteroaryl. In embodiments, two adjacent $R^1$ substituents may optionally be joined to form a substituted $C_3$-$C_8$ cycloalkyl. In embodiments, two adjacent $R^1$ substituents may optionally be joined to forma substituted 3 to 8 membered heterocycloalkyl. In embodiments, two adjacent $R^1$ substituents may optionally be joined to form a substituted $C_6$-$C_{10}$ aryl. In embodiments, two adjacent $R^1$ substituents may optionally be joined to form a substituted 5 to 10 membered heteroaryl. In embodiments, two adjacent $R^1$ substituents may optionally be joined to form an unsubstituted $C_3$-$C_8$ cycloalkyl. In embodiments, two adjacent $R^1$ substituents may optionally be joined to form an unsubstituted 3 to 8 membered heterocycloalkyl. In embodiments, two adjacent $R^1$ substituents may optionally be joined to form an unsubstituted $C_6$-$C_{10}$ aryl. In embodiments, two adjacent $R^1$ substituents may optionally be joined to form an unsubstituted 5 to 10 membered heteroaryl. In embodiments, two adjacent $R^1$ substituents may optionally be joined to form a substituted or unsubstituted $C_3$-$C_6$ cycloalkyl. In embodiments, two adjacent $R^1$ substituents may optionally be joined to form a substituted or unsubstituted 3 to 6 membered heterocycloalkyl. In embodiments, two adjacent $R^1$ substituents may optionally be joined to form a substituted or unsubstituted phenyl. In embodiments, two adjacent $R^1$ substituents may optionally be joined to form a substituted or unsubstituted 5 to 6 membered heteroaryl. In embodiments, two adjacent $R^1$ substituents may optionally be joined to forma substituted $C_3$-$C_6$ cycloalkyl. In embodiments, two adjacent $R^1$ substituents may optionally be joined to form a substituted 3 to 6 membered heterocycloalkyl. In embodiments, two adjacent $R^1$ substituents may optionally be joined to form a substituted phenyl. In embodiments, two adjacent $R^1$ substituents may optionally be joined to form a substituted 5 to 6 membered heteroaryl. In embodiments, two adjacent $R^1$ substituents may optionally be joined to form an unsubstituted $C_3$-$C_6$ cycloalkyl. In embodiments, two adjacent $R^1$ substituents may optionally be joined to form an unsubstituted 3 to 6 membered heterocycloalkyl. In embodiments, two adjacent $R^1$ substituents may optionally be joined to form an unsubstituted phenyl. In embodiments, two adjacent $R^1$ substituents may optionally be joined to form an unsubstituted 5 to 6 membered heteroaryl.

In embodiments, $R^{1A}$ is independently hydrogen. In embodiments, $R^{1A}$ is independently —$CX^{1A}_3$. In embodiments, $R^{1A}$ is independently —$CHX^{1A}_2$. In embodiments, $R^{1A}$ is independently —$CH_2X^{1A}$. In embodiments, $R^{1A}$ is independently —CN. In embodiments, $R^{1A}$ is independently —COOH. In embodiments, $R^{1A}$ is independently —$CONH_2$. In embodiments, $R^{1A}$ is independently substituted or unsubstituted alkyl. In embodiments, $R^{1A}$ is independently substituted or unsubstituted heteroalkyl. In embodiments, $R^{1A}$ is independently substituted or unsubstituted cycloalkyl. In embodiments, $R^{1A}$ is independently, substituted or unsubstituted heterocycloalkyl. In embodiments, $R^{1A}$ is independently substituted or unsubstituted aryl. In embodiments, $R^{1A}$ is independently substituted or unsubstituted heteroaryl. In embodiments, $R^{1A}$ is independently substituted alkyl. In embodiments, $R^{1A}$ is independently substituted heteroalkyl. In embodiments, $R^{1A}$ is independently substituted cycloalkyl. In embodiments, $R^{1A}$ is independently, substituted heterocycloalkyl. In embodiments, $R^{1A}$ is independently substituted aryl. In embodiments, $R^{1A}$ is independently substituted heteroaryl. In embodiments, $R^{1A}$ is independently unsubstituted alkyl. In embodiments, $R^{1A}$ is independently unsubstituted heteroalkyl. In embodiments, $R^{1A}$ is independently unsubstituted cycloalkyl. In embodiments, $R^{1A}$ is independently, unsubstituted heterocycloalkyl. In embodiments, $R^{1A}$ is independently unsubstituted aryl. In embodiments, $R^{1A}$ is independently unsubstituted heteroaryl. In embodiments, $R^{1A}$ is independently substituted or unsubstituted $C_1$-$C_8$ alkyl. In embodiments, $R^{1A}$ is independently substituted or unsubstituted 2 to 8 membered heteroalkyl. In embodiments, $R^{1A}$ is independently substituted or unsubstituted $C_3$-$C_8$ cycloalkyl. In embodiments, $R^{1A}$ is independently, substituted or unsubstituted 3 to 8 membered heterocycloalkyl. In embodiments, $R^{1A}$ is independently substituted or unsubstituted $C_6$-$C_{10}$ aryl. In embodiments, $R^{1A}$ is independently substituted or unsubstituted 5 to 10 membered heteroaryl. In embodiments, $R^{1A}$ is independently substituted $C_1$-$C_8$ alkyl. In embodiments, $R^{1A}$ is independently substituted 2 to 8 membered heteroalkyl. In embodiments, $R^{1A}$ is independently substituted $C_3$-$C_8$ cycloalkyl. In embodiments, $R^{1A}$ is independently, substituted 3 to 8 membered heterocycloalkyl. In embodiments, $R^{1A}$ is independently substituted $C_6$-$C_{10}$ aryl. In embodiments, $R^{1A}$ is independently substituted 5 to 10 membered heteroaryl. In embodiments, $R^{1A}$ is independently unsubstituted $C_1$-$C_8$ alkyl. In embodiments, $R^{1A}$ is independently unsubstituted 2 to 8 membered heteroalkyl. In embodiments, $R^{1A}$ is independently unsubstituted $C_3$-$C_8$ cycloalkyl. In embodiments, $R^{1A}$ is independently, unsubstituted 3 to 8 membered heterocycloalkyl. In embodiments, $R^{1A}$ is independently unsubstituted $C_6$-$C_{10}$ aryl. In embodiments, $R^{1A}$ is independently unsubstituted 5 to 10 membered heteroaryl. In embodiments, $R^{1A}$ is independently substituted or unsubstituted $C_1$-$C_4$ alkyl. In embodiments, $R^{1A}$ is independently substituted or unsubstituted 2 to 4 membered heteroalkyl. In embodiments, $R^{1A}$ is independently substituted or unsubstituted $C_3$-$C_6$ cycloalkyl. In embodiments, $R^{1A}$ is independently, substituted or unsubstituted 3 to 6 membered heterocycloalkyl. In embodiments, $R^{1A}$ is independently substituted or unsubstituted phenyl. In embodiments, $R^{1A}$ is independently substituted or unsubstituted 5 to 6 membered heteroaryl. In embodiments, $R^{1A}$ is independently substituted $C_1$-$C_4$ alkyl. In embodiments, $R^{1A}$ is independently substituted 2 to 4 membered heteroalkyl. In embodiments, $R^{1A}$ is independently substituted $C_3$-$C_6$ cycloalkyl. In embodiments, $R^{1A}$ is independently, substituted 3 to 6 membered heterocycloalkyl. In embodiments, $R^{1A}$ is independently substituted phenyl. In embodiments, $R^{1A}$ is independently substituted 5 to 6 membered heteroaryl. In embodiments, $R^{1A}$ is independently unsubstituted $C_1$-$C_4$ alkyl. In embodiments, $R^{1A}$ is independently unsubstituted 2 to 4 membered heteroalkyl. In embodiments, $R^{1A}$ is independently unsubstituted $C_3$-$C_6$ cycloalkyl. In embodiments, $R^{1A}$ is independently unsubstituted 3 to 6 membered heterocycloalkyl. In embodiments, $R^{1A}$ is independently unsubstituted phenyl. In embodiments, $R^{1A}$ is independently unsubstituted 5 to 6 membered heteroaryl. In embodiments, $R^{1A}$ is independently unsubstituted methyl. In embodiments, $R^{1A}$ is independently unsubstituted ethyl. In embodiments, $R^{1A}$ is independently unsubstituted propyl. In embodiments, $R^{1A}$ is independently unsubstituted isopropyl. In embodiments, $R^{1A}$ is independently unsubstituted tert-butyl.

In embodiments, $R^{1B}$ is independently hydrogen. In embodiments, $R^{1B}$ is independently —$CX^{1B}{}_3$. In embodiments, $R^{1B}$ is independently —$CHX^{1B}{}_2$. In embodiments, $R^{1B}$ is independently —$CH_2X^{1B}$. In embodiments, $R^{1B}$ is independently —CN. In embodiments, $R^{1B}$ is independently —COOH. In embodiments, $R^{1B}$ is independently —$CONH_2$. In embodiments, $R^{1B}$ is independently substituted or unsubstituted alkyl. In embodiments, $R^{1B}$ is independently substituted or unsubstituted heteroalkyl. In embodiments, $R^{1B}$ is independently substituted or unsubstituted cycloalkyl. In embodiments, $R^{1B}$ is independently, substituted or unsubstituted heterocycloalkyl. In embodiments, $R^{1B}$ is independently substituted or unsubstituted aryl. In embodiments, $R^{1B}$ is independently substituted or unsubstituted heteroaryl. In embodiments, $R^{1B}$ is independently substituted alkyl. In embodiments, $R^{1B}$ is independently substituted heteroalkyl. In embodiments, $R^{1B}$ is independently substituted cycloalkyl. In embodiments, $R^{1B}$ is independently, substituted heterocycloalkyl. In embodiments, $R^{1B}$ is independently substituted aryl. In embodiments, $R^{1B}$ is independently substituted heteroaryl. In embodiments, $R^{1B}$ is independently unsubstituted alkyl. In embodiments, $R^{1B}$ is independently unsubstituted heteroalkyl. In embodiments, $R^{1B}$ is independently unsubstituted cycloalkyl. In embodiments, $R^{1B}$ is independently, unsubstituted heterocycloalkyl. In embodiments, $R^{1B}$ is independently unsubstituted aryl. In embodiments, $R^{1B}$ is independently unsubstituted heteroaryl. In embodiments, $R^{1B}$ is independently substituted or unsubstituted $C_1$-$C_8$ alkyl. In embodiments, $R^{1B}$ is independently substituted or unsubstituted 2 to 8 membered heteroalkyl. In embodiments, $R^{1B}$ is independently substituted or unsubstituted $C_3$-$C_8$ cycloalkyl. In embodiments, $R^{1B}$ is independently, substituted or unsubstituted 3 to 8 membered heterocycloalkyl. In embodiments, $R^{1B}$ is independently substituted or unsubstituted $C_6$-$C_{10}$ aryl. In embodiments, $R^{1B}$ is independently substituted or unsubstituted 5 to 10 membered heteroaryl. In embodiments, $R^{1B}$ is independently substituted $C_1$-$C_8$ alkyl. In embodiments, $R^{1B}$ is independently substituted 2 to 8 membered heteroalkyl. In embodiments, $R^{1B}$ is independently substituted $C_3$-$C_8$ cycloalkyl. In embodiments, $R^{1B}$ is independently, substituted 3 to 8 membered heterocycloalkyl. In embodiments, $R^{1B}$ is independently substituted $C_6$-$C_{10}$ aryl. In embodiments, $R^{1B}$ is independently substituted 5 to 10 membered heteroaryl. In embodiments, $R^{1B}$ is independently unsubstituted $C_1$-$C_8$ alkyl. In embodiments, $R^{1B}$ is independently unsubstituted 2 to 8 membered heteroalkyl. In embodiments, $R^{1B}$ is independently unsubstituted $C_3$-$C_8$ cycloalkyl. In embodiments, $R^{1B}$ is independently, unsubstituted 3 to 8 membered heterocycloalkyl. In embodiments, $R^{1B}$ is independently unsubstituted $C_6$-$C_{10}$ aryl. In embodiments, $R^{1B}$ is independently unsubstituted 5 to 10 membered heteroaryl. In embodiments, $R^{1B}$ is independently substituted or unsubstituted $C_1$-$C_4$ alkyl. In embodiments, $R^{1B}$ is independently substituted or unsubstituted 2 to 4 membered heteroalkyl. In embodiments, $R^{1B}$ is independently substituted or unsubstituted $C_3$-$C_6$ cycloalkyl. In embodiments, $R^{1B}$ is independently, substituted or unsubstituted 3 to 6 membered heterocycloalkyl. In embodiments, $R^{1B}$ is independently substituted or unsubstituted phenyl. In embodiments, $R^{1B}$ is independently substituted or unsubstituted 5 to 6 membered heteroaryl. In embodiments, $R^{1B}$ is independently substituted $C_1$-$C_4$ alkyl. In embodiments, $R^{1B}$ is independently substituted 2 to 4 membered heteroalkyl. In embodiments, $R^{1B}$ is independently substituted $C_3$-$C_6$ cycloalkyl. In embodiments, $R^{1B}$ is independently, substituted 3 to 6 membered heterocycloalkyl. In embodiments, $R^{1B}$ is independently substituted phenyl. In embodiments, $R^{1B}$ is independently substituted 5 to 6 membered heteroaryl. In embodiments, $R^{1B}$ is independently unsubstituted $C_1$-$C_4$ alkyl. In embodiments, $R^{1B}$ is independently unsubstituted 2 to 4 membered heteroalkyl. In embodiments, $R^{1B}$ is independently unsubstituted $C_3$-$C_6$ cycloalkyl. In embodiments, $R^{1B}$ is independently unsubstituted 3 to 6 membered heterocycloalkyl. In embodiments, $R^{1B}$ is independently unsubstituted phenyl. In embodiments, $R^{1B}$ is independently unsubstituted 5 to 6 membered heteroaryl. In embodiments, $R^{1B}$ is independently unsubstituted methyl. In embodiments, $R^{1B}$ is independently unsubstituted ethyl. In embodiments, $R^{1B}$ is independently unsubstituted propyl. In embodiments, $R^{1B}$ is independently unsubstituted isopropyl. In embodiments, $R^{1B}$ is independently unsubstituted tert-butyl.

In embodiments, $R^{1A}$ and $R^{1B}$ substituents bonded to the same nitrogen atom may be joined to form a substituted or unsubstituted heterocycloalkyl. In embodiments, $R^{1A}$ and $R^{1B}$ substituents bonded to the same nitrogen atom may be joined to form a substituted or unsubstituted heteroaryl. In embodiments, $R^{1A}$ and $R^{1B}$ substituents bonded to the same nitrogen atom may be joined to form a substituted heterocycloalkyl. In embodiments, $R^{1A}$ and $R^{1B}$ substituents bonded to the same nitrogen atom may be joined to form a substituted heteroaryl. In embodiments, $R^{1A}$ and $R^{1B}$ substituents bonded to the same nitrogen atom may be joined to form an unsubstituted heterocycloalkyl. In embodiments, $R^{1A}$ and $R^{1B}$ substituents bonded to the same nitrogen atom may be joined to form an unsubstituted heteroaryl. In embodiments, $R^{1A}$ and $R^{1B}$ substituents bonded to the same nitrogen atom may be joined to form a substituted or unsubstituted 3 to 8 membered heterocycloalkyl. In embodiments, $R^{1A}$ and $R^{1B}$ substituents bonded to the same nitrogen atom may be joined to form a substituted or unsubstituted 5 to 10 membered heteroaryl. In embodiments, $R^{1A}$ and $R^{1B}$ substituents bonded to the same nitrogen atom may be joined to form a substituted 3 to 8 membered heterocycloalkyl. In embodiments, $R^{1A}$ and $R^{1B}$ substituents bonded to the same nitrogen atom may be joined to form a substituted 5 to 10 membered heteroaryl. In embodiments, $R^{1A}$ and $R^{1B}$ substituents bonded to the same nitrogen atom may be joined to form an unsubstituted 3 to 8 membered heterocycloalkyl. In embodiments, $R^{1A}$ and $R^{1B}$ substituents bonded to the same nitrogen atom may be joined to form an unsubstituted 5 to 10 membered heteroaryl. In embodiments, $R^{1A}$ and $R^{1B}$ substituents bonded to the same nitrogen atom may be joined to form a substituted or unsubstituted 3 to 6 membered heterocycloalkyl. In embodiments, $R^{1A}$ and $R^{1B}$ substituents bonded to the same nitrogen atom may be joined to form a substituted or unsubstituted 5 to 6 membered heteroaryl. In embodiments, $R^{1A}$ and $R^{1B}$ substituents bonded to the same nitrogen atom may be joined to form a substituted 3 to 6 membered heterocycloalkyl. In embodiments, $R^{1A}$ and $R^{1B}$ substituents bonded to the same nitrogen atom may be joined to form a substituted 5 to 6 membered heteroaryl. In embodiments, $R^{1A}$ and $R^{1B}$ substituents bonded to the same nitrogen atom may be joined to form an unsubstituted 3 to 6 membered heterocycloalkyl. In embodiments, $R^{1A}$ and $R^{1B}$ substituents bonded to the same nitrogen atom may be joined to form an unsubstituted 5 to 6 membered heteroaryl.

In embodiments, $R^{1C}$ is independently hydrogen. In embodiments, $R^{1C}$ is independently $-CX^{1C}_3$. In embodiments, $R^{1C}$ is independently $-CHX^{1C}_2$. In embodiments, $R^{1C}$ is independently $-CH_2X^{1C}$. In embodiments, $R^{1C}$ is independently $-CN$. In embodiments, $R^{1C}$ is independently $-COOH$. In embodiments, $R^{1C}$ is independently $-CONH_2$. In embodiments, $R^{1C}$ is independently substituted or unsubstituted alkyl. In embodiments, $R^{1C}$ is independently substituted or unsubstituted heteroalkyl. In embodiments, $R^{1C}$ is independently substituted or unsubstituted cycloalkyl. In embodiments, $R^{1C}$ is independently, substituted or unsubstituted heterocycloalkyl. In embodiments, $R^{1C}$ is independently substituted or unsubstituted aryl. In embodiments, $R^{1C}$ is independently substituted or unsubstituted heteroaryl. In embodiments, $R^{1C}$ is independently substituted alkyl. In embodiments, $R^{1C}$ is independently substituted heteroalkyl. In embodiments, $R^{1C}$ is independently substituted cycloalkyl. In embodiments, $R^{1C}$ is independently, substituted heterocycloalkyl. In embodiments, $R^{1C}$ is independently substituted aryl. In embodiments, $R^{1C}$ is independently substituted heteroaryl. In embodiments, $R^{1C}$ is independently unsubstituted alkyl. In embodiments, $R^{1C}$ is independently unsubstituted heteroalkyl. In embodiments, $R^{1C}$ is independently unsubstituted cycloalkyl. In embodiments, $R^{1C}$ is independently, unsubstituted heterocycloalkyl. In embodiments, $R^{1C}$ is independently unsubstituted aryl. In embodiments, $R^{1C}$ is independently unsubstituted heteroaryl. In embodiments, $R^{1C}$ is independently substituted or unsubstituted $C_1$-$C_8$ alkyl. In embodiments, $R^{1C}$ is independently substituted or unsubstituted 2 to 8 membered heteroalkyl. In embodiments, $R^{1C}$ is independently substituted or unsubstituted $C_3$-$C_8$ cycloalkyl. In embodiments, $R^{1C}$ is independently, substituted or unsubstituted 3 to 8 membered heterocycloalkyl. In embodiments, $R^{1C}$ is independently substituted or unsubstituted $C_6$-$C_{10}$ aryl. In embodiments, $R^{1C}$ is independently substituted or unsubstituted 5 to 10 membered heteroaryl. In embodiments, $R^{1C}$ is independently substituted $C_1$-$C_8$ alkyl. In embodiments, $R^{1C}$ is independently substituted 2 to 8 membered heteroalkyl. In embodiments, $R^{1C}$ is independently substituted $C_3$-$C_8$ cycloalkyl. In embodiments, $R^{1C}$ is independently, substituted 3 to 8 membered heterocycloalkyl. In embodiments, $R^{1C}$ is independently substituted $C_6$-$C_{10}$ aryl. In embodiments, $R^{1C}$ is independently substituted 5 to 10 membered heteroaryl. In embodiments, $R^{1C}$ is independently unsubstituted $C_1$-$C_8$ alkyl. In embodiments, $R^{1C}$ is independently unsubstituted 2 to 8 membered heteroalkyl. In embodiments, $R^{1C}$ is independently unsubstituted $C_3$-$C_8$ cycloalkyl. In embodiments, $R^{1C}$ is independently, unsubstituted 3 to 8 membered heterocycloalkyl. In embodiments, $R^{1C}$ is independently unsubstituted $C_6$-$C_{10}$ aryl. In embodiments, $R^{1C}$ is independently unsubstituted 5 to 10 membered heteroaryl. In embodiments, $R^{1C}$ is independently substituted or unsubstituted $C_1$-$C_4$ alkyl. In embodiments, $R^{1C}$ is independently substituted or unsubstituted 2 to 4 membered heteroalkyl. In embodiments, $R^{1C}$ is independently substituted or unsubstituted $C_3$-$C_6$ cycloalkyl. In embodiments, $R^{1C}$ is independently, substituted or unsubstituted 3 to 6 membered heterocycloalkyl. In embodiments, $R^{1C}$ is independently substituted or unsubstituted phenyl. In embodiments, $R^{1C}$ is independently substituted or unsubstituted 5 to 6 membered heteroaryl. In embodiments, $R^{1C}$ is independently substituted $C_1$-$C_4$ alkyl. In embodiments, $R^{1C}$ is independently substituted 2 to 4 membered heteroalkyl. In embodiments, $R^{1C}$ is independently substituted $C_3$-$C_6$ cycloalkyl. In embodiments, $R^{1C}$ is independently, substituted 3 to 6 membered heterocycloalkyl. In embodiments, $R^{1C}$ is independently substituted phenyl. In embodiments, $R^{1C}$ is independently substituted 5 to 6 membered heteroaryl. In embodiments, $R^{1C}$ is independently unsubstituted $C_1$-$C_4$ alkyl. In embodiments, $R^{1C}$ is independently unsubstituted 2 to 4 membered heteroalkyl. In embodiments, $R^{1C}$ is independently unsubstituted $C_3$-$C_6$ cycloalkyl. In embodiments, $R^{1C}$ is independently unsubstituted 3 to 6 membered heterocycloalkyl. In embodiments, $R^{1C}$ is independently unsubstituted phenyl. In embodiments, $R^{1C}$ is independently unsubstituted 5 to 6 membered heteroaryl. In embodiments, $R^{1C}$ is independently unsubstituted methyl. In embodiments, $R^{1C}$ is independently unsubstituted ethyl. In embodiments, $R^{1C}$ is independently unsubstituted propyl. In embodiments, $R^{1C}$ is independently unsubstituted isopropyl. In embodiments, $R^{1C}$ is independently unsubstituted tert-butyl.

In embodiments, $R^{1D}$ is independently hydrogen. In embodiments, $R^{1D}$ is independently —$CX^{1D}_3$. In embodiments, $R^{1D}$ is independently —$CHX^{1D}_2$. In embodiments, $R^{1D}$ is independently —$CH_2X^{1D}$. In embodiments, $R^{1D}$ is independently —CN. In embodiments, $R^{1D}$ is independently —COOH. In embodiments, $R^{1D}$ is independently —$CONH_2$. In embodiments, $R^{1D}$ is independently substituted or unsubstituted alkyl. In embodiments, $R^{1D}$ is independently substituted or unsubstituted heteroalkyl. In embodiments, $R^{1D}$ is independently substituted or unsubstituted cycloalkyl. In embodiments, $R^{1D}$ is independently, substituted or unsubstituted heterocycloalkyl. In embodiments, $R^{1D}$ is independently substituted or unsubstituted aryl. In embodiments, $R^{1D}$ is independently substituted or unsubstituted heteroaryl. In embodiments, $R^{1D}$ is independently substituted alkyl. In embodiments, $R^{1D}$ is independently substituted heteroalkyl. In embodiments, $R^{1D}$ is independently substituted cycloalkyl. In embodiments, $R^{1D}$ is independently, substituted heterocycloalkyl. In embodiments, $R^{1D}$ is independently substituted aryl. In embodiments, $R^{1D}$ is independently substituted heteroaryl. In embodiments, $R^{1D}$ is independently unsubstituted alkyl. In embodiments, $R^{1D}$ is independently unsubstituted heteroalkyl. In embodiments, $R^{1D}$ is independently unsubstituted cycloalkyl. In embodiments, $R^{1D}$ is independently, unsubstituted heterocycloalkyl. In embodiments, $R^{1D}$ is independently unsubstituted aryl. In embodiments, $R^{1D}$ is independently unsubstituted heteroaryl. In embodiments, $R^{1D}$ is independently substituted or unsubstituted $C_1$-$C_8$ alkyl. In embodiments, $R^{1D}$ is independently substituted or unsubstituted 2 to 8 membered heteroalkyl. In embodiments, $R^{1D}$ is independently substituted or unsubstituted $C_3$-$C_8$ cycloalkyl. In embodiments, $R^{1D}$ is independently, substituted or unsubstituted 3 to 8 membered heterocycloalkyl. In embodiments, $R^{1D}$ is independently substituted or unsubstituted $C_6$-$C_{10}$ aryl. In embodiments, $R^{1D}$ is independently substituted or unsubstituted 5 to 10 membered heteroaryl. In embodiments, $R^{1D}$ is independently substituted $C_1$-$C_8$ alkyl. In embodiments, $R^{1D}$ is independently substituted 2 to 8 membered heteroalkyl. In embodiments, $R^{1D}$ is independently substituted $C_3$-$C_8$ cycloalkyl. In embodiments, $R^{1D}$ is independently, substituted 3 to 8 membered heterocycloalkyl. In embodiments, $R^{1D}$ is independently substituted $C_6$-$C_{10}$ aryl. In embodiments, $R^{1D}$ is independently substituted 5 to 10 membered heteroaryl. In embodiments, $R^{1D}$ is independently unsubstituted $C_1$-$C_8$ alkyl. In embodiments, $R^{1D}$ is independently unsubstituted 2 to 8 membered heteroalkyl. In embodiments, $R^{1D}$ is independently unsubstituted $C_3$-$C_8$ cycloalkyl. In embodiments, $R^{1D}$ is independently, unsubstituted 3 to 8 membered heterocycloalkyl. In embodiments, $R^{1D}$ is independently unsubstituted $C_6$-$C_{10}$ aryl. In embodiments, $R^{1D}$ is independently unsubstituted 5 to 10 membered heteroaryl. In embodiments, $R^{1D}$ is independently substituted or unsubstituted $C_1$-$C_4$ alkyl. In embodiments, $R^{1D}$ is independently substituted or unsubstituted 2 to 4 membered heteroalkyl. In embodiments, $R^{1D}$ is independently substituted or unsubstituted $C_3$-$C_6$ cycloalkyl. In embodiments, $R^{1D}$ is independently, substituted or unsubstituted 3 to 6 membered heterocycloalkyl. In embodiments, $R^{1D}$ is independently substituted or unsubstituted phenyl. In embodiments, $R^{1D}$ is independently substituted or unsubstituted 5 to 6 membered heteroaryl. In embodiments, $R^{1D}$ is independently substituted $C_1$-$C_4$ alkyl. In embodiments, $R^{1D}$ is independently substituted 2 to 4 membered heteroalkyl. In embodiments, $R^{1D}$ is independently substituted $C_3$-$C_6$ cycloalkyl. In embodiments, $R^{1D}$ is independently, substituted 3 to 6 membered heterocycloalkyl. In embodiments, $R^{1D}$ is independently substituted phenyl. In embodiments, $R^{1D}$ is independently substituted 5 to 6 membered heteroaryl. In embodiments, $R^{1D}$ is independently unsubstituted $C_1$-$C_4$ alkyl. In embodiments, $R^{1D}$ is independently unsubstituted 2 to 4 membered heteroalkyl. In embodiments, $R^{1D}$ is independently unsubstituted $C_3$-$C_6$ cycloalkyl. In embodiments, $R^{1D}$ is independently unsubstituted 3 to 6 membered heterocycloalkyl. In embodiments, $R^{1D}$ is independently unsubstituted phenyl. In embodiments, $R^{1D}$ is independently unsubstituted 5 to 6 membered heteroaryl. In embodiments, $R^{1D}$ is independently unsubstituted methyl. In embodiments, $R^{1D}$ is independently unsubstituted ethyl. In embodiments, $R^{1D}$ is independently unsubstituted propyl. In embodiments, $R^{1D}$ is independently unsubstituted isopropyl. In embodiments, $R^{1D}$ is independently unsubstituted tert-butyl.

In embodiments, $R^1$ is independently halogen, —$CX^1_3$, —$CHX^1_2$, —$CH_2X^1$, —$OCX^1_3$, —$OCH_2X^1$, —$OCHX^1_2$, —CN, —$SO_nR^{1D}$, —$SO_{v1}NR^{1A}R^{1B}$, —$NHC(O)NR^{1A}R_{1B}$, —$N(O)_{m1}$, —$NR^{1A}R^{1B}$, —$C(O)R^{1C}$, —$C(O)OR^{1C}$, —$C(O)NR^{1A}R^{1B}$, —$OR^{1D}$, —$NR^{1A}SO_2R^{1D}$, —$NR^{1A}C(O)R^{1C}$, —$NR^{1A}C(O)OR^{1C}$, —$NR^{1A}OR^{1C}$, $R^{20}$-substituted or unsubstituted alkyl, $R^{20}$-substituted or unsubstituted heteroalkyl, $R^{20}$-substituted or unsubstituted cycloalkyl, $R^{20}$-substituted or unsubstituted heterocycloalkyl, $R^{20}$-substituted or unsubstituted aryl, or $R^{20}$-substituted or unsubstituted heteroaryl. In embodiments, $R^1$ is independently halogen, —$CX^1_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH$_2$, —NHC(O)NH$_2$, —$NHSO_2H$, —NHC(O)H, —NHC(O)OH, —NHOH, —$OCX^1_3$, —$OCHX^1_2$, $R^{20}$-substituted or unsubstituted alkyl, $R^{20}$-substituted or unsubstituted heteroalkyl, $R^{20}$-substituted or unsubstituted cycloalkyl, $R^{20}$-substituted or unsubstituted heterocycloalkyl, $R^{20}$-substituted or unsubstituted aryl, or $R^{20}$-substituted or unsubstituted heteroaryl. In embodiments, $R^1$ is independently halogen, —$CX^1_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH$_2$, —NHC(O)NH$_2$, —$NHSO_2H$, —NHC(O)H, —NHC(O)OH, —NHOH, —$OCX_3$, —$OCHX_2$, $R^{20}$-substituted or unsubstituted $C_1$-$C_8$ alkyl, $R^{20}$-substituted or unsubstituted 2 to 8 membered heteroalkyl, $R^{20}$-substituted or unsubstituted $C_3$-$C_8$ cycloalkyl, $R^{20}$-substituted or unsubstituted 3 to 6 membered heterocycloalkyl, $R^{20}$-substituted or unsubstituted phenyl, or $R^{20}$-substituted or unsubstituted 5 to 6 membered heteroaryl. $X^1$ is —F, —Cl, —Br, or —I. In embodiments, $R^1$ is independently hydrogen. In embodiments, $R^1$ is independently methyl. In embodiments, $R^1$ is independently ethyl. In embodiments, $R^1$ is $CX_3$. In embodiments, $R^1$ is $CHX_2$. In embodiments, $R^1$ is $CH_2X$. In embodiments, $R^1$ is $CF_3$. In embodiments, $R^1$ is $CHF_2$. In embodiments, $R^1$ is $CH_2F$.

In embodiments, two adjacent $R^1$ substituents may optionally be joined to form a $R^{20}$-substituted or unsubstituted cycloalkyl, $R^{20}$-substituted or unsubstituted heterocycloalkyl, $R^{20}$-substituted or unsubstituted aryl, or $R^{20}$-substituted or unsubstituted heteroaryl. In embodiments, two adjacent $R^1$ substituents may optionally be joined to form a $R^{20}$-substituted or unsubstituted $C_3$-$C_8$ cycloalkyl, $R^{20}$-substituted or unsubstituted 3 to 6 membered heterocycloalkyl, $R^{20}$-substituted or unsubstituted phenyl, or $R^{20}$-substituted or unsubstituted 5 to 6 membered heteroaryl.

$R^{20}$ is independently oxo, halogen, —$CX^{20}_3$, —CN, —OH, —$NH_2$, —COOH, —$CONH_2$, —$NO_2$, —SH, —$SO_3H$, —$SO_4H$, —$SO_2NH_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{20}$$_3$, —OCHX$^{20}$$_2$, R$^{21}$-substituted or unsubstituted alkyl, R$^{21}$-substituted or unsubstituted heteroalkyl, R$^{21}$-substituted or unsubstituted cycloalkyl, R$^{21}$-substituted or unsubstituted heterocycloalkyl, R$^{21}$-substituted or unsubstituted aryl, or R$^{21}$-substituted or unsubstituted heteroaryl. In embodiments, R$^{20}$ is independently oxo, halogen, —CX$^{20}$$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{20}$$_3$, —OCHX$^{20}$$_2$, R$^{21}$-substituted or unsubstituted C$_1$-C$_8$ alkyl, R$^{21}$-substituted or unsubstituted 2 to 8 membered heteroalkyl, R$^{21}$-substituted or unsubstituted C$_3$-C$_8$ cycloalkyl, R$^{21}$-substituted or unsubstituted 3 to 6 membered heterocycloalkyl, R$^{21}$-substituted or unsubstituted phenyl, or R$^{21}$-substituted or unsubstituted 5 to 6 membered heteroaryl. X$^{20}$ is —F, —C, —Br, or —I.

R$^{21}$ is independently oxo, halogen, —CX$^{21}$$_3$, —CN, —OH, —NH$_2$, —COOH, —CONH$_2$, —NO$_2$, —SH, —SO$_3$H, —SO$_4$H, —S$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{21}$$_3$, —OCHX$^{22}$, R$^{22}$-substituted or unsubstituted alkyl, R$^{22}$-substituted or unsubstituted heteroalkyl, R$^{22}$-substituted or unsubstituted cycloalkyl, R$^{22}$-substituted or unsubstituted heterocycloalkyl, R$^{22}$-substituted or unsubstituted aryl, or R$^{22}$-substituted or unsubstituted heteroaryl. In embodiments, R$^{21}$ is independently oxo, halogen, —CX$^{21}$$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{21}$$_3$, —OCHX$^{21}$$_2$, R$^{22}$-substituted or unsubstituted C$_1$-C$_8$ alkyl, R$^{22}$-substituted or unsubstituted 2 to 8 membered heteroalkyl, R$^{22}$-substituted or unsubstituted C$_3$-C$_8$ cycloalkyl, R$^{22}$-substituted or unsubstituted 3 to 6 membered heterocycloalkyl, R$^{22}$-substituted or unsubstituted phenyl, or R$^{22}$-substituted or unsubstituted 5 to 6 membered heteroaryl. X$^{21}$ is —F, —Cl, —Br, or —I.

In embodiments, R$^{1A}$ is independently hydrogen, —CX$^{1A}$$_3$, —CN, —COOH, —CONH$_2$, —CHX$^{A2}$, —CH$_2$X$^{1A}$, R$^{20A}$-substituted or unsubstituted alkyl, R$^{20A}$-substituted or unsubstituted heteroalkyl, R$^{20A}$-substituted or unsubstituted cycloalkyl, R$^{20A}$-substituted or unsubstituted heterocycloalkyl, R$^{20A}$-substituted or unsubstituted aryl, or R$^{20A}$-substituted or unsubstituted heteroaryl. In embodiments, R$^{1A}$ is independently hydrogen, —CX$^{1A}$$_3$, —CN, —COOH, —CONH$_2$, —CHX$^{A2}$, —CH$_2$X$^{1A}$, R$^{20A}$-substituted or unsubstituted C$_1$-C$_8$ alkyl, R$^{20A}$-substituted or unsubstituted 2 to 8 membered heteroalkyl, R$^{20A}$-substituted or unsubstituted C$_3$-C$_8$ cycloalkyl, R$^{20A}$-substituted or unsubstituted 3 to 6 membered heterocycloalkyl, R$^{20A}$-substituted or unsubstituted phenyl, or R$^{20A}$-substituted or unsubstituted 5 to 6 membered heteroaryl. X$^{1A}$ is —F, —Cl, —Br, or —I. In embodiments, R$^{1A}$ is independently hydrogen. In embodiments, R$^{1A}$ is independently methyl. In embodiments, R$^{1A}$ is independently ethyl.

In embodiments, R$^{1A}$ and R$^{1B}$ substituents bonded to the same nitrogen atom may optionally be joined to form a R$^{20A}$-substituted or unsubstituted heterocycloalkyl or R$^{20A}$-substituted or unsubstituted heteroaryl. In embodiments, R$^{1A}$ and R$^{1B}$ substituents bonded to the same nitrogen atom may optionally be joined to form a R$^{20A}$-substituted or unsubstituted 3 to 6 membered heterocycloalkyl or R$^{20A}$-substituted or unsubstituted 5 to 6 membered heteroaryl.

R$^{20A}$ is independently oxo, halogen, —CX$^{20A}$$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{20A}$$_3$, —OCHX$^{20A}$$_2$, R$^{21A}$-substituted or unsubstituted alkyl, R$^{21A}$-substituted or unsubstituted heteroalkyl, R$^{21A}$-substituted or unsubstituted cycloalkyl, R$^{21A}$-substituted or unsubstituted heterocycloalkyl, R$^{21A}$-substituted or unsubstituted aryl, or R$^{21A}$-substituted or unsubstituted heteroaryl. In embodiments, R$^{20A}$ is independently oxo, halogen, —CX$^{20A}$$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{20A}$$_3$, —OCHX$^{20A}$$_2$, R$^{21A}$-substituted or unsubstituted C$_1$-C$_8$ alkyl, R$^{21A}$-substituted or unsubstituted 2 to 8 membered heteroalkyl, R$^{21A}$-substituted or unsubstituted C$_3$-C$_8$ cycloalkyl, R$^{21A}$-substituted or unsubstituted 3 to 6 membered heterocycloalkyl, R$^{21A}$-substituted or unsubstituted phenyl, or R$^{21A}$-substituted or unsubstituted 5 to 6 membered heteroaryl. X$^{20A}$ is —F, —Cl, —Br, or —I.

R$^{21A}$ is independently oxo, halogen, —CX$^{21A}$$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{21A}$$_3$, —OCHX$^{21A}$$_2$, R$^{22A}$-substituted or unsubstituted alkyl, R$^{22A}$-substituted or unsubstituted heteroalkyl, R$^{22A}$-substituted or unsubstituted cycloalkyl, R$^{22A}$-substituted or unsubstituted heterocycloalkyl, R$^{22A}$-substituted or unsubstituted aryl, or R$^{22A}$-substituted or unsubstituted heteroaryl. In embodiments, R$^{21A}$ is independently oxo, halogen, —CX$^{21A}$$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{21A}$$_3$, —OCHX$^{21A}$$_2$, R$^{22A}$-substituted or unsubstituted C$_1$-C$_8$ alkyl, R$^{22A}$-substituted or unsubstituted 2 to 8 membered heteroalkyl, R$^{22A}$-substituted or unsubstituted C$_3$-C$_8$ cycloalkyl, R$^{22A}$-substituted or unsubstituted 3 to 6 membered heterocycloalkyl, R$^{22A}$-substituted or unsubstituted phenyl, or R$^{22A}$-substituted or unsubstituted 5 to 6 membered heteroaryl. X$^{21A}$ is —F, —Cl, —Br, or —I.

In embodiments, R$^{1B}$ is independently hydrogen, —CX$^{1B}$$_3$, —CN, —COOH, —CONH$_2$, —CHX$^{1B}$$_2$, —CH$_2$X$^{1B}$, R$^{20B}$-substituted or unsubstituted alkyl, R$^{20B}$-substituted or unsubstituted heteroalkyl, R$^{20B}$-substituted or unsubstituted cycloalkyl, R$^{20B}$-substituted or unsubstituted heterocycloalkyl, R$^{20B}$ substituted or unsubstituted aryl, or R$^{20B}$-substituted or unsubstituted heteroaryl. In embodiments, R$^{1B}$ is independently hydrogen, —CX$^{1B}$$_3$, —CN, —COOH, —CONH$_2$, —CHX$^{1B}$$_2$, —CH$_2$X$^{1B}$, R$^{2B}$-substituted or unsubstituted C$_1$-C$_8$ alkyl, R$^{20B}$-substituted or unsubstituted 2 to 8 membered heteroalkyl, R$^{20B}$-substituted or unsubstituted C$_3$-C$_8$ cycloalkyl, R$^{20B}$-substituted or unsubstituted 3 to 6 membered heterocycloalkyl, R$^{20B}$-substituted or unsubstituted phenyl, or R$^{20B}$-substituted or unsubstituted 5 to 6 membered heteroaryl. X$^{1B}$ is —F, —Cl, —Br, or —I. In embodiments, R$^{1B}$ is independently hydrogen. In embodiments, R$^{1B}$ is independently methyl. In embodiments, R$^{1B}$ is independently ethyl.

In embodiments, R$^{1A}$ and R$^{1B}$ substituents bonded to the same nitrogen atom may optionally be joined to form a R$^{20B}$-substituted or unsubstituted heterocycloalkyl or R$^{20B}$-substituted or unsubstituted heteroaryl. In embodiments, R$^{1A}$ and R$^{1B}$ substituents bonded to the same nitrogen atom may optionally be joined to form a $R^{20B}$-substituted or unsubstituted 3 to 6 membered heterocycloalkyl or $R^{20B}$-substituted or unsubstituted 5 to 6 membered heteroaryl.

$R^{20B}$ is independently oxo, halogen, —$CX^{20B}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{20B}_3$, —$OCHX^{20B}_2$, $R^{21B}$-substituted or unsubstituted alkyl, $R^{21B}$-substituted or unsubstituted heteroalkyl, $R^{21B}$-substituted or unsubstituted cycloalkyl, $R^{21B}$-substituted or unsubstituted heterocycloalkyl, $R^{21B}$-substituted or unsubstituted aryl, or $R^{21B}$-substituted or unsubstituted heteroaryl. In embodiments, $R^{20B}$ is independently oxo, halogen, —$CX^{20B}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{20B}_3$, —$OCHX^{20B}_2$, $R^{21B}$-substituted or unsubstituted $C_1$-$C_8$ alkyl, $R^{21B}$-substituted or unsubstituted 2 to 8 membered heteroalkyl, $R^{21B}$-substituted or unsubstituted $C_3$-$C_8$ cycloalkyl, $R^{21B}$-substituted or unsubstituted 3 to 6 membered heterocycloalkyl, $R^{21B}$-substituted or unsubstituted phenyl, or $R^{21B}$-substituted or unsubstituted 5 to 6 membered heteroaryl. $X^{20B}$ is —F, —Cl, —Br, or —I.

$R^{21B}$ is independently oxo, halogen, —$CX^{21B}_3$, —CN, —OH, —$NH_2$, —COOH, —$CONH_2$, —$NO_2$, —SH, —$SO_3H$, —$SO_4H$, —$S_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{21B}_3$, —$OCHX^{21B}_2$, $R^{22B}$-substituted or unsubstituted alkyl, $R^{22B}$-substituted or unsubstituted heteroalkyl, $R^{22B}$-substituted or unsubstituted cycloalkyl, $R^{22B}$-substituted or unsubstituted heterocycloalkyl, $R^{22B}$-substituted or unsubstituted aryl, or $R^{22B}$-substituted or unsubstituted heteroaryl. In embodiments, $R^{21B}$ is independently oxo, halogen, —$CX^{21B}_3$, —CN, —OH, —$NH_2$, —COOH, —$CONH_2$, —$NO_2$, —SH, —$SO_3H$, —$SO_4H$, —$S_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{21B}_3$, —$OCHX^{21B}2$, $R^{22B}$-substituted or unsubstituted $C_1$-$C_8$ alkyl, $R^{22B}$-substituted or unsubstituted 2 to 8 membered heteroalkyl, $R^{22B}$-substituted or unsubstituted $C_3$-$C_8$ cycloalkyl, $R^{22B}$-substituted or unsubstituted 3 to 6 membered heterocycloalkyl, $R^{22B}$-substituted or unsubstituted phenyl, or $R^{22B}$-substituted or unsubstituted 5 to 6 membered heteroaryl. $X^{21B}$ is —F, —Cl, —Br, or —I.

In embodiments, $R^{1C}$ is independently hydrogen, —$CX^{1C}_3$, —CN, —COOH, —$CONH_2$, —$CHX^{1C}_2$, —$CH_2X^{1C}$, $R^{20C}$-substituted or unsubstituted alkyl, $R^{20C}$-substituted or unsubstituted heteroalkyl, $R^{20C}$-substituted or unsubstituted cycloalkyl, $R^{20C}$-substituted or unsubstituted heterocycloalkyl, $R^{20C}$-substituted or unsubstituted aryl, or $R^{20C}$-substituted or unsubstituted heteroaryl. In embodiments, $R^{1C}$ is independently hydrogen, —$CX^{1C}_3$, —CN, —COOH, —$CONH_2$, —$CHX^{1C}_2$, —$CH_2X^{1C}$, $R^{20C}$-substituted or unsubstituted $C_1$-$C_8$ alkyl, $R^{20C}$-substituted or unsubstituted 2 to 8 membered heteroalkyl, $R^{20C}$-substituted or unsubstituted $C_3$-$C_8$ cycloalkyl, $R^{20C}$-substituted or unsubstituted 3 to 6 membered heterocycloalkyl, $R^{20C}$-substituted or unsubstituted phenyl, or $R^{20C}$-substituted or unsubstituted 5 to 6 membered heteroaryl. $X^{1C}$ is —F, —Cl, —Br, or —I. In embodiments, $R^{1C}$ is independently hydrogen. In embodiments, $R^{1C}$ is independently methyl. In embodiments, $R^{1C}$ is independently ethyl.

$R^{20C}$ is independently oxo, halogen, —$CX^{20C}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{20C}_3$, —$OCHX^{20C}_2$, $R^{21C}$-substituted or unsubstituted alkyl, $R^{21C}$-substituted or unsubstituted heteroalkyl, $R^{21C}$-substituted or unsubstituted cycloalkyl, $R^{21C}$-substituted or unsubstituted heterocycloalkyl, $R^{21C}$-substituted or unsubstituted aryl, or $R^{21C}$-substituted or unsubstituted heteroaryl. In embodiments, $R^{20C}$ is independently oxo, halogen, —$CX^{20C}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{20C}_3$, —$OCHX^{20C}_2$, $R^{21C}$-substituted or unsubstituted $C_1$-$C_8$ alkyl, $R^{21C}$-substituted or unsubstituted 2 to 8 membered heteroalkyl, $R^{21C}$-substituted or unsubstituted $C_3$-$C_8$ cycloalkyl, $R^{21C}$-substituted or unsubstituted 3 to 6 membered heterocycloalkyl, $R^{21C}$-substituted or unsubstituted phenyl, or $R^{21C}$-substituted or unsubstituted 5 to 6 membered heteroaryl. $X^{20C}$ is —F, —Cl, —Br, or —I.

$R^{21C}$ is independently oxo, halogen, —$CX^{21C}_3$, —CN, —OH, —$NH_2$, —COOH, —$CONH_2$, —$NO_2$, —SH, —$S_3H$, —$SO_4H$, —$S_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{21C}_3$, —$OCHX^{21C}_2$, $R^{22C}$-substituted or unsubstituted alkyl, $R^{22C}$-substituted or unsubstituted heteroalkyl, $R^{22C}$-substituted or unsubstituted cycloalkyl, $R^{22C}$-substituted or unsubstituted heterocycloalkyl, $R^{22C}$-substituted or unsubstituted aryl, or $R^{22C}$-substituted or unsubstituted heteroaryl. In embodiments, $R^{21C}$ is independently oxo, halogen, —$CX^{21C}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{21C}_3$, —$OCHX^{21C}_2$, $R^{22C}$-substituted or unsubstituted $C_1$-$C_8$ alkyl, $R^{22C}$-substituted or unsubstituted 2 to 8 membered heteroalkyl, $R^{22C}$-substituted or unsubstituted $C_3$-$C_8$ cycloalkyl, $R^{22C}$-substituted or unsubstituted 3 to 6 membered heterocycloalkyl, $R^{22C}$-substituted or unsubstituted phenyl, or $R^{22C}$-substituted or unsubstituted 5 to 6 membered heteroaryl. $X^{21C}$ is —F, —Cl, —Br, or —I.

In embodiments, $R^{1D}$ is independently hydrogen, —$CX^{1D}_3$, —CN, —COOH, —$CONH_2$, —$CHX^{1D}_2$, —$CH_2X^{1D}$, $R^{20D}$-substituted or unsubstituted alkyl, $R^{20D}$-substituted or unsubstituted heteroalkyl, $R^{20D}$-substituted or unsubstituted cycloalkyl, $R^{20D}$-substituted or unsubstituted heterocycloalkyl, $R^{20D}$ substituted or unsubstituted aryl, or $R^{20D}$-substituted or unsubstituted heteroaryl. In embodiments, $R^{1D}$ independently hydrogen, —$CX^{1D}_3$, —CN, —COOH, —$CONH_2$, —$CHX^{1D}_2$, —$CH_2X^{1D}$, $R^{20D}$-substituted or unsubstituted $C_1$-$C_8$ alkyl, $R^{20D}$-substituted or unsubstituted 2 to 8 membered heteroalkyl, $R^{20D}$-substituted or unsubstituted $C_3$-$C_8$ cycloalkyl, $R^{20D}$-substituted or unsubstituted 3 to 6 membered heterocycloalkyl, $R^{20D}$-substituted or unsubstituted phenyl, or $R^{20D}$-substituted or unsubstituted 5 to 6 membered heteroaryl. $X^1$ is —F, —Cl, —Br, or —I. In embodiments, $R^{1D}$ is independently hydrogen. In embodiments, $R^{1D}$ is independently methyl. In embodiments, $R^{1D}$ is independently ethyl.

$R^{20D}$ is independently oxo, halogen, —$CX^{20D}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{20D}_3$, —$OCHX^{20D}_2$, $R^{21D}$-substituted or unsubstituted alkyl, $R^{21D}$-substituted or unsubstituted heteroalkyl, $R^{21D}$-substituted or unsubstituted cycloalkyl, $R^{21D}$-substituted or unsubstituted heterocycloalkyl, $R^{21D}$-substituted or unsubstituted aryl, or $R^{21D}$-substituted or unsubstituted heteroaryl. In embodiments, $R^{20D}$ is independently oxo,
halogen, $-CX^{20D}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{20D}_3$, $-OCHX^{20D}_2$, $R^{20D}$-substituted or unsubstituted $C_1$-$C_8$ alkyl, $R^{21D}$-substituted or unsubstituted 2 to 8 membered heteroalkyl, $R^{21D}$-substituted or unsubstituted $C_3$-$C_8$ cycloalkyl, $R^{21D}$-substituted or unsubstituted 3 to 6 membered heterocycloalkyl, $R^{21D}$-substituted or unsubstituted phenyl, or $R^{21D}$-substituted or unsubstituted 5 to 6 membered heteroaryl. $X^{20D}$ is $-F$, $-Cl$, $-Br$, or $-I$.

$R^{21D}$ is independently oxo,
halogen, $-CX^{21D}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{21D}_3$, $-OCHX^{21D}_2$, $R^{22D}$-substituted or unsubstituted alkyl, $R^{22D}$-substituted or unsubstituted heteroalkyl, $R^{22D}$-substituted or unsubstituted cycloalkyl, $R^{22D}$-substituted or unsubstituted heterocycloalkyl, $R^{22D}$-substituted or unsubstituted aryl, or $R^{22D}$-substituted or unsubstituted heteroaryl. In embodiments, $R^{21D}$ is independently oxo,
halogen, $-CX^{21D}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{21D}_3$, $-OCHX^{21D}_2$, $R^{22D}$-substituted or unsubstituted $C_1$-$C_8$ alkyl, $R^{22D}$-substituted or unsubstituted 2 to 8 membered heteroalkyl, $R^{22D}$-substituted or unsubstituted $C_3$-$C_8$ cycloalkyl, $R^{22D}$-substituted or unsubstituted 3 to 6 membered heterocycloalkyl, $R^{22D}$-substituted or unsubstituted phenyl, or $R^{22D}$-substituted or unsubstituted 5 to 6 membered heteroaryl. $X^{21D}$ is $-F$, $-Cl$, $-Br$, or $-I$.

$R^{22}$, $R^{22A}$, $R^{22B}$, $R^{22C}$, and $R^{22D}$ are independently hydrogen, oxo,
halogen, $-CCl_3$, $-CBr_3$, $-CF_3$, $-Cl_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)$ $NHNH_2$,
$-NHC(O)NH_2$, $-NHSO_2H$, $-NHC(O)H$, $-NHC(O)OH$, $-NHOH$, $-OCCl_3$, $-OCF_3$, $-OCBr_3$, $-OCl_3$, $-OCHCl_2$, $-OCHBr_2$, $-OCHI_2$, $-OCHF_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{22}$, $R^{22A}$, $R^{22B}$, $R^{22C}$, and $R^{22D}$ are independently oxo,
halogen, $-CF_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCF_3$, $-OCHF_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{22}$, $R^{22A}$, $R^{22B}$, $R^{22C}$, and $R^{22D}$ are independently oxo,
halogen, $-CF_3$, $-CN$, $-OH$, $-NH_2$, $-COOH$, $-CONH_2$, $-NO_2$, $-SH$, $-SO_3H$, $-SO_4H$, $-S_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCF_3$, $-OCHF_2$, unsubstituted $C_1$-$C_8$ alkyl, unsubstituted 2 to 8 membered heteroalkyl, unsubstituted $C_3$-$C_8$ cycloalkyl, unsubstituted 3 to 6 membered heterocycloalkyl, unsubstituted phenyl, or unsubstituted 5 to 6 membered heteroaryl.

In embodiments, $R^1$ is independently halogen. In embodiments, $R^1$ is independently hydrogen. In embodiments, z1 is 2 and $R^1$ is independently hydrogen or halogen. In embodiments, z1 is 2 and one $R^1$ is independently hydrogen and one $R^1$ is halogen.

In embodiments, $R^1$ is independently methyl. In embodiments, $R^1$ is independently $C_1$-$C_4$ alkyl. In embodiments, z1 is 2 and one $R^1$ is independently halogen and one $R^1$ is unsubstituted $C_1$-$C_4$ alkyl. In embodiments, z1 is 2 and one $R^1$ is independently halogen and one $R^1$ is unsubstituted $C_1$-$C_3$ alkyl. In embodiments, z1 is 2 and one $R^1$ is independently halogen and one $R^1$ is unsubstituted $C_1$-$C_2$ alkyl. In embodiments, $R^1$ is independently halogen or unsubstituted $C_1$-$C_3$ alkyl. In embodiments, z1 is 2 and one $R^1$ is independently halogen and one $R^1$ is methyl.

In embodiments, $R^1$ is independently substituted or unsubstituted methyl. In embodiments, $R^1$ is independently substituted or unsubstituted $C_1$-$C_4$ alkyl. In embodiments, $R^1$ is independently halogen or substituted or unsubstituted $C_1$-$C_4$ alkyl. In embodiments, $R^1$ is independently halogen or substituted or unsubstituted $C_1$-$C_3$ alkyl. In embodiments, $R^1$ is independently halogen or substituted or unsubstituted $C_1$-$C_2$ alkyl. In embodiments, $R^1$ is independently halogen or substituted or unsubstituted methyl. In embodiments, $R^1$ is independently substituted methyl. In embodiments, $R^1$ is independently substituted $C_1$-$C_4$ alkyl. In embodiments, z1 is 2 and one $R^1$ is independently halogen and one $R^1$ is substituted $C_1$-$C_4$ alkyl. In embodiments, z1 is 2 and one $R^1$ is independently halogen and one $R^1$ is substituted $C_1$-$C_3$ alkyl. In embodiments, z1 is 2 and one $R^1$ is independently halogen and one $R^1$ is substituted $C_1$-$C_2$ alkyl. In embodiments, z1 is 2 and one $R^1$ is independently halogen and one $R^1$ is substituted methyl. In embodiments, $R^1$ is independently unsubstituted methyl. In embodiments, z1 is 2 and one $R^1$ is independently halogen and one $R^1$ is unsubstituted $C_1$-$C_4$ alkyl. In embodiments, z1 is 2 and one $R^1$ is independently halogen and one $R^1$ is unsubstituted $C_1$-$C_3$ alkyl. In embodiments, z1 is 2 and one $R^1$ is independently halogen and one $R^1$ is unsubstituted $C_1$-$C_2$ alkyl. In embodiments, z1 is 2 and one $R^1$ is independently halogen and one $R^1$ is unsubstituted methyl.

In embodiments, z1 is 2 and one $R^1$ is independently substituted or unsubstituted $C_1$-$C_4$ alkyl and one $R^1$ is substituted or unsubstituted $C_3$ alkyl. In embodiments, z1 is 2 and one $R^1$ is independently substituted or unsubstituted $C_1$-$C_3$ alkyl and one $R^1$ is substituted or unsubstituted $C_3$ alkyl. In embodiments, z1 is 2 and one $R^1$ is independently substituted or unsubstituted $C_1$-$C_2$ alkyl and one $R^1$ is substituted or unsubstituted $C_3$ alkyl. In embodiments, z1 is 2 and one $R^1$ is independently substituted or unsubstituted methyl and one $R^1$ is substituted or unsubstituted $C_3$ alkyl. In embodiments, z1 is 2 and one $R^1$ is independently substituted or unsubstituted methyl and one $R^1$ is substituted or unsubstituted isopropyl.

In embodiments, z1 is 2 and one $R^1$ is independently unsubstituted $C_1$-$C_4$ alkyl and one $R^1$ is unsubstituted $C_3$ alkyl. In embodiments, z1 is 2 and one $R^1$ is independently unsubstituted $C_1$-$C_3$ alkyl and one $R^1$ is unsubstituted $C_3$ alkyl. In embodiments, z1 is 2 and one $R^1$ is independently unsubstituted $C_1$-$C_2$ alkyl and one $R^1$ is unsubstituted $C_3$ alkyl. In embodiments, z1 is 2 and one $R^1$ is independently unsubstituted methyl and one $R^1$ is unsubstituted $C_3$ alkyl. In embodiments, z1 is 2 and one $R^1$ is independently unsubstituted methyl and one $R^1$ is unsubstituted isopropyl.

In embodiments, z1 is 2 and one $R^1$ is independently substituted $C_1$-$C_4$ alkyl and one $R^1$ substituted $C_3$ alkyl. In embodiments, z1 is 2 and one $R^1$ is independently substituted $C_1$-$C_3$ alkyl and one $R^1$ is substituted $C_3$ alkyl. In embodiments, z1 is 2 and one $R^1$ is independently substituted $C_1$-$C_2$ alkyl and one $R^1$ is substituted $C_3$ alkyl. In embodiments, z1 is 2 and one $R^1$ is independently substituted methyl and one $R^1$ is substituted $C_3$ alkyl. In embodiments, z1 is 2 and one $R^1$ is independently substituted methyl and one $R^1$ is substituted isopropyl.

In embodiments, z1 is 2 and one $R^1$ is independently substituted $C_1$-$C_4$ alkyl and one $R^1$ is unsubstituted $C_3$ alkyl. In embodiments, z1 is 2 and one $R^1$ is independently substituted $C_1$-$C_3$ alkyl and one $R^1$ is unsubstituted $C_3$ alkyl. In embodiments, z1 is 2 and one $R^1$ is independently substituted $C_1$-$C_2$ alkyl and one $R^1$ is unsubstituted $C_3$ alkyl. In embodiments, z1 is 2 and one $R^1$ is independently substituted methyl and one $R^1$ is unsubstituted $C_3$ alkyl. In embodiments, z1 is 2 and one $R^1$ is independently substituted methyl and one $R^1$ is unsubstituted isopropyl.

In embodiments, z1 is 2 and one $R^1$ is independently unsubstituted $C_1$-$C_4$ alkyl and one $R^1$ is substituted $C_3$ alkyl. In embodiments, z1 is 2 and one $R^1$ is independently unsubstituted $C_1$-$C_3$ alkyl and one $R^1$ is substituted $C_3$ alkyl. In embodiments, z1 is 2 and one $R^1$ is independently unsubstituted $C_1$-$C_2$ alkyl and one $R^1$ is substituted $C_3$ alkyl. In embodiments, z1 is 2 and one $R^1$ is independently unsubstituted methyl and one $R^1$ is substituted $C_3$ alkyl. In embodiments, z1 is 2 and one $R^1$ is independently unsubstituted methyl and one $R^1$ is substituted isopropyl.

In embodiments, z1 is 0. In embodiments, z1 is 1. In embodiments, z1 is 2. In embodiments, z1 is 3. In embodiments, z1 is 4. In embodiments, z1 is 5.

In embodiments, $R^2$ is independently halogen, $-CX^2_3$, $-CN$, $-OH$, $-NH_2$, $-COOH$, $-CONH_2$, $-NO_2$, $-SH$, $-OCX^2_3$, $-OCHX^2_2$, $-CHX^2_2$, $-CH_2X^2$, substituted or unsubstituted $C_1$-$C_8$ alkyl, or substituted or unsubstituted 2 to 8 membered heteroalkyl; two adjacent $R^2$ substituents may optionally be joined to form a substituted or unsubstituted $C_3$-$C_8$ cycloalkyl, substituted or unsubstituted 3 to 8 membered heterocycloalkyl, substituted or unsubstituted phenyl, or substituted or unsubstituted 5 to 6 membered heteroaryl. In embodiments, $R^2$ is independently halogen, $-CX^2_3$, $-CN$, unsubstituted $C_1$-$C_4$ alkyl, or unsubstituted 2 to 4 membered heteroalkyl. In embodiments, $R^2$ is independently halogen, $-CX^2_3$, $-CN$, unsubstituted methyl, unsubstituted ethyl, unsubstituted methoxy, or unsubstituted ethoxy. In embodiments, $R^2$ is independently unsubstituted methyl. In embodiments, $R^2$ is independently unsubstituted ethyl. In embodiments, $R^2$ is independently unsubstituted propyl. In embodiments, $R^2$ is independently unsubstituted n-propyl. In embodiments, $R^2$ is independently unsubstituted isopropyl. In embodiments, $R^2$ is independently unsubstituted butyl. In embodiments, $R^2$ is independently unsubstituted n-butyl. In embodiments, $R^2$ is independently unsubstituted isobutyl. In embodiments, $R^2$ is independently unsubstituted tert-butyl. In embodiments, $R^2$ is independently unsubstituted pentyl. In embodiments, $R^2$ is independently unsubstituted hexyl. In embodiments, $R^2$ is independently unsubstituted heptyl. In embodiments, $R^2$ is independently unsubstituted octyl. In embodiments, $R^2$ is independently $-F$. In embodiments, $R^2$ is independently $-Cl$. In embodiments, $R^2$ is independently $-Br$. In embodiments, $R^2$ is independently $-I$. In embodiments, $R^2$ is independently methoxy. In embodiments, $R^2$ is independently unsubstituted ethoxy. In embodiments, $R^2$ is independently halogen. In embodiments, $R^2$ is independently $-CF_3$. In embodiments, $R^2$ is independently $-CCl_3$.

In embodiments, $R^2$ is independently halogen, $-CX^2$. In embodiments, $R^2$ is independently $-CHX^2_2$. In embodiments, $R^2$ is independently $-CH_2X^2$. In embodiments, $R^2$ is independently $-OCX^2_3$. In embodiments, $R^2$ is independently $-OCH_2X^2$. In embodiments, $R^2$ is independently $-OCHX^2_2$. In embodiments, $R^2$ is independently $-CN$. In embodiments, $R^2$ is independently $-SO_{n2}R^{2D}$. In embodiments, $R^2$ is independently $-SO_{v2}NR^{2A}R^{2B}$. In embodiments, $R^2$ is independently $-NHC(O)NR^{2A}R^{2B}$. In embodiments, $R^2$ is independently $-N(O)_{m2}$. In embodiments, $R^2$ is independently $-NR^{2A}R^{2B}$. In embodiments, $R^2$ is independently $-C(O)R^{2C}$. In embodiments, $R^2$ is independently $-C(O)-OR^{2C}$. In embodiments, $R^2$ is independently $-C(O)NR^{2A}R^{2B}$. In embodiments, $R^2$ is independently $-OR^{2D}$. In embodiments, $R^2$ is independently $-NR^{2A}SO_2R^{2D}$. In embodiments, $R^2$ is independently $-NR^{2A}C(O)R^{2C}$. In embodiments, $R^2$ is independently $-NR^{2A}C(O)OR^{2C}$. In embodiments, $R^2$ is independently $-NR^{2A}OR^{2C}$. In embodiments, $R^2$ is independently $-OH$. In embodiments, $R^2$ is independently $-NH_2$. In embodiments, $R^2$ is independently $-COOH$. In embodiments, $R^2$ is independently $-CONH_2$. In embodiments, $R^2$ is independently $-NO_2$. In embodiments, $R^2$ is independently $-SH$.

In embodiments, $R^2$ is independently substituted or unsubstituted alkyl. In embodiments, $R^2$ is independently substituted or unsubstituted heteroalkyl. In embodiments, $R^2$ is independently substituted or unsubstituted cycloalkyl. In embodiments, $R^2$ is independently, substituted or unsubstituted heterocycloalkyl. In embodiments, $R^2$ is independently substituted or unsubstituted aryl. In embodiments, $R^2$ is independently substituted or unsubstituted heteroaryl. In embodiments, $R^2$ is independently substituted alkyl. In embodiments, $R^2$ is independently substituted heteroalkyl. In embodiments, $R^2$ is independently substituted cycloalkyl. In embodiments, $R^2$ is independently, substituted heterocycloalkyl. In embodiments, $R^2$ is independently substituted aryl. In embodiments, $R^2$ is independently substituted heteroaryl. In embodiments, $R^2$ is independently unsubstituted alkyl. In embodiments, $R^2$ is independently unsubstituted heteroalkyl. In embodiments, $R^2$ is independently unsubstituted cycloalkyl. In embodiments, $R^2$ is independently, unsubstituted heterocycloalkyl. In embodiments, $R^2$ is independently unsubstituted aryl. In embodiments, $R^2$ is independently unsubstituted heteroaryl. In embodiments, $R^2$ is independently substituted or unsubstituted $C_1$-$C_8$ alkyl. In embodiments, $R^2$ is independently substituted or unsubstituted 2 to 8 membered heteroalkyl. In embodiments, $R^2$ is independently substituted or unsubstituted $C_3$-$C_8$ cycloalkyl. In embodiments, $R^2$ is independently, substituted or unsubstituted 3 to 8 membered heterocycloalkyl. In embodiments, $R^2$ is independently substituted or unsubstituted $C_6$-$C_{10}$ aryl. In embodiments, $R^2$ is independently substituted or unsubstituted 5 to 10 membered heteroaryl. In embodiments, $R^2$ is independently substituted $C_1$-$C_8$ alkyl. In embodiments, $R^2$ is independently substituted 2 to 8 membered heteroalkyl. In embodiments, $R^2$ is independently substituted $C_3$-$C_8$ cycloalkyl. In embodiments, $R^2$ is independently, substituted 3 to 8 membered heterocycloalkyl. In embodiments, $R^2$ is independently substituted $C_6$-$C_{10}$ aryl. In embodiments, $R^2$ is independently substituted 5 to 10 membered heteroaryl. In embodiments, $R^2$ is independently unsubstituted $C_1$-$C_8$ alkyl. In embodiments, $R^2$ is independently unsubstituted 2 to 8 membered heteroalkyl. In embodiments, $R^2$ is independently unsubstituted $C_3$-$C_8$ cycloalkyl. In embodiments, $R^2$ is independently, unsubstituted 3 to 8 membered heterocycloalkyl. In embodiments, $R^2$ is independently unsubstituted $C_6$-$C_{10}$ aryl. In embodiments, $R^2$ is independently unsubstituted 5 to 10 membered heteroaryl. In embodiments, $R^2$ is independently substituted or unsubstituted $C_1$-$C_4$ alkyl. In embodiments, $R^2$ is independently substituted or unsubstituted 2 to 4 membered heteroalkyl. In embodiments, $R^2$ is independently substituted or unsubstituted $C_3$-$C_6$ cycloalkyl. In embodiments, $R^2$ is independently, substituted or unsubstituted 3 to 6 membered heterocycloalkyl. In embodiments, $R^2$ is independently substituted or unsubstituted phenyl. In embodiments, $R^2$ is independently substituted or unsubstituted 5 to 6 membered heteroaryl. In embodiments, $R^2$ is independently substituted $C_1$-$C_4$ alkyl. In embodiments, $R^2$ is independently substituted 2 to 4 membered heteroalkyl. In embodiments, $R^2$ is independently substituted $C_3$-$C_6$ cycloalkyl. In embodiments, $R^2$ is independently, substituted 3 to 6 membered heterocycloalkyl. In embodiments, $R^2$ is independently substituted phenyl. In embodiments, $R^2$ is independently substituted 5 to 6 membered heteroaryl. In embodiments, $R^2$ is independently unsubstituted $C_1$-$C_4$ alkyl. In embodiments, $R^2$ is independently unsubstituted 2 to 4 membered heteroalkyl. In embodiments, $R^2$ is independently unsubstituted $C_3$-$C_6$ cycloalkyl. In embodiments, $R^2$ is independently unsubstituted 3 to 6 membered heterocycloalkyl. In embodiments, $R^2$ is independently unsubstituted phenyl. In embodiments, $R^2$ is independently unsubstituted 5 to 6 membered heteroaryl.

In embodiments, two adjacent $R^2$ substituents may optionally be joined to form a substituted or unsubstituted cycloalkyl. In embodiments, two adjacent $R^2$ substituents may optionally be joined to form a substituted or unsubstituted heterocycloalkyl. In embodiments, two adjacent $R^2$ substituents may optionally be joined to form a substituted or unsubstituted aryl. In embodiments, two adjacent $R^2$ substituents may optionally be joined to form a substituted or unsubstituted heteroaryl. In embodiments, two adjacent $R^2$ substituents may optionally be joined to form a substituted cycloalkyl. In embodiments, two adjacent $R^2$ substituents may optionally be joined to form a substituted heterocycloalkyl. In embodiments, two adjacent $R^2$ substituents may optionally be joined to form a substituted aryl. In embodiments, two adjacent $R^2$ substituents may optionally be joined to form a substituted heteroaryl. In embodiments, two adjacent $R^2$ substituents may optionally be joined to form an unsubstituted cycloalkyl. In embodiments, two adjacent $R^2$ substituents may optionally be joined to form an unsubstituted heterocycloalkyl. In embodiments, two adjacent $R^2$ substituents may optionally be joined to form an unsubstituted aryl. In embodiments, two adjacent $R^2$ substituents may optionally be joined to form an unsubstituted heteroaryl. In embodiments, two adjacent $R^2$ substituents may optionally be joined to form a substituted or unsubstituted $C_3$-$C_8$ cycloalkyl. In embodiments, two adjacent $R^2$ substituents may optionally be joined to form a substituted or unsubstituted 3 to 8 membered heterocycloalkyl. In embodiments, two adjacent $R^2$ substituents may optionally be joined to form a substituted or unsubstituted $C_6$-$C_{10}$ aryl. In embodiments, two adjacent $R^2$ substituents may optionally be joined to form a substituted or unsubstituted 5 to 10 membered heteroaryl. In embodiments, two adjacent $R^2$ substituents may optionally be joined to forma substituted $C_3$-$C_8$ cycloalkyl. In embodiments, two adjacent $R^2$ substituents may optionally be joined to form a substituted 3 to 8 membered heterocycloalkyl. In embodiments, two adjacent $R^2$ substituents may optionally be joined to form a substituted $C_6$-$C_{10}$ aryl. In embodiments, two adjacent $R^2$ substituents may optionally be joined to form a substituted 5 to 10 membered heteroaryl. In embodiments, two adjacent $R^2$ substituents may optionally be joined to form an unsubstituted $C_3$-$C_8$ cycloalkyl. In embodiments, two adjacent $R^2$ substituents may optionally be joined to form an unsubstituted 3 to 8 membered heterocycloalkyl. In embodiments, two adjacent $R^2$ substituents may optionally be joined to form an unsubstituted $C_6$-$C_{10}$ aryl. In embodiments, two adjacent $R^2$ substituents may optionally be joined to form an unsubstituted 5 to 10 membered heteroaryl. In embodiments, two adjacent $R^2$ substituents may optionally be joined to form a substituted or unsubstituted $C_3$-$C_6$ cycloalkyl. In embodiments, two adjacent $R^2$ substituents may optionally be joined to form a substituted or unsubstituted 3 to 6 membered heterocycloalkyl. In embodiments, two adjacent $R^2$ substituents may optionally be joined to form a substituted or unsubstituted phenyl. In embodiments, two adjacent $R^2$ substituents may optionally be joined to form a substituted or unsubstituted 5 to 6 membered heteroaryl. In embodiments, two adjacent $R^2$ substituents may optionally be joined to forma substituted $C_3$-$C_6$ cycloalkyl. In embodiments, two adjacent $R^2$ substituents may optionally be joined to form a substituted 3 to 6 membered heterocycloalkyl. In embodiments, two adjacent $R^2$ substituents may optionally be joined to forma substituted phenyl. In embodiments, two adjacent $R^2$ substituents may optionally be joined to forma substituted 5 to 6 membered heteroaryl. In embodiments, two adjacent $R^2$ substituents may optionally be joined to form an unsubstituted $C_3$-$C_6$ cycloalkyl. In embodiments, two adjacent $R^2$ substituents may optionally be joined to form an unsubstituted 3 to 6 membered heterocycloalkyl. In embodiments, two adjacent $R^2$ substituents may optionally be joined to form an unsubstituted phenyl. In embodiments, two adjacent $R^2$ substituents may optionally be joined to form an unsubstituted 5 to 6 membered heteroaryl.

In embodiments, $R^{2A}$ is independently hydrogen. In embodiments, $R^{2A}$ is independently —$CX^{2A}{}_3$. In embodiments, $R^{2A}$ is independently —$CHX^{2A}{}_2$. In embodiments, $R^{2A}$ is independently —$CH_2X^{2A}$. In embodiments, $R^{2A}$ is independently —CN. In embodiments, $R^{2A}$ is independently —COOH. In embodiments, $R^{2A}$ is independently —$CONH_2$. In embodiments, $R^{2A}$ is independently substituted or unsubstituted alkyl. In embodiments, $R^{2A}$ is independently substituted or unsubstituted heteroalkyl. In embodiments, $R^{2A}$ is independently substituted or unsubstituted cycloalkyl. In embodiments, $R^{2A}$ is independently, substituted or unsubstituted heterocycloalkyl. In embodiments, $R^{2A}$ is independently substituted or unsubstituted aryl. In embodiments, $R^{2A}$ is independently substituted or unsubstituted heteroaryl. In embodiments, $R^{2A}$ is independently substituted alkyl. In embodiments, $R^{2A}$ is independently substituted heteroalkyl. In embodiments, $R^{2A}$ is independently substituted cycloalkyl. In embodiments, $R^{2A}$ is independently, substituted heterocycloalkyl. In embodiments, $R^{2A}$ is independently substituted aryl. In embodiments, $R^{2A}$ is independently substituted heteroaryl. In embodiments, $R^{2A}$ is independently unsubstituted alkyl. In embodiments, $R^{2A}$ is independently unsubstituted heteroalkyl. In embodiments, $R^{2A}$ is independently unsubstituted cycloalkyl. In embodiments, $R^{2A}$ is independently, unsubstituted heterocycloalkyl. In embodiments, $R^{2A}$ is independently unsubstituted aryl. In embodiments, $R^{2A}$ is independently unsubstituted heteroaryl. In embodiments, $R^{2A}$ is independently substituted or unsubstituted $C_1$-$C_8$ alkyl. In embodiments, $R^{2A}$ is independently substituted or unsubstituted 2 to 8 membered heteroalkyl. In embodiments, $R^{2A}$ is independently substituted or unsubstituted $C_3$-$C_8$ cycloalkyl.

In embodiments, $R^{2A}$ is independently, substituted or unsubstituted 3 to 8 membered heterocycloalkyl. In embodiments, $R^{2A}$ is independently substituted or unsubstituted $C_6$-$C_{10}$ aryl. In embodiments, $R^{2A}$ is independently substituted or unsubstituted 5 to 10 membered heteroaryl. In embodiments, $R^{2A}$ is independently substituted $C_1$-$C_8$ alkyl. In embodiments, $R^{2A}$ is independently substituted 2 to 8 membered heteroalkyl. In embodiments, $R^{2A}$ is independently substituted $C_3$-$C_8$ cycloalkyl. In embodiments, $R^{2A}$ is independently, substituted 3 to 8 membered heterocycloalkyl. In embodiments, $R^{2A}$ is independently substituted $C_6$-$C_{10}$ aryl. In embodiments, $R^{2A}$ is independently substituted 5 to 10 membered heteroaryl. In embodiments, $R^{2A}$ is independently unsubstituted $C_1$-$C_8$ alkyl. In embodiments, $R^{2A}$ is independently unsubstituted 2 to 8 membered heteroalkyl. In embodiments, $R^{2A}$ is independently unsubstituted $C_3$-$C_8$ cycloalkyl. In embodiments, $R^{2A}$ is independently, unsubstituted 3 to 8 membered heterocycloalkyl. In embodiments, $R^{2A}$ is independently unsubstituted $C_6$-$C_{10}$ aryl. In embodiments, $R^{2A}$ is independently unsubstituted 5 to 10 membered heteroaryl. In embodiments, $R^{2A}$ is independently substituted or unsubstituted $C_1$-$C_4$ alkyl. In embodiments, $R^{2A}$ is independently substituted or unsubstituted 2 to 4 membered heteroalkyl. In embodiments, $R^{2A}$ is independently substituted or unsubstituted $C_3$-$C_6$ cycloalkyl. In embodiments, $R^{2A}$ is independently, substituted or unsubstituted 3 to 6 membered heterocycloalkyl. In embodiments, $R^{2A}$ is independently substituted or unsubstituted phenyl. In embodiments, $R^{2A}$ is independently substituted or unsubstituted 5 to 6 membered heteroaryl. In embodiments, $R^2$ is independently substituted $C_1$-$C_4$ alkyl. In embodiments, $R^{2A}$ is independently substituted 2 to 4 membered heteroalkyl. In embodiments, $R^{2A}$ is independently substituted $C_3$-$C_6$ cycloalkyl. In embodiments, $R^{2A}$ is independently, substituted 3 to 6 membered heterocycloalkyl. In embodiments, $R^{2A}$ is independently substituted phenyl. In embodiments, $R^{2A}$ is independently substituted 5 to 6 membered heteroaryl. In embodiments, $R^{2A}$ is independently unsubstituted $C_1$-$C_4$ alkyl. In embodiments, $R^{2A}$ is independently unsubstituted 2 to 4 membered heteroalkyl. In embodiments, $R^{2A}$ is independently unsubstituted $C_3$-$C_6$ cycloalkyl. In embodiments, $R^{2A}$ is independently unsubstituted 3 to 6 membered heterocycloalkyl. In embodiments, $R^{2A}$ is independently unsubstituted phenyl. In embodiments, $R^{2A}$ is independently unsubstituted 5 to 6 membered heteroaryl. In embodiments, $R^{2A}$ is independently unsubstituted methyl. In embodiments, $R^{2A}$ is independently unsubstituted ethyl. In embodiments, $R^{2A}$ is independently unsubstituted propyl. In embodiments, $R^{2A}$ is independently unsubstituted isopropyl. In embodiments, $R^{2A}$ is independently unsubstituted tert-butyl.

In embodiments, $R^{2B}$ is independently hydrogen. In embodiments, $R^{2B}$ is independently —$CX^{2B}_3$. In embodiments, $R^{2B}$ is independently —$CHX^{2B}_2$. In embodiments, $R^{2B}$ is independently —$CH_2X^{2B}$. In embodiments, $R^{2B}$ is independently —CN. In embodiments, $R^{2B}$ is independently —COOH. In embodiments, $R^{2B}$ is independently —$CONH_2$. In embodiments, $R^{2B}$ is independently substituted or unsubstituted alkyl. In embodiments, $R^{2B}$ is independently substituted or unsubstituted heteroalkyl. In embodiments, $R^{2B}$ is independently substituted or unsubstituted cycloalkyl. In embodiments, $R^{2B}$ is independently, substituted or unsubstituted heterocycloalkyl. In embodiments, $R^{2B}$ is independently substituted or unsubstituted aryl. In embodiments, $R^{2B}$ is independently substituted or unsubstituted heteroaryl. In embodiments, $R^{2B}$ is independently substituted alkyl. In embodiments, $R^{2B}$ is independently substituted heteroalkyl. In embodiments, $R^{2B}$ is independently substituted cycloalkyl. In embodiments, $R^{2B}$ is independently, substituted heterocycloalkyl. In embodiments, $R^{2B}$ is independently substituted aryl. In embodiments, $R^{2B}$ is independently substituted heteroaryl. In embodiments, $R^{2B}$ is independently unsubstituted alkyl. In embodiments, $R^{2B}$ is independently unsubstituted heteroalkyl. In embodiments, $R^{2B}$ is independently unsubstituted cycloalkyl. In embodiments, $R^{2B}$ is independently, unsubstituted heterocycloalkyl. In embodiments, $R^{2B}$ is independently unsubstituted aryl. In embodiments, $R^{2B}$ is independently unsubstituted heteroaryl. In embodiments, $R^{2B}$ is independently substituted or unsubstituted $C_1$-$C_8$ alkyl. In embodiments, $R^{2B}$ is independently substituted or unsubstituted 2 to 8 membered heteroalkyl. In embodiments, $R^{2B}$ is independently substituted or unsubstituted $C_3$-$C_8$ cycloalkyl. In embodiments, $R^{2B}$ is independently, substituted or unsubstituted 3 to 8 membered heterocycloalkyl. In embodiments, $R^{2B}$ is independently substituted or unsubstituted $C_6$-$C_{10}$ aryl. In embodiments, $R^{2B}$ is independently substituted or unsubstituted 5 to 10 membered heteroaryl. In embodiments, $R^{2B}$ is independently substituted $C_1$-$C_8$ alkyl. In embodiments, $R^{2B}$ is independently substituted 2 to 8 membered heteroalkyl. In embodiments, $R^{2B}$ is independently substituted $C_3$-$C_8$ cycloalkyl. In embodiments, $R^{2B}$ is independently, substituted 3 to 8 membered heterocycloalkyl. In embodiments, $R^{2B}$ is independently substituted $C_6$-$C_{10}$ aryl. In embodiments, $R^{2B}$ is independently substituted 5 to 10 membered heteroaryl. In embodiments, $R^{2B}$ is independently unsubstituted $C_1$-$C_8$ alkyl. In embodiments, $R^{2B}$ is independently unsubstituted 2 to 8 membered heteroalkyl. In embodiments, $R^{2B}$ is independently unsubstituted $C_3$-$C_8$ cycloalkyl. In embodiments, $R^{2B}$ is independently, unsubstituted 3 to 8 membered heterocycloalkyl. In embodiments, $R^{2B}$ is independently unsubstituted $C_6$-$C_{10}$ aryl. In embodiments, $R^{2B}$ is independently unsubstituted 5 to 10 membered heteroaryl. In embodiments, $R^{2B}$ is independently substituted or unsubstituted $C_1$-$C_4$ alkyl. In embodiments, $R^{2B}$ is independently substituted or unsubstituted 2 to 4 membered heteroalkyl. In embodiments, $R^{2B}$ is independently substituted or unsubstituted $C_3$-$C_6$ cycloalkyl. In embodiments, $R^{2B}$ is independently, substituted or unsubstituted 3 to 6 membered heterocycloalkyl. In embodiments, $R^{2B}$ is independently substituted or unsubstituted phenyl. In embodiments, $R^{2B}$ is independently substituted or unsubstituted 5 to 6 membered heteroaryl. In embodiments, $R^{2B}$ is independently substituted $C_1$-$C_4$ alkyl. In embodiments, $R^{2B}$ is independently substituted 2 to 4 membered heteroalkyl. In embodiments, $R^{2B}$ is independently substituted $C_3$-$C_6$ cycloalkyl. In embodiments, $R^{2B}$ is independently, substituted 3 to 6 membered heterocycloalkyl. In embodiments, $R^{2B}$ is independently substituted phenyl. In embodiments, $R^{2B}$ is independently substituted 5 to 6 membered heteroaryl. In embodiments, $R^{2B}$ is independently unsubstituted $C_1$-$C_4$ alkyl. In embodiments, $R^{2B}$ is independently unsubstituted 2 to 4 membered heteroalkyl. In embodiments, $R^{2B}$ is independently unsubstituted $C_3$-$C_6$ cycloalkyl. In embodiments, $R^{2B}$ is independently unsubstituted 3 to 6 membered heterocycloalkyl. In embodiments, $R^{2B}$ is independently unsubstituted phenyl. In embodiments, $R^{2B}$ is independently unsubstituted 5 to 6 membered heteroaryl. In embodiments, $R^{2B}$ is independently unsubstituted methyl. In embodiments, $R^{2B}$ is independently unsubstituted ethyl. In embodiments, $R^{2B}$ is independently unsubstituted propyl. In embodiments, $R^{2B}$ is independently unsubstituted isopropyl. In embodiments, $R^{2B}$ is independently unsubstituted tert-butyl.

In embodiments, $R^{2A}$ and $R^{2B}$ substituents bonded to the same nitrogen atom may be joined to form a substituted or unsubstituted heterocycloalkyl. In embodiments, $R^{2A}$ and $R^{2B}$ substituents bonded to the same nitrogen atom may be joined to form a substituted or unsubstituted heteroaryl. In embodiments, $R^{2A}$ and $R^{2B}$ substituents bonded to the same nitrogen atom may be joined to form a substituted heterocycloalkyl. In embodiments, $R^{2A}$ and $R^{2B}$ substituents bonded to the same nitrogen atom may be joined to form a substituted heteroaryl. In embodiments, $R^{2A}$ and $R^{2B}$ substituents bonded to the same nitrogen atom may be joined to form an unsubstituted heterocycloalkyl. In embodiments, $R^{2A}$ and $R^{2B}$ substituents bonded to the same nitrogen atom may be joined to form an unsubstituted heteroaryl. In embodiments, $R^{2A}$ and $R^{2B}$ substituents bonded to the same nitrogen atom may be joined to form a substituted or unsubstituted 3 to 8 membered heterocycloalkyl. In embodiments, $R^{2A}$ and $R^{2B}$ substituents bonded to the same nitrogen atom may be joined to form a substituted or unsubstituted 5 to 10 membered heteroaryl. In embodiments, $R^{2A}$ and $R^{2B}$ substituents bonded to the same nitrogen atom may be joined to form a substituted 3 to 8 membered heterocycloalkyl. In embodiments, $R^{2A}$ and $R^{2B}$ substituents bonded to the same nitrogen atom may be joined to form a substituted 5 to 10 membered heteroaryl. In embodiments, $R^{2A}$ and $R^{2B}$ substituents bonded to the same nitrogen atom may be joined to form an unsubstituted 3 to 8 membered heterocycloalkyl. In embodiments, $R^{2A}$ and $R^{2B}$ substituents bonded to the same nitrogen atom may be joined to form an unsubstituted 5 to 10 membered heteroaryl. In embodiments, $R^{2A}$ and $R^{2B}$ substituents bonded to the same nitrogen atom may be joined to form a substituted or unsubstituted 3 to 6 membered heterocycloalkyl. In embodiments, $R^{2A}$ and $R^{2B}$ substituents bonded to the same nitrogen atom may be joined to form a substituted or unsubstituted 5 to 6 membered heteroaryl. In embodiments, $R^{2A}$ and $R^{2B}$ substituents bonded to the same nitrogen atom may be joined to form a substituted 3 to 6 membered heterocycloalkyl. In embodiments, $R^{2A}$ and $R^{2B}$ substituents bonded to the same nitrogen atom may be joined to form a substituted 5 to 6 membered heteroaryl. In embodiments, $R^{2A}$ and $R^{2B}$ substituents bonded to the same nitrogen atom may be joined to form an unsubstituted 3 to 6 membered heterocycloalkyl. In embodiments, $R^{2A}$ and $R^{2B}$ substituents bonded to the same nitrogen atom may be joined to form an unsubstituted 5 to 6 membered heteroaryl.

In embodiments, $R^{2C}$ is independently hydrogen. In embodiments, $R^{2C}$ is independently $-CX^{2C}_3$. In embodiments, $R^{2C}$ is independently $-CHX^{2C}_2$. In embodiments, $R^{2C}$ is independently $-CH_2X^{2C}$. In embodiments, $R^{2C}$ is independently $-CN$. In embodiments, $R^{2C}$ is independently $-COOH$. In embodiments, $R^{2C}$ is independently $-CONH_2$. In embodiments, $R^{2C}$ is independently substituted or unsubstituted alkyl. In embodiments, $R^{2C}$ is independently substituted or unsubstituted heteroalkyl. In embodiments, $R^{2C}$ is independently substituted or unsubstituted cycloalkyl. In embodiments, $R^{2C}$ is independently, substituted or unsubstituted heterocycloalkyl. In embodiments, $R^{2C}$ is independently substituted or unsubstituted aryl. In embodiments, $R^{2C}$ is independently substituted or unsubstituted heteroaryl. In embodiments, $R^{2C}$ is independently substituted alkyl. In embodiments, $R^{2C}$ is independently substituted heteroalkyl. In embodiments, $R^{2C}$ is independently substituted cycloalkyl. In embodiments, $R^{2C}$ is independently, substituted heterocycloalkyl. In embodiments, $R^{2C}$ is independently substituted aryl. In embodiments, $R^{2C}$ is independently substituted heteroaryl. In embodiments, $R^{2C}$ is independently unsubstituted alkyl. In embodiments, $R^{2C}$ is independently unsubstituted heteroalkyl. In embodiments, $R^{2C}$ is independently unsubstituted cycloalkyl. In embodiments, $R^{2C}$ is independently, unsubstituted heterocycloalkyl. In embodiments, $R^{2C}$ is independently unsubstituted aryl. In embodiments, $R^{2C}$ is independently unsubstituted heteroaryl. In embodiments, $R^{2C}$ is independently substituted or unsubstituted $C_1$-$C_8$ alkyl. In embodiments, $R^{2C}$ is independently substituted or unsubstituted 2 to 8 membered heteroalkyl. In embodiments, $R^{2C}$ is independently substituted or unsubstituted $C_3$-$C_8$ cycloalkyl. In embodiments, $R^{2C}$ is independently, substituted or unsubstituted 3 to 8 membered heterocycloalkyl. In embodiments, $R^{2C}$ is independently substituted or unsubstituted $C_6$-$C_{10}$ aryl. In embodiments, $R^{2C}$ is independently substituted or unsubstituted 5 to 10 membered heteroaryl. In embodiments, $R^{2C}$ is independently substituted $C_1$-$C_8$ alkyl. In embodiments, $R^{2C}$ is independently substituted 2 to 8 membered heteroalkyl. In embodiments, $R^{2C}$ is independently substituted $C_3$-$C_8$ cycloalkyl. In embodiments, $R^{2C}$ is independently, substituted 3 to 8 membered heterocycloalkyl. In embodiments, $R^{2C}$ is independently substituted $C_6$-$C_{10}$ aryl. In embodiments, $R^{2C}$ is independently substituted 5 to 10 membered heteroaryl. In embodiments, $R^{2C}$ is independently unsubstituted $C_1$-$C_8$ alkyl. In embodiments, $R^{2C}$ is independently unsubstituted 2 to 8 membered heteroalkyl. In embodiments, $R^{2C}$ is independently unsubstituted $C_3$-$C_8$ cycloalkyl. In embodiments, $R^{2C}$ is independently, unsubstituted 3 to 8 membered heterocycloalkyl. In embodiments, $R^{2C}$ is independently unsubstituted $C_6$-$C_{10}$ aryl. In embodiments, $R^{2C}$ is independently unsubstituted 5 to 10 membered heteroaryl. In embodiments, $R^{2C}$ is independently substituted or unsubstituted $C_1$-$C_4$ alkyl. In embodiments, $R^{2C}$ is independently substituted or unsubstituted 2 to 4 membered heteroalkyl. In embodiments, $R^{2C}$ is independently substituted or unsubstituted $C_3$-$C_6$ cycloalkyl. In embodiments, $R^{2C}$ is independently, substituted or unsubstituted 3 to 6 membered heterocycloalkyl. In embodiments, $R^{2C}$ is independently substituted or unsubstituted phenyl. In embodiments, $R^{2C}$ is independently substituted or unsubstituted 5 to 6 membered heteroaryl. In embodiments, $R^{2C}$ is independently substituted $C_1$-$C_4$ alkyl. In embodiments, $R^{2C}$ is independently substituted 2 to 4 membered heteroalkyl. In embodiments, $R^{2C}$ is independently substituted $C_3$-$C_6$ cycloalkyl. In embodiments, $R^{2C}$ is independently, substituted 3 to 6 membered heterocycloalkyl. In embodiments, $R^{2C}$ is independently substituted phenyl. In embodiments, $R^{2C}$ is independently substituted 5 to 6 membered heteroaryl. In embodiments, $R^{2C}$ is independently unsubstituted $C_1$-$C_4$ alkyl. In embodiments, $R^{2C}$ is independently unsubstituted 2 to 4 membered heteroalkyl. In embodiments, $R^{2C}$ is independently unsubstituted $C_3$-$C_6$ cycloalkyl. In embodiments, $R^{2C}$ is independently unsubstituted 3 to 6 membered heterocycloalkyl. In embodiments, $R^{2C}$ is independently unsubstituted phenyl. In embodiments, $R^{2C}$ is independently unsubstituted 5 to 6 membered heteroaryl. In embodiments, $R^{2C}$ is independently unsubstituted methyl. In embodiments, $R^{2C}$ is independently unsubstituted ethyl. In embodiments, $R^{2C}$ is independently unsubstituted propyl. In embodiments, $R^{2C}$ is independently unsubstituted isopropyl. In embodiments, $R^{2C}$ is independently unsubstituted tert-butyl.

In embodiments, $R^{2D}$ is independently hydrogen. In embodiments, $R^{2D}$ is independently $-CX^{2D}_3$. In embodiments, $R^{2D}$ is independently $-CHX^{2D}_2$. In embodiments, $R^{2D}$ is independently $-CH_2X^{2D}$. In embodiments, $R^{2D}$ is independently $-CN$. In embodiments, $R^{2D}$ is independently $-COOH$. In embodiments, $R^{2D}$ is independently $-CONH_2$. In embodiments, $R^{2D}$ is independently substituted or unsubstituted alkyl. In embodiments, $R^{2D}$ is independently substituted or unsubstituted heteroalkyl. In embodiments, $R^{2D}$ is independently substituted or unsubstituted cycloalkyl. In embodiments, $R^{2D}$ is independently, substituted or unsubstituted heterocycloalkyl. In embodiments, $R^{2D}$ is independently substituted or unsubstituted aryl. In embodiments, $R^{2D}$ is independently substituted or unsubstituted heteroaryl. In embodiments, $R^{2D}$ is independently substituted alkyl. In embodiments, $R^{2D}$ is independently substituted heteroalkyl. In embodiments, $R^{2D}$ is independently substituted cycloalkyl. In embodiments, $R^{2D}$ is independently, substituted heterocycloalkyl. In embodiments, $R^{2D}$ is independently substituted aryl. In embodiments, $R^{2D}$ is independently substituted heteroaryl. In embodiments, $R^{2D}$ is independently unsubstituted alkyl. In embodiments, $R^{2D}$ is independently unsubstituted heteroalkyl. In embodiments, $R^{2D}$ is independently unsubstituted cycloalkyl. In embodiments, $R^{2D}$ is independently, unsubstituted heterocycloalkyl. In embodiments, $R^{2D}$ is independently unsubstituted aryl. In embodiments, $R^{2D}$ is independently unsubstituted heteroaryl. In embodiments, $R^{2D}$ is independently substituted or unsubstituted $C_1$-$C_8$ alkyl. In embodiments, $R^{2D}$ is independently substituted or unsubstituted 2 to 8 membered heteroalkyl. In embodiments, $R^{2D}$ is independently substituted or unsubstituted $C_3$-$C_8$ cycloalkyl. In embodiments, $R^{2D}$ is independently, substituted or unsubstituted 3 to 8 membered heterocycloalkyl. In embodiments, $R^{2D}$ is independently substituted or unsubstituted $C_6$-$C_{10}$ aryl. In embodiments, $R^{2D}$ is independently substituted or unsubstituted 5 to 10 membered heteroaryl. In embodiments, $R^{2D}$ is independently substituted $C_1$-$C_8$ alkyl. In embodiments, $R^{2D}$ is independently substituted 2 to 8 membered heteroalkyl. In embodiments, $R^{2D}$ is independently substituted $C_3$-$C_8$ cycloalkyl. In embodiments, $R^{2D}$ is independently, substituted 3 to 8 membered heterocycloalkyl. In embodiments, $R^{2D}$ is independently substituted $C_6$-$C_{10}$ aryl. In embodiments, $R^{2D}$ is independently substituted 5 to 10 membered heteroaryl. In embodiments, $R^{2D}$ is independently unsubstituted $C_1$-$C_8$ alkyl. In embodiments, $R^{2D}$ is independently unsubstituted 2 to 8 membered heteroalkyl. In embodiments, $R^{2D}$ is independently unsubstituted $C_3$-$C_8$ cycloalkyl. In embodiments, $R^{2D}$ is independently, unsubstituted 3 to 8 membered heterocycloalkyl. In embodiments, $R^{2D}$ is independently unsubstituted $C_6$-$C_{10}$ aryl. In embodiments, $R^{2D}$ is independently unsubstituted 5 to 10 membered heteroaryl. In embodiments, $R^{2D}$ is independently substituted or unsubstituted $C_1$-$C_4$ alkyl. In embodiments, $R^{2D}$ is independently substituted or unsubstituted 2 to 4 membered heteroalkyl. In embodiments, $R^{2D}$ is independently substituted or unsubstituted $C_3$-$C_6$ cycloalkyl. In embodiments, $R^{2D}$ is independently, substituted or unsubstituted 3 to 6 membered heterocycloalkyl. In embodiments, $R^{2D}$ is independently substituted or unsubstituted phenyl. In embodiments, $R^{2D}$ is independently substituted or unsubstituted 5 to 6 membered heteroaryl. In embodiments, $R^{2D}$ is independently substituted $C_1$-$C_4$ alkyl. In embodiments, $R^{2D}$ is independently substituted 2 to 4 membered heteroalkyl. In embodiments, $R^{2D}$ is independently substituted $C_3$-$C_6$ cycloalkyl. In embodiments, $R^{2D}$ is independently, substituted 3 to 6 membered heterocycloalkyl. In embodiments, $R^{2D}$ is independently substituted phenyl. In embodiments, $R^{2D}$ is independently substituted 5 to 6 membered heteroaryl. In embodiments, $R^{2D}$ is independently unsubstituted $C_1$-$C_4$ alkyl. In embodiments, $R^{2D}$ is independently unsubstituted 2 to 4 membered heteroalkyl. In embodiments, $R^{2D}$ is independently unsubstituted $C_3$-$C_6$ cycloalkyl. In embodiments, $R^{2D}$ is independently unsubstituted 3 to 6 membered heterocycloalkyl. In embodiments, $R^{2D}$ is independently unsubstituted phenyl. In embodiments, $R^{2D}$ is independently unsubstituted 5 to 6 membered heteroaryl. In embodiments, $R^{2D}$ is independently unsubstituted methyl. In embodiments, $R^{2D}$ is independently unsubstituted ethyl. In embodiments, $R^{2D}$ is independently unsubstituted propyl. In embodiments, $R^{2D}$ is independently unsubstituted isopropyl. In embodiments, $R^{2D}$ is independently unsubstituted tert-butyl.

In embodiments, $R^2$ is independently halogen, —$CX^2_3$, —$CHX^2_2$, —$CH_2X^2$, —$OCX^2_3$, —$OCH_2X^2$, —$OCHX^2_2$, —CN, —$SO_{n2}R^{2D}$, —$SO_{v2}NR^{2A}R^{2B}$, —$NHC(O)NR^{2A}R^{2B}$, —$N(O)_{m2}$, —$NR^{2A}R^{2B}$, —$C(O)R^{2C}$, —$C(O)OR^{2C}$, —$C(O)NR^{2A}R^{2B}$, —$OR^{2D}$, —$NR^{2A}SO_2R^{2D}$, —$NR^{2A}C(O)R^{2C}$, —$NR^{2A}C(O)OR^{2C}$, —$NR^{2A}OR^{2C}$, $R^{23}$-substituted or unsubstituted alkyl, $R^{23}$-substituted or unsubstituted heteroalkyl, $R^{23}$-substituted or unsubstituted cycloalkyl, $R^{23}$-substituted or unsubstituted heterocycloalkyl, $R^{23}$-substituted or unsubstituted aryl, or $R^{23}$-substituted or unsubstituted heteroaryl. In embodiments, $R^2$ is independently halogen, —$CX^2_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH$_2$, —NHC(O)NH$_2$, —NHSO$_2$H, —NHC(O)H, —NHC(O)OH, —NHOH, —$OCX^{23}$, —$OCHX^{22}$, $R^{23}$-substituted or unsubstituted alkyl, $R^{23}$-substituted or unsubstituted heteroalkyl, $R^{23}$-substituted or unsubstituted cycloalkyl, $R^{23}$-substituted or unsubstituted heterocycloalkyl, $R^{23}$-substituted or unsubstituted aryl, or $R^{23}$-substituted or unsubstituted heteroaryl. In embodiments, $R^2$ is independently halogen, —$CX^{23}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH$_2$, —NHC(O)NH$_2$, —NHSO$_2$H, —NHC(O)H, —NHC(O)OH, —NHOH, —$OCX^2_3$, —$OCHX^2_2$, $R^{23}$-substituted or unsubstituted $C_1$-$C_8$ alkyl, $R^{23}$-substituted or unsubstituted 2 to 8 membered heteroalkyl, $R^{23}$-substituted or unsubstituted $C_3$-$C_8$ cycloalkyl, $R^{23}$-substituted or unsubstituted 3 to 6 membered heterocycloalkyl, $R^{23}$-substituted or unsubstituted phenyl, or $R^{23}$-substituted or unsubstituted 5 to 6 membered heteroaryl. $X^2$ is —F, —Cl, —Br, or —I. In embodiments, $R^2$ is independently hydrogen. In embodiments, $R^2$ is independently methyl. In embodiments, $R^2$ is independently ethyl.

In embodiments, two adjacent $R^2$ substituents may optionally be joined to form a $R^{23}$-substituted or unsubstituted cycloalkyl, $R^{23}$-substituted or unsubstituted heterocycloalkyl, $R^{23}$-substituted or unsubstituted aryl, or $R^{23}$-substituted or unsubstituted heteroaryl. In embodiments, two adjacent $R^2$ substituents may optionally be joined to form a $R^{23}$-substituted or unsubstituted $C_3$-$C_8$ cycloalkyl, $R^{23}$-substituted or unsubstituted 3 to 6 membered heterocycloalkyl, $R^{23}$-substituted or unsubstituted phenyl, or $R^{23}$-substituted or unsubstituted 5 to 6 membered heteroaryl.

$R^{23}$ is independently oxo, halogen, —$CX^{23}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH$_2$, —NHC(O)NH$_2$, —NHSO$_2$H, —NHC(O)H, —NHC(O)OH, —NHOH, —$OCX^{23}_3$, —$OCHX^{23}_2$, $R^{24}$-substituted or unsubstituted alkyl, $R^{24}$-substituted or unsubstituted heteroalkyl, $R^{24}$-substituted or unsubstituted cycloalkyl, $R^{24}$-substituted or unsubstituted heterocycloalkyl, $R^{24}$-substituted or unsubstituted aryl, or $R^{24}$-substituted or unsubstituted heteroaryl. In embodiments, $R^{23}$ is independently oxo, halogen, —$CX^{23}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH$_2$, —NHC(O)NH$_2$, —NHSO$_2$H, —NHC(O)H, —NHC(O)OH, —NHOH, —OCX$^{23}_3$, —OCHX$^{23}_2$, R$^{24}$-substituted or unsubstituted C$_1$-C$_8$ alkyl, R$^{24}$-substituted or unsubstituted 2 to 8 membered heteroalkyl, R$^{24}$-substituted or unsubstituted C$_3$-C$_8$ cycloalkyl, R$^{24}$-substituted or unsubstituted 3 to 6 membered heterocycloalkyl, R$^{24}$-substituted or unsubstituted phenyl, or R$^{24}$-substituted or unsubstituted 5 to 6 membered heteroaryl. X$^{23}$ is —F, —Cl, —Br, or —I.

R$^{24}$ is independently oxo, halogen, —CX$^{24}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{24}_3$, —OCHX$^{24}_2$, R$^{25}$-substituted or unsubstituted alkyl, R$^{25}$-substituted or unsubstituted heteroalkyl, R$^{25}$-substituted or unsubstituted cycloalkyl, R$^{25}$-substituted or unsubstituted heterocycloalkyl, R$^{25}$-substituted or unsubstituted aryl, or R$^{25}$-substituted or unsubstituted heteroaryl. In embodiments, R$^{24}$ is independently oxo, halogen, —CX$^{24}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{24}_3$, —OCHX$^{24}_2$, R$^{25}$-substituted or unsubstituted C$_1$-C$_8$ alkyl, R$^{25}$-substituted or unsubstituted 2 to 8 membered heteroalkyl, R$^{25}$-substituted or unsubstituted C$_3$-C$_8$ cycloalkyl, R$^{25}$-substituted or unsubstituted 3 to 6 membered heterocycloalkyl, R$^{25}$-substituted or unsubstituted phenyl, or R$^{25}$-substituted or unsubstituted 5 to 6 membered heteroaryl. X$^{24}$ is —F, —Cl, —Br, or —I.

In embodiments, R$^{2A}$ is independently hydrogen, —CX$^{2A}_3$, —CN, —COOH, —CONH$_2$, —CHX$^{2A}_2$, —CH$_2$X$^{2A}$, R$^{23A}$-substituted or unsubstituted alkyl, R$^{23A}$-substituted or unsubstituted heteroalkyl, R$^{23A}$-substituted or unsubstituted cycloalkyl, R$^{23A}$-substituted or unsubstituted heterocycloalkyl, R$^{23A}$-substituted or unsubstituted aryl, or R$^{23A}$-substituted or unsubstituted heteroaryl. In embodiments, R$^{2A}$ is independently hydrogen, —CX$^{2A}_3$, —CN, —COOH, —CONH$_2$, —CHX$^{2A}_2$, —CH$_2$X$^{2A}$, R$^{23A}$-substituted or unsubstituted C$_1$-C$_8$ alkyl, R$^{23A}$-substituted or unsubstituted 2 to 8 membered heteroalkyl, R$^{23A}$-substituted or unsubstituted C$_3$-C$_8$ cycloalkyl, R$^{23A}$-substituted or unsubstituted 3 to 6 membered heterocycloalkyl, R$^{23A}$-substituted or unsubstituted phenyl, or R$^{23A}$-substituted or unsubstituted 5 to 6 membered heteroaryl. X$^2$ is —F, —Cl, —Br, or —I. In embodiments, R$^{2A}$ is independently hydrogen. In embodiments, R$^{2A}$ is independently methyl. In embodiments, R$^{2A}$ is independently ethyl.

In embodiments, R$^{2A}$ and R$^{2B}$ substituents bonded to the same nitrogen atom may optionally be joined to form a R$^{23A}$-substituted or unsubstituted heterocycloalkyl or R$^{23A}$-substituted or unsubstituted heteroaryl. In embodiments, R$^{2A}$ and R$^{2B}$ substituents bonded to the same nitrogen atom may optionally be joined to form a R$^{23A}$-substituted or unsubstituted 3 to 6 membered heterocycloalkyl or R$^{23A}$-substituted or unsubstituted 5 to 6 membered heteroaryl.

R$^{23A}$ is independently oxo, halogen, —CX$^{23A}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{23A}_3$, —OCHX$^{23A}_2$, R$^{24A}$-substituted or unsubstituted alkyl, R$^{24A}$-substituted or unsubstituted heteroalkyl, R$^{24A}$-substituted or unsubstituted cycloalkyl, R$^{24A}$-substituted or unsubstituted heterocycloalkyl, R$^{24A}$-substituted or unsubstituted aryl, or R$^{24A}$-substituted or unsubstituted heteroaryl. In embodiments, R$^{23A}$ is independently oxo, halogen, —CX$^{23A}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{23A}_3$, —OCHX$^{23A}_2$, R$^{24A}$-substituted or unsubstituted C$_1$-C$_8$ alkyl, R$^{24A}$-substituted or unsubstituted 2 to 8 membered heteroalkyl, R$^{24A}$-substituted or unsubstituted C$_3$-C$_8$ cycloalkyl, R$^{24A}$-substituted or unsubstituted 3 to 6 membered heterocycloalkyl, R$^{24A}$. substituted or unsubstituted phenyl, or R$^{24A}$-substituted or unsubstituted 5 to 6 membered heteroaryl. X$^{23A}$ is —F, —Cl, —Br, or —I.

R$^{24A}$ is independently oxo, halogen, —CX$^{24A}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{24A}_3$, —OCHX$^{24A}_2$, R$^{25A}$-substituted or unsubstituted alkyl, R$^{25A}$-substituted or unsubstituted heteroalkyl, R$^{25A}$-substituted or unsubstituted cycloalkyl, R$^{25A}$-substituted or unsubstituted heterocycloalkyl, R$^{25A}$-substituted or unsubstituted aryl, or R$^{25A}$ substituted or unsubstituted heteroaryl. In embodiments, R$^{24A}$ is independently oxo, halogen, —CX$^{24A}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{24A}_3$, —OCHX$^{24A}_2$, R$^{25A}$-substituted or unsubstituted C$_1$-C$_8$ alkyl, R$^{25A}$-substituted or unsubstituted 2 to 8 membered heteroalkyl, R$^{25A}$-substituted or unsubstituted C$_3$-C$_8$ cycloalkyl, R$^{25A}$-substituted or unsubstituted 3 to 6 membered heterocycloalkyl, R$^{25A}$-substituted or unsubstituted phenyl, or R$^{25A}$-substituted or unsubstituted 5 to 6 membered heteroaryl. X$^{24A}$ is —F, —Cl, —Br, or —I.

In embodiments, R$^{2B}$ is independently hydrogen, —CX$^{2B}_3$, —CN, —COOH, —CONH$_2$, —CHX$^{2B}_2$, —CH$_2$X$^{2B}$, R$^{23B}$-substituted or unsubstituted alkyl, R$^{23B}$-substituted or unsubstituted heteroalkyl, R$^{23B}$-substituted or unsubstituted cycloalkyl, R$^{23B}$-substituted or unsubstituted heterocycloalkyl, R$^{23B}$-substituted or unsubstituted aryl, or R$^{23B}$-substituted or unsubstituted heteroaryl. In embodiments, R$^{2B}$ is independently hydrogen, —CX$^{2B}_3$, —CN, —COOH, —CONH$_2$, —CHX$^{2B}_2$, —CH$_2$X$^{2B}$, R$^{23B}$-substituted or unsubstituted C$_1$-C$_8$ alkyl, R$^{23B}$-substituted or unsubstituted 2 to 8 membered heteroalkyl, R$^{23B}$-substituted or unsubstituted C$_3$-C$_8$ cycloalkyl, R$^{23B}$-substituted or unsubstituted 3 to 6 membered heterocycloalkyl, R$^{23B}$-substituted or unsubstituted phenyl, or R$^{23B}$-substituted or unsubstituted 5 to 6 membered heteroaryl. X$^{2B}$ is —F, —Cl, —Br, or —I. In embodiments, R$^{2B}$ is independently hydrogen. In embodiments, R$^{2B}$ is independently methyl. In embodiments, R$^{2B}$ is independently ethyl.

In embodiments, R$^{2A}$ and R$^{2B}$ substituents bonded to the same nitrogen atom may optionally be joined to form a R$^{23B}$-substituted or unsubstituted heterocycloalkyl or R$^{23B}$-substituted or unsubstituted heteroaryl. In embodiments, R$^{2A}$ and R$^{2B}$ substituents bonded to the same nitrogen atom may optionally be joined to form a R$^{23B}$-substituted or unsubstituted 3 to 6 membered heterocycloalkyl or R$^{23B}$-substituted or unsubstituted 5 to 6 membered heteroaryl.

R$^{23B}$ is independently oxo, halogen, —CX$^{23B}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{23B}_3$, —OCHX$^{23B}_2$, R$^{24B}$-substituted or unsubstituted alkyl, R$^{24B}$-substituted or unsubstituted heteroalkyl, R$^{24B}$-substituted or unsubstituted cycloalkyl, R$^{24B}$-substituted or unsubstituted heterocycloalkyl, $R^{24B}$-substituted or unsubstituted aryl, or $R^{24B}$-substituted or unsubstituted heteroaryl. In embodiments, $R^{23B}$ is independently oxo, halogen, $-CX^{23B}{}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{23B}{}_3$, $-OCHX^{23B}{}_2$, $R^{24B}$-substituted or unsubstituted $C_1$-$C_8$ alkyl, $R^{24B}$-substituted or unsubstituted 2 to 8 membered heteroalkyl, $R^{24B}$-substituted or unsubstituted $C_3$-$C_8$ cycloalkyl, $R^{24B}$-substituted or unsubstituted 3 to 6 membered heterocycloalkyl, $R^{24B}$-substituted or unsubstituted phenyl, or $R^{24B}$-substituted or unsubstituted 5 to 6 membered heteroaryl. $X^{23B}$ is $-F$, $-Cl$, $-Br$, or $-I$.

$R^{24B}$ is independently oxo, halogen, $-CX^{24B}{}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{24B}{}_3$, $-OCHX^{24B}{}_2$, $R^{25B}$-substituted or unsubstituted alkyl, $R^{25B}$-substituted or unsubstituted heteroalkyl, $R^{25B}$-substituted or unsubstituted cycloalkyl, $R^{25}$-substituted or unsubstituted heterocycloalkyl, $R^{25B}$-substituted or unsubstituted aryl, or $R^{25B}$-substituted or unsubstituted heteroaryl. In embodiments, $R^{24B}$ is independently oxo, halogen, $-CX^{24B}{}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{24B}{}_3$, $-OCHX^{24B}{}_2$, $R^{25B}$-substituted or unsubstituted $C_1$-$C_8$ alkyl, $R^{25B}$-substituted or unsubstituted 2 to 8 membered heteroalkyl, $R^{25B}$-substituted or unsubstituted $C_3$-$C_8$ cycloalkyl, $R^{25B}$-substituted or unsubstituted 3 to 6 membered heterocycloalkyl, $R^{25B}$-substituted or unsubstituted phenyl, or $R^{25B}$-substituted or unsubstituted 5 to 6 membered heteroaryl. $X^{24B}$ is $-F$, $-Cl$, $-Br$, or $-I$.

In embodiments, $R^{2C}$ is independently hydrogen, $-CX^{2C}{}_3$, $-CN$, $-COOH$, $-CONH_2$, $-CHX^{2C}{}_2$, $-CH_2X^{2C}$, $R^{23C}$-substituted or unsubstituted alkyl, $R^{23C}$-substituted or unsubstituted heteroalkyl, $R^{23C}$-substituted or unsubstituted cycloalkyl, $R^{23C}$-substituted or unsubstituted heterocycloalkyl, $R^{23}$-substituted or unsubstituted aryl, or $R^{23C}$-substituted or unsubstituted heteroaryl. In embodiments, $R^{2C}$ is independently hydrogen, $-CX^{2C}{}_3$, $-CN$, $-COOH$, $-CONH_2$, $-CHX^{22}$, $-CH_2X^{2C}$, $R^{23}$-substituted or unsubstituted $C_1$-$C_8$ alkyl, $R^{23C}$-substituted or unsubstituted 2 to 8 membered heteroalkyl, $R^{23C}$-substituted or unsubstituted $C_3$-$C_8$ cycloalkyl, $R^{23C}$-substituted or unsubstituted 3 to 6 membered heterocycloalkyl, $R^{23C}$-substituted or unsubstituted phenyl, or $R^{23C}$-substituted or unsubstituted 5 to 6 membered heteroaryl. $X^2$ is $-F$, $-Cl$, $-Br$, or $-I$. In embodiments, $R^{2C}$ is independently hydrogen. In embodiments, $R^{2C}$ is independently methyl. In embodiments, $R^{2C}$ is independently ethyl.

$R^{23C}$ is independently oxo, halogen, $-CX^{23C}{}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{23C}{}_3$, $-OCHX^{23C}{}_2$, $R^{24C}$-substituted or unsubstituted alkyl, $R^{24C}$-substituted or unsubstituted heteroalkyl, $R^{24C}$-substituted or unsubstituted cycloalkyl, $R^{24C}$-substituted or unsubstituted heterocycloalkyl, $R^{24C}$-substituted or unsubstituted aryl, or $R^{24C}$-substituted or unsubstituted heteroaryl. In embodiments, $R^{23C}$ is independently oxo, halogen, $-CX^{23C}{}_3$, $-CN$, $-OH$, $-NH_2$, $-COOH$, $-CONH_2$, $-NO_2$, $-SH$, $-S_3H$, $-SO_4H$, $-S_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{23C}{}_3$, $-OCHX^{23C}{}_2$, $R^{24C}$-substituted or unsubstituted $C_1$-$C_8$ alkyl, $R^{24C}$-substituted or unsubstituted 2 to 8 membered heteroalkyl, $R^{24C}$-substituted or unsubstituted $C_3$-$C_8$ cycloalkyl, $R^{24C}$-substituted or unsubstituted 3 to 6 membered heterocycloalkyl, $R^{24}$-substituted or unsubstituted phenyl, or $R^{24C}$-substituted or unsubstituted 5 to 6 membered heteroaryl. $X^{23C}$ is $-F$, $-Cl$, $-Br$, or $-I$.

$R^{24C}$ is independently oxo, halogen, $-CX^{24}{}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{24C}{}_3$, $-OCHX^{24C}{}_2$, $R^{25C}$-substituted or unsubstituted alkyl, $R^{25C}$-substituted or unsubstituted heteroalkyl, $R^{25C}$-substituted or unsubstituted cycloalkyl, $R^{25C}$-substituted or unsubstituted heterocycloalkyl, $R^{25C}$-substituted or unsubstituted aryl, or $R^{25C}$-substituted or unsubstituted heteroaryl. In embodiments, $R^{24C}$ is independently oxo, halogen, $-CX^{24}{}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{24C}{}_3$, $-OCHX^{24C}{}_2$, $R^{25C}$-substituted or unsubstituted $C_1$-$C_8$ alkyl, $R^{25C}$-substituted or unsubstituted 2 to 8 membered heteroalkyl, $R^{25C}$-substituted or unsubstituted $C_3$-$C_8$ cycloalkyl, $R^{25C}$-substituted or unsubstituted 3 to 6 membered heterocycloalkyl, $R^{25C}$-substituted or unsubstituted phenyl, or $R^{25C}$-substituted or unsubstituted 5 to 6 membered heteroaryl. $X^{24C}$ is $-F$, $-Cl$, $-Br$, or $-I$.

In embodiments, $R^{2D}$ is independently hydrogen, $-CX^{2D}{}_3$, $-CN$, $-COOH$, $-CONH_2$, $-CHX^{2D}{}_2$, $-CH_2X^{2D}$, $R^{23D}$-substituted or unsubstituted alkyl, $R^{23D}$-substituted or unsubstituted heteroalkyl, $R^{23D}$-substituted or unsubstituted cycloalkyl, $R^{23D}$-substituted or unsubstituted heterocycloalkyl, $R^{23D}$-substituted or unsubstituted aryl, or $R^{23D}$-substituted or unsubstituted heteroaryl. In embodiments, $R^{2D}$ is independently hydrogen, $-CX^{2D}{}_3$, $-CN$, $-COOH$, $-CONH_2$, $-CHX^{2D}{}_2$, $-CH_2X^{2D}$, $R^{23D}$-substituted or unsubstituted $C_1$-$C_8$ alkyl, $R^{23D}$-substituted or unsubstituted 2 to 8 membered heteroalkyl, $R^{23D}$-substituted or unsubstituted $C_3$-$C_8$ cycloalkyl, $R^{23D}$-substituted or unsubstituted 3 to 6 membered heterocycloalkyl, $R^{23D}$-substituted or unsubstituted phenyl, or $R^{23D}$-substituted or unsubstituted 5 to 6 membered heteroaryl. $X^{2D}$ is $-F$, $-Cl$, $-Br$, or $-I$. In embodiments, $R^{2D}$ is independently hydrogen. In embodiments, $R^{2D}$ is independently methyl. In embodiments, $R^{2D}$ is independently ethyl.

$R^{23D}$ is independently oxo, halogen, $-CX^{23D}{}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{23D}{}_3$, $-OCHX^{23D}{}_2$, $R^{24D}$-substituted or unsubstituted alkyl, $R^{24D}$-substituted or unsubstituted heteroalkyl, $R^{24D}$-substituted or unsubstituted cycloalkyl, $R^{24D}$-substituted or unsubstituted heterocycloalkyl, $R^{24D}$-substituted or unsubstituted aryl, or $R^{24D}$-substituted or unsubstituted heteroaryl. In embodiments, $R^{23D}$ is independently oxo, halogen, $-CX^{23D}{}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{23D}{}_3$, $-OCHX^{23D}{}_2$, $R^{24D}$-substituted or unsubstituted $C_1$-$C_8$ alkyl, $R^{24D}$-substituted or unsubstituted 2 to 8 membered heteroalkyl, $R^{24D}$-substituted or unsubstituted $C_3$-$C_8$ cycloalkyl, $R^{24D}$-substituted or unsubstituted 3 to 6 membered heterocycloalkyl, $R^{24D}$-substituted or unsubstituted phenyl, or $R^{24D}$-substituted or unsubstituted 5 to 6 membered heteroaryl. $X^{23D}$ is —F, —Cl, —Br, or —I.

$R^{24D}$ is independently oxo, halogen, —$CX^{24D}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{24D}_3$, —$OCHX^{24D}_2$, $R^{25D}$-substituted or unsubstituted alkyl, $R^{25D}$-substituted or unsubstituted heteroalkyl, $R^{25D}$-substituted or unsubstituted cycloalkyl, $R^{25D}$-substituted or unsubstituted heterocycloalkyl, $R^{25D}$-substituted or unsubstituted aryl, or $R^{25D}$-substituted or unsubstituted heteroaryl. In embodiments, $R^{24D}$ is independently oxo, halogen, —$CX^{24D}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{24D}_3$, —$OCHX^{24D}_2$, $R^{25D}$-substituted or unsubstituted $C_1$-$C_8$ alkyl, $R^{25D}$-substituted or unsubstituted 2 to 8 membered heteroalkyl, $R^{25D}$-substituted or unsubstituted $C_3$-$C_8$ cycloalkyl, $R^{25D}$-substituted or unsubstituted 3 to 6 membered heterocycloalkyl, $R^{25D}$-substituted or unsubstituted phenyl, or $R^{25D}$-substituted or unsubstituted 5 to 6 membered heteroaryl. $X^{24D}$ is —F, —Cl, —Br, or —I.

$R^{25}$, $R^{25A}$, $R^{25B}$, $R^{25C}$, and $R^{25D}$ are independently hydrogen, oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$,
—NHC(O)$NH_2$, —$NHSO_2H$, —NHC(O)H,
—NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{25}$, $R^{25A}R^{25B}$, $R^{25C}$, and $R^{25D}$ are independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{25}$, $R^{25A}$, $R^{25B}$, $R^{25C}$, and $R^{25D}$ are independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, unsubstituted $C_1$-$C_8$ alkyl, unsubstituted 2 to 8 membered heteroalkyl, unsubstituted $C_3$-$C_8$ cycloalkyl, unsubstituted 3 to 6 membered heterocycloalkyl, unsubstituted phenyl, or unsubstituted 5 to 6 membered heteroaryl.

In embodiments, $R^2$ is independently halogen. In embodiments, $R^2$ is independently hydrogen. In embodiments, $R^2$ is independently hydrogen or halogen. In embodiments, $R^2$ is independently methyl. In embodiments, $R^2$ is independently $C_1$-$C_4$ alkyl. In embodiments, $R^2$ is independently halogen or $C_1$-$C_4$ alkyl. In embodiments, $R^2$ is independently halogen or $C_1$-$C_3$ alkyl. In embodiments, $R^2$ is independently halogen or $C_1$-$C_2$ alkyl. In embodiments, $R^2$ is independently halogen or methyl. In embodiments, $R^2$ is independently substituted methyl. In embodiments, $R^2$ is independently substituted or unsubstituted $C_1$-$C_4$ alkyl. In embodiments, $R^2$ is independently halogen or substituted or unsubstituted $C_1$-$C_4$ alkyl. In embodiments, $R^2$ is independently halogen or substituted or unsubstituted $C_1$-$C_3$ alkyl. In embodiments, $R^2$ is independently halogen or substituted or unsubstituted $C_1$-$C_2$ alkyl. In embodiments, $R^2$ is independently halogen or substituted or unsubstituted methyl. In embodiments, $R^2$ is independently substituted methyl. In embodiments, $R^2$ is independently substituted $C_1$-$C_4$ alkyl. In embodiments, $R^2$ is independently halogen or substituted $C_1$-$C_4$ alkyl. In embodiments, $R^2$ is independently halogen or substituted $C_1$-$C_3$ alkyl. In embodiments, $R^2$ is independently halogen or substituted $C_1$-$C_2$ alkyl. In embodiments, $R^2$ is independently halogen or substituted methyl. In embodiments, $R^2$ is independently unsubstituted methyl. In embodiments, $R^2$ is independently unsubstituted $C_1$-$C_4$ alkyl. In embodiments, $R^2$ is independently halogen or unsubstituted $C_1$-$C_4$ alkyl. In embodiments, $R^2$ is independently halogen or unsubstituted $C_1$-$C_3$ alkyl. In embodiments, $R^2$ is independently halogen or unsubstituted $C_1$-$C_2$ alkyl. In embodiments, $R^2$ is independently halogen or unsubstituted methyl.

In embodiments, $R^2$ is independently $C_1$-$C_4$ alkyl. In embodiments, $R^2$ is independently $C_1$-$C_3$ alkyl. In embodiments, $R^2$ is independently $C_1$-$C_2$ alkyl. In embodiments, $R^2$ is independently methyl. In embodiments, $R^2$ is independently ispropyl. In embodiments, $R^2$ is independently substituted or unsubstituted methyl or substituted or unsubstituted isopropyl.

In embodiments, $R^2$ is independently substituted or unsubstituted $C_1$-$C_4$ alkyl. In embodiments, $R^2$ is independently substituted or unsubstituted $C_1$-$C_3$ alkyl. In embodiments, $R^2$ is independently substituted or unsubstituted $C_1$-$C_2$ alkyl. In embodiments, $R^2$ is independently substituted or unsubstituted methyl.

In embodiments, z2 is 0. In embodiments, z2 is 1. In embodiments, z2 is 2. In embodiments, z2 is 3. In embodiments, z2 is 4.

In embodiments, $R^3$ is hydrogen. In embodiments, $R^3$ is —$NH_2$.

In embodiments, the symbol $Y^1$ is N. In embodiments, the symbol $Y^1$ is $C(R^4)$.

In embodiments, $R^4$ is hydrogen, substituted or unsubstituted $C_1$-$C_8$ alkyl, or substituted or unsubstituted 2 to 8 membered heteroalkyl.

In embodiments, $R^4$ is independently hydrogen. In embodiments, $R^4$ is independently halogen. In embodiments, $R^4$ is independently —$CX^{43}$. In embodiments, $R^4$ is independently —$CHX^{42}$. In embodiments, $R^4$ is independently —$CH_2X^4$. In embodiments, $R^4$ is independently —$OCX^{43}$. In embodiments, $R^4$ is independently —$OCH_2X^4$. In embodiments, $R^4$ is independently —$OCHX^{42}$. In embodiments, $R^4$ is independently —CN. In embodiments, $R^4$ is independently —$SO_{n4}R^{4D}$. In embodiments, $R^4$ is independently —$SO_{n4}$ $NR^{4A}R^{4B}$. In embodiments, $R^4$ is independently —NHC(O)$NR^{4A}R^{4B}$. In embodiments, $R^4$ is independently —$N(O)_{m4}$. In embodiments, $R^4$ is independently —$NR^{4A}R^{4B}$. In embodiments, $R^4$ is independently —C(O)$R^{4C}$. In embodiments, $R^4$ is independently —C(O)—$OR^{4C}$. In embodiments, $R^4$ is independently —C(O)$NR^{4A}R^{4B}$. In embodiments, $R^4$ is independently —$OR^{4D}$. In embodiments, $R^4$ is independently —$NR^{4A}SO_2R^{4D}$. In embodiments, $R^4$ is independently —$NR^{4A}C(O)R^{4C}$. In embodiments, $R^4$ is independently —$NR^{4A}C(O)OR^{4C}$ In embodiments, $R^4$ is independently —$NR^{4A}OR^{4C}$. In embodiments, $R^4$ is independently —OH. In embodiments, $R^4$ is independently —$NH_2$. In embodiments, $R^4$ is independently —COOH. In embodiments, $R^4$ is independently —CONH$_2$. In embodiments, $R^4$ is independently —NO$_2$. In embodiments, $R^4$ is independently —SH.

In embodiments, $R^4$ is independently substituted or unsubstituted alkyl. In embodiments, $R^4$ is independently substituted or unsubstituted heteroalkyl. In embodiments, $R^4$ is independently substituted or unsubstituted cycloalkyl. In embodiments, $R^4$ is independently, substituted or unsubstituted heterocycloalkyl. In embodiments, $R^4$ is independently substituted or unsubstituted aryl. In embodiments, $R^4$ is independently substituted or unsubstituted heteroaryl. In embodiments, $R^4$ is independently substituted alkyl. In embodiments, $R^4$ is independently substituted heteroalkyl. In embodiments, $R^4$ is independently substituted cycloalkyl. In embodiments, $R^4$ is independently, substituted heterocycloalkyl. In embodiments, $R^4$ is independently substituted aryl. In embodiments, $R^4$ is independently substituted heteroaryl. In embodiments, $R^4$ is independently unsubstituted alkyl. In embodiments, $R^4$ is independently unsubstituted heteroalkyl. In embodiments, $R^4$ is independently unsubstituted cycloalkyl. In embodiments, $R^4$ is independently, unsubstituted heterocycloalkyl. In embodiments, $R^4$ is independently unsubstituted aryl. In embodiments, $R^4$ is independently unsubstituted heteroaryl. In embodiments, $R^4$ is independently substituted or unsubstituted $C_1$-$C_8$ alkyl. In embodiments, $R^4$ is independently substituted or unsubstituted 2 to 8 membered heteroalkyl. In embodiments, $R^4$ is independently substituted or unsubstituted $C_3$-$C_8$ cycloalkyl. In embodiments, $R^4$ is independently, substituted or unsubstituted 3 to 8 membered heterocycloalkyl. In embodiments, $R^4$ is independently substituted or unsubstituted $C_6$-$C_{10}$ aryl. In embodiments, $R^4$ is independently substituted or unsubstituted 5 to 10 membered heteroaryl. In embodiments, $R^4$ is independently substituted $C_1$-$C_8$ alkyl. In embodiments, $R^4$ is independently substituted 2 to 8 membered heteroalkyl. In embodiments, $R^4$ is independently substituted $C_3$-$C_8$ cycloalkyl. In embodiments, $R^4$ is independently, substituted 3 to 8 membered heterocycloalkyl. In embodiments, $R^4$ is independently substituted $C_6$-$C_{10}$ aryl. In embodiments, $R^4$ is independently substituted 5 to 10 membered heteroaryl. In embodiments, $R^4$ is independently unsubstituted $C_1$-$C_8$ alkyl. In embodiments, $R^4$ is independently unsubstituted 2 to 8 membered heteroalkyl. In embodiments, $R^4$ is independently unsubstituted $C_3$-$C_8$ cycloalkyl. In embodiments, $R_4$ is independently, unsubstituted 3 to 8 membered heterocycloalkyl. In embodiments, $R^4$ is independently unsubstituted $C_6$-$C_{10}$ aryl. In embodiments, $R^4$ is independently unsubstituted 5 to 10 membered heteroaryl. In embodiments, $R^4$ is independently substituted or unsubstituted $C_1$-$C_4$ alkyl. In embodiments, $R^4$ is independently substituted or unsubstituted 2 to 4 membered heteroalkyl. In embodiments, $R^4$ is independently substituted or unsubstituted $C_3$-$C_6$ cycloalkyl. In embodiments, $R^4$ is independently, substituted or unsubstituted 3 to 6 membered heterocycloalkyl. In embodiments, $R^4$ is independently substituted or unsubstituted phenyl. In embodiments, $R^4$ is independently substituted or unsubstituted 5 to 6 membered heteroaryl. In embodiments, $R^4$ is independently substituted $C_1$-$C_4$ alkyl. In embodiments, $R^4$ is independently substituted 2 to 4 membered heteroalkyl. In embodiments, $R^4$ is independently substituted $C_3$-$C_6$ cycloalkyl. In embodiments, $R^4$ is independently, substituted 3 to 6 membered heterocycloalkyl. In embodiments, $R^4$ is independently substituted phenyl. In embodiments, $R^4$ is independently substituted 5 to 6 membered heteroaryl. In embodiments, $R^4$ is independently unsubstituted $C_1$-$C_4$ alkyl. In embodiments, $R^4$ is independently unsubstituted 2 to 4 membered heteroalkyl. In embodiments, $R^4$ is independently unsubstituted $C_3$-$C_6$ cycloalkyl. In embodiments, $R^4$ is independently unsubstituted 3 to 6 membered heterocycloalkyl. In embodiments, $R^4$ is independently unsubstituted phenyl. In embodiments, $R^4$ is independently unsubstituted 5 to 6 membered heteroaryl.

In embodiments, $R^{4A}$ is independently hydrogen. In embodiments, $R^{4A}$ is independently —$CX^{4A}_3$. In embodiments, $R^{4A}$ is independently —$CHX^{4A}_2$. In embodiments, $R^{4A}$ is independently —$CH_2X^{4A}$. In embodiments, $R^{4A}$ is independently —CN. In embodiments, $R^{4A}$ is independently —COOH. In embodiments, $R^{4A}$ is independently —CONH$_2$. In embodiments, $R^{4A}$ is independently substituted or unsubstituted alkyl. In embodiments, $R^{4A}$ is independently substituted or unsubstituted heteroalkyl. In embodiments, $R^{4A}$ is independently substituted or unsubstituted cycloalkyl. In embodiments, $R^{4A}$ is independently, substituted or unsubstituted heterocycloalkyl. In embodiments, $R^{4A}$ is independently substituted or unsubstituted aryl. In embodiments, $R^{4A}$ is independently substituted or unsubstituted heteroaryl. In embodiments, $R^{4A}$ is independently substituted alkyl. In embodiments, $R^{4A}$ is independently substituted heteroalkyl. In embodiments, $R^{4A}$ is independently substituted cycloalkyl. In embodiments, $R^{4A}$ is independently, substituted heterocycloalkyl. In embodiments, $R^{4A}$ is independently substituted aryl. In embodiments, $R^{4A}$ is independently substituted heteroaryl. In embodiments, $R^{4A}$ is independently unsubstituted alkyl. In embodiments, $R^{4A}$ is independently unsubstituted heteroalkyl. In embodiments, $R^{4A}$ is independently unsubstituted cycloalkyl. In embodiments, $R^{4A}$ is independently, unsubstituted heterocycloalkyl. In embodiments, $R^{4A}$ is independently unsubstituted aryl. In embodiments, $R^{4A}$ is independently unsubstituted heteroaryl. In embodiments, $R^{4A}$ is independently substituted or unsubstituted $C_1$-$C_8$ alkyl. In embodiments, $R^{4A}$ is independently substituted or unsubstituted 2 to 8 membered heteroalkyl. In embodiments, $R^{4A}$ is independently substituted or unsubstituted $C_3$-$C_8$ cycloalkyl. In embodiments, $R^{4A}$ is independently, substituted or unsubstituted 3 to 8 membered heterocycloalkyl. In embodiments, $R^{4A}$ is independently substituted or unsubstituted $C_6$-$C_{10}$ aryl. In embodiments, $R^{4A}$ is independently substituted or unsubstituted 5 to 10 membered heteroaryl. In embodiments, $R^{4A}$ is independently substituted $C_1$-$C_8$ alkyl. In embodiments, $R^{4A}$ is independently substituted 2 to 8 membered heteroalkyl. In embodiments, $R^{4A}$ is independently substituted $C_3$-$C_8$ cycloalkyl. In embodiments, $R^{4A}$ is independently, substituted 3 to 8 membered heterocycloalkyl. In embodiments, $R^{4A}$ is independently substituted $C_6$-$C_{10}$ aryl. In embodiments, $R^{4A}$ is independently substituted 5 to 10 membered heteroaryl. In embodiments, $R^{4A}$ is independently unsubstituted $C_1$-$C_8$ alkyl. In embodiments, $R^{4A}$ is independently unsubstituted 2 to 8 membered heteroalkyl. In embodiments, $R^{4A}$ is independently unsubstituted $C_3$-$C_8$ cycloalkyl. In embodiments, $R^{4A}$ is independently, unsubstituted 3 to 8 membered heterocycloalkyl. In embodiments, $R^{4A}$ is independently unsubstituted $C_6$-$C_{10}$ aryl. In embodiments, $R^{4A}$ is independently unsubstituted 5 to 10 membered heteroaryl. In embodiments, $R^{4A}$ is independently substituted or unsubstituted $C_1$-$C_4$ alkyl. In embodiments, $R^{4A}$ is independently substituted or unsubstituted 2 to 4 membered heteroalkyl. In embodiments, $R^{4A}$ is independently substituted or unsubstituted $C_3$-$C_6$ cycloalkyl. In embodiments, $R^{4A}$ is independently, substituted or unsubstituted 3 to 6 membered heterocycloalkyl. In embodiments, $R^{4A}$ is independently substituted or unsubstituted phenyl. In embodiments, $R^{4A}$ is independently substituted or unsubstituted 5 to 6 membered heteroaryl. In embodiments, $R^{4A}$ is independently substituted $C_1$-$C_4$ alkyl. In embodiments, $R^{4A}$ is independently substituted 2 to 4 membered heteroalkyl. In embodiments, $R^{4A}$ is independently substituted $C_3$-$C_6$ cycloalkyl. In embodiments, $R^{4A}$ is independently, substituted 3 to 6 membered heterocycloalkyl. In embodiments, $R^{4A}$ is independently substituted phenyl. In embodiments, $R^{4A}$ is independently substituted 5 to 6 membered heteroaryl. In embodiments, $R^{4A}$ is independently unsubstituted $C_1$-$C_4$ alkyl. In embodiments, $R^{4A}$ is independently unsubstituted 2 to 4 membered heteroalkyl. In embodiments, $R^{4A}$ is independently unsubstituted $C_3$-$C_6$ cycloalkyl. In embodiments, $R^{4A}$ is independently unsubstituted 3 to 6 membered heterocycloalkyl. In embodiments, $R^{4A}$ is independently unsubstituted phenyl. In embodiments, $R^{4A}$ is independently unsubstituted 5 to 6 membered heteroaryl. In embodiments, $R^{4A}$ is independently unsubstituted methyl. In embodiments, $R^{4A}$ is independently unsubstituted ethyl. In embodiments, $R^{4A}$ is independently unsubstituted propyl. In embodiments, $R^{4A}$ is independently unsubstituted isopropyl. In embodiments, $R^{4A}$ is independently unsubstituted tert-butyl.

In embodiments, $R^{41}$ is independently hydrogen. In embodiments, $R^{4B}$ is independently —$CX^{4B}_3$. In embodiments, $R^{4B}$ is independently —$CHX^{4B}_2$. In embodiments, $R^{4B}$ is independently —$CH_2X^{4B}$. In embodiments, $R^{4B}$ is independently —CN. In embodiments, $R^{4B}$ is independently —COOH. In embodiments, $R^{4B}$ is independently —$CONH_2$. In embodiments, $R^{4B}$ is independently substituted or unsubstituted alkyl. In embodiments, $R^{4B}$ is independently substituted or unsubstituted heteroalkyl. In embodiments, $R^{4B}$ is independently substituted or unsubstituted cycloalkyl. In embodiments, $R^{4B}$ is independently, substituted or unsubstituted heterocycloalkyl. In embodiments, $R^{4B}$ is independently substituted or unsubstituted aryl. In embodiments, $R^{4B}$ is independently substituted or unsubstituted heteroaryl. In embodiments, $R^{4B}$ is independently substituted alkyl. In embodiments, $R^{4B}$ is independently substituted heteroalkyl. In embodiments, $R^{4B}$ is independently substituted cycloalkyl. In embodiments, $R^{4B}$ is independently, substituted heterocycloalkyl. In embodiments, $R^{4B}$ is independently substituted aryl. In embodiments, $R^{4B}$ is independently substituted heteroaryl. In embodiments, $R^{4B}$ is independently unsubstituted alkyl. In embodiments, $R^{4B}$ is independently unsubstituted heteroalkyl. In embodiments, $R^{4B}$ is independently unsubstituted cycloalkyl. In embodiments, $R^{4B}$ is independently, unsubstituted heterocycloalkyl. In embodiments, $R^{4B}$ is independently unsubstituted aryl. In embodiments, $R^{4B}$ is independently unsubstituted heteroaryl. In embodiments, $R^{4B}$ is independently substituted or unsubstituted $C_1$-$C_8$ alkyl. In embodiments, $R^{4B}$ is independently substituted or unsubstituted 2 to 8 membered heteroalkyl. In embodiments, $R^{4B}$ is independently substituted or unsubstituted $C_3$-$C_8$ cycloalkyl. In embodiments, $R^{4B}$ is independently, substituted or unsubstituted 3 to 8 membered heterocycloalkyl. In embodiments, $R^{4B}$ is independently substituted or unsubstituted $C_6$-$C_{10}$ aryl. In embodiments, $R^{4B}$ is independently substituted or unsubstituted 5 to 10 membered heteroaryl. In embodiments, $R^{4B}$ is independently substituted $C_1$-$C_8$ alkyl. In embodiments, $R^{4B}$ is independently substituted 2 to 8 membered heteroalkyl. In embodiments, $R^{4B}$ is independently substituted $C_3$-$C_8$ cycloalkyl. In embodiments, $R^{4B}$ is independently, substituted 3 to 8 membered heterocycloalkyl. In embodiments, $R^{4B}$ is independently substituted $C_6$-$C_{10}$ aryl. In embodiments, $R^{4B}$ is independently substituted 5 to 10 membered heteroaryl. In embodiments, $R^{4B}$ is independently unsubstituted $C_1$-$C_8$ alkyl. In embodiments, $R^{4B}$ is independently unsubstituted 2 to 8 membered heteroalkyl. In embodiments, $R^{4B}$ is independently unsubstituted $C_3$-$C_8$ cycloalkyl. In embodiments, $R^{4B}$ is independently, unsubstituted 3 to 8 membered heterocycloalkyl. In embodiments, $R^{4B}$ is independently unsubstituted $C_6$-$C_{10}$ aryl. In embodiments, $R^{4B}$ is independently unsubstituted 5 to 10 membered heteroaryl. In embodiments, $R^{4B}$ is independently substituted or unsubstituted $C_1$-$C_4$ alkyl. In embodiments, $R^{4B}$ is independently substituted or unsubstituted 2 to 4 membered heteroalkyl. In embodiments, $R^{4B}$ is independently substituted or unsubstituted $C_3$-$C_6$ cycloalkyl. In embodiments, $R^{4B}$ is independently, substituted or unsubstituted 3 to 6 membered heterocycloalkyl. In embodiments, $R^{4B}$ is independently substituted or unsubstituted phenyl. In embodiments, $R^{4B}$ is independently substituted or unsubstituted 5 to 6 membered heteroaryl. In embodiments, $R^{4B}$ is independently substituted $C_1$-$C_4$ alkyl. In embodiments, $R^{4B}$ is independently substituted 2 to 4 membered heteroalkyl. In embodiments, $R^{4B}$ is independently substituted $C_3$-$C_6$ cycloalkyl. In embodiments, $R^{4B}$ is independently, substituted 3 to 6 membered heterocycloalkyl. In embodiments, $R^{4B}$ is independently substituted phenyl. In embodiments, $R^{4B}$ is independently substituted 5 to 6 membered heteroaryl. In embodiments, $R^{4B}$ is independently unsubstituted $C_1$-$C_4$ alkyl. In embodiments, $R^{4B}$ is independently unsubstituted 2 to 4 membered heteroalkyl. In embodiments, $R^{4B}$ is independently unsubstituted $C_3$-$C_6$ cycloalkyl. In embodiments, $R^{4B}$ is independently unsubstituted 3 to 6 membered heterocycloalkyl. In embodiments, $R^{4B}$ is independently unsubstituted phenyl. In embodiments, $R^{4B}$ is independently unsubstituted 5 to 6 membered heteroaryl. In embodiments, $R^{4B}$ is independently unsubstituted methyl. In embodiments, $R^{4B}$ is independently unsubstituted ethyl. In embodiments, $R^{4B}$ is independently unsubstituted propyl. In embodiments, $R^{4B}$ is independently unsubstituted isopropyl. In embodiments, $R^{4B}$ is independently unsubstituted tert-butyl.

In embodiments, $R^{4A}$ and $R^{4B}$ substituents bonded to the same nitrogen atom may be joined to form a substituted or unsubstituted heterocycloalkyl. In embodiments, $R^{4A}$ and $R^{4B}$ substituents bonded to the same nitrogen atom may be joined to form a substituted or unsubstituted heteroaryl. In embodiments, $R^{4A}$ and $R^{4B}$ substituents bonded to the same nitrogen atom may be joined to form a substituted heterocycloalkyl. In embodiments, $R^{4A}$ and $R^{4B}$ substituents bonded to the same nitrogen atom may be joined to form a substituted heteroaryl. In embodiments, $R^{4A}$ and $R^{4B}$ substituents bonded to the same nitrogen atom may be joined to form an unsubstituted heterocycloalkyl. In embodiments, $R^{4A}$ and $R^{4B}$ substituents bonded to the same nitrogen atom may be joined to form an unsubstituted heteroaryl. In embodiments, $R^{4A}$ and $R^{4B}$ substituents bonded to the same nitrogen atom may be joined to form a substituted or unsubstituted 3 to 8 membered heterocycloalkyl. In embodiments, $R^{4A}$ and $R^{4B}$ substituents bonded to the same nitrogen atom may be joined to form a substituted or unsubstituted 5 to 10 membered heteroaryl. In embodiments, $R^{4A}$ and $R^{4B}$ substituents bonded to the same nitrogen atom may be joined to form a substituted 3 to 8 membered heterocycloalkyl. In embodiments, $R^{4A}$ and $R^{4B}$ substituents bonded to the same nitrogen atom may be joined to form a substituted 5 to 10 membered heteroaryl. In embodiments, $R^{4A}$ and $R^{4B}$ substituents bonded to the same nitrogen atom may be joined to form an unsubstituted 3 to 8 membered heterocycloalkyl. In embodiments, $R^{4A}$ and $R^{4B}$ substituents bonded to the same nitrogen atom may be joined to form an unsubstituted 5 to 10 membered heteroaryl. In embodiments, $R^{4A}$ and $R^{4B}$ substituents bonded to the same nitrogen atom may be joined to form a substituted or unsubstituted 3 to 6 membered heterocycloalkyl. In embodiments, $R^{4A}$ and $R^{4B}$ substituents bonded to the same nitrogen atom may be joined to form a substituted or unsubstituted 5 to 6 membered heteroaryl. In embodiments, $R^{4A}$ and $R^{4B}$ substituents bonded to the same nitrogen atom may be joined to form a substituted 3 to 6 membered heterocycloalkyl. In embodiments, $R^{4A}$ and $R^{4B}$ substituents bonded to the same nitrogen atom may be joined to form a substituted 5 to 6 membered heteroaryl. In embodiments, $R^{4A}$ and $R^{4B}$ substituents bonded to the same nitrogen atom may be joined to form an unsubstituted 3 to 6 membered heterocycloalkyl. In embodiments, $R^{4A}$ and $R^{4B}$ substituents bonded to the same nitrogen atom may be joined to form an unsubstituted 5 to 6 membered heteroaryl.

In embodiments, $R^{4C}$ is independently hydrogen. In embodiments, $R^{4C}$ is independently $-CX^{4C}_3$. In embodiments, $R^{4C}$ is independently $-CHX^{4C}_2$. In embodiments, $R^{4C}$ is independently $-CH_2X^{4C}$. In embodiments, $R^{4C}$ is independently $-CN$. In embodiments, $R^{4C}$ is independently $-COOH$. In embodiments, $R^{4C}$ is independently $-CONH_2$. In embodiments, $R^{4C}$ is independently substituted or unsubstituted alkyl. In embodiments, $R^{4C}$ is independently substituted or unsubstituted heteroalkyl. In embodiments, $R^{4C}$ is independently substituted or unsubstituted cycloalkyl. In embodiments, $R^{4C}$ is independently, substituted or unsubstituted heterocycloalkyl. In embodiments, $R^{4C}$ is independently substituted or unsubstituted aryl. In embodiments, $R^{4C}$ is independently substituted or unsubstituted heteroaryl. In embodiments, $R^{4C}$ is independently substituted alkyl. In embodiments, $R^{4C}$ is independently substituted heteroalkyl. In embodiments, $R^{4C}$ is independently substituted cycloalkyl. In embodiments, $R^{4C}$ is independently, substituted heterocycloalkyl. In embodiments, $R^{4C}$ is independently substituted aryl. In embodiments, $R^{4C}$ is independently substituted heteroaryl. In embodiments, $R^{4C}$ is independently unsubstituted alkyl. In embodiments, $R^{4C}$ is independently unsubstituted heteroalkyl. In embodiments, $R^{4C}$ is independently unsubstituted cycloalkyl. In embodiments, $R^{4C}$ is independently, unsubstituted heterocycloalkyl. In embodiments, $R^{4C}$ is independently unsubstituted aryl. In embodiments, $R^{4C}$ is independently unsubstituted heteroaryl. In embodiments, $R^{4C}$ is independently substituted or unsubstituted $C_1$-$C_8$ alkyl. In embodiments, $R^{4C}$ is independently substituted or unsubstituted 2 to 8 membered heteroalkyl. In embodiments, $R^{4C}$ is independently substituted or unsubstituted $C_3$-$C_8$ cycloalkyl. In embodiments, $R^{4C}$ is independently, substituted or unsubstituted 3 to 8 membered heterocycloalkyl. In embodiments, $R^{4C}$ is independently substituted or unsubstituted $C_6$-$C_{10}$ aryl. In embodiments, $R^{4C}$ is independently substituted or unsubstituted 5 to 10 membered heteroaryl. In embodiments, $R^{4C}$ is independently substituted $C_1$-$C_8$ alkyl. In embodiments, $R^{4C}$ is independently substituted 2 to 8 membered heteroalkyl. In embodiments, $R^{4C}$ is independently substituted $C_3$-$C_8$ cycloalkyl. In embodiments, $R^{4C}$ is independently, substituted 3 to 8 membered heterocycloalkyl. In embodiments, $R^{4C}$ is independently substituted $C_6$-$C_{10}$ aryl. In embodiments, $R^{4C}$ is independently substituted 5 to 10 membered heteroaryl. In embodiments, $R^{4C}$ is independently unsubstituted $C_1$-$C_8$ alkyl. In embodiments, $R^{4C}$ is independently unsubstituted 2 to 8 membered heteroalkyl. In embodiments, $R^{4C}$ is independently unsubstituted $C_3$-$C_8$ cycloalkyl. In embodiments, $R^{4C}$ is independently, unsubstituted 3 to 8 membered heterocycloalkyl. In embodiments, $R^{4C}$ is independently unsubstituted $C_6$-$C_{10}$ aryl. In embodiments, $R^{4C}$ is independently unsubstituted 5 to 10 membered heteroaryl. In embodiments, $R^{4C}$ is independently substituted or unsubstituted $C_1$-$C_4$ alkyl. In embodiments, $R^{4C}$ is independently substituted or unsubstituted 2 to 4 membered heteroalkyl. In embodiments, $R^{4C}$ is independently substituted or unsubstituted $C_3$-$C_6$ cycloalkyl. In embodiments, $R^{4C}$ is independently, substituted or unsubstituted 3 to 6 membered heterocycloalkyl. In embodiments, $R^{4C}$ is independently substituted or unsubstituted phenyl. In embodiments, $R^{4C}$ is independently substituted or unsubstituted 5 to 6 membered heteroaryl. In embodiments, $R^{4C}$ is independently substituted $C_1$-$C_4$ alkyl. In embodiments, $R^{4C}$ is independently substituted 2 to 4 membered heteroalkyl. In embodiments, $R^{4C}$ is independently substituted $C_3$-$C_6$ cycloalkyl. In embodiments, $R^{4C}$ is independently, substituted 3 to 6 membered heterocycloalkyl. In embodiments, $R^{4C}$ is independently substituted phenyl. In embodiments, $R^{4C}$ is independently substituted 5 to 6 membered heteroaryl. In embodiments, $R^{4C}$ is independently unsubstituted $C_1$-$C_4$ alkyl. In embodiments, $R^{4C}$ is independently unsubstituted 2 to 4 membered heteroalkyl. In embodiments, $R^{4C}$ is independently unsubstituted $C_3$-$C_6$ cycloalkyl. In embodiments, $R^{4C}$ is independently unsubstituted 3 to 6 membered heterocycloalkyl. In embodiments, $R^{4C}$ is independently unsubstituted phenyl. In embodiments, $R^{4C}$ is independently unsubstituted 5 to 6 membered heteroaryl. In embodiments, $R^{4C}$ is independently unsubstituted methyl. In embodiments, $R^{4C}$ is independently unsubstituted ethyl. In embodiments, $R^{4C}$ is independently unsubstituted propyl. In embodiments, $R^{4C}$ is independently unsubstituted isopropyl. In embodiments, $R^{4C}$ is independently unsubstituted tert-butyl.

In embodiments, $R^{4D}$ is independently hydrogen. In embodiments, $R^{4D}$ is independently $-CX^{4D}_3$. In embodiments, $R^{4D}$ is independently $-CHX^{4D}_2$. In embodiments, $R^{4D}$ is independently $-CH_2X^{4D}$. In embodiments, $R^{4D}$ is independently $-CN$. In embodiments, $R^{4D}$ is independently $-COOH$. In embodiments, $R^{4D}$ is independently $-CONH_2$. In embodiments, $R^{4D}$ is independently substituted or unsubstituted alkyl. In embodiments, $R^{4D}$ is independently substituted or unsubstituted heteroalkyl. In embodiments, $R^{4D}$ is independently substituted or unsubstituted cycloalkyl. In embodiments, $R^{4D}$ is independently, substituted or unsubstituted heterocycloalkyl. In embodiments, $R^{4D}$ is independently substituted or unsubstituted aryl. In embodiments, $R^{4D}$ is independently substituted or unsubstituted heteroaryl. In embodiments, $R^{4D}$ is independently substituted alkyl. In embodiments, $R^{4D}$ is independently substituted heteroalkyl. In embodiments, $R^{4D}$ is independently substituted cycloalkyl. In embodiments, $R^{4D}$ is independently, substituted heterocycloalkyl. In embodiments, $R^{4D}$ is independently substituted aryl. In embodiments, $R^{4D}$ is independently substituted heteroaryl. In embodiments, $R^{4D}$ is independently unsubstituted alkyl. In embodiments, $R^{4D}$ is independently unsubstituted heteroalkyl. In embodiments, $R^{4D}$ is independently unsubstituted cycloalkyl. In embodiments, $R^{4D}$ is independently, unsubstituted heterocycloalkyl. In embodiments, $R^{4D}$ is independently unsubstituted aryl. In embodiments, $R^{4D}$ is independently unsubstituted heteroaryl. In embodiments, $R^{4D}$ is independently substituted or unsubstituted $C_1$-$C_8$ alkyl. In embodiments, $R^{4D}$ is independently substituted or unsubstituted 2 to 8 membered heteroalkyl. In embodiments, $R^{4D}$ is independently substituted or unsubstituted $C_3$-$C_8$ cycloalkyl. In embodiments, $R^{4D}$ is independently, substituted or unsubstituted 3 to 8 membered heterocycloalkyl. In embodiments, $R^{4D}$ is independently substituted or unsubstituted $C_6$-$C_{10}$ aryl. In embodiments, $R^{4D}$ is independently substituted or unsubstituted 5 to 10 membered heteroaryl. In embodiments, $R^{4D}$ is independently substituted $C_1$-$C_8$ alkyl. In embodiments, $R^{4D}$ is independently substituted 2 to 8 membered heteroalkyl. In embodiments, $R^{4D}$ is independently substituted $C_3$-$C_8$ cycloalkyl. In embodiments, $R^{4D}$ is independently, substituted 3 to 8 membered heterocycloalkyl. In embodiments, $R^{4D}$ is independently substituted $C_6$-$C_{10}$ aryl. In embodiments, $R^{4D}$ is independently substituted 5 to 10 membered heteroaryl. In embodiments, $R^{4D}$ is independently unsubstituted $C_1$-$C_8$ alkyl. In embodiments, $R^{4D}$ is independently unsubstituted 2 to 8 membered heteroalkyl. In embodiments, $R^{4D}$ is independently unsubstituted $C_3$-$C_8$ cycloalkyl. In embodiments, $R^{4D}$ is independently, unsubstituted 3 to 8 membered heterocycloalkyl. In embodiments, $R^{4D}$ is independently unsubstituted $C_6$-$C_{10}$ aryl. In embodiments, $R^{4D}$ is independently unsubstituted 5 to 10 membered heteroaryl. In embodiments, $R^{4D}$ is independently substituted or unsubstituted $C_1$-$C_4$ alkyl. In embodiments, $R^{4D}$ is independently substituted or unsubstituted 2 to 4 membered heteroalkyl. In embodiments, $R^{4D}$ is independently substituted or unsubstituted $C_3$-$C_6$ cycloalkyl. In embodiments, $R^{4D}$ is independently, substituted or unsubstituted 3 to 6 membered heterocycloalkyl. In embodiments, $R^{4D}$ is independently substituted or unsubstituted phenyl. In embodiments, $R^{4D}$ is independently substituted or unsubstituted 5 to 6 membered heteroaryl. In embodiments, $R^{4D}$ is independently substituted $C_1$-$C_4$ alkyl. In embodiments, $R^{4D}$ is independently substituted 2 to 4 membered heteroalkyl. In embodiments, $R^{4D}$ is independently substituted $C_3$-$C_6$ cycloalkyl. In embodiments, $R^{4D}$ is independently, substituted 3 to 6 membered heterocycloalkyl. In embodiments, $R^{4D}$ is independently substituted phenyl. In embodiments, $R^{4D}$ is independently substituted 5 to 6 membered heteroaryl. In embodiments, $R^{4D}$ is independently unsubstituted $C_1$-$C_4$ alkyl. In embodiments, $R^{4D}$ is independently unsubstituted 2 to 4 membered heteroalkyl. In embodiments, $R^{4D}$ is independently unsubstituted $C_3$-$C_6$ cycloalkyl. In embodiments, $R^{4D}$ is independently unsubstituted 3 to 6 membered heterocycloalkyl. In embodiments, $R^{4D}$ is independently unsubstituted phenyl. In embodiments, $R^{4D}$ is independently unsubstituted 5 to 6 membered heteroaryl. In embodiments, $R^{4D}$ is independently unsubstituted methyl. In embodiments, $R^{4D}$ is independently unsubstituted ethyl. In embodiments, $R^{4D}$ is independently unsubstituted propyl. In embodiments, $R^{4D}$ is independently unsubstituted isopropyl. In embodiments, $R^{4D}$ is independently unsubstituted tert-butyl.

In embodiments, $R^4$ is independently hydrogen, halogen, —$CX^4_3$, —$CHX^4_2$, —$CH_2X^4$, —$OCX^4_3$, —$OCH_2X^4$, —$OCHX^4_2$, —CN, —$SO_{n4}R^{4D}$, —$SO_{v4}NR^{4A}R^{4B}$, —$NHC(O)NR^{4A}R^{4B}$, —$N(O)_{m4}$, —$NR^{4A}R^{4B}$, —$C(O)R^{4C}$, —$C(O)OR^{4C}$, —$C(O)NR^{4A}R^{4B}$, —$OR^{4D}$, —$NR^{4A}SO_2R^{4D}$, —$NR^{4A}C(O)R^{4C}$, —$NR^{4A}C(O)OR^{4C}$, —$NR^{4A}OR^{4C}$, $R^{29}$-substituted or unsubstituted alkyl, $R^{29}$-substituted or unsubstituted heteroalkyl, $R^{29}$-substituted or unsubstituted cycloalkyl, $R^{29}$-substituted or unsubstituted heterocycloalkyl, $R^{29}$-substituted or unsubstituted aryl, or $R^{29}$-substituted or unsubstituted heteroaryl. In embodiments, $R^4$ is independently halogen, —$CX^4_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O) $NHNH_2$, —$NHC(O)NH_2$, —$NHSO_2H$, —NHC(O)H, —NHC(O)OH, —NHOH, —$OCX^4_3$, —$OCHX^4_2$, $R^{29}$-substituted or unsubstituted alkyl, $R^{29}$-substituted or unsubstituted heteroalkyl, $R^{29}$-substituted or unsubstituted cycloalkyl, $R^{29}$-substituted or unsubstituted heterocycloalkyl, $R^{29}$-substituted or unsubstituted aryl, or $R^{29}$-substituted or unsubstituted heteroaryl. In embodiments, $R^4$ is independently halogen, —$CX^4_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^4_3$, —$OCHX^4_2$, $R^{29}$-substituted or unsubstituted $C_1$-$C_8$ alkyl, $R^{29}$-substituted or unsubstituted 2 to 8 membered heteroalkyl, $R^{29}$-substituted or unsubstituted $C_3$-$C_8$ cycloalkyl, $R^{29}$-substituted or unsubstituted 3 to 6 membered heterocycloalkyl, $R^{29}$-substituted or unsubstituted phenyl, or $R^{29}$-substituted or unsubstituted 5 to 6 membered heteroaryl. $X^4$ is —F, —Cl, —Br, or —I. In embodiments, $R^4$ is independently hydrogen. In embodiments, $R^4$ is independently methyl. In embodiments, $R^4$ is independently ethyl.

$R^{29}$ is independently oxo, halogen, —$CX^{29}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{29}_3$, —$OCHX^{29}_2$, $R^{30}$-substituted or unsubstituted alkyl, $R^{30}$-substituted or unsubstituted heteroalkyl, $R^{30}$-substituted or unsubstituted cycloalkyl, $R^{30}$-substituted or unsubstituted heterocycloalkyl, $R^{30}$-substituted or unsubstituted aryl, or $R^{30}$-substituted or unsubstituted heteroaryl. In embodiments, $R^{29}$ is independently oxo, halogen, —$CX^{29}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{29}_3$, —$OCHX^{29}_2$, $R^{30}$-substituted or unsubstituted $C_1$-$C_8$ alkyl, $R^{30}$-substituted or unsubstituted 2 to 8 membered heteroalkyl, $R^{30}$-substituted or unsubstituted $C_3$-$C_8$ cycloalkyl, $R^{30}$-substituted or unsubstituted 3 to 6 membered heterocycloalkyl, $R^{30}$-substituted or unsubstituted phenyl, or $R^{30}$-substituted or unsubstituted 5 to 6 membered heteroaryl. $X^{29}$ is —F, —Cl, —Br, or —I.

$R^{30}$ is independently oxo, halogen, —$CX^{30}_3$, —CN, —OH, —$NH_2$, —COOH, —$CONH_2$, —$NO_2$, —SH, —$S_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{30}_3$, —$OCHX^{30}_2$, $R^{31}$-substituted or unsubstituted alkyl, $R^{31}$-substituted or unsubstituted heteroalkyl, $R^{31}$-substituted or unsubstituted cycloalkyl, $R^{31}$-substituted or unsubstituted heterocycloalkyl, $R^{31}$-substituted or unsubstituted aryl, or $R^{31}$-substituted or unsubstituted heteroaryl. In embodiments, $R^{30}$ is independently oxo, halogen, —$CX^{30}_3$, —CN, —OH, —$NH_2$, —COOH, —$CONH_2$, —$NO_2$, —SH, —$SO_3H$, —$SO_4H$, —$S_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{30}_3$, —$OCHX^{30}_2$, $R^{31}$-substituted or unsubstituted $C_1$-$C_8$ alkyl, $R^{31}$-substituted or unsubstituted 2 to 8 membered heteroalkyl, $R^{31}$-substituted or unsubstituted $C_3$-$C_8$ cycloalkyl, $R^{31}$-substituted or unsubstituted 3 to 6 membered heterocycloalkyl, $R^{31}$-substituted or unsubstituted phenyl, or $R^{31}$-substituted or unsubstituted 5 to 6 membered heteroaryl. $X^{30}$ is —F, —Cl, —Br, or —I.

In embodiments, $R^{4A}$ is independently hydrogen, —$CX^{4A}_3$, —CN, —COOH, —$CONH_2$, —$CHX^{4A}_2$, —$CH_2X^{4A}$, $R^{29A}$-substituted or unsubstituted alkyl, $R^{29A}$-substituted or unsubstituted heteroalkyl, $R^{29A}$-substituted or unsubstituted cycloalkyl, $R^{29A}$-substituted or unsubstituted heterocycloalkyl, $R^{29A}$-substituted or unsubstituted aryl, or $R^{29A}$-substituted or unsubstituted heteroaryl. In embodiments, $R^{4A}$ is independently hydrogen, —$CX^{4A}_3$, —CN, —COOH, —$CONH_2$, —$CHX^{4A}_2$, —$CH_2X^{4A}$, $R^{29A}$-substituted or unsubstituted $C_1$-$C_8$ alkyl, $R^{29A}$-substituted or unsubstituted 2 to 8 membered heteroalkyl, $R^{29A}$-substituted or unsubstituted $C_3$-$C_8$ cycloalkyl, $R^{29A}$-substituted or unsubstituted 3 to 6 membered heterocycloalkyl, $R^{29A}$-substituted or unsubstituted phenyl, or $R^{29A}$-substituted or unsubstituted 5 to 6 membered heteroaryl. $X^{4A}$ is —F, —Cl, —Br, or —I. In embodiments, $R^{4A}$ is independently hydrogen. In embodiments, $R^{4A}$ is independently methyl. In embodiments, $R^{4A}$ is independently ethyl.

In embodiments, $R^{4A}$ and $R^{4B}$ substituents bonded to the same nitrogen atom may optionally be joined to form a $R^{29A}$-substituted or unsubstituted heterocycloalkyl or $R^{29A}$-substituted or unsubstituted heteroaryl. In embodiments, $R^{4A}$ and $R^{4B}$ substituents bonded to the same nitrogen atom may optionally be joined to form a $R^{29A}$-substituted or unsubstituted 3 to 6 membered heterocycloalkyl or $R^{29A}$-substituted or unsubstituted 5 to 6 membered heteroaryl.

$R^{29A}$ is independently oxo, halogen, —$CX^{29A}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{29A}_3$, —$OCHX^{29A}_2$, $R^{30A}$-substituted or unsubstituted alkyl, $R^{30A}$-substituted or unsubstituted heteroalkyl, $R^{30A}$-substituted or unsubstituted cycloalkyl, $R^{30A}$-substituted or unsubstituted heterocycloalkyl, $R^{30A}$-substituted or unsubstituted aryl, or $R^{30A}$-substituted or unsubstituted heteroaryl. In embodiments, $R^{29A}$ is independently oxo, halogen, —$CX^{29A}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{29A}_3$, —$OCHX^{29A}_2$, $R^{30A}$-substituted or unsubstituted $C_1$-$C_8$ alkyl, $R^{3A}$-substituted or unsubstituted 2 to 8 membered heteroalkyl, $R^{3A}$-substituted or unsubstituted $C_3$-$C_8$ cycloalkyl, $R^{30A}$-substituted or unsubstituted 3 to 6 membered heterocycloalkyl, $R^{30A}$-substituted or unsubstituted phenyl, or $R^{30A}$-substituted or unsubstituted 5 to 6 membered heteroaryl. $X^{29A}$ is —F, —Cl, —Br, or —I.

$R^{30A}$ is independently oxo, halogen, —$CX^{30A}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{30A}_3$, —$OCHX^{30A}_2$, $R^{31A}$-substituted or unsubstituted alkyl, $R^{31A}$-substituted or unsubstituted heteroalkyl, $R^{31A}$-substituted or unsubstituted cycloalkyl, $R^{31A}$-substituted or unsubstituted heterocycloalkyl, $R^{31A}$-substituted or unsubstituted aryl, or $R^{31A}$-substituted or unsubstituted heteroaryl. In embodiments, $R^{30A}$ is independently oxo, halogen, —$CX^{30A}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{30A}_3$, —$OCHX^{30A}_2$, $R^{30A}$-substituted or unsubstituted $C_1$-$C_8$ alkyl, $R^{31A}$-substituted or unsubstituted 2 to 8 membered heteroalkyl, $R^{31A}$-substituted or unsubstituted $C_3$-$C_8$ cycloalkyl, $R^{31A}$-substituted or unsubstituted 3 to 6 membered heterocycloalkyl, $R^{31A}$-substituted or unsubstituted phenyl, or $R^{31A}$-substituted or unsubstituted 5 to 6 membered heteroaryl. $X^{30A}$ is —F, —Cl, —Br, or —I.

In embodiments, $R^{4B}$ is independently hydrogen, —$CX^{4B}_3$, —CN, —COOH, —$CONH_2$, —$CHX^{4B}_2$, —$CH_2X^{4B}$, $R^{29B}$-substituted or unsubstituted alkyl, $R^{29B}$-substituted or unsubstituted heteroalkyl, $R^{29B}$-substituted or unsubstituted cycloalkyl, $R^{29B}$-substituted or unsubstituted heterocycloalkyl, $R^{29B}$-substituted or unsubstituted aryl, or $R^{29B}$-substituted or unsubstituted heteroaryl. In embodiments, $R^{4B}$ is independently hydrogen, —$CX^{4B}_3$, —CN, —COOH, —$CONH_2$, —$CHX^{4B}_2$, —$CH_2X^{4B}$, $R^{29B}$-substituted or unsubstituted $C_1$-$C_8$ alkyl, $R^{29B}$-substituted or unsubstituted 2 to 8 membered heteroalkyl, $R^{29B}$-substituted or unsubstituted $C_3$-$C_8$ cycloalkyl, $R^{29B}$-substituted or unsubstituted 3 to 6 membered heterocycloalkyl, $R^{29B}$-substituted or unsubstituted phenyl, or $R^{29B}$-substituted or unsubstituted 5 to 6 membered heteroaryl. $X^{4B}$ is —F, —Cl, —Br, or —I. In embodiments, $R^{4B}$ is independently hydrogen. In embodiments, $R^{4B}$ is independently methyl. In embodiments, $R^{4B}$ is independently ethyl.

In embodiments, $R^{4A}$ and $R^{4B}$ substituents bonded to the same nitrogen atom may optionally be joined to form a $R^{29B}$-substituted or unsubstituted heterocycloalkyl or $R^{29B}$-substituted or unsubstituted heteroaryl. In embodiments, $R^{4A}$ and $R^{4B}$ substituents bonded to the same nitrogen atom may optionally be joined to form a $R^{29B}$-substituted or unsubstituted 3 to 6 membered heterocycloalkyl or $R^{29B}$-substituted or unsubstituted 5 to 6 membered heteroaryl.

$R^{29B}$ is independently oxo, halogen, —$CX^{29B}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{29B}_3$, —$OCHX^{29B}_2$, $R^{30B}$-substituted or unsubstituted alkyl, $R^{30B}$-substituted or unsubstituted heteroalkyl, $R^{30B}$-substituted or unsubstituted cycloalkyl, $R^{30B}$-substituted or unsubstituted heterocycloalkyl, $R^{30B}$-substituted or unsubstituted aryl, or $R^{30B}$-substituted or unsubstituted heteroaryl. In embodiments, $R^{29B}$ is independently oxo, halogen, —$CX^{29B}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{29B}_3$, —$OCHX^{29B}_2$, $R^{30B}$-substituted or unsubstituted $C_1$-$C_8$ alkyl, $R^{30B}$-substituted or unsubstituted 2 to 8 membered heteroalkyl, $R^{30B}$-substituted or unsubstituted $C_3$-$C_8$ cycloalkyl, $R^{30B}$-substituted or unsubstituted 3 to 6 membered heterocycloalkyl, $R^{30B}$-substituted or unsubstituted phenyl, or $R^{30B}$-substituted or unsubstituted 5 to 6 membered heteroaryl. $X^{29B}$ is —F, —Cl, —Br, or —I.

$R^{30B}$ is independently oxo, halogen, —$CX^{30B}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{30B}_3$, —$OCHX^{30B}_2$, $R^{31B}$-substituted or unsubstituted alkyl, $R^{31B}$-substituted or unsubstituted heteroalkyl, $R^{31B}$-substituted or unsubstituted cycloalkyl, $R^{31B}$-substituted or unsubstituted heterocycloalkyl, $R^{31B}$-substituted or unsubstituted aryl, or $R^{31B}$-substituted or unsubstituted heteroaryl. In embodiments, $R^{30B}$ is independently oxo, halogen, —$CX^{30B}_3$, —CN, —OH, —$NH_2$, —COOH, —$CONH_2$, —$NO_2$, —SH, —$SO_3H$, —$SO_4H$, —$S_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{30B}_3$, —$OCHX^{30B}_2$, $R^{31B}$-substituted or unsubstituted $C_1$-$C_8$ alkyl, $R^{31B}$-substituted or unsubstituted 2 to 8 membered heteroalkyl, $R^{31B}$-substituted or unsubstituted $C_3$-$C_8$ cycloalkyl, $R^{31B}$-substituted or unsubstituted 3 to 6 membered heterocycloalkyl, $R^{31B}$-substituted or unsubstituted phenyl, or $R^{31B}$-substituted or unsubstituted 5 to 6 membered heteroaryl. $X^{30B}$ is —F, —Cl, —Br, or —I.

In embodiments, $R^{4C}$ is independently hydrogen, —$CX^{4C}_3$, —CN, —COOH, —$CONH_2$, —$CHX^{42}$, —$CH_2X^{4C}$, $R^{29C}$-substituted or unsubstituted alkyl, $R^{29C}$-substituted or unsubstituted heteroalkyl, $R^{29C}$-substituted or unsubstituted cycloalkyl, $R^{29C}$-substituted or unsubstituted heterocycloalkyl, $R^{29C}$-substituted or unsubstituted aryl, or $R^{29C}$-substituted or unsubstituted heteroaryl. In embodiments, $R^{4C}$ is independently hydrogen, —$CX^{4C}_3$, —CN, —COOH, —CONH$_2$, —CHX$^{4C}_2$, —CH$_2$X$^{4C}$, $R^{29C}$-substituted or unsubstituted C$_1$-C$_8$ alkyl, $R^{29C}$-substituted or unsubstituted 2 to 8 membered heteroalkyl, $R^{29C}$-substituted or unsubstituted C$_3$-C$_8$ cycloalkyl, $R^{29C}$-substituted or unsubstituted 3 to 6 membered heterocycloalkyl, $R^{29C}$-substituted or unsubstituted phenyl, or $R^{29C}$-substituted or unsubstituted 5 to 6 membered heteroaryl. $X^{4C}$ is —F, —Cl, —Br, or —I. In embodiments, $R^{4C}$ is independently hydrogen. In embodiments, $R^{4C}$ is independently methyl. In embodiments, $R^{4C}$ is independently ethyl.

$R^{29C}$ is independently oxo, halogen, —CX$^{29C}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{29C}_3$, —OCHX$^{29C}_2$, $R^{30C}$-substituted or unsubstituted alkyl, $R^{30C}$-substituted or unsubstituted heteroalkyl, $R^{30C}$-substituted or unsubstituted cycloalkyl, $R^{30C}$-substituted or unsubstituted heterocycloalkyl, $R^{30C}$-substituted or unsubstituted aryl, or $R^{30C}$-substituted or unsubstituted heteroaryl. In embodiments, $R^{29C}$ is independently oxo, halogen, —CX$^{29C}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{29C}_3$, —OCHX$^{29C}_2$, $R^{30C}$ substituted or unsubstituted C$_1$-C$_8$ alkyl, $R^{30C}$-substituted or unsubstituted 2 to 8 membered heteroalkyl, $R^{30C}$-substituted or unsubstituted C$_3$-C$_8$ cycloalkyl, $R^{30C}$-substituted or unsubstituted 3 to 6 membered heterocycloalkyl, $R^{30C}$-substituted or unsubstituted phenyl, or $R^{30C}$-substituted or unsubstituted 5 to 6 membered heteroaryl. $X^{29C}$ is —F, —Cl, —Br, or —I.

$R^{30C}$ is independently oxo, halogen, —CX$^{30C}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{30C}_3$, —OCHX$^{30C}_2$, $R^{31C}$-substituted or unsubstituted alkyl, $R^{31C}$-substituted or unsubstituted heteroalkyl, $R^{31C}$-substituted or unsubstituted cycloalkyl, $R^{31C}$-substituted or unsubstituted heterocycloalkyl, $R^{31C}$-substituted or unsubstituted aryl, or $R^{31C}$-substituted or unsubstituted heteroaryl. In embodiments, $R^{31C}$ is independently oxo, halogen, —CX$^{30C}_3$, —CN, —OH, —NH$_2$, —COOH, —CONH$_2$, —NO$_2$, —SH, —S$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{30C}_3$, —OCHX$^{30C}_2$, $R^{31C}$-substituted or unsubstituted C$_1$-C$_8$ alkyl, $R^{31C}$ substituted or unsubstituted 2 to 8 membered heteroalkyl, $R^{31C}$-substituted or unsubstituted C$_3$-C$_8$ cycloalkyl, $R^{31C}$-substituted or unsubstituted 3 to 6 membered heterocycloalkyl, $R^{31C}$-substituted or unsubstituted phenyl, or $R^{31C}$-substituted or unsubstituted 5 to 6 membered heteroaryl. $X^{30C}$ is —F, —Cl, —Br, or —I.

In embodiments, $R^{4D}$ is independently hydrogen, —CX$^{4D}_3$, —CN, —COOH, —CONH$_2$, —CHX$^{4D}_2$, —CH$_2$X$^{4D}$, $R^{29D}$-substituted or unsubstituted alkyl, $R^{29D}$-substituted or unsubstituted heteroalkyl, $R^{29D}$-substituted or unsubstituted cycloalkyl, $R^{29D}$-substituted or unsubstituted heterocycloalkyl, $R^{29D}$-substituted or unsubstituted aryl, or $R^{29D}$-substituted or unsubstituted heteroaryl. In embodiments, $R^{4D}$ is independently hydrogen, —CX$^{4D}_3$, —CN, —COOH, —CONH$_2$, —CHX$^{4D}_2$, —CH$_2$X$^{4D}$, $R^{29D}$-substituted or unsubstituted C$_1$-C$_8$ alkyl, $R^{29D}$-substituted or unsubstituted 2 to 8 membered heteroalkyl, $R^{29D}$-substituted or unsubstituted C$_3$-C$_8$ cycloalkyl, $R^{29D}$-substituted or unsubstituted 3 to 6 membered heterocycloalkyl, $R^{29D}$-substituted or unsubstituted phenyl, or $R^{29D}$-substituted or unsubstituted 5 to 6 membered heteroaryl. $X^{4D}$ is —F, —Cl, —Br, or —I. In embodiments, $R^{4D}$ is independently hydrogen. In embodiments, $R^{4D}$ is independently methyl. In embodiments, $R^{4D}$ is independently ethyl.

$R^{29D}$ is independently oxo, halogen, —CX$^{29D}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{29D}_3$, —OCHX$^{29D}_2$, $R^{30D}$-substituted or unsubstituted alkyl, $R^{30D}$-substituted or unsubstituted heteroalkyl, $R^{30D}$-substituted or unsubstituted cycloalkyl, $R^{30D}$-substituted or unsubstituted heterocycloalkyl, $R^{30D}$-substituted or unsubstituted aryl, or $R^{30D}$-substituted or unsubstituted heteroaryl. In embodiments, $R^{29D}$ is independently oxo, halogen, —CX$^{29D}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{29D}_3$, —OCHX$^{29D}_2$, $R^{30D}$-substituted or unsubstituted C$_1$-C$_8$ alkyl, $R^{30D}$-substituted or unsubstituted 2 to 8 membered heteroalkyl, $R^{30D}$-substituted or unsubstituted C$_3$-C$_8$ cycloalkyl, $R^{30D}$-substituted or unsubstituted 3 to 6 membered heterocycloalkyl, $R^{30D}$-substituted or unsubstituted phenyl, or $R^{30D}$-substituted or unsubstituted 5 to 6 membered heteroaryl. $X^{29D}$ is —F, —Cl, —Br, or —I.

$R^{30D}$ is independently oxo, halogen, —CX$^{30D}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{30D}_3$, —OCHX$^{30D}_2$, $R^{31D}$-substituted or unsubstituted alkyl, $R^{31D}$-substituted or unsubstituted heteroalkyl, $R^{31D}$-substituted or unsubstituted cycloalkyl, $R^{31D}$-substituted or unsubstituted heterocycloalkyl, $R^{31D}$-substituted or unsubstituted aryl, or $R^{31D}$-substituted or unsubstituted heteroaryl. In embodiments, $R^{30D}$ is independently oxo, halogen, —CX$^{30D}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{30D}_3$, —OCHX$^{30D}_2$, $R^{31D}$-substituted or unsubstituted C$_1$-C$_8$ alkyl, $R^{31D}$-substituted or unsubstituted 2 to 8 membered heteroalkyl, $R^{31D}$-substituted or unsubstituted C$_3$-C$_8$ cycloalkyl, $R^{31D}$-substituted or unsubstituted 3 to 6 membered heterocycloalkyl, $R^{31D}$-substituted or unsubstituted phenyl, or $R^{31D}$-substituted or unsubstituted 5 to 6 membered heteroaryl. $X^{30D}$ is —F, —Cl, —Br, or —I.

$R^{31}$, $R^{31A}$, $R^{31B}$, $R^{31C}$, and $R^{31D}$ are independently hydrogen, oxo, halogen, —CCl$_3$, —CBr$_3$, —CF$_3$, —Cl$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCl$_3$, —OCHCl$_2$, —OCHBr$_2$, —OCHI$_2$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{31}$, $R^{31A}$, $R^{31B}$, $R^{31C}$, and $R^{31D}$ are independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{31}$, $R^{31A}$, $R^{31B}$, $R^{31C}$, and $R^{31D}$ are independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCHF$_2$, unsubstituted $C_1$-$C_8$ alkyl, unsubstituted 2 to 8 membered heteroalkyl, unsubstituted $C_3$-$C_8$ cycloalkyl, unsubstituted 3 to 6 membered heterocycloalkyl, unsubstituted phenyl, or unsubstituted 5 to 6 membered heteroaryl.

In embodiments, the symbol $Y^2$ is N. In embodiments, the symbol $Y^2$ is C($R^5$).

In embodiments, $R^5$ is hydrogen, substituted or unsubstituted $C_1$-$C_8$ alkyl, or substituted or unsubstituted 2 to 8 membered heteroalkyl.

In embodiments, $R^5$ is independently hydrogen. In embodiments, $R^5$ is independently halogen. In embodiments, $R^5$ is independently —CX$^5_3$. In embodiments, $R^5$ is independently —CHX$^5_2$. In embodiments, $R^5$ is independently —CH$_2$X$^5$. In embodiments, $R^5$ is independently —OCX$^{53}$. In embodiments, $R^5$ is independently —OCH$_2$X$^5$. In embodiments, $R^5$ is independently —OCHX$^5_2$. In embodiments, $R^5$ is independently —CN. In embodiments, $R^5$ is independently —SO$_n$R$^{5D}$. In embodiments, $R^5$ is independently —SO$_{v5}$NR$^{5A}$R$^{5B}$. In embodiments, $R^5$ is independently —NHC(O)NR$^{5A}$R$^{5B}$. In embodiments, $R^5$ is independently —N(O)$_{m5}$. In embodiments, $R^5$ is independently —NR$^{5A}$R$^{5B}$. In embodiments, $R^5$ is independently —C(O)R$^{5C}$. In embodiments, $R^5$ is independently —C(O)—OR$^{5C}$. In embodiments, $R^5$ is independently —C(O)NR$^{5A}$R$^{5B}$. In embodiments, $R^5$ is independently —OR$^{5D}$. In embodiments, $R^5$ is independently —NR$^{5A}$SO$_2$R$^{5D}$. In embodiments, $R^5$ is independently —NR$^{5A}$C(O)R$^{5C}$. In embodiments, $R^5$ is independently —NR$^{5A}$C(O)OR$^{5C}$. In embodiments, $R^5$ is independently —NR$^{5A}$OR$^{5C}$. In embodiments, $R^5$ is independently —OH. In embodiments, $R^5$ is independently —NH$_2$. In embodiments, $R^5$ is independently —COOH. In embodiments, $R^5$ is independently —CONH$_2$. In embodiments, $R^5$ is independently —NO$_2$. In embodiments, $R^5$ is independently —SH. In embodiments, $R^5$ is independently —F.

In embodiments, $R^5$ is independently substituted or unsubstituted alkyl. In embodiments, $R^5$ is independently substituted or unsubstituted heteroalkyl. In embodiments, $R^5$ is independently substituted or unsubstituted cycloalkyl. In embodiments, $R^5$ is independently, substituted or unsubstituted heterocycloalkyl. In embodiments, $R^5$ is independently substituted or unsubstituted aryl. In embodiments, $R^5$ is independently substituted or unsubstituted heteroaryl. In embodiments, $R^5$ is independently substituted alkyl. In embodiments, $R^5$ is independently substituted heteroalkyl. In embodiments, $R^5$ is independently substituted cycloalkyl. In embodiments, $R^5$ is independently, substituted heterocycloalkyl. In embodiments, $R^5$ is independently substituted aryl. In embodiments, $R^5$ is independently substituted heteroaryl. In embodiments, $R^5$ is independently unsubstituted alkyl. In embodiments, $R^5$ is independently unsubstituted heteroalkyl. In embodiments, $R^5$ is independently unsubstituted cycloalkyl. In embodiments, $R^5$ is independently, unsubstituted heterocycloalkyl. In embodiments, $R^5$ is independently unsubstituted aryl. In embodiments, $R^5$ is independently unsubstituted heteroaryl. In embodiments, $R^5$ is independently substituted or unsubstituted $C_1$-$C_8$ alkyl. In embodiments, $R^5$ is independently substituted or unsubstituted 2 to 8 membered heteroalkyl. In embodiments, $R^5$ is independently substituted or unsubstituted $C_3$-$C_8$ cycloalkyl. In embodiments, $R^5$ is independently, substituted or unsubstituted 3 to 8 membered heterocycloalkyl. In embodiments, $R^5$ is independently substituted or unsubstituted $C_6$-$C_{10}$ aryl. In embodiments, $R^5$ is independently substituted or unsubstituted 5 to 10 membered heteroaryl. In embodiments, $R^5$ is independently substituted $C_1$-$C_8$ alkyl. In embodiments, $R^5$ is independently substituted 2 to 8 membered heteroalkyl. In embodiments, $R^5$ is independently substituted $C_3$-$C_8$ cycloalkyl. In embodiments, $R^5$ is independently, substituted 3 to 8 membered heterocycloalkyl. In embodiments, $R^5$ is independently substituted $C_6$-$C_{10}$ aryl. In embodiments, $R^5$ is independently substituted 5 to 10 membered heteroaryl. In embodiments, $R^5$ is independently unsubstituted $C_1$-$C_8$ alkyl. In embodiments, $R^5$ is independently unsubstituted 2 to 8 membered heteroalkyl. In embodiments, $R^5$ is independently unsubstituted $C_3$-$C_8$ cycloalkyl. In embodiments, $R^5$ is independently, unsubstituted 3 to 8 membered heterocycloalkyl. In embodiments, $R^5$ is independently unsubstituted $C_6$-$C_{10}$ aryl. In embodiments, $R^5$ is independently unsubstituted 5 to 10 membered heteroaryl. In embodiments, $R^5$ is independently substituted or unsubstituted $C_1$-$C_4$ alkyl. In embodiments, $R^5$ is independently substituted or unsubstituted 2 to 4 membered heteroalkyl. In embodiments, $R^5$ is independently substituted or unsubstituted $C_3$-$C_6$ cycloalkyl. In embodiments, $R^5$ is independently, substituted or unsubstituted 3 to 6 membered heterocycloalkyl. In embodiments, $R^5$ is independently substituted or unsubstituted phenyl. In embodiments, $R^5$ is independently substituted or unsubstituted 5 to 6 membered heteroaryl. In embodiments, $R^5$ is independently substituted $C_1$-$C_4$ alkyl. In embodiments, $R^5$ is independently substituted 2 to 4 membered heteroalkyl. In embodiments, $R^5$ is independently substituted $C_3$-$C_6$ cycloalkyl. In embodiments, $R^5$ is independently, substituted 3 to 6 membered heterocycloalkyl. In embodiments, $R^5$ is independently substituted phenyl. In embodiments, $R^5$ is independently substituted 5 to 6 membered heteroaryl. In embodiments, $R^5$ is independently unsubstituted $C_1$-$C_4$ alkyl. In embodiments, $R^5$ is independently unsubstituted 2 to 4 membered heteroalkyl. In embodiments, $R^5$ is independently unsubstituted $C_3$-$C_6$ cycloalkyl. In embodiments, $R^5$ is independently unsubstituted 3 to 6 membered heterocycloalkyl. In embodiments, $R^5$ is independently unsubstituted phenyl. In embodiments, $R^5$ is independently unsubstituted 5 to 6 membered heteroaryl.

In embodiments, $R^{5A}$ is independently hydrogen. In embodiments, $R^{5A}$ is independently —CX$^{5A}_3$. In embodiments, $R^{5A}$ is independently —CHX$^{5A}_2$. In embodiments, $R^{5A}$ is independently —CH$_2$X$^{5A}$. In embodiments, $R^{5A}$ is independently —CN. In embodiments, $R^{5A}$ is independently —COOH. In embodiments, $R^{5A}$ is independently —CONH$_2$. In embodiments, $R^{5A}$ is independently substituted or unsubstituted alkyl. In embodiments, $R^{5A}$ is independently substituted or unsubstituted heteroalkyl. In embodiments, $R^{5A}$ is independently substituted or unsubstituted cycloalkyl. In embodiments, $R^{5A}$ is independently, substituted or unsubstituted heterocycloalkyl. In embodiments, $R^{5A}$ is independently substituted or unsubstituted aryl. In embodiments, $R^{5A}$ is independently substituted or unsubstituted heteroaryl. In embodiments, $R^{5A}$ is independently substituted alkyl. In embodiments, $R^{5A}$ is independently substituted heteroalkyl. In embodiments, $R^{5A}$ is independently substituted cycloalkyl. In embodiments, $R^{5A}$ is independently, substituted heterocycloalkyl. In embodiments, $R^{5A}$ is independently substituted aryl. In embodiments, $R^{5A}$ is independently substituted heteroaryl. In embodiments, $R^{5A}$ is independently unsubstituted alkyl. In embodiments, $R^{5A}$ is independently unsubstituted heteroalkyl. In embodiments, $R^{5A}$ is independently unsubstituted cycloalkyl. In embodiments, $R^{5A}$ is independently, unsubstituted heterocycloalkyl. In embodiments, $R^{5A}$ is independently unsubstituted aryl. In embodiments, $R^{5A}$ is independently unsubstituted heteroaryl. In embodiments, $R^{5A}$ is independently substituted or unsubstituted $C_1$-$C_8$ alkyl. In embodiments, $R^{5A}$ is independently substituted or unsubstituted 2 to 8 membered heteroalkyl. In embodiments, $R^{5A}$ is independently substituted or unsubstituted $C_3$-$C_8$ cycloalkyl. In embodiments, $R^{5A}$ is independently, substituted or unsubstituted 3 to 8 membered heterocycloalkyl. In embodiments, $R^{5A}$ is independently substituted or unsubstituted $C_6$-$C_{10}$ aryl. In embodiments, $R^{5A}$ is independently substituted or unsubstituted 5 to 10 membered heteroaryl. In embodiments, $R^{5A}$ is independently substituted $C_1$-$C_8$ alkyl. In embodiments, $R^{5A}$ is independently substituted 2 to 8 membered heteroalkyl. In embodiments, $R^{5A}$ is independently substituted $C_3$-$C_8$ cycloalkyl. In embodiments, $R^{5A}$ is independently, substituted 3 to 8 membered heterocycloalkyl. In embodiments, $R^{5A}$ is independently substituted $C_6$-$C_{10}$ aryl. In embodiments, $R^{5A}$ is independently substituted 5 to 10 membered heteroaryl. In embodiments, $R^{5A}$ is independently unsubstituted $C_1$-$C_8$ alkyl. In embodiments, $R^{5A}$ is independently unsubstituted 2 to 8 membered heteroalkyl. In embodiments, $R^{5A}$ is independently unsubstituted $C_3$-$C_8$ cycloalkyl. In embodiments, $R^{5A}$ is independently, unsubstituted 3 to 8 membered heterocycloalkyl. In embodiments, $R^{5A}$ is independently unsubstituted $C_6$-$C_{10}$ aryl. In embodiments, $R^{5A}$ is independently unsubstituted 5 to 10 membered heteroaryl. In embodiments, $R^{5A}$ is independently substituted or unsubstituted $C_1$-$C_4$ alkyl. In embodiments, $R^{5A}$ is independently substituted or unsubstituted 2 to 4 membered heteroalkyl. In embodiments, $R^{5A}$ is independently substituted or unsubstituted $C_3$-$C_6$ cycloalkyl. In embodiments, $R^{5A}$ is independently, substituted or unsubstituted 3 to 6 membered heterocycloalkyl. In embodiments, $R^{5A}$ is independently substituted or unsubstituted phenyl. In embodiments, $R^{5A}$ is independently substituted or unsubstituted 5 to 6 membered heteroaryl. In embodiments, $R^{5A}$ is independently substituted $C_1$-$C_4$ alkyl. In embodiments, $R^{5A}$ is independently substituted 2 to 4 membered heteroalkyl. In embodiments, $R^{5A}$ is independently substituted $C_3$-$C_6$ cycloalkyl. In embodiments, $R^{5A}$ is independently, substituted 3 to 6 membered heterocycloalkyl. In embodiments, $R^{5A}$ is independently substituted phenyl. In embodiments, $R^{5A}$ is independently substituted 5 to 6 membered heteroaryl. In embodiments, $R^{5A}$ is independently unsubstituted $C_1$-$C_4$ alkyl. In embodiments, $R^{5A}$ is independently unsubstituted 2 to 4 membered heteroalkyl. In embodiments, $R^{5A}$ is independently unsubstituted $C_3$-$C_6$ cycloalkyl. In embodiments, $R^{5A}$ is independently unsubstituted 3 to 6 membered heterocycloalkyl. In embodiments, $R^{5A}$ is independently unsubstituted phenyl. In embodiments, $R^{5A}$ is independently unsubstituted 5 to 6 membered heteroaryl. In embodiments, $R^{5A}$ is independently unsubstituted methyl. In embodiments, $R^{5A}$ is independently unsubstituted ethyl. In embodiments, $R^{5A}$ is independently unsubstituted propyl. In embodiments, $R^{5A}$ is independently unsubstituted isopropyl. In embodiments, $R^{5A}$ is independently unsubstituted tert-butyl.

In embodiments, $R^{5B}$ is independently hydrogen. In embodiments, $R^{5B}$ is independently —$CX^{5B}_3$. In embodiments, $R^{5B}$ is independently —$CHX^{5B2}$. In embodiments, $R^{5B}$ is independently —$CH_2X^{5B}$. In embodiments, $R^{5B}$ is independently —CN. In embodiments, $R^{5B}$ is independently —COOH. In embodiments, $R^{5B}$ is independently —$CONH_2$. In embodiments, $R^{5B}$ is independently substituted or unsubstituted alkyl. In embodiments, $R^{5B}$ is independently substituted or unsubstituted heteroalkyl. In embodiments, $R^{5B}$ is independently substituted or unsubstituted cycloalkyl. In embodiments, $R^{5B}$ is independently, substituted or unsubstituted heterocycloalkyl. In embodiments, $R^{5B}$ is independently substituted or unsubstituted aryl. In embodiments, $R^{5B}$ is independently substituted or unsubstituted heteroaryl. In embodiments, $R^{5B}$ is independently substituted alkyl. In embodiments, $R^{5B}$ is independently substituted heteroalkyl. In embodiments, $R^{5B}$ is independently substituted cycloalkyl. In embodiments, $R^{5B}$ is independently, substituted heterocycloalkyl. In embodiments, $R^{5B}$ is independently substituted aryl. In embodiments, $R^{5B}$ is independently substituted heteroaryl. In embodiments, $R^{5B}$ is independently unsubstituted alkyl. In embodiments, $R^{5B}$ is independently unsubstituted heteroalkyl. In embodiments, $R^{5B}$ is independently unsubstituted cycloalkyl. In embodiments, $R^{5B}$ is independently, unsubstituted heterocycloalkyl. In embodiments, $R^{5B}$ is independently unsubstituted aryl. In embodiments, $R^{5B}$ is independently unsubstituted heteroaryl. In embodiments, $R^{5B}$ is independently substituted or unsubstituted $C_1$-$C_8$ alkyl. In embodiments, $R^{5B}$ is independently substituted or unsubstituted 2 to 8 membered heteroalkyl. In embodiments, $R^{5B}$ is independently substituted or unsubstituted $C_3$-$C_8$ cycloalkyl. In embodiments, $R^{5B}$ is independently, substituted or unsubstituted 3 to 8 membered heterocycloalkyl. In embodiments, $R^{5B}$ is independently substituted or unsubstituted $C_6$-$C_{10}$ aryl. In embodiments, $R^{5B}$ is independently substituted or unsubstituted 5 to 10 membered heteroaryl. In embodiments, $R^{5B}$ is independently substituted $C_1$-$C_8$ alkyl. In embodiments, $R^{5B}$ is independently substituted 2 to 8 membered heteroalkyl. In embodiments, $R^{5B}$ is independently substituted $C_3$-$C_8$ cycloalkyl. In embodiments, $R^{5B}$ is independently, substituted 3 to 8 membered heterocycloalkyl. In embodiments, $R^{5B}$ is independently substituted $C_6$-$C_{10}$ aryl. In embodiments, $R^{5B}$ is independently substituted 5 to 10 membered heteroaryl. In embodiments, $R^{5B}$ is independently unsubstituted $C_1$-$C_8$ alkyl. In embodiments, $R^{5B}$ is independently unsubstituted 2 to 8 membered heteroalkyl. In embodiments, $R^{5B}$ is independently unsubstituted $C_3$-$C_8$ cycloalkyl. In embodiments, $R^{5B}$ is independently, unsubstituted 3 to 8 membered heterocycloalkyl. In embodiments, $R^{5B}$ is independently unsubstituted $C_6$-$C_{10}$ aryl. In embodiments, $R^{5B}$ is independently unsubstituted 5 to 10 membered heteroaryl. In embodiments, $R^{5B}$ is independently substituted or unsubstituted $C_1$-$C_4$ alkyl. In embodiments, $R^{5B}$ is independently substituted or unsubstituted 2 to 4 membered heteroalkyl. In embodiments, $R^{5B}$ is independently substituted or unsubstituted $C_3$-$C_6$ cycloalkyl. In embodiments, $R^{5B}$ is independently, substituted or unsubstituted 3 to 6 membered heterocycloalkyl. In embodiments, $R^{5B}$ is independently substituted or unsubstituted phenyl. In embodiments, $R^{5B}$ is independently substituted or unsubstituted 5 to 6 membered heteroaryl. In embodiments, $R^{5B}$ is independently substituted $C_1$-$C_4$ alkyl. In embodiments, $R^{5B}$ is independently substituted 2 to 4 membered heteroalkyl. In embodiments, $R^{5B}$ is independently substituted $C_3$-$C_6$ cycloalkyl. In embodiments, $R^{5B}$ is independently, substituted 3 to 6 membered heterocycloalkyl. In embodiments, $R^{5B}$ is independently substituted phenyl. In embodiments, $R^{5B}$ is independently substituted 5 to 6 membered heteroaryl. In embodiments, $R^{5B}$ is independently unsubstituted $C_1$-$C_4$ alkyl. In embodiments, $R^{5B}$ is independently unsubstituted 2 to 4 membered heteroalkyl. In embodiments, $R^{5B}$ is independently unsubstituted $C_3$-$C_6$ cycloalkyl. In embodiments, $R^{5B}$ is independently unsubstituted 3 to 6 membered heterocycloalkyl. In embodiments, $R^{5B}$ is independently unsubstituted phenyl. In embodiments, $R^{5B}$ is independently unsubstituted 5 to 6 membered heteroaryl. In embodiments, $R^{5B}$ is independently unsubstituted methyl. In embodiments, $R^{5B}$ is independently unsubstituted ethyl. In embodiments, $R^{5B}$ is independently unsubstituted propyl. In embodiments, $R^{5B}$ is independently unsubstituted isopropyl. In embodiments, $R^{5B}$ is independently unsubstituted tert-butyl.

In embodiments, $R^{5A}$ and $R^{5B}$ substituents bonded to the same nitrogen atom may be joined to form a substituted or unsubstituted heterocycloalkyl. In embodiments, $R^{5A}$ and $R^{5B}$ substituents bonded to the same nitrogen atom may be joined to form a substituted or unsubstituted heteroaryl. In embodiments, $R^{5A}$ and $R^{5B}$ substituents bonded to the same nitrogen atom may be joined to form a substituted heterocycloalkyl. In embodiments, $R^{5A}$ and $R^{5B}$ substituents bonded to the same nitrogen atom may be joined to form a substituted heteroaryl. In embodiments, $R^{5A}$ and $R^{5B}$ substituents bonded to the same nitrogen atom may be joined to form an unsubstituted heterocycloalkyl. In embodiments, $R^{5A}$ and $R^{5B}$ substituents bonded to the same nitrogen atom may be joined to form an unsubstituted heteroaryl. In embodiments, $R^{5A}$ and $R^{5B}$ substituents bonded to the same nitrogen atom may be joined to form a substituted or unsubstituted 3 to 8 membered heterocycloalkyl. In embodiments, $R^{5A}$ and $R^{5B}$ substituents bonded to the same nitrogen atom may be joined to form a substituted or unsubstituted 5 to 10 membered heteroaryl. In embodiments, $R^{5A}$ and $R^{5B}$ substituents bonded to the same nitrogen atom may be joined to form a substituted 3 to 8 membered heterocycloalkyl. In embodiments, $R^{5A}$ and $R^{5B}$ substituents bonded to the same nitrogen atom may be joined to form a substituted 5 to 10 membered heteroaryl. In embodiments, $R^{5A}$ and $R^{5B}$ substituents bonded to the same nitrogen atom may be joined to form an unsubstituted 3 to 8 membered heterocycloalkyl. In embodiments, $R^{5A}$ and $R^{5B}$ substituents bonded to the same nitrogen atom may be joined to form an unsubstituted 5 to 10 membered heteroaryl. In embodiments, $R^{5A}$ and $R^{5B}$ substituents bonded to the same nitrogen atom may be joined to form a substituted or unsubstituted 3 to 6 membered heterocycloalkyl. In embodiments, $R^{5A}$ and $R^{5B}$ substituents bonded to the same nitrogen atom may be joined to form a substituted or unsubstituted 5 to 6 membered heteroaryl. In embodiments, $R^{5A}$ and $R^{5B}$ substituents bonded to the same nitrogen atom may be joined to form a substituted 3 to 6 membered heterocycloalkyl. In embodiments, $R^{5A}$ and $R^{5B}$ substituents bonded to the same nitrogen atom may be joined to form a substituted 5 to 6 membered heteroaryl. In embodiments, $R^{5A}$ and $R^{5B}$ substituents bonded to the same nitrogen atom may be joined to form an unsubstituted 3 to 6 membered heterocycloalkyl. In embodiments, $R^{5A}$ and $R^{5B}$ substituents bonded to the same nitrogen atom may be joined to form an unsubstituted 5 to 6 membered heteroaryl.

In embodiments, $R^{5C}$ is independently hydrogen. In embodiments, $R^{5C}$ is independently —$CX^{5C}_3$. In embodiments, $R_{5C}$ is independently —$CHX^{5C}_2$. In embodiments, $R^{5C}$ is independently —$CH_2X^{5C}$. In embodiments, $R^{5C}$ is independently —CN. In embodiments, $R^{5C}$ is independently —COOH. In embodiments, $R^{5C}$ is independently —$CONH_2$. In embodiments, $R^{5C}$ is independently substituted or unsubstituted alkyl. In embodiments, $R_{5C}$ is independently substituted or unsubstituted heteroalkyl. In embodiments, $R^{5C}$ is independently substituted or unsubstituted cycloalkyl. In embodiments, $R^{5C}$ is independently, substituted or unsubstituted heterocycloalkyl. In embodiments, $R^{5C}$ is independently substituted or unsubstituted aryl. In embodiments, $R^{5C}$ is independently substituted or unsubstituted heteroaryl. In embodiments, $R^{5C}$ is independently substituted alkyl. In embodiments, $R^{5C}$ is independently substituted heteroalkyl. In embodiments, $R^{5C}$ is independently substituted cycloalkyl. In embodiments, $R^{5C}$ is independently, substituted heterocycloalkyl. In embodiments, $R^{5C}$ is independently substituted aryl. In embodiments, $R^{5C}$ is independently substituted heteroaryl. In embodiments, $R^{5C}$ is independently unsubstituted alkyl. In embodiments, $R^{5C}$ is independently unsubstituted heteroalkyl. In embodiments, $R^{5C}$ is independently unsubstituted cycloalkyl. In embodiments, $R^{5C}$ is independently, unsubstituted heterocycloalkyl. In embodiments, $R^{5C}$ is independently unsubstituted aryl. In embodiments, $R^{5C}$ is independently unsubstituted heteroaryl. In embodiments, $R^{5C}$ is independently substituted or unsubstituted $C_1$-$C_8$ alkyl. In embodiments, $R^{5C}$ is independently substituted or unsubstituted 2 to 8 membered heteroalkyl. In embodiments, $R^{5C}$ is independently substituted or unsubstituted $C_3$-$C_8$ cycloalkyl. In embodiments, $R^{5C}$ is independently, substituted or unsubstituted 3 to 8 membered heterocycloalkyl. In embodiments, $R^{5C}$ is independently substituted or unsubstituted $C_6$-$C_{10}$ aryl. In embodiments, $R^{5C}$ is independently substituted or unsubstituted 5 to 10 membered heteroaryl. In embodiments, $R^{5C}$ is independently substituted $C_1$-$C_8$ alkyl. In embodiments, $R^{5C}$ is independently substituted 2 to 8 membered heteroalkyl. In embodiments, $R^{5C}$ is independently substituted $C_3$-$C_8$ cycloalkyl. In embodiments, $R^{5C}$ is independently, substituted 3 to 8 membered heterocycloalkyl. In embodiments, $R^{5C}$ is independently substituted $C_6$-$C_{10}$ aryl. In embodiments, $R^{5C}$ is independently substituted 5 to 10 membered heteroaryl. In embodiments, $R^{5C}$ is independently unsubstituted $C_1$-$C_8$ alkyl. In embodiments, $R^{5C}$ is independently unsubstituted 2 to 8 membered heteroalkyl. In embodiments, $R^{5C}$ is independently unsubstituted $C_3$-$C_8$ cycloalkyl. In embodiments, $R^{5C}$ is independently, unsubstituted 3 to 8 membered heterocycloalkyl. In embodiments, $R^{5C}$ is independently unsubstituted $C_6$-$C_{10}$ aryl. In embodiments, $R^{5C}$ is independently unsubstituted 5 to 10 membered heteroaryl. In embodiments, $R^{5C}$ is independently substituted or unsubstituted $C_1$-$C_4$ alkyl. In embodiments, $R^{5C}$ is independently substituted or unsubstituted 2 to 4 membered heteroalkyl. In embodiments, $R^{5C}$ is independently substituted or unsubstituted $C_3$-$C_6$ cycloalkyl. In embodiments, $R^{5C}$ is independently, substituted or unsubstituted 3 to 6 membered heterocycloalkyl. In embodiments, $R^{5C}$ is independently substituted or unsubstituted phenyl. In embodiments, $R^{5C}$ is independently substituted or unsubstituted 5 to 6 membered heteroaryl. In embodiments, $R^{5C}$ is independently substituted $C_1$-$C_4$ alkyl. In embodiments, $R^{5C}$ is independently substituted 2 to 4 membered heteroalkyl. In embodiments, $R^{5C}$ is independently substituted $C_3$-$C_6$ cycloalkyl. In embodiments, $R_{5C}$ is independently, substituted 3 to 6 membered heterocycloalkyl. In embodiments, $R^{5C}$ is independently substituted phenyl. In embodiments, $R^{5C}$ is independently substituted 5 to 6 membered heteroaryl. In embodiments, $R^{5C}$ is independently unsubstituted $C_1$-$C_4$ alkyl. In embodiments, $R^{5C}$ is independently unsubstituted 2 to 4 membered heteroalkyl. In embodiments, $R^{5C}$ is independently unsubstituted $C_3$-$C_6$ cycloalkyl. In embodiments, $R^{5C}$ is independently unsubstituted 3 to 6 membered heterocycloalkyl. In embodiments, $R^{5C}$ is independently unsubstituted phenyl. In embodiments, $R^{5C}$ is independently unsubstituted 5 to 6 membered heteroaryl. In embodiments, $R^{5C}$ is independently unsubstituted methyl. In embodiments, $R^{5C}$ is independently unsubstituted ethyl. In embodiments, $R^{5C}$ is independently unsubstituted propyl. In embodiments, $R^{5C}$ is independently unsubstituted isopropyl. In embodiments, $R^{5C}$ is independently unsubstituted tert-butyl.

In embodiments, $R^{5D}$ is independently hydrogen. In embodiments, $R^{5D}$ is independently —$CX^{5D}_3$. In embodiments, $R^{5D}$ is independently —$CHX^{5D}_2$. In embodiments, $R^{5D}$ is independently —$CH_2X^{5D}$. In embodiments, $R^{5D}$ is independently —CN. In embodiments, $R^{5D}$ is independently —COOH. In embodiments, $R^{5D}$ is independently —$CONH_2$. In embodiments, $R^{5D}$ is independently substituted or unsubstituted alkyl. In embodiments, $R^{5D}$ is independently substituted or unsubstituted heteroalkyl. In embodiments, $R^{5D}$ is independently substituted or unsubstituted cycloalkyl. In embodiments, $R^{5D}$ is independently, substituted or unsubstituted heterocycloalkyl. In embodiments, $R^{5D}$ is independently substituted or unsubstituted aryl. In embodiments, $R^{5D}$ is independently substituted or unsubstituted heteroaryl. In embodiments, $R^{5D}$ is independently substituted alkyl. In embodiments, $R^{5D}$ is independently substituted heteroalkyl. In embodiments, $R^{5D}$ is independently substituted cycloalkyl. In embodiments, $R^{5D}$ is independently, substituted heterocycloalkyl. In embodiments, $R^{5D}$ is independently substituted aryl. In embodiments, $R^{5D}$ is independently substituted heteroaryl. In embodiments, $R^{5D}$ is independently unsubstituted alkyl. In embodiments, $R^{5D}$ is independently unsubstituted heteroalkyl. In embodiments, $R^{5D}$ is independently unsubstituted cycloalkyl. In embodiments, $R^{5D}$ is independently, unsubstituted heterocycloalkyl. In embodiments, $R^{5D}$ is independently unsubstituted aryl. In embodiments, $R^{5D}$ is independently unsubstituted heteroaryl. In embodiments, $R^{5D}$ is independently substituted or unsubstituted $C_1$-$C_8$ alkyl. In embodiments, $R^{5D}$ is independently substituted or unsubstituted 2 to 8 membered heteroalkyl. In embodiments, $R^{5D}$ is independently substituted or unsubstituted $C_3$-$C_8$ cycloalkyl. In embodiments, $R^{5D}$ is independently, substituted or unsubstituted 3 to 8 membered heterocycloalkyl. In embodiments, $R^{5D}$ is independently substituted or unsubstituted $C_6$-$C_{10}$ aryl. In embodiments, $R^{5D}$ is independently substituted or unsubstituted 5 to 10 membered heteroaryl. In embodiments, $R^{5D}$ is independently substituted $C_1$-$C_8$ alkyl. In embodiments, $R^{5D}$ is independently substituted 2 to 8 membered heteroalkyl. In embodiments, $R^{5D}$ is independently substituted $C_3$-$C_8$ cycloalkyl. In embodiments, $R^{5D}$ is independently, substituted 3 to 8 membered heterocycloalkyl. In embodiments, $R^{5D}$ is independently substituted $C_6$-$C_{10}$ aryl. In embodiments, $R^{5D}$ is independently substituted 5 to 10 membered heteroaryl. In embodiments, $R^{5D}$ is independently unsubstituted $C_1$-$C_8$ alkyl. In embodiments, $R^{5D}$ is independently unsubstituted 2 to 8 membered heteroalkyl. In embodiments, $R^{5D}$ is independently unsubstituted $C_3$-$C_8$ cycloalkyl. In embodiments, $R^{5D}$ is independently, unsubstituted 3 to 8 membered heterocycloalkyl. In embodiments, $R^{5D}$ is independently unsubstituted $C_6$-$C_{10}$ aryl. In embodiments, $R^{5D}$ is independently unsubstituted 5 to 10 membered heteroaryl. In embodiments, $R^{5D}$ is independently substituted or unsubstituted $C_1$-$C_4$ alkyl. In embodiments, $R^{5D}$ is independently substituted or unsubstituted 2 to 4 membered heteroalkyl. In embodiments, $R^{5D}$ is independently substituted or unsubstituted $C_3$-$C_6$ cycloalkyl. In embodiments, $R^{5D}$ is independently, substituted or unsubstituted 3 to 6 membered heterocycloalkyl. In embodiments, $R^{5D}$ is independently substituted or unsubstituted phenyl. In embodiments, $R^{5D}$ is independently substituted or unsubstituted 5 to 6 membered heteroaryl. In embodiments, $R^{5D}$ is independently substituted $C_1$-$C_4$ alkyl. In embodiments, $R^{5D}$ is independently substituted 2 to 4 membered heteroalkyl. In embodiments, $R^{5D}$ is independently substituted $C_3$-$C_6$ cycloalkyl. In embodiments, $R^{5D}$ is independently, substituted 3 to 6 membered heterocycloalkyl. In embodiments, $R^{5D}$ is independently substituted phenyl. In embodiments, $R^{5D}$ is independently substituted 5 to 6 membered heteroaryl. In embodiments, $R^{5D}$ is independently unsubstituted $C_1$-$C_4$ alkyl. In embodiments, $R^{5D}$ is independently unsubstituted 2 to 4 membered heteroalkyl. In embodiments, $R^{5D}$ is independently unsubstituted $C_3$-$C_6$ cycloalkyl. In embodiments, $R^{5D}$ is independently unsubstituted 3 to 6 membered heterocycloalkyl. In embodiments, $R^{5D}$ is independently unsubstituted phenyl. In embodiments, $R^{5D}$ is independently unsubstituted 5 to 6 membered heteroaryl. In embodiments, $R^{5D}$ is independently unsubstituted methyl. In embodiments, $R^{5D}$ is independently unsubstituted ethyl. In embodiments, $R^{5D}$ is independently unsubstituted propyl. In embodiments, $R^5$ is independently unsubstituted isopropyl. In embodiments, $R^{5D}$ is independently unsubstituted tert-butyl.

In embodiments, $R^5$ is independently hydrogen, halogen, —$CX^5_3$, —$CHX^5_2$, —$CH_2X^5$, —$OCX^5_3$, —$OCH_2X^5$, —$OCHX^5_2$, —CN, —$SO_{n5}R^{5D}$, —$SO_{v5}NR^{5A}R^{5B}$, —$NHC(O)NR^{5A}R^{5B}$, —$N(O)_{m5}$, —$NR^{5A}R^{5B}$, —$C(O)R^{5C}$, —$C(O)OR^{5C}$, —$C(O)NR^{5A}R^{5B}$, —$OR^{5D}$, —$NR^{5A}SO_2R^{5D}$, —$NR^{5A}C(O)R^{5C}$, —$NR^{5A}C(O)OR^{5C}$, —$NR^{5A}OR^{5C}$, $R^{32}$-substituted or unsubstituted alkyl, $R^{32}$-substituted or unsubstituted heteroalkyl, $R^{32}$-substituted or unsubstituted cycloalkyl, $R^{32}$-substituted or unsubstituted heterocycloalkyl, $R^{32}$-substituted or unsubstituted aryl, or $R^{32}$-substituted or unsubstituted heteroaryl. In embodiments, $R^5$ is independently halogen, —$CX^5_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O) $NHNH_2$, —$NHC(O)NH_2$, —$NHSO_2H$, —NHC(O)H, —NHC(O)OH, —NHOH, —$OCX^5_3$, —$OCHX_2$, $R^{32}$-substituted or unsubstituted alkyl, $R^{32}$-substituted or unsubstituted heteroalkyl, $R^{32}$-substituted or unsubstituted cycloalkyl, $R^{32}$-substituted or unsubstituted heterocycloalkyl, $R^{32}$-substituted or unsubstituted aryl, or $R^{32}$-substituted or unsubstituted heteroaryl. In embodiments, $R^5$ is independently halogen, —$CX^5_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{53}$, —$OCHX^{52}$, $R^{32}$-substituted or unsubstituted $C_1$-$C_8$ alkyl, $R^{32}$-substituted or unsubstituted 2 to 8 membered heteroalkyl, $R^{32}$-substituted or unsubstituted $C_3$-$C_8$ cycloalkyl, $R^{32}$-substituted or unsubstituted 3 to 6 membered heterocycloalkyl, $R^{32}$-substituted or unsubstituted phenyl, or $R^{32}$-substituted or unsubstituted 5 to 6 membered heteroaryl. $X^5$ is —F, —Cl, —Br, or —I. In embodiments, $R^5$ is independently methyl. In embodiments, $R^5$ is independently ethyl.

$R^{32}$ is independently oxo, halogen, —$CX^{32}_3$, —CN, —OH, —$NH_2$, —COOH, —$CONH_2$, —$NO_2$, —SH, —$SO_3H$, —$SO_4H$, —$S_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{32}_3$, —$OCHX^{32}_2$, $R^{33}$-substituted or unsubstituted alkyl, $R^{33}$-substituted or unsubstituted heteroalkyl, $R^{33}$-substituted or unsubstituted cycloalkyl, $R^{33}$-substituted or unsubstituted heterocycloalkyl, $R^{33}$-substituted or unsubstituted aryl, or $R^{33}$-substituted or unsubstituted heteroaryl. In embodiments, $R^{32}$ is independently oxo, halogen, $-CX^{32}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{32}_3$, $-OCHX^{32}_2$, $R^{33}$-substituted or unsubstituted $C_1$-$C_8$ alkyl, $R^{33}$-substituted or unsubstituted 2 to 8 membered heteroalkyl, $R^{33}$-substituted or unsubstituted $C_3$-$C_8$ cycloalkyl, $R^{33}$-substituted or unsubstituted 3 to 6 membered heterocycloalkyl, $R^{33}$-substituted or unsubstituted phenyl, or $R^{33}$-substituted or unsubstituted 5 to 6 membered heteroaryl. $X^{32}$ is $-F$, $-Cl$, $-Br$, or $-I$.

$R^{33}$ is independently oxo, halogen, $-CX^{33}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{33}_3$, $-OCHX^{33}_2$, $R^{34}$-substituted or unsubstituted alkyl, $R^{34}$-substituted or unsubstituted heteroalkyl, $R^{34}$-substituted or unsubstituted cycloalkyl, $R^{34}$-substituted or unsubstituted heterocycloalkyl, $R^{34}$-substituted or unsubstituted aryl, or $R^{34}$-substituted or unsubstituted heteroaryl. In embodiments, $R^{33}$ is independently oxo, halogen, $-CX^{33}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{33}_3$, $-OCHX^{32}$, $R^{34}$-substituted or unsubstituted $C_1$-$C_8$ alkyl, $R^{34}$-substituted or unsubstituted 2 to 8 membered heteroalkyl, $R^{34}$-substituted or unsubstituted $C_3$-$C_8$ cycloalkyl, $R^{34}$-substituted or unsubstituted 3 to 6 membered heterocycloalkyl, $R^{34}$-substituted or unsubstituted phenyl, or $R^{34}$-substituted or unsubstituted 5 to 6 membered heteroaryl. $X^{33}$ is $-F$, $-Cl$, $-Br$, or $-I$.

In embodiments, $R^{5A}$ is independently hydrogen, $-CX^{5A}_3$, $-CN$, $-COOH$, $-CONH_2$, $-CHX^{5A}_2$, $-CH_2X^{5A}$, $R^{32A}$-substituted or unsubstituted alkyl, $R^{32A}$-substituted or unsubstituted heteroalkyl, $R^{32A}$-substituted or unsubstituted cycloalkyl, $R^{32A}$-substituted or unsubstituted heterocycloalkyl, $R^{32A}$-substituted or unsubstituted aryl, or $R^{32A}$-substituted or unsubstituted heteroaryl. In embodiments, $R^{5A}$ is independently hydrogen, $-CX^{5A}_3$, $-CN$, $-COOH$, $-CONH_2$, $-CHX^{5A}_2$, $-CH_2X^{5A}$, $R^{32A}$-substituted or unsubstituted $C_1$-$C_8$ alkyl, $R^{32A}$-substituted or unsubstituted 2 to 8 membered heteroalkyl, $R^{32A}$-substituted or unsubstituted $C_3$-$C_8$ cycloalkyl, $R^{32A}$-substituted or unsubstituted 3 to 6 membered heterocycloalkyl, $R^{32A}$-substituted or unsubstituted phenyl, or $R^{32A}$-substituted or unsubstituted 5 to 6 membered heteroaryl. $X^{5A}$ is $-F$, $-Cl$, $-Br$, or $-I$. In embodiments, $R^{5A}$ is independently hydrogen. In embodiments, $R^{5A}$ is independently methyl. In embodiments, $R^{5A}$ is independently ethyl.

In embodiments, $R^{5A}$ and $R^{5B}$ substituents bonded to the same nitrogen atom may optionally be joined to form a $R^{32A}$-substituted or unsubstituted heterocycloalkyl or $R^{32A}$-substituted or unsubstituted heteroaryl. In embodiments, $R^{5A}$ and $R^{5B}$ substituents bonded to the same nitrogen atom may optionally be joined to form a $R^{32A}$-substituted or unsubstituted 3 to 6 membered heterocycloalkyl or $R^{32A}$-substituted or unsubstituted 5 to 6 membered heteroaryl.

$R^{32A}$ is independently oxo, halogen, $-CX^{32A}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{32A}_3$, $-OCHX^{32A}_2$, $R^{33A}$-substituted or unsubstituted alkyl, $R^{33A}$-substituted or unsubstituted heteroalkyl, $R^{33A}$-substituted or unsubstituted cycloalkyl, $R^{33A}$-substituted or unsubstituted heterocycloalkyl, $R^{33A}$-substituted or unsubstituted aryl, or $R^{33A}$-substituted or unsubstituted heteroaryl. In embodiments, $R^{32A}$ is independently oxo, halogen, $-CX^{32A}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{32A}_3$, $-OCHX^{32A}_2$, $R^{33A}$-substituted or unsubstituted $C_1$-$C_8$ alkyl, $R^{33A}$-substituted or unsubstituted 2 to 8 membered heteroalkyl, $R^{33A}$-substituted or unsubstituted $C_3$-$C_8$ cycloalkyl, $R^{33A}$-substituted or unsubstituted 3 to 6 membered heterocycloalkyl, $R^{33A}$-substituted or unsubstituted phenyl, or $R^{33A}$-substituted or unsubstituted 5 to 6 membered heteroaryl. $X^{32A}$ is $-F$, $-Cl$, $-Br$, or $-I$.

$R^{33A}$ is independently oxo, halogen, $-CX^{33A}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{33A}_3$, $-OCHX^{33A}_2$, $R^{34A}$-substituted or unsubstituted alkyl, $R^{34A}$-substituted or unsubstituted heteroalkyl, $R^{34A}$-substituted or unsubstituted cycloalkyl, $R^{34A}$-substituted or unsubstituted heterocycloalkyl, $R^{34A}$-substituted or unsubstituted aryl, or $R^{34A}$-substituted or unsubstituted heteroaryl. In embodiments, $R^{33A}$ is independently oxo, halogen, $-CX^{33A}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{33A}_3$, $-OCHX^{33A}_2$, $R^{34A}$-substituted or unsubstituted $C_1$-$C_8$ alkyl, $R^{34A}$-substituted or unsubstituted 2 to 8 membered heteroalkyl, $R^{34A}$-substituted or unsubstituted $C_3$-$C_8$ cycloalkyl, $R^{34A}$-substituted or unsubstituted 3 to 6 membered heterocycloalkyl, $R^{34A}$-substituted or unsubstituted phenyl, or $R^{34A}$-substituted or unsubstituted 5 to 6 membered heteroaryl. $X^{33A}$ is $-F$, $-Cl$, $-Br$, or $-I$.

In embodiments, $R^{5B}$ is independently hydrogen, $-CX^{5B}_3$, $-CN$, $-COOH$, $-CONH_2$, $-CHX^{5B}_2$, $-CH_2X^{5B}$, $R^{32B}$-substituted or unsubstituted alkyl, $R^{32B}$-substituted or unsubstituted heteroalkyl, $R^{32B}$-substituted or unsubstituted cycloalkyl, $R^{32B}$-substituted or unsubstituted heterocycloalkyl, $R^{32B}$-substituted or unsubstituted aryl, or $R^{32B}$-substituted or unsubstituted heteroaryl. In embodiments, $R^{5B}$ is independently hydrogen, $-CX^{5B}_3$, $-CN$, $-COOH$, $-CONH_2$, $-CHX^{5B}_2$, $-CH_2X^{5B}$, $R^{32B}$-substituted or unsubstituted $C_1$-$C_8$ alkyl, $R^{32B}$-substituted or unsubstituted 2 to 8 membered heteroalkyl, $R^{32B}$-substituted or unsubstituted $C_3$-$C_8$ cycloalkyl, $R^{32B}$-substituted or unsubstituted 3 to 6 membered heterocycloalkyl, $R^{32B}$-substituted or unsubstituted phenyl, or $R^{32B}$-substituted or unsubstituted 5 to 6 membered heteroaryl. $X^{5B}$ is $-F$, $-Cl$, $-Br$, or $-I$. In embodiments, $R^{5B}$ is independently hydrogen. In embodiments, $R^{5B}$ is independently methyl. In embodiments, $R^{5B}$ is independently ethyl.

In embodiments, $R^{5A}$ and $R^{5B}$ substituents bonded to the same nitrogen atom may optionally be joined to form a $R^{32B}$-substituted or unsubstituted heterocycloalkyl or $R^{32B}$-substituted or unsubstituted heteroaryl. In embodiments, $R^{5A}$ and $R^{5B}$ substituents bonded to the same nitrogen atom may optionally be joined to form a $R^{32B}$-substituted or unsubstituted 3 to 6 membered heterocycloalkyl or $R^{32B}$-substituted or unsubstituted 5 to 6 membered heteroaryl.

$R^{32B}$ is independently oxo, halogen, —$CX^{32B}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{32B3}$, —OCHX$^{32B2}$, $R^{33B}$-substituted or unsubstituted alkyl, $R^{33B}$-substituted or unsubstituted heteroalkyl, $R^{33B}$-substituted or unsubstituted cycloalkyl, $R^{33B}$-substituted or unsubstituted heterocycloalkyl, $R^{33B}$-substituted or unsubstituted aryl, or $R^{33B}$-substituted or unsubstituted heteroaryl. In embodiments, $R^{32B}$ is independently oxo, halogen, —$CX^{32B3}_3$, —CN, —OH, —NH$_2$, —COOH, —CONH$_2$, —NO$_2$, —SH, —SO$_3$H, —SO$_4$H, —S$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{32B}_3$, —OCHX$^{32B}_2$, $R^{33B}$-substituted or unsubstituted C$_1$-C$_8$ alkyl, $R^{33B}$-substituted or unsubstituted 2 to 8 membered heteroalkyl, $R^{33B}$-substituted or unsubstituted C$_3$-C$_8$ cycloalkyl, $R^{33B}$-substituted or unsubstituted 3 to 6 membered heterocycloalkyl, $R^{33B}$-substituted or unsubstituted phenyl, or $R^{33B}$-substituted or unsubstituted 5 to 6 membered heteroaryl. X$^{32B}$ is —F, —Cl, —Br, or —I.

$R^{33B}$ is independently oxo, halogen, —$CX^{33B}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{33B}_3$, —OCHX$^{33B}_2$, $R^{34B}$-substituted or unsubstituted alkyl, $R^{34B}$-substituted or unsubstituted heteroalkyl, $R^{34B}$-substituted or unsubstituted cycloalkyl, $R^{34B}$-substituted or unsubstituted heterocycloalkyl, $R^{34B}$-substituted or unsubstituted aryl, or $R^{34B}$-substituted or unsubstituted heteroaryl. In embodiments, $R^{33B}$ is independently oxo, halogen, —$CX^{33B}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{33B}_3$, —OCHX$^{33B}_2$, $R^{34B}$-substituted or unsubstituted C$_1$-C$_8$ alkyl, $R^{34B}$-substituted or unsubstituted 2 to 8 membered heteroalkyl, $R^{34B}$-substituted or unsubstituted C$_3$-C$_8$ cycloalkyl, $R^{34B}$-substituted or unsubstituted 3 to 6 membered heterocycloalkyl, $R^{34B}$-substituted or unsubstituted phenyl, or $R^{34B}$-substituted or unsubstituted 5 to 6 membered heteroaryl. X$^{33B}$ is —F, —Cl, —Br, or —I.

In embodiments, $R^{5C}$ is independently hydrogen, —$CX^{5C}_3$, —CN, —COOH, —CONH$_2$, —CHX$^{5C}_2$, —CH$_2$X$^{5C}$, $R^{32C}$-substituted or unsubstituted alkyl, $R^{32C}$-substituted or unsubstituted heteroalkyl, $R^{32C}$-substituted or unsubstituted cycloalkyl, $R^{32C}$-substituted or unsubstituted heterocycloalkyl, $R^{32C}$-substituted or unsubstituted aryl, or $R^{32C}$-substituted or unsubstituted heteroaryl. In embodiments, $R^{5C}$ is independently hydrogen, —$CX^{5C}_3$, —CN, —COOH, —CONH$_2$, —CHX$^{5C}_2$, —CH$_2$X$^{5C}$, $R^{32C}$-substituted or unsubstituted C$_1$-C$_8$ alkyl, $R^{32C}$-substituted or unsubstituted 2 to 8 membered heteroalkyl, $R^{32C}$-substituted or unsubstituted C$_3$-C$_8$ cycloalkyl, $R^{32C}$-substituted or unsubstituted 3 to 6 membered heterocycloalkyl, $R^{32C}$-substituted or unsubstituted phenyl, or $R^{32C}$-substituted or unsubstituted 5 to 6 membered heteroaryl. X$^{5C}$ is —F, —Cl, —Br, or —I. In embodiments, $R^{5C}$ is independently hydrogen. In embodiments, $R^{5C}$ is independently methyl. In embodiments, $R^{5C}$ is independently ethyl.

$R^{32C}$ is independently oxo, halogen, —$CX^{32C}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{32}_3$, —OCHX$^{32}_2$, $R^{33C}$-substituted or unsubstituted alkyl, $R^{33C}$-substituted or unsubstituted heteroalkyl, $R^{33C}$-substituted or unsubstituted cycloalkyl, $R^{33C}$-substituted or unsubstituted heterocycloalkyl, $R^{33C}$-substituted or unsubstituted aryl, or $R^{33C}$-substituted or unsubstituted heteroaryl. In embodiments, $R^{32C}$ is independently oxo, halogen, —$CX^{32C}_3$, —CN, —OH, —NH$_2$, —COOH, —CONH$_2$, —NO$_2$, —SH, —S$_3$H, —SO$_4$H, —S$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{32}_3$, —OCHX$^{32}_2$, $R^{33C}$-substituted or unsubstituted C$_1$-C$_8$ alkyl, $R^{33C}$-substituted or unsubstituted 2 to 8 membered heteroalkyl, $R^{33C}$-substituted or unsubstituted C$_3$-C$_8$ cycloalkyl, $R^{33C}$-substituted or unsubstituted 3 to 6 membered heterocycloalkyl, $R^{33C}$-substituted or unsubstituted phenyl, or $R^{33C}$-substituted or unsubstituted 5 to 6 membered heteroaryl. X$^{32C}$ is —F, —Cl, —Br, or —I.

$R^{33C}$ is independently oxo, halogen, —$CX^{33C}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{33}_3$, —OCHX$^{33C}_2$, $R^{34C}$-substituted or unsubstituted alkyl, $R^{34C}$-substituted or unsubstituted heteroalkyl, $R^{34C}$-substituted or unsubstituted cycloalkyl, $R^{34C}$-substituted or unsubstituted heterocycloalkyl, $R^{34C}$-substituted or unsubstituted aryl, or $R^{34C}$-substituted or unsubstituted heteroaryl. In embodiments, $R^{33C}$ is independently oxo, halogen, —$CX^{33}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{33}_3$, —OCHX$^{33}_2$, $R^{34C}$-substituted or unsubstituted C$_1$-C$_8$ alkyl, $R^{34C}$-substituted or unsubstituted 2 to 8 membered heteroalkyl, $R^{34C}$-substituted or unsubstituted C$_3$-C$_8$ cycloalkyl, $R^{34C}$-substituted or unsubstituted 3 to 6 membered heterocycloalkyl, $R^{34C}$-substituted or unsubstituted phenyl, or $R^{34C}$-substituted or unsubstituted 5 to 6 membered heteroaryl. X$^{33C}$ is —F, —Cl, —Br, or —I.

In embodiments, $R^{5D}$ is independently hydrogen, —$CX^{5D}_3$, —CN, —COOH, —CONH$_2$, —CHX$^{5D}_2$, —CH$_2$X$^{5D}$, $R^{32D}$-substituted or unsubstituted alkyl, $R^{32D}$-substituted or unsubstituted heteroalkyl, $R^{32D}$-substituted or unsubstituted cycloalkyl, $R^{32D}$-substituted or unsubstituted heterocycloalkyl, $R^{32D}$-substituted or unsubstituted aryl, or $R^{32D}$-substituted or unsubstituted heteroaryl. In embodiments, $R^{5D}$ is independently hydrogen, —$CX^{5D}_3$, —CN, —COOH, —CONH$_2$, —CHX$^{5D}_2$, —CH$_2$X$^{5D}$, $R^{32D}$-substituted or unsubstituted C$_1$-C$_8$ alkyl, $R^{32D}$-substituted or unsubstituted 2 to 8 membered heteroalkyl, $R^{32D}$-substituted or unsubstituted C$_3$-C$_8$ cycloalkyl, $R^{32D}$-substituted or unsubstituted 3 to 6 membered heterocycloalkyl, $R^{32D}$-substituted or unsubstituted phenyl, or $R^{32D}$-substituted or unsubstituted 5 to 6 membered heteroaryl. X$^{5D}$ is —F, —Cl, —Br, or —I. In embodiments, $R^{5D}$ is independently hydrogen. In embodiments, $R^{5D}$ is independently methyl. In embodiments, $R^{5D}$ is independently ethyl.

$R^{32D}$ is independently oxo, halogen, —$CX^{32D}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{32D}_3$, —OCHX$^{32D}_2$, R$^{33D}$-substituted or unsubstituted alkyl, R$^{33D}$-substituted or unsubstituted heteroalkyl, R$^{33D}$-substituted or unsubstituted cycloalkyl, R$^{33D}$-substituted or unsubstituted heterocycloalkyl, R$^{33D}$-substituted or unsubstituted aryl, or R$^{33D}$-substituted or unsubstituted heteroaryl. In embodiments, R$^{32D}$ is independently oxo, halogen, —CX$^{32D}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{32D}_3$, —OCHX$^{32D}_2$, R$^{33D}$-substituted or unsubstituted C$_1$-C$_8$ alkyl, R$^{33D}$-substituted or unsubstituted 2 to 8 membered heteroalkyl, R$^{33D}$-substituted or unsubstituted C$_3$-C$_8$ cycloalkyl, R$^{33}$-substituted or unsubstituted 3 to 6 membered heterocycloalkyl, R$^{33D}$-substituted or unsubstituted phenyl, or R$^{33D}$-substituted or unsubstituted 5 to 6 membered heteroaryl. X$^{32D}$ is —F, —Cl, —Br, or —I.

R$^{33D}$ is independently oxo, halogen, —CX$^{33D}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{33D}_3$, —OCHX$^{33D}_2$, R$^{34D}$-substituted or unsubstituted alkyl, R$^{34D}$-substituted or unsubstituted heteroalkyl, R$^{34D}$-substituted or unsubstituted cycloalkyl, R$^{34D}$-substituted or unsubstituted heterocycloalkyl, R$^{34D}$-substituted or unsubstituted aryl, or R$^{34D}$-substituted or unsubstituted heteroaryl. In embodiments, R$^{33D}$ is independently oxo, halogen, —CX$^{33D}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{33D}_3$, —OCHX$^{33D}_2$, R$^{34D}$-substituted or unsubstituted C$_1$-C$_8$ alkyl, R$^{34D}$-substituted or unsubstituted 2 to 8 membered heteroalkyl, R$^{34D}$-substituted or unsubstituted C$_3$-C$_8$ cycloalkyl, R$^{34D}$-substituted or unsubstituted 3 to 6 membered heterocycloalkyl, R$^{34D}$-substituted or unsubstituted phenyl, or R$^{34D}$-substituted or unsubstituted 5 to 6 membered heteroaryl. X$^{33D}$ is —F, —Cl, —Br, or —I.

R$^{34}$, R$^{34A}$, R$^{34B}$, R$^{34C}$, and R$^{34D}$ are independently hydrogen, oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl. In embodiments, R$^{34}$, R$^{34A}$R$^{34B}$, R$^{34C}$, and R$^{34D}$ are independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl. In embodiments, R$^{34}$, R$^{34A}$, R$^{34B}$, R$^{34C}$, and R$^{34D}$ are independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCHF$_2$, unsubstituted C$_1$-C$_8$ alkyl, unsubstituted 2 to 8 membered heteroalkyl, unsubstituted C$_3$-C$_8$ cycloalkyl, unsubstituted 3 to 6 membered heterocycloalkyl, unsubstituted phenyl, or unsubstituted 5 to 6 membered heteroaryl.

In embodiments, L$^1$ is a bond, —S(O)$_2$—, —S(O)$_2$-Ph-, substituted or unsubstituted C$_1$-C$_8$ alkylene, substituted or unsubstituted 2 to 8 membered heteroalkylene, substituted or unsubstituted C$_3$-C$_8$ cycloalkylene, substituted or unsubstituted 3 to 8 membered heterocycloalkylene, substituted or unsubstituted phenylene, or substituted or unsubstituted 5 to 6 membered heteroarylene. In embodiments, L$^1$ is a bond. In embodiments, L$^1$ is a substituted or unsubstituted C$_1$-C$_6$ alkylene, substituted or unsubstituted 2 to 6 membered heteroalkylene, substituted or unsubstituted C$_3$-C$_6$ cycloalkylene, substituted or unsubstituted 3 to 6 membered heterocycloalkylene, substituted or unsubstituted phenylene, or substituted or unsubstituted 5 to 6 membered heteroarylene. In embodiments, L$^1$ is an unsubstituted C$_1$-C$_6$ alkylene, unsubstituted 2 to 6 membered heteroalkylene, or unsubstituted C$_3$-C$_6$ cycloalkylene. In embodiments, L$^1$ is an unsubstituted methylene.

In embodiments, L$^1$ is a bond. In embodiments, L$^1$ is —S(O)$_2$—. In embodiments, L$^1$ is —S(O)$_2$-Ph-. In embodiments, L$^1$ is —NR$^6$—. In embodiments, L$^1$ is —O—. In embodiments, L$^1$ is —S—. In embodiments, L$^1$ is —C(O)—. In embodiments, L$^1$ is —C(O)NR$^6$—. In embodiments, L$^1$ is —NR$^6$C(O)—. In embodiments, L$^1$ is —NR$^6$C(O)NH—. In embodiments, L$^1$ is —NHC(O)NR$^6$—. In embodiments, L$^1$ is —C(O)O—. In embodiments, L$^1$ is —OC(O)—. In embodiments, L$^1$ is —NH—. In embodiments, L$^1$ is —C(O)NH—. In embodiments, L$^1$ is —NHC(O)—. In embodiments, L$^1$ is —NHC(O)NH—. In embodiments, L$^1$ is —CH$_2$—. In embodiments, L$^1$ is —OCH$_2$—. In embodiments, L$^1$ is —CH$_2$O—. In embodiments, L$^1$ is —CH$_2$CH$_2$—. In embodiments, L$^1$ is —SCH$_2$—. In embodiments, L$^1$ is —CH$_2$S—. In embodiments, L$^1$ is —CHCH—. In embodiments, L$^1$ is —CC—. In embodiments, L$^1$ is —NHCH$_2$—. In embodiments, L$^1$ is —CH$_2$NH—.

In embodiments, L$^1$ is a substituted or unsubstituted alkylene. In embodiments, L$^1$ is a substituted or unsubstituted heteroalkylene. In embodiments, L$^1$ is a substituted or unsubstituted cycloalkylene. In embodiments, L$^1$ is a substituted or unsubstituted heterocycloalkylene. In embodiments, L$^1$ is a substituted or unsubstituted arylene. In embodiments, L$^1$ is a substituted or unsubstituted heteroarylene. In embodiments, L$^1$ is a substituted alkylene. In embodiments, L$^1$ is a substituted heteroalkylene. In embodiments, L$^1$ is a substituted cycloalkylene. In embodiments, L$^1$ is a substituted heterocycloalkylene. In embodiments, L$^1$ is a substituted arylene. In embodiments, L$^1$ is a substituted heteroarylene. In embodiments, L$^1$ is an unsubstituted alkylene. In embodiments, L$^1$ is an unsubstituted heteroalkylene. In embodiments, L$^1$ is an unsubstituted cycloalkylene. In embodiments, L$^1$ is an unsubstituted heterocycloalkylene. In embodiments, L$^1$ is an unsubstituted arylene. In embodiments, L$^1$ is an unsubstituted heteroarylene. In embodiments, L$^1$ is a substituted or unsubstituted C$_1$-C$_8$ alkylene. In embodiments, L$^1$ is a substituted or unsubstituted 2 to 8 membered heteroalkylene. In embodiments, L$^1$ is a substituted or unsubstituted C$_3$-C$_8$ cycloalkylene. In embodiments, L$^1$ is a substituted or unsubstituted 3 to 8 membered heterocycloalkylene. In embodiments, L$^1$ is a substituted or unsubstituted C$_6$-C$_{10}$ arylene. In embodiments, L$^1$ is a substituted or unsubstituted 5 to 10 membered heteroarylene. In embodiments, L$^1$ is a substituted C$_1$-C$_8$ alkylene. In embodiments, $L^1$ is a substituted 2 to 8 membered heteroalkylene. In embodiments, $L^1$ is a substituted $C_3$-$C_8$ cycloalkylene. In embodiments, $L^1$ is a substituted 3 to 8 membered heterocycloalkylene. In embodiments, $L^1$ is a substituted $C_6$-$C_{10}$ arylene. In embodiments, $L^1$ is a substituted 5 to 10 membered heteroarylene. In embodiments, $L^1$ is an unsubstituted $C_1$-$C_8$ alkylene. In embodiments, $L^1$ is an unsubstituted 2 to 8 membered heteroalkylene. In embodiments, $L^1$ is an unsubstituted $C_3$-$C_8$ cycloalkylene. In embodiments, $L^1$ is an unsubstituted 3 to 8 membered heterocycloalkylene. In embodiments, $L^1$ is an unsubstituted $C_6$-$C_{10}$ arylene. In embodiments, $L^1$ is an unsubstituted 5 to 10 membered heteroarylene. In embodiments, $L^1$ is a substituted or unsubstituted $C_1$-$C_4$ alkylene. In embodiments, $L^1$ is a substituted or unsubstituted 2 to 4 membered heteroalkylene. In embodiments, $L^1$ is a substituted or unsubstituted $C_3$-$C_6$ cycloalkylene. In embodiments, $L^1$ is a substituted or unsubstituted 3 to 6 membered heterocycloalkylene. In embodiments, $L^1$ is a substituted or unsubstituted phenylene. In embodiments, $L^1$ is a substituted or unsubstituted 5 to 6 membered heteroarylene. In embodiments, $L^1$ is a substituted $C_1$-$C_4$ alkylene. In embodiments, $L^1$ is a substituted 2 to 4 membered heteroalkylene. In embodiments, $L^1$ is a substituted $C_3$-$C_6$ cycloalkylene. In embodiments, $L^1$ is a substituted 3 to 6 membered heterocycloalkylene. In embodiments, $L^1$ is a substituted phenylene. In embodiments, $L^1$ is a substituted 5 to 6 membered heteroarylene. In embodiments, $L^1$ is an unsubstituted $C_1$-$C_4$ alkylene. In embodiments, $L^1$ is an unsubstituted 2 to 4 membered heteroalkylene. In embodiments, $L^1$ is an unsubstituted $C_3$-$C_6$ cycloalkylene. In embodiments, $L^1$ is an unsubstituted 3 to 6 membered heterocycloalkylene. In embodiments, $L^1$ is an unsubstituted phenylene. In embodiments, $L^1$ is an unsubstituted 5 to 6 membered heteroarylene.

In embodiments, $L^1$ is a bond, —S(O)$_2$—, —S(O)$_2$-Ph-, —NR$^6$—, —O—, —S—, —C(O)—, —C(O)NR$^6$—, —NR$^6$C(O)—, —NR$^6$C(O)NH—, —NHC(O)NR—, —C(O)O—, —OC(O)—, $R^{41}$-substituted or unsubstituted alkylene, $R^{41}$-substituted or unsubstituted heteroalkylene, $R^{41}$-substituted or unsubstituted cycloalkylene, $R^{41}$-substituted or unsubstituted heterocycloalkylene, $R^{41}$-substituted or unsubstituted arylene, or $R^{41}$-substituted or unsubstituted heteroarylene. In embodiments, $L^1$ is a bond, —S(O)$_2$—, —S(O)$_2$-Ph-, —NH—, —O—, —S—, —C(O)—, —C(O)NH—, —NHC(O)—, —NHC(O)NH—, —C(O)O—, —OC(O)—, $R^{41}$-substituted or unsubstituted alkylene, $R^{41}$-substituted or unsubstituted heteroalkylene, $R^{41}$-substituted or unsubstituted cycloalkylene, $R^{41}$-substituted or unsubstituted heterocycloalkylene, $R^{41}$-substituted or unsubstituted arylene, or $R^{41}$-substituted or unsubstituted heteroarylene. In embodiments, $L^1$ is a bond, —S(O)$_2$—, —S(O)$_2$-Ph-, —NH—, —O—, —S—, —C(O)—, —C(O)NH—, —NHC(O)—, —NHC(O)NH—, —C(O)O—, —OC(O)—, $R^{41}$-substituted or unsubstituted $C_1$-$C_8$ alkylene, $R^{41}$-substituted or unsubstituted 2 to 8 membered heteroalkylene, $R^{41}$-substituted or unsubstituted $C_3$-$C_8$ cycloalkylene, $R^{41}$-substituted or unsubstituted 3 to 6 membered heterocycloalkylene, $R^{41}$-substituted or unsubstituted phenylene, or $R^{41}$-substituted or unsubstituted 5 to 6 membered heteroarylene.

$R^{41}$ is independently oxo, halogen, —CX$^{41}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{41}_3$, —OCHX$^{41}_2$, $R^{42}$-substituted or unsubstituted alkyl, $R^{42}$-substituted or unsubstituted heteroalkyl, $R^{42}$-substituted or unsubstituted cycloalkyl, $R^{42}$-substituted or unsubstituted heterocycloalkyl, $R^{42}$-substituted or unsubstituted aryl, or $R^{42}$-substituted or unsubstituted heteroaryl. In embodiments, $R^{41}$ is independently oxo, halogen, —CX$^{41}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{41}_3$, —OCHX$^{41}_2$, $R^{42}$-substituted or unsubstituted $C_1$-$C_8$ alkyl, $R^{42}$-substituted or unsubstituted 2 to 8 membered heteroalkyl, $R^{42}$-substituted or unsubstituted $C_3$-$C_8$ cycloalkyl, $R^{42}$-substituted or unsubstituted 3 to 6 membered heterocycloalkyl, $R^{42}$-substituted or unsubstituted phenyl, or $R^{42}$-substituted or unsubstituted 5 to 6 membered heteroaryl. $X^{41}$ is —F, —Cl, —Br, or —I.

$R^{42}$ is independently oxo, halogen, —CX$^4_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{42}_3$, —OCHX$^{42}_2$, $R^{43}$-substituted or unsubstituted alkyl, $R^{43}$-substituted or unsubstituted heteroalkyl, $R^{43}$-substituted or unsubstituted cycloalkyl, $R^{43}$-substituted or unsubstituted heterocycloalkyl, $R^{43}$-substituted or unsubstituted aryl, or $R^{43}$-substituted or unsubstituted heteroaryl. In embodiments, $R^{42}$ is independently oxo, halogen, —CX$^{42}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{42}_3$, —OCHX$^{42}_2$, $R^{43}$-substituted or unsubstituted $C_1$-$C_8$ alkyl, $R^{43}$-substituted or unsubstituted 2 to 8 membered heteroalkyl, $R^{43}$-substituted or unsubstituted $C_3$-$C_8$ cycloalkyl, $R^{43}$-substituted or unsubstituted 3 to 6 membered heterocycloalkyl, $R^{43}$-substituted or unsubstituted phenyl, or $R^{43}$-substituted or unsubstituted 5 to 6 membered heteroaryl. $X^{42}$ is —F, —Cl, —Br, or —I.

$R^{43}$ is independently hydrogen, oxo, halogen, —CCl$_3$, —CBr$_3$, —CF$_3$, —Cl$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCl$_3$, —OCHCl$_2$, —OCHBr$_2$, —OCHI$_2$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{43}$ is independently oxo, halogen, —CF$_3$, —CN, —OH, —NH$_2$, —COOH, —CONH$_2$, —NO$_2$, —SH, —S$_3$H, —SO$_4$H, —S$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{43}$ is independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCHF$_2$, unsubstituted $C_1$-$C_8$ alkyl, unsubstituted 2 to 8 membered heteroalkyl, unsubstituted $C_3$-$C_8$ cycloalkyl, unsubstituted 3 to 6 membered heterocycloalkyl, unsubstituted phenyl, or unsubstituted 5 to 6 membered heteroaryl.

In embodiments, $L^1$ is a bond. In embodiments, $L^1$ is $R^{41}$-substituted or unsubstituted $C_1$-$C_2$ alkylene. In embodiments, $L^1$ is $R^{41}$-substituted or unsubstituted $C_1$-$C_4$ alkylene. In embodiments, $L^1$ is $R^{41}$-substituted or unsubstituted $C_1$-$C_6$ alkylene. In embodiments, $L^1$ is $R^{41}$-substituted or unsubstituted $C_1$-$C_8$ alkylene. In embodiments, $L^1$ is $R^{41}$-substituted or unsubstituted alkylene (e.g., $C_1$-$C_8$ alkylene, $C_1$-$C_6$ alkylene, $C_1$-$C_4$ alkylene, $C_1$-$C_2$ alkylene). In embodiments, $L^1$ is $R^{41}$-substituted $C_1$-$C_2$ alkylene. In embodiments, $L^1$ is $R^{41}$-substituted $C_1$-$C_4$ alkylene. In embodiments, $L^1$ is $R^{41}$-substituted $C_1$-$C_6$ alkylene. In embodiments, $L^1$ is $R^{41}$-substituted $C_1$-$C_8$ alkylene. In embodiments, $L^1$ is $R^{41}$-substituted alkylene (e.g., $C_1$-$C_8$ alkylene, $C_1$-$C_6$ alkylene, $C_1$-$C_4$ alkylene, $C_1$-$C_2$ alkylene). In embodiments, $L^1$ is $R^{41}$-substituted methylene. In embodiments, $L^1$ is unsubstituted $C_1$-$C_2$ alkylene. In embodiments, $L^1$ is unsubstituted $C_1$-$C_4$ alkylene. In embodiments, $L^1$ is unsubstituted $C_1$-$C_6$ alkylene. In embodiments, $L^1$ is unsubstituted $C_1$-$C_8$ alkylene. In embodiments, $L^1$ is unsubstituted alkylene (e.g., $C_1$-$C_8$ alkylene, $C_1$-$C_6$ alkylene, $C_1$-$C_4$ alkylene, $C_1$-$C_2$ alkylene). In embodiments, $L^1$ is $R^{41}$-substituted or unsubstituted methylene. In embodiments, $L^1$ is $R^{41}$-substituted methylene. In embodiments, $L^1$ is unsubstituted methylene.

In embodiments, $L^1$ is $R^{41}$-substituted or unsubstituted 2 to 4 membered heteroalkylene. In embodiments, $L^1$ is $R^{41}$-substituted or unsubstituted 2 to 6 membered heteroalkylene. In embodiments, $L^1$ is $R^{41}$-substituted or unsubstituted 2 to 8 membered heteroalkylene. In embodiments, $L^1$ is $R^{41}$-substituted or unsubstituted heteroalkylene (e.g., 2 to 8 membered heteroalkylene, 2 to 6 membered heteroalkylene, 2 to 4 membered heteroalkylene). In embodiments, $L^1$ is $R^{41}$-substituted 2 to 4 membered heteroalkylene. In embodiments, $L^1$ is $R^{41}$-substituted 2 to 6 membered heteroalkylene. In embodiments, $L^1$ is $R^{41}$-substituted 2 to 8 membered heteroalkylene. In embodiments, $L^1$ is $R^{41}$-substituted heteroalkylene (e.g., 2 to 8 membered heteroalkylene, 2 to 6 membered heteroalkylene, 2 to 4 membered heteroalkylene). In embodiments, $L^1$ is unsubstituted 2 to 4 membered heteroalkylene. In embodiments, $L^1$ is unsubstituted 2 to 6 membered heteroalkylene. In embodiments, $L^1$ is unsubstituted 2 to 8 membered heteroalkylene. In embodiments, $L^1$ is unsubstituted heteroalkylene (e.g., 2 to 8 membered heteroalkylene, 2 to 6 membered heteroalkylene, 2 to 4 membered heteroalkylene).

In embodiments, $L^1$ is $R^{41}$-substituted or unsubstituted ethylaminylene. In embodiments, $L^1$ is $R^{41}$-substituted ethylaminylene. In embodiments, $L^1$ is unsubstituted ethylaminylene. In embodiments, $L^1$ is $R^{41}$-substituted or unsubstituted propylaminylene. In embodiments, $L^1$ is $R^{41}$-substituted propyl aminylene. In embodiments, $L^1$ is unsubstituted propylaminylene. In embodiments, $L^1$ is $R^{41}$-substituted or unsubstituted butylaminylene. In embodiments, $L^1$ is $R^{41}$-substituted butylaminylene. In embodiments, $L^1$ is unsubstituted butylaminylene.

In embodiments, $L^1$ is $R^{41}$-substituted or unsubstituted $C_3$-$C_8$ cycloalkylene. In embodiments, $L^1$ is $R^{41}$-substituted or unsubstituted $C_4$-$C_6$ cycloalkylene. In embodiments, $L^1$ is $R^{41}$-substituted or unsubstituted $C_5$-$C_6$ cycloalkylene. In embodiments, $L^1$ is $R^{41}$-substituted or unsubstituted cycloalkylene (e.g., $C_3$-$C_8$ cycloalkylene, $C_4$-$C_6$ cycloalkylene, or $C_5$-$C_6$ cycloalkylene). In embodiments, $L^1$ is $R^{41}$-substituted $C_3$-$C_8$ cycloalkylene. In embodiments, $L^1$ is $R^{41}$-substituted $C_4$-$C_6$ cycloalkylene. In embodiments, $L^1$ is $R^{41}$-substituted $C_5$-$C_6$ cycloalkylene. In embodiments, $L^1$ is $R^{41}$-substituted cycloalkylene (e.g., $C_3$-$C_8$ cycloalkylene, $C_4$-$C_6$ cycloalkylene, or $C_5$-$C_6$ cycloalkylene). In embodiments, $L^1$ is unsubstituted $C_3$-$C_8$ cycloalkylene. In embodiments, $L^1$ is unsubstituted $C_4$-$C_6$ cycloalkylene. In embodiments, $L^1$ is unsubstituted $C_5$-$C_6$ cycloalkylene. In embodiments, $L^1$ is unsubstituted cycloalkylene (e.g., $C_3$-$C_8$ cycloalkylene, $C_4$-$C_6$ cycloalkylene, or $C_5$-$C_6$ cycloalkylene).

In embodiments, $L^1$ is $R^{41}$-substituted or unsubstituted 4 membered heterocycloalkylene. In embodiments, $L^1$ is $R^{41}$-substituted or unsubstituted 5 membered heterocycloalkylene. In embodiments, $L^1$ is $R^{41}$-substituted or unsubstituted 6 membered heterocycloalkylene. In embodiments, $L^1$ is $R^{41}$-substituted or unsubstituted heterocycloalkylene (e.g., 3 to 6 membered heterocycloalkylene, 4 to 6 membered heterocycloalkylene, or 5 to 6 membered heterocycloalkylene). In embodiments, $L^1$ is $R^{41}$-substituted 4 membered heterocycloalkylene. In embodiments, $L^1$ is $R^{41}$-substituted 5 membered heterocycloalkylene. In embodiments, $L^1$ is $R^{41}$-substituted 6 membered heterocycloalkylene. In embodiments, $L^1$ is $R^{41}$-substituted heterocycloalkylene (e.g., 3 to 6 membered heterocycloalkylene, 4 to 6 membered heterocycloalkylene, or 5 to 6 membered heterocycloalkylene). In embodiments, $L^1$ is unsubstituted 4 membered heterocycloalkylene. In embodiments, $L^1$ is unsubstituted 5 membered heterocycloalkylene. In embodiments, L unsubstituted 6 membered heterocycloalkylene. In embodiments, $L^1$ is unsubstituted heterocycloalkylene (e.g., 3 to 6 membered heterocycloalkylene, 4 to 6 membered heterocycloalkylene, or 5 to 6 membered heterocycloalkylene).

In embodiments, $L^1$ is $R^{41}$-substituted or unsubstituted arylene (e.g. $C_6$-$C_{10}$ arylene or $C_6$ arylene). In embodiments, $L^1$ is $R^{41}$-substituted or unsubstituted $C_6$-$C_{10}$ arylene. In embodiments, $L^1$ is $R^{41}$-substituted or unsubstituted $C_6$ arylene. In embodiments, $L^1$ is $R^{41}$-substituted arylene (e.g. $C_6$-$C_{10}$ arylene or $C_6$ arylene). In embodiments, $L^1$ is $R^{41}$-substituted $C_6$-$C_{10}$ arylene. In embodiments, $L^1$ is $R^{41}$-substituted $C_6$ arylene. In embodiments, $L^1$ is unsubstituted $C_6$-$C_{10}$ arylene. In embodiments, $L^1$ is unsubstituted $C_6$ arylene.

In embodiments, $L^1$ is $R^{41}$-substituted or unsubstituted heteroarylene (e.g. 5 to 10 membered heteroarylene, 5 to 9 membered heteroarylene, or 5 to 6 membered heteroarylene). In embodiments, $L^1$ is $R^{41}$-substituted or unsubstituted 5 to 10 membered heteroarylene. In embodiments, $L^1$ is $R^{41}$-substituted or unsubstituted 5 to 9 membered heteroarylene. In embodiments, $L^1$ is $R^{41}$-substituted or unsubstituted 5 to 6 membered heteroarylene. In embodiments, $L^1$ is $R^{41}$-substituted heteroarylene (e.g. 5 to 10 membered heteroarylene, 5 to 9 membered heteroarylene, or 5 to 6 membered heteroarylene). In embodiments, $L^1$ is $R^{41}$-substituted 5 to 10 membered heteroarylene. In embodiments, $L^1$ is $R^{41}$-substituted 5 to 9 membered heteroarylene. In embodiments, $L^1$ is $R^{41}$-substituted 5 to 6 membered heteroarylene. In embodiments, $L^1$ is unsubstituted heteroarylene (e.g. 5 to 10 membered heteroarylene, 5 to 9 membered heteroarylene, or 5 to 6 membered heteroarylene). In embodiments, $L^1$ is unsubstituted 5 to 10 membered heteroarylene. In embodiments, $L^1$ is unsubstituted 5 to 9 membered heteroarylene. In embodiments, $L^1$ is unsubstituted 5 to 6 membered heteroarylene. In embodiments, $L^1$ is $R^{41}$-substituted or unsubstituted indolinylene. In embodiments, $L^1$ is $R^{41}$-substituted or unsubstituted indazolylene. In embodiments, $L^1$ is $R^{41}$-substituted or unsubstituted benzimidazolylene. In embodiments, $L^1$ is $R^{41}$-substituted or unsubstituted benzoxazolylene. In embodiments, $L^1$ is $R^{41}$-substituted or unsubstituted azaindolylene. In embodiments, $L^1$ is $R^{41}$-substituted or unsubstituted purinylene. In embodiments, $L^1$ is $R^{41}$-substituted or unsubstituted indolylene. In embodiments, $L^1$ is $R^{41}$-substituted or unsubstituted pyrazinylene. In embodiments, $L^1$ is $R^{41}$-substituted or unsubstituted pyrrolylene. In embodiments, $L^1$ is $R^{41}$-substituted or unsubstituted imidazolylene. In embodiments, $L^1$ is $R^4$-substituted or unsubstituted pyrazolylene. In embodiments, $L^1$ is $R^{41}$-substituted or unsubstituted triazolylene. In embodiments, $L^1$ is $R^{41}$-substituted or unsubstituted tetrazolylene.

In embodiments, $L^1$ is $R^{41}$-substituted indolinylene. In embodiments, $L^1$ is $R^{41}$-substituted indazolylene. In embodiments, $L^1$ is $R^{41}$-substituted benzimidazolylene. In embodiments, $L^1$ is $R^{41}$-substituted benzoxazolylene. In embodiments, $L^1$ is $R^{41}$-substituted azaindolylene. In embodiments, $L^1$ is $R^{41}$-substituted purinylene. In embodiments, $L^1$ is $R^{41}$-substituted indolylene. In embodiments, $L^1$ is $R^{41}$-substituted pyrazinylene. In embodiments, $L^1$ is $R^{41}$-substituted pyrrolylene. In embodiments, $L^1$ is $R^{41}$-substituted imidazolylene. In embodiments, $L^1$ is $R^{41}$-substituted pyrazolylene. In embodiments, $L^1$ is $R^{41}$-substituted triazolylene. In embodiments, $L^1$ is $R^{41}$-substituted tetrazolylene.

In embodiments, $L^1$ is unsubstituted indolinylene. In embodiments, $L^1$ is unsubstituted indazolylene. In embodiments, $L^1$ is unsubstituted benzimidazolylene. In embodiments, $L^1$ is unsubstituted benzoxazolylene. In embodiments, $L^1$ is unsubstituted azaindolylene. In embodiments, $L^1$ is unsubstituted purinylene. In embodiments, $L^1$ is unsubstituted indolylene. In embodiments, $L^1$ is unsubstituted pyrazinylene. In embodiments, $L^1$ is unsubstituted pyrrolylene. In embodiments, $L^1$ is unsubstituted imidazolylene. In embodiments, $L^1$ is unsubstituted pyrazolylene. In embodiments, $L^1$ is unsubstituted triazolylene. In embodiments, $L^1$ is unsubstituted tetrazolylene.

In embodiments, $R^6$ is independently hydrogen. In embodiments, $R^6$ is independently halogen. In embodiments, $R^6$ is independently $-CX^6_3$. In embodiments, $R^6$ is independently $-CHX^6_2$. In embodiments, $R^6$ is independently $-CH_2X^6$. In embodiments, $R^6$ is independently $-OCX^6_3$. In embodiments, $R^6$ is independently $-OCH_2X^6$. In embodiments, $R^6$ is independently $-OCHX^6_2$. In embodiments, $R^6$ is independently $-CN$. In embodiments, $R^6$ is independently $-SO_{n6}R^{6D}$. In embodiments, $R^6$ is independently $-SO_{v6}NR^{6A}R^{6B}$. In embodiments, $R^6$ is independently $-NHC(O)NR^{6A}R^{6B}$. In embodiments, $R^6$ is independently $-N(O)_{m6}$. In embodiments, $R^6$ is independently $-NR^{6A}R^{6B}$. In embodiments, $R^6$ is independently $-C(O)R^{6C}$. In embodiments, $R^6$ is independently $-C(O)-OR^{6C}$. In embodiments, $R^6$ is independently $-C(O)NR^{6A}R^{6B}$. In embodiments, $R^6$ is independently $-OR^{6D}$. In embodiments, $R^6$ is independently $-NR^{6A}SO_2R^{6D}$. In embodiments, $R^6$ is independently $-NR^{6A}C(O)R^{6C}$. In embodiments, $R^6$ is independently $-NR^{6A}C(O)OR^{6C}$. In embodiments, $R^6$ is independently $-NR^{6A}OR^{6C}$. In embodiments, $R^6$ is independently $-OH$. In embodiments, $R^6$ is independently $-NH_2$. In embodiments, $R^6$ is independently $-COOH$. In embodiments, $R^6$ is independently $-CONH_2$. In embodiments, $R^6$ is independently $-NO_2$. In embodiments, $R^6$ is independently $-SH$.

In embodiments, $R^6$ is independently substituted or unsubstituted alkyl. In embodiments, $R^6$ is independently substituted or unsubstituted heteroalkyl. In embodiments, $R^6$ is independently substituted or unsubstituted cycloalkyl. In embodiments, $R^6$ is independently, substituted or unsubstituted heterocycloalkyl. In embodiments, $R^6$ is independently substituted or unsubstituted aryl. In embodiments, $R^6$ is independently substituted or unsubstituted heteroaryl. In embodiments, $R^6$ is independently substituted alkyl. In embodiments, $R^6$ is independently substituted heteroalkyl. In embodiments, $R^6$ is independently substituted cycloalkyl. In embodiments, $R^6$ is independently, substituted heterocycloalkyl. In embodiments, $R^6$ is independently substituted aryl. In embodiments, $R^6$ is independently substituted heteroaryl. In embodiments, $R^6$ is independently unsubstituted alkyl. In embodiments, $R^6$ is independently unsubstituted heteroalkyl. In embodiments, $R^6$ is independently unsubstituted cycloalkyl. In embodiments, $R^6$ is independently, unsubstituted heterocycloalkyl. In embodiments, $R^6$ is independently unsubstituted aryl. In embodiments, $R^6$ is independently unsubstituted heteroaryl. In embodiments, $R^6$ is independently substituted or unsubstituted $C_1$-$C_8$ alkyl. In embodiments, $R^6$ is independently substituted or unsubstituted 2 to 8 membered heteroalkyl. In embodiments, $R^6$ is independently substituted or unsubstituted $C_3$-$C_8$ cycloalkyl. In embodiments, $R^6$ is independently, substituted or unsubstituted 3 to 8 membered heterocycloalkyl. In embodiments, $R^6$ is independently substituted or unsubstituted $C_6$-$C_{10}$ aryl. In embodiments, $R^6$ is independently substituted or unsubstituted 5 to 10 membered heteroaryl. In embodiments, $R^6$ is independently substituted $C_1$-$C_8$ alkyl. In embodiments, $R^6$ is independently substituted 2 to 8 membered heteroalkyl. In embodiments, $R^6$ is independently substituted $C_3$-$C_8$ cycloalkyl. In embodiments, $R^6$ is independently, substituted 3 to 8 membered heterocycloalkyl. In embodiments, $R^6$ is independently substituted $C_6$-$C_{10}$ aryl. In embodiments, $R^6$ is independently substituted 5 to 10 membered heteroaryl. In embodiments, $R^6$ is independently unsubstituted $C_1$-$C_8$ alkyl. In embodiments, $R^6$ is independently unsubstituted 2 to 8 membered heteroalkyl. In embodiments, $R^6$ is independently unsubstituted $C_3$-$C_8$ cycloalkyl. In embodiments, $R^6$ is independently, unsubstituted 3 to 8 membered heterocycloalkyl. In embodiments, $R^6$ is independently unsubstituted $C_6$-$C_{10}$ aryl. In embodiments, $R^6$ is independently unsubstituted 5 to 10 membered heteroaryl. In embodiments, $R^6$ is independently substituted or unsubstituted $C_1$-$C_4$ alkyl. In embodiments, $R^6$ is independently substituted or unsubstituted 2 to 4 membered heteroalkyl. In embodiments, $R^6$ is independently substituted or unsubstituted $C_3$-$C_6$ cycloalkyl. In embodiments, $R^6$ is independently, substituted or unsubstituted 3 to 6 membered heterocycloalkyl. In embodiments, $R^6$ is independently substituted or unsubstituted phenyl. In embodiments, $R^6$ is independently substituted or unsubstituted 5 to 6 membered heteroaryl. In embodiments, $R^6$ is independently substituted $C_1$-$C_4$ alkyl. In embodiments, $R^6$ is independently substituted 2 to 4 membered heteroalkyl. In embodiments, $R^6$ is independently substituted $C_3$-$C_6$ cycloalkyl. In embodiments, $R^6$ is independently, substituted 3 to 6 membered heterocycloalkyl. In embodiments, $R^6$ is independently substituted phenyl. In embodiments, $R^6$ is independently substituted 5 to 6 membered heteroaryl. In embodiments, $R^6$ is independently unsubstituted $C_1$-$C_4$ alkyl. In embodiments, $R^6$ is independently unsubstituted 2 to 4 membered heteroalkyl. In embodiments, $R^6$ is independently unsubstituted $C_3$-$C_6$ cycloalkyl. In embodiments, $R^6$ is independently unsubstituted 3 to 6 membered heterocycloalkyl. In embodiments, $R^6$ is independently unsubstituted phenyl. In embodiments, $R^6$ is independently unsubstituted 5 to 6 membered heteroaryl.

In embodiments, $R^{6A}$ is independently hydrogen. In embodiments, $R^{6A}$ is independently $-CX^{6A}_3$. In embodiments, $R^{6A}$ is independently $-CHX^{6A2}$. In embodiments, $R^{6A}$ is independently $-CH_2X^{6A}$. In embodiments, $R^{6A}$ is independently —CN. In embodiments, $R^{6A}$ is independently —COOH. In embodiments, $R^{6A}$ is independently —CONH$_2$. In embodiments, $R^{6A}$ is independently substituted or unsubstituted alkyl. In embodiments, $R^{6A}$ is independently substituted or unsubstituted heteroalkyl. In embodiments, $R^{6A}$ is independently substituted or unsubstituted cycloalkyl. In embodiments, $R^{6A}$ is independently, substituted or unsubstituted heterocycloalkyl. In embodiments, $R^{6A}$ is independently substituted or unsubstituted aryl. In embodiments, $R^{6A}$ is independently substituted or unsubstituted heteroaryl. In embodiments, $R^{6A}$ is independently substituted alkyl. In embodiments, $R^{6A}$ is independently substituted heteroalkyl. In embodiments, $R^{6A}$ is independently substituted cycloalkyl. In embodiments, $R^{6A}$ is independently, substituted heterocycloalkyl. In embodiments, $R^{6A}$ is independently substituted aryl. In embodiments, $R^{6A}$ is independently substituted heteroaryl. In embodiments, $R^{6A}$ is independently unsubstituted alkyl. In embodiments, $R^{6A}$ is independently unsubstituted heteroalkyl. In embodiments, $R^{6A}$ is independently unsubstituted cycloalkyl. In embodiments, $R^{6A}$ is independently, unsubstituted heterocycloalkyl. In embodiments, $R^{6A}$ is independently unsubstituted aryl. In embodiments, $R^{6A}$ is independently unsubstituted heteroaryl. In embodiments, $R^{6A}$ is independently substituted or unsubstituted $C_1$-$C_8$ alkyl. In embodiments, $R^{6A}$ is independently substituted or unsubstituted 2 to 8 membered heteroalkyl. In embodiments, $R^{6A}$ is independently substituted or unsubstituted $C_3$-$C_8$ cycloalkyl. In embodiments, $R^{6A}$ is independently, substituted or unsubstituted 3 to 8 membered heterocycloalkyl. In embodiments, $R^{6A}$ is independently substituted or unsubstituted $C_6$-$C_{10}$ aryl. In embodiments, $R^{6A}$ is independently substituted or unsubstituted 5 to 10 membered heteroaryl. In embodiments, $R^{6A}$ is independently substituted $C_1$-$C_8$ alkyl. In embodiments, $R^{6A}$ is independently substituted 2 to 8 membered heteroalkyl. In embodiments, $R^{6A}$ is independently substituted $C_3$-$C_8$ cycloalkyl. In embodiments, $R^{6A}$ is independently, substituted 3 to 8 membered heterocycloalkyl. In embodiments, $R^{6A}$ is independently substituted $C_6$-$C_{10}$ aryl. In embodiments, $R^{6A}$ is independently substituted 5 to 10 membered heteroaryl. In embodiments, $R^{6A}$ is independently unsubstituted $C_1$-$C_8$ alkyl. In embodiments, $R^{6A}$ is independently unsubstituted 2 to 8 membered heteroalkyl. In embodiments, $R^{6A}$ is independently unsubstituted $C_3$-$C_8$ cycloalkyl. In embodiments, $R^{6A}$ is independently, unsubstituted 3 to 8 membered heterocycloalkyl. In embodiments, $R^{6A}$ is independently unsubstituted $C_6$-$C_{10}$ aryl. In embodiments, $R^{6A}$ is independently unsubstituted 5 to 10 membered heteroaryl. In embodiments, $R^{6A}$ is independently substituted or unsubstituted $C_1$-$C_4$ alkyl. In embodiments, $R^{6A}$ is independently substituted or unsubstituted 2 to 4 membered heteroalkyl. In embodiments, $R^{6A}$ is independently substituted or unsubstituted $C_3$-$C_6$ cycloalkyl. In embodiments, $R^{6A}$ is independently, substituted or unsubstituted 3 to 6 membered heterocycloalkyl. In embodiments, $R^{6A}$ is independently substituted or unsubstituted phenyl. In embodiments, $R^{6A}$ is independently substituted or unsubstituted 5 to 6 membered heteroaryl. In embodiments, $R^{6A}$ is independently substituted $C_1$-$C_4$ alkyl. In embodiments, $R^{6A}$ is independently substituted 2 to 4 membered heteroalkyl. In embodiments, $R^{6A}$ is independently substituted $C_3$-$C_6$ cycloalkyl. In embodiments, $R^{6A}$ is independently, substituted 3 to 6 membered heterocycloalkyl. In embodiments, $R^{6A}$ is independently substituted phenyl. In embodiments, $R^{6A}$ is independently substituted 5 to 6 membered heteroaryl. In embodiments, $R^{6A}$ is independently unsubstituted $C_1$-$C_4$ alkyl. In embodiments, $R^{6A}$ is independently unsubstituted 2 to 4 membered heteroalkyl. In embodiments, $R^{6A}$ is independently unsubstituted $C_3$-$C_6$ cycloalkyl. In embodiments, $R^{6A}$ is independently unsubstituted 3 to 6 membered heterocycloalkyl. In embodiments, $R^{6A}$ is independently unsubstituted phenyl. In embodiments, $R^{6A}$ is independently unsubstituted 5 to 6 membered heteroaryl. In embodiments, $R^{6A}$ is independently unsubstituted methyl. In embodiments, $R^{6A}$ is independently unsubstituted ethyl. In embodiments, $R^{6A}$ is independently unsubstituted propyl. In embodiments, $R^{6A}$ is independently unsubstituted isopropyl. In embodiments, $R^{6A}$ is independently unsubstituted tert-butyl.

In embodiments, $R^{6B}$ is independently hydrogen. In embodiments, $R^{6B}$ is independently —$CX^{6B}_3$. In embodiments, $R^{6B}$ is independently —$CHX^{6B}_2$. In embodiments, $R^{6B}$ is independently —$CH_2X^{6B}$. In embodiments, $R^{6B}$ is independently —CN. In embodiments, $R^{6B}$ is independently —COOH. In embodiments, $R^{6B}$ is independently —CONH$_2$. In embodiments, $R^{6B}$ is independently substituted or unsubstituted alkyl. In embodiments, $R^{6B}$ is independently substituted or unsubstituted heteroalkyl. In embodiments, $R^{6B}$ is independently substituted or unsubstituted cycloalkyl. In embodiments, $R^{6B}$ is independently, substituted or unsubstituted heterocycloalkyl. In embodiments, $R^{6B}$ is independently substituted or unsubstituted aryl. In embodiments, $R^{6B}$ is independently substituted or unsubstituted heteroaryl. In embodiments, $R^{6B}$ is independently substituted alkyl. In embodiments, $R^{6B}$ is independently substituted heteroalkyl. In embodiments, $R^{6B}$ is independently substituted cycloalkyl. In embodiments, $R^{6B}$ is independently, substituted heterocycloalkyl. In embodiments, $R^{6B}$ is independently substituted aryl. In embodiments, $R^{6B}$ is independently substituted heteroaryl. In embodiments, $R^{6B}$ is independently unsubstituted alkyl. In embodiments, $R^{6B}$ is independently unsubstituted heteroalkyl. In embodiments, $R^{6B}$ is independently unsubstituted cycloalkyl. In embodiments, $R^{6B}$ is independently, unsubstituted heterocycloalkyl. In embodiments, $R^{6B}$ is independently unsubstituted aryl. In embodiments, $R^{6B}$ is independently unsubstituted heteroaryl. In embodiments, $R^{6B}$ is independently substituted or unsubstituted $C_1$-$C_8$ alkyl. In embodiments, $R^{6B}$ is independently substituted or unsubstituted 2 to 8 membered heteroalkyl. In embodiments, $R^{6B}$ is independently substituted or unsubstituted $C_3$-$C_8$ cycloalkyl. In embodiments, $R^{6B}$ is independently, substituted or unsubstituted 3 to 8 membered heterocycloalkyl. In embodiments, $R^{6B}$ is independently substituted or unsubstituted $C_6$-$C_{10}$ aryl. In embodiments, $R^{6B}$ is independently substituted or unsubstituted 5 to 10 membered heteroaryl. In embodiments, $R^{6B}$ is independently substituted $C_1$-$C_8$ alkyl. In embodiments, $R^{6B}$ is independently substituted 2 to 8 membered heteroalkyl. In embodiments, $R^{6B}$ is independently substituted $C_3$-$C_8$ cycloalkyl. In embodiments, $R^{6B}$ is independently, substituted 3 to 8 membered heterocycloalkyl. In embodiments, $R^{6B}$ is independently substituted $C_6$-$C_{10}$ aryl. In embodiments, $R^{6B}$ is independently substituted 5 to 10 membered heteroaryl. In embodiments, $R^{6B}$ is independently unsubstituted $C_1$-$C_8$ alkyl. In embodiments, $R^{6B}$ is independently unsubstituted 2 to 8 membered heteroalkyl. In embodiments, $R^{6B}$ is independently unsubstituted $C_3$-$C_8$ cycloalkyl. In embodiments, $R^{6B}$ is independently, unsubstituted 3 to 8 membered heterocycloalkyl. In embodiments, $R^{6B}$ is independently unsubstituted $C_6$-$C_{10}$ aryl. In embodiments, $R^{6B}$ is independently unsubstituted 5 to 10 membered heteroaryl. In embodiments, $R^{6B}$ is independently substituted or unsubstituted $C_1$-$C_4$ alkyl. In embodiments, $R^{6B}$ is independently substituted or unsubstituted 2 to 4 membered heteroalkyl. In embodiments, $R^{6B}$ is independently substituted or unsubstituted $C_3$-$C_6$ cycloalkyl. In embodiments, $R^{6B}$ is independently, substituted or unsubstituted 3 to 6 membered heterocycloalkyl. In embodiments, $R^{6B}$ is independently substituted or unsubstituted phenyl. In embodiments, $R^{6B}$ is independently substituted or unsubstituted 5 to 6 membered heteroaryl. In embodiments, $R^{6B}$ is independently substituted $C_1$-$C_4$ alkyl. In embodiments, $R^{6B}$ is independently substituted 2 to 4 membered heteroalkyl. In embodiments, $R^{6B}$ is independently substituted $C_3$-$C_6$ cycloalkyl. In embodiments, $R^{6B}$ is independently, substituted 3 to 6 membered heterocycloalkyl. In embodiments, $R^{6B}$ is independently substituted phenyl. In embodiments, $R^{6B}$ is independently substituted 5 to 6 membered heteroaryl. In embodiments, $R^{6B}$ is independently unsubstituted $C_1$-$C_4$ alkyl. In embodiments, $R^{6B}$ is independently unsubstituted 2 to 4 membered heteroalkyl. In embodiments, $R^{6B}$ is independently unsubstituted $C_3$-$C_6$ cycloalkyl. In embodiments, $R^{6B}$ is independently unsubstituted 3 to 6 membered heterocycloalkyl. In embodiments, $R^{6B}$ is independently unsubstituted phenyl. In embodiments, $R^{6B}$ is independently unsubstituted 5 to 6 membered heteroaryl. In embodiments, $R^{6B}$ is independently unsubstituted methyl. In embodiments, $R^{6B}$ is independently unsubstituted ethyl. In embodiments, $R^{6B}$ is independently unsubstituted propyl. In embodiments, $R^{6B}$ is independently unsubstituted isopropyl. In embodiments, $R^{6B}$ is independently unsubstituted tert-butyl.

In embodiments, $R^{6A}$ and $R^{6B}$ substituents bonded to the same nitrogen atom may be joined to form a substituted or unsubstituted heterocycloalkyl. In embodiments, $R^{6A}$ and $R^{6B}$ substituents bonded to the same nitrogen atom may be joined to form a substituted or unsubstituted heteroaryl. In embodiments, $R^{6A}$ and $R^{6B}$ substituents bonded to the same nitrogen atom may be joined to form a substituted heterocycloalkyl. In embodiments, $R^{6A}$ and $R^{6B}$ substituents bonded to the same nitrogen atom may be joined to form a substituted heteroaryl. In embodiments, $R^{6A}$ and $R^{6B}$ substituents bonded to the same nitrogen atom may be joined to form an unsubstituted heterocycloalkyl. In embodiments, $R^{6A}$ and $R^{6B}$ substituents bonded to the same nitrogen atom may be joined to form an unsubstituted heteroaryl. In embodiments, $R^{6A}$ and $R^{6B}$ substituents bonded to the same nitrogen atom may be joined to forma substituted or unsubstituted 3 to 8 membered heterocycloalkyl. In embodiments, $R^{6A}$ and $R^{6B}$ substituents bonded to the same nitrogen atom may be joined to form a substituted or unsubstituted 5 to 10 membered heteroaryl. In embodiments, $R^{6A}$ and $R^{6B}$ substituents bonded to the same nitrogen atom may be joined to form a substituted 3 to 8 membered heterocycloalkyl. In embodiments, $R^{6A}$ and $R^{6B}$ substituents bonded to the same nitrogen atom may be joined to form a substituted 5 to 10 membered heteroaryl. In embodiments, $R^{6A}$ and $R^{6B}$ substituents bonded to the same nitrogen atom may be joined to form an unsubstituted 3 to 8 membered heterocycloalkyl. In embodiments, $R^{6A}$ and $R^{6B}$ substituents bonded to the same nitrogen atom may be joined to form an unsubstituted 5 to 10 membered heteroaryl. In embodiments, $R^{6A}$ and $R^{6B}$ substituents bonded to the same nitrogen atom may be joined to form a substituted or unsubstituted 3 to 6 membered heterocycloalkyl. In embodiments, $R^{6A}$ and $R^{6B}$ substituents bonded to the same nitrogen atom may be joined to form a substituted or unsubstituted 5 to 6 membered heteroaryl. In embodiments, $R^{6A}$ and $R^{6B}$ substituents bonded to the same nitrogen atom may be joined to form a substituted 3 to 6 membered heterocycloalkyl. In embodiments, $R^{6A}$ and $R^{6B}$ substituents bonded to the same nitrogen atom may be joined to form a substituted 5 to 6 membered heteroaryl. In embodiments, $R^{6A}$ and $R^{6B}$ substituents bonded to the same nitrogen atom may be joined to form an unsubstituted 3 to 6 membered heterocycloalkyl. In embodiments, $R^{6A}$ and $R^{6B}$ substituents bonded to the same nitrogen atom may be joined to form an unsubstituted 5 to 6 membered heteroaryl.

In embodiments, $R^{6C}$ is independently hydrogen. In embodiments, $R^{6C}$ is independently —$CX^{6C}_3$. In embodiments, $R^{6C}$ is independently —$CHX^{6C}_2$. In embodiments, $R^{6C}$ is independently —$CH_2X^{6C}$. In embodiments, $R^{6C}$ is independently —CN. In embodiments, $R^{6C}$ is independently —COOH. In embodiments, $R^{6C}$ is independently —$CONH_2$. In embodiments, $R^{6C}$ is independently substituted or unsubstituted alkyl. In embodiments, $R^{6C}$ is independently substituted or unsubstituted heteroalkyl. In embodiments, $R^{6C}$ is independently substituted or unsubstituted cycloalkyl. In embodiments, $R^{6C}$ is independently, substituted or unsubstituted heterocycloalkyl. In embodiments, $R^{6C}$ is independently substituted or unsubstituted aryl. In embodiments, $R^{6C}$ is independently substituted or unsubstituted heteroaryl. In embodiments, $R^{6C}$ is independently substituted alkyl. In embodiments, $R^{6C}$ is independently substituted heteroalkyl. In embodiments, $R^{6C}$ is independently substituted cycloalkyl. In embodiments, $R^{6C}$ is independently, substituted heterocycloalkyl. In embodiments, $R^{6C}$ is independently substituted aryl. In embodiments, $R^{6C}$ is independently substituted heteroaryl. In embodiments, $R^{6C}$ is independently unsubstituted alkyl. In embodiments, $R^{6C}$ is independently unsubstituted heteroalkyl. In embodiments, $R^{6C}$ is independently unsubstituted cycloalkyl. In embodiments, $R^{6C}$ is independently, unsubstituted heterocycloalkyl. In embodiments, $R^{6C}$ is independently unsubstituted aryl. In embodiments, $R^{6C}$ is independently unsubstituted heteroaryl. In embodiments, $R^{6C}$ is independently substituted or unsubstituted $C_1$-$C_8$ alkyl. In embodiments, $R^{6C}$ is independently substituted or unsubstituted 2 to 8 membered heteroalkyl. In embodiments, $R^{6C}$ is independently substituted or unsubstituted $C_3$-$C_8$ cycloalkyl. In embodiments, $R^{6C}$ is independently, substituted or unsubstituted 3 to 8 membered heterocycloalkyl. In embodiments, $R^{6C}$ is independently substituted or unsubstituted $C_6$-$C_{10}$ aryl. In embodiments, $R^{6C}$ is independently substituted or unsubstituted 5 to 10 membered heteroaryl. In embodiments, $R^{6C}$ is independently substituted $C_1$-$C_8$ alkyl. In embodiments, $R^{6C}$ is independently substituted 2 to 8 membered heteroalkyl. In embodiments, $R^{6C}$ is independently substituted $C_3$-$C_8$ cycloalkyl. In embodiments, $R^{6C}$ is independently, substituted 3 to 8 membered heterocycloalkyl. In embodiments, $R^{6C}$ is independently substituted $C_6$-$C_{10}$ aryl. In embodiments, $R^{6C}$ is independently substituted 5 to 10 membered heteroaryl. In embodiments, $R^{6C}$ is independently unsubstituted $C_1$-$C_8$ alkyl. In embodiments, $R^{6C}$ is independently unsubstituted 2 to 8 membered heteroalkyl. In embodiments, $R^{6C}$ is independently unsubstituted $C_3$-$C_8$ cycloalkyl. In embodiments, $R^{6C}$ is independently, unsubstituted 3 to 8 membered heterocycloalkyl. In embodiments, $R^{6C}$ is independently unsubstituted $C_6$-$C_{10}$ aryl. In embodiments, $R^{6C}$ is independently unsubstituted 5 to 10 membered heteroaryl. In embodiments, $R^{6C}$ is independently substituted or unsubstituted $C_1$-$C_4$ alkyl. In embodiments, $R^{6C}$ is independently substituted or unsubstituted 2 to 4 membered heteroalkyl. In embodiments, $R^{6C}$ is independently substituted or unsubstituted $C_3$-$C_6$ cycloalkyl. In embodiments, $R^{6C}$ is independently, substituted or unsubstituted 3 to 6 membered heterocycloalkyl. In embodiments, $R^{6C}$ is independently substituted or unsubstituted phenyl. In embodiments, $R^{6C}$ is independently substituted or unsubstituted 5 to 6 membered heteroaryl. In embodiments, $R^{6C}$ is independently substituted $C_1$-$C_4$ alkyl. In embodiments, $R^{6C}$ is independently substituted 2 to 4 membered heteroalkyl. In embodiments, $R^{6C}$ is independently substituted $C_3$-$C_6$ cycloalkyl. In embodiments, $R^{6C}$ is independently, substituted 3 to 6 membered heterocycloalkyl. In embodiments, $R^{6C}$ is independently substituted phenyl. In embodiments, $R^{6C}$ is independently substituted 5 to 6 membered heteroaryl. In embodiments, $R^{6C}$ is independently unsubstituted $C_1$-$C_4$ alkyl. In embodiments, $R^{6C}$ is independently unsubstituted 2 to 4 membered heteroalkyl. In embodiments, $R^{6C}$ is independently unsubstituted $C_3$-$C_6$ cycloalkyl. In embodiments, $R^{6C}$ is independently unsubstituted 3 to 6 membered heterocycloalkyl. In embodiments, $R^{6C}$ is independently unsubstituted phenyl. In embodiments, $R^{6C}$ is independently unsubstituted 5 to 6 membered heteroaryl. In embodiments, $R^{6C}$ is independently unsubstituted methyl. In embodiments, $R^{6C}$ is independently unsubstituted ethyl. In embodiments, $R^{6C}$ is independently unsubstituted propyl. In embodiments, $R^{6C}$ is independently unsubstituted isopropyl. In embodiments, $R^{6C}$ is independently unsubstituted tert-butyl.

In embodiments, $R^{6D}$ is independently hydrogen. In embodiments, $R^{6D}$ is independently —$CX^{6D}_3$. In embodiments, $R^{6D}$ is independently —$CHX^{6D}_2$. In embodiments, $R^{6D}$ is independently —$CH_2X^{6D}$. In embodiments, $R^{6D}$ is independently —CN. In embodiments, $R^{6D}$ is independently —COOH. In embodiments, $R^{6D}$ is independently —$CONH_2$. In embodiments, $R^{6D}$ is independently substituted or unsubstituted alkyl. In embodiments, $R^{6D}$ is independently substituted or unsubstituted heteroalkyl. In embodiments, $R^{6D}$ is independently substituted or unsubstituted cycloalkyl. In embodiments, $R^{6D}$ is independently, substituted or unsubstituted heterocycloalkyl. In embodiments, $R^{6D}$ is independently substituted or unsubstituted aryl. In embodiments, $R^{6D}$ is independently substituted or unsubstituted heteroaryl. In embodiments, $R^{6D}$ is independently substituted alkyl. In embodiments, $R^{6D}$ is independently substituted heteroalkyl. In embodiments, $R^{6D}$ is independently substituted cycloalkyl. In embodiments, $R^{6D}$ is independently, substituted heterocycloalkyl. In embodiments, $R^{6D}$ is independently substituted aryl. In embodiments, $R^{6D}$ is independently substituted heteroaryl. In embodiments, $R^{6D}$ is independently unsubstituted alkyl. In embodiments, $R^{6D}$ is independently unsubstituted heteroalkyl. In embodiments, $R^{6D}$ is independently unsubstituted cycloalkyl. In embodiments, $R^{6D}$ is independently, unsubstituted heterocycloalkyl. In embodiments, $R^{6D}$ is independently unsubstituted aryl. In embodiments, $R^{6D}$ is independently unsubstituted heteroaryl. In embodiments, $R^{6D}$ is independently substituted or unsubstituted $C_1$-$C_8$ alkyl. In embodiments, $R^{6D}$ is independently substituted or unsubstituted 2 to 8 membered heteroalkyl. In embodiments, $R^{6D}$ is independently substituted or unsubstituted $C_3$-$C_8$ cycloalkyl. In embodiments, $R^{6D}$ is independently, substituted or unsubstituted 3 to 8 membered heterocycloalkyl. In embodiments, $R^{6D}$ is independently substituted or unsubstituted $C_6$-$C_{10}$ aryl. In embodiments, $R^{6D}$ is independently substituted or unsubstituted 5 to 10 membered heteroaryl. In embodiments, $R^{6D}$ is independently substituted $C_1$-$C_8$ alkyl. In embodiments, $R^{6D}$ is independently substituted 2 to 8 membered heteroalkyl. In embodiments, $R^{6D}$ is independently substituted $C_3$-$C_8$ cycloalkyl. In embodiments, $R^{6D}$ is independently, substituted 3 to 8 membered heterocycloalkyl. In embodiments, $R^{6D}$ is independently substituted $C_6$-$C_{10}$ aryl. In embodiments, $R^{6D}$ is independently substituted 5 to 10 membered heteroaryl. In embodiments, $R^{6D}$ is independently unsubstituted $C_1$-$C_8$ alkyl. In embodiments, $R^{6D}$ is independently unsubstituted 2 to 8 membered heteroalkyl. In embodiments, $R^{6D}$ is independently unsubstituted $C_3$-$C_8$ cycloalkyl. In embodiments, $R^{6D}$ is independently, unsubstituted 3 to 8 membered heterocycloalkyl. In embodiments, $R^{6D}$ is independently unsubstituted $C_6$-$C_{10}$ aryl. In embodiments, $R^{6D}$ is independently unsubstituted 5 to 10 membered heteroaryl. In embodiments, $R^{6D}$ is independently substituted or unsubstituted $C_1$-$C_4$ alkyl. In embodiments, $R^{6D}$ is independently substituted or unsubstituted 2 to 4 membered heteroalkyl. In embodiments, $R^{6D}$ is independently substituted or unsubstituted $C_3$-$C_6$ cycloalkyl. In embodiments, $R^{6D}$ is independently, substituted or unsubstituted 3 to 6 membered heterocycloalkyl. In embodiments, $R^{6D}$ is independently substituted or unsubstituted phenyl. In embodiments, $R^{6D}$ is independently substituted or unsubstituted 5 to 6 membered heteroaryl. In embodiments, $R^{6D}$ is independently substituted $C_1$-$C_4$ alkyl. In embodiments, $R^{6D}$ is independently substituted 2 to 4 membered heteroalkyl. In embodiments, $R^{6D}$ is independently substituted $C_3$-$C_6$ cycloalkyl. In embodiments, $R^{6D}$ is independently, substituted 3 to 6 membered heterocycloalkyl. In embodiments, $R^{6D}$ is independently substituted phenyl. In embodiments, $R^{6D}$ is independently substituted 5 to 6 membered heteroaryl. In embodiments, $R^{6D}$ is independently unsubstituted $C_1$-$C_4$ alkyl. In embodiments, $R^{6D}$ is independently unsubstituted 2 to 4 membered heteroalkyl. In embodiments, $R^{6D}$ is independently unsubstituted $C_3$-$C_6$ cycloalkyl. In embodiments, $R^{6D}$ is independently unsubstituted 3 to 6 membered heterocycloalkyl. In embodiments, $R^{6D}$ is independently unsubstituted phenyl. In embodiments, $R^{6D}$ is independently unsubstituted 5 to 6 membered heteroaryl. In embodiments, $R^{6D}$ is independently unsubstituted methyl. In embodiments, $R^{6D}$ is independently unsubstituted ethyl. In embodiments, $R^{6D}$ is independently unsubstituted propyl. In embodiments, $R^{6D}$ is independently unsubstituted isopropyl. In embodiments, $R^{6D}$ is independently unsubstituted tert-butyl.

In embodiments, $R^6$ is independently hydrogen, halogen, —$CX^6_3$, —$CHX^6_2$, —$CH_2X^6$, —$OCX^6_3$, —$OCH_2X^6$, —$OCHX^6_2$, —CN, —$SO_{n6}R^{6D}$, —$SO_{v6}NR^{6A}R^{6B}$, —$NHC(O)NR^{6A}R^{6B}$, —$N(O)_{m6}$, —$NR^{6A}R^{6B}$, —$C(O)R^{6C}$, —$C(O)OR^{6C}$, —$C(O)NR^{6A}R^{6B}$, —$OR^{6D}$, —$NR^{6A}SO_2R^{6D}$, —$NR^{6A}C(O)R^{6C}$, —$NR^{6A}C(O)OR^{6C}$, —$NR^{6A}OR^{6C}$, $R^{35}$-substituted or unsubstituted alkyl, $R^{35}$-substituted or unsubstituted heteroalkyl, $R^{35}$-substituted or unsubstituted cycloalkyl, $R^{35}$-substituted or unsubstituted heterocycloalkyl, $R^{35}$-substituted or unsubstituted aryl, or $R^{35}$-substituted or unsubstituted heteroaryl. In embodiments, $R^6$ is independently halogen, —$CX^6_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH$_2$, —$NHC(O)NH_2$, —$NHSO_2H$, —NHC(O)H, —NHC(O)OH, —NHOH, —$OCX^6_3$, —$OCHX^6_2$, $R^{35}$-substituted or unsubstituted alkyl, $R^{35}$-substituted or unsubstituted heteroalkyl, $R^{35}$-substituted or unsubstituted cycloalkyl, $R^{35}$-substituted or unsubstituted heterocycloalkyl, $R^{35}$-substituted or unsubstituted aryl, or $R^{35}$-substituted or unsubstituted heteroaryl. In embodiments, $R^6$ is independently halogen, —$CX^6_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH$_2$, —NHC(O)NH$_2$, —$NHSO_2H$, —NHC(O)H, —NHC(O)OH, —NHOH, —$OCX^6_3$, —$OCHX^6_2$, $R^{35}$-substituted or unsubstituted $C_1$-$C_8$ alkyl, $R^{35}$-substituted or unsubstituted 2 to 8 membered heteroalkyl, $R^{35}$-substituted or unsubstituted $C_3$-$C_8$ cycloalkyl, $R^{35}$-substituted or unsubstituted 3 to 6 membered heterocycloalkyl, $R^{35}$-substituted or unsubstituted phenyl, or $R^{35}$-substituted or unsubstituted 5 to 6 membered heteroaryl. $X^6$ is —F, —Cl, —Br, or —I. In embodiments, $R^6$ is independently hydrogen. In embodiments, $R^6$ is independently methyl. In embodiments, $R^6$ is independently ethyl.

$R^{35}$ is independently oxo, halogen, —$CX^{35}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{35}_3$, —$OCHX^{35}_2$, $R^{36}$-substituted or unsubstituted alkyl, $R^{36}$-substituted or unsubstituted heteroalkyl, $R^{36}$-substituted or unsubstituted cycloalkyl, $R^{36}$-substituted or unsubstituted heterocycloalkyl, $R^{36}$-substituted or unsubstituted aryl, or $R^{36}$-substituted or unsubstituted heteroaryl. In embodiments, $R^{35}$ is independently oxo, halogen, —$CX^{35}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{35}_3$, —$OCHX^{35}_2$, $R^{36}$-substituted or unsubstituted $C_1$-$C_8$ alkyl, $R^{36}$-substituted or unsubstituted 2 to 8 membered heteroalkyl, $R^{36}$-substituted or unsubstituted $C_3$-$C_8$ cycloalkyl, $R^{36}$-substituted or unsubstituted 3 to 6 membered heterocycloalkyl, $R^{36}$-substituted or unsubstituted phenyl, or $R^{36}$-substituted or unsubstituted 5 to 6 membered heteroaryl. $X^{35}$ is —F, —Cl, —Br, or —I.

$R^{36}$ is independently oxo, halogen, —$CX^{36}_3$, —CN, —OH, —$NH_2$, —COOH, —$CONH_2$, —$NO_2$, —SH, —$S_3H$, —$SO_4H$, —$S_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{36}_3$, —$OCHX^{36}_2$, $R^{37C}$-substituted or unsubstituted alkyl, $R^{37C}$-substituted or unsubstituted heteroalkyl, $R^{37C}$-substituted or unsubstituted cycloalkyl, $R^{37C}$-substituted or unsubstituted heterocycloalkyl, $R^{37C}$-substituted or unsubstituted aryl, or $R^{37C}$-substituted or unsubstituted heteroaryl. In embodiments, $R^{36}$ is independently oxo, halogen, —$CX^{36}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{36}_3$, —$OCHX^{36}_2$, $R^{37C}$-substituted or unsubstituted $C_1$-$C_8$ alkyl, $R^{37C}$-substituted or unsubstituted 2 to 8 membered heteroalkyl, $R^{37C}$-substituted or unsubstituted $C_3$-$C_8$ cycloalkyl, $R^{37C}$-substituted or unsubstituted 3 to 6 membered heterocycloalkyl, $R^{37C}$-substituted or unsubstituted phenyl, or $R^{37C}$-substituted or unsubstituted 5 to 6 membered heteroaryl. $X^{36}$ is —F, —Cl, —Br, or —I.

In embodiments, $R^{6A}$ is independently hydrogen, —$CX^{6A}_3$, —CN, —COOH, —$CONH_2$, —$CHX^{6A}_2$, —$CH_2X^{6A}$, $R^{35A}$-substituted or unsubstituted alkyl, $R^{35A}$-substituted or unsubstituted heteroalkyl, $R^{35A}$-substituted or unsubstituted cycloalkyl, $R^{35A}$-substituted or unsubstituted heterocycloalkyl, $R^{35A}$-substituted or unsubstituted aryl, or $R^{35A}$-substituted or unsubstituted heteroaryl. In embodiments, $R^{6A}$ is independently hydrogen, —$CX^{6A}_3$, —CN, —COOH, —$CONH_2$, —$CHX^{6A}_2$, —$CH_2X^{6A}$, $R^{35A}$-substituted or unsubstituted $C_1$-$C_8$ alkyl, $R^{35A}$-substituted or unsubstituted 2 to 8 membered heteroalkyl, $R^{35A}$-substituted or unsubstituted $C_3$-$C_8$ cycloalkyl, $R^{35A}$-substituted or unsubstituted 3 to 6 membered heterocycloalkyl, $R^{35A}$-substituted or unsubstituted phenyl, or $R^{35A}$-substituted or unsubstituted 5 to 6 membered heteroaryl. $X^{6A}$ is —F, —Cl, —Br, or —I. In embodiments, $R^{6A}$ is independently hydrogen. In embodiments, $R^{6A}$ is independently methyl. In embodiments, $R^{6A}$ is independently ethyl.

In embodiments, $R^{6A}$ and $R^{6B}$ substituents bonded to the same nitrogen atom may optionally be joined to form a $R^{35A}$-substituted or unsubstituted heterocycloalkyl or $R^{35A}$-substituted or unsubstituted heteroaryl. In embodiments, $R^{6A}$ and $R^{6B}$ substituents bonded to the same nitrogen atom may optionally be joined to form a $R^{35A}$-substituted or unsubstituted 3 to 6 membered heterocycloalkyl or $R^{35A}$-substituted or unsubstituted 5 to 6 membered heteroaryl.

$R^{35A}$ is independently oxo, halogen, —$CX^{35A}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{35A}_3$, —$OCHX^{35A}_2$, $R^{36A}$-substituted or unsubstituted alkyl, $R^{36A}$-substituted or unsubstituted heteroalkyl, $R^{36A}$-substituted or unsubstituted cycloalkyl, $R^{36A}$-substituted or unsubstituted heterocycloalkyl, $R^{36A}$-substituted or unsubstituted aryl, or $R^{36A}$-substituted or unsubstituted heteroaryl. In embodiments, $R^{35A}$ is independently oxo, halogen, —$CX^{35A}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{35A}_3$, —$OCHX^{35A}_2$, $R^{36A}$-substituted or unsubstituted $C_1$-$C_8$ alkyl, $R^{36A}$-substituted or unsubstituted 2 to 8 membered heteroalkyl, $R^{36A}$-substituted or unsubstituted $C_3$-$C_8$ cycloalkyl, $R^{36A}$-substituted or unsubstituted 3 to 6 membered heterocycloalkyl, $R^{36A}$-substituted or unsubstituted phenyl, or $R^{36A}$-substituted or unsubstituted 5 to 6 membered heteroaryl. $X^{35A}$ is —F, —Cl, —Br, or —I.

$R^{36A}$ is independently oxo, halogen, —$CX^{36A}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{36A}_3$, —$OCHX^{36A}_2$, $R^{37A}$-substituted or unsubstituted alkyl, $R^{37A}$-substituted or unsubstituted heteroalkyl, $R^{37A}$-substituted or unsubstituted cycloalkyl, $R^{37A}$-substituted or unsubstituted heterocycloalkyl, $R^{37A}$-substituted or unsubstituted aryl, or $R^{37A}$-substituted or unsubstituted heteroaryl. In embodiments, $R^{36A}$ is independently oxo, halogen, —$CX^{36A}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{36A}_3$, —$OCHX^{36A}_2$, $R^{37A}$-substituted or unsubstituted $C_1$-$C_8$ alkyl, $R^{37A}$-substituted or unsubstituted 2 to 8 membered heteroalkyl, $R^{37A}$-substituted or unsubstituted $C_3$-$C_8$ cycloalkyl, $R^{37A}$-substituted or unsubstituted 3 to 6 membered heterocycloalkyl, $R^{37A}$-substituted or unsubstituted phenyl, or $R^{37A}$-substituted or unsubstituted 5 to 6 membered heteroaryl. $X^{36A}$ is —F, —Cl, —Br, or —I.

In embodiments, $R^{6B}$ is independently hydrogen, —$CX^{6B}_3$, —CN, —COOH, —$CONH_2$, —$CHX^{6B}_2$, —$CH_2X^{6B}$, $R^{35B}$-substituted or unsubstituted alkyl, $R^{35B}$-substituted or unsubstituted heteroalkyl, $R^{35B}$-substituted or unsubstituted cycloalkyl, $R^{35B}$-substituted or unsubstituted heterocycloalkyl, $R^{35B}$-substituted or unsubstituted aryl, or $R^{35B}$-substituted or unsubstituted heteroaryl. In embodiments, $R^{6B}$ is independently hydrogen, —$CX^{6B}_3$, —CN, —COOH, —$CONH_2$, —$CHX^{6B}_2$, —$CH_2X^{6B}$, $R^{35B}$-substituted or unsubstituted $C_1$-$C_8$ alkyl, $R^{35B}$-substituted or unsubstituted 2 to 8 membered heteroalkyl, $R^{35B}$-substituted or unsubstituted $C_3$-$C_8$ cycloalkyl, $R^{35B}$-substituted or unsubstituted 3 to 6 membered heterocycloalkyl, $R^{35B}$-substituted or unsubstituted phenyl, or $R^{35B}$-substituted or unsubstituted 5 to 6 membered heteroaryl. $X^{6B}$ is —F, —Cl, —Br, or —I. In embodiments, $R^{6B}$ is independently hydrogen. In embodiments, $R^{6B}$ is independently methyl. In embodiments, $R^{6B}$ is independently ethyl.

In embodiments, $R^{6A}$ and $R^{6B}$ substituents bonded to the same nitrogen atom may optionally be joined to form a $R^{35B}$-substituted or unsubstituted heterocycloalkyl or $R^{35B}$-substituted or unsubstituted heteroaryl. In embodiments, $R^{6A}$ and $R^{6B}$ substituents bonded to the same nitrogen atom may optionally be joined to form a $R^{35B}$-substituted or unsubstituted 3 to 6 membered heterocycloalkyl or $R^{35B}$-substituted or unsubstituted 5 to 6 membered heteroaryl.

$R^{35B}$ is independently oxo, halogen, —$CX^{35B}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{35B}_3$, —$OCHX^{35B}_2$, $R^{36B}$-substituted or unsubstituted alkyl, $R^{36B}$-substituted or unsubstituted heteroalkyl, $R^{36B}$-substituted or unsubstituted cycloalkyl, $R^{36B}$-substituted or unsubstituted heterocycloalkyl, $R^{36B}$-substituted or unsubstituted aryl, or $R^{36B}$-substituted or unsubstituted heteroaryl. In embodiments, $R^{35B}$ is independently oxo, halogen, —$CX^{35B}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{35B}_3$, —$OCHX^{35B}_2$, $R^{36B}$-substituted or unsubstituted $C_1$-$C_8$ alkyl, $R^{36B}$-substituted or unsubstituted 2 to 8 membered heteroalkyl, $R^{36B}$-substituted or unsubstituted $C_3$-$C_8$ cycloalkyl, $R^{36B}$-substituted or unsubstituted 3 to 6 membered heterocycloalkyl, $R^{36B}$-substituted or unsubstituted phenyl, or $R^{36B}$-substituted or unsubstituted 5 to 6 membered heteroaryl. $X^{35B}$ is —F, —Cl, —Br, or —I.

$R^{36B}$ is independently oxo, halogen, —$CX^{36B}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{36B}_3$, —$OCHX^{36B}_2$, $R^{37B}$-substituted or unsubstituted alkyl, $R^{37B}$-substituted or unsubstituted heteroalkyl, $R^{37B}$-substituted or unsubstituted cycloalkyl, $R^{37B}$-substituted or unsubstituted heterocycloalkyl, $R^{37B}$-substituted or unsubstituted aryl, or $R^{37B}$-substituted or unsubstituted heteroaryl. In embodiments, $R^{36B}$ is independently oxo, halogen, —$CX^{36B}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{36B}_3$, —$OCHX^{36B}_2$, $R^{37B}$-substituted or unsubstituted $C_1$-$C_8$ alkyl, $R^{37B}$-substituted or unsubstituted 2 to 8 membered heteroalkyl, $R^{37B}$-substituted or unsubstituted $C_3$-$C_8$ cycloalkyl, $R^{37B}$-substituted or unsubstituted 3 to 6 membered heterocycloalkyl, $R^{37B}$-substituted or unsubstituted phenyl, or $R^{37B}$-substituted or unsubstituted 5 to 6 membered heteroaryl. $X^{36B}$ is —F, —Cl, —Br, or —I.

In embodiments, $R^{6C}$ is independently hydrogen, —$CX^{6C}_3$, —CN, —COOH, —$CONH_2$, —$CHX^{62}$, —$CH_2X^{6C}$, $R^{35C}$-substituted or unsubstituted alkyl, $R^{35C}$-substituted or unsubstituted heteroalkyl, $R^{35C}$-substituted or unsubstituted cycloalkyl, $R^{35C}$-substituted or unsubstituted heterocycloalkyl, $R^{35C}$-substituted or unsubstituted aryl, or $R^{35C}$-substituted or unsubstituted heteroaryl. In embodiments, $R^{6C}$ is independently hydrogen, —$CX^{6C}_3$, —CN, —COOH, —$CONH_2$, —$CHX^{62}$, —$CH_2X^{6C}$, $R^{35C}$-substituted or unsubstituted $C_1$-$C_8$ alkyl, $R^{35C}$-substituted or unsubstituted 2 to 8 membered heteroalkyl, $R^{35C}$-substituted or unsubstituted $C_3$-$C_8$ cycloalkyl, $R^{35C}$-substituted or unsubstituted 3 to 6 membered heterocycloalkyl, $R^{35C}$-substituted or unsubstituted phenyl, or $R^{35C}$-substituted or unsubstituted 5 to 6 membered heteroaryl. $X^{6C}$ is —F, —Cl, —Br, or —I. In embodiments, $R^{6C}$ is independently hydrogen. In embodiments, $R^{6C}$ is independently methyl. In embodiments, $R^{6C}$ is independently ethyl.

$R^{35C}$ is independently oxo, halogen, —$CX^{35C}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{35C}_3$, —$OCHX^{35}_2$, $R^{36C}$-substituted or unsubstituted alkyl, $R^{36C}$-substituted or unsubstituted heteroalkyl, $R^{36C}$-substituted or unsubstituted cycloalkyl, $R^{36C}$-substituted or unsubstituted heterocycloalkyl, $R^{36C}$-substituted or unsubstituted aryl, or $R^{36C}$-substituted or unsubstituted heteroaryl. In embodiments, $R^{35C}$ is independently oxo, halogen, —$CX^{35C}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{35C}_3$, $OCHX^{35C}_2$, $R^{36C}$-substituted or unsubstituted $C_1$-$C_8$ alkyl, $R^{36}$-substituted or unsubstituted 2 to 8 membered heteroalkyl, $R^{36C}$-substituted or unsubstituted $C_3$-$C_8$ cycloalkyl, $R^{36C}$-substituted or unsubstituted 3 to 6 membered heterocycloalkyl, $R^{36}$-substituted or unsubstituted phenyl, or $R^{36C}$-substituted or unsubstituted 5 to 6 membered heteroaryl. $X^{35C}$ is —F, —Cl, —Br, or —I.

$R^{36C}$ is independently oxo, halogen, —$CX^{36}_3$, —CN, —OH, —$NH_2$, —COOH, —$CONH_2$, —$NO_2$, —SH, —$SO_3H$, —$SO_4H$, —$S_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{36C}_3$, —$OCHX^{36}_2$, $R^{37C}$-substituted or unsubstituted alkyl, $R^{37C}$-substituted or unsubstituted heteroalkyl, $R^{37C}$-substituted or unsubstituted cycloalkyl, $R^{37C}$-substituted or unsubstituted heterocycloalkyl, $R^{37C}$-substituted or unsubstituted aryl, or $R^{37C}$-substituted or unsubstituted heteroaryl. In embodiments, $R^{36C}$ is independently oxo, halogen, —$CX^{36}_3$, —CN, —OH, —$NH_2$, —COOH, —$CONH_2$, —$NO_2$, —SH, —$S_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{36C}_3$, —$OCHX^{36}_2$, $R^{37C}$-substituted or unsubstituted $C_1$-$C_8$ alkyl, $R^{37C}$-substituted or unsubstituted 2 to 8 membered heteroalkyl, $R^{37C}$-substituted or unsubstituted $C_3$-$C_8$ cycloalkyl, $R^{37C}$-substituted or unsubstituted 3 to 6 membered heterocycloalkyl, $R^{37C}$-substituted or unsubstituted phenyl, or $R^{37C}$-substituted or unsubstituted 5 to 6 membered heteroaryl. $X^{36C}$ is —F, —Cl, —Br, or —I.

In embodiments, $R^{6D}$ is independently hydrogen, —$CX^{6D}_3$, —CN, —COOH, —$CONH_2$, —$CHX^{6D2}$, —$CH_2X^{6D}$, $R^{3D}$-substituted or unsubstituted alkyl, $R^{35D}$-substituted or unsubstituted heteroalkyl, $R^{35D}$-substituted or unsubstituted cycloalkyl, $R^{35D}$-substituted or unsubstituted heterocycloalkyl, $R^{35D}$-substituted or unsubstituted aryl, or $R^{35D}$-substituted or unsubstituted heteroaryl. In embodiments, $R^{6D}$ is independently hydrogen, —$CX^{6D}_3$, —CN, —COOH, —$CONH_2$, —$CHX^{6D}_2$, —$CH_2X^{6D}$, $R^{35D}$-substituted or unsubstituted $C_1$-$C_8$ alkyl, $R^{35D}$-substituted or unsubstituted 2 to 8 membered heteroalkyl, $R^{35D}$-substituted or unsubstituted $C_3$-$C_8$ cycloalkyl, $R^{35D}$-substituted or unsubstituted 3 to 6 membered heterocycloalkyl, $R^{3D}$-substituted or unsubstituted phenyl, or $R^{35D}$-substituted or unsubstituted 5 to 6 membered heteroaryl. $X^{6D}$ is —F, —Cl, —Br, or —I. In embodiments, $R^{6D}$ is independently hydrogen. In embodiments, $R^{6D}$ is independently methyl. In embodiments, $R^{6D}$ is independently ethyl.

$R^{35D}$ is independently oxo, halogen, $-CX^{35D}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{35D}_3$, $-OCHX^{35D}_2$, $R^{36D}$-substituted or unsubstituted alkyl, $R^{36D}$-substituted or unsubstituted heteroalkyl, $R^{36D}$-substituted or unsubstituted cycloalkyl, $R^{36D}$-substituted or unsubstituted heterocycloalkyl, $R^{36D}$-substituted or unsubstituted aryl, or $R^{36D}$-substituted or unsubstituted heteroaryl. In embodiments, $R^{35D}$ is independently oxo, halogen, $-CX^{35D}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{35D}_3$, $-OCHX^{35D}_2$, $R^{36D}$-substituted or unsubstituted $C_1$-$C_8$ alkyl, $R^{36D}$-substituted or unsubstituted 2 to 8 membered heteroalkyl, $R^{36D}$-substituted or unsubstituted $C_3$-$C_8$ cycloalkyl, $R^{36D}$-substituted or unsubstituted 3 to 6 membered heterocycloalkyl, $R^{36D}$-substituted or unsubstituted phenyl, or $R^{36D}$-substituted or unsubstituted 5 to 6 membered heteroaryl. $X^{35D}$ is $-F$, $-Cl$, $-Br$, or $-I$.

$R^{36D}$ is independently oxo, halogen, $-CX^{36D}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{36D}_3$, $-OCHX^{36D}_2$, $R^{37D}$-substituted or unsubstituted alkyl, $R^{37D}$-substituted or unsubstituted heteroalkyl, $R^{37D}$-substituted or unsubstituted cycloalkyl, $R^{37D}$-substituted or unsubstituted heterocycloalkyl, $R^{37D}$-substituted or unsubstituted aryl, or $R^{37D}$-substituted or unsubstituted heteroaryl. In embodiments, $R^{36D}$ is independently oxo, halogen, $-CX^{36D}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{36D}_3$, $-OCHX^{36D}_2$, $R^{37D}$-substituted or unsubstituted $C_1$-$C_8$ alkyl, $R^{37D}$-substituted or unsubstituted 2 to 8 membered heteroalkyl, $R^{37D}$-substituted or unsubstituted $C_3$-$C_8$ cycloalkyl, $R^{37D}$-substituted or unsubstituted 3 to 6 membered heterocycloalkyl, $R^{37D}$-substituted or unsubstituted phenyl, or $R^{37D}$-substituted or unsubstituted 5 to 6 membered heteroaryl. $X^{36D}$ is $-F$, $-Cl$, $-Br$, or $-I$.

$R^{37}$, $R^{37A}$, $R^{37B}$, $R^{37C}$, and $R^{37D}$ are independently hydrogen, oxo, halogen, $-CCl_3$, $-CBr_3$, $-CF_3$, $-CI_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{37}$, $R^{37A}$, $R^{37B}$, $R^{37C}$, and $R^{37D}$ are independently oxo, halogen, $-CF_3$, $-CN$, $-OH$, $-NH_2$, $-COOH$, $-CONH_2$, $-NO_2$, $-SH$, $-S_3H$, $-SO_4H$, $-S_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCF_3$, $-OCHF_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{37}$, $R^{37A}$, $R^{37B}$, $R^{37C}$, and $R^{37D}$ are independently oxo, halogen, $-CF_3$, $-CN$, $-OH$, $-NH_2$, $-COOH$, $-CONH_2$, $-NO_2$, $-SH$, $-SO_3H$, $-SO_4H$, $-S_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCF_3$, $-OCHF_2$, unsubstituted $C_1$-$C_8$ alkyl, unsubstituted 2 to 8 membered heteroalkyl, unsubstituted $C_3$-$C_8$ cycloalkyl, unsubstituted 3 to 6 membered heterocycloalkyl, unsubstituted phenyl, or unsubstituted 5 to 6 membered heteroaryl.

In embodiments, $L^1$ is given by the formula $L^{100}$-$L^{108}$.

$L^{100}$ is a bond, $-S(O)_2-$, $-S(O)_2$-Ph-, $-NR^{101}-$, $-O-$, $-S-$, $-C(O)-$, $-C(O)NR^{101}-$, $-NR^{101}C(O)-$, $-NR^{101}C(O)NH-$, $-NHC(O)NR^{101}-$, $-C(O)O-$, $-OC(O)-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^{101}$ is hydrogen, halogen, $-CX^{101}_3$, $-CHX^{101}_2$, $-CH_2X^{101}$, $-OCX^{101}_3$, $-OCH_2X^{101}$, $-OCHX^{101}_2$, $-CN$, $-SO_{n101}R^{101D}$, $-SO_{v101}NR^{101A}R^{101B}$, $-NHC(O)NR^{101A}R^{101B}$, $-N(O)_{m101}$, $-NR^{101A}R^{101B}$, $-C(O)R^{101C}$, $-C(O)-OR^{101C}$, $-C(O)NR^{101A}R^{101B}$, $-OR^{101D}$, $-NR^{101A}SO_2R^{101D}$, $-NR^{101A}C(O)R^{101C}$, $-NR^{101A}C(O)OR^{101C}$, $-NR^{101A}OR^{101C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbols v101 and m101 are independently an integer from 1 to 2. The symbol n101 is an integer from 0 to 4.

$L^{108}$ is a bond, $-S(O)_2-$, $-S(O)_2$-Ph-, $-NR^{109A}-$, $-O-$, $-S-$, $-C(O)-$, $-C(O)NR^{109A}-$, $-NR^{109}C(O)-$, $-NR^{109}C(O)NH-$, $-NHC(O)NR^{109A}-$, $-C(O)O-$, $-OC(O)-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^{109}$ is hydrogen, halogen, $-CX^{109}_3$, $-CHX^{109}_2$, $-CH_2X^{109}$, $-OCX^{109}_3$, $-OCH_2X^{109}$, $-OCHX^{109}_2$, $-CN$, $-SO_{n109}R^{109D}$, $-SO_{v109}NR^{109A}R^{109B}$, $-NHC(O)NR^{109A}R^{109B}$, $-N(O)_{m109}$, $-NR^{109A}R^{109B}$, $-C(O)R^{109C}$, $-C(O)-OR^{109C}$, $-C(O)NR^{109A}R^{109B}$, $-OR^{109D}$, $-NR^{109A}SO_2R^{109D}$, $-NR^{109A}C(O)R^{109C}$, $-NR^{109A}C(O)OR^{109C}$, $-NR^{109A}OR^{109C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbols v109 and m109 are independently an integer from 1 to 2. The symbol n109 is an integer from 0 to 4.

In embodiments, $L^{100}$ is a bond, $-S(O)_2-$, $-S(O)_2$-Ph-, substituted or unsubstituted $C_1$-$C_8$ alkylene, substituted or unsubstituted 2 to 8 membered heteroalkylene, substituted or unsubstituted $C_3$-$C_8$ cycloalkylene, substituted or unsubstituted 3 to 8 membered heterocycloalkylene, substituted or unsubstituted phenylene, or substituted or unsubstituted 5 to 6 membered heteroarylene. In embodiments, $L^{100}$ is a bond. In embodiments, $L^{100}$ is a substituted or unsubstituted $C_1$-$C_6$ alkylene, substituted or unsubstituted 2 to 6 membered heteroalkylene, substituted or unsubstituted $C_3$-$C_6$ cycloalkylene, substituted or unsubstituted 3 to 6 membered heterocycloalkylene, substituted or unsubstituted phenylene, or substituted or unsubstituted 5 to 6 membered heteroarylene. In embodiments, $L^{100}$ is an unsubstituted $C_1$-$C_6$ alkylene, unsubstituted 2 to 6 membered heteroalkylene, or unsubstituted $C_3$-$C_6$ cycloalkylene. In embodiments, $L^{100}$ is an unsubstituted methylene.

In embodiments, $L^{100}$ is a bond. In embodiments, $L^{100}$ is —S(O)$_2$—. In embodiments, $L^{100}$ is —S(O)$_2$-Ph-. In embodiments, $L^{100}$ is —NR$^{101}$—. In embodiments, $L^{100}$ is —O—. In embodiments, $L^{100}$ is —S—. In embodiments, $L^{100}$ is —C(O)—. In embodiments, $L^{100}$ is —C(O)NR$^{101}$—. In embodiments, $L^{100}$ is —NR$^{101}$C(O)—. In embodiments, $L^{100}$ is —NR$^{10}$C(O)NH—. In embodiments, $L^{100}$ is —NHC(O)NR$^{101}$—. In embodiments, $L^{100}$ is —C(O)O—. In embodiments, $L^{100}$ is —OC(O)—. In embodiments, $L^{100}$ is —NH—. In embodiments, $L^{100}$ is —C(O)NH—. In embodiments, $L^{100}$ is —NHC(O)—. In embodiments, $L^{100}$ is —NHC(O)NH—. In embodiments, $L^{100}$ is —CH$_2$—. In embodiments, $L^{100}$ is —OCH$_2$—. In embodiments, $L^{100}$ is —CH$_2$O—. In embodiments, $L^{100}$ is —CH$_2$CH$_2$—. In embodiments, $L^{100}$ is —SCH$_2$—. In embodiments, $L^{100}$ is —CH$_2$S—. In embodiments, $L^{100}$ is —CHCH—. In embodiments, $L^{100}$ is —CC—. In embodiments, $L^{100}$ is —NHCH$_2$—. In embodiments, $L^{100}$ is —CH$_2$NH—.

In embodiments, $L^{100}$ is a substituted or unsubstituted alkylene. In embodiments, $L^{100}$ is a substituted or unsubstituted heteroalkylene. In embodiments, $L^{100}$ is a substituted or unsubstituted cycloalkylene. In embodiments, $L^{100}$ is a substituted or unsubstituted heterocycloalkylene. In embodiments, $L^{100}$ is a substituted or unsubstituted arylene. In embodiments, $L^{100}$ is a substituted or unsubstituted heteroarylene. In embodiments, $L^{100}$ is a substituted alkylene. In embodiments, $L^{100}$ is a substituted heteroalkylene. In embodiments, $L^{100}$ is a substituted cycloalkylene. In embodiments, $L^{100}$ is a substituted heterocycloalkylene. In embodiments, $L^{100}$ is a substituted arylene. In embodiments, $L^{100}$ is a substituted heteroarylene. In embodiments, $L^{100}$ is an unsubstituted alkylene. In embodiments, $L^{100}$ is an unsubstituted heteroalkylene. In embodiments, $L^{100}$ is an unsubstituted cycloalkylene. In embodiments, $L^{100}$ is an unsubstituted heterocycloalkylene. In embodiments, $L^{100}$ is an unsubstituted arylene. In embodiments, $L^{100}$ is an unsubstituted heteroarylene. In embodiments, $L^{100}$ is a substituted or unsubstituted $C_1$-$C_8$ alkylene. In embodiments, $L^{100}$ is a substituted or unsubstituted 2 to 8 membered heteroalkylene. In embodiments, $L^{100}$ is a substituted or unsubstituted $C_3$-$C_8$ cycloalkylene. In embodiments, $L^{100}$ is a substituted or unsubstituted 3 to 8 membered heterocycloalkylene. In embodiments, $L^{100}$ is a substituted or unsubstituted $C_6$-$C_{10}$ arylene. In embodiments, $L^{100}$ is a substituted or unsubstituted 5 to 10 membered heteroarylene. In embodiments, $L^{100}$ is a substituted $C_1$-$C_8$ alkylene. In embodiments, $L^{100}$ is a substituted 2 to 8 membered heteroalkylene. In embodiments, $L^{100}$ is a substituted $C_3$-$C_8$ cycloalkylene. In embodiments, $L^{100}$ is a substituted 3 to 8 membered heterocycloalkylene. In embodiments, $L^{100}$ is a substituted $C_6$-$C_{10}$ arylene. In embodiments, $L^{100}$ is a substituted 5 to 10 membered heteroarylene. In embodiments, $L^{100}$ is an unsubstituted $C_1$-$C_8$ alkylene. In embodiments, $L^{100}$ is an unsubstituted 2 to 8 membered heteroalkylene. In embodiments, $L^{100}$ is an unsubstituted $C_3$-$C_8$ cycloalkylene. In embodiments, $L^{100}$ is an unsubstituted 3 to 8 membered heterocycloalkylene. In embodiments, $L^{100}$ is an unsubstituted $C_6$-$C_{10}$ arylene. In embodiments, $L^{100}$ is an unsubstituted 5 to 10 membered heteroarylene. In embodiments, $L^{100}$ is a substituted or unsubstituted $C_1$-$C_4$ alkylene. In embodiments, $L^{100}$ is a substituted or unsubstituted 2 to 4 membered heteroalkylene. In embodiments, $L^{100}$ is a substituted or unsubstituted $C_3$-$C_6$ cycloalkylene. In embodiments, $L^{100}$ is a substituted or unsubstituted 3 to 6 membered heterocycloalkylene. In embodiments, $L^{100}$ is a substituted or unsubstituted phenylene. In embodiments, $L^{100}$ is a substituted or unsubstituted 5 to 6 membered heteroarylene. In embodiments, $L^{100}$ is a substituted $C_1$-$C_4$ alkylene. In embodiments, $L^{100}$ is a substituted 2 to 4 membered heteroalkylene. In embodiments, $L^{100}$ is a substituted $C_3$-$C_6$ cycloalkylene. In embodiments, $L^{100}$ is a substituted 3 to 6 membered heterocycloalkylene. In embodiments, $L^{100}$ is a substituted phenylene. In embodiments, $L^{100}$ is a substituted 5 to 6 membered heteroarylene. In embodiments, $L^{100}$ is an unsubstituted $C_1$-$C_4$ alkylene. In embodiments, $L^{100}$ is an unsubstituted 2 to 4 membered heteroalkylene. In embodiments, $L^{100}$ is an unsubstituted $C_3$-$C_6$ cycloalkylene. In embodiments, $L^{100}$ is an unsubstituted 3 to 6 membered heterocycloalkylene. In embodiments, $L^{100}$ is an unsubstituted phenylene. In embodiments, $L^{100}$ is an unsubstituted 5 to 6 membered heteroarylene.

In embodiments, $L^{100}$ is a
bond, —S(O)$_2$—, —S(O)$_2$-Ph-, —NR$^{101}$—, —O—, —S—, —C(O)—, —C(O)NR$^{101}$—, —NR$^{101}$C(O)—, —NR$^{101}$C(O)NH—, —NHC(O)NR$^{101}$—, —C(O)O—, —OC(O)—, $R^{105}$-substituted or unsubstituted alkylene, $R^{105}$-substituted or unsubstituted heteroalkylene, $R^{105}$-substituted or unsubstituted cycloalkylene, $R^{105}$-substituted or unsubstituted heterocycloalkylene, $R^{105}$-substituted or unsubstituted arylene, or $R^{105}$-substituted or unsubstituted heteroarylene. In embodiments, $L^{100}$ is a bond, —S(O)$_2$—, —S(O)$_2$-Ph-, —NH—, —O—, —S—, —C(O)—, —C(O)NH—, —NHC(O)—, —NHC(O)NH—, —C(O)O—, —OC(O)—, $R^{105}$-substituted or unsubstituted alkylene, $R^{105}$-substituted or unsubstituted heteroalkylene, $R^{105}$-substituted or unsubstituted cycloalkylene, $R^{105}$-substituted or unsubstituted heterocycloalkylene, $R^{105}$-substituted or unsubstituted arylene, or $R^{105}$-substituted or unsubstituted heteroarylene. In embodiments, $L^{100}$ is a bond, —S(O)$_2$—, —S(O)$_2$-Ph-, —NH—, —O—, —S—, —C(O)—, —C(O)NH—, —NHC(O)—, —NHC(O)NH—, —C(O)O—, —OC(O)—, $R^{10}$-substituted or unsubstituted $C_1$-$C_8$ alkylene, $R^{105}$-substituted or unsubstituted 2 to 8 membered heteroalkylene, $R^{105}$-substituted or unsubstituted $C_3$-$C_8$ cycloalkylene, $R^{105}$-substituted or unsubstituted 3 to 6 membered heterocycloalkylene, $R^{105}$-substituted or unsubstituted phenylene, or $R^{105}$-substituted or unsubstituted 5 to 6 membered heteroarylene.

$R^{105}$ is independently oxo,
halogen, —CX$^{105}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{105}_3$, —OCHX$^{105}_2$, $R^{106}$-substituted or unsubstituted alkyl, $R^{106}$-substituted or unsubstituted heteroalkyl, $R^{106}$-substituted or unsubstituted cycloalkyl, $R^{106}$-substituted or unsubstituted heterocycloalkyl, $R^{106}$-substituted or unsubstituted aryl, or $R^{106}$-substituted or unsubstituted heteroaryl. In embodiments, $R^{105}$ is independently oxo,
halogen, —CX$^{105}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{105}_3$, —OCHX$^{105}_2$, $R^{106}$-substituted or unsubstituted $C_1$-$C_8$ alkyl, $R^{106}$-substituted or unsubstituted 2 to 8 membered heteroalkyl, $R^{106}$-substituted or unsubstituted $C_3$-$C_8$ cycloalkyl, $R^{106}$-substituted or unsubstituted 3 to 6 membered heterocycloalkyl, $R^{106}$-substituted or unsubstituted phenyl, or $R^{106}$-substituted or unsubstituted 5 to 6 membered heteroaryl. $X^{105}$ is —F, —Cl, —Br, or —I.

$R^{106}$ is independently oxo, halogen, —$CX^{106}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{106}_3$, —$OCHX^{106}_2$, $R^{107}$-substituted or unsubstituted alkyl, $R^{107}$-substituted or unsubstituted heteroalkyl, $R^{107}$-substituted or unsubstituted cycloalkyl, $R^{107}$-substituted or unsubstituted heterocycloalkyl, $R^{107}$-substituted or unsubstituted aryl, or $R^{107}$-substituted or unsubstituted heteroaryl. In embodiments, $R^{106}$ is independently oxo, halogen, —$CX^{106}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{106}_3$, —$OCHX^{106}_2$, $R^{107}$-substituted or unsubstituted $C_1$-$C_8$ alkyl, $R^{107}$-substituted or unsubstituted 2 to 8 membered heteroalkyl, $R^{107}$-substituted or unsubstituted $C_3$-$C_8$ cycloalkyl, $R^{107}$-substituted or unsubstituted 3 to 6 membered heterocycloalkyl, $R^{107}$-substituted or unsubstituted phenyl, or $R^{107}$-substituted or unsubstituted 5 to 6 membered heteroaryl. $X^{106}$ is —F, —Cl, —Br, or —I.

$R^{107}$ is independently hydrogen, oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCl_3$, —$OCHCl_2$, —$OCHBr_2$, —$OCHI_2$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{107}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{107}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCHF_2$, unsubstituted $C_1$-$C_8$ alkyl, unsubstituted 2 to 8 membered heteroalkyl, unsubstituted $C_3$-$C_8$ cycloalkyl, unsubstituted 3 to 6 membered heterocycloalkyl, unsubstituted phenyl, or unsubstituted 5 to 6 membered heteroaryl.

In embodiments, $L^{100}$ is a bond. In embodiments, $L^{100}$ is $R^{105}$-substituted or unsubstituted $C_1$-$C_2$ alkylene. In embodiments, $L^{100}$ is $R^{105}$-substituted or unsubstituted $C_1$-$C_4$ alkylene. In embodiments, $L^{100}$ is $R^{105}$-substituted or unsubstituted $C_1$-$C_6$ alkylene. In embodiments, $L^{100}$ is $R^{105}$-substituted or unsubstituted $C_1$-$C_8$ alkylene. In embodiments, $L^{100}$ is $R^{105}$-substituted or unsubstituted alkylene (e.g., $C_1$-$C_8$ alkylene, $C_1$-$C_6$ alkylene, $C_1$-$C_4$ alkylene, $C_1$-$C_2$ alkylene). In embodiments, $L^{100}$ is $R^{105}$-substituted $C_1$-$C_2$ alkylene. In embodiments, $L^{100}$ is $R^{105}$-substituted $C_1$-$C_4$ alkylene. In embodiments, $L^{100}$ is $R^{105}$-substituted $C_1$-$C_6$ alkylene. In embodiments, $L^{100}$ is $R^{105}$-substituted $C_1$-$C_8$ alkylene. In embodiments, $L^{100}$ is $R^{105}$-substituted alkylene (e.g., $C_1$-$C_8$ alkylene, $C_1$-$C_6$ alkylene, $C_1$-$C_4$ alkylene, $C_1$-$C_2$ alkylene). In embodiments, $L^{100}$ is $R^{105}$-substituted methylene. In embodiments, $L^{100}$ is unsubstituted $C_1$-$C_2$ alkylene. In embodiments, $L^{100}$ is unsubstituted $C_1$-$C_4$ alkylene. In embodiments, $L^{100}$ is unsubstituted $C_1$-$C_6$ alkylene. In embodiments, $L^{100}$ is unsubstituted $C_1$-$C_8$ alkylene. In embodiments, $L^{100}$ is unsubstituted alkylene (e.g., $C_1$-$C_8$ alkylene, $C_1$-$C_6$ alkylene, $C_1$-$C_4$ alkylene, $C_1$-$C_2$ alkylene). In embodiments, $L^{100}$ is $R^{105}$-substituted or unsubstituted methylene. In embodiments, $L^{100}$ is $R^{105}$-substituted methylene. In embodiments, $L^{100}$ is unsubstituted methylene.

In embodiments, $L^{100}$ is $R^{105}$-substituted or unsubstituted 2 to 4 membered heteroalkylene. In embodiments, $L^{100}$ is $R^{105}$-substituted or unsubstituted 2 to 6 membered heteroalkylene. In embodiments, $L^{100}$ is $R^{105}$-substituted or unsubstituted 2 to 8 membered heteroalkylene. In embodiments, $L^{100}$ is $R^{105}$-substituted or unsubstituted heteroalkylene (e.g., 2 to 8 membered heteroalkylene, 2 to 6 membered heteroalkylene, 2 to 4 membered heteroalkylene). In embodiments, $L^{100}$ is $R^{105}$-substituted 2 to 4 membered heteroalkylene. In embodiments, $L^{100}$ is $R^{105}$-substituted 2 to 6 membered heteroalkylene. In embodiments, $L^{100}$ is $R^{105}$-substituted 2 to 8 membered heteroalkylene. In embodiments, $L^{100}$ is $R^{105}$-substituted heteroalkylene (e.g., 2 to 8 membered heteroalkylene, 2 to 6 membered heteroalkylene, 2 to 4 membered heteroalkylene). In embodiments, $L^{100}$ is unsubstituted 2 to 4 membered heteroalkylene. In embodiments, $L^{100}$ is unsubstituted 2 to 6 membered heteroalkylene. In embodiments, $L^{100}$ is unsubstituted 2 to 8 membered heteroalkylene. In embodiments, $L^{100}$ is unsubstituted heteroalkylene (e.g., 2 to 8 membered heteroalkylene, 2 to 6 membered heteroalkylene, 2 to 4 membered heteroalkylene).

In embodiments, $L^{100}$ is $R^{105}$-substituted or unsubstituted ethylaminylene. In embodiments, $L^{100}$ is $R^{105}$-substituted ethylaminylene. In embodiments, $L^{100}$ is unsubstituted ethylaminylene. In embodiments, $L^{100}$ is $R^{105}$-substituted or unsubstituted propylaminylene. In embodiments, $L^{100}$ is $R^{105}$-substituted propyl aminylene. In embodiments, $L^{100}$ is unsubstituted propylaminylene. In embodiments, $L^{100}$ is $R^{105}$-substituted or unsubstituted butylaminylene. In embodiments, $L^{100}$ is $R^{105}$-substituted butylaminylene. In embodiments, $L^{100}$ is unsubstituted butylaminylene.

In embodiments, $L^{100}$ is $R^{105}$-substituted or unsubstituted $C_3$-$C_8$ cycloalkylene. In embodiments, $L^{100}$ is $R^{105}$-substituted or unsubstituted $C_4$-$C_6$ cycloalkylene. In embodiments, $L^{100}$ is $R^{105}$-substituted or unsubstituted $C_5$-$C_6$ cycloalkylene. In embodiments, $L^{100}$ is $R^{105}$-substituted or unsubstituted cycloalkylene (e.g., $C_3$-$C_8$ cycloalkylene, $C_4$-$C_6$ cycloalkylene, or $C_5$-$C_6$ cycloalkylene). In embodiments, $L^{100}$ is $R^{105}$-substituted $C_3$-$C_8$ cycloalkylene. In embodiments, $L^{100}$ is $R^{105}$-substituted $C_4$-$C_6$ cycloalkylene. In embodiments, $L^{100}$ is $R^{105}$-substituted $C_5$-$C_6$ cycloalkylene. In embodiments, $L^{100}$ is $R^{105}$-substituted cycloalkylene (e.g., $C_3$-$C_8$ cycloalkylene, $C_4$-$C_6$ cycloalkylene, or $C_5$-$C_6$ cycloalkylene). In embodiments, $L^{100}$ is unsubstituted $C_3$-$C_8$ cycloalkylene. In embodiments, $L^{100}$ is unsubstituted $C_4$-$C_6$ cycloalkylene. In embodiments, $L^{100}$ is unsubstituted $C_5$-$C_6$ cycloalkylene. In embodiments, $L^{100}$ is unsubstituted cycloalkylene (e.g., $C_3$-$C_8$ cycloalkylene, $C_4$-$C_6$ cycloalkylene, or $C_5$-$C_6$ cycloalkylene).

In embodiments, $L^{100}$ is $R^{105}$-substituted or unsubstituted 4 membered heterocycloalkylene. In embodiments, $L^{100}$ is $R^{105}$-substituted or unsubstituted 5 membered heterocycloalkylene. In embodiments, $L^{100}$ is $R^{105}$-substituted or unsubstituted 6 membered heterocycloalkylene. In embodiments, $L^{100}$ is $R^{105}$-substituted or unsubstituted heterocycloalkylene (e.g., 3 to 6 membered heterocycloalkylene, 4 to 6 membered heterocycloalkylene, or 5 to 6 membered heterocycloalkylene). In embodiments, $L^{100}$ is $R^{105}$-substituted 4 membered heterocycloalkylene. In embodiments, $L^{100}$ is $R^{105}$-substituted 5 membered heterocycloalkylene. In embodiments, $L^{100}$ is $R^{105}$-substituted 6 membered heterocycloalkylene. In embodiments, $L^{100}$ is $R^{105}$-substituted heterocycloalkylene (e.g., 3 to 6 membered heterocycloalkylene, 4 to 6 membered heterocycloalkylene, or 5 to 6 membered heterocycloalkylene). In embodiments, $L^{100}$ is unsubstituted 4 membered heterocycloalkylene. In embodiments, $L^{100}$ is unsubstituted 5 membered heterocycloalkylene. In embodiments, $L^{100}$ unsubstituted 6 membered heterocycloalkylene. In embodiments, $L^{100}$ is unsubstituted heterocycloalkylene (e.g., 3 to 6 membered heterocycloalkylene, 4 to 6 membered heterocycloalkylene, or 5 to 6 membered heterocycloalkylene).

In embodiments, $L^{100}$ is $R^{105}$-substituted or unsubstituted arylene (e.g. $C_6$-$C_{10}$ arylene or $C_6$ arylene). In embodiments, $L^{100}$ is $R^{105}$-substituted or unsubstituted $C_6$-$C_{10}$ arylene. In embodiments, $L^{100}$ is $R^{105}$-substituted or unsubstituted $C_6$ arylene. In embodiments, $L^{100}$ is $R^{105}$-substituted arylene (e.g. $C_6$-$C_{10}$ arylene or $C_6$ arylene). In embodiments, $L^{100}$ is $R^{105}$-substituted $C_6$-$C_{10}$ arylene. In embodiments, $L^{100}$ is $R^{105}$-substituted $C_6$ arylene. In embodiments, $L^{100}$ is unsubstituted $C_6$-$C_{10}$ arylene. In embodiments, $L^{100}$ is unsubstituted $C_6$ arylene.

In embodiments, $L^{100}$ is $R^{105}$-substituted or unsubstituted heteroarylene (e.g. 5 to 10 membered heteroarylene, 5 to 9 membered heteroarylene, or 5 to 6 membered heteroarylene). In embodiments, $L^{100}$ is $R^{105}$-substituted or unsubstituted 5 to 10 membered heteroarylene. In embodiments, $L^{100}$ is $R^{105}$-substituted or unsubstituted 5 to 9 membered heteroarylene. In embodiments, $L^{100}$ is $R^{105}$-substituted or unsubstituted 5 to 6 membered heteroarylene. In embodiments, $L^{100}$ is $R^{105}$-substituted heteroarylene (e.g. 5 to 10 membered heteroarylene, 5 to 9 membered heteroarylene, or 5 to 6 membered heteroarylene). In embodiments, $L^{100}$ is $R^{105}$-substituted 5 to 10 membered heteroarylene. In embodiments, $L^{100}$ is $R^{105}$-substituted 5 to 9 membered heteroarylene. In embodiments, $L^{100}$ is $R^{105}$-substituted 5 to 6 membered heteroarylene. In embodiments, $L^{100}$ is unsubstituted heteroarylene (e.g. 5 to 10 membered heteroarylene, 5 to 9 membered heteroarylene, or 5 to 6 membered heteroarylene). In embodiments, $L^{100}$ is unsubstituted 5 to 10 membered heteroarylene. In embodiments, $L^{100}$ is unsubstituted 5 to 9 membered heteroarylene. In embodiments, $L^{100}$ is unsubstituted 5 to 6 membered heteroarylene. In embodiments, $L^{100}$ is $R^{105}$-substituted or unsubstituted indolinylene. In embodiments, $L^{100}$ is $R^{105}$-substituted or unsubstituted indazolylene. In embodiments, $L^{100}$ is $R^{105}$-substituted or unsubstituted benzimidazolylene. In embodiments, $L^{100}$ is $R^{105}$-substituted or unsubstituted benzoxazolylene. In embodiments, $L^{100}$ is $R^{105}$-substituted or unsubstituted azaindolylene. In embodiments, $L^{100}$ is $R^{105}$-substituted or unsubstituted purinylene. In embodiments, $L^{100}$ is $R^{105}$-substituted or unsubstituted indolylene. In embodiments, $L^{100}$ is $R^{05}$-substituted or unsubstituted pyrazinylene. In embodiments, $L^{100}$ is $R^{105}$-substituted or unsubstituted pyrrolylene. In embodiments, $L^{100}$ is $R^{105}$-substituted or unsubstituted imidazolylene. In embodiments, $L^{100}$ is $R^{105}$-substituted or unsubstituted pyrazolylene. In embodiments, $L^{100}$ is $R^{105}$-substituted or unsubstituted triazolylene. In embodiments, $L^{100}$ is $R^{105}$-substituted or unsubstituted tetrazolylene.

In embodiments, $L^{100}$ is $R^{105}$-substituted indolinylene. In embodiments, $L^{100}$ is $R^{105}$-substituted indazolylene. In embodiments, $L^{100}$ is $R^{105}$-substituted benzimidazolylene. In embodiments, $L^{100}$ is $R^{105}$-substituted benzoxazolylene. In embodiments, $L^{100}$ is $R^{105}$-substituted azaindolylene. In embodiments, $L^{100}$ is $R^{105}$-substituted purinylene. In embodiments, $L^{100}$ is $R^{105}$-substituted indolylene. In embodiments, $L^{100}$ is $R^{105}$-substituted pyrazinylene. In embodiments, $L^{100}$ is $R^{105}$-substituted pyrrolylene. In embodiments, $L^{100}$ is $R^{105}$-substituted imidazolylene. In embodiments, $L^{100}$ is $R^{105}$-substituted pyrazolylene. In embodiments, $L^{100}$ is $R^{105}$-substituted triazolylene. In embodiments, $L^{100}$ is $R^{105}$-substituted tetrazolylene.

In embodiments, $L^{100}$ is unsubstituted indolinylene. In embodiments, $L^{100}$ is unsubstituted indazolylene. In embodiments, $L^{100}$ is unsubstituted benzimidazolylene. In embodiments, $L^{100}$ is unsubstituted benzoxazolylene. In embodiments, $L^{100}$ is unsubstituted azaindolylene. In embodiments, $L^{100}$ is unsubstituted purinylene. In embodiments, $L^{100}$ is unsubstituted indolylene. In embodiments, $L^{100}$ is unsubstituted pyrazinylene. In embodiments, $L^{100}$ is unsubstituted pyrrolylene. In embodiments, $L^{100}$ is unsubstituted imidazolylene. In embodiments, $L^{100}$ is unsubstituted pyrazolylene. In embodiments, $L^{100}$ is unsubstituted triazolylene. In embodiments, $L^{100}$ is unsubstituted tetrazolylene.

In embodiments, $R^{101}$ is independently hydrogen. In embodiments, $R^{101}$ is independently halogen. In embodiments, $R^{101}$ is independently —$CX^{103}$. In embodiments, $R^{101}$ is independently —$CHX^{101}_2$. In embodiments, $R^{101}$ is independently —$CH_2X^{101}$. In embodiments, $R^{101}$ is independently —$OCX^{101}_3$. In embodiments, $R^{101}$ is independently —$OCH_2X^{101}$. In embodiments, $R^{101}$ is independently —$OCHX^{101}_2$. In embodiments, $R^{101}$ is independently —CN. In embodiments, $R^{101}$ is independently —$SO_{n101}R^{101D}$. In embodiments, $R^{101}$ is independently —$SO_{n101}NR^{101A}R^{101B}$. In embodiments, $R^{101}$ is independently —NHC(O)NR$^{101A}$R$^{101B}$. In embodiments, $R^{101}$ is independently —$N(O)_{m101}$. In embodiments, $R^{101}$ is independently —NR$^{101A}$R$^{101B}$. In embodiments, $R^{101}$ is independently —C(O)R$^{101C}$. In embodiments, $R^{101}$ is independently —C(O)—OR$^{101C}$. In embodiments, $R^{101}$ is independently —C(O)NR$^{101A}$R$^{101B}$. In embodiments, $R^{101}$ is independently —OR$^{101D}$. In embodiments, $R^{101}$ is independently —NR$^{101A}$SO$_2$R$^{101D}$. In embodiments, $R^{101}$ is independently —NR$^{101A}$C(O)R$^{101C}$. In embodiments, $R^{101}$ is independently —NR$^{101A}$C(O)OR$^{101C}$. In embodiments, $R^{101}$ is independently —NR$^{101A}$OR$^{101C}$. In embodiments, $R^{101}$ is independently —OH. In embodiments, $R^{101}$ is independently —NH$_2$. In embodiments, $R^{101}$ is independently —COOH. In embodiments, $R^{101}$ is independently —CONH$_2$. In embodiments, $R^{101}$ is independently —NO$_2$. In embodiments, $R^{101}$ is independently —SH.

In embodiments, $R^{101}$ is independently substituted or unsubstituted alkyl. In embodiments, $R^{101}$ is independently substituted or unsubstituted heteroalkyl. In embodiments, $R^{101}$ is independently substituted or unsubstituted cycloalkyl. In embodiments, $R^{101}$ is independently, substituted or unsubstituted heterocycloalkyl. In embodiments, $R^{101}$ is independently substituted or unsubstituted aryl. In embodiments, $R^{101}$ is independently substituted or unsubstituted heteroaryl. In embodiments, $R^{101}$ is independently substituted alkyl. In embodiments, $R^{101}$ is independently substituted heteroalkyl. In embodiments, $R^{101}$ is independently substituted cycloalkyl. In embodiments, $R^{101}$ is independently, substituted heterocycloalkyl. In embodiments, $R^{101}$ is independently substituted aryl. In embodiments, $R^{101}$ is independently substituted heteroaryl. In embodiments, $R^{101}$ is independently unsubstituted alkyl. In embodiments, $R^{101}$ is independently unsubstituted heteroalkyl. In embodiments, $R^{101}$ is independently unsubstituted cycloalkyl. In embodiments, $R^{101}$ is independently, unsubstituted heterocycloalkyl. In embodiments, $R^{101}$ is independently unsubstituted aryl. In embodiments, $R^{101}$ is independently unsubstituted heteroaryl. In embodiments, $R^{101}$ is independently substituted or unsubstituted $C_1$-$C_8$ alkyl. In embodiments, $R^{101}$ is independently substituted or unsubstituted 2 to 8 membered heteroalkyl. In embodiments, $R^{101}$ is independently substituted or unsubstituted $C_3$-$C_8$ cycloalkyl. In embodiments, $R^{101}$ is independently, substituted or unsubstituted 3 to 8 membered heterocycloalkyl. In embodiments, $R^{101}$ is independently substituted or unsubstituted $C_6$-$C_{10}$ aryl. In embodiments, $R^{101}$ is independently substituted or unsubstituted 5 to 10 membered heteroaryl. In embodiments, $R^{101}$ is independently substituted $C_1$-$C_8$ alkyl. In embodiments, $R^{101}$ is independently substituted 2 to 8 membered heteroalkyl. In embodiments, $R^{101}$ is independently substituted $C_3$-$C_8$ cycloalkyl. In embodiments, $R^{101}$ is independently, substituted 3 to 8 membered heterocycloalkyl. In embodiments, $R^{101}$ is independently substituted $C_6$-$C_{10}$ aryl. In embodiments, $R^{101}$ is independently substituted 5 to 10 membered heteroaryl. In embodiments, $R^{101}$ is independently unsubstituted $C_1$-$C_8$ alkyl. In embodiments, $R^{101}$ is independently unsubstituted 2 to 8 membered heteroalkyl. In embodiments, $R^{101}$ is independently unsubstituted $C_3$-$C_8$ cycloalkyl. In embodiments, $R^{101}$ is independently, unsubstituted 3 to 8 membered heterocycloalkyl. In embodiments, $R^{101}$ is independently unsubstituted $C_6$-$C_{10}$ aryl. In embodiments, $R^{101}$ is independently unsubstituted 5 to 10 membered heteroaryl. In embodiments, $R^{101}$ is independently substituted or unsubstituted $C_1$-$C_4$ alkyl. In embodiments, $R^{101}$ is independently substituted or unsubstituted 2 to 4 membered heteroalkyl. In embodiments, $R^{101}$ is independently substituted or unsubstituted $C_3$-$C_6$ cycloalkyl. In embodiments, $R^{101}$ is independently, substituted or unsubstituted 3 to 6 membered heterocycloalkyl. In embodiments, $R^{101}$ is independently substituted or unsubstituted phenyl. In embodiments, $R^{101}$ is independently substituted or unsubstituted 5 to 6 membered heteroaryl. In embodiments, $R^{101}$ is independently substituted $C_1$-$C_4$ alkyl. In embodiments, $R^{101}$ is independently substituted 2 to 4 membered heteroalkyl. In embodiments, $R^{101}$ is independently substituted $C_3$-$C_6$ cycloalkyl. In embodiments, $R^{101}$ is independently, substituted 3 to 6 membered heterocycloalkyl. In embodiments, $R^{101}$ is independently substituted phenyl. In embodiments, $R^{101}$ is independently substituted 5 to 6 membered heteroaryl. In embodiments, $R^{101}$ is independently unsubstituted $C_1$-$C_4$ alkyl. In embodiments, $R^{101}$ is independently unsubstituted 2 to 4 membered heteroalkyl. In embodiments, $R^{101}$ is independently unsubstituted $C_3$-$C_6$ cycloalkyl. In embodiments, $R^{101}$ is independently unsubstituted 3 to 6 membered heterocycloalkyl. In embodiments, $R^{101}$ is independently unsubstituted phenyl. In embodiments, $R^{101}$ is independently unsubstituted 5 to 6 membered heteroaryl.

In embodiments, $R^{101A}$ is independently hydrogen. In embodiments, $R^{101A}$ is independently —$CX^{101A}_3$. In embodiments, $R^{101A}$ is independently —$CHX^{101A}_2$. In embodiments, $R^{101A}$ is independently —$CH_2X^{101A}$. In embodiments, $R^{101A}$ is independently —CN. In embodiments, $R^{101A}$ is independently —COOH. In embodiments, $R^{101A}$ is independently —$CONH_2$. In embodiments, $R^{101A}$ is independently substituted or unsubstituted alkyl. In embodiments, $R^{101A}$ is independently substituted or unsubstituted heteroalkyl. In embodiments, $R^{101A}$ is independently substituted or unsubstituted cycloalkyl. In embodiments, $R^{101A}$ is independently, substituted or unsubstituted heterocycloalkyl. In embodiments, $R^{101A}$ is independently substituted or unsubstituted aryl. In embodiments, $R^{101A}$ is independently substituted or unsubstituted heteroaryl. In embodiments, $R^{101A}$ is independently substituted alkyl. In embodiments, $R^{101A}$ is independently substituted heteroalkyl. In embodiments, $R^{101A}$ is independently substituted cycloalkyl. In embodiments, $R^{101A}$ is independently, substituted heterocycloalkyl. In embodiments, $R^{101A}$ is independently substituted aryl. In embodiments, $R^{101A}$ is independently substituted heteroaryl. In embodiments, $R^{101A}$ is independently unsubstituted alkyl. In embodiments, $R^{101A}$ is independently unsubstituted heteroalkyl. In embodiments, $R^{101A}$ is independently unsubstituted cycloalkyl. In embodiments, $R^{101A}$ is independently, unsubstituted heterocycloalkyl. In embodiments, $R^{101A}$ is independently unsubstituted aryl. In embodiments, $R^{101A}$ is independently unsubstituted heteroaryl. In embodiments, $R^{101A}$ is independently substituted or unsubstituted $C_1$-$C_8$ alkyl. In embodiments, $R^A$ is independently substituted or unsubstituted 2 to 8 membered heteroalkyl. In embodiments, $R^{101A}$ is independently substituted or unsubstituted $C_3$-$C_8$ cycloalkyl. In embodiments, $R^{101A}$ is independently, substituted or unsubstituted 3 to 8 membered heterocycloalkyl. In embodiments, $R^{101A}$ is independently substituted or unsubstituted $C_6$-$C_{10}$ aryl. In embodiments, $R^{101A}$ is independently substituted or unsubstituted 5 to 10 membered heteroaryl. In embodiments, $R^{101A}$ is independently substituted $C_1$-$C_8$ alkyl. In embodiments, $R^{101A}$ is independently substituted 2 to 8 membered heteroalkyl. In embodiments, $R^{101A}$ is independently substituted $C_3$-$C_8$ cycloalkyl. In embodiments, $R^{101A}$ is independently, substituted 3 to 8 membered heterocycloalkyl. In embodiments, $R^{101A}$ is independently substituted $C_6$-$C_{10}$ aryl. In embodiments, $R^{101A}$ is independently substituted 5 to 10 membered heteroaryl. In embodiments, $R^{101A}$ is independently unsubstituted $C_1$-$C_8$ alkyl. In embodiments, $R^{101A}$ is independently unsubstituted 2 to 8 membered heteroalkyl. In embodiments, $R^{101A}$ is independently unsubstituted $C_3$-$C_8$ cycloalkyl. In embodiments, $R^{101A}$ is independently, unsubstituted 3 to 8 membered heterocycloalkyl. In embodiments, $R^{101A}$ is independently unsubstituted $C_6$-$C_{10}$ aryl. In embodiments, $R^{101A}$ is independently unsubstituted 5 to 10 membered heteroaryl. In embodiments, $R^{101A}$ is independently substituted or unsubstituted $C_1$-$C_4$ alkyl. In embodiments, $R^{101A}$ is independently substituted or unsubstituted 2 to 4 membered heteroalkyl. In embodiments, $R^{101A}$ is independently substituted or unsubstituted $C_3$-$C_6$ cycloalkyl. In embodiments, $R^{101A}$ is independently, substituted or unsubstituted 3 to 6 membered heterocycloalkyl. In embodiments, $R^{101A}$ is independently substituted or unsubstituted phenyl. In embodiments, $R^{101A}$ is independently substituted or unsubstituted 5 to 6 membered heteroaryl. In embodiments, $R^{101A}$ is independently substituted $C_1$-$C_4$ alkyl. In embodiments, $R^{101A}$ is independently substituted 2 to 4 membered heteroalkyl. In embodiments, $R^{101A}$ is independently substituted $C_3$-$C_6$ cycloalkyl. In embodiments, $R^{101A}$ is independently, substituted 3 to 6 membered heterocycloalkyl. In embodiments, $R^{101A}$ is independently substituted phenyl. In embodiments, $R^{101A}$ is independently substituted 5 to 6 membered heteroaryl. In embodiments, $R^{101A}$ is independently unsubstituted $C_1$-$C_4$ alkyl. In embodiments, $R^{101A}$ is independently unsubstituted 2 to 4 membered heteroalkyl. In embodiments, $R^{1A}$ is independently unsubstituted $C_3$-$C_6$ cycloalkyl. In embodiments, $R^{101A}$ is independently unsubstituted 3 to 6 membered heterocycloalkyl. In embodiments, $R^{101A}$ is independently unsubstituted phenyl. In embodiments, $R^{101A}$ is independently unsubstituted 5 to 6 membered heteroaryl. In embodiments, $R^{101A}$ is independently unsubstituted methyl. In embodiments, $R^{101A}$ is independently unsubstituted ethyl. In embodiments, $R^{101A}$ is independently unsubstituted propyl. In embodiments, $R^{101A}$ is independently unsubstituted isopropyl. In embodiments, $R^{101A}$ is independently unsubstituted tert-butyl.

In embodiments, $R^{101B}$ is independently hydrogen. In embodiments, $R^{101B}$ is independently —$CX^{101B}_3$. In embodiments, $R^{101B}$ is independently —$CHX^{101B}_2$. In embodiments, $R^{101B}$ is independently —$CH_2X^{101B}$. In embodiments, $R^{101B}$ is independently —CN. In embodiments, $R^{101B}$ is independently —COOH. In embodiments, $R^{101B}$ is independently —$CONH_2$. In embodiments, $R^{101B}$ is independently substituted or unsubstituted alkyl. In embodiments, $R^{101B}$ is independently substituted or unsubstituted heteroalkyl. In embodiments, $R^{101B}$ is independently substituted or unsubstituted cycloalkyl. In embodiments, $R^{101B}$ is independently, substituted or unsubstituted heterocycloalkyl. In embodiments, $R^{101B}$ is independently substituted or unsubstituted aryl. In embodiments, $R^{101B}$ is independently substituted or unsubstituted heteroaryl. In embodiments, $R^{101B}$ is independently substituted alkyl. In embodiments, $R^{101B}$ is independently substituted heteroalkyl. In embodiments, $R^{101B}$ is independently substituted cycloalkyl. In embodiments, $R^{101B}$ is independently, substituted heterocycloalkyl. In embodiments, $R^{101B}$ is independently substituted aryl. In embodiments, $R^{101B}$ is independently substituted heteroaryl. In embodiments, $R^{101B}$ is independently unsubstituted alkyl. In embodiments, $R^{101B}$ is independently unsubstituted heteroalkyl. In embodiments, $R^{101B}$ is independently unsubstituted cycloalkyl. In embodiments, $R^{101B}$ is independently, unsubstituted heterocycloalkyl. In embodiments, $R^{101B}$ is independently unsubstituted aryl. In embodiments, $R^{101B}$ is independently unsubstituted heteroaryl. In embodiments, $R^{101B}$ is independently substituted or unsubstituted $C_1$-$C_8$ alkyl. In embodiments, $R^{101B}$ is independently substituted or unsubstituted 2 to 8 membered heteroalkyl. In embodiments, $R^{101B}$ is independently substituted or unsubstituted $C_3$-$C_8$ cycloalkyl. In embodiments, $R^{101B}$ is independently, substituted or unsubstituted 3 to 8 membered heterocycloalkyl. In embodiments, $R^{101B}$ is independently substituted or unsubstituted $C_6$-$C_{10}$ aryl. In embodiments, $R^{101B}$ is independently substituted or unsubstituted 5 to 10 membered heteroaryl. In embodiments, $R_{101B}$ is independently substituted $C_1$-$C_8$ alkyl. In embodiments, $R^{101B}$ is independently substituted 2 to 8 membered heteroalkyl. In embodiments, $R^{101B}$ is independently substituted $C_3$-$C_8$ cycloalkyl. In embodiments, $R^{101B}$ is independently, substituted 3 to 8 membered heterocycloalkyl. In embodiments, $R^{101B}$ is independently substituted $C_6$-$C_{10}$ aryl. In embodiments, $R^{101B}$ is independently substituted 5 to 10 membered heteroaryl. In embodiments, $R^{101B}$ is independently unsubstituted $C_1$-$C_8$ alkyl. In embodiments, $R^{101B}$ is independently unsubstituted 2 to 8 membered heteroalkyl. In embodiments, $R^{101B}$ is independently unsubstituted $C_3$-$C_8$ cycloalkyl. In embodiments, $R^{101B}$ is independently, unsubstituted 3 to 8 membered heterocycloalkyl. In embodiments, $R^{101B}$ is independently unsubstituted $C_6$-$C_{10}$ aryl. In embodiments, $R^{101B}$ is independently unsubstituted 5 to 10 membered heteroaryl. In embodiments, $R^{101B}$ is independently substituted or unsubstituted $C_1$-$C_4$ alkyl. In embodiments, $R^{101B}$ is independently substituted or unsubstituted 2 to 4 membered heteroalkyl. In embodiments, $R^{101B}$ is independently substituted or unsubstituted $C_3$-$C_6$ cycloalkyl. In embodiments, $R^{101B}$ is independently, substituted or unsubstituted 3 to 6 membered heterocycloalkyl. In embodiments, $R^{101B}$ is independently substituted or unsubstituted phenyl. In embodiments, $R^{101B}$ is independently substituted or unsubstituted 5 to 6 membered heteroaryl. In embodiments, $R^{101B}$ is independently substituted $C_1$-$C_4$ alkyl. In embodiments, $R^{101B}$ is independently substituted 2 to 4 membered heteroalkyl. In embodiments, $R^{101B}$ is independently substituted $C_3$-$C_6$ cycloalkyl. In embodiments, $R^{101B}$ is independently, substituted 3 to 6 membered heterocycloalkyl. In embodiments, $R^{101B}$ is independently substituted phenyl. In embodiments, $R^{101B}$ is independently substituted 5 to 6 membered heteroaryl. In embodiments, $R^{101B}$ is independently unsubstituted $C_1$-$C_4$ alkyl. In embodiments, $R^{101B}$ is independently unsubstituted 2 to 4 membered heteroalkyl. In embodiments, $R^{101B}$ is independently unsubstituted $C_3$-$C_6$ cycloalkyl. In embodiments, $R^{101B}$ is independently unsubstituted 3 to 6 membered heterocycloalkyl. In embodiments, $R^{101B}$ is independently unsubstituted phenyl. In embodiments, $R^{101B}$ is independently unsubstituted 5 to 6 membered heteroaryl. In embodiments, $R^{101B}$ is independently unsubstituted methyl. In embodiments, $R^{101B}$ is independently unsubstituted ethyl. In embodiments, $R^{101B}$ is independently unsubstituted propyl. In embodiments, $R^{101B}$ is independently unsubstituted isopropyl. In embodiments, $R^{101B}$ is independently unsubstituted tert-butyl.

In embodiments, $R^{101A}$ and $R^{101B}$ substituents bonded to the same nitrogen atom may be joined to form a substituted or unsubstituted heterocycloalkyl. In embodiments, $R^{101A}$ and $R^{101B}$ substituents bonded to the same nitrogen atom may be joined to form a substituted or unsubstituted heteroaryl. In embodiments, $R^{101A}$ and $R^{101B}$ substituents bonded to the same nitrogen atom may be joined to form a substituted heterocycloalkyl. In embodiments, $R^{101A}$ and $R^{101B}$ substituents bonded to the same nitrogen atom may be joined to form a substituted heteroaryl. In embodiments, $R^{101A}$ and $R^{101B}$ substituents bonded to the same nitrogen atom may be joined to form an unsubstituted heterocycloalkyl. In embodiments, $R^{101A}$ and $R^{101B}$ substituents bonded to the same nitrogen atom may be joined to form an unsubstituted heteroaryl. In embodiments, $R^{101A}$ and $R^{101B}$ substituents bonded to the same nitrogen atom may be joined to form a substituted or unsubstituted 3 to 8 membered heterocycloalkyl. In embodiments, $R^{101A}$ and $R^{101B}$ substituents bonded to the same nitrogen atom may be joined to form a substituted or unsubstituted 5 to 10 membered heteroaryl. In embodiments, $R^{101A}$ and $R^{101B}$ substituents bonded to the same nitrogen atom may be joined to form a substituted 3 to 8 membered heterocycloalkyl. In embodiments, $R^{101A}$ and $R^{101B}$ substituents bonded to the same nitrogen atom may be joined to form a substituted 5 to 10 membered heteroaryl. In embodiments, $R^{101A}$ and $R^{101B}$ substituents bonded to the same nitrogen atom may be joined to form an unsubstituted 3 to 8 membered heterocycloalkyl. In embodiments, $R^{101A}$ and $R^{101B}$ substituents bonded to the same nitrogen atom may be joined to form an unsubstituted 5 to 10 membered heteroaryl. In embodiments, $R^{101A}$ and $R^{101B}$ substituents bonded to the same nitrogen atom may be joined to form a substituted or unsubstituted 3 to 6 membered heterocycloalkyl. In embodiments, $R^{101A}$ and $R^{101B}$ substituents bonded to the same nitrogen atom may be joined to form a substituted or unsubstituted 5 to 6 membered heteroaryl. In embodiments, $R^{101A}$ and $R^{101B}$ substituents bonded to the same nitrogen atom may be joined to form a substituted 3 to 6 membered heterocycloalkyl. In embodiments, $R^{101A}$ and $R^{101B}$ substituents bonded to the same nitrogen atom may be joined to form a substituted 5 to 6 membered heteroaryl. In embodiments, $R^{101A}$ and $R^{101B}$ substituents bonded to the same nitrogen atom may be joined to form an unsubstituted 3 to 6 membered heterocycloalkyl. In embodiments, $R^{101A}$ and $R^{101B}$ substituents bonded to the same nitrogen atom may be joined to form an unsubstituted 5 to 6 membered heteroaryl.

In embodiments, $R^{101C}$ is independently hydrogen. In embodiments, $R^{101C}$ is independently —$CX^{101C}_3$. In embodiments, $R^{101C}$ is independently —$CHX^{101C}_2$. In embodiments, $R^{101C}$ is independently —$CH_2X^{101C}$. In embodiments, $R^{101C}$ is independently —CN. In embodiments, $R^{101C}$ is independently —COOH. In embodiments, $R^{101C}$ is independently —$CONH_2$. In embodiments, $R^{101C}$ is independently substituted or unsubstituted alkyl. In embodiments, $R^{101C}$ is independently substituted or unsubstituted heteroalkyl. In embodiments, $R^{101C}$ is independently substituted or unsubstituted cycloalkyl. In embodiments, $R_{101C}$ is independently, substituted or unsubstituted heterocycloalkyl. In embodiments, $R_{101C}$ is independently substituted or unsubstituted aryl. In embodiments, $R^{101C}$ is independently substituted or unsubstituted heteroaryl. In embodiments, $R^{101C}$ is independently substituted alkyl. In embodiments, $R^{101C}$ is independently substituted heteroalkyl. In embodiments, $R^{101C}$ is independently substituted cycloalkyl. In embodiments, $R^{101C}$ is independently, substituted heterocycloalkyl. In embodiments, $R^{101C}$ is independently substituted aryl. In embodiments, $R^{101C}$ is independently substituted heteroaryl. In embodiments, $R_{101C}$ is independently unsubstituted alkyl. In embodiments, $R^{101C}$ is independently unsubstituted heteroalkyl. In embodiments, $R^{101C}$ is independently unsubstituted cycloalkyl. In embodiments, $R^{101C}$ is independently, unsubstituted heterocycloalkyl. In embodiments, $R_{101C}$ is independently unsubstituted aryl. In embodiments, $R^{101C}$ is independently unsubstituted heteroaryl. In embodiments, $R^{101C}$ is independently substituted or unsubstituted $C_1$-$C_8$ alkyl. In embodiments, $R^{101C}$ is independently substituted or unsubstituted 2 to 8 membered heteroalkyl. In embodiments, $R^{101C}$ is independently substituted or unsubstituted $C_3$-$C_8$ cycloalkyl. In embodiments, $R^{101C}$ is independently, substituted or unsubstituted 3 to 8 membered heterocycloalkyl. In embodiments, $R^{101C}$ is independently substituted or unsubstituted $C_6$-$C_{10}$ aryl. In embodiments, $R^{101C}$ is independently substituted or unsubstituted 5 to 10 membered heteroaryl. In embodiments, $R^{101C}$ is independently substituted $C_1$-$C_8$ alkyl. In embodiments, $R^{101C}$ is independently substituted 2 to 8 membered heteroalkyl. In embodiments, $R^{101C}$ is independently substituted $C_3$-$C_8$ cycloalkyl. In embodiments, $R^{101C}$ is independently, substituted 3 to 8 membered heterocycloalkyl. In embodiments, $R^{101C}$ is independently substituted $C_6$-$C_{10}$ aryl. In embodiments, $R^{101C}$ is independently substituted 5 to 10 membered heteroaryl. In embodiments, $R^{101C}$ is independently unsubstituted $C_1$-$C_8$ alkyl. In embodiments, $R^{101C}$ is independently unsubstituted 2 to 8 membered heteroalkyl. In embodiments, $R^{101C}$ is independently unsubstituted $C_3$-$C_8$ cycloalkyl. In embodiments, $R^{101C}$ is independently, unsubstituted 3 to 8 membered heterocycloalkyl. In embodiments, $R^{101C}$ is independently unsubstituted $C_6$-$C_{10}$ aryl. In embodiments, $R^{101C}$ is independently unsubstituted 5 to 10 membered heteroaryl. In embodiments, $R^{101C}$ is independently substituted or unsubstituted $C_1$-$C_4$ alkyl. In embodiments, $R^{101C}$ is independently substituted or unsubstituted 2 to 4 membered heteroalkyl. In embodiments, $R^{101C}$ is independently substituted or unsubstituted $C_3$-$C_6$ cycloalkyl. In embodiments, $R^{101C}$ is independently, substituted or unsubstituted 3 to 6 membered heterocycloalkyl. In embodiments, $R^{101C}$ is independently substituted or unsubstituted phenyl. In embodiments, $R^{101C}$ is independently substituted or unsubstituted 5 to 6 membered heteroaryl. In embodiments, $R^{101C}$ is independently substituted $C_1$-$C_4$ alkyl. In embodiments, $R^{101C}$ is independently substituted 2 to 4 membered heteroalkyl. In embodiments, $R^{101C}$ is independently substituted $C_3$-$C_6$ cycloalkyl. In embodiments, $R^{101C}$ is independently, substituted 3 to 6 membered heterocycloalkyl. In embodiments, $R^{101C}$ is independently substituted phenyl. In embodiments, $R^{101C}$ is independently substituted 5 to 6 membered heteroaryl. In embodiments, $R^{101C}$ is independently unsubstituted $C_1$-$C_4$ alkyl. In embodiments, $R^{101C}$ is independently unsubstituted 2 to 4 membered heteroalkyl. In embodiments, $R^{101C}$ is independently unsubstituted $C_3$-$C_6$ cycloalkyl. In embodiments, $R^{101C}$ is independently unsubstituted 3 to 6 membered heterocycloalkyl. In embodiments, $R^{101C}$ is independently unsubstituted phenyl. In embodiments, $R^{101C}$ is independently unsubstituted 5 to 6 membered heteroaryl. In embodiments, $R^{101C}$ is independently unsubstituted methyl. In embodiments, $R^{101C}$ is independently unsubstituted ethyl. In embodiments, $R^{101C}$ is independently unsubstituted propyl. In embodiments, $R^{101C}$ is independently unsubstituted isopropyl. In embodiments, $R^{101C}$ is independently unsubstituted tert-butyl.

In embodiments, $R^{101D}$ is independently hydrogen. In embodiments, $R^{101D}$ is independently —$CX^{101D}_3$. In embodiments, $R^{101D}$ is independently —$CHX^{101D}_2$. In embodiments, $R^{101D}$ is independently —$CH_2X^{101D}$. In embodiments, $R^{101D}$ is independently —CN. In embodiments, $R^{101D}$ is independently —COOH. In embodiments, $R^{101D}$ is independently —$CONH_2$. In embodiments, $R^{101D}$ is independently substituted or unsubstituted alkyl. In embodiments, $R^{101D}$ is independently substituted or unsubstituted heteroalkyl. In embodiments, $R^{101D}$ is independently substituted or unsubstituted cycloalkyl. In embodiments, $R^{101D}$ is independently, substituted or unsubstituted heterocycloalkyl. In embodiments, $R^{101D}$ is independently substituted or unsubstituted aryl. In embodiments, $R^{101D}$ is independently substituted or unsubstituted heteroaryl. In embodiments, $R^{101D}$ is independently substituted alkyl. In embodiments, $R^{101D}$ is independently substituted heteroalkyl. In embodiments, $R^{101D}$ is independently substituted cycloalkyl. In embodiments, $R^{101D}$ is independently, substituted heterocycloalkyl. In embodiments, $R^{101D}$ is independently substituted aryl. In embodiments, $R^{101D}$ is independently substituted heteroaryl. In embodiments, $R^{101D}$ is independently unsubstituted alkyl. In embodiments, $R^{101D}$ is independently unsubstituted heteroalkyl. In embodiments, $R^{101D}$ is independently unsubstituted cycloalkyl. In embodiments, $R^{101D}$ is independently, unsubstituted heterocycloalkyl. In embodiments, $R^{101D}$ is independently unsubstituted aryl. In embodiments, $R^{101D}$ is independently unsubstituted heteroaryl. In embodiments, $R^{101D}$ is independently substituted or unsubstituted $C_1$-$C_8$ alkyl. In embodiments, $R^{101D}$ is independently substituted or unsubstituted 2 to 8 membered heteroalkyl. In embodiments, $R^{101D}$ is independently substituted or unsubstituted $C_3$-$C_8$ cycloalkyl. In embodiments, $R^{101D}$ is independently, substituted or unsubstituted 3 to 8 membered heterocycloalkyl. In embodiments, $R^{101D}$ is independently substituted or unsubstituted $C_6$-$C_{10}$ aryl. In embodiments, $R^{101D}$ is independently substituted or unsubstituted 5 to 10 membered heteroaryl. In embodiments, $R^{101D}$ is independently substituted $C_1$-$C_8$ alkyl. In embodiments, $R^{101D}$ is independently substituted 2 to 8 membered heteroalkyl. In embodiments, $R^{101D}$ is independently substituted $C_3$-$C_8$ cycloalkyl. In embodiments, $R^{101D}$ is independently, substituted 3 to 8 membered heterocycloalkyl. In embodiments, $R^{101D}$ is independently substituted $C_6$-$C_{10}$ aryl. In embodiments, $R^{101D}$ is independently substituted 5 to 10 membered heteroaryl. In embodiments, $R^{101D}$ is independently unsubstituted $C_1$-$C_8$ alkyl. In embodiments, $R^{101D}$ is independently unsubstituted 2 to 8 membered heteroalkyl. In embodiments, $R^{101D}$ is independently unsubstituted $C_3$-$C_8$ cycloalkyl. In embodiments, $R^{101D}$ is independently, unsubstituted 3 to 8 membered heterocycloalkyl. In embodiments, $R^{101D}$ is independently unsubstituted $C_6$-$C_{10}$ aryl. In embodiments, $R^{101D}$ is independently unsubstituted 5 to 10 membered heteroaryl. In embodiments, $R^{101D}$ is independently substituted or unsubstituted $C_1$-$C_4$ alkyl. In embodiments, $R^{101D}$ is independently substituted or unsubstituted 2 to 4 membered heteroalkyl. In embodiments, $R^{101D}$ is independently substituted or unsubstituted $C_3$-$C_6$ cycloalkyl. In embodiments, $R^{101D}$ is independently, substituted or unsubstituted 3 to 6 membered heterocycloalkyl. In embodiments, $R^{101D}$ is independently substituted or unsubstituted phenyl. In embodiments, $R^{101D}$ is independently substituted or unsubstituted 5 to 6 membered heteroaryl. In embodiments, $R^{101D}$ is independently substituted $C_1$-$C_4$ alkyl. In embodiments, $R^{101D}$ is independently substituted 2 to 4 membered heteroalkyl. In embodiments, $R^{101D}$ is independently substituted $C_3$-$C_6$ cycloalkyl. In embodiments, substituted 3 to 6 membered heterocycloalkyl. In embodiments, $R^{101D}$ is independently substituted phenyl. In embodiments, $R^{101D}$ is independently substituted 5 to 6 membered heteroaryl. In embodiments, $R^{101D}$ is independently unsubstituted $C_1$-$C_4$ alkyl. In embodiments, $R^{101D}$ is independently unsubstituted 2 to 4 membered heteroalkyl. In embodiments, $R^{101D}$ is independently unsubstituted $C_3$-$C_6$ cycloalkyl. In embodiments, $R^{101D}$ is independently unsubstituted 3 to 6 membered heterocycloalkyl. In embodiments, $R^{101D}$ is independently unsubstituted phenyl. In embodiments, $R^{101D}$ is independently unsubstituted 5 to 6 membered heteroaryl. In embodiments, $R^{101D}$ is independently unsubstituted methyl. In embodiments, $R^{101D}$ is independently unsubstituted ethyl. In embodiments, $R^{101D}$ is independently unsubstituted propyl. In embodiments, $R^{101D}$ is independently unsubstituted isopropyl. In embodiments, $R^{101D}$ is independently unsubstituted tert-butyl.

In embodiments, $R^{101}$ is independently hydrogen, halogen, —$CX^{101}_3$, —$CHX^{101}_2$, —$CH_2X^{101}$, —$OCX^{101}_3$, —$OCH_2X^{101}$, —$OCHX^{101}_2$, —CN, —$SO_{n101}R^{101D}$, —$SO_{v101}NR^{101A}R^{101B}$, —$NHC(O)NR^{101A}R^{101B}$, —$N(O)_{m101}$, —$NR^{101A}R^{101B}$, —$C(O)R^{101C}$, —$C(O)OR^{101C}$, —$C(O)NR^{101A}R^{101B}$, —$OR^{101D}$, —$NR^{101A}SO_2R^{101D}$, —$NR^{101A}C(O)R^{101C}$, —$NR^{101A}C(O)OR^{101C}$, —$NR^{101A}OR^{101C}$, $R^{102}$-substituted or unsubstituted alkyl, $R^{102}$-substituted or unsubstituted heteroalkyl, $R^{102}$-substituted or unsubstituted cycloalkyl, $R^{102}$-substituted or unsubstituted heterocycloalkyl, $R^{102}$-substituted or unsubstituted aryl, or $R^{102}$-substituted or unsubstituted heteroaryl. In embodiments, $R^{101}$ is independently halogen, —$CX^{101}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCX^{101}_3$, —$OCHX^{101}_2$, $R^{102}$-substituted or unsubstituted alkyl, $R^{102}$-substituted or unsubstituted heteroalkyl, $R^{102}$-substituted or unsubstituted cycloalkyl, $R^{102}$-substituted or unsubstituted heterocycloalkyl, $R^{102}$-substituted or unsubstituted aryl, or $R^{102}$-substituted or unsubstituted heteroaryl. In embodiments, $R^{102}$ is independently halogen, —$CX^{101}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCX^{101}_3$, —$OCHX^{102}_2$, $R^{102}$-substituted or unsubstituted $C_1$-$C_8$ alkyl, $R^{102}$-substituted or unsubstituted 2 to 8 membered heteroalkyl, $R^{102}$-substituted or unsubstituted $C_3$-$C_8$ cycloalkyl, $R^{102}$-substituted or unsubstituted 3 to 6 membered heterocycloalkyl, $R^{102}$-substituted or unsubstituted phenyl, or $R^{102}$-substituted or unsubstituted 5 to 6 membered heteroaryl. $X^{101}$ is —F, —Cl, —Br, or —I. In embodiments, $R^{101}$ is independently hydrogen. In embodiments, $R^{101}$ is independently methyl. In embodiments, $R^{101}$ is independently ethyl.

In embodiments, $R^{101}$ is independently halogen, —$CX^{101}_3$, —CN, —OH, —COOH, —$CONH_2$, —$OCX^{101}_3$, —$OCHX^{101}_2$, $R^{102}$-substituted or unsubstituted $C_1$-$C_8$ alkyl, $R^{102}$-substituted or unsubstituted 2 to 8 membered heteroalkyl, $R^{102}$-substituted or unsubstituted $C_3$-$C_8$ cycloalkyl, $R^{102}$-substituted or unsubstituted 3 to 6 membered heterocycloalkyl, $R^{102}$-substituted or unsubstituted phenyl, or $R^{102}$-substituted or unsubstituted 5 to 6 membered heteroaryl. $X^{101}$ is —F, —Cl, —Br, or —I. In embodiments, $R^{101}$ is independently hydrogen. In embodiments, $R^{101}$ is independently methyl. In embodiments, $R^{101}$ is independently ethyl.

$R^{102}$ is independently oxo, halogen, —$CX^{102}_3$, —CN, —OH, —$NH_2$, —COOH, —$CONH_2$, —$NO_2$, —SH, —$SO_3H$, —$SO_4H$, —$S_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCX^{102}_3$, —$OCHX^{102}_2$, $R^{103}$-substituted or unsubstituted alkyl, $R^{103}$-substituted or unsubstituted heteroalkyl, $R^{103}$-substituted or unsubstituted cycloalkyl, $R^{103}$-substituted or unsubstituted heterocycloalkyl, $R^{103}$-substituted or unsubstituted aryl, or $R^{103}$-substituted or unsubstituted heteroaryl. In embodiments, $R^{102}$ is independently oxo, halogen, —$CX^{102}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCX^{102}_3$, —$OCHX^{102}_2$, $R^{103}$-substituted or unsubstituted $C_1$-$C_8$ alkyl, $R^{103}$-substituted or unsubstituted 2 to 8 membered heteroalkyl, $R^{103}$-substituted or unsubstituted $C_3$-$C_8$ cycloalkyl, $R^{103}$-substituted or unsubstituted 3 to 6 membered heterocycloalkyl, $R^{103}$-substituted or unsubstituted phenyl, or $R^{103}$-substituted or unsubstituted 5 to 6 membered heteroaryl. $X^{102}$ is —F, —Cl, —Br, or —I.

$R^{103}$ is independently oxo, halogen, —$CX^{103}_3$, —CN, —OH, —$NH_2$, —COOH, —$CONH_2$, —$NO_2$, —SH, —$S_3H$, —$SO_4H$, —$S_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCX^{103}_3$, —$OCHX^{103}_2$, $R^{104}$-substituted or unsubstituted alkyl, $R^{104}$-substituted or unsubstituted heteroalkyl, $R^{104}$-substituted or unsubstituted cycloalkyl, $R^{104}$-substituted or unsubstituted heterocycloalkyl, $R^{104}$-substituted or unsubstituted aryl, or $R^{104}$-substituted or unsubstituted heteroaryl. In embodiments, $R^{103}$ is independently oxo, halogen, —$CX^{103}_3$, —CN, —OH, —$NH_2$, —COOH, —$CONH_2$, —$NO_2$, —SH, —$S_3H$, —$SO_4H$, —$S_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCX^{103}_3$, —$OCHX^{103}_2$, $R^{104}$-substituted or unsubstituted $C_1$-$C_8$ alkyl, $R^{104}$-substituted or unsubstituted 2 to 8 membered heteroalkyl, $R^{104}$-substituted or unsubstituted $C_3$-$C_8$ cycloalkyl, $R^{104}$-substituted or unsubstituted 3 to 6 membered heterocycloalkyl, $R^{104}$-substituted or unsubstituted phenyl, or $R^{104}$-substituted or unsubstituted 5 to 6 membered heteroaryl. $X^{103}$ is —F, —Cl, —Br, or —I.

In embodiments, $R^{101A}$ is independently hydrogen, $-CX^{101A}_3$, $-CN$, $-COOH$, $-CONH_2$, $-CHX^{101A}_2$, $-CH_2X^{101A}$, $R^{102A}$-substituted or unsubstituted alkyl, $R^{102A}$-substituted or unsubstituted heteroalkyl, $R^{102A}$-substituted or unsubstituted cycloalkyl, $R^{102A}$-substituted or unsubstituted heterocycloalkyl, $R^{102A}$-substituted or unsubstituted aryl, or $R^{102A}$-substituted or unsubstituted heteroaryl. In embodiments, $R^{101A}$ is independently hydrogen, $-CX^{101A}_3$, $-CN$, $-COOH$, $-CONH_2$, $-CHX^{101A}_2$, $-CH_2X^{101A}$, $R^{102A}$-substituted or unsubstituted $C_1$-$C_8$ alkyl, $R^{102A}$-substituted or unsubstituted 2 to 8 membered heteroalkyl, $R^{102A}$-substituted or unsubstituted $C_3$-$C_8$ cycloalkyl, $R^{102A}$-substituted or unsubstituted 3 to 6 membered heterocycloalkyl, $R^{102A}$-substituted or unsubstituted phenyl, or $R^{102A}$-substituted or unsubstituted 5 to 6 membered heteroaryl. $X^{101A}$ is $-F$, $-Cl$, $-Br$, or $-I$. In embodiments, $R^{101A}$ is independently hydrogen. In embodiments, $R^{101A}$ is independently methyl. In embodiments, $R^{101A}$ is independently ethyl.

In embodiments, $R^{101A}$ and $R^{101B}$ substituents bonded to the same nitrogen atom may optionally be joined to form a $R^{102A}$-substituted or unsubstituted heterocycloalkyl or $R^{102A}$-substituted or unsubstituted heteroaryl. In embodiments, $R^{101A}$ and $R^{101B}$ substituents bonded to the same nitrogen atom may optionally be joined to form a $R^{102A}$-substituted or unsubstituted 3 to 6 membered heterocycloalkyl or $R^{102A}$-substituted or unsubstituted 5 to 6 membered heteroaryl.

$R^{102A}$ is independently oxo, halogen, $-CX^{102A}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{102A}_3$, $-OCHX^{102A}_2$, $R^{103A}$-substituted or unsubstituted alkyl, $R^{103A}$-substituted or unsubstituted heteroalkyl, $R^{103A}$-substituted or unsubstituted cycloalkyl, $R^{103A}$-substituted or unsubstituted heterocycloalkyl, $R^{13A}$-substituted or unsubstituted aryl, or $R^{103A}$-substituted or unsubstituted heteroaryl. In embodiments, $R^{102A}$ is independently oxo, halogen, $-CX^{102A}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{102A}_3$, $-OCHX^{102A}_2$, $R^{103A}$-substituted or unsubstituted $C_1$-$C_8$ alkyl, $R^{103A}$-substituted or unsubstituted 2 to 8 membered heteroalkyl, $R^{103A}$-substituted or unsubstituted $C_3$-$C_8$ cycloalkyl, $R^{103A}$-substituted or unsubstituted 3 to 6 membered heterocycloalkyl, $R^{103A}$-substituted or unsubstituted phenyl, or $R^{103A}$-substituted or unsubstituted 5 to 6 membered heteroaryl. $X^{102A}$ is $-F$, $-Cl$, $-Br$, or $-I$.

$R^{103A}$ is independently oxo, halogen, $-CX^{103A}_3$, $-CN$, $-OH$, $-NH_2$, $-COOH$, $-CONH_2$, $-NO_2$, $-SH$, $-SO_3H$, $-SO_4H$, $-S_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{103A}_3$, $-OCHX^{103A}_2$, $R^{104A}$-substituted or unsubstituted alkyl, $R^{104A}$-substituted or unsubstituted heteroalkyl, $R^{104A}$-substituted or unsubstituted cycloalkyl, $R^{104A}$-substituted or unsubstituted heterocycloalkyl, $R^{104A}$-substituted or unsubstituted aryl, or $R^{104A}$-substituted or unsubstituted heteroaryl. In embodiments, $R^{103A}$ is independently oxo, halogen, $-CX^{103A}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{103A}_3$, $-OCHX^{103A}_2$, $R^{104A}$-substituted or unsubstituted $C_1$-$C_8$ alkyl, $R^{104A}$-substituted or unsubstituted 2 to 8 membered heteroalkyl, $R^{104A}$-substituted or unsubstituted $C_3$-$C_8$ cycloalkyl, $R^{104A}$-substituted or unsubstituted 3 to 6 membered heterocycloalkyl, $R^{104A}$-substituted or unsubstituted phenyl, or $R^{104A}$-substituted or unsubstituted 5 to 6 membered heteroaryl. $X^{103A}$ is $-F$, $-Cl$, $-Br$, or $-I$.

In embodiments, $R^{101B}$ is independently hydrogen, $-CX^{101B}_3$, $-CN$, $-COOH$, $-CONH_2$, $-CHX^{101B}_2$, $-CH_2X^{101B}$, $R^{102B}$-substituted or unsubstituted alkyl, $R^{102B}$-substituted or unsubstituted heteroalkyl, $R^{102B}$-substituted or unsubstituted cycloalkyl, $R^{102B}$-substituted or unsubstituted heterocycloalkyl, $R^{102B}$-substituted or unsubstituted aryl, or $R^{102B}$-substituted or unsubstituted heteroaryl. In embodiments, $R^{101B}$ is independently hydrogen, $-CX^{101B}_3$, $-CN$, $-COOH$, $-CONH_2$, $-CHX^{101B}_2$, $-CH_2X^{101B}$, $R^{102B}$-substituted or unsubstituted $C_1$-$C_8$ alkyl, $R^{102B}$-substituted or unsubstituted 2 to 8 membered heteroalkyl, $R^{102B}$-substituted or unsubstituted $C_3$-$C_8$ cycloalkyl, $R^{102B}$-substituted or unsubstituted 3 to 6 membered heterocycloalkyl, $R^{102B}$-substituted or unsubstituted phenyl, or $R^{102B}$-substituted or unsubstituted 5 to 6 membered heteroaryl. $X^{101B}$ is $-F$, $-Cl$, $-Br$, or $-I$. In embodiments, $R^{101B}$ is independently hydrogen. In embodiments, $R^{101B}$ is independently methyl. In embodiments, $R^{101B}$ is independently ethyl.

In embodiments, $R^{101A}$ and $R^{101B}$ substituents bonded to the same nitrogen atom may optionally be joined to form a $R^{102B}$-substituted or unsubstituted heterocycloalkyl or $R^{102B}$-substituted or unsubstituted heteroaryl. In embodiments, $R^{101A}$ and $R^{101B}$ substituents bonded to the same nitrogen atom may optionally be joined to form a $R^{102B}$-substituted or unsubstituted 3 to 6 membered heterocycloalkyl or $R^{102B}$-substituted or unsubstituted 5 to 6 membered heteroaryl.

$R^{102B}$ is independently oxo, halogen, $-CX^{102B}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{102B}_3$, $-OCHX^{102B}_2$, $R^{103B}$-substituted or unsubstituted alkyl, $R^{103B}$-substituted or unsubstituted heteroalkyl, $R^{103B}$-substituted or unsubstituted cycloalkyl, $R^{103B}$-substituted or unsubstituted heterocycloalkyl, $R^{103B}$-substituted or unsubstituted aryl, or $R^{103B}$-substituted or unsubstituted heteroaryl. In embodiments, $R^{102B}$ is independently oxo, halogen, $-CX^{102B}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{102B}_3$, $-OCHX^{102B}_2$, $R^{103B}$-substituted or unsubstituted $C_1$-$C_8$ alkyl, $R^{103B}$-substituted or unsubstituted 2 to 8 membered heteroalkyl, $R^{103B}$-substituted or unsubstituted $C_3$-$C_8$ cycloalkyl, $R^{103B}$-substituted or unsubstituted 3 to 6 membered heterocycloalkyl, $R^{103B}$-substituted or unsubstituted phenyl, or $R^{103B}$-substituted or unsubstituted 5 to 6 membered heteroaryl. $X^{102B}$ is $-F$, $-Cl$, $-Br$, or $-I$.

$R^{103B}$ is independently oxo, halogen, $-CX^{103B}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{103B}_3$, $-OCHX^{103B}_2$, $R^{104B}$-substituted or unsubstituted alkyl, $R^{104B}$-substituted or unsubstituted heteroalkyl, $R^{104B}$-substituted or unsubstituted cycloalkyl, $R^{104B}$-substituted or unsubstituted heterocycloalkyl, $R^{104B}$-substituted or unsubstituted aryl, or $R^{104B}$-substituted or unsubstituted heteroaryl. In embodiments, $R^{103B}$ is independently oxo, halogen, —$CX^{103B}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{103B}_3$, —$OCHX^{103B}_2$, $R^{104B}$-substituted or unsubstituted $C_1$-$C_8$ alkyl, $R^{104B}$-substituted or unsubstituted 2 to 8 membered heteroalkyl, $R^{104B}$-substituted or unsubstituted $C_3$-$C_8$ cycloalkyl, $R^{104B}$-substituted or unsubstituted 3 to 6 membered heterocycloalkyl, $R^{104B}$-substituted or unsubstituted phenyl, or $R^{104B}$-substituted or unsubstituted 5 to 6 membered heteroaryl. $X^{103B}$ is —F, —Cl, —Br, or —I.

In embodiments, $R^{101C}$ is independently hydrogen, —$CX^{101C}_3$, —CN, —COOH, —$CONH_2$, —$CHX^{101C}_2$, —$CH_2X^{101C}$, $R^{102C}$-substituted or unsubstituted alkyl, $R^{102C}$-substituted or unsubstituted heteroalkyl, $R^{102C}$-substituted or unsubstituted cycloalkyl, $R^{102C}$-substituted or unsubstituted heterocycloalkyl, $R^{102C}$-substituted or unsubstituted aryl, or $R^{102C}$-substituted or unsubstituted heteroaryl. In embodiments, $R^{101C}$ is independently hydrogen, —$CX^{101C}_3$, —CN, —COOH, —$CONH_2$, —$CHX^{101C}_2$, —$CH_2X^{101C}$, $R^{102C}$-substituted or unsubstituted $C_1$-$C_8$ alkyl, $R^{102C}$-substituted or unsubstituted 2 to 8 membered heteroalkyl, $R^{102C}$-substituted or unsubstituted $C_3$-$C_8$ cycloalkyl, $R^{102C}$-substituted or unsubstituted 3 to 6 membered heterocycloalkyl, $R^{102C}$-substituted or unsubstituted phenyl, or $R^{102C}$-substituted or unsubstituted 5 to 6 membered heteroaryl. $X^{101C}$ is —F, —Cl, —Br, or —I. In embodiments, $R^{101C}$ is independently hydrogen. In embodiments, $R^{101C}$ is independently methyl. In embodiments, $R^{101C}$ is independently ethyl.

$R^{102C}$ is independently oxo, halogen, —$CX^{102C}_3$, —CN, —OH, —$NH_2$, —COOH, —$CONH_2$, —$NO_2$, —SH, —$SO_3H$, —$SO_4H$, —$S_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{102C}_3$, —$OCHX^{102C}_2$, $R^{103C}$-substituted or unsubstituted alkyl, $R^{103C}$-substituted or unsubstituted heteroalkyl, $R^{103C}$-substituted or unsubstituted cycloalkyl, $R^{103C}$-substituted or unsubstituted heterocycloalkyl, $R^{103C}$-substituted or unsubstituted aryl, or $R^{103C}$-substituted or unsubstituted heteroaryl. In embodiments, $R^{102C}$ is independently oxo, halogen, —$CX^{102C}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{102C}_3$, —$OCHX^{102C}_2$, $R^{103C}$-substituted or unsubstituted $C_1$-$C_8$ alkyl, $R^{103C}$-substituted or unsubstituted 2 to 8 membered heteroalkyl, $R^{103C}$-substituted or unsubstituted $C_3$-$C_8$ cycloalkyl, $R^{103C}$-substituted or unsubstituted 3 to 6 membered heterocycloalkyl, $R^{103C}$-substituted or unsubstituted phenyl, or $R^{103C}$-substituted or unsubstituted 5 to 6 membered heteroaryl. $X^{102C}$ is —F, —Cl, —Br, or —I.

$R^{103C}$ is independently oxo, halogen, —$CX^{103C}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{103C}_3$, —$OCHX^{103C}_2$$R^{104C}$-substituted or unsubstituted alkyl, $R^{104C}$-substituted or unsubstituted heteroalkyl, $R^{104C}$-substituted or unsubstituted cycloalkyl, $R^{104C}$-substituted or unsubstituted heterocycloalkyl, $R^{104C}$-substituted or unsubstituted aryl, or $R^{104C}$-substituted or unsubstituted heteroaryl. In embodiments, $R^{103C}$ is independently oxo, halogen, —$CX^{103C}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{103C}_3$, —$OCHX^{103C}_2$, $R^{104C}$-substituted or unsubstituted $C_1$-$C_8$ alkyl, $R^{104C}$-substituted or unsubstituted 2 to 8 membered heteroalkyl, $R^{104C}$-substituted or unsubstituted $C_3$-$C_8$ cycloalkyl, $R^{104C}$-substituted or unsubstituted 3 to 6 membered heterocycloalkyl, $R^{104C}$-substituted or unsubstituted phenyl, or $R^{104C}$-substituted or unsubstituted 5 to 6 membered heteroaryl. $X^{103C}$ is —F, —Cl, —Br, or —I.

In embodiments, $R^{101D}$ is independently hydrogen, —$CX^{101D}_3$, —CN, —COOH, —$CONH_2$, —$CHX^{101D}_2$, —$CH_2X^{101D}$, $R^{102D}$-substituted or unsubstituted alkyl, $R^{102D}$-substituted or unsubstituted heteroalkyl, $R^{102D}$-substituted or unsubstituted cycloalkyl, $R^{102D}$-substituted or unsubstituted heterocycloalkyl, $R^{102D}$-substituted or unsubstituted aryl, or $R^{102D}$-substituted or unsubstituted heteroaryl. In embodiments, $R^{101D}$ is independently hydrogen, —$CX^{101D}_3$, —CN, —COOH, —$CONH_2$, —$CHX^{101D}_2$, —$CH_2X^{101D}$, $R^{102D}$-substituted or unsubstituted $C_1$-$C_8$ alkyl, $R^{102D}$-substituted or unsubstituted 2 to 8 membered heteroalkyl, $R^{102D}$-substituted or unsubstituted $C_3$-$C_8$ cycloalkyl, $R^{102D}$-substituted or unsubstituted 3 to 6 membered heterocycloalkyl, $R^{102D}$-substituted or unsubstituted phenyl, or $R^{102D}$-substituted or unsubstituted 5 to 6 membered heteroaryl. $X^{101D}$ is —F, —Cl, —Br, or —I. In embodiments, $R^{101D}$ is independently hydrogen. In embodiments, $R^{101D}$ is independently methyl. In embodiments, $R^{101D}$ is independently ethyl.

$R^{102D}$ is independently oxo, halogen, —$CX^{102D}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{102D}_3$, —$OCHX^{102D}_2$, $R^{103D}$-substituted or unsubstituted alkyl, $R^{103D}$-substituted or unsubstituted heteroalkyl, $R^{103D}$-substituted or unsubstituted cycloalkyl, $R^{103D}$-substituted or unsubstituted heterocycloalkyl, $R^{103D}$-substituted or unsubstituted aryl, or $R^{103D}$-substituted or unsubstituted heteroaryl. In embodiments, $R^{102D}$ is independently oxo, halogen, —$CX^{102D}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{102D}_3$, —$OCHX^{102D}_2$, $R^{103D}$-substituted or unsubstituted $C_1$-$C_8$ alkyl, $R^{103D}$-substituted or unsubstituted 2 to 8 membered heteroalkyl, $R^{103D}$-substituted or unsubstituted $C_3$-$C_8$ cycloalkyl, $R^{103D}$-substituted or unsubstituted 3 to 6 membered heterocycloalkyl, $R^{103D}$-substituted or unsubstituted phenyl, or $R^{103D}$-substituted or unsubstituted 5 to 6 membered heteroaryl. $X^{102D}$ is —F, —Cl, —Br, or —I.

$R^{103D}$ is independently oxo, halogen, —$CX^{103D}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{103D}_3$, —$OCHX^{103D}_2$, $R^{104D}$-substituted or unsubstituted alkyl, $R^{104D}$-substituted or unsubstituted heteroalkyl, $R^{104D}$-substituted or unsubstituted cyclalkyl, $R^{104D}$-substituted or unsubstituted heterocycloalkyl, $R^{104D}$-substituted or unsubstituted aryl, or $R^{104D}$-substituted or unsubstituted heteroaryl. In embodiments, $R^{103D}$ is independently oxo, halogen, —$CX^{103D}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{103D}_3$, —$OCHX^{103D}_2$, $R^{104D}$-substituted or unsubstituted $C_1$-$C_8$ alkyl, $R^{104D}$-substituted or unsubstituted 2 to 8 membered heteroalkyl, $R^{104D}$-substituted or unsubstituted $C_3$-$C_8$ cycloalkyl, $R^{104D}$-substituted or unsubstituted 3 to 6 membered heterocycloalkyl, $R^{104D}$-substituted or unsubstituted phenyl, or $R^{104D}$-substituted or unsubstituted 5 to 6 membered heteroaryl. $X^{103D}$ is —F, —Cl, —Br, or —I.

$R^{104}$, $R^{104A}$, $R^{104B}$, $R^{104C}$, and $R^{104D}$ are hydrogen, oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCl$_3$, —OCHCl$_2$, —OCHBr$_2$, —OCHI$_2$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{104}$, $R^{104A}$, $R^{104B}$, $R^{104C}$, and $R^{104D}$ are independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCl$_3$, —OCHCl$_2$, —OCHBr$_2$, —OCHI$_2$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{104}$, $R^{104A}$, $R^{104B}$, $R^{104C}$, and $R^{104D}$ are independently hydrogen, oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCl$_3$, —OCHCl$_2$, —OCHBr$_2$, —OCHI$_2$, —OCHF$_2$, unsubstituted $C_1$-$C_8$ alkyl, unsubstituted 2 to 8 membered heteroalkyl, unsubstituted $C_3$-$C_8$ cycloalkyl, unsubstituted 3 to 6 membered heterocycloalkyl, unsubstituted phenyl, or unsubstituted 5 to 6 membered heteroaryl.

In embodiments, $L^{108}$ is a bond, —S(O)$_2$—, —S(O)$_2$-Ph-, substituted or unsubstituted $C_1$-$C_8$ alkylene, substituted or unsubstituted 2 to 8 membered heteroalkylene, substituted or unsubstituted $C_3$-$C_8$ cycloalkylene, substituted or unsubstituted 3 to 8 membered heterocycloalkylene, substituted or unsubstituted phenylene, or substituted or unsubstituted 5 to 6 membered heteroarylene. In embodiments, $L^{108}$ is a bond. In embodiments, $L^{108}$ is a substituted or unsubstituted $C_1$-$C_6$ alkylene, substituted or unsubstituted 2 to 6 membered heteroalkylene, substituted or unsubstituted $C_3$-$C_6$ cycloalkylene, substituted or unsubstituted 3 to 6 membered heterocycloalkylene, substituted or unsubstituted phenylene, or substituted or unsubstituted 5 to 6 membered heteroarylene. In embodiments, $L^{108}$ is an unsubstituted $C_1$-$C_6$ alkylene, unsubstituted 2 to 6 membered heteroalkylene, or unsubstituted $C_3$-$C_6$ cycloalkylene. In embodiments, $L^{108}$ is an unsubstituted methylene.

In embodiments, $L^{108}$ is a bond. In embodiments, $L^{108}$ is —S(O)$_2$—. In embodiments, $L^{108}$ is —S(O)$_2$-Ph-. In embodiments, $L^{108}$ is —NR$^{109A}$—. In embodiments, $L^{108}$ is —O—. In embodiments, $L^{108}$ is —S—. In embodiments, $L^{108}$ is —C(O)—. In embodiments, $L^{108}$ is —C(O)NR$^{109A}$—. In embodiments, $L^{108}$ is —NR$^{109}$C(O)—. In embodiments, $L^{108}$ is —NR$^{109}$C(O)NH—. In embodiments, $L^{108}$ is —NHC(O)NR$^{109A}$—. In embodiments, $L^{108}$ is —C(O)O—. In embodiments, $L^{108}$ is —OC(O)—. In embodiments, $L^{108}$ is —NH—. In embodiments, $L^{108}$ is —C(O)NH—. In embodiments, $L^{108}$ is —NHC(O)—. In embodiments, $L^{108}$ is —NHC(O)NH—. In embodiments, $L^{108}$ is —CH$_2$—. In embodiments, $L^{108}$ is —OCH$_2$—. In embodiments, $L^{108}$ is —CH$_2$O—. In embodiments, $L^{108}$ is —CH$_2$CH$_2$—. In embodiments, $L^{108}$ is —SCH$_2$—. In embodiments, $L^{108}$ is —CH$_2$S—. In embodiments, $L^{108}$ is —CHCH—. In embodiments, $L^{108}$ is —CC—. In embodiments, $L^{108}$ is —NHCH$_2$—. In embodiments, $L^{108}$ is —CH$_2$NH—.

In embodiments, $L^{108}$ is a substituted or unsubstituted alkylene. In embodiments, $L^{108}$ is a substituted or unsubstituted heteroalkylene. In embodiments, $L^{108}$ is a substituted or unsubstituted cycloalkylene. In embodiments, $L^{108}$ is a substituted or unsubstituted heterocycloalkylene. In embodiments, $L^{108}$ is a substituted or unsubstituted arylene. In embodiments, $L^{108}$ is a substituted or unsubstituted heteroarylene. In embodiments, $L^{108}$ is a substituted alkylene. In embodiments, $L^{108}$ is a substituted heteroalkylene. In embodiments, $L^{108}$ is a substituted cycloalkylene. In embodiments, $L^{108}$ is a substituted heterocycloalkylene. In embodiments, $L^{108}$ is a substituted arylene. In embodiments, $L^{108}$ is a substituted heteroarylene. In embodiments, $L^{108}$ is an unsubstituted alkylene. In embodiments, $L^{108}$ is an unsubstituted heteroalkylene. In embodiments, $L^{108}$ is an unsubstituted cycloalkylene. In embodiments, $L^{108}$ is an unsubstituted heterocycloalkylene. In embodiments, $L^{108}$ is an unsubstituted arylene. In embodiments, $L^{108}$ is an unsubstituted heteroarylene. In embodiments, $L^{108}$ is a substituted or unsubstituted $C_1$-$C_8$ alkylene. In embodiments, $L^{108}$ is a substituted or unsubstituted 2 to 8 membered heteroalkylene. In embodiments, $L^{108}$ is a substituted or unsubstituted $C_3$-$C_8$ cycloalkylene. In embodiments, $L^{108}$ is a substituted or unsubstituted 3 to 8 membered heterocycloalkylene. In embodiments, $L^{108}$ is a substituted or unsubstituted $C_6$-$C_{10}$ arylene. In embodiments, $L^{108}$ is a substituted or unsubstituted 5 to 10 membered heteroarylene. In embodiments, $L^{108}$ is a substituted $C_1$-$C_8$ alkylene. In embodiments, $L^{108}$ is a substituted 2 to 8 membered heteroalkylene. In embodiments, $L^{108}$ is a substituted $C_3$-$C_8$ cycloalkylene. In embodiments, $L^{108}$ is a substituted 3 to 8 membered heterocycloalkylene. In embodiments, $L^{108}$ is a substituted $C_6$-$C_{10}$ arylene. In embodiments, $L^{108}$ is a substituted 5 to 10 membered heteroarylene. In embodiments, $L^{108}$ is an unsubstituted $C_1$-$C_8$ alkylene. In embodiments, $L^{108}$ is an unsubstituted 2 to 8 membered heteroalkylene. In embodiments, $L^{108}$ is an unsubstituted $C_3$-$C_8$ cycloalkylene. In embodiments, $L^{108}$ is an unsubstituted 3 to 8 membered heterocycloalkylene. In embodiments, $L^{108}$ is an unsubstituted $C_6$-$C_{10}$ arylene. In embodiments, $L^{108}$ is an unsubstituted 5 to 10 membered heteroarylene. In embodiments, $L^{108}$ is a substituted or unsubstituted $C_1$-$C_4$ alkylene. In embodiments, $L^{108}$ is a substituted or unsubstituted 2 to 4 membered heteroalkylene. In embodiments, $L^{108}$ is a substituted or unsubstituted $C_3$-$C_6$ cycloalkylene. In embodiments, $L^{108}$ is a substituted or unsubstituted 3 to 6 membered heterocycloalkylene. In embodiments, $L^{108}$ is a substituted or unsubstituted phenylene. In embodiments, $L^{108}$ is a substituted or unsubstituted 5 to 6 membered heteroarylene. In embodiments, $L^{108}$ is a substituted $C_1$-$C_4$ alkylene. In embodiments, $L^{108}$ is a substituted 2 to 4 membered heteroalkylene. In embodiments, $L^{108}$ is a substituted $C_3$-$C_6$ cycloalkylene. In embodiments, $L^{108}$ is a substituted 3 to 6 membered heterocycloalkylene. In embodiments, $L^{108}$ is a substituted phenylene. In embodiments, $L^{108}$ is a substituted 5 to 6 membered heteroarylene. In embodiments, $L^{108}$ is an unsubstituted $C_1$-$C_4$ alkylene. In embodiments, $L^{108}$ is an unsubstituted 2 to 4 membered heteroalkylene. In embodiments, $L^{108}$ is an unsubstituted $C_3$-$C_6$ cycloalkylene. In embodiments, $L^{108}$ is an unsubstituted 3 to 6 membered heterocycloalkylene. In embodiments, $L^{108}$ is an unsubstituted phenylene. In embodiments, $L^{108}$ is an unsubstituted 5 to 6 membered heteroarylene.

In embodiments, $L^{108}$ is a bond, —S(O)$_2$—, —S(O)$_2$-Ph-, —NR$^{109A}$—, —O—, —S—, —C(O)—, —C(O)NR$^{109A}$—, —NR$^{109}$C(O)—, —NR$^{109}$C(O)NH—, —NHC(O)NR$^{109A}$—, —C(O)O—, —OC(O)—, $R^{113}$-substituted or unsubstituted alkylene, $R^{113}$-substituted or unsubstituted heteroalkylene, $R^{113}$-substituted or unsubstituted cycloalkylene, $R^{113}$-substituted or unsubstituted heterocycloalkylene, $R^{113}$-substituted or unsubstituted arylene, or $R^{113}$-substituted or unsubstituted heteroarylene. In embodiments, $L^{108}$ is a bond, —S(O)$_2$—, —S(O)$_2$-Ph-, —NH—, —O—, —S—, —C(O)—, —C(O)NH—, —NHC(O)—, —NHC(O)NH—, —C(O)O—, —OC(O)—, $R^{113}$-substituted or unsubstituted alkylene, $R^{113}$-substituted or unsubstituted heteroalkylene, $R^{113}$-substituted or unsubstituted cycloalkylene, $R^{113}$-substituted or unsubstituted heterocycloalkylene, $R^{113}$-substituted or unsubstituted arylene, or $R^{113}$-substituted or unsubstituted heteroarylene. In embodiments, $L^{108}$ is a bond, —S(O)$_2$—, —S(O)$_2$-Ph-, —NH—, —O—, —S—, —C(O)—, —C(O)NH—, —NHC(O)—, —NHC(O)NH—, —C(O)O—, —OC(O)—, $R^{113}$-substituted or unsubstituted $C_1$-$C_8$ alkylene, $R^{113}$-substituted or unsubstituted 2 to 8 membered heteroalkylene, $R^{113}$-substituted or unsubstituted $C_3$-$C_8$ cycloalkylene, $R^{113}$-substituted or unsubstituted 3 to 6 membered heterocycloalkylene, $R^{113}$-substituted or unsubstituted phenylene, or $R^{113}$-substituted or unsubstituted 5 to 6 membered heteroarylene.

In embodiments, $L^{108}$ has the formula

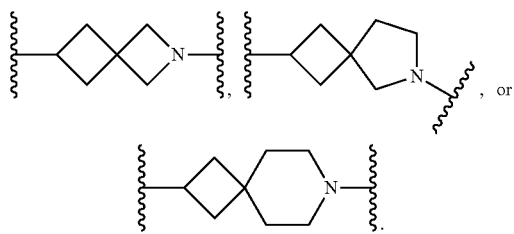

$R^{113}$ is independently oxo, halogen, —CX$^{113}$$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{113}$$_3$, —OCHX$^{113}$$_2$, $R^{114}$-substituted or unsubstituted alkyl, $R^{114}$-substituted or unsubstituted heteroalkyl, $R^{114}$-substituted or unsubstituted cycloalkyl, $R^{114}$-substituted or unsubstituted heterocycloalkyl, $R^{114}$-substituted or unsubstituted aryl, or $R^{114}$-substituted or unsubstituted heteroaryl. In embodiments, $R^{113}$ is independently oxo, halogen, —CX$^{113}$$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{113}$$_3$, —OCHX$^{113}$$_2$, $R^{114}$-substituted or unsubstituted $C_1$-$C_8$ alkyl, $R^{114}$-substituted or unsubstituted 2 to 8 membered heteroalkyl, $R^{114}$-substituted or unsubstituted $C_3$-$C_8$ cycloalkyl, $R^{114}$-substituted or unsubstituted 3 to 6 membered heterocycloalkyl, $R^{114}$-substituted or unsubstituted phenyl, or $R^{114}$-substituted or unsubstituted 5 to 6 membered heteroaryl. $X^{113}$ is —F, —Cl, —Br, or —I.

$R^{114}$ is independently oxo, halogen, —CX$^{114}$$_3$, —CN, —OH, —NH$_2$, —COOH, —CONH$_2$, —NO$_2$, —SH, —SO$_3$H, —SO$_4$H, —S$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{114}$$_3$, —OCHX$^{114}$$_2$, $R^{115}$-substituted or unsubstituted alkyl, $R^{15}$-substituted or unsubstituted heteroalkyl, $R^{115}$-substituted or unsubstituted cycloalkyl, $R^{115}$-substituted or unsubstituted heterocycloalkyl, $R^{115}$-substituted or unsubstituted aryl, or $R^{115}$-substituted or unsubstituted heteroaryl. In embodiments, $R^{114}$ is independently oxo, halogen, —CX$^{114}$$_3$, —CN, —OH, —NH$_2$, —COOH, —CONH$_2$, —NO$_2$, —SH, —SO$_3$H, —SO$_4$H, —S$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{114}$$_3$, —OCHX$^{114}$$_2$, $R^{115}$-substituted or unsubstituted $C_1$-$C_8$ alkyl, $R^{115}$-substituted or unsubstituted 2 to 8 membered heteroalkyl, $R^{115}$-substituted or unsubstituted $C_3$-$C_8$ cycloalkyl, $R^{115}$-substituted or unsubstituted 3 to 6 membered heterocycloalkyl, $R^{115}$-substituted or unsubstituted phenyl, or $R^{115}$-substituted or unsubstituted 5 to 6 membered heteroaryl. $X^{114}$ is —F, —Cl, —Br, or —I.

$R^{115}$ is independently hydrogen, oxo, halogen, —CCl$_3$, —CBr$_3$, —CF$_3$, —Cl$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCl$_3$, —OCHCl$_2$, —OCHBr$_2$, —OCHI$_2$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R_5$ is independently oxo, halogen, —CF$_3$, —CN, —OH, —NH$_2$, —COOH, —CONH$_2$, —NO$_2$, —SH, —S$_3$H, —SO$_4$H, —S$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{115}$ is independently oxo, halogen, —CF$_3$, —CN, —OH, —NH$_2$, —COOH, —CONH$_2$, —NO$_2$, —SH, —S$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCHF$_2$, unsubstituted $C_1$-$C_8$ alkyl, unsubstituted 2 to 8 membered heteroalkyl, unsubstituted $C_3$-$C_8$ cycloalkyl, unsubstituted 3 to 6 membered heterocycloalkyl, unsubstituted phenyl, or unsubstituted 5 to 6 membered heteroaryl.

In embodiments, $L^{108}$ is a bond. In embodiments, $L^{108}$ is $R^{113}$-substituted or unsubstituted $C_1$-$C_2$ alkylene. In embodiments, $L^{108}$ is $R^{113}$-substituted or unsubstituted $C_1$-$C_4$ alkylene. In embodiments, $L^{108}$ is $R^{113}$-substituted or unsubstituted $C_1$-$C_6$ alkylene. In embodiments, $L^{108}$ is $R^{113}$-substituted or unsubstituted $C_1$-$C_8$ alkylene. In embodiments, $L^{108}$ is $R^{113}$-substituted or unsubstituted alkylene (e.g., $C_1$-$C_8$ alkylene, $C_1$-$C_6$ alkylene, $C_1$-$C_4$ alkylene, $C_1$-$C_2$ alkylene). In embodiments, $L^{108}$ is $R^{113}$-substituted $C_1$-$C_2$ alkylene. In embodiments, $L^{108}$ is $R^{113}$-substituted $C_1$-$C_4$ alkylene. In embodiments, $L^{108}$ is $R^{113}$-substituted $C_1$-$C_6$ alkylene. In embodiments, $L^{108}$ is $R^{113}$-substituted $C_1$-$C_8$ alkylene. In embodiments, $L^{108}$ is $R^{113}$-substituted alkylene (e.g., $C_1$-$C_8$ alkylene, $C_1$-$C_6$ alkylene, $C_1$-$C_4$ alkylene, $C_1$-$C_2$ alkylene). In embodiments, $L^{108}$ is $R^{113}$-substituted methylene. In embodiments, $L^{108}$ is unsubstituted $C_1$-$C_2$ alkylene. In embodiments, $L^{108}$ is unsubstituted $C_1$-$C_4$ alkylene. In embodiments, $L^{108}$ is unsubstituted $C_1$-$C_6$ alkylene. In embodiments, $L^{108}$ is unsubstituted $C_1$-$C_8$ alkylene. In embodiments, $L^{108}$ is unsubstituted alkylene (e.g., $C_1$-$C_8$ alkylene, $C_1$-$C_6$ alkylene, $C_1$-$C_4$ alkylene, $C_1$-$C_2$ alkylene). In embodiments, $L^{108}$ is $R^{113}$-substituted or unsubstituted methylene. In embodiments, $L^{108}$ is $R^{113}$-substituted methylene. In embodiments, $L^{108}$ is unsubstituted methylene.

In embodiments, $L^{108}$ is $R^{113}$-substituted or unsubstituted 2 to 4 membered heteroalkylene. In embodiments, $L^{108}$ is $R^{113}$-substituted or unsubstituted 2 to 6 membered heteroalkylene. In embodiments, $L^{108}$ is $R^{113}$-substituted or unsubstituted 2 to 8 membered heteroalkylene. In embodiments, $L^{108}$ is $R^{113}$-substituted or unsubstituted heteroalkylene (e.g., 2 to 8 membered heteroalkylene, 2 to 6 membered heteroalkylene, 2 to 4 membered heteroalkylene). In embodiments, $L^{108}$ is $R^{113}$-substituted 2 to 4 membered heteroalkylene. In embodiments, $L^{108}$ is $R^{113}$-substituted 2 to 6 membered heteroalkylene. In embodiments, $L^{108}$ is $R^{113}$-substituted 2 to 8 membered heteroalkylene. In embodiments, $L^{108}$ is $R^{113}$-substituted heteroalkylene (e.g., 2 to 8 membered heteroalkylene, 2 to 6 membered heteroalkylene, 2 to 4 membered heteroalkylene). In embodiments, $L^{108}$ is unsubstituted 2 to 4 membered heteroalkylene. In embodiments, $L^{108}$ is unsubstituted 2 to 6 membered heteroalkylene. In embodiments, $L^{108}$ is unsubstituted 2 to 8 membered heteroalkylene. In embodiments, $L^{108}$ is unsubstituted heteroalkylene (e.g., 2 to 8 membered heteroalkylene, 2 to 6 membered heteroalkylene, 2 to 4 membered heteroalkylene).

In embodiments, $L^{108}$ is $R^{113}$-substituted or unsubstituted ethylaminylene. In embodiments, $L^{108}$ is $R^{113}$-substituted ethylaminylene. In embodiments, $L^{108}$ is unsubstituted ethylaminylene. In embodiments, $L^{108}$ is $R^{113}$-substituted or unsubstituted propylaminylene. In embodiments, $L^{108}$ is $R^{113}$-substituted propyl aminylene. In embodiments, $L^{108}$ is unsubstituted propylaminylene. In embodiments, $L^{108}$ is $R^{113}$-substituted or unsubstituted butylaminylene. In embodiments, $L^{108}$ is $R^{113}$-substituted butylaminylene. In embodiments, $L^{108}$ is unsubstituted butylaminylene.

In embodiments, $L^{108}$ is $R^{113}$-substituted or unsubstituted $C_3$-$C_8$ cycloalkylene. In embodiments, $L^{108}$ is $R^{113}$-substituted or unsubstituted $C_4$-$C_6$ cycloalkylene. In embodiments, $L^{108}$ is $R^{113}$-substituted or unsubstituted $C_5$-$C_6$ cycloalkylene. In embodiments, $L^{108}$ is $R^{113}$-substituted or unsubstituted cycloalkylene (e.g., $C_3$-$C_8$ cycloalkylene, $C_4$-$C_6$ cycloalkylene, or $C_5$-$C_6$ cycloalkylene). In embodiments, $L^{108}$ is $R^{113}$-substituted $C_3$-$C_8$ cycloalkylene. In embodiments, $L^{108}$ is $R^{113}$-substituted $C_4$-$C_6$ cycloalkylene. In embodiments, $L^{108}$ is $R^{113}$-substituted $C_5$-$C_6$ cycloalkylene. In embodiments, $L^{108}$ is $R^{113}$-substituted cycloalkylene (e.g., $C_3$-$C_8$ cycloalkylene, $C_4$-$C_6$ cycloalkylene, or $C_5$-$C_6$ cycloalkylene). In embodiments, $L^{108}$ is unsubstituted $C_3$-$C_8$ cycloalkylene. In embodiments, $L^{108}$ is unsubstituted $C_4$-$C_6$ cycloalkylene. In embodiments, $L^{108}$ is unsubstituted $C_5$-$C_6$ cycloalkylene. In embodiments, $L^{108}$ is unsubstituted cycloalkylene (e.g., $C_3$-$C_8$ cycloalkylene, $C_4$-$C_6$ cycloalkylene, or $C_5$-$C_6$ cycloalkylene).

In embodiments, $L^{108}$ is $R^{113}$-substituted or unsubstituted 4 membered heterocycloalkylene. In embodiments, $L^{108}$ is $R^{113}$-substituted or unsubstituted 5 membered heterocycloalkylene. In embodiments, $L^{108}$ is $R^{113}$-substituted or unsubstituted 6 membered heterocycloalkylene. In embodiments, $L^{108}$ is $R^{113}$-substituted or unsubstituted heterocycloalkylene (e.g., 3 to 6 membered heterocycloalkylene, 4 to 6 membered heterocycloalkylene, or 5 to 6 membered heterocycloalkylene). In embodiments, $L^{108}$ is $R^{113}$-substituted 4 membered heterocycloalkylene. In embodiments, $L^{108}$ is $R^{113}$-substituted 5 membered heterocycloalkylene. In embodiments, $L^{108}$ is $R^{113}$-substituted 6 membered heterocycloalkylene. In embodiments, $L^{108}$ is $R^{113}$-substituted heterocycloalkylene (e.g., 3 to 6 membered heterocycloalkylene, 4 to 6 membered heterocycloalkylene, or 5 to 6 membered heterocycloalkylene). In embodiments, $L^{108}$ is unsubstituted 4 membered heterocycloalkylene. In embodiments, $L^{108}$ is unsubstituted 5 membered heterocycloalkylene. In embodiments, $L^{108}$ unsubstituted 6 membered heterocycloalkylene. In embodiments, $L^{108}$ is unsubstituted heterocycloalkylene (e.g., 3 to 6 membered heterocycloalkylene, 4 to 6 membered heterocycloalkylene, or 5 to 6 membered heterocycloalkylene).

In embodiments, $L^{108}$ is $R^{113}$-substituted or unsubstituted arylene (e.g. $C_6$-$C_{10}$ arylene or $C_6$ arylene). In embodiments, $L^{108}$ is $R^{113}$-substituted or unsubstituted $C_6$-$C_{10}$ arylene. In embodiments, $L^{108}$ is $R^{113}$-substituted or unsubstituted $C_6$ arylene. In embodiments, $L^{108}$ is $R^{113}$-substituted arylene (e.g. $C_6$-$C_{10}$ arylene or $C_6$ arylene). In embodiments, $L^{108}$ is $R^{113}$-substituted $C_6$-$C_{10}$ arylene. In embodiments, $L^{108}$ is $R^{113}$-substituted $C_6$ arylene. In embodiments, $L^{108}$ is unsubstituted $C_6$-$C_{10}$ arylene. In embodiments, $L^{108}$ is unsubstituted $C_6$ arylene.

In embodiments, $L^{108}$ is $R^{113}$-substituted or unsubstituted heteroarylene (e.g. 5 to 10 membered heteroarylene, 5 to 9 membered heteroarylene, or 5 to 6 membered heteroarylene). In embodiments, $L^{108}$ is $R^{113}$-substituted or unsubstituted 5 to 10 membered heteroarylene. In embodiments, $L^{108}$ is $R^{113}$-substituted or unsubstituted 5 to 9 membered heteroarylene. In embodiments, $L^{108}$ is $R^{113}$-substituted or unsubstituted 5 to 6 membered heteroarylene. In embodiments, $L^{108}$ is $R^{113}$-substituted heteroarylene (e.g. 5 to 10 membered heteroarylene, 5 to 9 membered heteroarylene, or 5 to 6 membered heteroarylene). In embodiments, $L^{108}$ is $R^{113}$-substituted 5 to 10 membered heteroarylene. In embodiments, $L^{108}$ is $R^{113}$-substituted 5 to 9 membered heteroarylene. In embodiments, $L^{108}$ is $R^{113}$-substituted 5 to 6 membered heteroarylene. In embodiments, $L^{108}$ is unsubstituted heteroarylene (e.g. 5 to 10 membered heteroarylene, 5 to 9 membered heteroarylene, or 5 to 6 membered heteroarylene). In embodiments, $L^{108}$ is unsubstituted 5 to 10 membered heteroarylene. In embodiments, $L^{108}$ is unsubstituted 5 to 9 membered heteroarylene. In embodiments, $L^{108}$ is unsubstituted 5 to 6 membered heteroarylene. In embodiments, $L^{108}$ is $R^{113}$-substituted or unsubstituted indolinylene. In embodiments, $L^{108}$ is $R^{13}$-substituted or unsubstituted indazolylene. In embodiments, $L^{108}$ is $R^{113}$-substituted or unsubstituted benzimidazolylene. In embodiments, $L^{108}$ is $R^{113}$-substituted or unsubstituted benzoxazolylene. In embodiments, $L^{108}$ is $R^{113}$-substituted or unsubstituted azaindolylene. In embodiments, $L^{108}$ is $R^{113}$-substituted or unsubstituted purinylene. In embodiments, $L^{108}$ is $R^{113}$-substituted or unsubstituted indolylene. In embodiments, $L^{108}$ is $R^{113}$-substituted or unsubstituted pyrazinylene. In embodiments, $L^{108}$ is $R^{113}$-substituted or unsubstituted pyrrolylene. In embodiments, $L^{108}$ is $R^{113}$-substituted or unsubstituted imidazolylene. In embodiments, $L^{108}$ is $R^{113}$-substituted or unsubstituted pyrazolylene. In embodiments, $L^{108}$ is $R^{113}$-substituted or unsubstituted triazolylene. In embodiments, $L^{108}$ is $R^{113}$-substituted or unsubstituted tetrazolylene.

In embodiments, $L^{108}$ is $R^{113}$-substituted indolinylene. In embodiments, $L^{108}$ is $R^{113}$ substituted indazolylene. In embodiments, $L^{108}$ is $R^{113}$-substituted benzimidazolylene. In embodiments, $L^{108}$ is $R^{113}$-substituted benzoxazolylene. In embodiments, $L^{108}$ is $R^{113}$-substituted azaindolylene. In embodiments, $L^{108}$ is $R^{113}$-substituted purinylene. In embodiments, $L^{108}$ is $R^{113}$-substituted indolylene. In embodiments, $L^{108}$ is $R^{113}$-substituted pyrazinylene. In embodiments, $L^{108}$ is $R^{113}$-substituted pyrrolylene. In embodiments, $L^{108}$ is $R^{113}$-substituted imidazolylene. In embodiments, $L^{108}$ is $R^{113}$-substituted pyrazolylene. In embodiments, $L^{108}$ is $R^{113}$-substituted triazolylene. In embodiments, $L^{108}$ is $R^{113}$-substituted tetrazolylene.

In embodiments, $L^{108}$ is unsubstituted indolinylene. In embodiments, $L^{108}$ is unsubstituted indazolylene. In embodiments, $L^{108}$ is unsubstituted benzimidazolylene. In embodiments, $L^{108}$ is unsubstituted benzoxazolylene. In embodiments, $L^{108}$ is unsubstituted azaindolylene. In embodiments, $L^{108}$ is unsubstituted purinylene. In embodiments, $L^{108}$ is unsubstituted indolylene. In embodiments, $L^{108}$ is unsubstituted pyrazinylene. In embodiments, $L^{108}$ is unsubstituted pyrrolylene. In embodiments, $L^{108}$ is unsubstituted imidazolylene. In embodiments, $L^{108}$ is unsubstituted pyrazolylene. In embodiments, $L^{108}$ is unsubstituted triazolylene. In embodiments, $L^{108}$ is unsubstituted tetrazolylene.

In embodiments, $R^{109}$ is independently hydrogen. In embodiments, $R^{109}$ is independently halogen. In embodiments, $R^{109}$ is independently $-CX^{109}{}_3$. In embodiments, $R^{109}$ is independently $-CHX^{109}{}_2$. In embodiments, $R^{109}$ is independently $-CH_2X^{109}$. In embodiments, $R^{109}$ is independently $-OCX^{109}{}_3$. In embodiments, $R^{109}$ is independently $-OCH_2X^{109}$. In embodiments, $R^{109}$ is independently $-OCHX^{109}{}_2$. In embodiments, $R^{109}$ is independently $-CN$. In embodiments, $R^{109}$ is independently $-SO_{n109}R^{109D}$. In embodiments, $R^{109}$ is independently $-SO_{v109}NR^{109A}R^{109B}$. In embodiments, $R^{109}$ is independently $-NHC(O)NR^{109A}R^{109B}$. In embodiments, $R^{109}$ is independently $-N(O)_{m109}$. In embodiments, $R^{109}$ is independently $-NR^{109A}R^{109B}$. In embodiments, $R^{109}$ is independently $-C(O)R^{109C}$. In embodiments, $R^{109}$ is independently $-C(O)-OR^{109C}$. In embodiments, $R^{109}$ is independently $-C(O)NR^{109A}R^{109B}$. In embodiments, $R^{109}$ is independently $-OR^{109D}$. In embodiments, $R^{109}$ is independently $-NR^{109A}SO_2R^{109D}$. In embodiments, $R^{109}$ is independently $-NR^{109A}C(O)R^{109C}$. In embodiments, $R^{109}$ is independently $-NR^{109A}C(O)OR^{109C}$. In embodiments, $R^{109}$ is independently $-NR^{109A}OR^{109C}$. In embodiments, $R^{109}$ is independently $-OH$. In embodiments, $R^{109}$ is independently $-NH_2$. In embodiments, $R^{109}$ is independently $-COOH$. In embodiments, $R^{109}$ is independently $-CONH_2$. In embodiments, $R^{109}$ is independently $-NO_2$. In embodiments, $R^{109}$ is independently $-SH$.

In embodiments, $R^{109}$ is independently substituted or unsubstituted alkyl. In embodiments, $R^{109}$ is independently substituted or unsubstituted heteroalkyl. In embodiments, $R^{109}$ is independently substituted or unsubstituted cycloalkyl. In embodiments, $R^{109}$ is independently, substituted or unsubstituted heterocycloalkyl. In embodiments, $R^{109}$ is independently substituted or unsubstituted aryl. In embodiments, $R^{109}$ is independently substituted or unsubstituted heteroaryl. In embodiments, $R^{109}$ is independently substituted alkyl. In embodiments, $R^{109}$ is independently substituted heteroalkyl. In embodiments, $R^{109}$ is independently substituted cycloalkyl. In embodiments, $R^{109}$ is independently, substituted heterocycloalkyl. In embodiments, $R^{109}$ is independently substituted aryl. In embodiments, $R^{109}$ is independently substituted heteroaryl. In embodiments, $R^{109}$ is independently unsubstituted alkyl. In embodiments, $R^{109}$ is independently unsubstituted heteroalkyl. In embodiments, $R^{109}$ is independently unsubstituted cycloalkyl. In embodiments, $R^{109}$ is independently, unsubstituted heterocycloalkyl. In embodiments, $R^{109}$ is independently unsubstituted aryl. In embodiments, $R^{109}$ is independently unsubstituted heteroaryl. In embodiments, $R^{109}$ is independently substituted or unsubstituted $C_1$-$C_8$ alkyl. In embodiments, $R^{109}$ is independently substituted or unsubstituted 2 to 8 membered heteroalkyl. In embodiments, $R^{109}$ is independently substituted or unsubstituted $C_3$-$C_8$ cycloalkyl. In embodiments, $R^{109}$ is independently, substituted or unsubstituted 3 to 8 membered heterocycloalkyl. In embodiments, $R^{109}$ is independently substituted or unsubstituted $C_6$-$C_{10}$ aryl. In embodiments, $R^{109}$ is independently substituted or unsubstituted 5 to 10 membered heteroaryl. In embodiments, $R^{109}$ is independently substituted $C_1$-$C_8$ alkyl. In embodiments, $R^{109}$ is independently substituted 2 to 8 membered heteroalkyl. In embodiments, $R^{109}$ is independently substituted $C_3$-$C_8$ cycloalkyl. In embodiments, $R^{109}$ is independently, substituted 3 to 8 membered heterocycloalkyl. In embodiments, $R^{109}$ is independently substituted $C_6$-$C_{10}$ aryl. In embodiments, $R^{109}$ is independently substituted 5 to 10 membered heteroaryl. In embodiments, $R^{109}$ is independently unsubstituted $C_1$-$C_8$ alkyl. In embodiments, $R^{109}$ is independently unsubstituted 2 to 8 membered heteroalkyl. In embodiments, $R^{109}$ is independently unsubstituted $C_3$-$C_8$ cycloalkyl. In embodiments, $R^{109}$ is independently, unsubstituted 3 to 8 membered heterocycloalkyl. In embodiments, $R^{109}$ is independently unsubstituted $C_6$-$C_{10}$ aryl. In embodiments, $R^{109}$ is independently unsubstituted 5 to 10 membered heteroaryl. In embodiments, $R^{109}$ is independently substituted or unsubstituted $C_1$-$C_4$ alkyl. In embodiments, $R^{109}$ is independently substituted or unsubstituted 2 to 4 membered heteroalkyl. In embodiments, $R^{109}$ is independently substituted or unsubstituted $C_3$-$C_6$ cycloalkyl. In embodiments, $R^{109}$ is independently, substituted or unsubstituted 3 to 6 membered heterocycloalkyl. In embodiments, $R^{109}$ is independently substituted or unsubstituted phenyl. In embodiments, $R^{109}$ is independently substituted or unsubstituted 5 to 6 membered heteroaryl. In embodiments, $R^{109}$ is independently substituted $C_1$-$C_4$ alkyl. In embodiments, $R^{109}$ is independently substituted 2 to 4 membered heteroalkyl. In embodiments, $R^{109}$ is independently substituted $C_3$-$C_6$ cycloalkyl. In embodiments, $R^{109}$ is independently, substituted 3 to 6 membered heterocycloalkyl. In embodiments, $R^{109}$ is independently substituted phenyl. In embodiments, $R^{109}$ is independently substituted 5 to 6 membered heteroaryl. In embodiments, $R^{109}$ is independently unsubstituted $C_1$-$C_4$ alkyl. In embodiments, $R^{109}$ is independently unsubstituted 2 to 4 membered heteroalkyl. In embodiments, $R^{109}$ is independently unsubstituted $C_3$-$C_6$ cycloalkyl. In embodiments, $R^{109}$ is independently unsubstituted 3 to 6 membered heterocycloalkyl. In embodiments, $R^{109}$ is independently unsubstituted phenyl. In embodiments, $R^{109}$ is independently unsubstituted 5 to 6 membered heteroaryl.

In embodiments, $R^{109A}$ is independently hydrogen. In embodiments, $R^{109A}$ is independently $-CX^{109A}{}_3$. In embodiments, $R^{109A}$ is independently $-CHX^{109A}{}_2$. In embodiments, $R^{109A}$ is independently $-CH_2X^{109A}$. In embodiments, $R^{109A}$ is independently $-CN$. In embodiments, $R^{109A}$ is independently $-COOH$. In embodiments, $R^{109A}$ is independently $-CONH_2$. In embodiments, $R^{109A}$ is independently substituted or unsubstituted alkyl. In embodiments, $R^{109A}$ is independently substituted or unsubstituted heteroalkyl. In embodiments, $R^{109A}$ is independently substituted or unsubstituted cycloalkyl. In embodiments, $R^{109A}$ is independently, substituted or unsubstituted heterocycloalkyl. In embodiments, $R^{109A}$ is independently substituted or unsubstituted aryl. In embodiments, $R^{109A}$ is independently substituted or unsubstituted heteroaryl. In embodiments, $R^{109A}$ is independently substituted alkyl. In embodiments, $R^{109A}$ is independently substituted heteroalkyl. In embodiments, $R^{109A}$ is independently substituted cycloalkyl. In embodiments, $R^{109A}$ is independently, substituted heterocycloalkyl. In embodiments, $R^{109A}$ is independently substituted aryl. In embodiments, $R^{109A}$ is independently substituted heteroaryl. In embodiments, $R^{109A}$ is independently unsubstituted alkyl. In embodiments, $R^{109A}$ is independently unsubstituted heteroalkyl. In embodiments, $R^{109A}$ is independently unsubstituted cycloalkyl. In embodiments, $R^{109A}$ is independently, unsubstituted heterocycloalkyl. In embodiments, $R^{109A}$ is independently unsubstituted aryl. In embodiments, $R^{109A}$ is independently unsubstituted heteroaryl. In embodiments, $R^{109A}$ is independently substituted or unsubstituted $C_1$-$C_8$ alkyl. In embodiments, $R^{109A}$ is independently substituted or unsubstituted 2 to 8 membered heteroalkyl. In embodiments, $R^{109A}$ is independently substituted or unsubstituted $C_3$-$C_8$ cycloalkyl. In embodiments, $R^{109A}$ is independently, substituted or unsubstituted 3 to 8 membered heterocycloalkyl. In embodiments, $R^{109A}$ is independently substituted or unsubstituted $C_6$-$C_{10}$ aryl. In embodiments, $R^{109A}$ is independently substituted or unsubstituted 5 to 10 membered heteroaryl. In embodiments, $R^{109A}$ is independently substituted $C_1$-$C_8$ alkyl. In embodiments, $R^{109A}$ is independently substituted 2 to 8 membered heteroalkyl. In embodiments, $R^{109A}$ is independently substituted $C_3$-$C_8$ cycloalkyl. In embodiments, $R^{109A}$ is independently, substituted 3 to 8 membered heterocycloalkyl. In embodiments, $R^{109A}$ is independently substituted $C_6$-$C_{10}$ aryl. In embodiments, $R^{109A}$ is independently substituted 5 to 10 membered heteroaryl. In embodiments, $R^{109A}$ is independently unsubstituted $C_1$-$C_8$ alkyl. In embodiments, $R^{109A}$ is independently unsubstituted 2 to 8 membered heteroalkyl. In embodiments, $R^{109A}$ is independently unsubstituted $C_3$-$C_8$ cycloalkyl. In embodiments, $R^{109A}$ is independently, unsubstituted 3 to 8 membered heterocycloalkyl. In embodiments, $R^{109A}$ is independently unsubstituted $C_6$-$C_{10}$ aryl. In embodiments, $R^{109A}$ is independently unsubstituted 5 to 10 membered heteroaryl. In embodiments, $R^{109A}$ is independently substituted or unsubstituted $C_1$-$C_4$ alkyl. In embodiments, $R^{109A}$ is independently substituted or unsubstituted 2 to 4 membered heteroalkyl. In embodiments, $R^{109A}$ is independently substituted or unsubstituted $C_3$-$C_6$ cycloalkyl. In embodiments, $R^{109A}$ is independently, substituted or unsubstituted 3 to 6 membered heterocycloalkyl. In embodiments, $R^{109A}$ is independently substituted or unsubstituted phenyl. In embodiments, $R^{109A}$ is independently substituted or unsubstituted 5 to 6 membered heteroaryl. In embodiments, $R^{109A}$ is independently substituted $C_1$-$C_4$ alkyl. In embodiments, $R^{109A}$ is independently substituted 2 to 4 membered heteroalkyl. In embodiments, $R^{109A}$ is independently substituted $C_3$-$C_6$ cycloalkyl. In embodiments, $R^{109A}$ is independently, substituted 3 to 6 membered heterocycloalkyl. In embodiments, $R^{109A}$ is independently substituted phenyl. In embodiments, $R^{109A}$ is independently substituted 5 to 6 membered heteroaryl. In embodiments, $R^{109A}$ is independently unsubstituted $C_1$-$C_4$ alkyl. In embodiments, $R^{109A}$ is independently unsubstituted 2 to 4 membered heteroalkyl. In embodiments, $R^{109A}$ is independently unsubstituted $C_3$-$C_6$ cycloalkyl. In embodiments, $R^{109A}$ is independently unsubstituted 3 to 6 membered heterocycloalkyl. In embodiments, $R^{109A}$ is independently unsubstituted phenyl. In embodiments, $R^{9A}$ is independently unsubstituted 5 to 6 membered heteroaryl. In embodiments, $R^{109A}$ is independently unsubstituted methyl. In embodiments, $R^{109A}$ is independently unsubstituted ethyl. In embodiments, $R^{19A}$ is independently unsubstituted propyl. In embodiments, $R^{109A}$ is independently unsubstituted isopropyl. In embodiments, $R^{109A}$ is independently unsubstituted tert-butyl.

In embodiments, $R^{109B}$ is independently hydrogen. In embodiments, $R^{109B}$ is independently —$CX^{109B}_3$. In embodiments, $R^{109B}$ is independently —$CHX^{109B}_2$. In embodiments, $R^{109B}$ is independently —$CH_2X^{109B}$. In embodiments, $R^{109B}$ is independently —CN. In embodiments, $R^{109B}$ is independently —COOH. In embodiments, $R^{109B}$ is independently —$CONH_2$. In embodiments, $R^{109B}$ is independently substituted or unsubstituted alkyl. In embodiments, $R^{109B}$ is independently substituted or unsubstituted heteroalkyl. In embodiments, $R^{109B}$ is independently substituted or unsubstituted cycloalkyl. In embodiments, $R^{109B}$ is independently, substituted or unsubstituted heterocycloalkyl. In embodiments, $R^{109B}$ is independently substituted or unsubstituted aryl. In embodiments, $R^{109B}$ is independently substituted or unsubstituted heteroaryl. In embodiments, $R^{109B}$ is independently substituted alkyl. In embodiments, $R^{109B}$ is independently substituted heteroalkyl. In embodiments, $R^{109B}$ is independently substituted cycloalkyl. In embodiments, $R^{109B}$ is independently, substituted heterocycloalkyl. In embodiments, $R^{109B}$ is independently substituted aryl. In embodiments, $R^{109B}$ is independently substituted heteroaryl. In embodiments, $R^{109B}$ is independently unsubstituted alkyl. In embodiments, $R^{109B}$ is independently unsubstituted heteroalkyl. In embodiments, $R^{109B}$ is independently unsubstituted cycloalkyl. In embodiments, $R^{109B}$ is independently, unsubstituted heterocycloalkyl. In embodiments, $R^{109B}$ is independently unsubstituted aryl. In embodiments, $R^{109B}$ is independently unsubstituted heteroaryl. In embodiments, $R^{109B}$ is independently substituted or unsubstituted $C_1$-$C_8$ alkyl. In embodiments, $R^{109B}$ is independently substituted or unsubstituted 2 to 8 membered heteroalkyl. In embodiments, $R^{109B}$ is independently substituted or unsubstituted $C_3$-$C_8$ cycloalkyl. In embodiments, $R^{109B}$ is independently, substituted or unsubstituted 3 to 8 membered heterocycloalkyl. In embodiments, $R^{109B}$ is independently substituted or unsubstituted $C_6$-$C_{10}$ aryl. In embodiments, $R^{109B}$ is independently substituted or unsubstituted 5 to 10 membered heteroaryl. In embodiments, $R^{109B}$ is independently substituted $C_1$-$C_8$ alkyl. In embodiments, $R^{109B}$ is independently substituted 2 to 8 membered heteroalkyl. In embodiments, $R^{109B}$ is independently substituted $C_3$-$C_8$ cycloalkyl. In embodiments, $R^{109B}$ is independently, substituted 3 to 8 membered heterocycloalkyl. In embodiments, $R^{109B}$ is independently substituted $C_6$-$C_{10}$ aryl. In embodiments, $R^{109B}$ is independently substituted 5 to 10 membered heteroaryl. In embodiments, $R^{109B}$ is independently unsubstituted $C_1$-$C_8$ alkyl. In embodiments, $R^{109B}$ is independently unsubstituted 2 to 8 membered heteroalkyl. In embodiments, $R^{109B}$ is independently unsubstituted $C_3$-$C_8$ cycloalkyl. In embodiments, $R^{109B}$ is independently, unsubstituted 3 to 8 membered heterocycloalkyl. In embodiments, $R^{109B}$ is independently unsubstituted $C_6$-$C_{10}$ aryl. In embodiments, $R^{109B}$ is independently unsubstituted 5 to 10 membered heteroaryl. In embodiments, $R^{109B}$ is independently substituted or unsubstituted $C_1$-$C_4$ alkyl. In embodiments, $R^{109B}$ is independently substituted or unsubstituted 2 to 4 membered heteroalkyl. In embodiments, $R^{109B}$ is independently substituted or unsubstituted $C_3$-$C_6$ cycloalkyl. In embodiments, $R^{109B}$ is independently, substituted or unsubstituted 3 to 6 membered heterocycloalkyl. In embodiments, $R^{109B}$ is independently substituted or unsubstituted phenyl. In embodiments, $R^{109}$ is independently substituted or unsubstituted 5 to 6 membered heteroaryl. In embodiments, $R^{109B}$ is independently substituted $C_1$-$C_4$ alkyl. In embodiments, $R^{109B}$ is independently substituted 2 to 4 membered heteroalkyl. In embodiments, $R^{109B}$ is independently substituted $C_3$-$C_6$ cycloalkyl. In embodiments, $R^{109B}$ is independently, substituted 3 to 6 membered heterocycloalkyl. In embodiments, $R^{109B}$ is independently substituted phenyl. In embodiments, $R^{109B}$ is independently substituted 5 to 6 membered heteroaryl. In embodiments, $R^{109B}$ is independently unsubstituted $C_1$-$C_4$ alkyl. In embodiments, $R^{109B}$ is independently unsubstituted 2 to 4 membered heteroalkyl. In embodiments, $R^{109B}$ is independently unsubstituted $C_3$-$C_6$ cycloalkyl. In embodiments, $R^{109B}$ is independently unsubstituted 3 to 6 membered heterocycloalkyl. In embodiments, $R^{109B}$ is independently unsubstituted phenyl. In embodiments, $R^{109B}$ is independently unsubstituted 5 to 6 membered heteroaryl. In embodiments, $R^{109B}$ is independently unsubstituted methyl. In embodiments, $R^{109B}$ is independently unsubstituted ethyl. In embodiments, $R^{109B}$ is independently unsubstituted propyl. In embodiments, $R^{109B}$ is independently unsubstituted isopropyl. In embodiments, $R^{109B}$ is independently unsubstituted tert-butyl.

In embodiments, $R^{109A}$ and $R^{109B}$ substituents bonded to the same nitrogen atom may be joined to form a substituted or unsubstituted heterocycloalkyl. In embodiments, $R^{109A}$ and $R^{109B}$ substituents bonded to the same nitrogen atom may be joined to form a substituted or unsubstituted heteroaryl. In embodiments, $R^{109A}$ and $R^{109B}$ substituents bonded to the same nitrogen atom may be joined to forma substituted heterocycloalkyl. In embodiments, $R^{109A}$ and $R^{109B}$ substituents bonded to the same nitrogen atom may be joined to form a substituted heteroaryl. In embodiments, $R^{109A}$ and $R^{109B}$ substituents bonded to the same nitrogen atom may be joined to form an unsubstituted heterocycloalkyl. In embodiments, $R^{109A}$ and $R^{109B}$ substituents bonded to the same nitrogen atom may be joined to form an unsubstituted heteroaryl. In embodiments, $R^{109A}$ and $R^{109B}$ substituents bonded to the same nitrogen atom may be joined to form a substituted or unsubstituted 3 to 8 membered heterocycloalkyl. In embodiments, $R^{109A}$ and $R^{109B}$ substituents bonded to the same nitrogen atom may be joined to form a substituted or unsubstituted 5 to 10 membered heteroaryl. In embodiments, $R^{109A}$ and $R^{109B}$ substituents bonded to the same nitrogen atom may be joined to form a substituted 3 to 8 membered heterocycloalkyl. In embodiments, $R^{109A}$ and $R^{109B}$ substituents bonded to the same nitrogen atom may be joined to form a substituted 5 to 10 membered heteroaryl. In embodiments, $R^{109A}$ and $R^{109B}$ substituents bonded to the same nitrogen atom may be joined to form an unsubstituted 3 to 8 membered heterocycloalkyl. In embodiments, $R^{109A}$ and $R^{109B}$ substituents bonded to the same nitrogen atom may be joined to form an unsubstituted 5 to 10 membered heteroaryl. In embodiments, $R^{109A}$ and $R^{109B}$ substituents bonded to the same nitrogen atom may be joined to form a substituted or unsubstituted 3 to 6 membered heterocycloalkyl. In embodiments, $R^{109A}$ and $R^{109B}$ substituents bonded to the same nitrogen atom may be joined to form a substituted or unsubstituted 5 to 6 membered heteroaryl. In embodiments, $R^{109A}$ and $R^{109B}$ substituents bonded to the same nitrogen atom may be joined to form a substituted 3 to 6 membered heterocycloalkyl. In embodiments, $R^{109A}$ and $R^{109B}$ substituents bonded to the same nitrogen atom may be joined to form a substituted 5 to 6 membered heteroaryl. In embodiments, $R^{109A}$ and $R^{109B}$ substituents bonded to the same nitrogen atom may be joined to form an unsubstituted 3 to 6 membered heterocycloalkyl. In embodiments, $R^{109A}$ and $R^{109B}$ substituents bonded to the same nitrogen atom may be joined to form an unsubstituted 5 to 6 membered heteroaryl.

In embodiments, $R^{109C}$ is independently hydrogen. In embodiments, $R^{109C}$ is independently $-CX^{109C}_3$. In embodiments, $R^{109C}$ is independently $-CHX^{109C}_2$. In embodiments, $R^{109C}$ is independently $-CH_2X^{109C}$. In embodiments, $R^{109C}$ is independently $-CN$. In embodiments, $R^{109C}$ is independently $-COOH$. In embodiments, $R^{109C}$ is independently $-CONH_2$. In embodiments, $R^{109C}$ is independently substituted or unsubstituted alkyl. In embodiments, $R^{109C}$ is independently substituted or unsubstituted heteroalkyl. In embodiments, $R_{109C}$ is independently substituted or unsubstituted cycloalkyl. In embodiments, $R^{109C}$ is independently, substituted or unsubstituted heterocycloalkyl. In embodiments, $R^{109C}$ is independently substituted or unsubstituted aryl. In embodiments, $R^{109C}$ is independently substituted or unsubstituted heteroaryl. In embodiments, $R^{109C}$ is independently substituted alkyl. In embodiments, $R^{109C}$ is independently substituted heteroalkyl. In embodiments, $R^{109C}$ is independently substituted cycloalkyl. In embodiments, $R^{109C}$ is independently, substituted heterocycloalkyl. In embodiments, $R^{109C}$ is independently substituted aryl. In embodiments, $R^{109C}$ is independently substituted heteroaryl. In embodiments, $R^{109C}$ is independently unsubstituted alkyl. In embodiments, $R^{109C}$ is independently unsubstituted heteroalkyl. In embodiments, $R^{109C}$ is independently unsubstituted cycloalkyl. In embodiments, $R^{109C}$ is independently, unsubstituted heterocycloalkyl. In embodiments, $R^{109C}$ is independently unsubstituted aryl. In embodiments, $R^{109C}$ is independently unsubstituted heteroaryl. In embodiments, $R^{109C}$ is independently substituted or unsubstituted $C_1$-$C_8$ alkyl. In embodiments, $R^{109C}$ is independently substituted or unsubstituted 2 to 8 membered heteroalkyl. In embodiments, $R^{109C}$ is independently substituted or unsubstituted $C_3$-$C_8$ cycloalkyl. In embodiments, $R^{109C}$ is independently, substituted or unsubstituted 3 to 8 membered heterocycloalkyl. In embodiments, $R^{109C}$ is independently substituted or unsubstituted $C_6$-$C_{10}$ aryl. In embodiments, $R^{109C}$ is independently substituted or unsubstituted 5 to 10 membered heteroaryl. In embodiments, $R^{109C}$ is independently substituted $C_1$-$C_8$ alkyl. In embodiments, $R^{109C}$ is independently substituted 2 to 8 membered heteroalkyl. In embodiments, $R^{109C}$ is independently substituted $C_3$-$C_8$ cycloalkyl. In embodiments, $R^{109C}$ is independently, substituted 3 to 8 membered heterocycloalkyl. In embodiments, $R^{109C}$ is independently substituted $C_6$-$C_{10}$ aryl. In embodiments, $R^{109C}$ is independently substituted 5 to 10 membered heteroaryl. In embodiments, $R^{109C}$ is independently unsubstituted $C_1$-$C_8$ alkyl. In embodiments, $R^{109C}$ is independently unsubstituted 2 to 8 membered heteroalkyl. In embodiments, $R^{109C}$ is independently unsubstituted $C_3$-$C_8$ cycloalkyl. In embodiments, $R^{109C}$ is independently, unsubstituted 3 to 8 membered heterocycloalkyl. In embodiments, $R^{109C}$ is independently unsubstituted $C_6$-$C_{10}$ aryl. In embodiments, $R^{109C}$ is independently unsubstituted 5 to 10 membered heteroaryl. In embodiments, $R^{109C}$ is independently substituted or unsubstituted $C_1$-$C_4$ alkyl. In embodiments, $R^{109C}$ is independently substituted or unsubstituted 2 to 4 membered heteroalkyl. In embodiments, $R^{109C}$ is independently substituted or unsubstituted $C_3$-$C_6$ cycloalkyl. In embodiments, $R^{109C}$ is independently, substituted or unsubstituted 3 to 6 membered heterocycloalkyl. In embodiments, $R^{109C}$ is independently substituted or unsubstituted phenyl. In embodiments, $R^{109C}$ is independently substituted or unsubstituted 5 to 6 membered heteroaryl. In embodiments, $R^{109C}$ is independently substituted $C_1$-$C_4$ alkyl. In embodiments, $R^{109C}$ is independently substituted 2 to 4 membered heteroalkyl. In embodiments, $R^{109C}$ is independently substituted $C_3$-$C_6$ cycloalkyl. In embodiments, $R^{109C}$ is independently, substituted 3 to 6 membered heterocycloalkyl. In embodiments, $R^{109C}$ is independently substituted phenyl. In embodiments, $R^{109C}$ is independently substituted 5 to 6 membered heteroaryl. In embodiments, $R^{109C}$ is independently unsubstituted $C_1$-$C_4$ alkyl. In embodiments, $R^{109C}$ is independently unsubstituted 2 to 4 membered heteroalkyl. In embodiments, $R^{109C}$ is independently unsubstituted $C_3$-$C_6$ cycloalkyl. In embodiments, $R^{109C}$ is independently unsubstituted 3 to 6 membered heterocycloalkyl. In embodiments, $R^{109C}$ is independently unsubstituted phenyl. In embodiments, $R^{109C}$ is independently unsubstituted 5 to 6 membered heteroaryl. In embodiments, $R^{109C}$ is independently unsubstituted methyl. In embodiments, $R^{109C}$ is independently unsubstituted ethyl. In embodiments, $R^{109C}$ is independently unsubstituted propyl. In embodiments, $R^{109C}$ is independently unsubstituted isopropyl. In embodiments, $R^{109C}$ is independently unsubstituted tert-butyl.

In embodiments, $R^{109D}$ is independently hydrogen. In embodiments, $R^{109D}$ is independently —$CX^{109D}_3$. In embodiments, $R^{109D}$ is independently —$CHX^{109D}_2$. In embodiments, $R^{109D}$ is independently —$CH_2X^{109D}$. In embodiments, $R^{109D}$ is independently —CN. In embodiments, $R^{109D}$ is independently —COOH. In embodiments, $R^{109D}$ is independently —$CONH_2$. In embodiments, $R^{109D}$ is independently substituted or unsubstituted alkyl. In embodiments, $R^{109D}$ is independently substituted or unsubstituted heteroalkyl. In embodiments, $R^{109D}$ is independently substituted or unsubstituted cycloalkyl. In embodiments, $R^{109D}$ is independently, substituted or unsubstituted heterocycloalkyl. In embodiments, $R^{109D}$ is independently substituted or unsubstituted aryl. In embodiments, $R^{109D}$ is independently substituted or unsubstituted heteroaryl. In embodiments, $R^{109D}$ is independently substituted alkyl. In embodiments, $R^{109D}$ is independently substituted heteroalkyl. In embodiments, $R^{109D}$ is independently substituted cycloalkyl. In embodiments, $R^{109D}$ is independently, substituted heterocycloalkyl. In embodiments, $R^{109D}$ is independently substituted aryl. In embodiments, $R^{109D}$ is independently substituted heteroaryl. In embodiments, $R^{109D}$ is independently unsubstituted alkyl. In embodiments, $R^{109D}$ is independently unsubstituted heteroalkyl. In embodiments, $R^{109D}$ is independently unsubstituted cycloalkyl. In embodiments, $R^{109D}$ is independently unsubstituted heterocycloalkyl. In embodiments, $R^{109D}$ is independently unsubstituted aryl. In embodiments, $R^{109D}$ is independently unsubstituted heteroaryl. In embodiments, $R^{109D}$ is independently substituted or unsubstituted $C_1$-$C_8$ alkyl. In embodiments, $R^{109D}$ is independently substituted or unsubstituted 2 to 8 membered heteroalkyl. In embodiments, $R^{109D}$ is independently substituted or unsubstituted $C_3$-$C_8$ cycloalkyl. In embodiments, $R^{109D}$ is independently, substituted or unsubstituted 3 to 8 membered heterocycloalkyl. In embodiments, $R^{109D}$ is independently substituted or unsubstituted $C_6$-$C_{10}$ aryl. In embodiments, $R^{109D}$ is independently substituted or unsubstituted 5 to 10 membered heteroaryl. In embodiments, $R^{109D}$ is independently substituted $C_1$-$C_8$ alkyl. In embodiments, $R^{109D}$ is independently substituted 2 to 8 membered heteroalkyl. In embodiments, $R^{109D}$ is independently substituted $C_3$-$C_8$ cycloalkyl. In embodiments, $R^{109D}$ is independently, substituted 3 to 8 membered heterocycloalkyl. In embodiments, $R^{109D}$ is independently substituted $C_6$-$C_{10}$ aryl. In embodiments, $R^{109D}$ is independently substituted 5 to 10 membered heteroaryl. In embodiments, $R^{109D}$ is independently unsubstituted $C_1$-$C_8$ alkyl. In embodiments, $R^{109D}$ is independently unsubstituted 2 to 8 membered heteroalkyl. In embodiments, $R^{109D}$ is independently unsubstituted $C_3$-$C_8$ cycloalkyl. In embodiments, $R^{109D}$ is independently unsubstituted 3 to 8 membered heterocycloalkyl. In embodiments, $R^{109D}$ is independently unsubstituted $C_6$-$C_{10}$ aryl. In embodiments, $R^{109D}$ is independently unsubstituted 5 to 10 membered heteroaryl. In embodiments, $R^{109D}$ is independently substituted or unsubstituted $C_1$-$C_4$ alkyl. In embodiments, $R^{109D}$ is independently substituted or unsubstituted 2 to 4 membered heteroalkyl. In embodiments, $R^{109D}$ is independently substituted or unsubstituted $C_3$-$C_6$ cycloalkyl. In embodiments, $R^{109D}$ is independently, substituted or unsubstituted 3 to 6 membered heterocycloalkyl. In embodiments, $R^{109D}$ is independently substituted or unsubstituted phenyl. In embodiments, $R^{109D}$ is independently substituted or unsubstituted 5 to 6 membered heteroaryl. In embodiments, $R^{109D}$ is independently substituted $C_1$-$C_4$ alkyl. In embodiments, $R^{109D}$ is independently substituted 2 to 4 membered heteroalkyl. In embodiments, $R^{109D}$ is independently substituted $C_3$-$C_6$ cycloalkyl. In embodiments, $R^{109D}$ is independently, substituted 3 to 6 membered heterocycloalkyl. In embodiments, $R^{109D}$ is independently substituted phenyl. In embodiments, $R^{109D}$ is independently substituted 5 to 6 membered heteroaryl. In embodiments, $R^{109D}$ is independently unsubstituted $C_1$-$C_4$ alkyl. In embodiments, $R^{109D}$ is independently unsubstituted 2 to 4 membered heteroalkyl. In embodiments, $R^{109D}$ is independently unsubstituted $C_3$-$C_6$ cycloalkyl. In embodiments, $R^{109D}$ is independently unsubstituted 3 to 6 membered heterocycloalkyl. In embodiments, $R^{109D}$ is independently unsubstituted phenyl. In embodiments, $R^{109D}$ is independently unsubstituted 5 to 6 membered heteroaryl. In embodiments, $R^{109D}$ is independently unsubstituted methyl. In embodiments, $R^{109D}$ is independently unsubstituted ethyl. In embodiments, $R^{109D}$ is independently unsubstituted propyl. In embodiments, $R^{109D}$ is independently unsubstituted isopropyl. In embodiments, $R^{109D}$ is independently unsubstituted tert-butyl.

In embodiments, $R^{109}$ is independently hydrogen, halogen, —$CX^{109}_3$, —$CHX^{109}_2$, —$CH_2X^{109}$, —$OCX^{109}_3$, —$OCH_2X^{109}$, —$OCHX^{109}_2$, —CN, —$SO_{n109}R^{109D}$, —$SO_{v109}NR^{109A}R^{109B}$, —NHC(O)$NR^{109A}R^{109B}$, —N(O)$_{m109}$, —$NR^{109A}R^{109B}$, —C(O)$R^{109C}$, —C(O)$OR^{109C}$, —C(O)$NR^{109A}R^{109B}$, —$OR^{109D}$, —$NR^{109A}SO_2R^{109D}$, —$NR^{109A}C(O)R^{109C}$, —$NR^{109A}C(O)OR^{109C}$, —$NR^{109A}OR^{109C}$, $R^{110}$-substituted or unsubstituted alkyl, $R^{110}$-substituted or unsubstituted heteroalkyl, $R^{110}$-substituted or unsubstituted cycloalkyl, $R^{110}$-substituted or unsubstituted heterocycloalkyl, $R^{110}$-substituted or unsubstituted aryl, or $R^{110}$-substituted or unsubstituted heteroaryl. In embodiments, $R^{109}$ is independently halogen, —$CX^{109}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{109}_3$, —$OCHX^{109}_2$, R-substituted or unsubstituted alkyl, $R^{110}$-substituted or unsubstituted heteroalkyl, $R^{110}$-substituted or unsubstituted cycloalkyl, $R^{110}$-substituted or unsubstituted heterocycloalkyl, $R^{110}$-substituted or unsubstituted aryl, or $R^{110}$-substituted or unsubstituted heteroaryl. In embodiments, $R^{109}$ is independently halogen, —$CX^{109}_3$, —CN, —OH, —$NH_2$, —COOH, —$CONH_2$, —$NO_2$, —SH, —$SO_3H$, —$SO_4H$, —$S_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{109}_3$, —$OCHX^{109}_2$, $R^{110}$-substituted or unsubstituted $C_1$-$C_8$ alkyl, $R^{110}$-substituted or unsubstituted 2 to 8 membered heteroalkyl, $R^{110}$-substituted or unsubstituted $C_3$-$C_8$ cycloalkyl, $R^{110}$-substituted or unsubstituted 3 to 6 membered heterocycloalkyl, $R^{110}$-substituted or unsubstituted phenyl, or $R^{110}$-substituted or unsubstituted 5 to 6 membered heteroaryl. $X^{109}$ is —F, —Cl, —Br, or —I. In embodiments, $R^{109}$ is independently hydrogen. In embodiments, $R^{109}$ is independently methyl. In embodiments, $R^{109}$ is independently ethyl.

In embodiments, $R^{109}$ is independently halogen, —$CX^{109}_3$, —CN, —OH, —COOH, —$CONH_2$, —$OCX^{109}_3$, —$OCHX^{109}_2$, $R^{109}$-substituted or unsubstituted $C_1$-$C_8$ alkyl, $R^{109}$-substituted or unsubstituted 2 to 8 membered heteroalkyl, $R^{109}$-substituted or unsubstituted $C_3$-$C_8$ cycloalkyl, $R^{109}$-substituted or unsubstituted 3 to 6 membered heterocycloalkyl, $R^{109}$-substituted or unsubstituted phenyl, or $R^{109}$-substituted or unsubstituted 5 to 6 membered heteroaryl.

$R^{110}$ is independently oxo, halogen, —$CX^{110}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{110}_3$, —$OCHX^{110}_2$, $R^{111}$-substituted or unsubstituted alkyl, $R^{111}$-substituted or unsubstituted heteroalkyl, $R^{111}$-substituted or unsubstituted cycloalkyl, $R^{111}$-substituted or unsubstituted heterocycloalkyl, $R^{111}$-substituted or unsubstituted aryl, or $R^{111}$-substituted or unsubstituted heteroaryl. In embodiments, $R^{110}$ is independently oxo, halogen, —$CX^{110}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{110}_3$, —$OCHX^{110}_2$, $R^{111}$-substituted or unsubstituted $C_1$-$C_8$ alkyl, $R^{111}$-substituted or unsubstituted 2 to 8 membered heteroalkyl, $R^{111}$-substituted or unsubstituted $C_3$-$C_8$ cycloalkyl, $R^{111}$-substituted or unsubstituted 3 to 6 membered heterocycloalkyl, $R^{111}$-substituted or unsubstituted phenyl, or $R^{111}$-substituted or unsubstituted 5 to 6 membered heteroaryl. $X^{110}$ is —F, —Cl, —Br, or —I.

$R^{111}$ is independently oxo, halogen, —$CX^{111}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{111}_3$, —$OCHX^{111}_2$, $R^{112}$-substituted or unsubstituted alkyl, $R^{112}$-substituted or unsubstituted heteroalkyl, $R^{112}$-substituted or unsubstituted cycloalkyl, $R^{112}$-substituted or unsubstituted heterocycloalkyl, $R^{112}$-substituted or unsubstituted aryl, or $R^{112}$-substituted or unsubstituted heteroaryl. In embodiments, $R^{111}$ is independently oxo, halogen, —$CX^{111}_3$, —CN, —OH, —$NH_2$, —COOH, —$CONH_2$, —$NO_2$, —SH, —$S_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{111}_3$, —$OCHX^{111}_2$, $R^{112}$-substituted or unsubstituted $C_1$-$C_8$ alkyl, $R^{112}$-substituted or unsubstituted 2 to 8 membered heteroalkyl, $R^{112}$-substituted or unsubstituted $C_3$-$C_8$ cycloalkyl, $R^{112}$-substituted or unsubstituted 3 to 6 membered heterocycloalkyl, $R^{112}$-substituted or unsubstituted phenyl, or $R^{112}$-substituted or unsubstituted 5 to 6 membered heteroaryl. $X^{111}$ is —F, —Cl, —Br, or —I.

In embodiments, $R^{109A}$ is independently hydrogen, —$CX^{109A}_3$, —CN, —COOH, —$CONH_2$, —$CHX^{109A}_2$, —$CH_2X^{109A}$, $R^{110A}$-substituted or unsubstituted alkyl, $R^{110A}$-substituted or unsubstituted heteroalkyl, $R^{110A}$-substituted or unsubstituted cycloalkyl, $R^{110A}$-substituted or unsubstituted heterocycloalkyl, $R^{110A}$-substituted or unsubstituted aryl, or $R^{110A}$-substituted or unsubstituted heteroaryl. In embodiments, $R^{109A}$ is independently hydrogen, —$CX^{109A}_3$, —CN, —COOH, —$CONH_2$, —$CHX^{109A}_2$, —$CH_2X^{109A}$, $R^{110A}$-substituted or unsubstituted $C_1$-$C_8$ alkyl, $R^{110A}$-substituted or unsubstituted 2 to 8 membered heteroalkyl, $R^{110A}$-substituted or unsubstituted $C_3$-$C_8$ cycloalkyl, $R^{110A}$-substituted or unsubstituted 3 to 6 membered heterocycloalkyl, $R^{110A}$-substituted or unsubstituted phenyl, or $R^{110A}$-substituted or unsubstituted 5 to 6 membered heteroaryl. $X^{109A}$ is —F, —Cl, —Br, or —I. In embodiments, $R^{109A}$ is independently hydrogen. In embodiments, $R^{109A}$ is independently methyl. In embodiments, $R^{109A}$ is independently ethyl.

In embodiments, $R^{109A}$ and $R^{109B}$ substituents bonded to the same nitrogen atom may optionally be joined to form a $R^{110A}$-substituted or unsubstituted heterocycloalkyl or $R^{110A}$-substituted or unsubstituted heteroaryl. In embodiments, $R^{109A}$ and $R^{109B}$ substituents bonded to the same nitrogen atom may optionally be joined to form a $R^{110A}$-substituted or unsubstituted 3 to 6 membered heterocycloalkyl or $R^{110A}$-substituted or unsubstituted 5 to 6 membered heteroaryl.

$R^{110A}$ is independently oxo, halogen, —$CX^{110A}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{110A}_3$, —$OCHX^{110A}_2$, $R^{111A}$-substituted or unsubstituted alkyl, $R^{111A}$-substituted or unsubstituted heteroalkyl, $R^{111A}$-substituted or unsubstituted cycloalkyl, $R^{111A}$-substituted or unsubstituted heterocycloalkyl, $R^{111A}$-substituted or unsubstituted aryl, or $R^{111A}$-substituted or unsubstituted heteroaryl. In embodiments, $R^{111A}$ is independently oxo, halogen, —$CX^{110A}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{110A}_3$, —$OCHX^{110A}_2$, $R^{111A}$-substituted or unsubstituted $C_1$-$C_8$ alkyl, $R^{111A}$-substituted or unsubstituted 2 to 8 membered heteroalkyl, $R^{111A}$-substituted or unsubstituted $C_3$-$C_8$ cycloalkyl, $R^{111A}$-substituted or unsubstituted 3 to 6 membered heterocycloalkyl, $R^{111A}$-substituted or unsubstituted phenyl, or $R^{111A}$-substituted or unsubstituted 5 to 6 membered heteroaryl. $X^{110A}$ is —F, —Cl, —Br, or —I.

$R^{111A}$ is independently oxo, halogen, —$CX^{111A}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{111A}_3$, —$OCHX^{111A}_2$, $R^{112A}$-substituted or unsubstituted alkyl, $R^{112A}$-substituted or unsubstituted heteroalkyl, $R^{112A}$-substituted or unsubstituted cycloalkyl, $R^{112A}$-substituted or unsubstituted heterocycloalkyl, $R^{112A}$-substituted or unsubstituted aryl, or $R^{112A}$-substituted or unsubstituted heteroaryl. In embodiments, $R^{111A}$ is independently oxo, halogen, —$CX^{111A}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{111A}_3$, —$OCHX^{111A}_2$, $R^{112A}$-substituted or unsubstituted $C_1$-$C_8$ alkyl, $R^{112A}$-substituted or unsubstituted 2 to 8 membered heteroalkyl, $R^{112A}$-substituted or unsubstituted $C_3$-$C_8$ cycloalkyl, $R^{112A}$-substituted or unsubstituted 3 to 6 membered heterocycloalkyl, $R^{112A}$-substituted or unsubstituted phenyl, or $R^{112A}$-substituted or unsubstituted 5 to 6 membered heteroaryl. $X^{111A}$ is —F, —Cl, —Br, or —I.

In embodiments, $R^{109B}$ is independently hydrogen, $-CX^{109B}{}_3$, $-CN$, $-COOH$, $-CONH_2$, $-CHX^{109B}{}_2$, $-CH_2X^{109B}$, $R^{110B}$-substituted or unsubstituted alkyl, $R^{110B}$-substituted or unsubstituted heteroalkyl, $R^{110B}$-substituted or unsubstituted cycloalkyl, $R^{110B}$-substituted or unsubstituted heterocycloalkyl, $R^{110B}$-substituted or unsubstituted aryl, or $R^{110B}$-substituted or unsubstituted heteroaryl. In embodiments, $R^{109B}$ is independently hydrogen, $-CX^{109B}{}_3$, $-CN$, $-COOH$, $-CONH_2$, $-CHX^{109B}{}_2$, $-CH_2X^{109B}$, $R^{110B}$-substituted or unsubstituted $C_1$-$C_8$ alkyl, $R^{110B}$-substituted or unsubstituted 2 to 8 membered heteroalkyl, $R^{110B}$-substituted or unsubstituted $C_3$-$C_8$ cycloalkyl, $R^{110B}$-substituted or unsubstituted 3 to 6 membered heterocycloalkyl, $R^{110B}$-substituted or unsubstituted phenyl, or $R^{110B}$-substituted or unsubstituted 5 to 6 membered heteroaryl. $X^{109B}$ is $-F$, $-Cl$, $-Br$, or $-I$. In embodiments, $R^{109B}$ is independently hydrogen. In embodiments, $R^{109B}$ is independently methyl. In embodiments, $R^{109B}$ is independently ethyl.

In embodiments, $R^{109A}$ and $R^{109B}$ substituents bonded to the same nitrogen atom may optionally be joined to form a $R^{110B}$-substituted or unsubstituted heterocycloalkyl or $R^{110B}$-substituted or unsubstituted heteroaryl. In embodiments, $R^{109A}$ and $R^{109B}$ substituents bonded to the same nitrogen atom may optionally be joined to form a $R^{110B}$-substituted or unsubstituted 3 to 6 membered heterocycloalkyl or $R^{110B}$-substituted or unsubstituted 5 to 6 membered heteroaryl.

$R^{110B}$ is independently oxo, halogen, $-CX^{110B}{}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{110B}{}_3$, $-OCHX^{110B}{}_2$, $R^{111B}$-substituted or unsubstituted alkyl, $R^{111B}$-substituted or unsubstituted heteroalkyl, $R^{111B}$-substituted or unsubstituted cycloalkyl, $R^{111B}$-substituted or unsubstituted heterocycloalkyl, $R^{111B}$-substituted or unsubstituted aryl, or $R^{111B}$-substituted or unsubstituted heteroaryl. In embodiments, $R^{110B}$ is independently oxo, halogen, $-CX^{110B}{}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{110B}{}_3$, $-OCHX^{110B}{}_2$, $R^{111B}$-substituted or unsubstituted $C_1$-$C_8$ alkyl, $R^{111B}$-substituted or unsubstituted 2 to 8 membered heteroalkyl, $R^{111B}$-substituted or unsubstituted $C_3$-$C_8$ cycloalkyl, $R^{111B}$-substituted or unsubstituted 3 to 6 membered heterocycloalkyl, $R^{111B}$-substituted or unsubstituted phenyl, or $R^{111B}$-substituted or unsubstituted 5 to 6 membered heteroaryl. $X^{110B}$ is $-F$, $-Cl$, $-Br$, or $-I$.

$R^{111B}$ is independently oxo, halogen, $-CX^{111B}{}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{111B}{}_3$, $-OCHX^{111B}{}_2$, $R^{112B}$-substituted or unsubstituted alkyl, $R^{112B}$-substituted or unsubstituted heteroalkyl, $R^{112B}$-substituted or unsubstituted cycloalkyl, $R^{112B}$-substituted or unsubstituted heterocycloalkyl, $R^{112B}$-substituted or unsubstituted aryl, or $R^{112B}$-substituted or unsubstituted heteroaryl. In embodiments, $R^{111B}$ is independently oxo, halogen, $-CX^{111B}{}_3$, $-CN$, $-OH$, $-NH_2$, $-COOH$, $-CONH_2$, $-NO_2$, $-SH$, $-SO_3H$, $-SO_4H$, $-S_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{111B}{}_3$, $-OCHX^{111B}{}_2$, $R^{112B}$-substituted or unsubstituted $C_1$-$C_8$ alkyl, $R^{112B}$-substituted or unsubstituted 2 to 8 membered heteroalkyl, $R^{112B}$-substituted or unsubstituted $C_3$-$C_8$ cycloalkyl, $R^{112B}$-substituted or unsubstituted 3 to 6 membered heterocycloalkyl, $R^{112B}$-substituted or unsubstituted phenyl, or $R^{112B}$-substituted or unsubstituted 5 to 6 membered heteroaryl. $X^{111B}$ is $-F$, $-Cl$, $-Br$, or $-I$.

In embodiments, $R^{109C}$ is independently hydrogen, $-CX^{109C}{}_3$, $-CN$, $-COOH$, $-CONH_2$, $-CHX^{109C}{}_2$, $-CH_2X^{109C}$, $R^{110C}$-substituted or unsubstituted alkyl, $R^{110C}$-substituted or unsubstituted heteroalkyl, $R^{110C}$-substituted or unsubstituted cycloalkyl, $R^{110C}$-substituted or unsubstituted heterocycloalkyl, $R^{110C}$-substituted or unsubstituted aryl, or $R^{110C}$-substituted or unsubstituted heteroaryl. In embodiments, $R^{109C}$ is independently hydrogen, $-CX^{109C}{}_3$, $-CN$, $-COOH$, $-CONH_2$, $-CHX^{109C}{}_2$, $-CH_2X^{109C}$, $R^{110C}$-substituted or unsubstituted $C_1$-$C_8$ alkyl, $R^{110C}$-substituted or unsubstituted 2 to 8 membered heteroalkyl, $R^{110C}$-substituted or unsubstituted $C_3$-$C_8$ cycloalkyl, $R^{110C}$-substituted or unsubstituted 3 to 6 membered heterocycloalkyl, $R^{110C}$-substituted or unsubstituted phenyl, or $R^{110C}$-substituted or unsubstituted 5 to 6 membered heteroaryl. $X^{109C}$ is $-F$, $-Cl$, $-Br$, or $-I$. In embodiments, $R^{109C}$ is independently hydrogen. In embodiments, $R^{109C}$ is independently methyl. In embodiments, $R^{109C}$ is independently ethyl.

$R^{110C}$ is independently oxo, halogen, $-CX^{110C}{}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{110C}{}_3$, $-OCHX^{110C}{}_2$, $R^{111C}$-substituted or unsubstituted alkyl, $R^{111C}$-substituted or unsubstituted heteroalkyl, $R^{111C}$-substituted or unsubstituted cycloalkyl, $R^{111C}$-substituted or unsubstituted heterocycloalkyl, $R^{111C}$-substituted or unsubstituted aryl, or $R^{111C}$-substituted or unsubstituted heteroaryl. In embodiments, $R^{110C}$ is independently oxo, halogen, $-CX^{110C}{}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{110C}{}_3$, $-OCHX^{110C}{}_2$, $R^{111C}$-substituted or unsubstituted $C_1$-$C_8$ alkyl, $R^{111C}$-substituted or unsubstituted 2 to 8 membered heteroalkyl, $R^{111C}$-substituted or unsubstituted $C_3$-$C_8$ cycloalkyl, $R^{111C}$-substituted or unsubstituted 3 to 6 membered heterocycloalkyl, $R^{111C}$-substituted or unsubstituted phenyl, or $R^{111C}$-substituted or unsubstituted 5 to 6 membered heteroaryl. $X^{110C}$ is $-F$, $-Cl$, $-Br$, or $-I$.

$R^{111C}$ is independently oxo, halogen, $-CX^{111C}{}_3$, $-CN$, $-OH$, $-NH_2$, $-COOH$, $-CONH_2$, $-NO_2$, $-SH$, $-SO_3H$, $-SO_4H$, $-S_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{111C}{}_3$, $-OCHX^{111C}{}_2$, $R^{112C}$-substituted or unsubstituted alkyl, $R^{112C}$-substituted or unsubstituted heteroalkyl, $R^{112C}$-substituted or unsubstituted cycloalkyl, $R^{112C}$-substituted or unsubstituted heterocycloalkyl, $R^{112C}$-substituted or unsubstituted aryl, or $R^{112C}$-substituted or unsubstituted heteroaryl. In embodiments, $R^{111C}$ is independently oxo, halogen, $-CX^{111C}{}_3$, $-CN$, $-OH$, $-NH_2$, $-COOH$, $-CONH_2$, $-NO_2$, $-SH$, $-SO_3H$, $-SO_4H$, $-S_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{111C}{}_3$, $-OCHX^{111C}{}_2$, $R^{112C}$-substituted or unsubstituted $C_1$-$C_8$ alkyl, $R^{112C}$-substituted or unsubstituted 2 to 8 membered heteroalkyl, $R^{112C}$-substituted or unsubstituted $C_3$-$C_8$ cycloalkyl, $R^{112C}$-substituted or unsubstituted 3 to 6 membered heterocycloalkyl, $R^{112C}$ substituted or unsubstituted phenyl, or $R^{112C}$-substituted or unsubstituted 5 to 6 membered heteroaryl. $X^{111C}$ is —F, —Cl, —Br, or —I.

In embodiments, $R^{109D}$ is independently hydrogen, —$CX^{109D}{}_3$, —CN, —COOH, —$CONH_2$, —$CHX^{109D}{}_2$, —$CH_2X^{109D}$, $R^{110D}$-substituted or unsubstituted alkyl, $R^{110D}$-substituted or unsubstituted heteroalkyl, $R^{110D}$-substituted or unsubstituted cycloalkyl, $R^{110D}$-substituted or unsubstituted heterocycloalkyl, $R^{110D}$-substituted or unsubstituted aryl, or $R^{110D}$-substituted or unsubstituted heteroaryl. In embodiments, $R^{109D}$ is independently hydrogen, —$CX^{109D}{}_3$, —CN, —COOH, —$CONH_2$, —$CHX^{109D}{}_2$, —$CH_2X^{109D}$, $R^{110D}$-substituted or unsubstituted $C_1$-$C_8$ alkyl, $R^{110D}$-substituted or unsubstituted 2 to 8 membered heteroalkyl, $R^{110D}$-substituted or unsubstituted $C_3$-$C_8$ cycloalkyl, $R^{110D}$-substituted or unsubstituted 3 to 6 membered heterocycloalkyl, $R^{110D}$-substituted or unsubstituted phenyl, or ROD-substituted or unsubstituted 5 to 6 membered heteroaryl. $X^{109D}$ is —F, —Cl, —Br, or —I. In embodiments, $R^{109D}$ is independently hydrogen. In embodiments, $R^{109D}$ is independently methyl. In embodiments, $R^{109D}$ is independently ethyl.

$R^{110D}$ is independently oxo, halogen, —$CX^{110D}{}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{110D}{}_3$, —$OCHX^{110D}{}_2$, $R^{111D}$-substituted or unsubstituted alkyl, $R^{111D}$-substituted or unsubstituted heteroalkyl, $R^{111D}$-substituted or unsubstituted cycloalkyl, $R^{111D}$-substituted or unsubstituted heterocycloalkyl, $R^{111D}$-substituted or unsubstituted aryl, or $R^{111D}$-substituted or unsubstituted heteroaryl. In embodiments, $R^{111D}$ is independently oxo, halogen, —$CX^{110D}{}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{110D}{}_3$, —$OCHX^{110D}{}_2$, $R^{111D}$-substituted or unsubstituted $C_1$-$C_8$ alkyl, $R^{111D}$-substituted or unsubstituted 2 to 8 membered heteroalkyl, $R^{111D}$-substituted or unsubstituted $C_3$-$C_8$ cycloalkyl, $R^{111D}$-substituted or unsubstituted 3 to 6 membered heterocycloalkyl, $R^{111D}$-substituted or unsubstituted phenyl, or $R^{111D}$-substituted or unsubstituted 5 to 6 membered heteroaryl. $X^{110D}$ is —F, —Cl, —Br, or —I.

$R^{111D}$ is independently oxo, halogen, —$CX^{111D}{}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{111D}{}_3$, —$OCHX^{111D}{}_2$, $R^{112D}$-substituted or unsubstituted alkyl, $R^{112D}$-substituted or unsubstituted heteroalkyl, $R^{112D}$-substituted or unsubstituted cycloalkyl, $R^{112D}$-substituted or unsubstituted heterocycloalkyl, $R^{112D}$-substituted or unsubstituted aryl, or $R^{112D}$-substituted or unsubstituted heteroaryl. In embodiments, $R^{111D}$ is independently oxo, halogen, —$CX^{111D}{}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{111D}{}_3$, —$OCHX^{111D}{}_2$, $R^{112D}$-substituted or unsubstituted $C_1$-$C_8$ alkyl, $R^{112D}$-substituted or unsubstituted 2 to 8 membered heteroalkyl, $R^{112D}$-substituted or unsubstituted $C_3$-$C_8$ cycloalkyl, $R^{112D}$-substituted or unsubstituted 3 to 6 membered heterocycloalkyl, $R^{112D}$-substituted or unsubstituted phenyl, or $R^{112D}$-substituted or unsubstituted 5 to 6 membered heteroaryl. $X^{111D}$ is —F, —Cl, —Br, or —I.

$R^{112}$, $R^{112A}$, $R^{112B}$, $R^{112C}$, and $R^{112D}$ are independently hydrogen, oxo, halogen, —$CCl_3$, —$CBr_3$, —$CF_3$, —$Cl_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH_2, —$NHC(O)NH_2$, —$NHSO_2H$, —NHC(O)H, —NHC(O)OH, —NHOH, —$OCCl_3$, —$OCF_3$, —$OCBr_3$, —$OCl_3$, —$OCHCl_2$, —$OCHBr_2$, —$OCHI_2$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{112}$, $R^{112A}$, $R^{112B}$, $R^{112C}$, and $R^{112D}$ are independently oxo, halogen, —$CF_3$, —CN, —OH, —$NH_2$, —COOH, —$CONH_2$, —$NO_2$, —SH, —$S_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{112}$, $R^{112A}$, $R^{112B}$, $R^{112C}$, and $R^{112D}$ are independently oxo, halogen, —$CF_3$, —CN, —OH, —$NH_2$, —COOH, —$CONH_2$, —$NO_2$, —SH, —$SO_3H$, —$SO_4H$, —$S_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCHF_2$, unsubstituted $C_1$-$C_8$ alkyl, unsubstituted 2 to 8 membered heteroalkyl, unsubstituted $C_3$-$C_8$ cycloalkyl, unsubstituted 3 to 6 membered heterocycloalkyl, unsubstituted phenyl, or unsubstituted 5 to 6 membered heteroaryl.

In embodiments, $L^2$ is —$NR^{7A}$— or substituted or unsubstituted heterocycloalkylene including a ring nitrogen bonded directly to E. In embodiments, $L^2$ is —$NR^{7A}$—. In embodiments, $L^2$ is substituted or unsubstituted heterocycloalkylene. In embodiments, $L^2$ is substituted or unsubstituted piperidinylene or substituted or unsubstituted pyrrolindinylene. In embodiments, $L^2$ is unsubstituted piperidinylene or unsubstituted pyrrolindinylene.

In embodiments, $L^2$ is a bond. In embodiments, $L^2$ is —$S(O)_2$—. In embodiments, $L^2$ is —$S(O)_2$-Ph-. In embodiments, $L^2$ is —$NR^{7A}$—. In embodiments, $L^2$ is —O—. In embodiments, $L^2$ is —S—. In embodiments, $L^2$ is —C(O)—. In embodiments, $L^2$ is —$C(O)NR^{7A}$—. In embodiments, $L^2$ is —$NR^7C(O)$—. In embodiments, $L^2$ is —NRC(O)NH—. In embodiments, $L^2$ is —NHC(O)$NR^{7A}$—. In embodiments, $L^2$ is —C(O)O—. In embodiments, $L^2$ is —OC(O)—. In embodiments, $L^2$ is —NH—. In embodiments, $L^2$ is —C(O)NH—. In embodiments, $L^2$ is —NHC(O)—. In embodiments, $L^2$ is —NHC(O)NH—. In embodiments, $L^2$ is —$CH_2$—. In embodiments, $L^2$ is —$OCH_2$—. In embodiments, $L^2$ is —$CH_2O$—. In embodiments, $L^2$ is —$CH_2CH_2$—. In embodiments, $L^2$ is —$SCH_2$—. In embodiments, $L^2$ is —$CH_2S$—. In embodiments, $L^2$ is —CHCH—. In embodiments, $L^2$ is —CC—. In embodiments, $L^2$ is —$NHCH_2$—. In embodiments, $L^2$ is —$CH_2NH$—.

In embodiments, $L^2$ is a substituted or unsubstituted alkylene. In embodiments, $L^2$ is a substituted or unsubstituted heteroalkylene. In embodiments, $L^2$ is a substituted or unsubstituted cycloalkylene. In embodiments, $L^2$ is a substituted or unsubstituted heterocycloalkylene. In embodiments, $L^2$ is a substituted or unsubstituted arylene. In embodiments, $L^2$ is a substituted or unsubstituted heteroarylene. In embodiments, $L^2$ is a substituted alkylene. In embodiments, $L^2$ is a substituted heteroalkylene. In embodiments, $L^2$ is a substituted cycloalkylene. In embodiments, $L^2$ is a substituted heterocycloalkylene. In embodiments, $L^2$ is a substituted arylene. In embodiments, $L^2$ is a substituted heteroarylene. In embodiments, $L^2$ is an unsubstituted alkylene. In embodiments, $L^2$ is an unsubstituted heteroalkylene. In embodiments, $L^2$ is an unsubstituted cycloalkylene. In embodiments, $L^2$ is an unsubstituted heterocycloalkylene. In embodiments, $L^2$ is an unsubstituted arylene. In embodiments, $L^2$ is an unsubstituted heteroarylene. In embodiments, $L^2$ is a substituted or unsubstituted $C_1$-$C_8$ alkylene. In embodiments, $L^2$ is a substituted or unsubstituted 2 to 8 membered heteroalkylene. In embodiments, $L^2$ is a substituted or unsubstituted $C_3$-$C_8$ cycloalkylene. In embodiments, $L^2$ is a substituted or unsubstituted 3 to 8 membered heterocycloalkylene. In embodiments, $L^2$ is a substituted or unsubstituted $C_6$-$C_{10}$ arylene. In embodiments, $L^2$ is a substituted or unsubstituted 5 to 10 membered heteroarylene. In embodiments, $L^2$ is a substituted $C_1$-$C_5$ alkylene. In embodiments, $L^2$ is a substituted 2 to 8 membered heteroalkylene. In embodiments, $L^2$ is a substituted $C_3$-$C_8$ cycloalkylene. In embodiments, $L^2$ is a substituted 3 to 8 membered heterocycloalkylene. In embodiments, $L^2$ is a substituted $C_6$-$C_{10}$ arylene. In embodiments, $L^2$ is a substituted 5 to 10 membered heteroarylene. In embodiments, $L^2$ is an unsubstituted $C_1$-$C_8$ alkylene. In embodiments, $L^2$ is an unsubstituted 2 to 8 membered heteroalkylene. In embodiments, $L^2$ is an unsubstituted $C_3$-$C_8$ cycloalkylene. In embodiments, $L^2$ is an unsubstituted 3 to 8 membered heterocycloalkylene. In embodiments, $L^2$ is an unsubstituted $C_6$-$C_{10}$ arylene. In embodiments, $L^2$ is an unsubstituted 5 to 10 membered heteroarylene. In embodiments, $L^2$ is a substituted or unsubstituted $C_1$-$C_4$ alkylene. In embodiments, $L^2$ is a substituted or unsubstituted 2 to 4 membered heteroalkylene. In embodiments, $L^2$ is a substituted or unsubstituted $C_3$-$C_6$ cycloalkylene. In embodiments, $L^2$ is a substituted or unsubstituted 3 to 6 membered heterocycloalkylene. In embodiments, $L^2$ is a substituted or unsubstituted phenylene. In embodiments, $L^2$ is a substituted or unsubstituted 5 to 6 membered heteroarylene. In embodiments, $L^2$ is a substituted $C_1$-$C_4$ alkylene. In embodiments, $L^2$ is a substituted 2 to 4 membered heteroalkylene. In embodiments, $L^2$ is a substituted $C_3$-$C_6$ cycloalkylene. In embodiments, $L^2$ is a substituted 3 to 6 membered heterocycloalkylene. In embodiments, $L^2$ is a substituted phenylene. In embodiments, $L^2$ is a substituted 5 to 6 membered heteroarylene. In embodiments, $L^2$ is an unsubstituted $C_1$-$C_4$ alkylene. In embodiments, $L^2$ is an unsubstituted 2 to 4 membered heteroalkylene. In embodiments, $L^2$ is an unsubstituted $C_3$-$C_6$ cycloalkylene. In embodiments, $L^2$ is an unsubstituted 3 to 6 membered heterocycloalkylene. In embodiments, $L^2$ is an unsubstituted phenylene. In embodiments, $L^2$ is an unsubstituted 5 to 6 membered heteroarylene.

In embodiments, $L^2$ is a bond, —S(O)$_2$—, —S(O)$_2$-Ph-, —NR$^{7A}$—, —O—, —S—, —C(O)—, —C(O)NR$^{7A}$—, —NR$^7$C(O)—, —NR$^7$C(O)NH—, —NHC(O)NR—, —C(O)O—, —OC(O)—, R$^{44}$-substituted or unsubstituted alkylene, R$^{44}$-substituted or unsubstituted heteroalkylene, R$^{44}$-substituted or unsubstituted cycloalkylene, R$^{44}$-substituted or unsubstituted heterocycloalkylene, R$^{44}$-substituted or unsubstituted arylene, or R$^{44}$-substituted or unsubstituted heteroarylene. In embodiments, $L^2$ is a bond, —S(O)$_2$—, —S(O)$_2$-Ph-, —NH—, —O—, —S—, —C(O)—, —C(O)NH—, —NHC(O)—, —NHC(O)NH—, —C(O)O—, —OC(O)—, R$^{44}$-substituted or unsubstituted alkylene, R$^{44}$-substituted or unsubstituted heteroalkylene, R$^{44}$-substituted or unsubstituted cycloalkylene, R$^{44}$-substituted or unsubstituted heterocycloalkylene, R$^{44}$-substituted or unsubstituted arylene, or R$^{44}$-substituted or unsubstituted heteroarylene. In embodiments, $L^2$ is a bond, —S(O)$_2$—, —S(O)$_2$-Ph-, —NH—, —O—, —S—, —C(O)—, —C(O)NH—, —NHC(O)—, —NHC(O)NH—, —C(O)O—, —OC(O)—, R$^{44}$-substituted or unsubstituted $C_1$-$C_8$ alkylene, R$^{44}$-substituted or unsubstituted 2 to 8 membered heteroalkylene, R$^{44}$-substituted or unsubstituted $C_3$-$C_8$ cycloalkylene, R$^{44}$-substituted or unsubstituted 3 to 6 membered heterocycloalkylene, R$^{44}$-substituted or unsubstituted phenylene, or R$^{44}$-substituted or unsubstituted 5 to 6 membered heteroarylene.

R$^{44}$ is independently oxo, halogen, —CX$^{44}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{44}_3$, —OCHX$^{44}_2$, R$^{45}$-substituted or unsubstituted alkyl, R$^{45}$-substituted or unsubstituted heteroalkyl, R$^5$-substituted or unsubstituted cycloalkyl, R$^{45}$-substituted or unsubstituted heterocycloalkyl, R$^{45}$-substituted or unsubstituted aryl, or R$^{45}$-substituted or unsubstituted heteroaryl. In embodiments, R$^{44}$ is independently oxo, halogen, —CX$^{44}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{44}_3$, —OCHX$^{44}_2$, R$^{45}$-substituted or unsubstituted $C_1$-$C_8$ alkyl, R$^{45}$-substituted or unsubstituted 2 to 8 membered heteroalkyl, R$^{45}$-substituted or unsubstituted $C_3$-$C_8$ cycloalkyl, R$^{45}$-substituted or unsubstituted 3 to 6 membered heterocycloalkyl, R$^{45}$-substituted or unsubstituted phenyl, or R$^{45}$-substituted or unsubstituted 5 to 6 membered heteroaryl. X$^{44}$ is —F, —Cl, —Br, or —I. In embodiments, R$^{44}$ is —CH$_3$. In embodiments, R$^{44}$ is —F.

R$^{45}$ is independently oxo, halogen, —CX$^{45}_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{45}_3$, —OCHX$^{45}_2$, R$^{46}$-substituted or unsubstituted alkyl, R$^{46}$-substituted or unsubstituted heteroalkyl, R$^{46}$-substituted or unsubstituted cycloalkyl, R$^{46}$-substituted or unsubstituted heterocycloalkyl, R$^{46}$-substituted or unsubstituted aryl, or R$^{46}$-substituted or unsubstituted heteroaryl. In embodiments, R$^{45}$ is independently oxo, halogen, —CX$^{45}_3$, —CN, —OH, —NH$_2$, —COOH, —CONH$_2$, —NO$_2$, —SH, —S$_3$H, —SO$_4$H, —S$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{45}_3$, —OCHX$^{45}_2$, R$^{46}$-substituted or unsubstituted $C_1$-$C_8$ alkyl, R$^{46}$-substituted or unsubstituted 2 to 8 membered heteroalkyl, R$^{46}$-substituted or unsubstituted $C_3$-$C_8$ cycloalkyl, R$^{46}$-substituted or unsubstituted 3 to 6 membered heterocycloalkyl, R$^{46}$-substituted or unsubstituted phenyl, or R$^{46}$-substituted or unsubstituted 5 to 6 membered heteroaryl. X$^{45}$ is —F, —Cl, —Br, or —I.

R$^{46}$ is independently hydrogen, oxo, halogen, —CCl$_3$, —CBr$_3$, —CF$_3$, —Cl$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCl$_3$, —OCHCl$_2$, —OCHBr$_2$, —OCHI$_2$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl. In embodiments, R$^{46}$ is independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{46}$ is independently oxo, halogen, —CF$_3$, —CN, —OH, —NH$_2$, —COOH, —CONH$_2$, —NO$_2$. —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCHF$_2$, unsubstituted C$_1$-C$_8$ alkyl, unsubstituted 2 to 8 membered heteroalkyl, unsubstituted C$_3$-C$_8$ cycloalkyl, unsubstituted 3 to 6 membered heterocycloalkyl, unsubstituted phenyl, or unsubstituted 5 to 6 membered heteroaryl.

In embodiments, L$^2$ is $R^{44}$-substituted or unsubstituted 4 membered heterocycloalkylene. In embodiments, L$^2$ is $R^{44}$-substituted or unsubstituted 5 membered heterocycloalkylene. In embodiments, L$^2$ is $R^{44}$-substituted or unsubstituted 6 membered heterocycloalkylene. In embodiments, L$^2$ is $R^{44}$-substituted or unsubstituted 7 membered heterocycloalkylene. In embodiments, L$^2$ is $R^{44}$-substituted or unsubstituted heterocycloalkylene (e.g., 3 to 6 membered heterocycloalkylene, 4 to 6 membered heterocycloalkylene, or 5 to 6 membered heterocycloalkylene). In embodiments, L$^2$ is $R^{44}$-substituted 4 membered heterocycloalkylene. In embodiments, L$^2$ is $R^{44}$-substituted 5 membered heterocycloalkylene. In embodiments, L$^2$ is $R^{44}$-substituted 6 membered heterocycloalkylene. In embodiments, L$^2$ is $R^{44}$-substituted 7 membered heterocycloalkylene. In embodiments, L$^2$ is $R^{44}$-substituted heterocycloalkylene (e.g., 3 to 6 membered heterocycloalkylene, 4 to 6 membered heterocycloalkylene, or 5 to 6 membered heterocycloalkylene). In embodiments, L$^2$ is unsubstituted 4 membered heterocycloalkylene. In embodiments, L$^2$ is unsubstituted 5 membered heterocycloalkylene. In embodiments, L$^2$ is unsubstituted 6 membered heterocycloalkylene. In embodiments, L$^2$ is unsubstituted 7 membered heterocycloalkylene. In embodiments, L$^2$ is unsubstituted heterocycloalkylene (e.g., 3 to 6 membered heterocycloalkylene, 4 to 6 membered heterocycloalkylene, or 5 to 6 membered heterocycloalkylene).

In embodiments, L$^2$ is $R^{44}$-substituted or unsubstituted piperidinylene. In embodiments, L$^2$ is $R^{44}$-substituted or unsubstituted pyrrolidinylene. In embodiments, L$^2$ is $R^{44}$-substituted or unsubstituted imidazolidinylene. In embodiments, L$^2$ is $R^{44}$-substituted or unsubstituted pyrazolidinylene. In embodiments, L$^2$ is $R^{44}$-substituted or unsubstituted piperazinylene. In embodiments, L$^2$ is $R^{44}$-substituted or unsubstituted piperazinylene. In embodiments, L$^2$ is $R^{44}$-substituted or unsubstituted azetidinylene. In embodiments, L$^2$ is $R^{44}$-substituted or unsubstituted aziridinylene. In embodiments, L$^2$ is $R^{44}$-substituted or unsubstituted morpholinylene.

In embodiments, L$^2$ is $R^{44}$-substituted piperidinylene. In embodiments, L$^2$ is $R^{44}$-substituted $R^{44}$-substituted pyrrolidinylene. In embodiments, L$^2$ is $R^{44}$-substituted imidazolidinylene. In embodiments, L$^2$ is $R^{44}$-substituted pyrazolidinylene. In embodiments, L$^2$ is $R^{44}$-substituted piperazinylene. In embodiments, L$^2$ is $R^{44}$-substituted azetidinylene. In embodiments, L$^2$ is $R^{44}$-substituted aziridinylene. In embodiments, L$^2$ is $R^{44}$-substituted morpholinylene.

In embodiments, L$^2$ is methyl-substituted piperidinylene. In embodiments, L$^2$ is methyl-substituted methyl-substituted pyrrolidinylene. In embodiments, L$^2$ is methyl-substituted imidazolidinylene. In embodiments, L$^2$ is methyl-substituted pyrazolidinylene. In embodiments, L$^2$ is methyl-substituted piperazinylene. In embodiments, L$^2$ is methyl-substituted azetidinylene. In embodiments, L$^2$ is methyl-substituted aziridinylene. In embodiments, L$^2$ is methyl-substituted morpholinylene.

In embodiments, L$^2$ is unsubstituted 5 membered heterocycloalkylene. In embodiments, L$^2$ unsubstituted 6 membered heterocycloalkylene. In embodiments, L$^2$ is unsubstituted heterocycloalkylene (e.g., 3 to 6 membered heterocycloalkylene, 4 to 6 membered heterocycloalkylene, or 5 to 6 membered heterocycloalkylene). In embodiments, L$^2$ is unsubstituted piperidinylene. In embodiments, L$^2$ is unsubstituted pyrrolidinylene. In embodiments, L$^2$ is unsubstituted imidazolidinylene. In embodiments, L$^2$ is unsubstituted pyrazolidinylene. In embodiments, L$^2$ is unsubstituted piperazinylene. In embodiments, L$^2$ is unsubstituted azetidinylene. In embodiments, L$^2$ is unsubstituted aziridinylene. In embodiments, L$^2$ is unsubstituted morpholinylene.

In embodiments, L$^2$ is a $R^{44}$-substituted or unsubstituted 5 to 10 membered heteroarylene. In embodiments, L$^2$ is a $R^{44}$-substituted or unsubstituted 5 to 6 membered heteroarylene. In embodiments, L$^2$ is a $R^{44}$-substituted or unsubstituted pyridinylene, pyridazinylene, pyrimidinylene, pyrazinylene, or triazinylene.

In embodiments, L$^2$ is a $R^{44}$-substituted 5 to 10 membered heteroarylene. In embodiments, L$^2$ is a $R^{44}$-substituted 5 to 6 membered heteroarylene. In embodiments, L$^2$ is a $R^{44}$-substituted pyridinylene, pyridazinylene, pyrimidinylene, pyrazinylene, or triazinylene. In embodiments, L$^2$ is unsubstituted 5 to 10 membered heteroarylene. In embodiments, L$^2$ is unsubstituted 5 to 6 membered heteroarylene. In embodiments, L$^2$ is unsubstituted pyridinylene, pyridazinylene, pyrimidinylene, pyrazinylene, or triazinylene. In embodiments, L$^2$ is $R^{44}$-substituted or unsubstituted indolinylene. In embodiments, L$^2$ is $R^{44}$-substituted or unsubstituted indazolylene. In embodiments, L$^2$ is $R^{44}$-substituted or unsubstituted benzimidazolylene. In embodiments, L$^2$ is $R^{44}$-substituted or unsubstituted benzoxazolylene. In embodiments, L$^2$ is $R^{44}$-substituted or unsubstituted azaindolylene. In embodiments, L$^2$ is $R^{44}$-substituted or unsubstituted purinylene. In embodiments, L$^2$ is $R^{44}$-substituted or unsubstituted indolylene. In embodiments, L$^2$ is $R^{44}$-substituted or unsubstituted pyrazinylene. In embodiments, L$^2$ is $R^{44}$-substituted or unsubstituted pyrrolylene. In embodiments, L$^2$ is $R^{44}$-substituted or unsubstituted imidazolylene. In embodiments, L$^2$ is $R^{44}$-substituted or unsubstituted pyrazolylene. In embodiments, L$^2$ is $R^{44}$-substituted or unsubstituted triazolylene. In embodiments, L$^2$ is $R^{44}$-substituted or unsubstituted tetrazolylene. In embodiments, L$^2$ is $R^{44}$-substituted or unsubstituted azepanylene. In embodiments, L$^2$ is $R^{44}$-substituted or unsubstituted azepinylene.

In embodiments, L$^2$ is $R^{44}$-substituted indolinylene. In embodiments, L$^2$ is $R^{44}$-substituted indazolylene. In embodiments, L$^2$ is $R^{44}$-substituted benzimidazolylene. In embodiments, L$^2$ is $R^{44}$-substituted benzoxazolylene. In embodiments, L$^2$ is $R^{44}$-substituted azaindolylene. In embodiments, L$^2$ is $R^{44}$-substituted purinylene. In embodiments, L$^2$ is $R^{44}$-substituted indolylene. In embodiments, L$^2$ is $R^{44}$-substituted pyrazinylene. In embodiments, L$^2$ is $R^{44}$-substituted pyrrolylene. In embodiments, L$^2$ is $R^{44}$-substituted imidazolylene. In embodiments, L$^2$ is $R^{44}$-substituted pyrazolylene. In embodiments, L$^2$ is $R^{44}$-substituted triazolylene. In embodiments, L$^2$ is $R^{44}$-substituted tetrazolylene. In embodiments, L$^2$ is $R^{44}$-substituted azepanylene. In embodiments, L$^2$ is $R^{44}$-substituted azepinylene.

In embodiments, $L^2$ is unsubstituted indolinylene. In embodiments, $L^2$ is unsubstituted indazolylene. In embodiments, $L^2$ is unsubstituted benzimidazolylene. In embodiments, $L^2$ is unsubstituted benzoxazolylene. In embodiments, $L^2$ is unsubstituted azaindolylene. In embodiments, $L^2$ is unsubstituted purinylene. In embodiments, $L^2$ is unsubstituted indolylene. In embodiments, $L^2$ is unsubstituted pyrazinylene. In embodiments, $L^2$ is unsubstituted pyrrolylene. In embodiments, $L^2$ is unsubstituted imidazolylene. In embodiments, $L^2$ is unsubstituted pyrazolylene. In embodiments, $L^2$ is unsubstituted triazolylene. In embodiments, $L^2$ is unsubstituted tetrazolylene. In embodiments, $L^2$ is unsubstituted azepanylene. In embodiments, $L^2$ is unsubstituted azepinylene.

In embodiments, $L^2$ is $R^{44}$-substituted or unsubstituted $C_3$-$C_8$ cycloalkylene. In embodiments, $L^2$ is $R^{44}$-substituted or unsubstituted $C_4$-$C_6$ cycloalkylene. In embodiments, $L^2$ is $R^{44}$-substituted or unsubstituted $C_5$-$C_6$ cycloalkylene. In embodiments, $L^2$ is $R^{44}$-substituted or unsubstituted cycloalkylene (e.g., $C_3$-$C_8$ cycloalkylene, $C_4$-$C_6$ cycloalkylene, or $C_5$-$C_6$ cycloalkylene). In embodiments, $L^2$ is $R^{44}$-substituted $C_3$-$C_8$ cycloalkylene. In embodiments, $L^2$ is $R^{44}$-substituted $C_4$-$C_6$ cycloalkylene. In embodiments, $L^2$ is $R^{44}$-substituted $C_5$-$C_6$ cycloalkylene. In embodiments, $L^2$ is $R^{44}$-substituted cycloalkylene (e.g., $C_3$-$C_8$ cycloalkylene, $C_4$-$C_6$ cycloalkylene, or $C_5$-$C_6$ cycloalkylene). In embodiments, $L^2$ is unsubstituted $C_3$-$C_8$ cycloalkylene. In embodiments, $L^2$ is unsubstituted $C_4$-$C_6$ cycloalkylene. In embodiments, $L^2$ is unsubstituted $C_5$-$C_6$ cycloalkylene. In embodiments, $L^2$ is unsubstituted cycloalkylene (e.g., $C_3$-$C_8$ cycloalkylene, $C_4$-$C_6$ cycloalkylene, or $C_5$-$C_6$ cycloalkylene).

In embodiments, $L^2$ is $R^{44}$-substituted or unsubstituted alkylene (e.g., $C_1$-$C_8$ alkylene, $C_1$-$C_6$ alkylene, $C_1$-$C_4$ alkylene, $C_1$-$C_2$ alkylene). In embodiments, $L^2$ is $R^{44}$-substituted or unsubstituted $C_1$-$C_8$ alkylene. In embodiments, $L^2$ is $R^{44}$-substituted or unsubstituted $C_1$-$C_6$ alkylene. In embodiments, $L^2$ is $R^{44}$-substituted or unsubstituted $C_1$-$C_4$ alkylene. In embodiments, $L^2$ is $R^{44}$-substituted or unsubstituted $C_1$-$C_2$ alkylene. In embodiments, $L^2$ is $R^{44}$-substituted alkylene (e.g., $C_1$-$C_8$ alkylene, $C_1$-$C_6$ alkylene, $C_1$-$C_4$ alkylene, $C_1$-$C_2$ alkylene). In embodiments, $L^2$ is $R^{44}$-substituted $C_1$-$C_8$ alkylene. In embodiments, $L^2$ is $R^{44}$-substituted $C_1$-$C_6$ alkylene. In embodiments, $L^2$ is $R^{44}$-substituted $C_1$-$C_4$ alkylene. In embodiments, $L^2$ is $R^{44}$-substituted $C_1$-$C_2$ alkylene. In embodiments, $L^2$ is unsubstituted alkylene (e.g., $C_1$-$C_8$ alkylene, $C_1$-$C_6$ alkylene, $C_1$-$C_4$ alkylene, $C_1$-$C_2$ alkylene). In embodiments, $L^2$ is unsubstituted $C_1$-$C_8$ alkylene. In embodiments, $L^2$ is unsubstituted $C_1$-$C_6$ alkylene. In embodiments, $L^2$ is unsubstituted $C_1$-$C_4$ alkylene. In embodiments, $L^2$ is unsubstituted $C_1$-$C_2$ alkylene. In embodiments, $L^2$ is $R^{44}$-substituted or unsubstituted methylene. In embodiments, $L^2$ is unsubstituted methylene.

In embodiments, $L^2$ is $R^{44}$-substituted or unsubstituted heteroalkylene (e.g., 2 to 8 membered heteroalkylene, 2 to 6 membered heteroalkylene, 2 to 4 membered heteroalkylene). In embodiments, $L^2$ is $R^{44}$-substituted or unsubstituted 2 to 8 membered heteroalkylene. In embodiments, $L^2$ is $R^{44}$-substituted or unsubstituted 2 to 6 membered heteroalkylene. In embodiments, $L^2$ is $R^{44}$-substituted or unsubstituted 2 to 4 membered heteroalkylene. In embodiments, $L^2$ is $R^{44}$-substituted heteroalkylene (e.g., 2 to 8 membered heteroalkylene, 2 to 6 membered heteroalkylene, 2 to 4 membered heteroalkylene). In embodiments, $L^2$ is $R^{44}$-substituted 2 to 8 membered heteroalkylene. In embodiments, $L^2$ is $R^{44}$-substituted 2 to 6 membered heteroalkylene. In embodiments, $L^2$ is $R^{44}$-substituted 2 to 4 membered heteroalkylene. In embodiments, $L^2$ is unsubstituted heteroalkylene (e.g., 2 to 8 membered heteroalkylene, 2 to 6 membered heteroalkylene, 2 to 4 membered heteroalkylene). In embodiments, $L^2$ is unsubstituted 2 to 8 membered heteroalkylene. In embodiments, $L^2$ is unsubstituted 2 to 6 membered heteroalkylene. In embodiments, $L^2$ is unsubstituted 2 to 4 membered heteroalkylene.

In embodiments, $L^2$ is

In embodiments, $L^2$ is

In embodiments, $L^2$ is

In embodiments, $L^1$ is

In embodiments, $L^2$ is

In embodiments, $L^2$-E is

In embodiments, L²
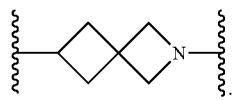 [SMILES: *C1CC2(C1)CN(*)C2]
In embodiment L² is
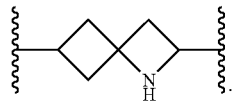 [SMILES: *C1CC2(C1)CC(*)N2]
In embodiments, L² is
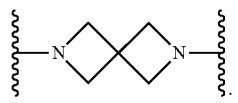 [SMILES: *N1CC2(C1)CN(*)C2]
In embodiments, L² is
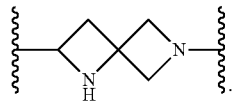 [SMILES: *C1CC2(CN(*)C2)N1]
In embodiments, L² is
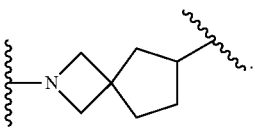 [SMILES: *C1CCC2(C1)CN(*)C2]
In embodiments, L² is
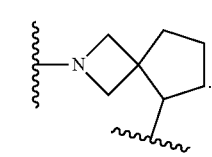 [SMILES: *C1CCCC12CN(*)C2]
In embodiments, L² is
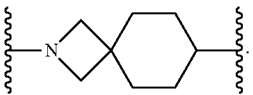 [SMILES: *C1CCC2(CC1)CN(*)C2]
In embodiments, L² is
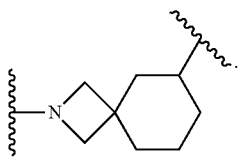 [SMILES: *C1CCCC2(C1)CN(*)C2]
In embodiments, L² is
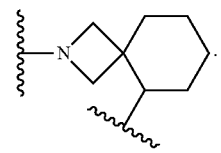 [SMILES: *C1CCCCC12CN(*)C2]
In embodiments, L² is
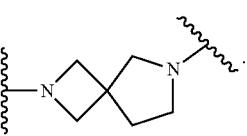 [SMILES: *N1CCC2(C1)CN(*)C2]
In embodiments, L² is
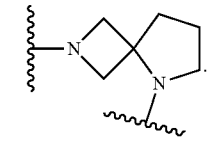 [SMILES: *N1CC2(CCCN2*)C1]
In embodiments, L² is
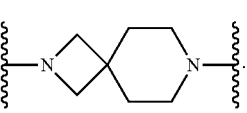
In embodiments L² is
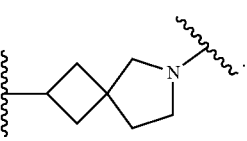 [SMILES: *C1CC2(CCN(*)C2)C1]
In embodiments, L² is
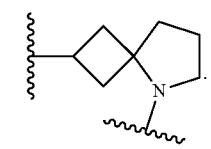 [SMILES: *C1CC2(CCCN2*)C1]

In embodiments, $L^2$ is

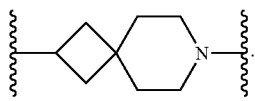 [SMILES: *C1CC2(CCN(*)CC2)C1]

In embodiments, $L^2$ is

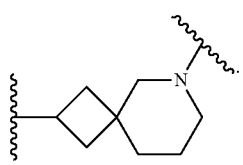 [SMILES: *C1CC2(CCCN(*)C2)C1]

In embodiments, $L^2$ is

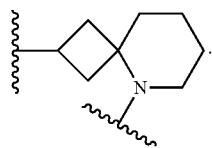 [SMILES: *C1CC2(CCCCN2*)C1]

In embodiments, $R^7$ is hydrogen, substituted or unsubstituted $C_1$-$C_6$ alkyl, or substituted or unsubstituted 2 to 6 membered heteroalkyl. In embodiments, $R^7$ is hydrogen or unsubstituted $C_1$-$C_3$ alkyl. In embodiments, $R^7$ is hydrogen.

In embodiments, $R^7$ is independently hydrogen. In embodiments, $R^7$ is independently halogen. In embodiments, $R^7$ is independently —$CX^7{}_3$. In embodiments, $R^7$ is independently —$CHX^7{}_2$. In embodiments, $R^7$ is independently —$CH_2X^7$. In embodiments, $R^7$ is independently —$OCX^7{}_3$. In embodiments, $R^7$ is independently —$OCH_2X^7$. In embodiments, $R^7$ is independently —$OCHX^7{}_2$. In embodiments, $R^7$ is independently —CN. In embodiments, $R^7$ is independently —$SO_{n7}R^{7D}$. In embodiments, $R^7$ is independently —$SO_{v7}NR^{7A}R^{7B}$. In embodiments, $R^7$ is independently —NHC(O)$NR^{7A}R^{7B}$. In embodiments, $R^7$ is independently —$N(O)_{m7}$. In embodiments, $R^7$ is independently —$NR^{7A}R^{7B}$. In embodiments, $R^7$ is independently —C(O)$R^{7C}$. In embodiments, $R^7$ is independently —C(O)—$OR^{7C}$. In embodiments, $R^7$ is independently —C(O)$NR^{7A}R^{7B}$. In embodiments, $R^7$ is independently —$OR^{7D}$. In embodiments, $R^7$ is independently —$NR^{7A}SO_2R^{7D}$. In embodiments, $R^7$ is independently —$NR^{7A}C(O)R^{7C}$. In embodiments, $R^7$ is independently —$NR^{7A}C(O)OR^{7C}$. In embodiments, $R^7$ is independently —$NR^{7A}OR^{7C}$. In embodiments, $R^7$ is independently —OH. In embodiments, $R^7$ is independently —$NH_2$. In embodiments, $R^7$ is independently —COOH. In embodiments, $R^7$ is independently —$CONH_2$. In embodiments, $R^7$ is independently —$NO_2$. In embodiments, $R^7$ is independently —SH.

In embodiments, $R^7$ is independently substituted or unsubstituted alkyl. In embodiments, $R^7$ is independently substituted or unsubstituted heteroalkyl. In embodiments, $R^7$ is independently substituted or unsubstituted cycloalkyl. In embodiments, $R^7$ is independently, substituted or unsubstituted heterocycloalkyl. In embodiments, $R^7$ is independently substituted or unsubstituted aryl. In embodiments, $R^7$ is independently substituted or unsubstituted heteroaryl. In embodiments, $R^7$ is independently substituted alkyl. In embodiments, $R^7$ is independently substituted heteroalkyl. In embodiments, $R^7$ is independently substituted cycloalkyl. In embodiments, $R^7$ is independently, substituted heterocycloalkyl. In embodiments, $R^1$ is independently substituted aryl. In embodiments, $R^7$ is independently substituted heteroaryl. In embodiments, $R^7$ is independently unsubstituted alkyl. In embodiments, $R^7$ is independently unsubstituted heteroalkyl. In embodiments, $R^7$ is independently unsubstituted cycloalkyl. In embodiments, $R^7$ is independently, unsubstituted heterocycloalkyl. In embodiments, $R^7$ is independently unsubstituted aryl. In embodiments, $R^1$ is independently unsubstituted heteroaryl. In embodiments, $R^7$ is independently substituted or unsubstituted $C_1$-$C_8$ alkyl. In embodiments, $R^1$ is independently substituted or unsubstituted 2 to 8 membered heteroalkyl. In embodiments, $R^7$ is independently substituted or unsubstituted $C_3$-$C_8$ cycloalkyl. In embodiments, $R^7$ is independently, substituted or unsubstituted 3 to 8 membered heterocycloalkyl. In embodiments, $R^7$ is independently substituted or unsubstituted $C_6$-$C_{10}$ aryl. In embodiments, $R^7$ is independently substituted or unsubstituted 5 to 10 membered heteroaryl. In embodiments, $R^1$ is independently substituted $C_1$-$C_8$ alkyl. In embodiments, $R^1$ is independently substituted 2 to 8 membered heteroalkyl. In embodiments, $R^7$ is independently substituted $C_3$-$C_8$ cycloalkyl. In embodiments, $R^7$ is independently, substituted 3 to 8 membered heterocycloalkyl. In embodiments, $R^7$ is independently substituted $C_6$-$C_{10}$ aryl. In embodiments, $R^7$ is independently substituted 5 to 10 membered heteroaryl. In embodiments, $R^7$ is independently unsubstituted $C_1$-$C_8$ alkyl. In embodiments, $R^1$ is independently unsubstituted 2 to 8 membered heteroalkyl. In embodiments, $R^7$ is independently unsubstituted $C_3$-$C_8$ cycloalkyl. In embodiments, $R^7$ is independently, unsubstituted 3 to 8 membered heterocycloalkyl. In embodiments, $R^7$ is independently unsubstituted $C_6$-$C_{10}$ aryl. In embodiments, $R^7$ is independently unsubstituted 5 to 10 membered heteroaryl. In embodiments, $R^7$ is independently substituted or unsubstituted $C_1$-$C_4$ alkyl. In embodiments, $R^7$ is independently substituted or unsubstituted 2 to 4 membered heteroalkyl. In embodiments, $R^7$ is independently substituted or unsubstituted $C_3$-$C_6$ cycloalkyl. In embodiments, $R^7$ is independently, substituted or unsubstituted 3 to 6 membered heterocycloalkyl. In embodiments, $R^7$ is independently substituted or unsubstituted phenyl. In embodiments, $R^7$ is independently substituted or unsubstituted 5 to 6 membered heteroaryl. In embodiments, $R^7$ is independently substituted $C_1$-$C_4$ alkyl. In embodiments, $R^7$ is independently substituted 2 to 4 membered heteroalkyl. In embodiments, $R^7$ is independently substituted $C_3$-$C_6$ cycloalkyl. In embodiments, $R^7$ is independently, substituted 3 to 6 membered heterocycloalkyl. In embodiments, $R^7$ is independently substituted phenyl. In embodiments, $R^7$ is independently substituted 5 to 6 membered heteroaryl. In embodiments, $R^7$ is independently unsubstituted $C_1$-$C_4$ alkyl. In embodiments, $R^7$ is independently unsubstituted 2 to 4 membered heteroalkyl. In embodiments, $R^7$ is independently unsubstituted $C_3$-$C_6$ cycloalkyl. In embodiments, $R^7$ is independently unsubstituted 3 to 6 membered heterocycloalkyl. In embodiments, $R^7$ is independently unsubstituted phenyl. In embodiments, $R^7$ is independently unsubstituted 5 to 6 membered heteroaryl.

In embodiments, $R^{7A}$ is independently hydrogen. In embodiments, $R^{7A}$ is independently —$CX^{7A}{}_3$. In embodiments, $R^{7A}$ is independently —$CHX^{7A}{}_2$. In embodiments, $R^{7A}$ is independently —$CH_2X^{7A}$. In embodiments, $R^{7A}$ is independently —CN. In embodiments, $R^{7A}$ is independently —COOH. In embodiments, $R^{7A}$ is independently —$CONH_2$. In embodiments, $R^{7A}$ is independently substituted or unsubstituted alkyl. In embodiments, $R^{7A}$ is independently substituted or unsubstituted heteroalkyl. In embodiments, $R^{7A}$ is independently substituted or unsubstituted cycloalkyl. In embodiments, $R^{7A}$ is independently, substituted or unsubstituted heterocycloalkyl. In embodiments, $R^{7A}$ is independently substituted or unsubstituted aryl. In embodiments, $R^{7A}$ is independently substituted or unsubstituted heteroaryl. In embodiments, $R^{7A}$ is independently substituted alkyl. In embodiments, $R^{7A}$ is independently substituted heteroalkyl. In embodiments, $R^{7A}$ is independently substituted cycloalkyl. In embodiments, $R^{7A}$ is independently, substituted heterocycloalkyl. In embodiments, $R^{7A}$ is independently substituted aryl. In embodiments, $R^{7A}$ is independently substituted heteroaryl. In embodiments, $R^{7A}$ is independently unsubstituted alkyl. In embodiments, $R^{7A}$ is independently unsubstituted heteroalkyl. In embodiments, $R^{7A}$ is independently unsubstituted cycloalkyl. In embodiments, $R^{7A}$ is independently, unsubstituted heterocycloalkyl. In embodiments, $R^{7A}$ is independently unsubstituted aryl. In embodiments, $R^{7A}$ is independently unsubstituted heteroaryl. In embodiments, $R^{7A}$ is independently substituted or unsubstituted $C_1$-$C_8$ alkyl. In embodiments, $R^{7A}$ is independently substituted or unsubstituted 2 to 8 membered heteroalkyl. In embodiments, $R^{7A}$ is independently substituted or unsubstituted $C_3$-$C_8$ cycloalkyl. In embodiments, $R^{7A}$ is independently, substituted or unsubstituted 3 to 8 membered heterocycloalkyl. In embodiments, $R^{7A}$ is independently substituted or unsubstituted $C_6$-$C_{10}$ aryl. In embodiments, $R^{7A}$ is independently substituted or unsubstituted 5 to 10 membered heteroaryl. In embodiments, $R^{7A}$ is independently substituted $C_1$-$C_8$ alkyl. In embodiments, $R^{7A}$ is independently substituted 2 to 8 membered heteroalkyl. In embodiments, $R^{7A}$ is independently substituted $C_3$-$C_8$ cycloalkyl. In embodiments, $R^{7A}$ is independently, substituted 3 to 8 membered heterocycloalkyl. In embodiments, $R^{7A}$ is independently substituted $C_6$-$C_{10}$ aryl. In embodiments, $R^{7A}$ is independently substituted 5 to 10 membered heteroaryl. In embodiments, $R^{7A}$ is independently unsubstituted $C_1$-$C_8$ alkyl. In embodiments, $R^{7A}$ is independently unsubstituted 2 to 8 membered heteroalkyl. In embodiments, $R^{7A}$ is independently unsubstituted $C_3$-$C_8$ cycloalkyl. In embodiments, $R^{7A}$ is independently, unsubstituted 3 to 8 membered heterocycloalkyl. In embodiments, $R^{7A}$ is independently unsubstituted $C_6$-$C_{10}$ aryl. In embodiments, $R^{7A}$ is independently unsubstituted 5 to 10 membered heteroaryl. In embodiments, $R^{7A}$ is independently substituted or unsubstituted $C_1$-$C_4$ alkyl. In embodiments, $R^{7A}$ is independently substituted or unsubstituted 2 to 4 membered heteroalkyl. In embodiments, $R^{7A}$ is independently substituted or unsubstituted $C_3$-$C_6$ cycloalkyl. In embodiments, $R^{7A}$ is independently, substituted or unsubstituted 3 to 6 membered heterocycloalkyl. In embodiments, $R^{7A}$ is independently substituted or unsubstituted phenyl. In embodiments, $R^{7A}$ is independently substituted or unsubstituted 5 to 6 membered heteroaryl. In embodiments, $R^{7A}$ is independently substituted $C_1$-$C_4$ alkyl. In embodiments, $R^{7A}$ is independently substituted 2 to 4 membered heteroalkyl. In embodiments, $R^{7A}$ is independently substituted $C_3$-$C_6$ cycloalkyl. In embodiments, $R^{7A}$ is independently, substituted 3 to 6 membered heterocycloalkyl. In embodiments, $R^{7A}$ is independently substituted phenyl. In embodiments, $R^{7A}$ is independently substituted 5 to 6 membered heteroaryl. In embodiments, $R^{7A}$ is independently unsubstituted $C_1$-$C_4$ alkyl. In embodiments, $R^{7A}$ is independently unsubstituted 2 to 4 membered heteroalkyl. In embodiments, $R^{7A}$ is independently unsubstituted $C_3$-$C_6$ cycloalkyl. In embodiments, $R^{7A}$ is independently unsubstituted 3 to 6 membered heterocycloalkyl. In embodiments, $R^{7A}$ is independently unsubstituted phenyl. In embodiments, $R^{7A}$ is independently unsubstituted 5 to 6 membered heteroaryl. In embodiments, $R^{7A}$ is independently unsubstituted methyl. In embodiments, $R^{7A}$ is independently unsubstituted ethyl. In embodiments, $R^{7A}$ is independently unsubstituted propyl. In embodiments, $R^{7A}$ is independently unsubstituted isopropyl. In embodiments, $R^{7A}$ is independently unsubstituted tert-butyl.

In embodiments, $R^{7B}$ is independently hydrogen. In embodiments, $R^{7B}$ is independently —$CX^{7B}_3$. In embodiments, $R^{7B}$ is independently —$CHX^{7B}_2$. In embodiments, $R^{7B}$ is independently —$CH_2X^{7B}$. In embodiments, $R^{7B}$ is independently —CN. In embodiments, $R^{7B}$ is independently —COOH. In embodiments, $R^{7B}$ is independently —$CONH_2$. In embodiments, $R^{7B}$ is independently substituted or unsubstituted alkyl. In embodiments, $R^{7B}$ is independently substituted or unsubstituted heteroalkyl. In embodiments, $R^{7B}$ is independently substituted or unsubstituted cycloalkyl. In embodiments, $R^{7B}$ is independently, substituted or unsubstituted heterocycloalkyl. In embodiments, $R^{7B}$ is independently substituted or unsubstituted aryl. In embodiments, $R^{7B}$ is independently substituted or unsubstituted heteroaryl. In embodiments, $R^{7B}$ is independently substituted alkyl. In embodiments, $R^{7B}$ is independently substituted heteroalkyl. In embodiments, $R^{7B}$ is independently substituted cycloalkyl. In embodiments, $R^{7B}$ is independently, substituted heterocycloalkyl. In embodiments, $R^{7B}$ is independently substituted aryl. In embodiments, $R^{7B}$ is independently substituted heteroaryl. In embodiments, $R^{1B}$ is independently unsubstituted alkyl. In embodiments, $R^{7B}$ is independently unsubstituted heteroalkyl. In embodiments, $R^{7B}$ is independently unsubstituted cycloalkyl. In embodiments, $R^{7B}$ is independently, unsubstituted heterocycloalkyl. In embodiments, $R^{7B}$ is independently unsubstituted aryl. In embodiments, $R^{7B}$ is independently unsubstituted heteroaryl. In embodiments, $R^{7B}$ is independently substituted or unsubstituted $C_1$-$C_8$ alkyl. In embodiments, $R^{7B}$ is independently substituted or unsubstituted 2 to 8 membered heteroalkyl. In embodiments, $R^{7B}$ is independently substituted or unsubstituted $C_3$-$C_8$ cycloalkyl. In embodiments, $R^{7B}$ is independently, substituted or unsubstituted 3 to 8 membered heterocycloalkyl. In embodiments, $R^{7B}$ is independently substituted or unsubstituted $C_6$-$C_{10}$ aryl. In embodiments, $R^{7B}$ is independently substituted or unsubstituted 5 to 10 membered heteroaryl. In embodiments, $R^{7B}$ is independently substituted $C_1$-$C_8$ alkyl. In embodiments, $R^{7B}$ is independently substituted 2 to 8 membered heteroalkyl. In embodiments, $R^{7B}$ is independently substituted $C_3$-$C_8$ cycloalkyl. In embodiments, $R^{7B}$ is independently, substituted 3 to 8 membered heterocycloalkyl. In embodiments, $R^{7B}$ is independently substituted $C_6$-$C_{10}$ aryl. In embodiments, $R^{7B}$ is independently substituted 5 to 10 membered heteroaryl. In embodiments, $R^{7B}$ is independently unsubstituted $C_1$-$C_8$ alkyl. In embodiments, $R^{7B}$ is independently unsubstituted 2 to 8 membered heteroalkyl. In embodiments, $R^{7B}$ is independently unsubstituted $C_3$-$C_8$ cycloalkyl. In embodiments, $R^{7B}$ is independently, unsubstituted 3 to 8 membered heterocycloalkyl. In embodiments, $R^{7B}$ is independently unsubstituted $C_6$-$C_{10}$ aryl. In embodiments, $R^{7B}$ is independently unsubstituted 5 to 10 membered heteroaryl. In embodiments, $R^{7B}$ is independently substituted or unsubstituted $C_1$-$C_4$ alkyl. In embodiments, $R^{7B}$ is independently substituted or unsubstituted 2 to 4 membered heteroalkyl. In embodiments, $R^{7B}$ is independently substituted or unsubstituted $C_3$-$C_6$ cycloalkyl. In embodiments, $R^{7B}$ is independently, substituted or unsubstituted 3 to 6 membered heterocycloalkyl. In embodiments, $R^{7B}$ is independently substituted or unsubstituted phenyl. In embodiments, $R^{7B}$ is independently substituted or unsubstituted 5 to 6 membered heteroaryl. In embodiments, $R^{7B}$ is independently substituted $C_1$-$C_4$ alkyl. In embodiments, $R^{7B}$ is independently substituted 2 to 4 membered heteroalkyl. In embodiments, $R^{7B}$ is independently substituted $C_3$-$C_6$ cycloalkyl. In embodiments, $R^{7B}$ is independently, substituted 3 to 6 membered heterocycloalkyl. In embodiments, $R^{7B}$ is independently substituted phenyl. In embodiments, $R^{7B}$ is independently substituted 5 to 6 membered heteroaryl. In embodiments, $R^{7B}$ is independently unsubstituted $C_1$-$C_4$ alkyl. In embodiments, $R^{7B}$ is independently unsubstituted 2 to 4 membered heteroalkyl. In embodiments, $R^{7B}$ is independently unsubstituted $C_3$-$C_6$ cycloalkyl. In embodiments, $R^{7B}$ is independently unsubstituted 3 to 6 membered heterocycloalkyl. In embodiments, $R^{7B}$ is independently unsubstituted phenyl. In embodiments, $R^{7B}$ is independently unsubstituted 5 to 6 membered heteroaryl. In embodiments, $R^{7B}$ is independently unsubstituted methyl. In embodiments, $R^{7B}$ is independently unsubstituted ethyl. In embodiments, $R^{7B}$ is independently unsubstituted propyl. In embodiments, $R^{7B}$ is independently unsubstituted isopropyl. In embodiments, $R^{7B}$ is independently unsubstituted tert-butyl.

In embodiments, $R^{7A}$ and $R^{7B}$ substituents bonded to the same nitrogen atom may be joined to form a substituted or unsubstituted heterocycloalkyl. In embodiments, $R^{7A}$ and $R^{7B}$ substituents bonded to the same nitrogen atom may be joined to form a substituted or unsubstituted heteroaryl. In embodiments, $R^{7A}$ and $R^{7B}$ substituents bonded to the same nitrogen atom may be joined to form a substituted heterocycloalkyl. In embodiments, $R^{7A}$ and $R^{7B}$ substituents bonded to the same nitrogen atom may be joined to form a substituted heteroaryl. In embodiments, $R^{7A}$ and $R^{7B}$ substituents bonded to the same nitrogen atom may be joined to form an unsubstituted heterocycloalkyl. In embodiments, $R^{7A}$ and $R^{7B}$ substituents bonded to the same nitrogen atom may be joined to form an unsubstituted heteroaryl. In embodiments, $R^{7A}$ and $R^{7B}$ substituents bonded to the same nitrogen atom may be joined to form a substituted or unsubstituted 3 to 8 membered heterocycloalkyl. In embodiments, $R^{7A}$ and $R^{1B}$ substituents bonded to the same nitrogen atom may be joined to form a substituted or unsubstituted 5 to 10 membered heteroaryl. In embodiments, $R^{7A}$ and $R^{7B}$ substituents bonded to the same nitrogen atom may be joined to form a substituted 3 to 8 membered heterocycloalkyl. In embodiments, $R^{7A}$ and $R^{7B}$ substituents bonded to the same nitrogen atom may be joined to form a substituted 5 to 10 membered heteroaryl. In embodiments, $R^{7A}$ and $R_{7B}$ substituents bonded to the same nitrogen atom may be joined to form an unsubstituted 3 to 8 membered heterocycloalkyl. In embodiments, $R^{7A}$ and $R^{7B}$ substituents bonded to the same nitrogen atom may be joined to form an unsubstituted 5 to 10 membered heteroaryl. In embodiments, $R^{7A}$ and $R^{7B}$ substituents bonded to the same nitrogen atom may be joined to form a substituted or unsubstituted 3 to 6 membered heterocycloalkyl. In embodiments, $R^{7A}$ and $R^{7B}$ substituents bonded to the same nitrogen atom may be joined to form a substituted or unsubstituted 5 to 6 membered heteroaryl. In embodiments, $R^{7A}$ and $R^{7B}$ substituents bonded to the same nitrogen atom may be joined to form a substituted 3 to 6 membered heterocycloalkyl. In embodiments, $R^{7A}$ and $R^{7B}$ substituents bonded to the same nitrogen atom may be joined to form a substituted 5 to 6 membered heteroaryl. In embodiments, $R^{7A}$ and $R^{7B}$ substituents bonded to the same nitrogen atom may be joined to form an unsubstituted 3 to 6 membered heterocycloalkyl. In embodiments, $R^{7A}$ and $R^{7B}$ substituents bonded to the same nitrogen atom may be joined to form an unsubstituted 5 to 6 membered heteroaryl.

In embodiments, $R^{7C}$ is independently hydrogen. In embodiments, $R^{7C}$ is independently —$CX^{7C}_3$. In embodiments, $R^{7C}$ is independently —$CHX^{7C}_2$. In embodiments, $R^{7C}$ is independently —$CH_2X^{7C}$. In embodiments, $R^{7C}$ is independently —CN. In embodiments, $R^{7C}$ is independently —COOH. In embodiments, $R^{7C}$ is independently —$CONH_2$. In embodiments, $R^{7C}$ is independently substituted or unsubstituted alkyl. In embodiments, $R^{7C}$ is independently substituted or unsubstituted heteroalkyl. In embodiments, $R^{7C}$ is independently substituted or unsubstituted cycloalkyl. In embodiments, $R^{7C}$ is independently, substituted or unsubstituted heterocycloalkyl. In embodiments, $R^{7C}$ is independently substituted or unsubstituted aryl. In embodiments, $R^{7C}$ is independently substituted or unsubstituted heteroaryl. In embodiments, $R^{7C}$ is independently substituted alkyl. In embodiments, $R^{7C}$ is independently substituted heteroalkyl. In embodiments, $R^{7C}$ is independently substituted cycloalkyl. In embodiments, $R^{7C}$ is independently, substituted heterocycloalkyl. In embodiments, $R^{7C}$ is independently substituted aryl. In embodiments, $R^{7C}$ is independently substituted heteroaryl. In embodiments, $R^{7C}$ is independently unsubstituted alkyl. In embodiments, $R^{7C}$ is independently unsubstituted heteroalkyl. In embodiments, $R^{7C}$ is independently unsubstituted cycloalkyl. In embodiments, $R^{7C}$ is independently, unsubstituted heterocycloalkyl. In embodiments, $R^{7C}$ is independently unsubstituted aryl. In embodiments, $R^{7C}$ is independently unsubstituted heteroaryl. In embodiments, $R^{7C}$ is independently substituted or unsubstituted $C_1$-$C_8$ alkyl. In embodiments, $R^{7C}$ is independently substituted or unsubstituted 2 to 8 membered heteroalkyl. In embodiments, $R^{7C}$ is independently substituted or unsubstituted $C_3$-$C_8$ cycloalkyl. In embodiments, $R^{7C}$ is independently, substituted or unsubstituted 3 to 8 membered heterocycloalkyl. In embodiments, $R^{7C}$ is independently substituted or unsubstituted $C_6$-$C_{10}$ aryl. In embodiments, $R^{7C}$ is independently substituted or unsubstituted 5 to 10 membered heteroaryl. In embodiments, $R^{7C}$ is independently substituted $C_1$-$C_8$ alkyl. In embodiments, $R^{7C}$ is independently substituted 2 to 8 membered heteroalkyl. In embodiments, $R^{7C}$ is independently substituted $C_3$-$C_8$ cycloalkyl. In embodiments, $R^{7C}$ is independently, substituted 3 to 8 membered heterocycloalkyl. In embodiments, $R^{7C}$ is independently substituted $C_6$-$C_{10}$ aryl. In embodiments, $R^{7C}$ is independently substituted 5 to 10 membered heteroaryl. In embodiments, $R^{7C}$ is independently unsubstituted $C_1$-$C_8$ alkyl. In embodiments, $R^{7C}$ is independently unsubstituted 2 to 8 membered heteroalkyl. In embodiments, $R^{7C}$ is independently unsubstituted $C_3$-$C_8$ cycloalkyl. In embodiments, $R^{7C}$ is independently, unsubstituted 3 to 8 membered heterocycloalkyl. In embodiments, $R^{7C}$ is independently unsubstituted $C_6$-$C_{10}$ aryl. In embodiments, $R^{7C}$ is independently unsubstituted 5 to 10 membered heteroaryl. In embodiments, $R^{7C}$ is independently substituted or unsubstituted $C_1$-$C_4$ alkyl. In embodiments, $R^{7C}$ is independently substituted or unsubstituted 2 to 4 membered heteroalkyl. In embodiments, $R^{7C}$ is independently substituted or unsubstituted $C_3$-$C_6$ cycloalkyl. In embodiments, $R^{7C}$ is independently, substituted or unsubstituted 3 to 6 membered heterocycloalkyl. In embodiments, $R^{7C}$ is independently substituted or unsubstituted phenyl. In embodiments, $R^{7C}$ is independently substituted or unsubstituted 5 to 6 membered heteroaryl. In embodiments, $R^{7C}$ is independently substituted $C_1$-$C_4$ alkyl. In embodiments, $R^{7C}$ is independently substituted 2 to 4 membered heteroalkyl. In embodiments, $R^{7C}$ is independently substituted $C_3$-$C_6$ cycloalkyl. In embodiments, $R_{7C}$ is independently, substituted 3 to 6 membered heterocycloalkyl. In embodiments, $R^{7C}$ is independently substituted phenyl. In embodiments, $R^{7C}$ is independently substituted 5 to 6 membered heteroaryl. In embodiments, $R^{7C}$ is independently unsubstituted $C_1$-$C_4$ alkyl. In embodiments, $R^{7C}$ is independently unsubstituted 2 to 4 membered heteroalkyl. In embodiments, $R^{7C}$ is independently unsubstituted $C_3$-$C_6$ cycloalkyl. In embodiments, $R^{7C}$ is independently unsubstituted 3 to 6 membered heterocycloalkyl. In embodiments, $R^{7C}$ is independently unsubstituted phenyl. In embodiments, $R^{7C}$ is independently unsubstituted 5 to 6 membered heteroaryl. In embodiments, $R^{7C}$ is independently unsubstituted methyl. In embodiments, $R^{7C}$ is independently unsubstituted ethyl. In embodiments, $R^{7C}$ is independently unsubstituted propyl. In embodiments, $R^{7C}$ is independently unsubstituted isopropyl. In embodiments, $R^{7C}$ is independently unsubstituted tert-butyl.

In embodiments, $R^{7D}$ is independently hydrogen. In embodiments, $R^{7D}$ is independently —$CX^{7D}_3$. In embodiments, $R^{7D}$ is independently —$CHX^{7D}_2$. In embodiments, $R^{7D}$ is independently —$CH_2X^{7D}$. In embodiments, $R^{7D}$ is independently —CN. In embodiments, $R^{7D}$ is independently —COOH. In embodiments, $R^{7D}$ is independently —$CONH_2$. In embodiments, $R^{7D}$ is independently substituted or unsubstituted alkyl. In embodiments, $R^{7D}$ is independently substituted or unsubstituted heteroalkyl. In embodiments, $R^{7D}$ is independently substituted or unsubstituted cycloalkyl. In embodiments, $R^{7D}$ is independently, substituted or unsubstituted heterocycloalkyl. In embodiments, $R^{7D}$ is independently substituted or unsubstituted aryl. In embodiments, $R^{7D}$ is independently substituted or unsubstituted heteroaryl. In embodiments, $R^{7D}$ is independently substituted alkyl. In embodiments, $R^{7D}$ is independently substituted heteroalkyl. In embodiments, $R^{7D}$ is independently substituted cycloalkyl. In embodiments, $R^{7D}$ is independently, substituted heterocycloalkyl. In embodiments, $R^{7D}$ is independently substituted aryl. In embodiments, $R^{7D}$ is independently substituted heteroaryl. In embodiments, $R^{7D}$ is independently unsubstituted alkyl. In embodiments, $R^{7D}$ is independently unsubstituted heteroalkyl. In embodiments, $R^{7D}$ is independently unsubstituted cycloalkyl. In embodiments, $R^{7D}$ is independently, unsubstituted heterocycloalkyl. In embodiments, $R^{7D}$ is independently unsubstituted aryl. In embodiments, $R^{7D}$ is independently unsubstituted heteroaryl. In embodiments, $R^{7D}$ is independently substituted or unsubstituted $C_1$-$C_8$ alkyl. In embodiments, $R^{7D}$ is independently substituted or unsubstituted 2 to 8 membered heteroalkyl. In embodiments, $R^{7D}$ is independently substituted or unsubstituted $C_3$-$C_8$ cycloalkyl. In embodiments, $R^{7D}$ is independently, substituted or unsubstituted 3 to 8 membered heterocycloalkyl. In embodiments, $R^{7D}$ is independently substituted or unsubstituted $C_6$-$C_{10}$ aryl. In embodiments, $R^{7D}$ is independently substituted or unsubstituted 5 to 10 membered heteroaryl. In embodiments, $R^{7D}$ is independently substituted $C_1$-$C_8$ alkyl. In embodiments, $R^{7D}$ is independently substituted 2 to 8 membered heteroalkyl. In embodiments, $R^{7D}$ is independently substituted $C_3$-$C_8$ cycloalkyl. In embodiments, $R^{7D}$ is independently, substituted 3 to 8 membered heterocycloalkyl. In embodiments, $R^{7D}$ is independently substituted $C_6$-$C_{10}$ aryl. In embodiments, $R^{7D}$ is independently substituted 5 to 10 membered heteroaryl. In embodiments, $R^{7D}$ is independently substituted $C_1$-$C_8$ alkyl. In embodiments, $R^{7D}$ is independently unsubstituted 2 to 8 membered heteroalkyl. In embodiments, $R^{7D}$ is independently unsubstituted $C_3$-$C_8$ cycloalkyl. In embodiments, $R^{7D}$ is independently, unsubstituted 3 to 8 membered heterocycloalkyl. In embodiments, $R^{7D}$ is independently unsubstituted $C_6$-$C_{10}$ aryl. In embodiments, $R^{7D}$ is independently unsubstituted 5 to 10 membered heteroaryl. In embodiments, $R^{7D}$ is independently substituted or unsubstituted $C_1$-$C_4$ alkyl. In embodiments, $R^{7D}$ is independently substituted or unsubstituted 2 to 4 membered heteroalkyl. In embodiments, $R^{7D}$ is independently substituted or unsubstituted $C_3$-$C_6$ cycloalkyl. In embodiments, $R^{7D}$ is independently, substituted or unsubstituted 3 to 6 membered heterocycloalkyl. In embodiments, $R^{7D}$ is independently substituted or unsubstituted phenyl. In embodiments, $R^{7D}$ is independently substituted or unsubstituted 5 to 6 membered heteroaryl. In embodiments, $R^{7D}$ is independently substituted $C_1$-$C_4$ alkyl. In embodiments, $R^{7D}$ is independently substituted 2 to 4 membered heteroalkyl. In embodiments, $R^{7D}$ is independently substituted $C_3$-$C_6$ cycloalkyl. In embodiments, $R^{7D}$ is independently, substituted 3 to 6 membered heterocycloalkyl. In embodiments, $R^{7D}$ is independently substituted phenyl. In embodiments, $R^{7D}$ is independently substituted 5 to 6 membered heteroaryl. In embodiments, $R^{7D}$ is independently unsubstituted $C_1$-$C_4$ alkyl. In embodiments, $R^{7D}$ is independently unsubstituted 2 to 4 membered heteroalkyl. In embodiments, $R^{7D}$ is independently unsubstituted $C_3$-$C_6$ cycloalkyl. In embodiments, $R^{7D}$ is independently unsubstituted 3 to 6 membered heterocycloalkyl. In embodiments, $R^{7D}$ is independently unsubstituted phenyl. In embodiments, $R^{7D}$ is independently unsubstituted 5 to 6 membered heteroaryl. In embodiments, $R^{7D}$ is independently unsubstituted methyl. In embodiments, $R^{7D}$ is independently unsubstituted ethyl. In embodiments, $R^{7D}$ is independently unsubstituted propyl. In embodiments, $R^{7D}$ is independently unsubstituted isopropyl. In embodiments, $R^{7D}$ is independently unsubstituted tert-butyl.

In embodiments, $R^7$ is independently hydrogen, halogen, —$CX^7_3$, —$CHX^7_2$, —$CH_2X^7$, —$OCX^7_3$, —$OCH_2X^7$, —$OCHX^7_2$, —CN, —$SO_{n7}R^{7D}$, —$SO_{v7}NR^{7A}R^{7B}$, —$NHC(O)NR^{7A}R^{7B}$, —$N(O)_m$, —$NR^{7A}R^{7B}$, —$C(O)R^{7C}$, —$C(O)OR^{7C}$, —$C(O)NR^{7A}R^{7B}$, —$OR^{7D}$, —$NR^{7A}SO_2R^{7D}$, —$NR^{7A}C(O)R^{7C}$, —$NR^{7A}C(O)OR^{7C}$, —$NR^{7A}OR^{7C}$, $R^{38}$-substituted or unsubstituted alkyl, $R^{38}$-substituted or unsubstituted heteroalkyl, $R^{38}$-substituted or unsubstituted cycloalkyl, $R^{38}$-substituted or unsubstituted heterocycloalkyl, $R^{38}$-substituted or unsubstituted aryl, or $R^{38}$-substituted or unsubstituted heteroaryl. In embodiments, $R^7$ is independently halogen, —$CX^7_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^7_3$, —$OCHX^7_2$, $R^{38}$-substituted or unsubstituted alkyl, $R^{38}$-substituted or unsubstituted heteroalkyl, $R^{38}$-substituted or unsubstituted cycloalkyl, $R^{38}$-substituted or unsubstituted heterocycloalkyl, $R^{38}$-substituted or unsubstituted aryl, or $R^{38}$-substituted or unsubstituted heteroaryl. In embodiments, $R^7$ is independently halogen, —$CX^7_3$, —CN, —OH, —$NH_2$, —COOH, —$CONH_2$, —$NO_2$, —SH, —$S_3H$, —$SO_4H$, —$S_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{73}$, —$OCHX^{72}$, $R^{38}$-substituted or unsubstituted $C_1$-$C_8$ alkyl, $R^{38}$-substituted or unsubstituted 2 to 8 membered heteroalkyl, $R^{38}$-substituted or unsubstituted $C_3$-$C_8$ cycloalkyl, $R^{38}$-substituted or unsubstituted 3 to 6 membered heterocycloalkyl, $R^{38}$-substituted or unsubstituted phenyl, or $R^{38}$-substituted or unsubstituted 5 to 6 membered heteroaryl. $X^7$ is —F, —Cl, —Br, or —I. In embodiments, $R^7$ is independently hydrogen. In embodiments, $R^7$ is independently methyl. In embodiments, $R^7$ is independently ethyl.

$R^{38}$ is independently oxo, halogen, —$CX^{38}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{38}_3$, —$OCHX^{38}_2$, $R^{39}$-substituted or unsubstituted alkyl, $R^{39}$-substituted or unsubstituted heteroalkyl, $R^{39}$-substituted or unsubstituted cycloalkyl, $R^{39}$-substituted or unsubstituted heterocycloalkyl, $R^{39}$-substituted or unsubstituted aryl, or $R^{39}$-substituted or unsubstituted heteroaryl. In embodiments, $R^{38}$ is independently oxo, halogen, —$CX^{38}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{38}_3$, —$OCHX^{38}_2$, $R^{39}$-substituted or unsubstituted $C_1$-$C_8$ alkyl, $R^{39}$-substituted or unsubstituted 2 to 8 membered heteroalkyl, $R^{39}$-substituted or unsubstituted $C_3$-$C_8$ cycloalkyl, $R^{39}$-substituted or unsubstituted 3 to 6 membered heterocycloalkyl, $R^{39}$-substituted or unsubstituted phenyl, or $R^{39}$-substituted or unsubstituted 5 to 6 membered heteroaryl. $X^{38}$ is —F, —Cl, —Br, or —I.

$R^{39}$ is independently oxo, halogen, —$CX^{39}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{39}_3$, —$OCHX^{39}_2$, $R^{40}$-substituted or unsubstituted alkyl, $R^{40}$-substituted or unsubstituted heteroalkyl, $R^{40}$-substituted or unsubstituted cycloalkyl, $R^{40}$-substituted or unsubstituted heterocycloalkyl, $R^{40}$-substituted or unsubstituted aryl, or $R^{40}$-substituted or unsubstituted heteroaryl. In embodiments, $R^{39}$ is independently oxo, halogen, —$CX^{39}_3$, —CN, —OH, —$NH_2$, —COOH, —$CONH_2$, —$NO_2$, —SH, —$S_3H$, —$SO_4H$, —$S_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{39}_3$, —$OCHX^{39}_2$, $R^{40}$-substituted or unsubstituted $C_1$-$C_8$ alkyl, $R^{40}$-substituted or unsubstituted 2 to 8 membered heteroalkyl, $R^{40}$-substituted or unsubstituted $C_3$-$C_8$ cycloalkyl, $R^{40}$-substituted or unsubstituted 3 to 6 membered heterocycloalkyl, $R^{40}$-substituted or unsubstituted phenyl, or $R^{40}$-substituted or unsubstituted 5 to 6 membered heteroaryl. $X^{39}$ is —F, —Cl, —Br, or —I.

In embodiments, $R^{7A}$ is independently hydrogen, —$CX^{7A}_3$, —CN, —COOH, —$CONH_2$, —$CHX^{7A}_2$, —$CH_2X^{7A}$, $R^{38A}$-substituted or unsubstituted alkyl, $R^{38A}$-substituted or unsubstituted heteroalkyl, $R^{38A}$-substituted or unsubstituted cycloalkyl, $R^{38A}$-substituted or unsubstituted heterocycloalkyl, $R^{38A}$-substituted or unsubstituted aryl, or $R^{38A}$-substituted or unsubstituted heteroaryl. In embodiments, $R^{7A}$ is independently hydrogen, —$CX^{7A}_3$, —CN, —COOH, —$CONH_2$, —$CHX^{7A}_2$, —$CH_2X^{7A}$, $R^{38A}$-substituted or unsubstituted $C_1$-$C_8$ alkyl, $R^{38A}$-substituted or unsubstituted 2 to 8 membered heteroalkyl, $R^{38A}$-substituted or unsubstituted $C_3$-$C_8$ cycloalkyl, $R^{38A}$-substituted 3 to 6 membered heterocycloalkyl, $R^{38A}$-substituted or unsubstituted phenyl, or $R^{38A}$-substituted or unsubstituted 5 to 6 membered heteroaryl. $X^{7A}$ is —F, —Cl, —Br, or —I. In embodiments, $R^{7A}$ is independently hydrogen. In embodiments, $R^{7A}$ is independently methyl. In embodiments, $R^{7A}$ is independently ethyl.

In embodiments, $R^{7A}$ and $R^{7B}$ substituents bonded to the same nitrogen atom may optionally be joined to form a $R^{38A}$-substituted or unsubstituted heterocycloalkyl or $R^{38A}$-substituted or unsubstituted heteroaryl. In embodiments, $R^{7A}$ and $R^{7B}$ substituents bonded to the same nitrogen atom may optionally be joined to form a $R^{38A}$-substituted or unsubstituted 3 to 6 membered heterocycloalkyl or $R^{38A}$-substituted or unsubstituted 5 to 6 membered heteroaryl.

$R^{38A}$ is independently oxo, halogen, —$CX^{38A}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{38A}_3$, —$OCHX^{38A}_2$, $R^{39A}$-substituted or unsubstituted alkyl, $R^{39A}$-substituted or unsubstituted heteroalkyl, $R^{39A}$-substituted or unsubstituted cycloalkyl, $R^{39A}$-substituted or unsubstituted heterocycloalkyl, $R^{39A}$-substituted or unsubstituted aryl, or $R^{39A}$-substituted or unsubstituted heteroaryl. In embodiments, $R^{38A}$ is independently oxo, halogen, —$CX^{38A}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{38A}_3$, —$OCHX^{38A}_2$, $R^{39A}$-substituted or unsubstituted $C_1$-$C_8$ alkyl, $R^{39A}$-substituted or unsubstituted 2 to 8 membered heteroalkyl, $R^{39}$-substituted or unsubstituted $C_3$-$C_8$ cycloalkyl, $R^{39A}$-substituted or unsubstituted 3 to 6 membered heterocycloalkyl, $R^{39A}$-substituted or unsubstituted phenyl, or $R^{39A}$-substituted or unsubstituted 5 to 6 membered heteroaryl. $X^{38A}$ is —F, —Cl, —Br, or —I.

$R^{39A}$ is independently oxo, halogen, —$CX^{39A}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{39A}_3$, —$OCHX^{39A}_2$, $R^{40A}$-substituted or unsubstituted alkyl, $R^{40A}$-substituted or unsubstituted heteroalkyl, $R^{40A}$-substituted or unsubstituted cycloalkyl, $R^{40A}$-substituted or unsubstituted heterocycloalkyl, $R^{40A}$-substituted or unsubstituted aryl, or $R^{40A}$-substituted or unsubstituted heteroaryl. In embodiments, $R^{39A}$ is independently oxo, halogen, —$CX^{39A}_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{39A}_3$, —$OCHX^{39A}_2$, $R^{40A}$-substituted or unsubstituted $C_1$-$C_8$ alkyl, $R^{40A}$-substituted or unsubstituted 2 to 8 membered heteroalkyl, $R^{40A}$-substituted or unsubstituted $C_3$-$C_8$ cycloalkyl, $R^{40A}$-substituted or unsubstituted 3 to 6 membered heterocycloalkyl, $R^{40A}$-substituted or unsubstituted phenyl, or $R^{40A}$-substituted or unsubstituted 5 to 6 membered heteroaryl. $X^{39A}$ is —F, —Cl, —Br, or —I.

In embodiments, $R^{7B}$ is independently hydrogen, —$CX^{7B}_3$, —CN, —COOH, —$CONH_2$, —$CHX^{7B}_2$, —$CH_2X^{7B}$, $R^{38B}$-substituted or unsubstituted alkyl, $R^{38B}$-substituted or unsubstituted heteroalkyl, $R^{38B}$-substituted or unsubstituted cycloalkyl, $R^{38B}$-substituted or unsubstituted heterocycloalkyl, $R^{38B}$-substituted or unsubstituted aryl, or $R^{38B}$-substituted or unsubstituted heteroaryl. In embodiments, $R^{7B}$ is independently hydrogen, —$CX^{7B}_3$, —CN, —COOH, —$CONH_2$, —$CHX^{7B}_2$, —$CH_2X^{7B}$, $R^{38B}$-substituted or unsubstituted $C_1$-$C_8$ alkyl, $R^{38B}$-substituted or unsubstituted 2 to 8 membered heteroalkyl, $R^{38B}$-substituted or unsubstituted $C_3$-$C_8$ cycloalkyl, $R^{38B}$-substituted or unsubstituted 3 to 6 membered heterocycloalkyl, $R^{38B}$-substituted or unsubstituted phenyl, or $R^{38B}$-substituted or unsubstituted 5 to 6 membered heteroaryl. $X^{7B}$ is —F, —Cl, —Br, or —I. In embodiments, $R^{7B}$ is independently hydrogen. In embodiments, $R^{7B}$ is independently methyl. In embodiments, $R^{7B}$ is independently ethyl.

In embodiments, $R^{7A}$ and $R^{7B}$ substituents bonded to the same nitrogen atom may optionally be joined to form a $R^{38B}$-substituted or unsubstituted heterocycloalkyl or $R^{38B}$-substituted or unsubstituted heteroaryl. In embodiments, $R^{7A}$ and $R^{7B}$ substituents bonded to the same nitrogen atom may optionally be joined to form a $R^{38B}$-substituted or unsubstituted 3 to 6 membered heterocycloalkyl or $R^{38B}$-substituted or unsubstituted 5 to 6 membered heteroaryl.

$R^{38B}$ is independently oxo, halogen, $-CX^{38B}{}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{38B}{}_3$, $-OCHX^{38B}{}_2$, $R^{39B}$-substituted or unsubstituted alkyl, $R^{39B}$-substituted or unsubstituted heteroalkyl, $R^{39B}$-substituted or unsubstituted cycloalkyl, $R^{39B}$-substituted or unsubstituted heterocycloalkyl, $R^{39B}$-substituted or unsubstituted aryl, or $R^{39B}$-substituted or unsubstituted heteroaryl. In embodiments, $R^{38B}$ is independently oxo, halogen, $-CX^{38B}{}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{38B}{}_3$, $-OCHX^{38B}{}_2$, $R^{39B}$-substituted or unsubstituted $C_1$-$C_8$ alkyl, $R^{39B}$-substituted or unsubstituted 2 to 8 membered heteroalkyl, $R^{39B}$-substituted or unsubstituted $C_3$-$C_8$ cycloalkyl, $R^{39B}$-substituted or unsubstituted 3 to 6 membered heterocycloalkyl, $R^{39B}$-substituted or unsubstituted phenyl, or $R^{39B}$-substituted or unsubstituted 5 to 6 membered heteroaryl. $X^{38B}$ is $-F$, $-Cl$, $-Br$, or $-I$.

$R^{39B}$ is independently oxo, halogen, $-CX^{39B}{}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{39B}{}_3$, $-OCHX^{39B}{}_2$, $R^{40B}$-substituted or unsubstituted alkyl, $R^{40B}$-substituted or unsubstituted heteroalkyl, $R^{40B}$-substituted or unsubstituted cycloalkyl, $R^{40B}$-substituted or unsubstituted heterocycloalkyl, $R^{40B}$-substituted or unsubstituted aryl, or $R^{40B}$-substituted or unsubstituted heteroaryl. In embodiments, $R^{39B}$ is independently oxo, halogen, $-CX^{39B}{}_3$, $-CN$, $-OH$, $-NH_2$, $-COOH$, $-CONH_2$, $-NO_2$, $-SH$, $-SO_3H$, $-SO_4H$, $-S_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{39B}{}_3$, $-OCHX^{39B}{}_2$, $R^{40B}$-substituted or unsubstituted $C_1$-$C_8$ alkyl, $R^{40B}$-substituted or unsubstituted 2 to 8 membered heteroalkyl, $R^{40B}$-substituted or unsubstituted $C_3$-$C_8$ cycloalkyl, $R^{40B}$-substituted or unsubstituted 3 to 6 membered heterocycloalkyl, $R^{40B}$-substituted or unsubstituted phenyl, or $R^{40B}$-substituted or unsubstituted 5 to 6 membered heteroaryl. $X^{39B}$ is $-F$, $-Cl$, $-Br$, or $-I$.

In embodiments, $R^{7C}$ is independently hydrogen, $-CX^{7C}{}_3$, $-CN$, $-COOH$, $-CONH_2$, $-CHX^{7C}{}_2$, $-CH_2X^{7C}$, $R^{38C}$-substituted or unsubstituted alkyl, $R^{38C}$-substituted or unsubstituted heteroalkyl, $R^{38C}$-substituted or unsubstituted cycloalkyl, $R^{38C}$-substituted or unsubstituted heterocycloalkyl, $R^{38C}$-substituted or unsubstituted aryl, or $R^{38C}$-substituted or unsubstituted heteroaryl. In embodiments, $R^{7C}$ is independently hydrogen, $-CX^{7C}{}_3$, $-CN$, $-COOH$, $-CONH_2$, $-CHX^{7C}{}_2$, $-CH_2X^{7C}$, $R^{38C}$-substituted or unsubstituted $C_1$-$C_8$ alkyl, $R^{38C}$-substituted or unsubstituted 2 to 8 membered heteroalkyl, $R^{38C}$-substituted or unsubstituted $C_3$-$C_8$ cycloalkyl, $R^{38C}$-substituted or unsubstituted 3 to 6 membered heterocycloalkyl, $R^{38C}$-substituted or unsubstituted phenyl, or $R^{38C}$-substituted or unsubstituted 5 to 6 membered heteroaryl. $X^{7C}$ is $-F$, $-Cl$, $-Br$, or $-I$. In embodiments, $R^{7C}$ is independently hydrogen. In embodiments, $R^{7C}$ is independently methyl. In embodiments, $R^{7C}$ is independently ethyl.

$R^{38C}$ is independently oxo, halogen, $-CX^{38C}{}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{38C}{}_3$, $-OCHX^{38C}{}_2$, $R^{39C}$-substituted or unsubstituted alkyl, $R^{39C}$-substituted or unsubstituted heteroalkyl, $R^{39C}$-substituted or unsubstituted cycloalkyl, $R^{39C}$-substituted or unsubstituted heterocycloalkyl, $R^{39C}$-substituted or unsubstituted aryl, or $R^{39C}$-substituted or unsubstituted heteroaryl. In embodiments, $R^{38C}$ is independently oxo, halogen, $-CX^{38C}{}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{38C}{}_3$, $-OCHX^{38C}{}_2$, $R^{39C}$-substituted or unsubstituted $C_1$-$C_8$ alkyl, $R^{39C}$-substituted or unsubstituted 2 to 8 membered heteroalkyl, $R^{39C}$-substituted or unsubstituted $C_3$-$C_8$ cycloalkyl, $R^{39C}$-substituted or unsubstituted 3 to 6 membered heterocycloalkyl, $R^{39C}$-substituted or unsubstituted phenyl, or $R^{39C}$-substituted or unsubstituted 5 to 6 membered heteroaryl. $X^{38C}$ is $-F$, $-Cl$, $-Br$, or $-I$.

$R^{39C}$ is independently oxo, halogen, $-CX^{39C}{}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{39C}{}_3$, $-OCHX^{39C}{}_2$, $R^{40C}$-substituted or unsubstituted alkyl, $R^{40C}$-substituted or unsubstituted heteroalkyl, $R^{40C}$-substituted or unsubstituted cycloalkyl, $R^{40C}$-substituted or unsubstituted heterocycloalkyl, $R^{40C}$-substituted or unsubstituted aryl, or $R^{40C}$-substituted or unsubstituted heteroaryl. In embodiments, $R^{39C}$ is independently oxo, halogen, $-CX^{39C}{}_3$, $-CN$, $-OH$, $-NH_2$, $-COOH$, $-CONH_2$, $-NO_2$, $-SH$, $-S_3H$, $-SO_4H$, $-S_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{39C}{}_3$, $-OCHX^{39C}{}_2$, $R^{40C}$-substituted or unsubstituted $C_1$-$C_8$ alkyl, $R^{40C}$-substituted or unsubstituted 2 to 8 membered heteroalkyl, $R^{40C}$-substituted or unsubstituted $C_3$-$C_8$ cycloalkyl, $R^{40C}$-substituted or unsubstituted 3 to 6 membered heterocycloalkyl, $R^{40C}$-substituted or unsubstituted phenyl, or $R^{40C}$-substituted or unsubstituted 5 to 6 membered heteroaryl. $X^{39C}$ is $-F$, $-Cl$, $-Br$, or $-I$.

In embodiments, $R^{7D}$ is independently hydrogen, $-CX^{7D}{}_3$, $-CN$, $-COOH$, $-CONH_2$, $-CHX^{7D}{}_2$, $-CH_2X^{7D}$, $R^{38D}$-substituted or unsubstituted alkyl, $R^{38D}$-substituted or unsubstituted heteroalkyl, $R^{38D}$-substituted or unsubstituted cycloalkyl, $R^{38D}$-substituted or unsubstituted heterocycloalkyl, $R^{38D}$-substituted or unsubstituted aryl, or $R^{38D}$-substituted or unsubstituted heteroaryl. In embodiments, $R^{7D}$ is independently hydrogen, $-CX^{7D}{}_3$, $-CN$, $-COOH$, $-CONH_2$, $-CHX^{7D}{}_2$, $-CH_2X^{7D}$, $R^{38D}$-substituted or unsubstituted $C_1$-$C_8$ alkyl, $R^{38D}$-substituted or unsubstituted 2 to 8 membered heteroalkyl, $R^{38D}$-substituted or unsubstituted $C_3$-$C_8$ cycloalkyl, $R^{38D}$-substituted or unsubstituted 3 to 6 membered heterocycloalkyl, $R^{38D}$-substituted or unsubstituted phenyl, or $R^{38D}$-substituted or unsubstituted 5 to 6 membered heteroaryl. $X^{7D}$ is $-F$, $-Cl$, $-Br$, or $-I$. In embodiments, $R^{7D}$ is independently hydrogen. In embodiments, $R^{7D}$ is independently methyl. In embodiments, $R^{7D}$ is independently ethyl.

$R^{38D}$ is independently oxo, halogen, $-CX^{38D}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{38D}_3$, $-OCHX^{38D}_2$, $R^{39D}$-substituted or unsubstituted alkyl, $R^{39D}$-substituted or unsubstituted heteroalkyl, $R^{39D}$-substituted or unsubstituted cycloalkyl, $R^{39D}$-substituted or unsubstituted heterocycloalkyl, $R^{39D}$-substituted or unsubstituted aryl, or $R^{39D}$-substituted or unsubstituted heteroaryl. In embodiments, $R^{38D}$ is independently oxo, halogen, $-CX^{38D}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{38D}_3$, $-OCHX^{38D}_2$, $R^{39D}$-substituted or unsubstituted $C_1$-$C_8$ alkyl, $R^{39D}$-substituted or unsubstituted 2 to 8 membered heteroalkyl, $R^{39D}$-substituted or unsubstituted $C_3$-$C_8$ cycloalkyl, $R^{39D}$-substituted or unsubstituted 3 to 6 membered heterocycloalkyl, $R^{39D}$-substituted or unsubstituted phenyl, or $R^{39D}$-substituted or unsubstituted 5 to 6 membered heteroaryl. $X^{38D}$ is $-F$, $-Cl$, $-Br$, or $-I$.

$R^{39D}$ is independently oxo, halogen, $-CX^{39D}_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{39D}_3$, $-OCHX^{39D}_2$, $R^{40D}$-substituted or unsubstituted alkyl, $R^{40D}$-substituted or unsubstituted heteroalkyl, $R^{40D}$-substituted or unsubstituted cycloalkyl, $R^{40D}$-substituted or unsubstituted heterocycloalkyl, $R^{40D}$-substituted or unsubstituted aryl, or $R^{40D}$-substituted or unsubstituted heteroaryl. In embodiments, $R^{39D}$ is independently oxo, halogen, $-CX^{39D}_3$, $-CN$, $-OH$, $-NH_2$, $-COOH$, $-CONH_2$, $-NO_2$, $-SH$, $-SO_3H$, $-SO_4H$, $-S_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{39D}_3$, $-OCHX^{39D}_2$, $R^{40D}$-substituted or unsubstituted $C_1$-$C_8$ alkyl, $R^{40D}$-substituted or unsubstituted 2 to 8 membered heteroalkyl, $R^{40D}$-substituted or unsubstituted $C_3$-$C_8$ cycloalkyl, $R^{40D}$-substituted or unsubstituted 3 to 6 membered heterocycloalkyl, $R^{40D}$-substituted or unsubstituted phenyl, or $R^{40D}$-substituted or unsubstituted 5 to 6 membered heteroaryl. $X^{39D}$ is $-F$, $-Cl$, $-Br$, or $-I$.

$R^{40}$, $R^{40A}$, $R^{40B}$, $R^{40C}$, and $R^{40D}$ are independently hydrogen, oxo, halogen, $-CCl_3$, $-CBr_3$, $-CF_3$, $-Cl_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCl_3$, $-OCHCl_2$, $-OCHBr_2$, $-OCHI_2$, $-OCHF_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{40}$, $R^{40A}$, $R^{40B}$, $R^{40C}$, and $R^{40D}$ are independently oxo, halogen, $-CF_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCF_3$, $-OCHF_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{40}$, $R^{40A}$, $R^{40B}$, $R^{40C}$, and $R^{40D}$ are independently oxo, halogen, $-CF_3$, $-CN$, $-OH$, $-NH_2$, $-COOH$, $-CONH_2$, $-NO_2$, $-SH$, $-S_3H$, $-SO_4H$, $-S_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCF_3$, $-OCHF_2$, unsubstituted $C_1$-$C_8$ alkyl, unsubstituted 2 to 8 membered heteroalkyl, unsubstituted $C_3$-$C_8$ cycloalkyl, unsubstituted 3 to 6 membered heterocycloalkyl, unsubstituted phenyl, or unsubstituted 5 to 6 membered heteroaryl.

In embodiments, X is $-F$. In embodiments, X is $-Cl$. In embodiments, X is $-Br$. In embodiments, X is $-I$. In embodiments, $X^1$ is $-F$. In embodiments, $X^1$ is $-Cl$. In embodiments, $X^1$ is $-Br$. In embodiments, $X^1$ is $-I$. In embodiments, $X^2$ is $-F$. In embodiments, $X^2$ is $-Cl$. In embodiments, $X^2$ is $-Br$. In embodiments, $X^2$ is $-I$. In embodiments, $X^4$ is $-F$. In embodiments, $X^4$ is $-Cl$. In embodiments, $X^4$ is $-Br$. In embodiments, $X^4$ is $-I$. In embodiments, $X^5$ is $-F$. In embodiments, $X^5$ is $-Cl$. In embodiments, $X^5$ is $-Br$. In embodiments, $X^5$ is $-I$. In embodiments, $X^6$ is $-F$. In embodiments, $X^6$ is $-Cl$. In embodiments, $X^6$ is $-Br$. In embodiments, $X^6$ is $-I$. In embodiments, $X^7$ is $-F$. In embodiments, $X^7$ is $-Cl$. In embodiments, $X^7$ is $-Br$. In embodiments, $X^7$ is $-I$.

In embodiments, n1 is 0. In embodiments, n1 is 1. In embodiments, n1 is 2. In embodiments, n1 is 3. In embodiments, n1 is 4. In embodiments, n2 is 0. In embodiments, n2 is 1. In embodiments, n2 is 2. In embodiments, n2 is 3. In embodiments, n2 is 4. In embodiments, n4 is 0. In embodiments, n4 is 1. In embodiments, n4 is 2. In embodiments, n4 is 3. In embodiments, n4 is 4. In embodiments, n5 is 0. In embodiments, n5 is 1. In embodiments, n5 is 2. In embodiments, n5 is 3. In embodiments, n5 is 4. In embodiments, n6 is 0. In embodiments, n6 is 1. In embodiments, n6 is 2. In embodiments, n6 is 3. In embodiments, n6 is 4. In embodiments, n7 is 0. In embodiments, n7 is 1. In embodiments, n7 is 2. In embodiments, n7 is 3. In embodiments, n7 is 4. In embodiments, n109 is 0. In embodiments, n109 is 1. In embodiments, n109 is 2. In embodiments, n109 is 3. In embodiments, n109 is 4. In embodiments, n101 is 0. In embodiments, n101 is 1. In embodiments, n101 is 2. In embodiments, n101 is 3. In embodiments, n101 is 4.

In embodiments, m1 is 1. In embodiments, m1 is 2. In embodiments, m2 is 1. In embodiments, m2 is 2. In embodiments, m4 is 1. In embodiments, m4 is 2. In embodiments, m5 is 1. In embodiments, m5 is 2. In embodiments, m6 is 1. In embodiments, m6 is 2. In embodiments, m7 is 1. In embodiments, m7 is 2. In embodiments, m109 is 1. In embodiments, m109 is 2. In embodiments, m101 is 1. In embodiments, m101 is 2.

In embodiments, v is 1. In embodiments, v1 is 2. In embodiments, v2 is 1. In embodiments, v2 is 2. In embodiments, v4 is 1. In embodiments, v4 is 2. In embodiments, v5 is 1. In embodiments, v5 is 2. In embodiments, v6 is 1. In embodiments, v6 is 2. In embodiments, v7 is 1. In embodiments, v7 is 2. In embodiments, v109 is 1. In embodiments, v109 is 2. In embodiments, v101 is 1. In embodiments, v101 is 2.

In embodiments, E is a covalent cysteine modifier moiety. In embodiments, E is:

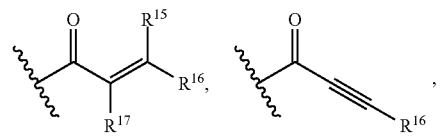

-continued

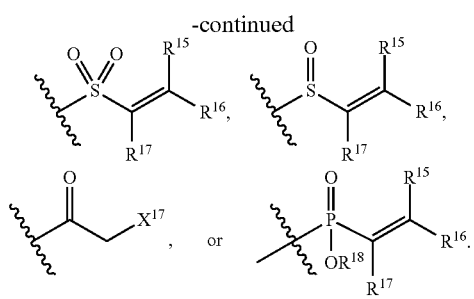

$R^{15}$ is independently hydrogen, halogen, $CX^{15}_3$, —$CHX^{15}_2$, —$CH_2X^{15}$, —CN, —$SO_{n15}R^{15D}$, —$SO_{v15}NR^{15A}R^{15B}$, —$NHNR^{15A}R^{15B}$, —$ONR^{15A}R^{15B}$, —$NHC=(O)NHNR^{15A}R^{15B}$, —$NHC(O)NR^{15A}R^{15B}$, —$N(O)_{m15}$, —$NR^{15A}R^{15B}$, —$C(O)R^{15C}$, —$C(O)$—$OR^{15C}$, —$C(O)NR^{15A}R^{15B}$, —$OR^{15D}$, —$NR^{15A}SO_2R^{15D}$, —$NR^{15A}C(O)R^{15C}$, —$NR^{15A}C(O)OR^{15C}$, —$NR^{15A}OR^{15C}$, —$OCX^{15}_3$, —$OCHX^{15}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. $R^{16}$ is independently hydrogen, halogen, $CX^{16}_3$, —$CHX^{16}_2$, —$CH_2X^{16}$, —CN, —$SO_{n16}R^{16D}$, —$SO_{v16}NR^{16A}R^{16B}$, —$NHNR^{16A}R^{16B}$, —$ONR^{16A}R^{16B}$, —$NHC=(O)NHNR^{16A}R^{16B}$, —$NHC(O)NR^{16A}R^{16B}$, —$N(O)_{m16}$, —$NR^{16A}R^{16B}$, —$C(O)R^{16C}$, —$C(O)$—$OR^{16C}$, —$C(O)NR^{16A}R^{16B}$, —$OR^{16D}$, —$NR^{16A}SO_2R^{16D}$, —$NR^{16A}C(O)R^{16C}$, —$NR^{16A}C(O)OR^{16C}$, —$NR^{16A}OR^{16C}$, —$OCX^{16}_3$, —$OCHX^{16}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. $R^{17}$ is independently hydrogen, halogen, $CX^{17}_3$, —$CHX^{17}_2$, —$CH_2X^{17}$, —CN, —$SO_{n17}R^{17D}$, —$SO_{v17}NR^{17A}R^{17B}$, —$NHNR^{17A}R^{17B}$, —$ONR^{17A}R^{17B}$, —$NHC=(O)NHNR^{17A}R^{17B}$, —$NHC(O)NR^{17A}R^{17B}$, —$N(O)_{m17}$, —$NR^{17A}R^{17B}$, —$C(O)R^{17C}$, —$C(O)$—$OR^{17C}$, —$C(O)NR^{17A}R^{17B}$, —$OR^{17D}$, —$NR^{17A}SO_2R^{17D}$, —$NR^{17A}C(O)R^{17C}$, —$NR^{17A}C(O)OR^{17C}$, —$NR^{17A}OR^{17C}$, —$OCX^{17}_3$, —$OCHX^{17}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. $R^{18}$ is independently hydrogen, —$CX^{18}_3$, —$CHX^{18}_2$, —$CH_2X^{18}$, —$C(O)R^{18C}$, —$C(O)OR^{18C}$, —$C(O)NR^{18A}R^{18B}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl.

Each $R^{15A}$, $R^{15B}$, $R^{15C}$, $R^{15D}$, $R^{16A}$, $R^{16B}$, $R^{16C}$, $R^{16D}$, $R^{17A}$, $R^{17B}$, $R^{17C}$, $R^{17D}$, $R^{18A}$, $R^{18B}$, $R^{18C}$, $R^{18D}$, is independently hydrogen, —$CX_3$, —CN, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{15A}$ and $R^{15B}$ substituents bonded to the same nitrogen atom may optionally be joined to form a substituted or unsubstituted heterocycloalkyl or substituted or unsubstituted heteroaryl; $R^{16A}$ and $R^{16B}$ substituents bonded to the same nitrogen atom may optionally be joined to form a substituted or unsubstituted heterocycloalkyl or substituted or unsubstituted heteroaryl; $R^{17A}$ and $R^{17B}$ substituents bonded to the same nitrogen atom may optionally be joined to form a substituted or unsubstituted heterocycloalkyl or substituted or unsubstituted heteroaryl; $R^{18A}$ and $R^{18B}$ substituents bonded to the same nitrogen atom may optionally be joined to form a substituted or unsubstituted heterocycloalkyl or substituted or unsubstituted heteroaryl. Each X, $X^{15}$, $X^{16}$, $X^{17}$ and $X^{18}$ is independently —F, —Cl, —Br, or —I. The symbols n15, n16, n17, v15, v16, and v17, are independently and integer from 0 to 4. The symbols m15, m16, and m17 are independently and integer between 1 and 2.

In embodiments, E is

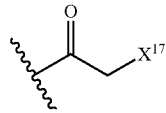

and $X^{17}$ is —Cl. In embodiments, E is:

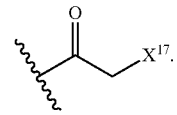

In embodiments, $X^{17}$ is —Cl.

In embodiments, E is:

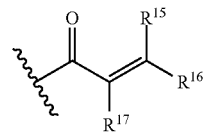

and $R^{15}$, $R^{16}$, and $R^{17}$ are independently hydrogen. In embodiments, E is:

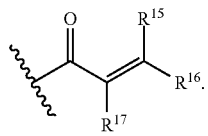

In embodiments, $R^{15}$, $R^{16}$, and $R^{17}$ are independently hydrogen.

In embodiments, E is:

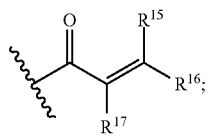

$R^{15}$ is independently hydrogen; $R^{16}$ is independently hydrogen or —$CH_2NR^{16A}R^{16B}$; $R^{17}$ is independently hydrogen; and $R^{16A}$ and $R^{16B}$ are independently hydrogen or unsubstituted alkyl. In embodiments, E is:

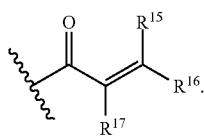

In embodiments, $R^{15}$ is independently hydrogen. In embodiments, $R^{16}$ is independently hydrogen or —$CH_2NR^{16A}R^{16B}$. In embodiments, $R^{17}$ is independently hydrogen. In embodiments, $R^{16A}$ and $R^{16B}$ are independently hydrogen or unsubstituted alkyl. In embodiments, $R^{16A}$ and $R^{16B}$ are independently unsubstituted methyl.

In embodiments, E is:

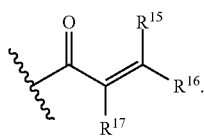

In embodiments, E is:

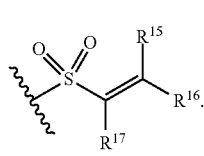

In embodiments, E is:

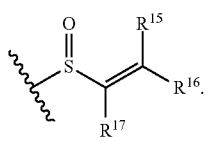

In embodiments, E is:

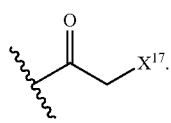

In embodiments, E is:

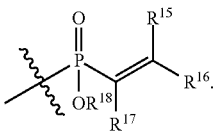

In embodiments, E is:

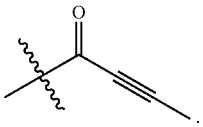 [SMILES: *C(=O)C#CC]

In embodiments, E is:

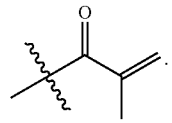 [SMILES: *C(=O)C(=C)C]

X may independently be —F. X may independently be —Cl. X may independently be —Br. X may independently be —I. $X^{15}$ may independently be —F. $X^{15}$ may independently be —Cl. $X^{15}$ may independently be —Br. $X^{15}$ may independently be —I. $X^{16}$ may independently be —F. $X^{16}$ may independently be —Cl. $X^{16}$ may independently be —Br. $X^{16}$ may independently be —I. $X^{17}$ may independently be —F. $X^{17}$ may independently be —Cl. $X^{17}$ may independently be —Br. $X^{17}$ may independently be —I. $X^{18}$ may independently be —F. $X^{18}$ may independently be —Cl. $X^{18}$ may independently be —Br. $X^{18}$ may independently be —I. n15 may independently be 0. n15 may independently be 1. n15 may independently be 2. n15 may independently be 3. n15 may independently be 4. n16 may independently be 0. n16 may independently be 1. n16 may independently be 2. n16 may independently be 3. n16 may independently be 4. n17 may independently be 0. n17 may independently be 1. n17 may independently be 2. n17 may independently be 3. n17 may independently be 4. v15 may independently be 0. v15 may independently be 1. v15 may independently be 2. v15 may independently be 3. v15 may independently be 4. v16 may independently be 0. v16 may independently be 1. v16 may independently be 2. v16 may independently be 3. v16 may independently be 4. m15 may independently be 1. m15 may independently be 2. m16 may independently be 1. m16 may independently be 2. m17 may independently be 1. m17 may independently be 2.

In embodiments, $R^1$ is hydrogen. In embodiments, $R^{15}$ is halogen. In embodiments, $R^{15}$ is $CX^{15}_3$. In embodiments, $R^1$ is —$CHX^{15}_2$. In embodiments, $R^{15}$ is —$CH_2X^{15}$. In embodiments, $R^{15}$ is —CN. In embodiments, $R^{15}$ is —$SO_{n15}R^{15D}$. In embodiments, $R^{15}$ is —$SO_{v15}NR^{15A}R^{15B}$. In embodiments, $R^{15}$ is —$NHNR^{15A}R^{15B}$. In embodiments, $R^{15}$ is —$ONR^{15A}R^{15B}$. In embodiments, $R^{15}$ is —NHC=(O)$NHNR^{15A}R^{15B}$. In embodiments, $R^{15}$ is —NHC(O)$NR^{15A}R^{15B}$. In embodiments, $R^{15}$ is —$N(O)^{m15}$. In embodiments, $R^{15}$ is —$NR^{15A}R^{15B}$. In embodiments, $R^{15}$ is —C(O)$R^{15C}$. In embodiments, $R^{15}$ is —C(O)—OR sc. In embodiments, $R^{15}$ is —C(O)$NR^{15A}R^{15B}$. In embodiments, $R^{15}$ is —$OR^{15D}$. In embodiments, $R^1$ is —$NR^{15A}SO_2R^{15D}$. In embodiments, $R^{15}$ is —$NR^{15A}C(O)R^{15C}$. In embodiments, $R^{15}$ is $-NR^{15A}C(O)OR^{15C}$. In embodiments, $R^{15}$ is $-NR^{15A}OR^{15C}$. In embodiments, $R^{15}$ is $-OCX^{15}_3$. In embodiments, $R^{15}$ is $-OCHX^{15}_2$. In embodiments, $R^{15}$ is substituted or unsubstituted alkyl. In embodiments, $R^{15}$ is substituted or unsubstituted heteroalkyl. In embodiments, $R^1$ is substituted or unsubstituted cycloalkyl. In embodiments, $R^{15}$ is substituted or unsubstituted heterocycloalkyl. In embodiments, $R^1$ is substituted or unsubstituted aryl. In embodiments, $R^{15}$ is substituted or unsubstituted heteroaryl. In embodiments, $R^{15}$ is substituted alkyl. In embodiments, $R^{15}$ is substituted heteroalkyl. In embodiments, $R^{15}$ is substituted cycloalkyl. In embodiments, $R^{15}$ is substituted heterocycloalkyl. In embodiments, $R^{15}$ is substituted aryl. In embodiments, $R^{15}$ is substituted heteroaryl. In embodiments, $R^{15}$ is unsubstituted alkyl. In embodiments, $R^{15}$ is unsubstituted heteroalkyl. In embodiments, $R^{15}$ is unsubstituted cycloalkyl. In embodiments, $R^{15}$ is unsubstituted heterocycloalkyl. In embodiments, $R^{15}$ is unsubstituted aryl. In embodiments, $R^{15}$ is unsubstituted heteroaryl. In embodiments, $R^{15}$ is unsubstituted methyl. In embodiments, $R^{15}$ is unsubstituted ethyl. In embodiments, $R^{15}$ is unsubstituted propyl. In embodiments, $R^{15}$ is unsubstituted isopropyl. In embodiments, $R^{15}$ is unsubstituted butyl. In embodiments, $R^{15}$ is unsubstituted tert-butyl.

In embodiments, $R^{15A}$ is hydrogen. In embodiments, $R^{15A}$ is $-CX_3$. In embodiments, $R^{15A}$ is $-CN$. In embodiments, $R^{15A}$ is $-COOH$. In embodiments, $R^{15A}$ is $-CONH_2$. In embodiments, $R^{15A}$ is $-CHX_2$. In embodiments, $R^{15A}$ is $-CH_2X$. In embodiments, $R^{15A}$ is unsubstituted methyl. In embodiments, $R^{15A}$ is unsubstituted ethyl. In embodiments, $R^{15A}$ is unsubstituted propyl. In embodiments, $R^{15A}$ is unsubstituted isopropyl. In embodiments, $R^{15A}$ is unsubstituted butyl. In embodiments, $R^{15A}$ is unsubstituted tert-butyl.

In embodiments, $R^{15B}$ is hydrogen. In embodiments, $R^{15B}$ is $-CX_3$. In embodiments, $R^{15B}$ is $-CN$. In embodiments, $R^{15B}$ is $-COOH$. In embodiments, $R^{15B}$ is $-CONH_2$. In embodiments, $R^{15B}$ is $-CHX_2$. In embodiments, $R^{15B}$ is $-CH_2X$. In embodiments, $R^{15B}$ is unsubstituted methyl. In embodiments, $R^{15B}$ is unsubstituted ethyl. In embodiments, $R^{15B}$ is unsubstituted propyl. In embodiments, $R^{15B}$ is unsubstituted isopropyl. In embodiments, $R^{15B}$ is unsubstituted butyl. In embodiments, $R^{15B}$ is unsubstituted tert-butyl.

In embodiments, $R^{15C}$ is hydrogen. In embodiments, $R^{15C}$ is $-CX_3$. In embodiments, $R^{15C}$ is $-CN$. In embodiments, $R^{15C}$ is $-COOH$. In embodiments, $R^{15C}$ is $-CONH_2$. In embodiments, $R^{15C}$ is $-CHX_2$. In embodiments, $R^{15C}$ is $-CH_2X$. In embodiments, $R^{15C}$ is unsubstituted methyl. In embodiments, $R^{15C}$ is unsubstituted ethyl. In embodiments, $R^{15C}$ is unsubstituted propyl. In embodiments, $R^{15C}$ is unsubstituted isopropyl. In embodiments, $R^{15C}$ is unsubstituted butyl. In embodiments, $R^{15C}$ is unsubstituted tert-butyl.

In embodiments, $R^{15D}$ is hydrogen. In embodiments, $R^{15D}$ is $-CX_3$. In embodiments, $R^{15D}$ is $-CN$. In embodiments, $R^{15D}$ is $-COOH$. In embodiments, $R^{15D}$ is $-CONH_2$. In embodiments, $R^{15D}$ is $-CHX_2$. In embodiments, $R^{15D}$ is $-CH_2X$. In embodiments, $R^{15D}$ is unsubstituted methyl. In embodiments, $R^{15D}$ is unsubstituted ethyl. In embodiments, $R^{15D}$ is unsubstituted propyl. In embodiments, $R^{15D}$ is unsubstituted isopropyl. In embodiments, $R^{15D}$ is unsubstituted butyl. In embodiments, $R^{15D}$ is unsubstituted tert-butyl.

In embodiments, $R^{15}$ is independently hydrogen, oxo, halogen, $-CX^{15}_3$, $-CHX^{15}_2$, $-OCH_2X^{15}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{15}_3$, $-OCHX^{15}_2$, $R^{72}$-substituted or unsubstituted alkyl, $R^{72}$-substituted or unsubstituted heteroalkyl, $R^{72}$-substituted or unsubstituted cycloalkyl, $R^{72}$-substituted or unsubstituted heterocycloalkyl, $R^{72}$-substituted or unsubstituted aryl, or $R^{72}$-substituted or unsubstituted heteroaryl. $X^{15}$ is halogen. In embodiments, $X^{15}$ is F.

$R^{72}$ is independently oxo, halogen, $-CX^{72}_3$, $-CHX^{72}_2$, $-OCH_2X^{72}$, $-OCHX^{72}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{72}_3$, $-OCHX^{72}_2$, $R^{73}$-substituted or unsubstituted alkyl, $R^{73}$-substituted or unsubstituted heteroalkyl, $R^{73}$-substituted or unsubstituted cycloalkyl, $R^{73}$-substituted or unsubstituted heterocycloalkyl, $R^{73}$-substituted or unsubstituted aryl, or $R^{73}$-substituted or unsubstituted heteroaryl. $X^{72}$ is halogen. In embodiments, $X^{72}$ is F.

$R^{73}$ is independently oxo, halogen, $-CX^{73}_3$, $-CHX^{73}_2$, $-OCH_2X^{73}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{73}_3$, $-OCHX^{73}_2$, $R^{74}$-substituted or unsubstituted alkyl, $R^{74}$-substituted or unsubstituted heteroalkyl, $R^{74}$-substituted or unsubstituted cycloalkyl, $R^{74}$-substituted or unsubstituted heterocycloalkyl, $R^{74}$-substituted or unsubstituted aryl, or $R^{74}$-substituted or unsubstituted heteroaryl. $X^{73}$ is halogen. In embodiments, $X^{73}$ is F.

In embodiments, $R^{15A}$ is independently hydrogen, oxo, halogen, $-CX^{15A}_3$, $-CHX^{15A}_2$, $-OCH_2X^{15A}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{15A}_3$, $-OCHX^{15A}_2$, $R^{72A}$-substituted or unsubstituted alkyl, $R^{72A}$-substituted or unsubstituted heteroalkyl, $R^{72A}$-substituted or unsubstituted cycloalkyl, $R^{72A}$-substituted or unsubstituted heterocycloalkyl, $R^{72A}$-substituted or unsubstituted aryl, or $R^{72A}$-substituted or unsubstituted heteroaryl. $X^{15A}$ is halogen. In embodiments, $X^{15A}$ is F.

$R^{72A}$ is independently oxo, halogen, $-CX^{72A}_3$, $-CHX^{72A}_2$, $-OCH_2X^{72A}$, $-OCHX^{72A}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{72A}_3$, $-OCHX^{72A}_2$, $R^{73A}$-substituted or unsubstituted alkyl, $R^{73A}$-substituted or unsubstituted heteroalkyl, $R^{73A}$-substituted or unsubstituted cycloalkyl, $R^{73A}$-substituted or unsubstituted heterocycloalkyl, $R^{73A}$-substituted or unsubstituted aryl, or $R^{73A}$-substituted or unsubstituted heteroaryl. $X^{72A}$ is halogen. In embodiments, $X^{72A}$ is F.

$R^{73A}$ is independently oxo, halogen, $-CX^{73A}_3$, $-CHX^{73A}_2$, $-OCH_2X^{73A}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{73A}_3$, $-OCHX^{73A}_2$, $R^{74A}$-substituted or unsubstituted alkyl, $R^{74A}$-substituted or unsubstituted heteroalkyl, $R^{74A}$-substituted or unsubstituted cycloalkyl, $R^{74A}$-substituted or unsubstituted heterocycloalkyl, $R^{74A}$-substituted or unsubstituted aryl, or $R^{74A}$-substituted or unsubstituted heteroaryl. $X^{73A}$ is halogen. In embodiments, $X^{73A}$ is F.

In embodiments, $R^{15B}$ is independently hydrogen, oxo, halogen, —$CX^{15B}_3$, —$CHX^{15B}_2$, —$OCH_2X^{15B}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{15B}_3$, —$OCHX^{15B}_2$, $R^{72B}$-substituted or unsubstituted alkyl, $R^{72B}$-substituted or unsubstituted heteroalkyl, $R^{72B}$-substituted or unsubstituted cycloalkyl, $R^{72B}$-substituted or unsubstituted heterocycloalkyl, $R^{72B}$-substituted or unsubstituted aryl, or $R^{72B}$-substituted or unsubstituted heteroaryl. $X^{15B}$ is halogen. In embodiments, $X^{15B}$ is F.

$R^{72B}$ is independently oxo, halogen, —$CX^{72B}_3$, —$CHX^{72B}_2$, —$OCH_2X^{72B}$, —$OCHX^{72B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{72B}_3$, —$OCHX^{72B}_2$, $R^{73B}$-substituted or unsubstituted alkyl, $R^{73B}$-substituted or unsubstituted heteroalkyl, $R^{73B}$-substituted or unsubstituted cycloalkyl, $R^{73B}$-substituted or unsubstituted heterocycloalkyl, $R^{73B}$-substituted or unsubstituted aryl, or $R^{73B}$-substituted or unsubstituted heteroaryl. $X^{72}B$ is halogen. In embodiments, $X^{72B}$ is F.

$R^{73B}$ is independently oxo, halogen, —$CX^{73B}_3$, —$CHX^{73B}_2$, —$OCH_2X^{73B}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{73B}_3$, —$OCHX^{73B}_2$, $R^{74B}$-substituted or unsubstituted alkyl, $R^{74B}$-substituted or unsubstituted heteroalkyl, $R^{74B}$-substituted or unsubstituted cycloalkyl, $R^{74B}$-substituted or unsubstituted heterocycloalkyl, $R^{74B}$-substituted or unsubstituted aryl, or $R^{74B}$-substituted or unsubstituted heteroaryl. $X^{73B}$ is halogen. In embodiments, $X^{73B}$ is F.

In embodiments, $R^{15C}$ is independently hydrogen, oxo, halogen, —$CX^{15C}_3$, —$CHX^{15C}_2$, —$OCH_2X^{15C}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{15C}_3$, —$OCHX^{15C}_2$, $R^{72C}$-substituted or unsubstituted alkyl, $R^{72C}$-substituted or unsubstituted heteroalkyl, $R^{72C}$-substituted or unsubstituted cycloalkyl, $R^{72C}$-substituted or unsubstituted heterocycloalkyl, $R^{72C}$-substituted or unsubstituted aryl, or $R^{72C}$-substituted or unsubstituted heteroaryl. $X^{15C}$ is halogen. In embodiments, $X^{15C}$ is F.

$R^{72C}$ is independently oxo, halogen, —$CX^{72C}_3$, —$CHX^{72C}_2$, —$OCH_2X^{72C}$, —$OCHX^{72C}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{72C}_3$, —$OCHX^{72C}_2$, $R^{73C}$-substituted or unsubstituted alkyl, $R^{73C}$-substituted or unsubstituted heteroalkyl, $R^{73}$-substituted or unsubstituted cycloalkyl, $R^{73C}$-substituted or unsubstituted heterocycloalkyl, $R^{73C}$-substituted or unsubstituted aryl, or $R^{73C}$-substituted or unsubstituted heteroaryl. $X^{72C}$ is halogen. In embodiments, $X^{72C}$ is F.

$R^{73C}$ is independently oxo, halogen, —$CX^{73C}_3$, —$CHX^{73C}_2$, —$OCH_2X^{73C}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{73}_3$, —$OCHX^{73}_2$, $R^{74C}$-substituted or unsubstituted alkyl, $R^{74C}$-substituted or unsubstituted heteroalkyl. $R^{74C}$-substituted or unsubstituted cycloalkyl, $R^{74C}$-substituted or unsubstituted heterocycloalkyl, $R^{74C}$-substituted or unsubstituted aryl, or $R^{74C}$-substituted or unsubstituted heteroaryl. $X^{73C}$ is halogen. In embodiments, $X^{73C}$ is F.

In embodiments, $R^{15D}$ is independently hydrogen, oxo, halogen, —$CX^{15D}_3$, —$CHX^{15D}_2$, —$OCH_2X^{15D}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{15D}_3$, —$OCHX^{15D}_2$, $R^{72D}$-substituted or unsubstituted alkyl, $R^{72D}$-substituted or unsubstituted heteroalkyl, $R^{72D}$-substituted or unsubstituted cycloalkyl, $R^{72D}$-substituted or unsubstituted heterocycloalkyl, $R^{72D}$-substituted or unsubstituted aryl, or $R^{72D}$-substituted or unsubstituted heteroaryl. $X^{15D}$ is halogen. In embodiments, $X^{15D}$ is F.

$R^{72D}$ is independently oxo, halogen, —$CX^{72D}_3$, —$CHX^{72D}_2$, —$OCH_2X^{72D}$, —$OCHX^{72D}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{72D}_3$, —$OCHX^{72D}_2$, $R^{73D}$-substituted or unsubstituted alkyl, $R^{73D}$-substituted or unsubstituted heteroalkyl, $R^{73D}$-substituted or unsubstituted cycloalkyl, $R^{73D}$-substituted or unsubstituted heterocycloalkyl, $R^{73D}$-substituted or unsubstituted aryl, or $R^{73D}$-substituted or unsubstituted heteroaryl. $X^{72D}$ is halogen. In embodiments, $X^{72D}$ is F.

$R^{73D}$ is independently oxo, halogen, —$CX^{73D}_3$, —$CHX^{73D}_2$, —$OCH_2X^{73D}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{73D}_3$, —$OCHX^{73D}_2$, $R^{74D}$-substituted or unsubstituted alkyl, $R^{74D}$-substituted or unsubstituted heteroalkyl, $R^{74D}$-substituted or unsubstituted cycloalkyl, $R^{74D}$-substituted or unsubstituted heterocycloalkyl, $R^{74D}$-substituted or unsubstituted aryl, or $R^{74D}$-substituted or unsubstituted heteroaryl. $X^{73D}$ is halogen. In embodiments, $X^{73D}$ is F.

In embodiments, $R^{16}$ is hydrogen. In embodiments, $R^{16}$ is halogen. In embodiments, $R^{16}$ is $CX^{16}_3$. In embodiments, $R^{16}$ is —$CHX^{16}_2$. In embodiments, $R^{16}$ is —$CH_2X^{16}$. In embodiments, $R^{16}$ is —CN. In embodiments, $R^{16}$ is —$SO_{n16}R^{16D}$. In embodiments, $R^{16}$ is —$SO_{v16}NR^{16A}R^{16B}$. In embodiments, $R^{16}$ is —$NHNR^{16A}R^{16B}$. In embodiments, $R^{16}$ is —$ONR^{16A}R^{16B}$. In embodiments, $R^{16}$ is —NHC=(O)$NHNR^{16A}R^{16B}$. In embodiments, $R^{16}$ is —NHC(O)$NR^{16A}R^{16B}$. In embodiments, $R^{16}$ is —$N(O)_{m16}$. In embodiments, $R^{16}$ is —$NR^{16A}R^{16B}$. In embodiments, $R^{16}$ is —C(O)$R^{16C}$. In embodiments, $R^{16}$ is —C(O)—$OR^{16C}$. In embodiments, $R^{16}$ is —C(O)$NR^{16A}R^{16B}$. In embodiments, $R^{16}$ is —$OR^{16D}$. In embodiments, $R^{16}$ is —$NR^{16A}SO_2R^{16D}$. In embodiments, $R^{16}$ is —$NR^{16A}C(O)R^{16C}$. In embodiments, $R^{16}$ is —$NR^{16A}C(O)OR^{16C}$. In embodiments, $R^{16}$ is —$NR^{16A}OR^{16C}$. In embodiments, $R^{16}$ is —$OCX^{16}_3$. In embodiments, $R^{16}$ is —$OCHX^{16}_2$. In embodiments, $R^{16}$ is substituted or unsubstituted alkyl. In embodiments, $R^{16}$ is substituted or unsubstituted heteroalkyl. In embodiments, $R^{16}$ is substituted or unsubstituted cycloalkyl. In embodiments, $R^{16}$ is substituted or unsubstituted heterocycloalkyl. In embodiments, $R^{16}$ is substituted or unsubstituted aryl. In embodiments, $R^{16}$ is substituted or unsubstituted heteroaryl. In embodiments, $R^{16}$ is substituted alkyl. In embodiments, $R^{16}$ is substituted heteroalkyl. In embodiments, $R^{16}$ is substituted cycloalkyl. In embodiments, $R^{16}$ is substituted heterocycloalkyl. In embodiments, $R^{16}$ is substituted aryl. In embodiments, $R^{16}$ is substituted heteroaryl. In embodiments, $R^{16}$ is unsubstituted alkyl. In embodiments, $R^{16}$ is unsubstituted heteroalkyl. In embodiments, $R^{16}$ is unsubstituted cycloalkyl. In embodiments, $R^{16}$ is unsubstituted heterocycloalkyl. In embodiments, $R^{16}$ is unsubstituted aryl. In embodiments, $R^{16}$ is unsubstituted heteroaryl. In embodiments, $R^{16}$ is unsubstituted methyl. In embodiments, $R^{16}$ is unsubstituted ethyl. In embodiments, $R^{16}$ is unsubstituted propyl. In embodiments, $R^{16}$ is unsubstituted isopropyl. In embodiments, $R^6$ is unsubstituted butyl. In embodiments, $R^{16}$ is unsubstituted tert-butyl. In embodiments, $R^{16}$ is

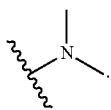 [SMILES: *N(C)C]

In embodiments $R^{16}$ is

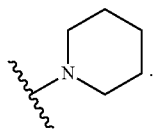 [SMILES: *N1CCCCC1]

In embodiments, $R^{16}$ is

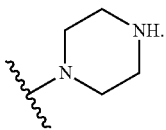 [SMILES: *N1CCNCC1]

In embodiments, $R^{16}$ is

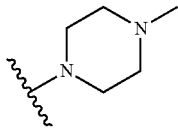

In embodiments, $R^{16A}$ is hydrogen. In embodiments, $R^{16A}$ is —$CX_3$. In embodiments, $R^{16A}$ is —CN. In embodiments, $R^{16A}$ is —COOH. In embodiments, $R^{16A}$ is —$CONH_2$. In embodiments, $R^{16A}$ is —$CHX_2$. In embodiments, $R^{16A}$ is —$CH_2X$. In embodiments, $R^{16A}$ is unsubstituted methyl. In embodiments, $R^{16A}$ is unsubstituted ethyl. In embodiments, $R^{16A}$ is unsubstituted propyl. In embodiments, $R^{16A}$ is unsubstituted isopropyl. In embodiments, $R^{16A}$ is unsubstituted butyl. In embodiments, $R^{16A}$ is unsubstituted tert-butyl.

In embodiments, $R^{16B}$ is hydrogen. In embodiments, $R^{16B}$ is —$CX_3$. In embodiments, $R^{16B}$ is —CN. In embodiments, $R^{16B}$ is —COOH. In embodiments, $R^{16B}$ is —$CONH_2$. In embodiments, $R^{16B}$ is —$CHX_2$. In embodiments, $R^{16B}$ is —$CH_2X$. In embodiments, $R^{16B}$ is unsubstituted methyl. In embodiments, $R^{16B}$ is unsubstituted ethyl. In embodiments, $R^{16B}$ is unsubstituted propyl. In embodiments, $R^{16B}$ is unsubstituted isopropyl. In embodiments, $R^{16B}$ is unsubstituted butyl. In embodiments, $R^{16B}$ is unsubstituted tert-butyl.

In embodiments, $R^{16C}$ is hydrogen. In embodiments, $R^{16C}$ is —$CX_3$. In embodiments, $R^{16C}$ is —CN. In embodiments, $R^{16C}$ is —COOH. In embodiments, $R^{16C}$ is —$CONH_2$. In embodiments, $R^{16C}$ is —$CHX_2$. In embodiments, $R^{16C}$ is —$CH_2X$. In embodiments, $R^{16C}$ is unsubstituted methyl. In embodiments, $R^{16C}$ is unsubstituted ethyl. In embodiments, $R^{16C}$ is unsubstituted propyl. In embodiments, $R^{16C}$ is unsubstituted isopropyl. In embodiments, $R^{16C}$ is unsubstituted butyl. In embodiments, $R^{16C}$ is unsubstituted tert-butyl.

In embodiments, $R^{16D}$ is hydrogen. In embodiments, $R^{16D}$ is —$CX_3$. In embodiments, $R^{16D}$ is —CN. In embodiments, $R^{16D}$ is —COOH. In embodiments, $R^{16D}$ is —$CONH_2$. In embodiments, $R^{16D}$ is —$CHX_2$. In embodiments, $R^{16D}$ is —$CH_2X$. In embodiments, $R^{16D}$ is unsubstituted methyl. In embodiments, $R^{16D}$ is unsubstituted ethyl. In embodiments, $R^{16D}$ is unsubstituted propyl. In embodiments, $R^{16D}$ is unsubstituted isopropyl. In embodiments, $R^{16D}$ is unsubstituted butyl. In embodiments, $R^{16D}$ is unsubstituted tert-butyl.

In embodiments, $R^{16}$ is independently hydrogen, oxo, halogen, —$CX^{16}_3$, —$CHX^{16}_2$, —$OCH_2X^{16}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{16}_3$, —$OCHX^{16}_2$, $R^{75}$-substituted or unsubstituted alkyl, $R^{75}$-substituted or unsubstituted heteroalkyl, $R^{75}$-substituted or unsubstituted cycloalkyl, $R^{75}$-substituted or unsubstituted heterocycloalkyl, $R^{75}$-substituted or unsubstituted aryl, or $R^{75}$-substituted or unsubstituted heteroaryl. $X^{16}$ is halogen. In embodiments, $X^{16}$ is F.

$R^{75}$ is independently oxo, halogen, —$CX^{75}_3$, —$CHX^{75}_2$, —$OCH_2X^{75}$, —$OCHX^{75}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{75}_3$, —$OCHX^{75}_2$, $R^{76}$-substituted or unsubstituted alkyl, $R^{76}$-substituted or unsubstituted heteroalkyl, $R^{76}$-substituted or unsubstituted cycloalkyl, $R^{76}$-substituted or unsubstituted heterocycloalkyl, $R^{76}$-substituted or unsubstituted aryl, or $R^{76}$-substituted or unsubstituted heteroaryl. $X^{75}$ is halogen. In embodiments, $X^{75}$ is F.

$R^{76}$ is independently oxo, halogen, —$CX^{76}_3$, —$CHX^{76}_2$, —$OCH_2X^{76}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{76}_{c3}$, —$OCHX^{76}_2$, $R^{77}$-substituted or unsubstituted alkyl, $R^{77}$-substituted or unsubstituted heteroalkyl, $R^{77}$-substituted or unsubstituted cycloalkyl, $R^{77}$-substituted or unsubstituted heterocycloalkyl, $R^{77}$-substituted or unsubstituted aryl, or $R^{77}$-substituted or unsubstituted heteroaryl. $X^{76}$ is halogen. In embodiments, $X^{76}$ is F.

In embodiments, $R^{16A}$ is independently hydrogen, oxo, halogen, —$CX^{16A}_3$, —$CHX^{16A}_2$, —$OCH_2X^{16A}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{16A}_3$, —$OCHX^{16A}_2$, $R^{75A}$-substituted or unsubstituted alkyl, $R^{75A}$-substituted or unsubstituted heteroalkyl, $R^{75A}$-substituted or unsubstituted cycloalkyl, $R^{75A}$-substituted or unsubstituted heterocycloalkyl, $R^{75A}$-substituted or unsubstituted aryl, or $R^{75A}$-substituted or unsubstituted heteroaryl. $X^{16A}$ is halogen. In embodiments, $X^{16A}$ is F.

$R^{75A}$ is independently oxo, halogen, $-CX^{75A}_3$, $-CHX^{75A}_2$, $-OCH_2X^{75A}$, $-OCHX^{75A}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{75A}_3$, $-OCHX^{75A}_2$, $R^{76A}$-substituted or unsubstituted alkyl, $R^{76A}$-substituted or unsubstituted heteroalkyl, $R^{76A}$-substituted or unsubstituted cycloalkyl, $R^{76A}$-substituted or unsubstituted heterocycloalkyl, $R^{76A}$-substituted or unsubstituted aryl, or $R^{76A}$-substituted or unsubstituted heteroaryl. $X^{75A}$ is halogen. In embodiments, $X^{75A}$ is F.

$R^{76A}$ is independently oxo, halogen, $-CX^{76A}_3$, $-CHX^{76A}_2$, $-OCH_2X^{76A}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{76A}_3$, $-OCHX^{76A}_2$, $R^{77A}$-substituted or unsubstituted alkyl, $R^{77A}$-substituted or unsubstituted heteroalkyl, $R^{77A}$-substituted or unsubstituted cycloalkyl, $R^{77A}$-substituted or unsubstituted heterocycloalkyl, $R^{77A}$-substituted or unsubstituted aryl, or $R^{77A}$-substituted or unsubstituted heteroaryl. $X^{76A}$ is halogen. In embodiments, $X^{76A}$ is F.

In embodiments, $R^{16B}$ is independently hydrogen, oxo, halogen, $-CX^{16B}_3$, $-CHX^{16B}_2$, $-OCH_2X^{16B}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{16B}_3$, $-OCHX^{16B}_2$, $R^{75B}$-substituted or unsubstituted alkyl, $R^{75B}$-substituted or unsubstituted heteroalkyl, $R^{75B}$-substituted or unsubstituted cycloalkyl, $R^{75B}$-substituted or unsubstituted heterocycloalkyl, $R^{75B}$-substituted or unsubstituted aryl, or $R^{75B}$-substituted or unsubstituted heteroaryl. $X^{16B}$ is halogen. In embodiments, $X^{16B}$ is F.

$R^{75B}$ is independently oxo, halogen, $-CX^{75B}_3$, $-CHX^{75B}_2$, $-OCH_2X^{75B}$, $-OCHX^{75B}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{75B}_3$, $-OCHX^{75B}_2$, $R^{76B}$-substituted or unsubstituted alkyl, $R^{76B}$-substituted or unsubstituted heteroalkyl, $R^{76B}$-substituted or unsubstituted cycloalkyl, $R^{76B}$-substituted or unsubstituted heterocycloalkyl, $R^{76B}$-substituted or unsubstituted aryl, or $R^{76B}$-substituted or unsubstituted heteroaryl. $X^{75B}$ is halogen. In embodiments, $X^{75B}$ is F.

$R^{76B}$ is independently oxo, halogen, $-CX^{76B}_3$, $-CHX^{76B}_2$, $-OCH_2X^{76B}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{76B}_3$, $-OCHX^{76B}_2$, $R^{77B}$-substituted or unsubstituted alkyl, $R^{77B}$-substituted or unsubstituted heteroalkyl, $R^{77B}$-substituted or unsubstituted cycloalkyl, $R^{77B}$-substituted or unsubstituted heterocycloalkyl, $R^{77B}$-substituted or unsubstituted aryl, or $R^{77B}$-substituted or unsubstituted heteroaryl. $X^{76B}$ is halogen. In embodiments, $X^{76B}$ is F.

In embodiments, $R^{16C}$ is independently hydrogen, oxo, halogen, $-CX^{16C}_3$, $CHX^{16C}_2$, $-OCH_2X^{16C}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{16C}_3$, $-OCHX^{16C}_2$, $R^{75C}$-substituted or unsubstituted alkyl, $R^{75C}$-substituted or unsubstituted heteroalkyl, $R^{75C}$-substituted or unsubstituted cycloalkyl, $R^{75C}$-substituted or unsubstituted heterocycloalkyl, $R^{75C}$-substituted or unsubstituted aryl, or $R^{75C}$-substituted or unsubstituted heteroaryl. $X^{16C}$ is halogen. In embodiments, $X^{16C}$ is F.

$R^{75C}$ is independently oxo, halogen, $-CX^{75C}_3$, $-CHX^{75C}_2$, $-OCH_2X^{75C}$, $-OCHX^{75C}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{75C}_3$, $-OCHX^{75C}_2$ $R^{76C}$-substituted or unsubstituted alkyl, $R^{76C}$-substituted or unsubstituted heteroalkyl, $R^{76C}$-substituted or unsubstituted cycloalkyl, $R^{76C}$-substituted or unsubstituted heterocycloalkyl, $R^{76C}$-substituted or unsubstituted aryl, or $R^{76C}$-substituted or unsubstituted heteroaryl. $X^{75C}$ is halogen. In embodiments, $X^{75C}$ is F.

$R^{76C}$ is independently oxo, halogen, $-CX^{76C}_3$, $-CHX^{76C}_2$, $-OCH_2X^{76C}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{76C}_3$, $-OCHX^{76C}_2$, $R^{77C}$-substituted or unsubstituted alkyl, $R^{77C}$-substituted or unsubstituted heteroalkyl, $R^{77C}$-substituted or unsubstituted cycloalkyl, $R^{77C}$-substituted or unsubstituted heterocycloalkyl, $R^{77C}$-substituted or unsubstituted aryl, or $R^{77C}$-substituted or unsubstituted heteroaryl. $X^{76C}$ is halogen. In embodiments, $X^{76C}$ is F.

In embodiments, $R^{16D}$ is independently hydrogen, oxo, halogen, $-CX^{16D}_3$, $-CHX^{16D}_2$, $-OCH_2X^{16D}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{16D}_3$, $-OCHX^{16D}_2$, $R^{75D}$-substituted or unsubstituted alkyl, $R^{75D}$-substituted or unsubstituted heteroalkyl, $R^{75D}$-substituted or unsubstituted cycloalkyl, $R^{75D}$-substituted or unsubstituted heterocycloalkyl, $R^{75D}$-substituted or unsubstituted aryl, or $R^{75D}$-substituted or unsubstituted heteroaryl. $X^{16D}$ is halogen. In embodiments, $X^{16D}$ is F.

$R^{75D}$ is independently oxo, halogen, $-CX^{75D}_3$, $-CHX^{75D}_2$, $-OCH_2X^{75D}$, $-OCHX^{75D}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{75D}_3$, $-OCHX^{75D}_2$, $R^{76D}$-substituted or unsubstituted alkyl, $R^{76D}$-substituted or unsubstituted heteroalkyl, $R^{76D}$-substituted or unsubstituted cycloalkyl, $R^{76D}$-substituted or unsubstituted heterocycloalkyl, $R^{76D}$-substituted or unsubstituted aryl, or $R^{76D}$-substituted or unsubstituted heteroaryl. $X^{76D}$ is halogen. In embodiments, $X^{75D}$ is F.

$R^{76D}$ is independently oxo, halogen, $-CX^{76D}_3$, $-CHX^{76D}_2$, $-OCH_2X^{76D}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{76D}_3$, $-OCHX^{76D}_2$, $R^{77D}$-substituted or unsubstituted alkyl, $R^{77D}$-substituted or unsubstituted heteroalkyl, $R^{77D}$-substituted or unsubstituted cycloalkyl, $R^{77D}$-substituted or unsubstituted heterocycloalkyl, $R^{77D}$-substituted or unsubstituted aryl, or $R^{77D}$-substituted or unsubstituted heteroaryl. $X^{76D}$ is halogen. In embodiments, $X^{76D}$ is F.

In embodiments, $R^{17}$ is hydrogen. In embodiments, $R^{17}$ is halogen. In embodiments, $R^{17}$ is $CX^{17}_3$. In embodiments, $R^{17}$ is —$CHX^{17}_2$. In embodiments, $R^{17}$ is —$CH_2X^{17}$. In embodiments, $R^{17}$ is —CN. In embodiments, $R^{17}$ is —$SO_{n17}R^{17D}$. In embodiments, $R^{17}$ is —$SO_{v17}NR^{17A}R^{17B}$. In embodiments, $R^{17}$ is —$NHNR^{17A}R^{17B}$. In embodiments, $R^{17}$ is —$ONR^{17A}R^{17B}$. In embodiments, $R^{17}$ is —NHC═(O)$NHNR^{17A}R^{17B}$. In embodiments, $R^{17}$ is —NHC(O)$NR^{17A}R^{17B}$. In embodiments, $R^{17}$ is —$N(O)_{m17}$. In embodiments, $R^{17}$ is —$NR^{17A}R^{17B}$. In embodiments, $R^{17}$ is —C(O)$R^{17C}$. In embodiments, $R^{17}$ is —C(O)—$OR^{17C}$. In embodiments, $R^{17}$ is —C(O)$NR^{17A}R^{17B}$. In embodiments, $R^{17}$ is —$OR^{17D}$. In embodiments, $R^{17}$ is —$NR^{17A}SO_2R^{17D}$. In embodiments, $R^{17}$ is —$NR^{17A}C(O)R^{17C}$. In embodiments, $R^{17}$ is —$NR^{17A}C(O)OR^{17C}$. In embodiments, $R^{17}$ is —$NR^{17A}OR^{17C}$. In embodiments, $R^{17}$ is —$OCX^{17}_3$. In embodiments, $R^{17}$ is —$OCHX^{17}_2$. In embodiments, $R^{17}$ is substituted or unsubstituted alkyl. In embodiments, $R^{17}$ is substituted or unsubstituted heteroalkyl. In embodiments, $R^{17}$ is substituted or unsubstituted cycloalkyl. In embodiments, $R^{17}$ is substituted or unsubstituted heterocycloalkyl. In embodiments, $R^{17}$ is substituted or unsubstituted aryl. In embodiments, $R^{17}$ is substituted or unsubstituted heteroaryl. In embodiments, $R^{17}$ is substituted alkyl. In embodiments, $R^{17}$ is substituted heteroalkyl. In embodiments, $R^{17}$ is substituted cycloalkyl. In embodiments, $R^{17}$ is substituted heterocycloalkyl. In embodiments, $R^{17}$ is substituted aryl. In embodiments, $R^{17}$ is substituted heteroaryl. In embodiments, $R^{17}$ is unsubstituted alkyl. In embodiments, $R^{17}$ is unsubstituted heteroalkyl. In embodiments, $R^{17}$ is unsubstituted cycloalkyl. In embodiments, $R^{17}$ is unsubstituted heterocycloalkyl. In embodiments, $R^{17}$ is unsubstituted aryl. In embodiments, $R^{17}$ is unsubstituted heteroaryl. In embodiments, $R^{17}$ is unsubstituted methyl. In embodiments, $R^{17}$ is unsubstituted ethyl. In embodiments, $R^{17}$ is unsubstituted propyl. In embodiments, $R^{17}$ is unsubstituted isopropyl. In embodiments, $R^{17}$ is unsubstituted butyl. In embodiments, $R^{17}$ is unsubstituted tert-butyl.

In embodiments, $R^{17A}$ is hydrogen. In embodiments, $R^{17A}$ is —$CX_3$. In embodiments, $R^{17A}$ is —CN. In embodiments, $R^{17A}$ is —COOH. In embodiments, $R^{17A}$ is —$CONH_2$. In embodiments, $R^{17A}$ is —$CHX_2$. In embodiments, $R^{17A}$ is —$CH_2X$. In embodiments, $R^{17A}$ is unsubstituted methyl. In embodiments, $R^{17A}$ is unsubstituted ethyl. In embodiments, $R^{17A}$ is unsubstituted propyl. In embodiments, $R^{17A}$ is unsubstituted isopropyl. In embodiments, $R^{17A}$ is unsubstituted butyl. In embodiments, $R^{17A}$ is unsubstituted tert-butyl.

In embodiments, $R^{17B}$ is hydrogen. In embodiments, $R^{17B}$ is —$CX_3$. In embodiments, $R^{17B}$ is —CN. In embodiments, $R^{17B}$ is —COOH. In embodiments, $R^{17B}$ is —$CONH_2$. In embodiments, $R^{17B}$ is —$CHX_2$. In embodiments, $R^{17B}$ is —$CH_2X$. In embodiments, $R^{17B}$ is unsubstituted methyl. In embodiments, $R^{17B}$ is unsubstituted ethyl. In embodiments, $R^{17B}$ is unsubstituted propyl. In embodiments, $R^{17B}$ is unsubstituted isopropyl. In embodiments, $R^{17B}$ is unsubstituted butyl. In embodiments, $R^{17B}$ is unsubstituted tert-butyl.

In embodiments, $R^{17C}$ is hydrogen. In embodiments, $R^{17C}$ is —$CX_3$. In embodiments, $R^{17C}$ is —CN. In embodiments, $R^{17C}$ is —COOH. In embodiments, $R^{17C}$ is —$CONH_2$. In embodiments, $R^{17C}$ is —$CHX_2$. In embodiments, $R^{17C}$ is —$CH_2X$. In embodiments, $R^{17C}$ is unsubstituted methyl. In embodiments, $R^{17C}$ is unsubstituted ethyl. In embodiments, $R^{17C}$ is unsubstituted propyl. In embodiments, $R^{17C}$ is unsubstituted isopropyl. In embodiments, $R^{17C}$ is unsubstituted butyl. In embodiments, $R^{17C}$ is unsubstituted tert-butyl.

In embodiments, $R^{17D}$ is hydrogen. In embodiments, $R^{17D}$ is —$CX_3$. In embodiments, $R^{17D}$ is —CN. In embodiments, $R^{17D}$ is —COOH. In embodiments, $R^{17D}$ is —$CONH_2$. In embodiments, $R^{17D}$ is —$CHX_2$. In embodiments, $R^{17D}$ is —$CH_2X$. In embodiments, $R^{17D}$ is unsubstituted methyl. In embodiments, $R^{17D}$ is unsubstituted ethyl. In embodiments, $R^{17D}$ is unsubstituted propyl. In embodiments, $R^{17D}$ is unsubstituted isopropyl. In embodiments, $R^{17D}$ is unsubstituted butyl. In embodiments, $R^{17D}$ is unsubstituted tert-butyl.

In embodiments, $R^{17}$ is independently hydrogen, oxo, halogen, —$CX^{17}_3$, —$CHX^{17}_2$, —$OCH_2X^{17}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, —$OCX^{17}_3$, —$OCHX^{17}_2$, $R^{78}$-substituted or unsubstituted alkyl, $R^{78}$-substituted or unsubstituted heteroalkyl, $R^{78}$-substituted or unsubstituted cycloalkyl, $R^{78}$-substituted or unsubstituted heterocycloalkyl, $R^{78}$-substituted or unsubstituted aryl, or $R^{78}$-substituted or unsubstituted heteroaryl. $X^{17}$ is halogen. In embodiments, $X^{17}$ is F.

$R^{78}$ is independently oxo, halogen, —$CX^{78}_3$, —$CHX^{78}_2$, —$OCH_2X^{78}$, —$OCHX^{78}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, —$OCX^{78}_3$, —$OCHX^{78}_2$, $R^{79}$-substituted or unsubstituted alkyl, $R^{79}$-substituted or unsubstituted heteroalkyl, $R^{79}$-substituted or unsubstituted cycloalkyl, $R^{79}$-substituted or unsubstituted heterocycloalkyl, $R^{79}$-substituted or unsubstituted aryl, or $R^{79}$-substituted or unsubstituted heteroaryl. $X^{78}$ is halogen. In embodiments, $X^{78}$ is F.

$R^{79}$ is independently oxo, halogen, —$CX^{79}_3$, —$CHX^{79}_2$, —$OCH_2X^{79}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, —$OCX^{79}_3$, —$OCHX^{79}_2$, $R^{80}$-substituted or unsubstituted alkyl, $R^{80}$-substituted or unsubstituted heteroalkyl, $R^{80}$-substituted or unsubstituted cycloalkyl, $R^{80}$-substituted or unsubstituted heterocycloalkyl, $R^{80}$-substituted or unsubstituted aryl, or $R^{80}$-substituted or unsubstituted heteroaryl. $X^{79}$ is halogen. In embodiments, $X^{79}$ is F.

In embodiments, $R^{17A}$ is independently hydrogen, oxo, halogen, —$CX^{17A}_3$, —$CHX^{17A}_2$, —$OCH_2X^{17A}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, —$OCX^{17A}_3$, —$OCHX^{17A}_2$, $R^{78A}$-substituted or unsubstituted alkyl, $R^{78A}$-substituted or unsubstituted heteroalkyl, $R^{78A}$-substituted or unsubstituted cycloalkyl, $R^{78A}$-substituted or unsubstituted heterocycloalkyl, $R^{78A}$-substituted or unsubstituted aryl, or $R^{78A}$-substituted or unsubstituted heteroaryl. $X^{17A}$ is halogen. In embodiments, $X^{17A}$ is F.

$R^{78A}$ is independently oxo, halogen, —$CX^{78A}_3$, —$CHX^{78A}_2$, —$OCH_2X^{78A}$, —$OCHX^{78A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, —OCX$^{78A}_3$, —OCHX$^{78A}_2$, R$^{79A}$-substituted or unsubstituted alkyl, R$^{79A}$-substituted or unsubstituted heteroalkyl, R$^{79A}$-substituted or unsubstituted cycloalkyl, R$^{79A}$-substituted or unsubstituted heterocycloalkyl, R$^{79A}$-substituted or unsubstituted aryl, or R$^{79A}$-substituted or unsubstituted heteroaryl. X$^{78A}$ is halogen. In embodiments, X$^{78A}$ is F.

R$^{79A}$ is independently oxo, halogen, —CX$^{79A}_3$, —CHX$^{79A}_2$, —OCH$_2$X$^{79A}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{79A}_3$, —OCHX$^{79A}_2$, R$^{80A}$-substituted or unsubstituted alkyl, R$^{80A}$-substituted or unsubstituted heteroalkyl, R$^{80A}$-substituted or unsubstituted cycloalkyl, R$^{80A}$-substituted or unsubstituted heterocycloalkyl, R$^{80A}$-substituted or unsubstituted aryl, or R$^{80A}$-substituted or unsubstituted heteroaryl. X$^{79A}$ is halogen. In embodiments, X$^{79A}$ is F.

In embodiments, R$^{17B}$ is independently hydrogen, oxo, halogen, —CX$^{17B}_3$, —CHX$^{17B}_2$, —OCH$_2$X$^{17B}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{7B3}$, —OCHX$^{17B}_2$, R$^{78B}$-substituted or unsubstituted alkyl, R$^{78B}$-substituted or unsubstituted heteroalkyl, R$^{78B}$-substituted or unsubstituted cycloalkyl, R$^{78B}$-substituted or unsubstituted heterocycloalkyl, R$^{78B}$-substituted or unsubstituted aryl, or R$^{17B}$-substituted or unsubstituted heteroaryl. X$^{78B}$ is halogen. In embodiments, X$^{17B}$ is F.

R$^{78B}$ is independently oxo, halogen, —CX$^{78B}_3$, —CHX$^{78B}_2$, —OCH$_2$X$^{78B}$, —OCHX$^{78B}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{78B}_3$, —OCHX$^{78B}_2$, R$^{79B}$-substituted or unsubstituted alkyl, R$^{798}$-substituted or unsubstituted heteroalkyl, R$^{79B}$-substituted or unsubstituted cycloalkyl, R$^{79B}$-substituted or unsubstituted heterocycloalkyl, R$^{79B}$-substituted or unsubstituted aryl, or R$^{79B}$-substituted or unsubstituted heteroaryl. X$^{78B}$ is halogen. In embodiments, X$^{78B}$ is F.

R$^{79B}$ is independently oxo, halogen, —CX$^{79B}_3$, —CHX$^{79B}_2$, —OCH$_2$X$^{79B}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{79B}_3$, —OCHX$^{79B}_2$, R$^{80B}$-substituted or unsubstituted alkyl, R$^{80B}$-substituted or unsubstituted heteroalkyl, R$^{80B}$-substituted or unsubstituted cycloalkyl, R$^{80B}$-substituted or unsubstituted heterocycloalkyl, R$^{80B}$-substituted or unsubstituted aryl, or R$^{80B}$-substituted or unsubstituted heteroaryl. X$^{79B}$ is halogen. In embodiments, X$^{79B}$ is F.

In embodiments, R$^{17C}$ is independently hydrogen, oxo, halogen, —CX$^{17C}_3$, —CHX$^{17C}_2$, —OCH$_2$X$^{17C}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{17C}_3$, —OCHX$^{17C}_2$, R$^{78C}$-substituted or unsubstituted alkyl, R$^{78C}$-substituted or unsubstituted heteroalkyl, R$^{78C}$-substituted or unsubstituted cycloalkyl, R$^{78C}$-substituted or unsubstituted heterocycloalkyl, R$^{78C}$-substituted or unsubstituted aryl, or R$^{78C}$-substituted or unsubstituted heteroaryl. X$^{17C}$ is halogen. In embodiments, X$^{17C}$ is F.

R$^{78C}$ is independently oxo, halogen, —CX$^{78C}_3$, —CHX$^{78C}_2$, —OCH$_2$X$^{78C}$, —OCHX$^{78C}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{78C}_3$, —OCHX$^{78C}_2$, R$^{79C}$-substituted or unsubstituted alkyl, R$^{79C}$-substituted or unsubstituted heteroalkyl, R$^{79C}$-substituted or unsubstituted cycloalkyl, R$^{79C}$-substituted or unsubstituted heterocycloalkyl, R$^{79C}$-substituted or unsubstituted aryl, or R$^{79C}$-substituted or unsubstituted heteroaryl. X$^{78C}$ is halogen. In embodiments, X$^{78C}$ is F.

R$^{79C}$ is independently oxo, halogen, —CX$^{79C}_3$, —CHX$^{79C}_2$, —OCH$_2$X$^{79C}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{793}$, —OCHX$^{79C}_2$, R$^{80C}$-substituted or unsubstituted alkyl, R$^{80C}$-substituted or unsubstituted heteroalkyl, R$^{80C}$-substituted or unsubstituted cycloalkyl, R$^{80C}$-substituted or unsubstituted heterocycloalkyl, R$^{80C}$-substituted or unsubstituted aryl, or R$^{80C}$-substituted or unsubstituted heteroaryl. X$^{79C}$ is halogen. In embodiments, X$^{79C}$ is F.

In embodiments, R$^{17D}$ is independently hydrogen, oxo, halogen, —CX$^{17D}_3$, —CHX$^{17D}_2$, —OCH$_2$X$^{17D}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{17D}_3$, —OCHX$^{17D}_2$, R$^{78D}$-substituted or unsubstituted alkyl, R$^{78D}$-substituted or unsubstituted heteroalkyl, R$^{78D}$-substituted or unsubstituted cycloalkyl, R$^{78D}$-substituted or unsubstituted heterocycloalkyl, R$^{78D}$-substituted or unsubstituted aryl, or R$^{78D}$-substituted or unsubstituted heteroaryl. X$^{17D}$ is halogen. In embodiments, X$^{17D}$ is F.

R$^{78D}$ is independently oxo, halogen, —CX$^{78D}_3$, —CHX$^{78D}_2$, —OCH$_2$X$^{78D}$, —OCHX$^{78D}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{78D}_3$, —OCHX$^{78D}_2$, R$^{79D}$-substituted or unsubstituted alkyl, R$^{79D}$-substituted or unsubstituted heteroalkyl, R$^{79D}$-substituted or unsubstituted cycloalkyl, R$^{79D}$-substituted or unsubstituted heterocycloalkyl, R$^{79D}$-substituted or unsubstituted aryl, or R$^{79D}$-substituted or unsubstituted heteroaryl. X$^{78D}$ is halogen. In embodiments, X$^{78D}$ is F.

R$^{79D}$ is independently oxo, halogen, —CX$^{79D}_3$, —CHX$^{79D}_2$, —OCH$_2$X$^{79D}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{79D}_3$, —OCHX$^{79D}_2$, R$^{80D}$-substituted or unsubstituted alkyl, R$^{80D}$-substituted or unsubstituted heteroalkyl, R$^{80D}$-substituted or unsubstituted cycloalkyl, R$^{80D}$-substituted or unsubstituted heterocycloalkyl, R$^{80D}$-substituted or unsubstituted aryl, or R$^{80D}$-substituted or unsubstituted heteroaryl. X$^{79D}$ is halogen. In embodiments, X$^{79D}$ is F.

In embodiments, R$^{18}$ is hydrogen. In embodiments, R$^{18}$ is halogen. In embodiments, R$^{18}$ is CX$^{18}_3$. In embodiments, R$^{18}$ is —CHX$^{18}_2$. In embodiments, R$^{18}$ is —CH$_2$X$^{18}$. In embodiments, R$^{18}$ is —CN. In embodiments, R$^{18}$ is —SO$_{18}$R$^{18D}$. In embodiments, R$^{18}$ is —SO$_{v18}$NR$^{18A}$R$^{18B}$. In embodiments, R$^{18}$ is —NHNR$^{18A}$R$^{18B}$. In embodiments, R$^{18}$ is —ONR$^{18A}$R$^{18B}$. In embodiments, R$^{18}$ is —NHC=(O)NHNR$^{18A}$R$^{18B}$. In embodiments, R$^{18}$ is —NHC(O)

$NR^{18A}R^{18B}$. In embodiments, $R^{18}$ is $-N(O)_{m18}$. In embodiments, $R^{18}$ is $-NR^{18A}R^{18B}$. In embodiments, $R^{18}$ is $-C(O)R^{18C}$. In embodiments, $R^{18}$ is $-C(O)-OR^{18C}$. In embodiments, $R^{18}$ is $-C(O)NR^{18A}R^{18B}$. In embodiments, $R^{18}$ is $-OR^{18D}$. In embodiments, $R^{18}$ is $-NR^{18A}SO_2R^{18D}$. In embodiments, $R^{18}$ is $-NR^{18A}C(O)R^{18C}$. In embodiments, $R^{18}$ is $-NR^{18A}C(O)OR^{18C}$. In embodiments, $R^{18}$ is $-NR^{18A}OR^{18C}$. In embodiments, $R^{18}$ is $-OCX^{18}_3$. In embodiments, $R^{18}$ is $-OCHX^{18}_2$. In embodiments, $R^{18}$ is substituted or unsubstituted alkyl. In embodiments, $R^{18}$ is substituted or unsubstituted heteroalkyl. In embodiments, $R^{18}$ is substituted or unsubstituted cycloalkyl. In embodiments, $R^{18}$ is substituted or unsubstituted heterocycloalkyl. In embodiments, $R^{18}$ is substituted or unsubstituted aryl. In embodiments, $R^{18}$ is substituted or unsubstituted heteroaryl. In embodiments, $R^{18}$ is substituted alkyl. In embodiments, $R^{18}$ is substituted heteroalkyl. In embodiments, $R^{18}$ is substituted cycloalkyl. In embodiments, $R^{18}$ is substituted heterocycloalkyl. In embodiments, $R^{18}$ is substituted aryl. In embodiments, $R^{18}$ is substituted heteroaryl. In embodiments, $R^{18}$ is unsubstituted alkyl. In embodiments, $R^{18}$ is unsubstituted heteroalkyl. In embodiments, $R^{18}$ is unsubstituted cycloalkyl. In embodiments, $R^{18}$ is unsubstituted heterocycloalkyl. In embodiments, $R^{18}$ is unsubstituted aryl. In embodiments, $R^{18}$ is unsubstituted heteroaryl. In embodiments, $R^{18}$ is unsubstituted methyl. In embodiments, $R^{18}$ is unsubstituted ethyl. In embodiments, $R^{18}$ is unsubstituted propyl. In embodiments, $R^{18}$ is unsubstituted isopropyl. In embodiments, $R^{18}$ is unsubstituted butyl. In embodiments, $R^{18}$ is unsubstituted tert-butyl.

In embodiments, $R^{18A}$ is hydrogen. In embodiments, $R^{18A}$ is $-CX_3$. In embodiments, $R^{18A}$ is $-CN$. In embodiments, $R^{18A}$ is $-COOH$. In embodiments, $R^{18A}$ is $-CONH_2$. In embodiments, $R^{18A}$ is $-CHX_2$. In embodiments, $R^{18A}$ is $-CH_2X$. In embodiments, $R^{18A}$ is unsubstituted methyl. In embodiments, $R^{18A}$ is unsubstituted ethyl. In embodiments, $R^{18A}$ is unsubstituted propyl. In embodiments, $R^{18A}$ is unsubstituted isopropyl. In embodiments, $R^{18A}$ is unsubstituted butyl. In embodiments, $R^{18A}$ is unsubstituted tert-butyl.

In embodiments, $R^{18B}$ is hydrogen. In embodiments, $R^{18B}$ is $-CX_3$. In embodiments, $R^{18B}$ is $-CN$. In embodiments, $R^{18B}$ is $-COOH$. In embodiments, $R^{18B}$ is $-CONH_2$. In embodiments, $R^{18B}$ is $-CHX_2$. In embodiments, $R^{18B}$ is $-CH_2X$. In embodiments, $R^{18B}$ is unsubstituted methyl. In embodiments, $R^{18B}$ is unsubstituted ethyl. In embodiments, $R^{18B}$ is unsubstituted propyl. In embodiments, $R^{18B}$ is unsubstituted isopropyl. In embodiments, $R^{18B}$ is unsubstituted butyl. In embodiments, $R^{18B}$ is unsubstituted tert-butyl.

In embodiments, $R^{18C}$ is hydrogen. In embodiments, $R^{18C}$ is $-CX_3$. In embodiments, $R^{18C}$ is $-CN$. In embodiments, $R^{18C}$ is $-COOH$. In embodiments, $R^{18C}$ is $-CONH_2$. In embodiments, $R^{1SC}$ is $-CHX_2$. In embodiments, $R^{18C}$ is $-CH_2X$. In embodiments, $R^{18C}$ is unsubstituted methyl. In embodiments, $R^{18C}$ is unsubstituted ethyl. In embodiments, $R^{18C}$ is unsubstituted propyl. In embodiments, $R^{18C}$ is unsubstituted isopropyl. In embodiments, $R^{18C}$ is unsubstituted butyl. In embodiments, $R^{18C}$ is unsubstituted tert-butyl.

In embodiments, $R^{18D}$ is hydrogen. In embodiments, $R^{18D}$ is $-CX_3$. In embodiments, $R^{18D}$ is $-CN$. In embodiments, $R^{18D}$ is $-COOH$. In embodiments, $R^{18D}$ is $-CONH_2$. In embodiments, $R^{18D}$ is $-CHX_2$. In embodiments, $R^{18D}$ is $-CH_2X$. In embodiments, $R^{18D}$ is unsubstituted methyl. In embodiments, $R^{18D}$ is unsubstituted ethyl. In embodiments, $R^{18D}$ is unsubstituted propyl. In embodiments, $R^{18D}$ is unsubstituted isopropyl. In embodiments, $R^{18D}$ is unsubstituted butyl. In embodiments, $R^{18D}$ is unsubstituted tert-butyl.

In embodiments, $R^{18}$ is independently hydrogen, oxo, halogen, $-CX^{18}_3$, $-CHX^{18}_2$, $-OCH_2X^{18}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{18}_3$, $-OCHX^{18}_2$, $R^{81}$-substituted or unsubstituted alkyl, $R^{81}$-substituted or unsubstituted heteroalkyl, $R^{81}$-substituted or unsubstituted cycloalkyl, $R^{81}$-substituted or unsubstituted heterocycloalkyl, $R^{81}$-substituted or unsubstituted aryl, or $R^{81}$-substituted or unsubstituted heteroaryl. $X^{18}$ is halogen. In embodiments, $X^{18}$ is F.

$R^{81}$ is independently oxo, halogen, $-CX^{81}_3$, $-CHX^{81}_2$, $-OCH_2X^{81}$, $-OCHX^{81}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX_3$, $-OCHX^{81}_2$, $R^{82}$-substituted or unsubstituted alkyl, $R^{82}$-substituted or unsubstituted heteroalkyl, $R^{82}$-substituted or unsubstituted cycloalkyl, $R^{82}$-substituted or unsubstituted heterocycloalkyl, $R^{82}$-substituted or unsubstituted aryl, or $R^{82}$-substituted or unsubstituted heteroaryl. $X^{81}$ is halogen. In embodiments, $X^{81}$ is F.

$R^{82}$ is independently oxo, halogen, $-CX^{82}_3$, $-CHX^{82}_2$, $-OCH_2X^{82}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{82}_3$, $-OCHX^{82}_2$, $R^{83}$-substituted or unsubstituted alkyl, $R^{83}$-substituted or unsubstituted heteroalkyl, $R^{83}$-substituted or unsubstituted cycloalkyl, $R^{83}$-substituted or unsubstituted heterocycloalkyl, $R^{83}$-substituted or unsubstituted aryl, or $R^{83}$-substituted or unsubstituted heteroaryl. $X^{82}$ is halogen. In embodiments, $X^{82}$ is F.

In embodiments, $R^{18A}$ is independently hydrogen, oxo, halogen, $-CX^{18A}_3$, $-CHX^{18A}_2$, $-OCH_2X^{18A}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{18A}_3$, $-OCHX^{18A}_2$, $R^{81A}$-substituted or unsubstituted alkyl, $R^{81A}$-substituted or unsubstituted heteroalkyl, $R^{81A}$-substituted or unsubstituted cycloalkyl, $R^{81A}$-substituted or unsubstituted heterocycloalkyl, $R^{81A}$-substituted or unsubstituted aryl, or $R^{81A}$-substituted or unsubstituted heteroaryl. $X^{18A}$ is halogen. In embodiments, $X^{18A}$ is F.

$R^{81A}$ is independently oxo, halogen, $-CX^{81A}_3$, $-CHX^{81A}_2$, $-OCH_2X^{81A}$, $-OCHX^{81A}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{81A}_3$, $-OCHX^{81A}_2$, $R^{82A}$-substituted or unsubstituted alkyl, $R^{82A}$-substituted or unsubstituted heteroalkyl, $R^{82A}$-substituted or unsubstituted cycloalkyl, $R^{82A}$-substituted or unsubstituted heterocycloalkyl, $R^{82A}$-substituted or unsubstituted aryl, or $R^{82A}$-substituted or unsubstituted heteroaryl. $X^{81A}$ is halogen. In embodiments, $X^{81A}$ is F.

$R^{82A}$ is independently oxo, halogen, $-CX^{82A}_3$, $-CHX^{82A}_2$, $-OCH_2X^{82A}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, —NHC=(O)NHNH$_2$, —NHC=(O)NH$_2$, —NHSO$_2$H, —NHC=(O)H, —NHC(O)—OH, —NHOH, —OCX$^{82A}_3$, —OCHX$^{82A}_2$, R$^{83A}$-substituted or unsubstituted alkyl, R$^{53A}$-substituted or unsubstituted heteroalkyl, R$^{83A}$-substituted or unsubstituted cycloalkyl, R$^{83A}$-substituted or unsubstituted heterocycloalkyl, R$^{83A}$-substituted or unsubstituted aryl, or R$^{83A}$-substituted or unsubstituted heteroaryl. X$^{82A}$ is halogen. In embodiments, X$^{82A}$ is F.

In embodiments, R$^{18B}$ is independently hydrogen, oxo, halogen, —CX$^{18B}_3$, —CHX$^{18B}_2$, —OCH$_2$X$^{18B}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{18B}_3$, —OCHX$^{18B}_2$, R$^{18B}$-substituted or unsubstituted alkyl, R$^{81B}$-substituted or unsubstituted heteroalkyl, R$^{81B}$-substituted or unsubstituted cycloalkyl, R$^{81B}$-substituted or unsubstituted heterocycloalkyl, R$^{81B}$-substituted or unsubstituted aryl, or R$^{81B}$-substituted or unsubstituted heteroaryl. X$^{81B}$ is halogen. In embodiments, X$^{18B}$ is F.

R$^{81B}$ is independently oxo, halogen, —CX$^{81B}_3$, —CHX$^{81B}_2$, —OCH$_2$X$^{81B}$, —OCHX$^{81B}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{81B}_3$, —OCHX$^{81B}_2$, R$^{82B}$-substituted or unsubstituted alkyl, R$^{82B}$-substituted or unsubstituted heteroalkyl, R$^{82B}$-substituted or unsubstituted cycloalkyl, R$^{82B}$-substituted or unsubstituted heterocycloalkyl, R$^{82B}$-substituted or unsubstituted aryl, or R$^{82B}$-substituted or unsubstituted heteroaryl. X$^{81B}$ is halogen. In embodiments, X$^{81B}$ is F.

R$^{82B}$ is independently oxo, halogen, —CX$^{82B}_3$, —CHX$^{82B}_2$, —OCH$_2$X$^{82B}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{82B}_3$, —OCHX$^{82B}_2$, R$^{83B}$-substituted or unsubstituted alkyl, R$^{83B}$-substituted or unsubstituted heteroalkyl, R$^{83B}$-substituted or unsubstituted cycloalkyl, R$^{83B}$-substituted or unsubstituted heterocycloalkyl, R$^{83B}$-substituted or unsubstituted aryl, or R$^{83B}$-substituted or unsubstituted heteroaryl. X$^{82B}$ is halogen. In embodiments, X$^{82B}$ is F.

In embodiments, R$^{18C}$ is independently hydrogen, oxo, halogen, —CX$^{18C}_3$, —CHX$^{18C}_2$, —OCH$_2$X$^{18C}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{18C}_3$, —OCHX$^{18C}_2$, R$^{81C}$-substituted or unsubstituted alkyl, R$^{81C}$-substituted or unsubstituted heteroalkyl, R$^{81C}$-substituted or unsubstituted cycloalkyl, R$^{81C}$-substituted or unsubstituted heterocycloalkyl, R$^{81C}$-substituted or unsubstituted aryl, or R$^{81C}$-substituted or unsubstituted heteroaryl. X$^{18C}$ is halogen. In embodiments, X$^{18C}$ is F.

R$^{81C}$ is independently oxo, halogen, —CX$^{81C}_3$, —CHX$^{81C}_2$, —OCH$_2$X$^{81C}$, —OCHX$^{81C}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{81C}_3$, —OCHX$^{81C}_2$, R$^{82C}$-substituted or unsubstituted alkyl, R$^{82C}$-substituted or unsubstituted heteroalkyl, R$^{82}$-substituted or unsubstituted cycloalkyl, R$^{82C}$-substituted or unsubstituted heterocycloalkyl, R$^{82C}$-substituted or unsubstituted aryl, or R$^{82C}$-substituted or unsubstituted heteroaryl. X$^{81C}$ is halogen. In embodiments, X$^{81C}$ is F.

R$^{82C}$ is independently oxo, halogen, —CX$^{82C}_3$, —CHX$^{82C}_2$, —OCH$_2$X$^{82C}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{82C}_3$, —OCHX$^{82C}_2$, R$^{83C}$-substituted or unsubstituted alkyl, R$^{83C}$-substituted or unsubstituted heteroalkyl, R$^{83C}$-substituted or unsubstituted cycloalkyl, R$^{83C}$-substituted or unsubstituted heterocycloalkyl, R$^{83C}$-substituted or unsubstituted aryl, or R$^{83C}$-substituted or unsubstituted heteroaryl. X$^{82C}$ is halogen. In embodiments, X$^{82C}$ is F.

In embodiments, R$^{18D}$ is independently hydrogen, oxo, halogen, —CX$^{18D}_3$, —CHX$^{18D}_2$, —OCH$_2$X$^{18D}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{18D}_3$, —OCHX$^{18D}_2$, R$^{81D}$-substituted or unsubstituted alkyl, R$^{81D}$-substituted or unsubstituted heteroalkyl, R$^{81D}$-substituted or unsubstituted cycloalkyl, R$^{81D}$-substituted or unsubstituted heterocycloalkyl, R$^{81D}$-substituted or unsubstituted aryl, or R$^{81D}$-substituted or unsubstituted heteroaryl. X$^{18D}$ is halogen. In embodiments, X$^{18D}$ is F.

R$^{81D}$ is independently oxo, halogen, —CX$^{81D}_3$, —CHX$^{81D}_2$, —OCH$_2$X$^{81D}$, —OCHX$^{81D}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{81D}_3$, —OCHX$^{81D}_2$, R$^{82D}$-substituted or unsubstituted alkyl, R$^{82D}$-substituted or unsubstituted heteroalkyl, R$^{82D}$-substituted or unsubstituted cycloalkyl, R$^{82D}$-substituted or unsubstituted heterocycloalkyl, R$^{82D}$-substituted or unsubstituted aryl, or R$^{82D}$-substituted or unsubstituted heteroaryl. X$^{81D}$ is halogen. In embodiments, X$^{81D}$ is F.

R$^{82D}$ is independently oxo, halogen, —CX$^{82D}_3$, —CHX$^{82D}_2$, —OCH$_2$X$^{82D}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{82D}_3$, —OCHX$^{82D}_2$, R$^{83D}$-substituted or unsubstituted alkyl, R$^{83D}$-substituted or unsubstituted heteroalkyl, R$^{83D}$-substituted or unsubstituted cycloalkyl, R$^{83D}$-substituted or unsubstituted heterocycloalkyl, R$^{83D}$-substituted or unsubstituted aryl, or R$^{83D}$-substituted or unsubstituted heteroaryl. X$^{82D}$ is halogen. In embodiments, X$^{82D}$ is F.

R$^{74}$, R$^{77}$, R$^{80}$, R$^{83}$, R$^{74A}$, R$^{77A}$, R$^{80A}$, R$^{83A}$, R$^{74B}$, R$^{77B}$, R$^{80B}$, R$^{83B}$, R$^{74C}$, R$^{77C}$, R$^{80C}$, R$^{83C}$, R$^{74D}$, R$^{77D}$, R$^{80D}$, and R$^{83D}$ are independently hydrogen, oxo, halogen, —CCl$_3$, —CBr$_3$, —CF$_3$, —Cl$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCl$_3$, —OCHCl$_2$, —OCHBr$_2$, —OCHI$_2$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl. In embodiments, R$^{74}$, R$^{77}$, R$^{80}$, R$^{83}$, R$^{74A}$, R$^{77A}$, R$^{80A}$, R$^{83A}$, R$^{74B}$, R$^{77B}$, R$^{80B}$, R$^{83B}$, R$^{74C}$, R$^{77C}$, R$^{80C}$, R$^{83C}$, R$^{74D}$, R$^{77D}$, R$^{80D}$, and R$^{83D}$ are independently oxo, halogen, —CF$_3$, —CN, —OH, —NH$_2$, —COOH, —CONH$_2$, —NO$_2$, —SH, —S$_3$H, —SO$_4$H, —S$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl. In embodiments, R$^{74}$, R$^{77}$, R$^{80}$, R$^{83}$, R$^{74A}$, R$^{77A}$, R$^{80A}$, R$^{83A}$, R$^{74B}$, R$^{77B}$, R$^{80B}$, R$^{83B}$, R$^{74C}$, R$^{77C}$, R$^{80C}$, R$^{83C}$, R$^{74D}$, R$^{77D}$, R$^{80D}$, R$^{83D}$, and R$^{86}$ are independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCHF$_2$, unsubstituted C$_1$-C$_8$ alkyl, unsubstituted 2 to 8 membered heteroalkyl, unsubstituted C$_3$-C$_8$ cycloalkyl, unsubstituted 3 to 6 membered heterocycloalkyl, unsubstituted phenyl, or unsubstituted 5 to 6 membered heteroaryl.

In embodiments, R$^{15}$, R$^{16}$, R$^{17}$, and R$^{18}$ are hydrogen. In embodiments, R$^{15}$ is hydrogen. In embodiments, R$^{16}$ is hydrogen, —CH$_3$, —CH$_2$NR$^{16A}$R$^{16B}$, or

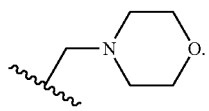 [SMILES: *CN1CCOCC1]

In embodiments, R$^{17}$ is hydrogen. In embodiments, R$^{16A}$ and R$^{16B}$ are independently hydrogen or unsubstituted alkyl. In embodiments, R$^{16A}$ and R$^{16B}$ are independently unsubstituted methyl. In embodiments, R$^{16A}$ is independently hydrogen. In embodiments, R$^{16A}$ is independently unsubstituted alkyl. In embodiments, R$^{16B}$ is independently hydrogen. In embodiments, R$^{16B}$ is independently unsubstituted alkyl. In embodiments, R$^{16A}$ is independently unsubstituted methyl. In embodiments, R$^{16B}$ is independently unsubstituted methyl. In embodiments, R$^{15}$ is hydrogen; R$^{16}$ is hydrogen, —CH$_3$, —CH$_2$NR$^{16A}$R$^{16B}$, or

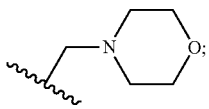 [SMILES: *CN1CCOCC1]

R$^{17}$ is hydrogen; and R$^{16A}$ and R$^{16B}$ are independently hydrogen or unsubstituted alkyl.

In embodiments, R$^{15}$ is hydrogen. In embodiments, R$^{16}$ is hydrogen. In embodiments, R$^{17}$ is hydrogen, —CH$_3$, —CH$_2$NR$^{17A}$R$^{17B}$, or

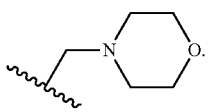 [SMILES: *CN1CCOCC1]

In embodiments, R$^{17A}$ and R$^{17B}$ are independently hydrogen or unsubstituted alkyl. In embodiments, R$^{17A}$ and R$^{17B}$ are independently unsubstituted methyl. In embodiments, R$^{15}$ is hydrogen; R$^{16}$ is hydrogen; R$^{17}$ is hydrogen, —CH$_3$, —CH$_2$NR$^{17A}$R$^{17B}$, or

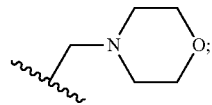 [SMILES: *CN1CCOCC1]

and R$^{17A}$ and R$^{17B}$ are independently hydrogen or unsubstituted alkyl. In embodiments, R$^{17A}$ is independently hydrogen. In embodiments, R$^{17A}$ is independently unsubstituted alkyl. In embodiments, R$^{17B}$ is independently hydrogen. In embodiments, R$^{17B}$ is independently unsubstituted alkyl. In embodiments, R$^{17A}$ is independently unsubstituted methyl. In embodiments, R$^{17B}$ is independently unsubstituted methyl.

In embodiments, R$^{15}$ is hydrogen, —CH$_3$, —CH$_2$NR$^{15A}$R$^{15B}$, or

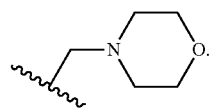 [SMILES: *CN1CCOCC1]

In embodiments, R$^{16}$ is hydrogen. In embodiments, R$^{17}$ is hydrogen. In embodiments, R$^{15A}$ and R$^{15B}$ are independently hydrogen or unsubstituted alkyl. In embodiments, R$^{15A}$ and R$^{15B}$ are independently unsubstituted methyl. In embodiments, R$^{15A}$ is independently hydrogen. In embodiments, R$^{15A}$ is independently unsubstituted alkyl. In embodiments, R$^{15B}$ is independently hydrogen. In embodiments, R$^{15B}$ is independently unsubstituted alkyl. In embodiments, R$^{15A}$ is independently unsubstituted methyl. In embodiments, R$^{15B}$ is independently unsubstituted methyl. In embodiments, R$^{15}$ is hydrogen, —CH$_3$, —CH$_2$NR$^{15A}$R$^{15B}$, or

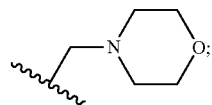 [SMILES: *CN1CCOCC1]

R$^{16}$ is hydrogen; R$^{17}$ is hydrogen; and R$^{15A}$ and R$^{15B}$ are independently hydrogen or unsubstituted alkyl.

In embodiments, E is:

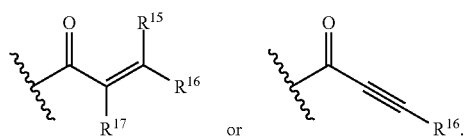

In embodiments, E is:

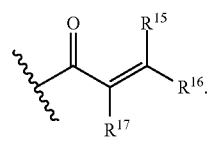

In embodiments, E is:
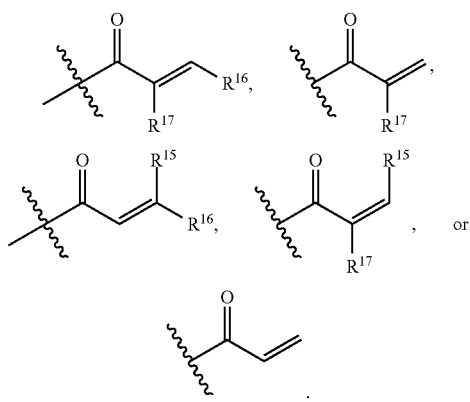
In embodiments, E is:
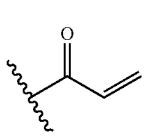
In embodiments, E is:
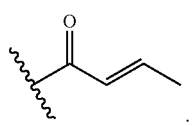 [SMILES: *C(=O)/C=C/C ; "."]
In embodiments, E is:
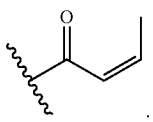
In embodiments, E is:
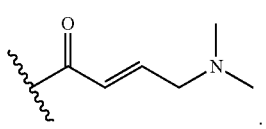 [SMILES: *C(=O)/C=C/CN(C)C ; "."]
In embodiments, E is
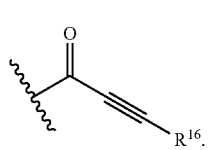
In embodiments, E is:
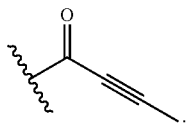 [SMILES: *C(=O)C#CC]
In embodiments, E is:
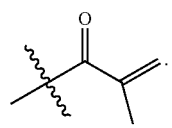 [SMILES: *C(=O)C(=C)C]
In embodiments, E is:
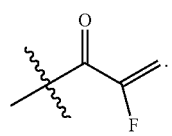 [SMILES: *C(=O)C(=C)F]
In embodiments, E is:
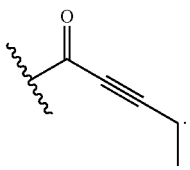 [SMILES: *C(=O)C#CCC]
In embodiments, E is:
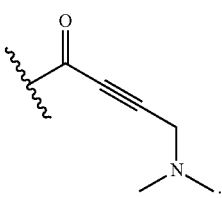 [SMILES: *C(=O)C#CCN(C)C]
In embodiments, E is:
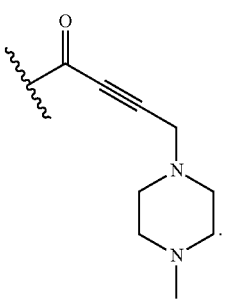 [SMILES: *C(=O)C#CCN1CCN(C)CC1]

In embodiments, E is:
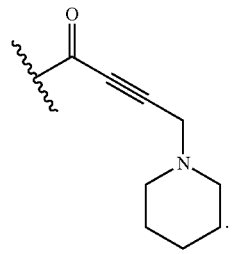 [SMILES: *C(=O)C#CCN1CCCCC1]
In embodiments, $L^1$-$L^2$-E is
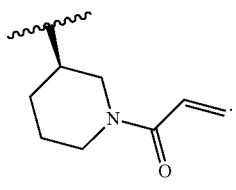 [SMILES: *[C@@H]1CCCN(C(=O)C=C)C1]
In embodiments, $L^1$-$L^2$-E is
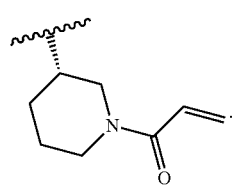 [SMILES: *[C@H]1CCCN(C(=O)C=C)C1]
In embodiments, $L^1$-$L^2$-E is
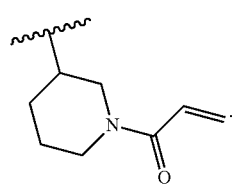 [SMILES: *C1CCCN(C(=O)C=C)C1]
In embodiments, $L^1$-$L^2$-E is $CH_2CH_2NHOCHCH_2$. In embodiments, $L^1$-$L^2$-E is
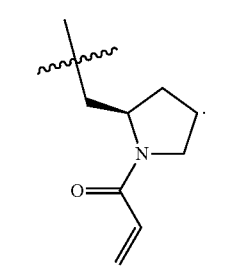 [SMILES: *C[C@H]1CCCN1C(=O)C=C]
In embodiments, $L^1$-$L^2$-E is
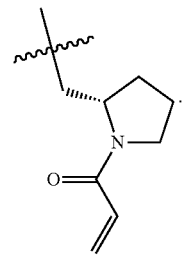 [SMILES: *C[C@@H]1CCCN1C(=O)C=C]
In embodiments, $L^1$-$L^2$-E is
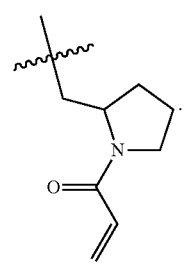 [SMILES: *CC1CCCN1C(=O)C=C]
In embodiments, $L^1$-$L^2$-E is
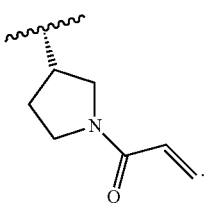
In embodiments, $L^1$-$L^2$-E is
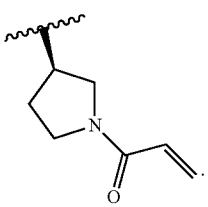 [SMILES: *[C@@H]1CCN(C(=O)C=C)C1]
In embodiments, $L^1$-$L^2$-E is
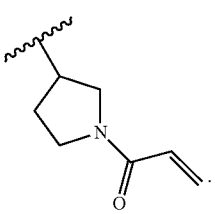 [SMILES: *C1CCN(C(=O)C=C)C1 ; "."]

In embodiments, L¹-L²-E is
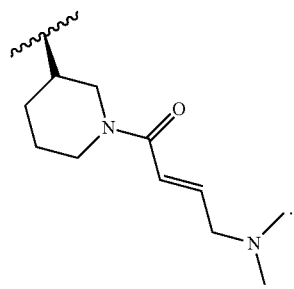
In embodiments, L¹-L²-E is
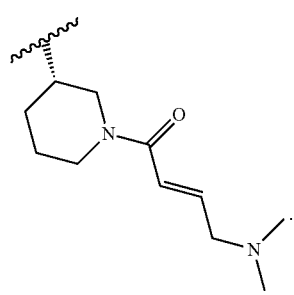 [SMILES: *[C@H]1CCCN(C(=O)/C=C/CN(C)C)C1 ; "."]
In embodiments, L¹-L²-E is
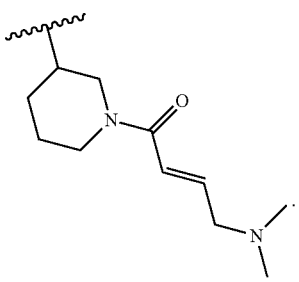 [SMILES: *C1CCCN(C(=O)/C=C/CN(C)C)C1 ; "."]
In embodiments, L¹-L²-E is
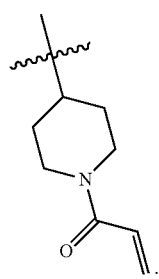 [SMILES: *C1CCN(C(=O)C=C)CC1 ; "."]
In embodiments, L¹-L²-E is
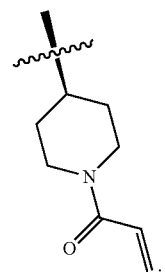
In embodiments, L¹-L²-E is
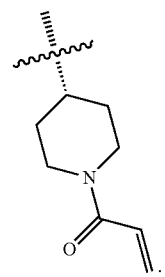
In embodiments, L¹-L²-E is —CH₂CH₂NHCOCHCHCH₂N(CH₃)₂. In embodiments, L¹-L²-E is
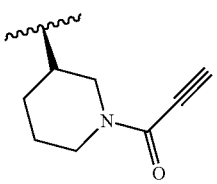
In embodiments, L¹-L²-E is
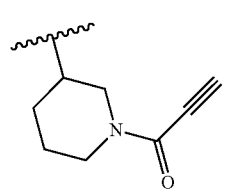
In embodiments, L¹-L²-E is In embodiments, L¹-L²-E is
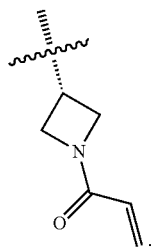
In embodiments, L¹-L²-E is
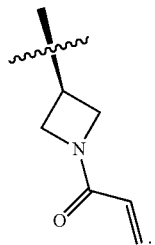
In embodiments, L¹-L²-E is
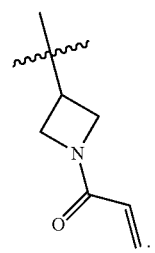 [SMILES: *C1CN(C(=O)C=C)C1 ; "."]
In embodiments, L¹-L²-E is
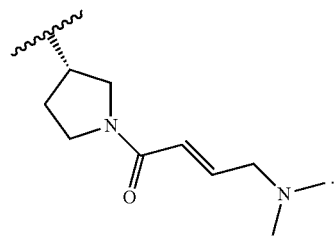 [SMILES: *[C@H]1CCN(C(=O)/C=C/CN(C)C)C1 ; "."]
In embodiments, L¹-L²-E is
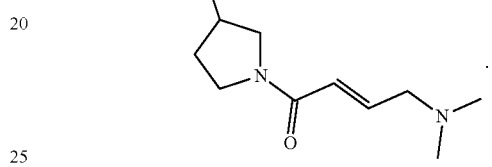
In embodiments, L¹-L²-E is
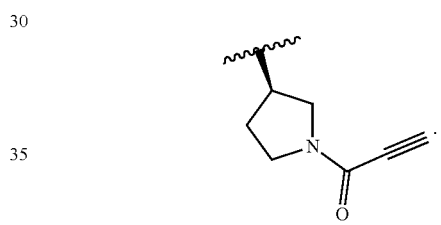
In embodiments, L¹-L²-E is
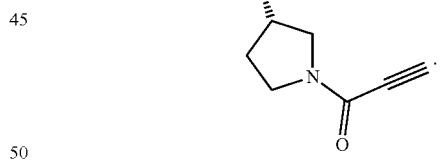
In embodiments, L¹-L²-E is
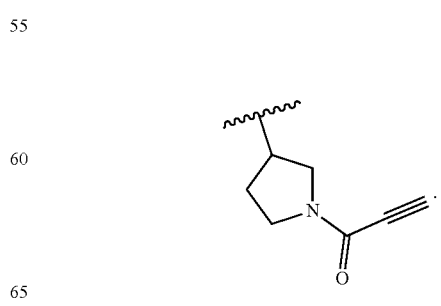

In embodiments, L¹-L²-E is
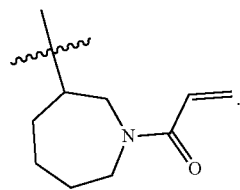 [SMILES: *C1CCCCN(C(=O)C=C)C1]
In embodiments, L¹-L²-E is
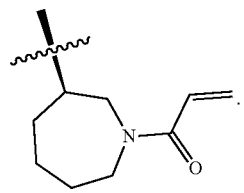
In embodiments, L¹-L²-E is
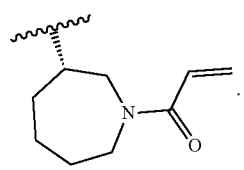 [SMILES: *[C@H]1CCCCN(C(=O)C=C)C1]
In embodiments, L¹-L²-E is
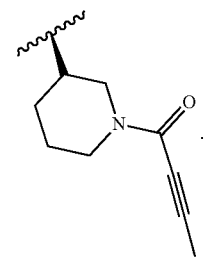
In embodiments, L¹-L²-E is
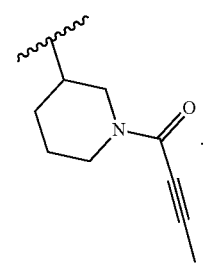 [SMILES: *C1CCCN(C(=O)C#CC)C1]
In embodiments, L¹-L²-E is
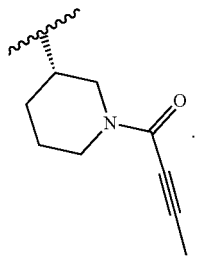 [SMILES: *[C@H]1CCCN(C(=O)C#CC)C1]
In embodiments, L¹-L²-E is
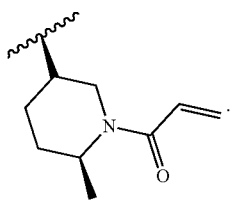
In embodiments, L¹-L²-E is
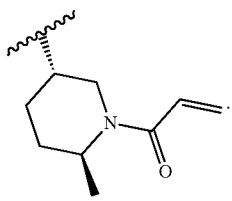 [SMILES: *[C@H]1CC[C@H](C)N(C(=O)C=C)C1]
In embodiments, L¹-L²-E is
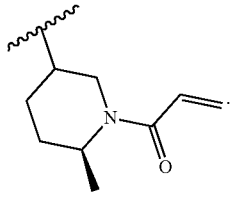 [SMILES: *C1CC[C@H](C)N(C(=O)C=C)C1]
In embodiments, L¹-L²-E is
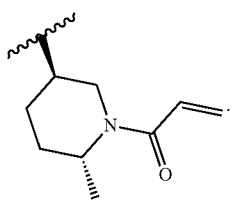 [SMILES: *[C@@H]1CC[C@@H](C)N(C(=O)C=C)C1]

In embodiments, L¹-L²-E is
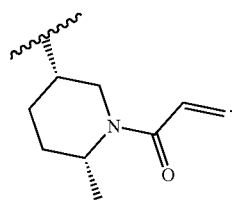 [SMILES: *[C@H]1CC[C@@H](C)N(C(=O)C=C)C1]
In embodiments, L¹-L²-E is
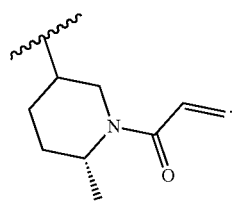
In embodiments, L¹-L²-E is
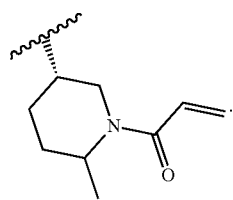 [SMILES: *[C@H]1CCC(C)N(C(=O)C=C)C1]
In embodiments, L¹-L²-E is
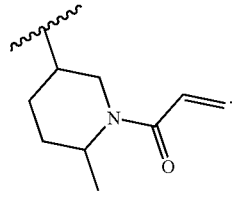 [SMILES: *C1CCC(C)N(C(=O)C=C)C1]
In embodiments, L¹-L²-E is
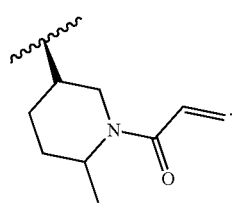
In embodiments, L¹-L²-E is
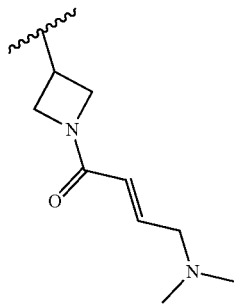
In embodiments, L¹-L²-E is
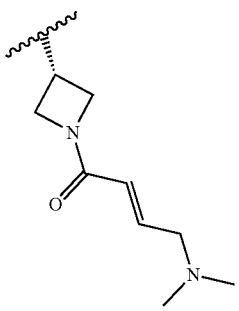
In embodiments, L¹-L²-E is
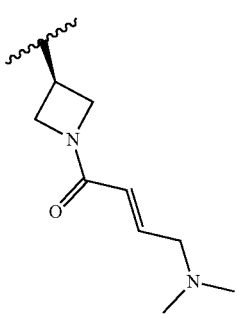
In embodiments, L¹-L²-E is
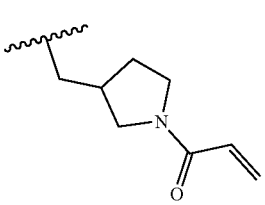

In embodiments, L¹-L²-E is
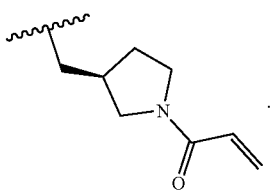 [SMILES: *C[C@H]1CCN(C(=O)C=C)C1]
In embodiments, L¹-L²-E is
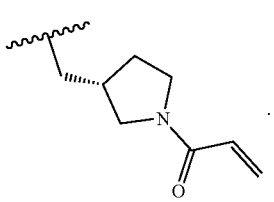 [SMILES: *C[C@@H]1CCN(C(=O)C=C)C1]
In embodiments, L¹-L²-E is
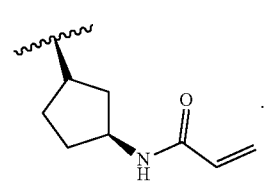
In embodiments, L¹-L²-E is
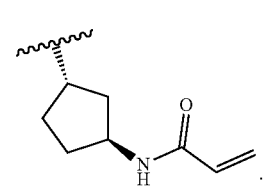 [SMILES: *[C@H]1CC[C@H](NC(=O)C=C)C1]
In embodiments, L¹-L²-E is
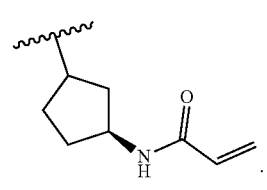 [SMILES: *C1CC[C@H](NC(=O)C=C)C1]
In embodiments, L¹-L²-E is
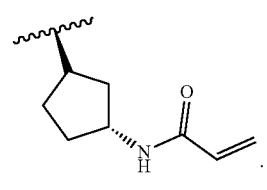
In embodiments L¹-L²-E
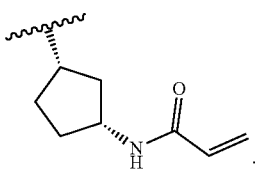 [SMILES: *[C@H]1CC[C@@H](NC(=O)C=C)C1]
In embodiments, L¹-L²-E is
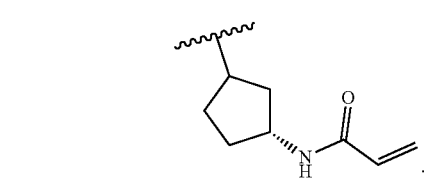 [SMILES: *C1CC[C@@H](NC(=O)C=C)C1]
In embodiments, L¹-L²-E is
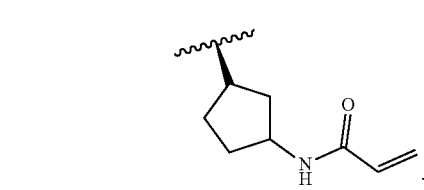
In embodiments, L¹-L²-E is
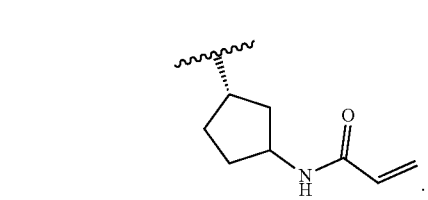 [SMILES: *[C@H]1CCC(NC(=O)C=C)C1]
In embodiments, L¹-L²-E is
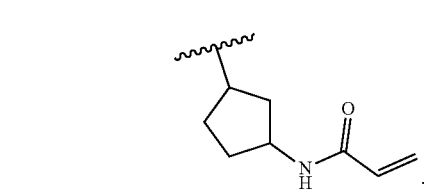 [SMILES: *C1CCC(NC(=O)C=C)C1]
In embodiments, L¹-L²-E is
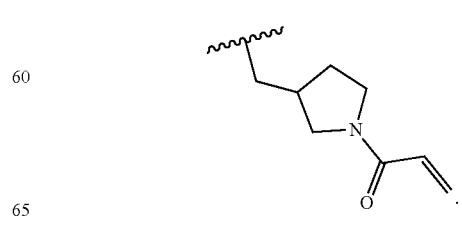

In embodiments, $L^1$-$L^2$-E is
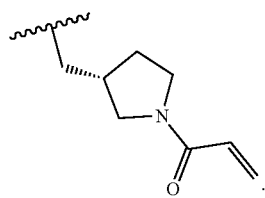 [SMILES: *C[C@@H]1CCN(C(=O)C=C)C1]
In embodiments, $L^1$-$L^2$-E is
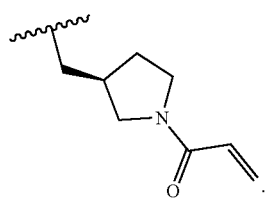 [SMILES: *C[C@H]1CCN(C(=O)C=C)C1]
In embodiments, $L^1$-$L^2$-E is
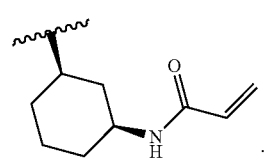 [SMILES: *[C@@H]1CCC[C@H](NC(=O)C=C)C1]
In embodiments, $L^1$-$L^2$-E
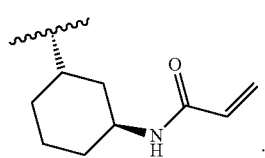
In embodiments, $L^1$-$L^2$-E
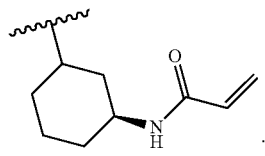 [SMILES: *C1CCC[C@H](NC(=O)C=C)C1]
In embodiments, $L^1$-$L^2$-E
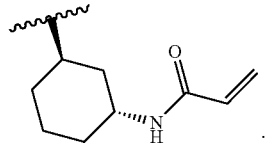 [SMILES: *[C@@H]1CCC[C@@H](NC(=O)C=C)C1]
In embodiments, $L^1$-$L^2$-E is
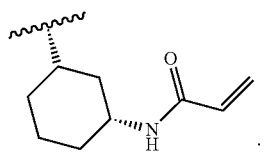
In embodiments, $L^1$-$L^2$-E is
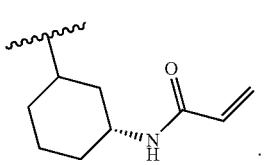 [SMILES: *C1CCC[C@@H](NC(=O)C=C)C1]
In embodiments, $L^1$-$L^2$-E is
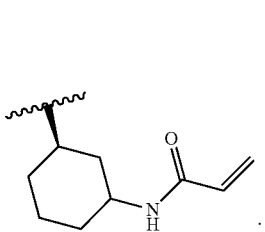 [SMILES: *[C@@H]1CCCC(NC(=O)C=C)C1]
In embodiments, $L^1$-$L^2$-E is
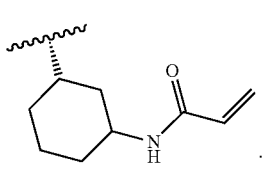
In embodiments, $L^1$-$L^2$-E is
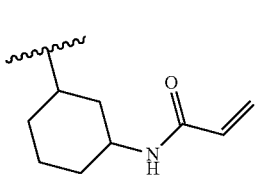
In embodiments, $L^1$-$L^2$-E is
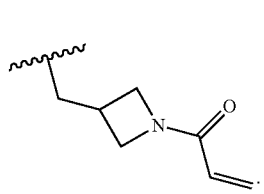 [SMILES: *CC1CN(C(=O)C=C)C1]

In embodiments, $L^1$-$L^2$-E is
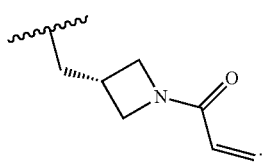
In embodiments, $L^1$-$L^2$-E is
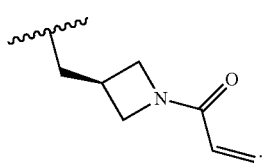
In embodiments, $L^1$-$L^2$-E is
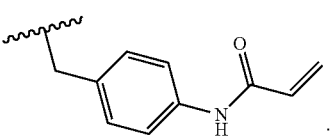 [SMILES: *Cc1ccc(NC(=O)C=C)cc1]
In embodiments, $L^1$-$L^2$-E is
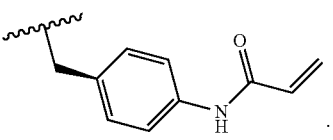
In embodiments, $L^1$-$L^2$-E is
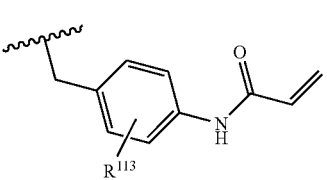
In embodiments, $L^1$-$L^2$-E is
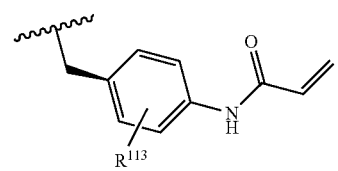
In embodiments, $L^1$-$L^2$-E is
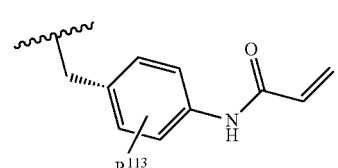
In embodiments, $L^1$-$L^2$-E is
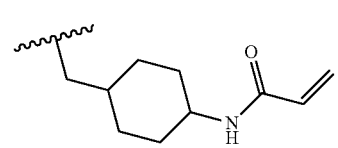
In embodiments, $L^1$-$L^2$-E is
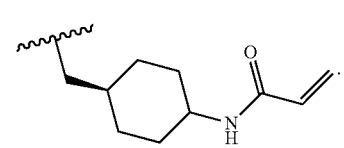
In embodiments, $L^1$-$L^2$-E is
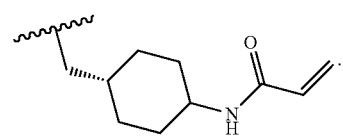
In embodiments, $L^1$-$L^2$-E is
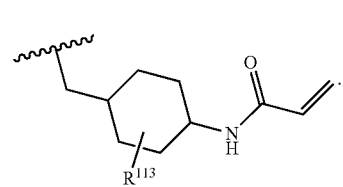

In embodiments, $L^1$-$L^2$-E is
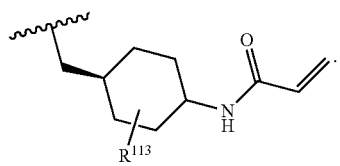
In embodiments, $L^1$-$L^2$-E is
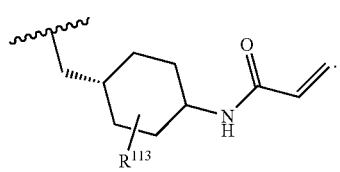
In embodiments, $L^1$-$L^2$-E is
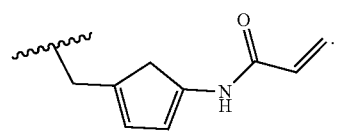 [SMILES: *CC1=CC=C(NC(=O)C=C)C1]
In embodiments, $L^1$-$L^2$-E is
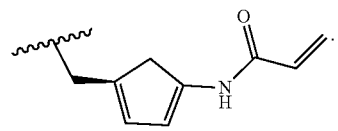
In embodiments, $L^1$-$L^2$-E is
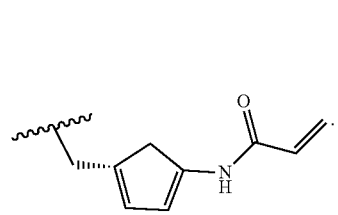
In embodiments, $L^1$-$L^2$-E is
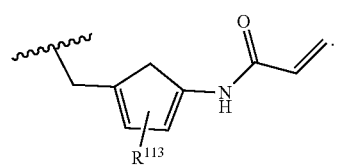
In embodiments, $L^1$-$L^2$-E is
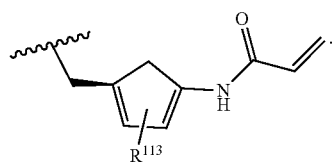
In embodiments, $L^1$-$L^2$-E is
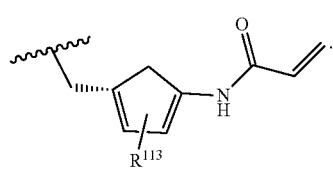
In embodiments, L-$L^2$-E is
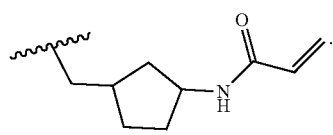
In embodiments, $L^1$-$L^2$-E is
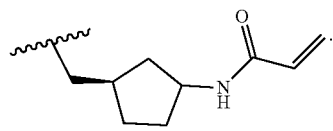 [SMILES: *C[C@@H]1CCC(NC(=O)C=C)C1]
In embodiments, $L^1$-$L^2$-E is
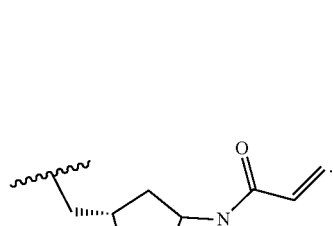
In embodiments, $L^1$-$L^2$-E is
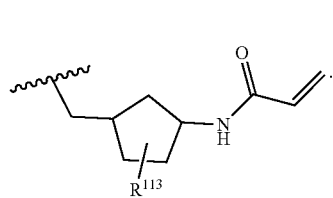

In embodiments, $L^1$-$L^2$-E is

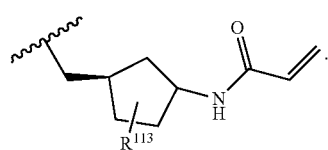

In embodiments, $L^1$-$L^2$-E is

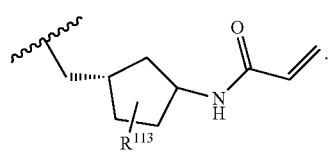

In embodiments, $L^1$-$L^2$-E is

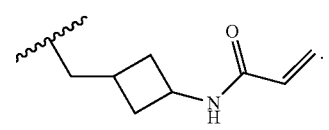 [SMILES: *CC1CC(NC(=O)C=C)C1]

In embodiments, $L^1$-$L^2$-E is

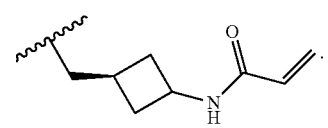

In embodiments, $L^1$-$L^2$-E is

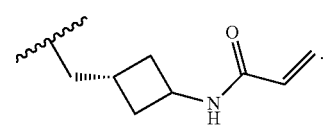

In embodiments, $L^1$-$L^2$-E is

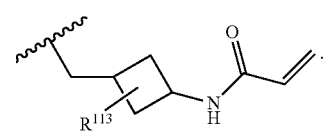

In embodiments, $L^1$-$L^2$-E is

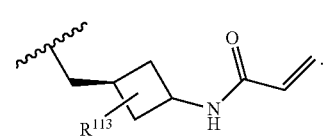

In embodiments, $L^1$-$L^2$-E is

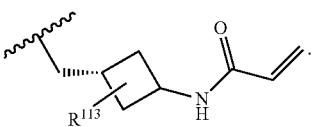

In embodiments, $L^1$-$L^2$-E is

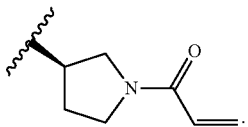 [SMILES: *[C@@H]1CCN(C(=O)C=C)C1]

In embodiments, $L^1$-$L^2$-E is

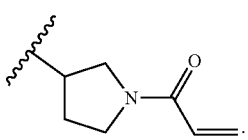 [SMILES: *C1CCN(C(=O)C=C)C1]

In embodiments, $L^1$-$L^2$-E is

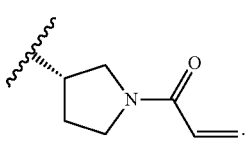 [SMILES: *[C@H]1CCN(C(=O)C=C)C1]

In embodiments, $L^1$-$L^2$-E is

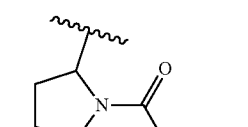

In embodiments, $L^1$-$L^2$-E is

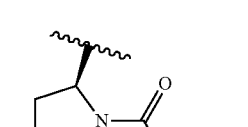

In embodiments, $L^1$-$L^2$-E is

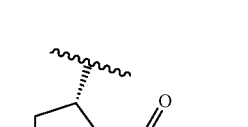

In embodiments $L^1$-$L^2$-E is
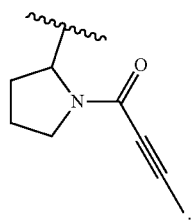 [SMILES: *C1CCCN1C(=O)C#CC]
In embodiments, $L^1$-$L^2$-E is
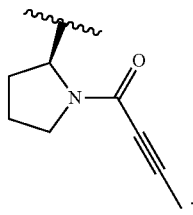 [SMILES: *[C@@H]1CCCN1C(=O)C#CC]
In embodiments, $L^1$-$L^2$-E is
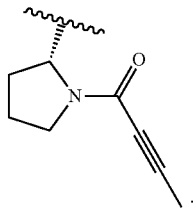 [SMILES: *[C@H]1CCCN1C(=O)C#CC]
In embodiments, $L^1$-$L^2$-E is
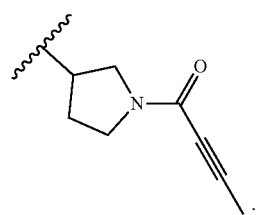 [SMILES: *C1CCN(C(=O)C#CC)C1]
In embodiments, $L^1$-$L^2$-E is
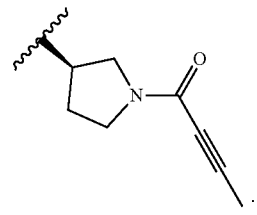 [SMILES: *[C@@H]1CCN(C(=O)C#CC)C1]
In embodiments, $L^1$-$L^2$-E is
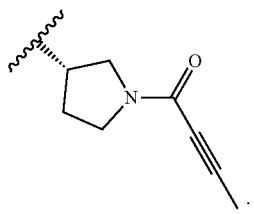 [SMILES: *[C@H]1CCN(C(=O)C#CC)C1]
In embodiments, $L^1$-$L^2$-E is
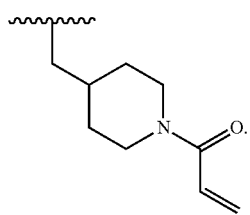 [SMILES: *CC1CCN(C(=O)C=C)CC1]
In embodiments, $L^1$-$L^2$-E is
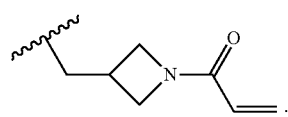 [SMILES: *CC1CN(C(=O)C=C)C1]
In embodiments, L-$L^2$-E is
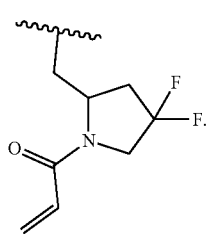 [SMILES: *CC1CC(F)(F)CN1C(=O)C=C]
In embodiments, $L^1$-$L^2$-E is
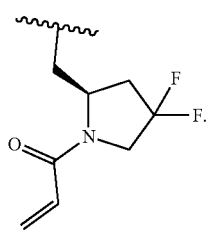 [SMILES: *C[C@H]1CC(F)(F)CN1C(=O)C=C]

In embodiments, L¹-L²-E is
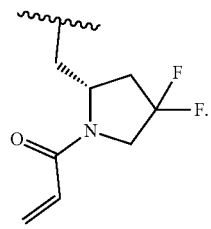 [SMILES: *C[C@@H]1CC(F)(F)CN1C(=O)C=C]
In embodiments, L¹-L²-E is
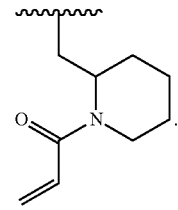
In embodiments, L¹-L²-E is
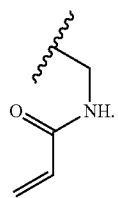
In embodiments, L¹-L²-E is
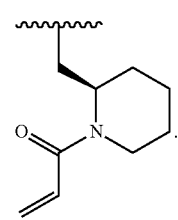 [SMILES: *C[C@H]1CCCCN1C(=O)C=C]
In embodiments, L¹-L²-E is
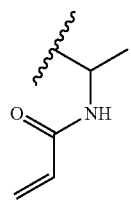
In embodiments, L¹-L²-E
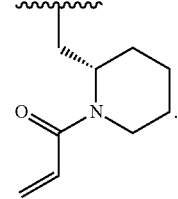
In embodiments, L¹-L²-E is
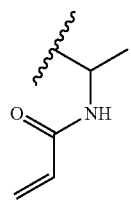
In embodiments, L¹-L²-E
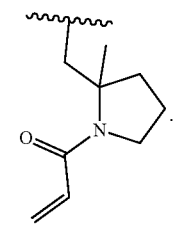 [SMILES: *CC1(C)CCCN1C(=O)C=C]
In embodiments, L¹-L²-E is
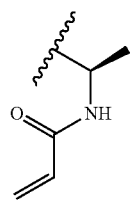
In embodiments, L¹-L²-E is
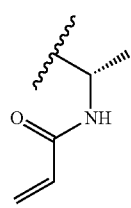
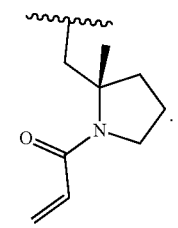 [SMILES: *C[C@]1(C)CCCN1C(=O)C=C]

In embodiments, $L^1$-$L^2$-E
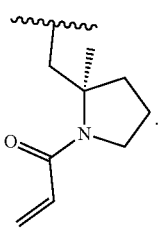
In embodiments, $L^1$-$L^2$-E is
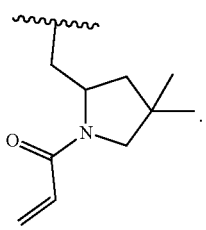 [SMILES: *CC1CC(C)(C)CN1C(=O)C=C]
In embodiments, $L^1$-$L^2$-E is
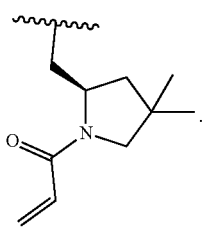 [SMILES: *C[C@H]1CC(C)(C)CN1C(=O)C=C]
In embodiments, $L^1$-$L^2$-E is
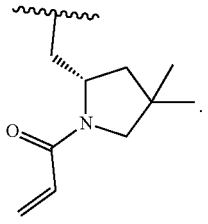
In embodiments, $L^1$-$L^2$-E is
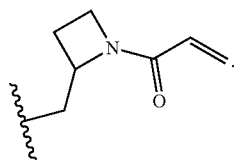 [SMILES: *CC1CCN1C(=O)C=C]
In embodiments, $L^1$-$L^2$-E is
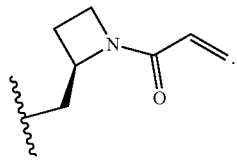 [SMILES: *C[C@H]1CCN1C(=O)C=C]
In embodiments, $L^1$-$L^2$-E is
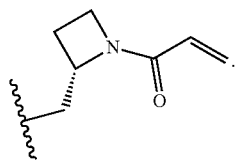 [SMILES: *C[C@@H]1CCN1C(=O)C=C]
In embodiments, $L^1$-$L^2$-E is
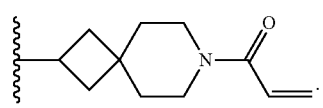
In embodiments, $L^1$-$L^2$-E is
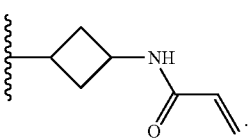
In embodiments, $L^1$-$L^2$-E is
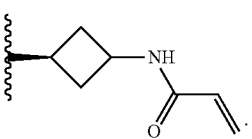
In embodiments, $L^1$-$L^2$-E is
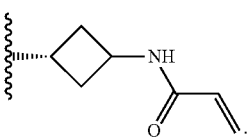 [SMILES: *C1CC(NC(=O)C=C)C1]
In embodiments, $L^1$-$L^2$-E is
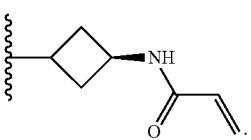

In embodiments, $L^1$-$L^2$-E is
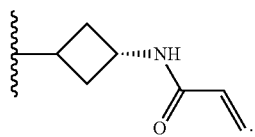
In embodiments, $L^1$-$L^2$-E is
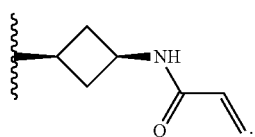 [SMILES: *[C@H]1C[C@@H](NC(=O)C=C)C1]
In embodiments, $L^1$-$L^2$-E is
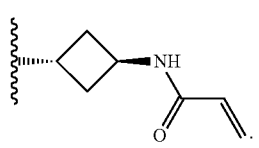 [SMILES: *[C@H]1C[C@H](NC(=O)C=C)C1]
In embodiments, $L^1$-$L^2$-E is
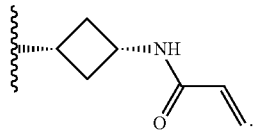
In embodiments, $L^1$-$L^2$-E is
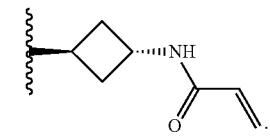
In embodiments, L-$L^2$-E is
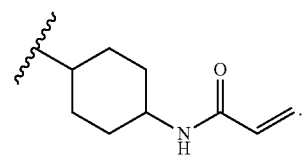
In embodiments, $L^1$-$L^2$-E is
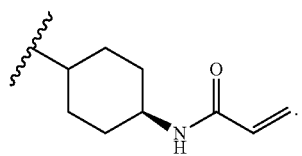
In embodiments, $L^1$-$L^2$-E is
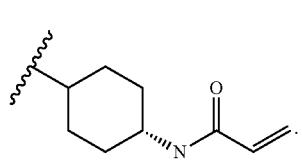
In embodiments, $L^1$-$L^2$-E is
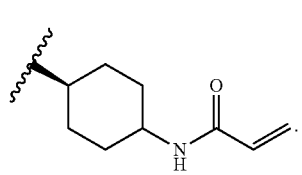
In embodiments, $L^1$-$L^2$-E is
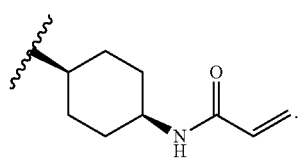 [SMILES: *[C@H]1CC[C@@H](NC(=O)C=C)CC1]
In embodiments, $L^1$-$L^2$-E is
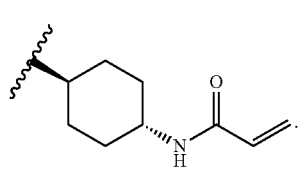 [SMILES: *[C@H]1CC[C@H](NC(=O)C=C)CC1]
In embodiments, $L^1$-$L^2$-E is
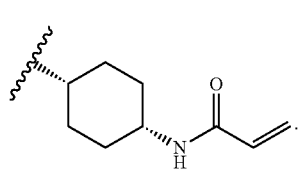 [SMILES: *[C@H]1CC[C@@H](NC(=O)C=C)CC1]

In embodiments, $L^1$-$L^2$-E is
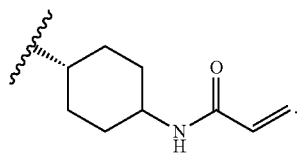
In embodiments, $L^1$-$L^2$-E is
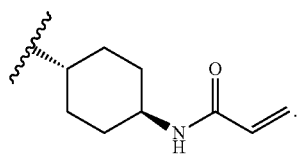 [SMILES: *[C@H]1CC[C@H](NC(=O)C=C)CC1]
In embodiments, $L^1$-$L^2$-E is
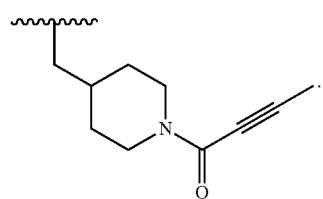 [SMILES: *CC1CCN(C(=O)C#CC)CC1]
In embodiments, $L^1$-$L^2$-E is
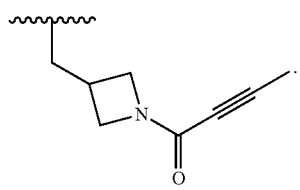 [SMILES: *CC1CN(C(=O)C#CC)C1]
In embodiments, $L^1$-$L^2$-E is
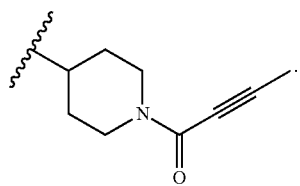 [SMILES: *C1CCN(C(=O)C#CC)CC1]
In embodiments, $L^1$-$L^2$-E is
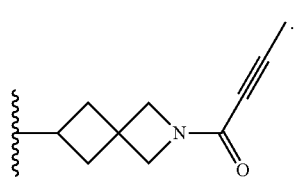 [SMILES: *C1CC2(C1)CN(C(=O)C#CC)C2]
In embodiments, $L^1$-$L^2$-E is
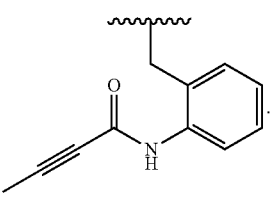 [SMILES: *Cc1ccccc1NC(=O)C#CC]
In embodiments, $L^1$-$L^2$-E is
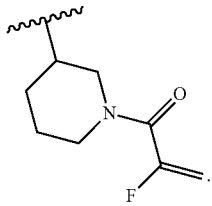 [SMILES: *C1CCCN(C(=O)C(=C)F)C1]
In embodiments, $L^1$-$L^2$-E is
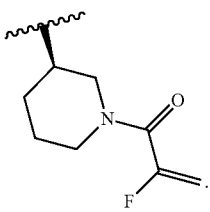 [SMILES: *[C@@H]1CCCN(C(=O)C(=C)F)C1]
In embodiments, $L^1$-$L^2$-E is
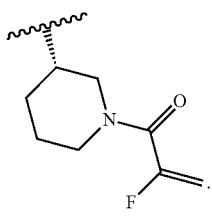 [SMILES: *[C@H]1CCCN(C(=O)C(=C)F)C1]
In embodiments, $L^1$-$L^2$-E is
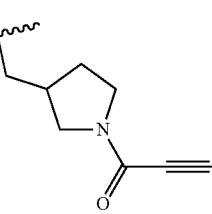

In embodiments, L¹-L²-E is
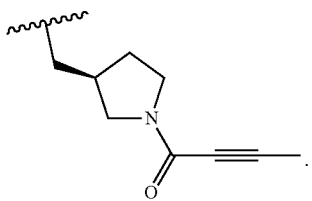 [SMILES: *C[C@H]1CCN(C(=O)C#CC)C1]
In embodiments, L¹-L²-E is
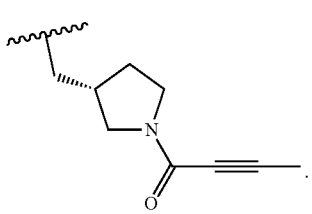 [SMILES: *C[C@@H]1CCN(C(=O)C#CC)C1]
In embodiments, L¹-L²-E is
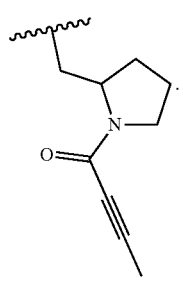 [SMILES: *CC1CCCN1C(=O)C#CC]
In embodiments, L¹-L²-E is
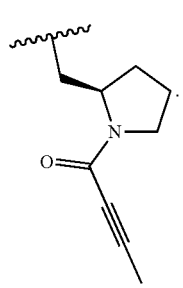 [SMILES: *C[C@H]1CCCN1C(=O)C#CC]
In embodiments, L¹-L²-E is
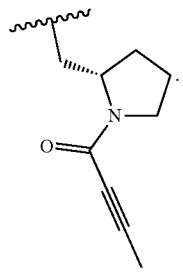 [SMILES: *C[C@@H]1CCCN1C(=O)C#CC]
In embodiments, L¹-L²-E is
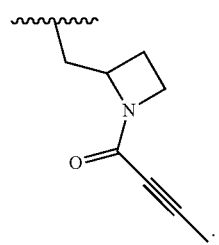 [SMILES: *CC1CCN1C(=O)C#CC]
In embodiments, L¹-L²-E is
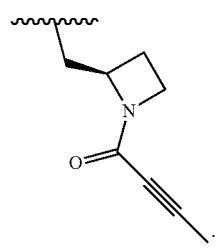 [SMILES: *C[C@H]1CCN1C(=O)C#CC]
In embodiments, L¹-L²-E is
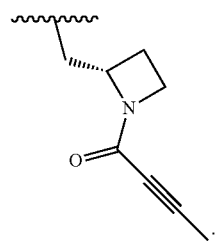 [SMILES: *C[C@@H]1CCN1C(=O)C#CC]
In embodiments, L¹-L²-E is
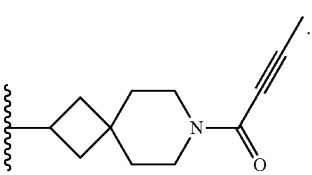 [SMILES: *C1CC2(CCN(C(=O)C#CC)CC2)C1]
In embodiments, L¹-L²-E is
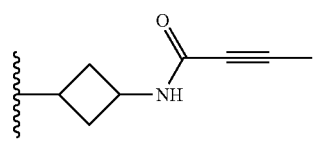

In embodiments, L¹-L²-E is
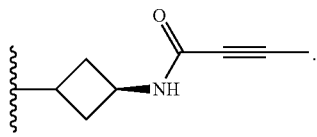
In embodiments, L-L²-E is
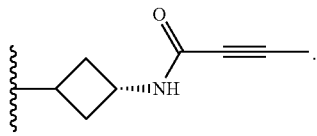
In embodiments L¹-L²-E is
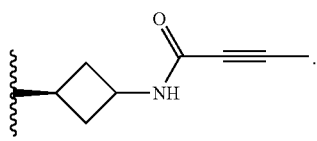
In embodiments, L¹-L²-E is
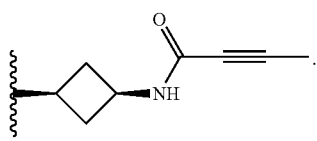 [SMILES: *[C@H]1C[C@@H](NC(=O)C#CC)C1]
In embodiments, L¹-L²-E is
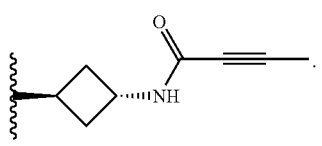 [SMILES: *[C@H]1C[C@H](NC(=O)C#CC)C1]
In embodiments, L¹-L²-E is
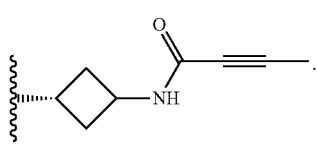
In embodiments, L¹-L²-E is
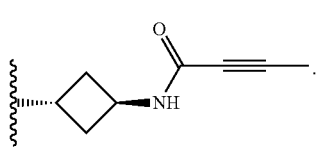 [SMILES: *[C@H]1C[C@H](NC(=O)C#CC)C1]
In embodiments, L¹-L²-E is
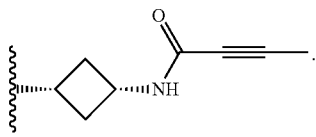
In embodiments, L¹-L²-E is
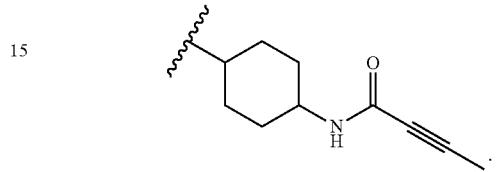
In embodiments, L¹-L²-E is
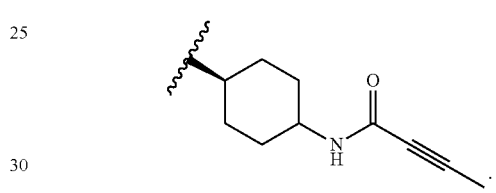
In embodiments, L¹-L²-E is
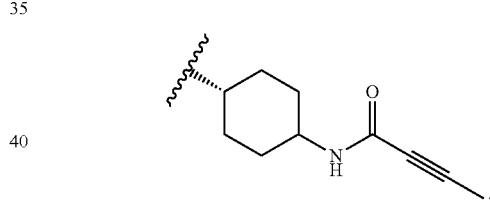
In embodiments, L¹-L²-E is
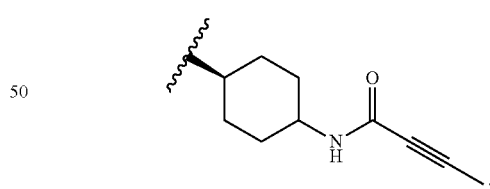
In embodiments, L¹-L²-E is
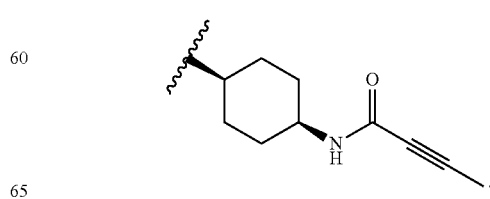

In embodiments, $L^1$-$L^2$-E is
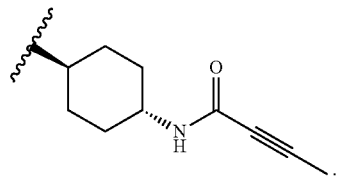 [SMILES: *[C@H]1CC[C@H](NC(=O)C#CC)CC1 ; "."]
In embodiments, $L^1$-$L^2$-E is
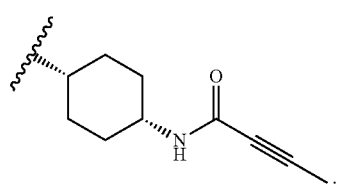 [SMILES: *[C@H]1CC[C@@H](NC(=O)C#CC)CC1 ; "."]
In embodiments, $L^1$-$L^2$-E is
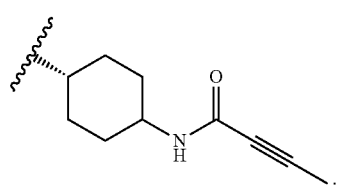
In embodiments, $L^1$-$L^2$-E is
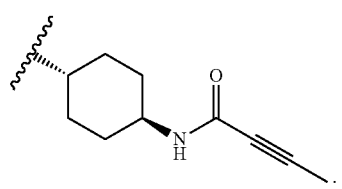 [SMILES: *[C@H]1CC[C@H](NC(=O)C#CC)CC1 ; "."]
In embodiments, $L^1$-$L^2$-E is
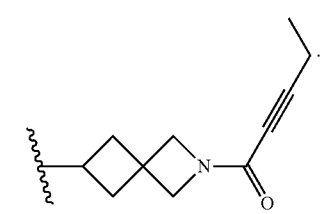 [SMILES: *C1CC2(C1)CN(C(=O)C#CCC)C2 ; "."]
In embodiments, $L^1$-$L^2$-E is
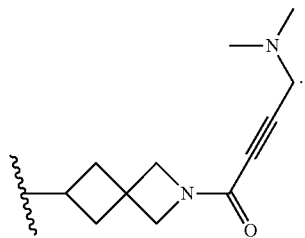 [SMILES: *C1CC2(C1)CN(C(=O)C#CCN(C)C)C2 ; "."]
In embodiments, $L^1$-$L^2$-E is
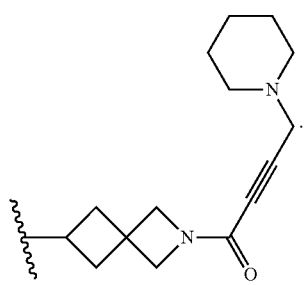 [SMILES: *C1CC2(C1)CN(C(=O)C#CCN1CCCCC1)C2 ; "."]
In embodiments, $L^1$-$L^2$-E is
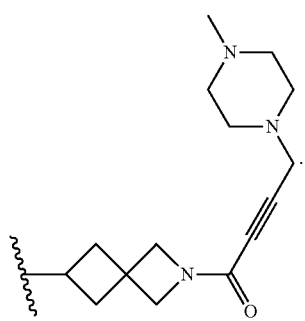 [SMILES: *C1CC2(C1)CN(C(=O)C#CCN1CCN(C)CC1)C2 ; "."]
In embodiments, $L^1$-$L^2$-E is
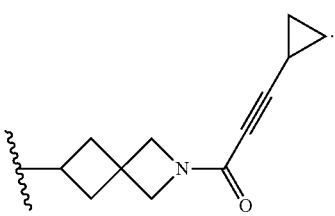 [SMILES: *C1CC2(C1)CN(C(=O)C#CC1CC1)C2 ; "."]

In embodiments, $L^1$-$L^2$-E is

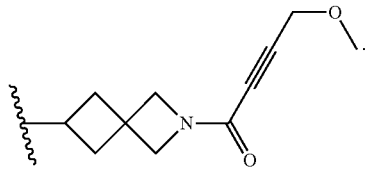 [SMILES: *C1CC2(C1)CN(C(=O)C#CCOC)C2 ; "."]

In embodiments, the compound (e.g, described herein) is capable of entering the central nervous system of a patient following administration outside of the central nervous system (e.g., systemic administration, i.v., or intrarterial). In embodiments, the compound (e.g., described herein) is capable of crossing the blood-brain barrier.

In embodiments, the compound has the formula

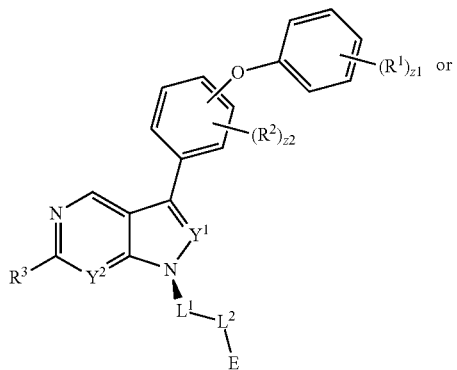

or

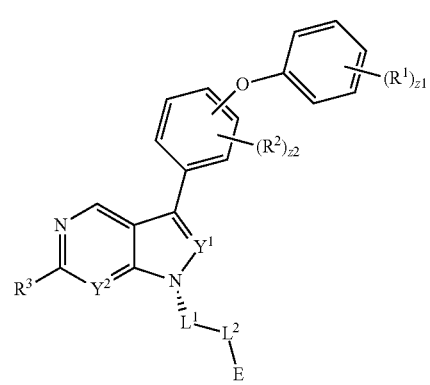

$R^1$, $R^2$, $R^3$, $L^1$, $L^2$, $Y^1$, $Y^2$, z1, z2, and E are as described herein.

In embodiments, the compound has the formula

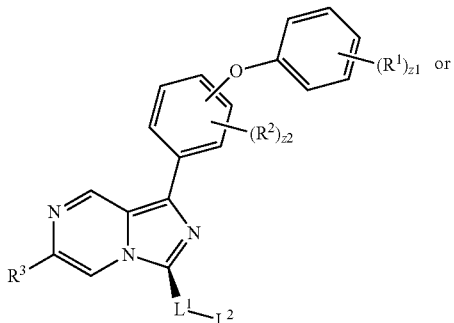

or

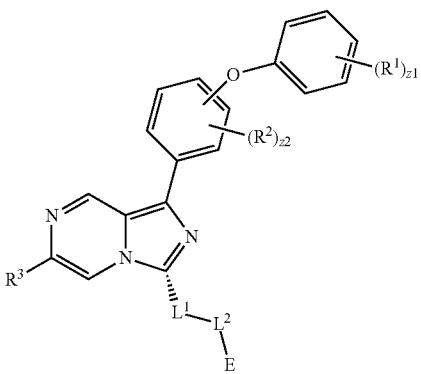

$R^1$, $R^2$, $R^3$, $L^1$, $L^2$, z1, z2, and E are as described herein.

In embodiments, the compound has the formula

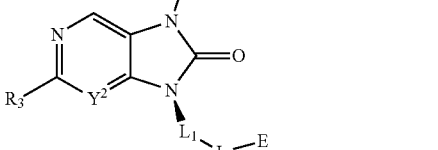

or

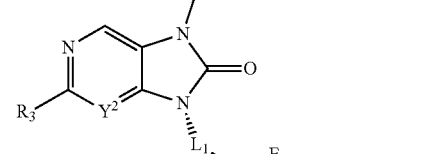

$R^1$, $R^2$, $R^3$, $L^1$, $L^2$, $Y^2$, z1, z2, and E are as described herein.

235
In embodiments, the compound has the formula
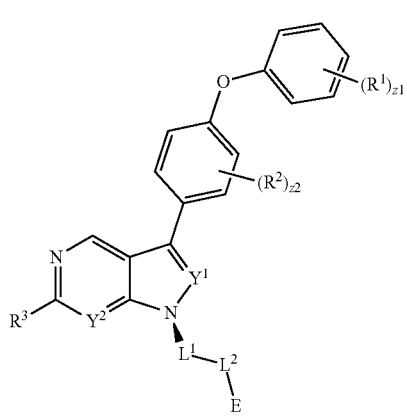
or
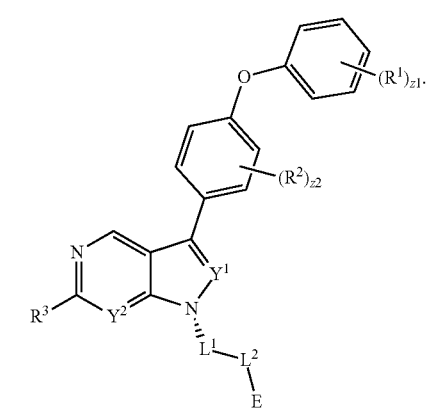
$R^1$, $R^2$, $R^3$, $L^1$, $L^2$, $Y^1$, $Y^2$, z1, z2, and E are as described herein.
In embodiments, the compound has the formula
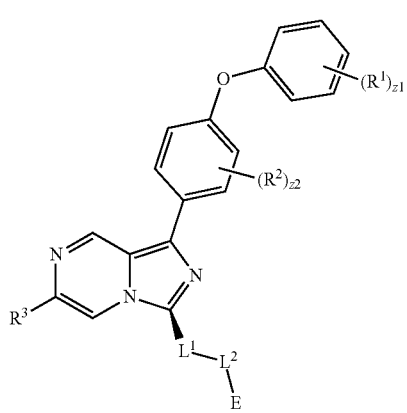
or
236
-continued
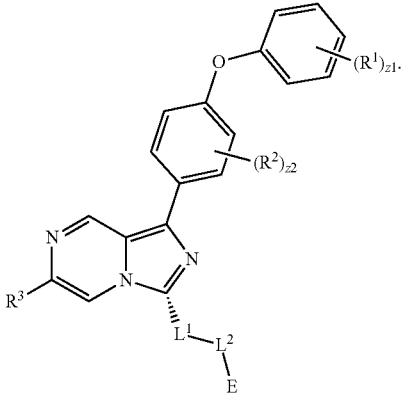
$R^1$, $R^2$, $R^3$, $L^1$, $L^2$, z1, z2, and E are as described herein.
In embodiments, the compound has the formula
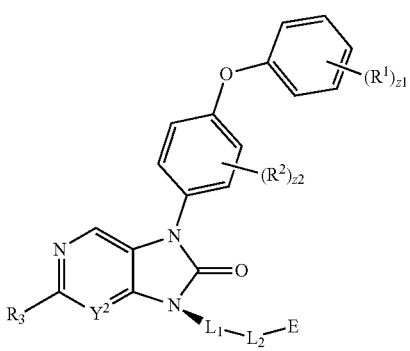
or
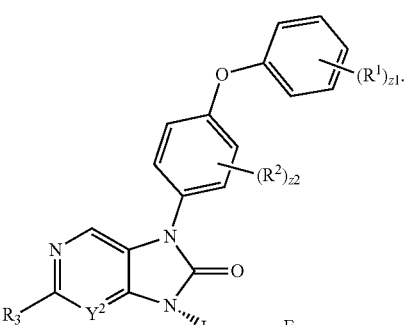
$R^1$, $R^2$, $R^3$, $L^1$, $L^2$, $Y^2$, z1, z2, and E are as described herein.

In embodiments, the compound has the formula
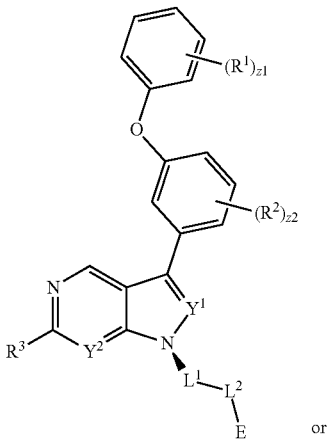
or
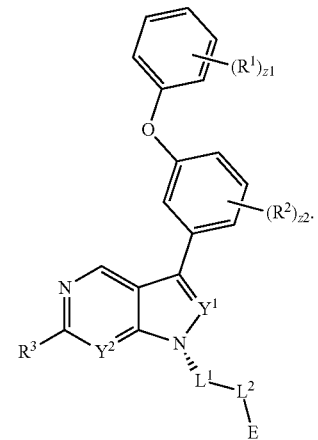
$R^1$, $R^2$, $R^3$, $L^1$, $L^2$, $Y^1$, $Y^2$, z1, z2, and E are as described herein.
In embodiments, the compound has the formula
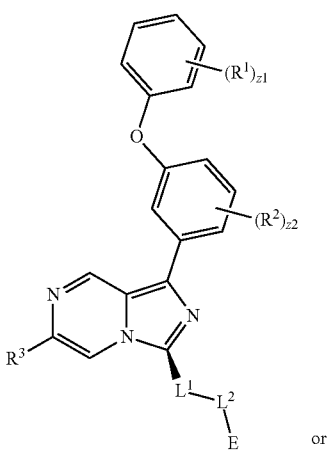
or
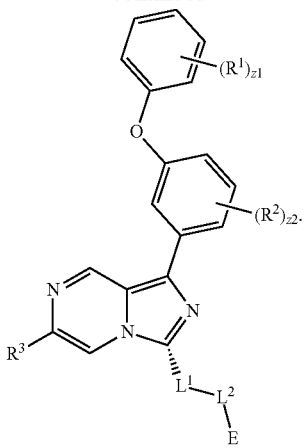
$R^1$, $R^2$, $R^3$, $L^1$, $L^2$, z1, z2, and E are as described herein.
In embodiments, the compound has the formula
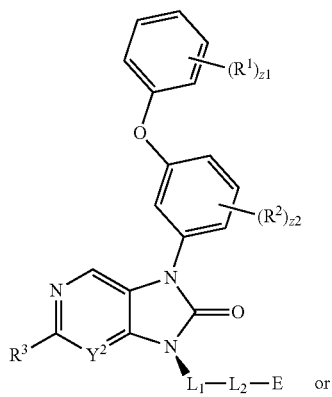
or
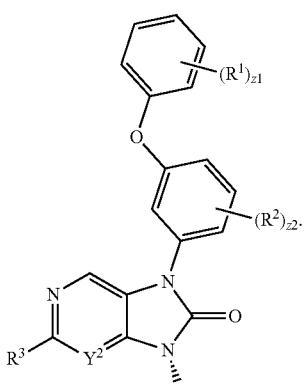
$R^1$, $R^2$, $R^3$, $L^1$, $L^2$, $Y^2$, z1, z2, and E are as described herein.

In embodiments, the compound has the formula

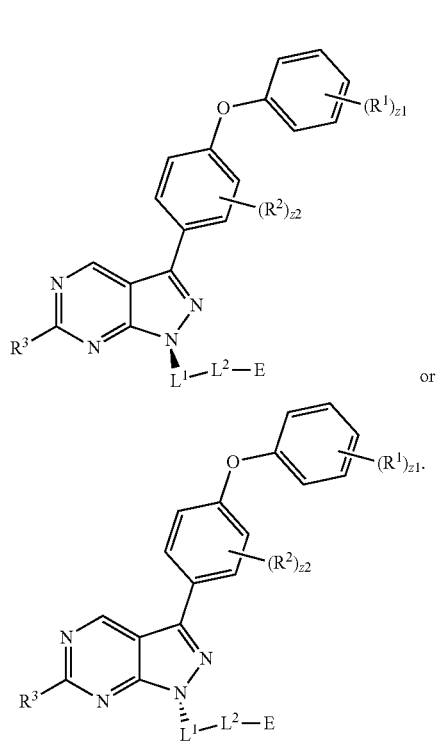

or

R¹, R², R³, L¹, L², z1, z2, and E are as described herein.

In embodiments, the compound has the formula

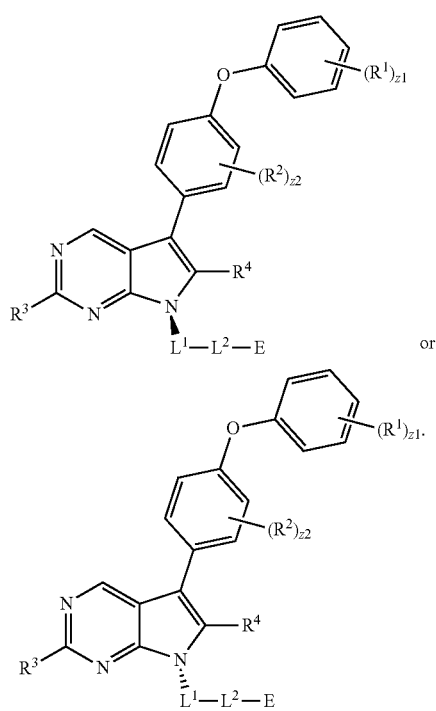

R¹, R², R³, R⁴, L¹, L², Y¹, Y², z1, z2, and E are as described herein.

In embodiments, the compound has the formula

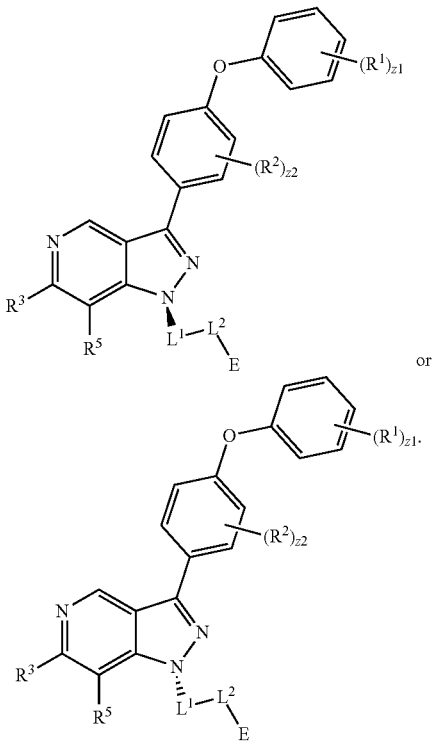

or

R¹, R², R³, R⁵, L¹, L², Y¹, Y², z1, z2, and E are as described herein.

In embodiments, the compound has the formula

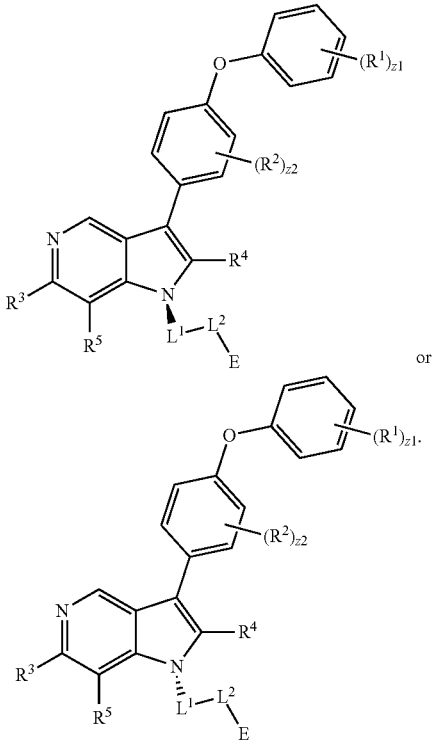

or

R¹, R², R³, R⁴, R, L¹, L², Y¹Y², z¹, z2, and E are as described herein.

241

In embodiments, the compound has the formula

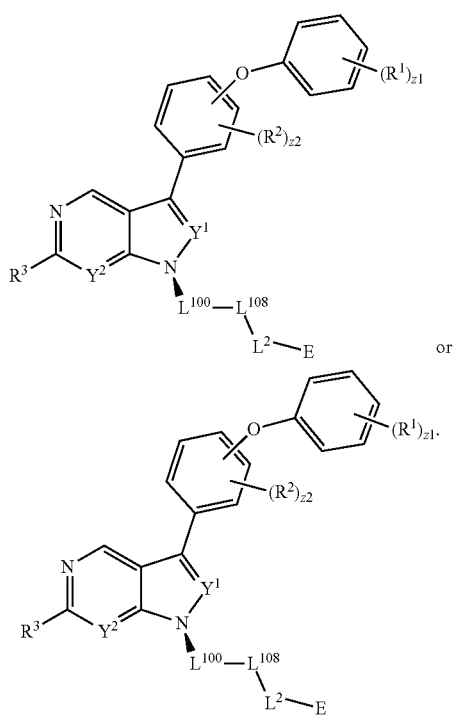

or

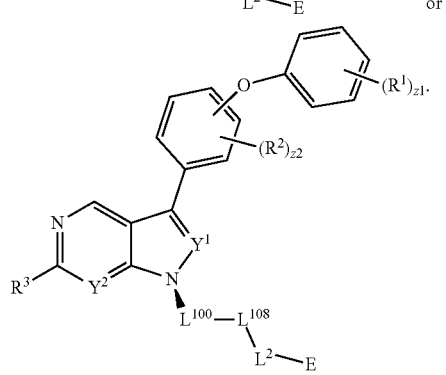

$R^1$, $R^2$, $R^3$, $L^{100}$, $L^{108}$, $L^2$, $Y^1$, $Y^2$, z1, z2, and E are as described herein.

In embodiments, the compound has the formula

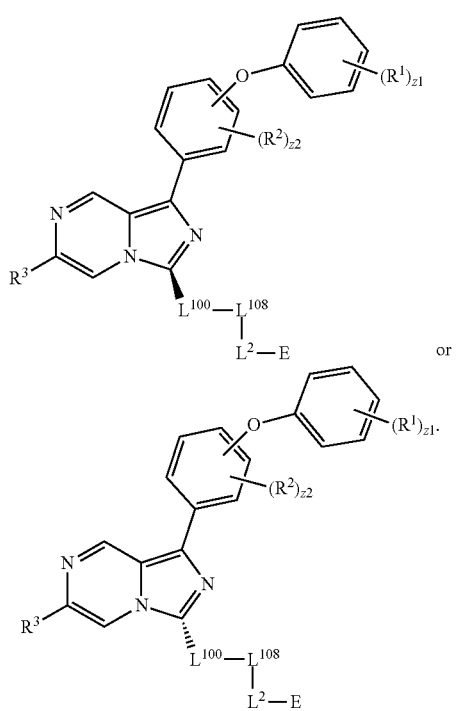

or

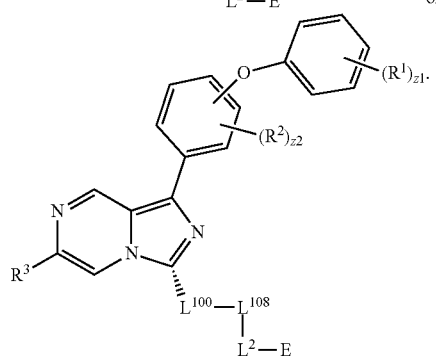

$R^1$, $R^2$, $R^3$, $L^{100}$, $L^{108}$, $L^2$, z1, z2, and E are as described herein.

242

In embodiments, the compound has the formula

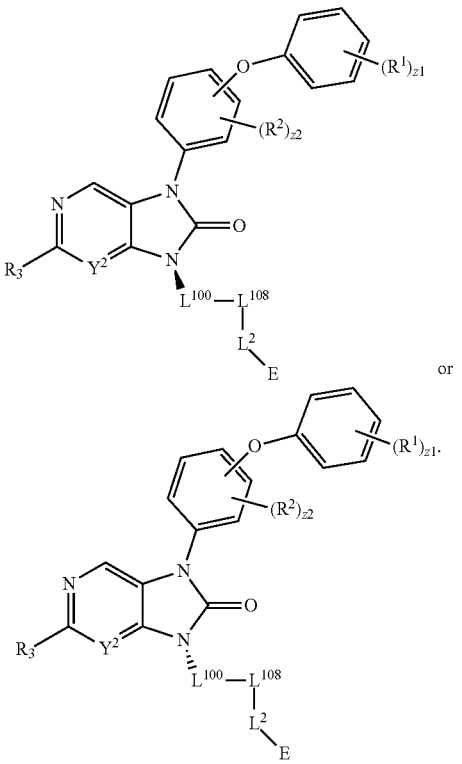

or $R^1$, $R^2$, $R^3$, $L^{100}$, $L^{108}$, $L^2$, $Y^2$, z1, z2, and E are as described herein.

In embodiments, the compound has the formula

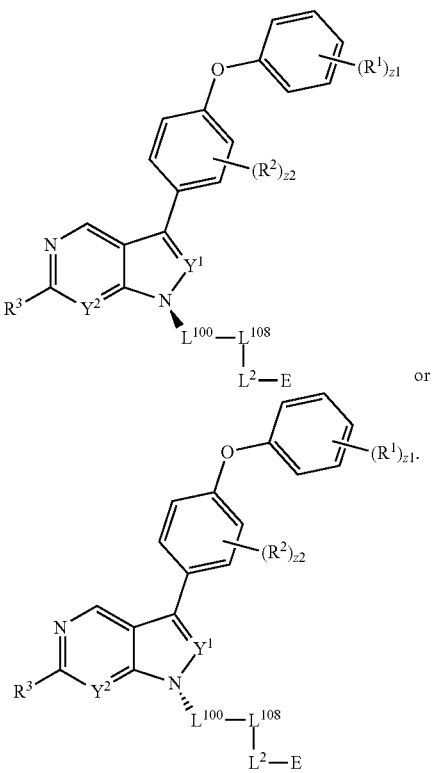

or $R^1$, $R^2$, $R^3$, $L^{100}$, $L^{108}$ $L^2$, $Y^1$, $Y^2$, z1, z2, and E are as described herein.

In embodiments, the compound has the formula

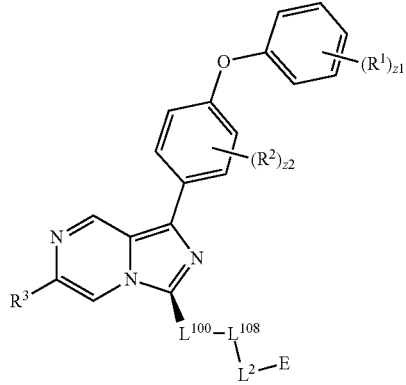

or

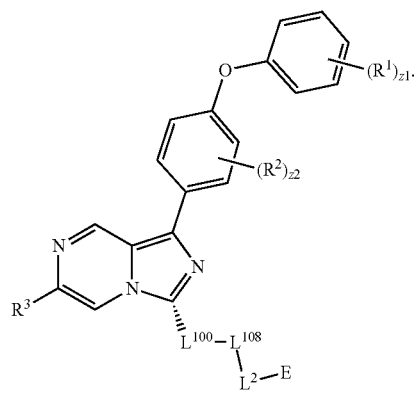

$R^1$, $R^2$, $R^3$, $L^{100}$, $L^{108}$, $L^2$, z1, z2, and E are as described herein.

In embodiments, the compound has the formula

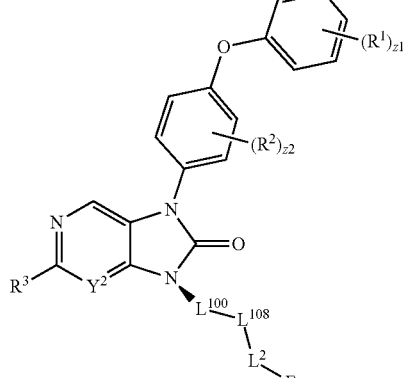

-continued

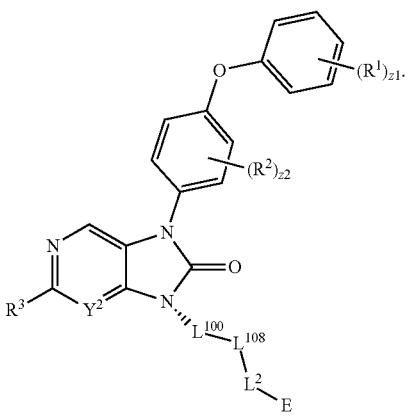

$R^1$, $R^2$, $R^3$, $L^{100}$, $L^{108}$, $L^2$, $Y^2$, z1, z2, and E are as described herein.

In embodiments, the compound has the formula

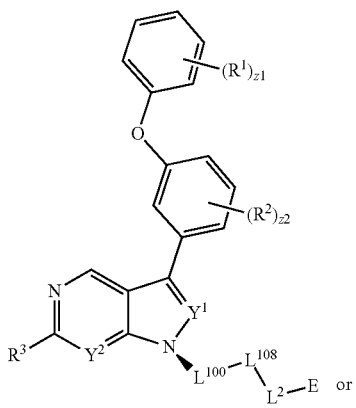 or

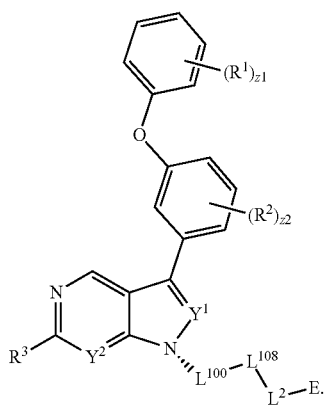

$R^1$, $R^2$, $R^3$, $L^{100}$, $L^{108}$, $L^2$, $Y^1$, $Y^2$, z1, z2, and E are as described herein.

In embodiments, the compound has the formula
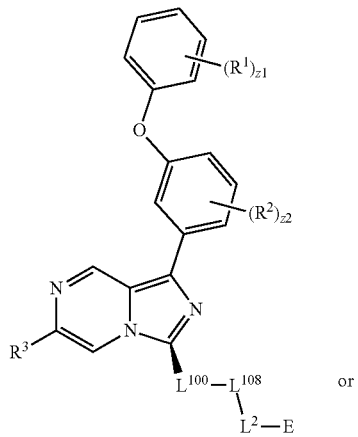 or
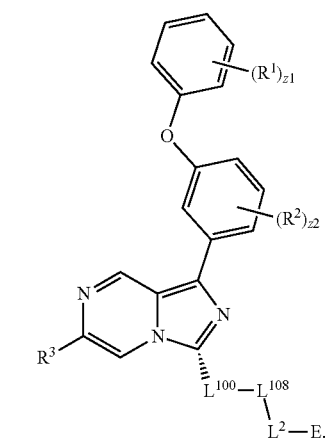
R¹, R², R³, $L^{100}$, $L^{108}$, $L^2$, z1, z2 and E are as described herein.
In embodiments, the compound has the formula
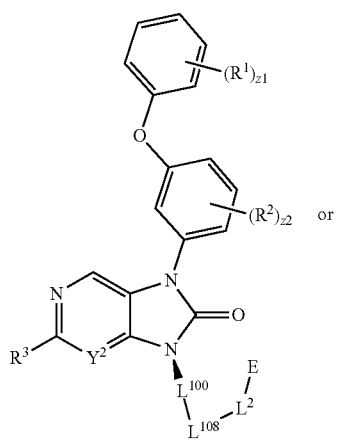 or
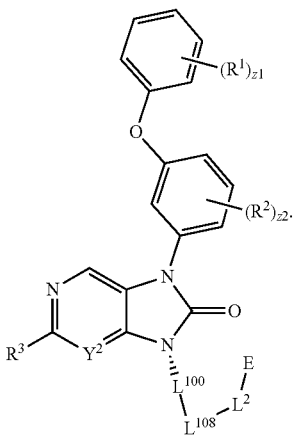
R¹, R², R³, $L^{100}$, $L^{108}$, $L^2$, $Y^2$, z1, z2, and E are as described herein.
In embodiments, the compound has the formula
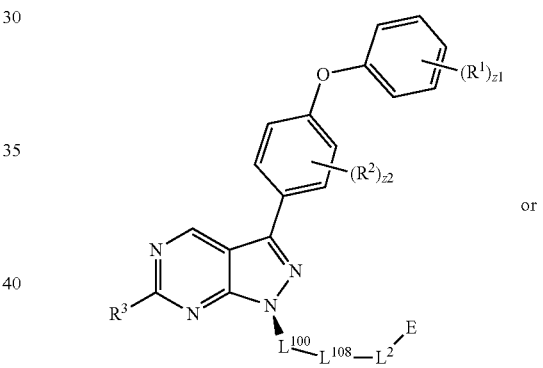
R¹, R², R³, $L^{100}$, $L^{108}$, $L^2$, z1, z2, and E are as described herein.

In embodiments, the compound has the formula

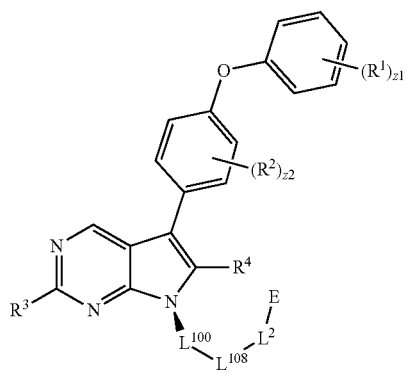

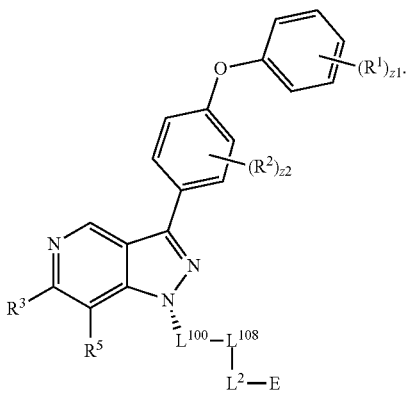

or $R^1$, $R^2$, $R^3$, $R^5$, $L^{100}$, $L^{108}$, $L^2$, $Y^1$, $Y^2$, z1, z2, and E are as described herein.

In embodiments, the compound has the formula

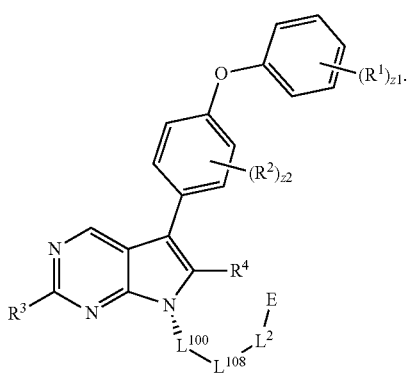

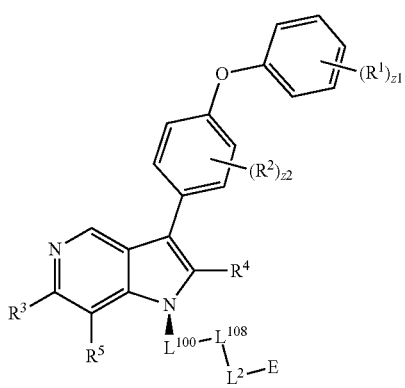

or $R^1$, $R^2$, $R^3$, $R^4$, $L^{100}$, $L^{108}$, $L^2$, $Y^1$, $Y^2$, z1, z2, and E are as described herein.

In embodiments, the compound has the formula

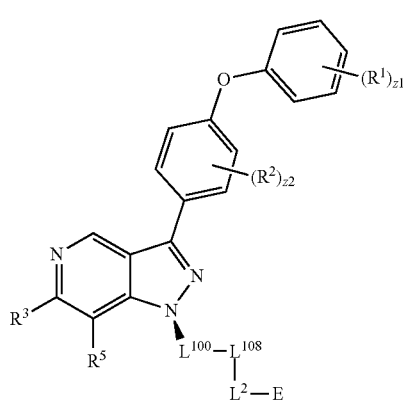

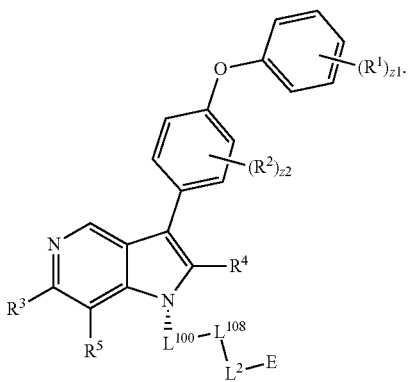

or $R^1$, $R^2$, $R^3$, $R^4$, $R^5$, $L^{100}$, $L^{108}$, $L^2$, $Y^1$, $Y^2$, z1, z2, and E are as described herein.

In embodiments, the compound has the formula:

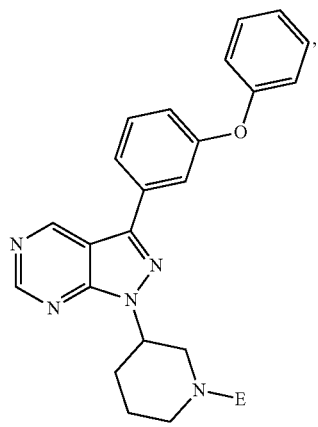

wherein E is as described herein. In embodiments, the compound has the formula:

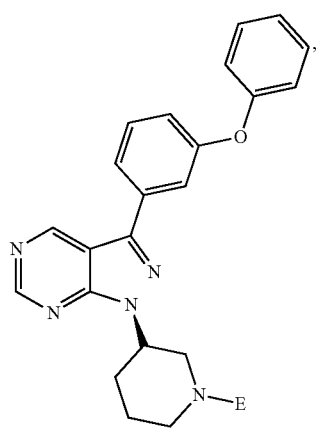

wherein E is as described herein. In embodiments, the compound has the formula:

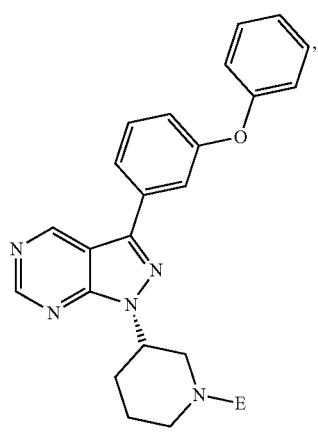

wherein E is as described herein.

In embodiments, the compound has the formula:

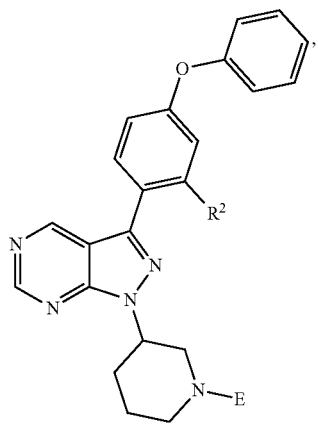

wherein $R^2$ and E are as described herein. In embodiments, the compound has the formula:

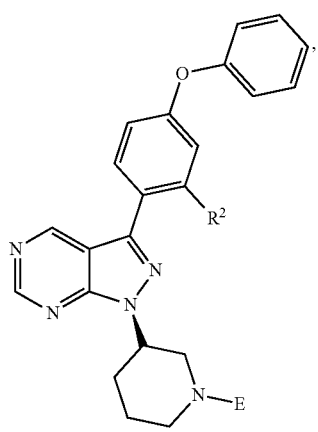

wherein $R^2$ and E are as described herein. In embodiments, the compound has the formula:

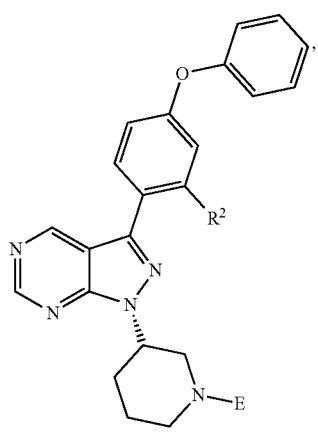

wherein $R^2$ and E are as described herein.

In embodiments, the compound has the formula:

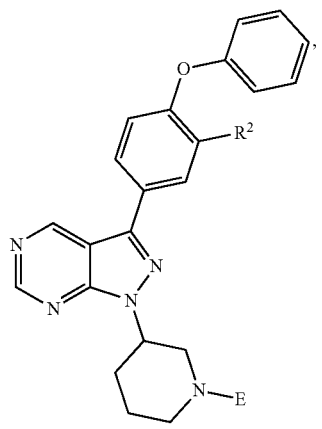

wherein $R^2$ and E are as described herein. In embodiments, the compound has the formula:

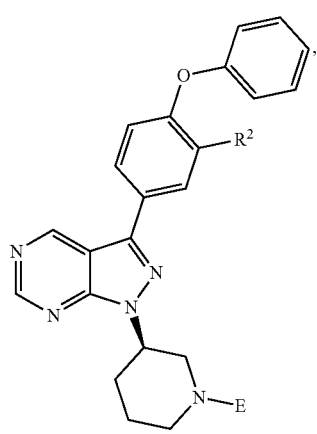

wherein $R^2$ and E are as described herein. In embodiments, the compound has the formula:

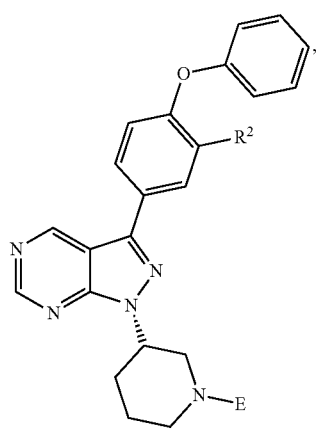

wherein $R^2$ and E are as described herein.

In embodiments, the compound has the formula:

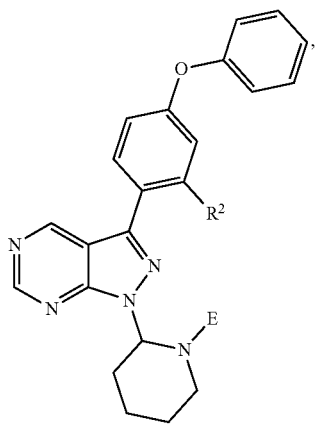

wherein $R^2$ and E are as described herein. In embodiments, the compound has the formula:

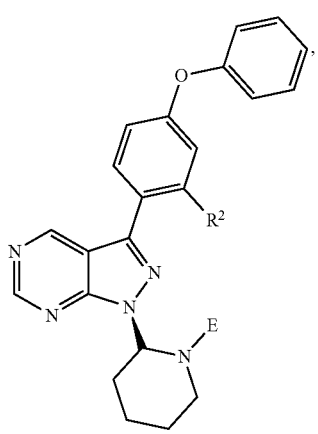

wherein $R^2$ and E are as described herein. In embodiments, the compound has the formula:

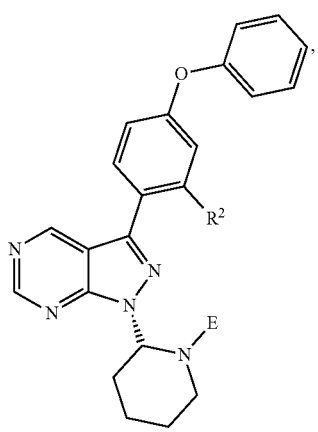

wherein $R^2$ and E are as described herein.

In embodiments, the compound has the formula:

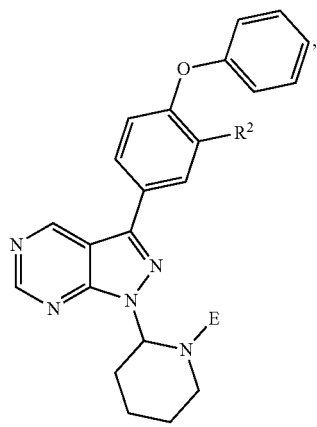

wherein $R^2$ and E are as described herein. In embodiments, the compound has the formula:

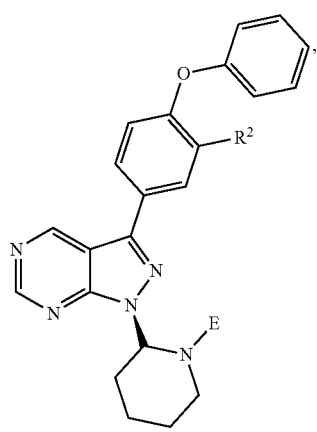

wherein $R^2$ and E are as described herein. In embodiments, the compound has the formula:

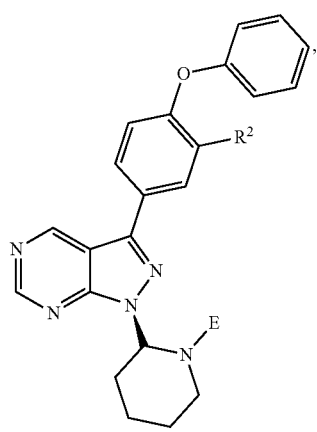

wherein $R^2$ and E are as described herein.

In embodiments, the compound has the formula:

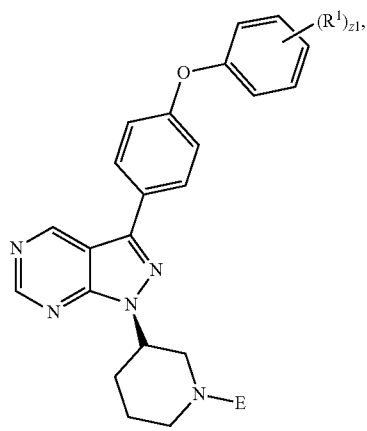

wherein R, z1, and E are as described herein. In embodiments, the compound has the formula:

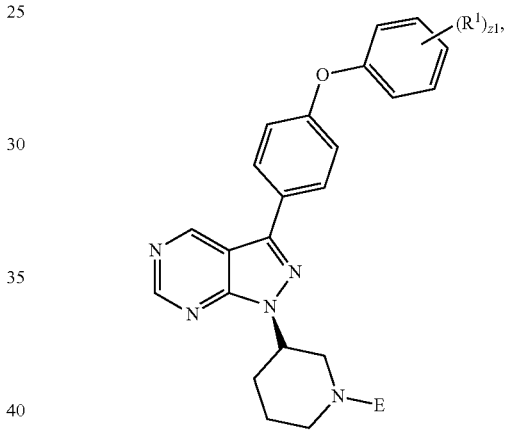

wherein $R^1$, z1, and E are as described herein. In embodiments, the compound has the formula:

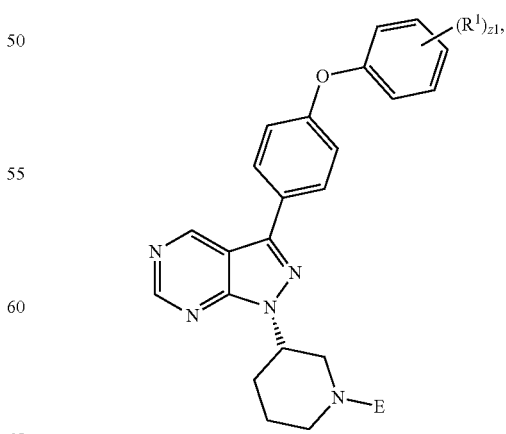

wherein $R^1$, z1, and E are as described herein.

In embodiments, the compound has the formula:

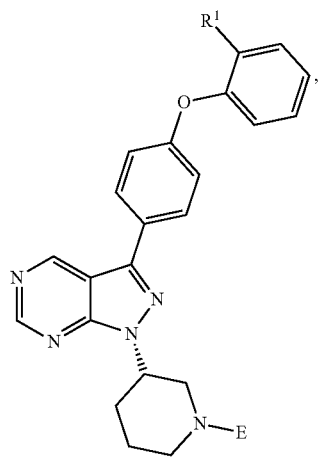

wherein $R^1$ and E are as described herein. In embodiments, the compound has the formula:

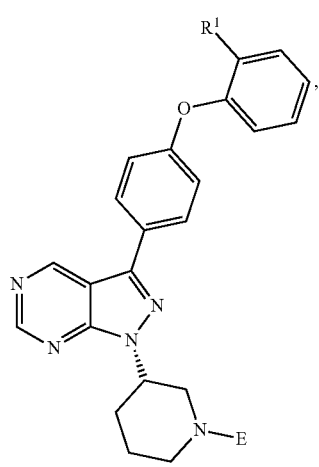

wherein $R^1$ and E are as described herein. In embodiments, the compound has the formula:

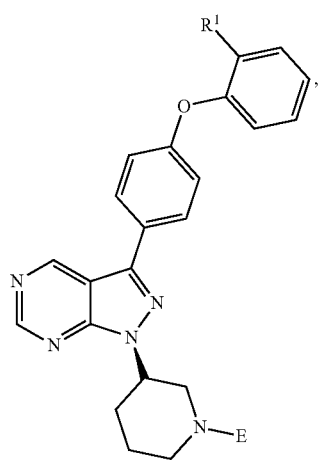

wherein $R^1$ and E are as described herein.

In embodiments, the compound has the formula:

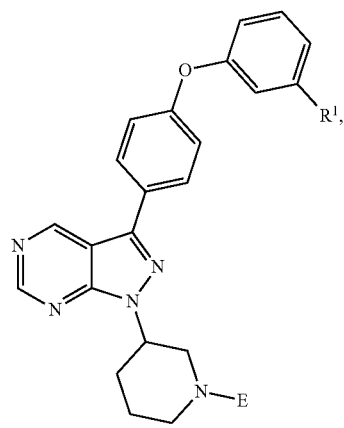

wherein $R^1$ and E are as described herein. In embodiments, the compound has the formula:

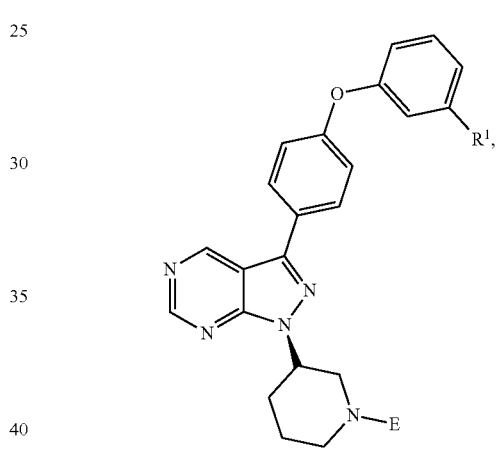

wherein $R^1$ and E are as described herein. In embodiments, the compound has the formula:

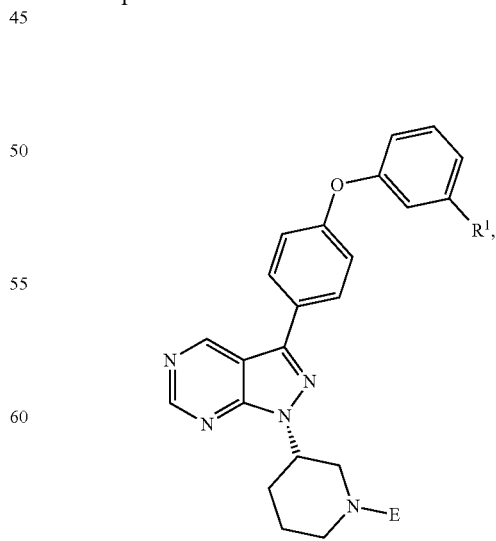

wherein $R^1$ and E are as described herein.

In embodiments, the compound has the formula:

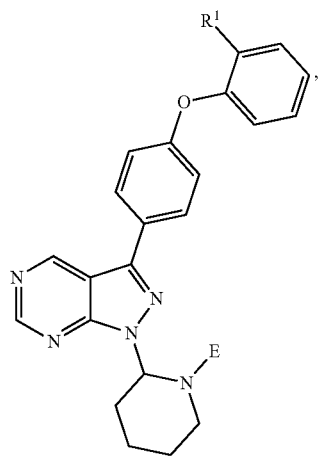

wherein R¹ and E are as described herein. In embodiments, the compound has the formula:

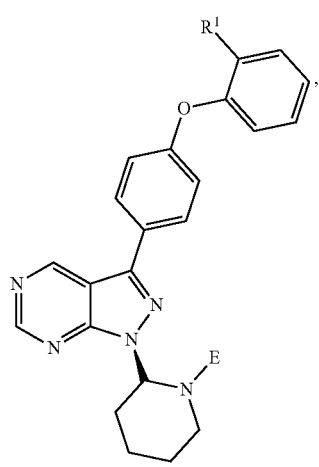

wherein R¹ and E are as described herein. In embodiments, the compound has the formula:

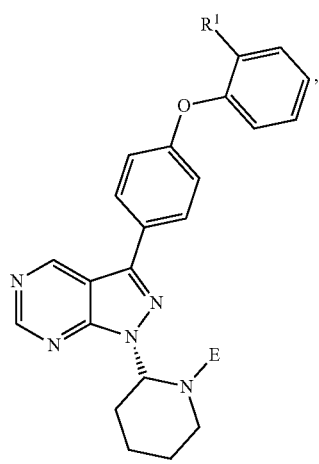

wherein R¹ and E are as described herein.

In embodiments, the compound has the formula:

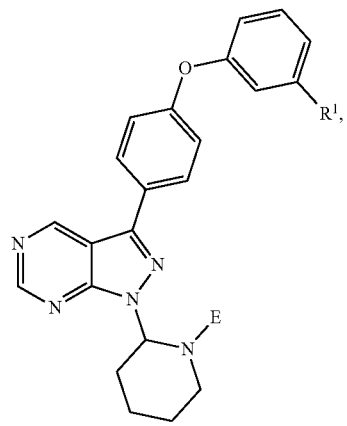

wherein R¹ and E are as described herein. In embodiments, the compound has the formula:

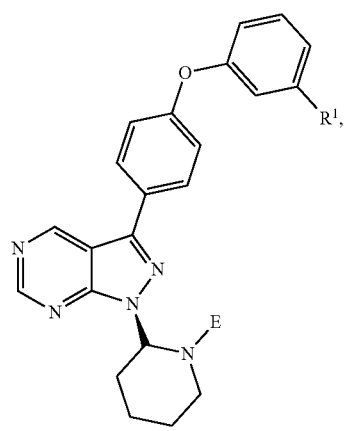

wherein R¹ and E are as described herein. In embodiments, the compound has the formula:

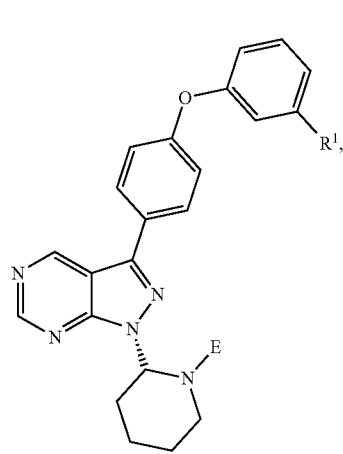

wherein R¹ and E are as described herein.

In embodiments, the compound has the formula:

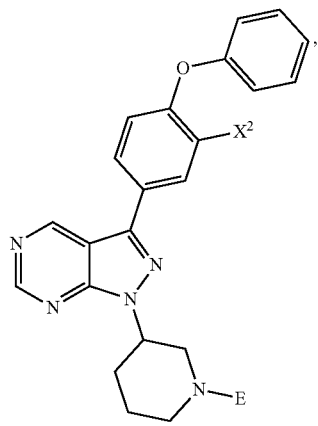

wherein $X^2$ and E are as described herein. In embodiments, the compound has the formula:

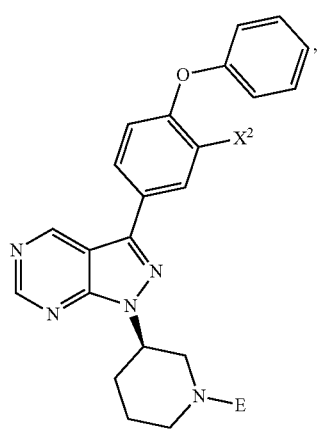

wherein $X^2$ and E are as described herein. In embodiments, the compound has the formula:

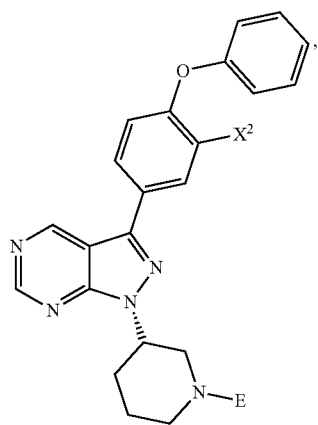

wherein $X^2$ and E are as described herein.

In embodiments, the compound has the formula:

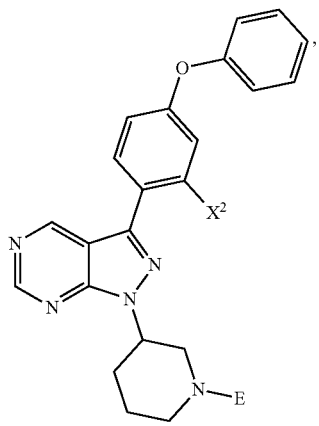

wherein $X^2$ and E are as described herein. In embodiments, the compound has the formula:

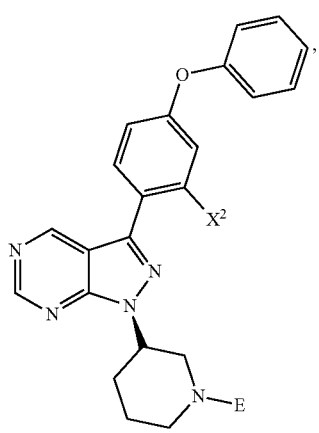

wherein $X^2$ and E are as described herein. In embodiments, the compound has the formula:

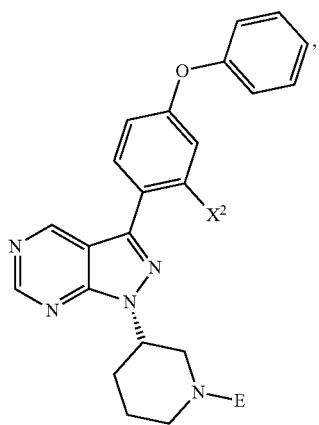

wherein $X^2$ and E are as described herein.

In embodiments, the compound has the formula:

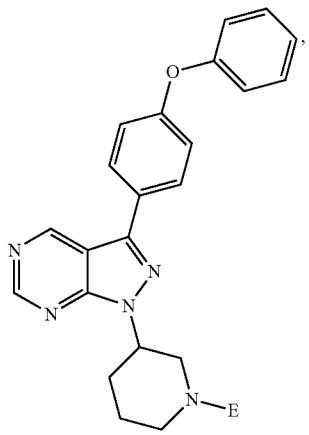

wherein R² and E are as described herein. In embodiments, the compound has the formula:

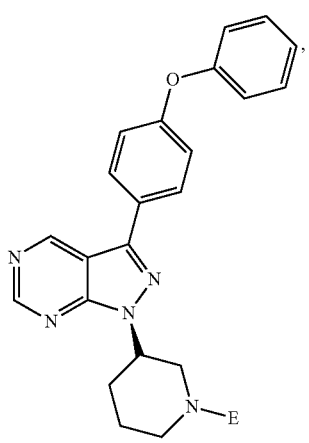

wherein R² and E are as described herein. In embodiments, the compound has the formula:

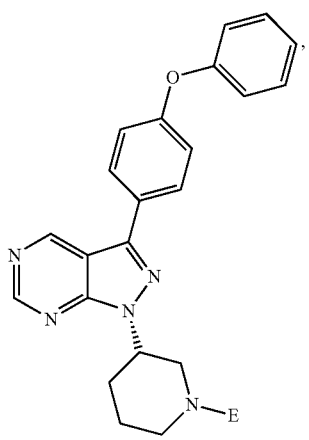

wherein R² and E are as described herein.

In embodiments, the compound has the formula:

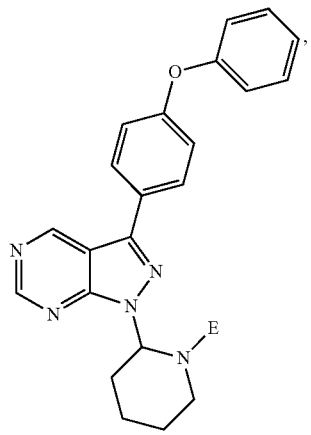

wherein R² and E are as described herein. In embodiments, the compound has the formula:

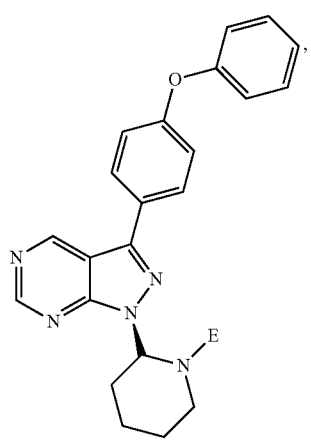

wherein R² and E are as described herein. In embodiments, the compound has the formula:

wherein R² and E are as described herein.

In embodiments, the compound has the formula:

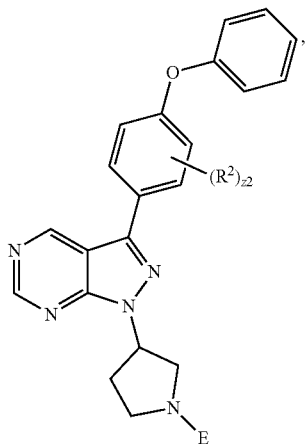

wherein $R^2$, z2, and E are as described herein. In embodiments, the compound has the formula:

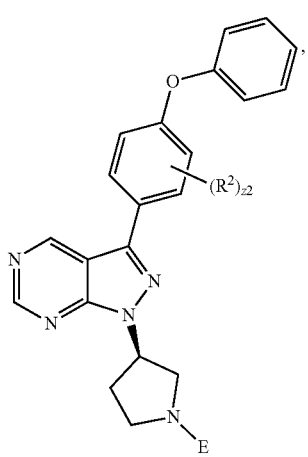

wherein $R^2$, z2, and E are as described herein. In embodiments, the compound has the formula:

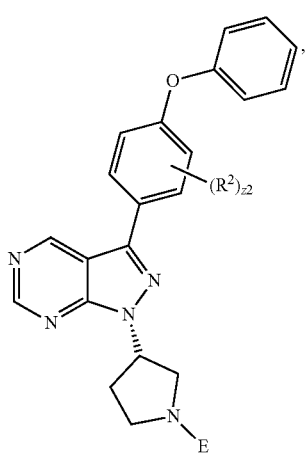

wherein $R^2$, z2, and E are as described herein.

In embodiments, the compound has the formula:

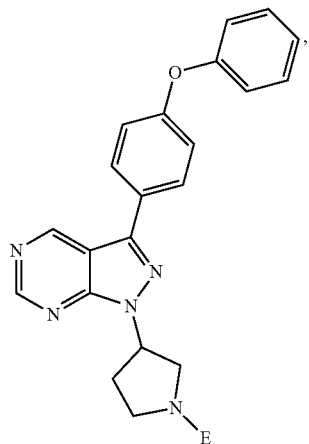

wherein E is as described herein. In embodiments, the compound has the formula:

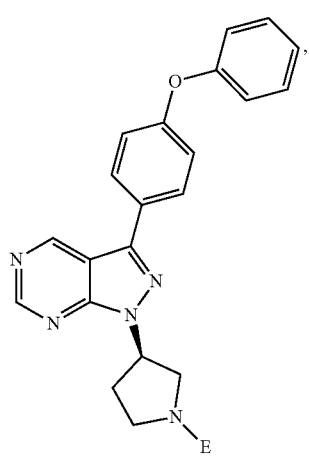

wherein E is as described herein, the compound has the formula:

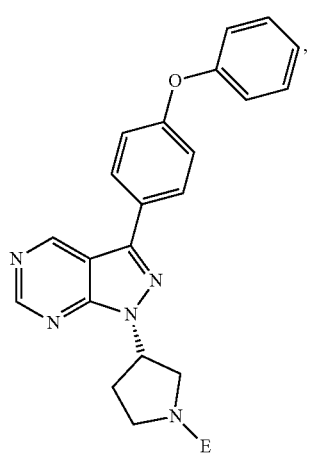

wherein E is as described herein.

In embodiments, the compound has the formula:

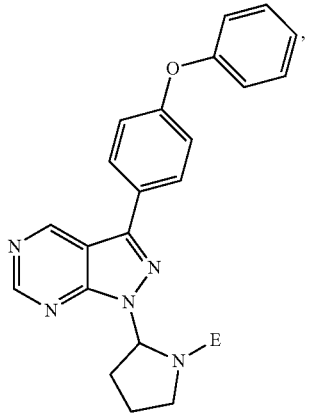

wherein E is as described herein. In embodiments, the compound has the formula:

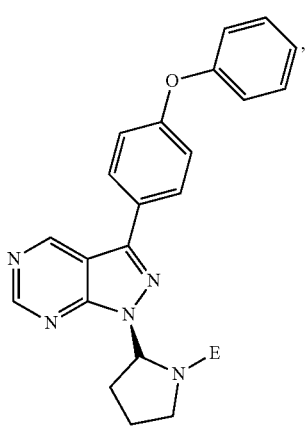

wherein E is as described herein. In embodiments, the compound has the formula:

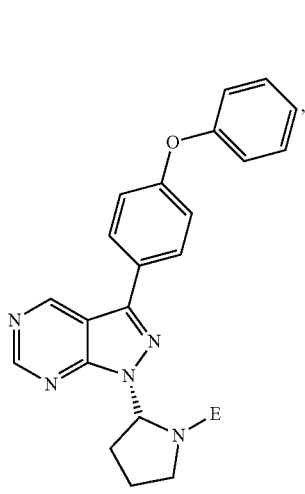

wherein E is as described herein.

In embodiments, the compound has the formula:

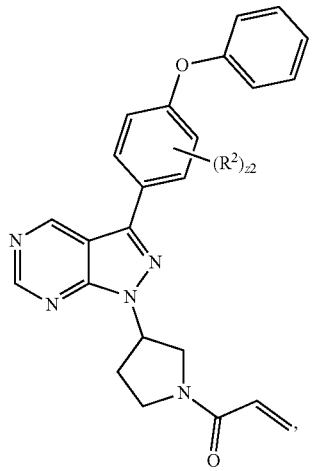

wherein $R^2$ and z2 are as described herein. In embodiments, the compound has the formula:

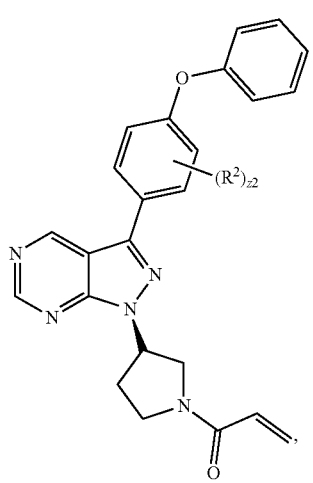

wherein $R^2$ and z2 are as described herein. In embodiments, the compound has the formula:

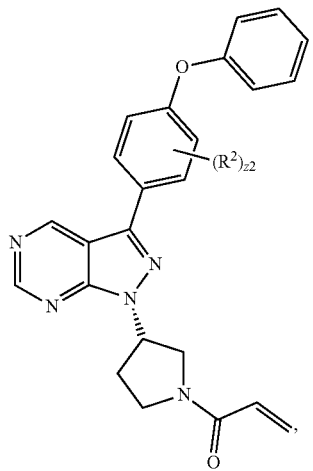

wherein $R^2$ and z2 are as described herein.

In embodiments, the compound has the formula:

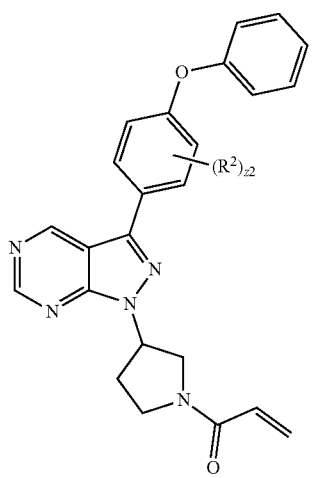

wherein $R^2$ and z2 are as described herein. In embodiments, the compound has the formula:


wherein $R^2$ and z2 are as described herein.

In embodiments, the compound has the formula:

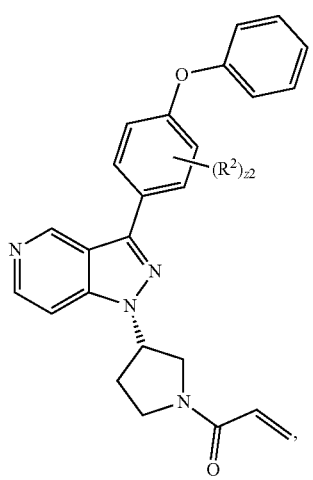

wherein $R^2$ and z2 are as described herein.

In embodiments, the compound has the formula:

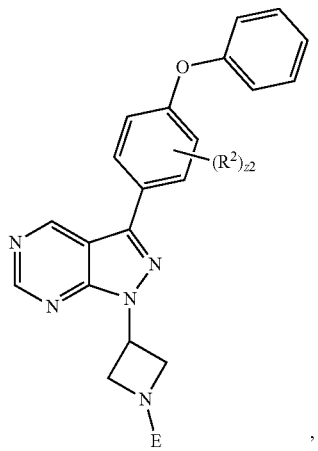

wherein $R^2$, z2, and E are as described herein.

In embodiments, the compound has the formula:

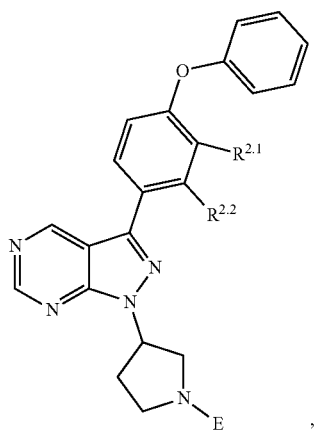

wherein E is as described herein. $R^{2.1}$ and $R^{2.2}$ are each $R^1$ at a fixed position on the attached ring. $R^{2.1}$ and $R^{2.2}$ may be any substituent of $R^2$ described herein, including in any aspect, embodiment, example, FIGURE, or claim. In embodiments, the compound has the formula:

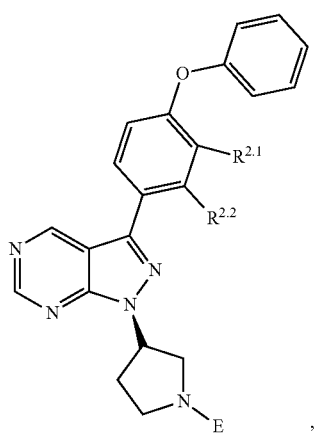

wherein E is as described herein. $R^{2.1}$ and $R^{2.2}$ are each $R^1$ at a fixed position on the attached ring. $R^{2.1}$ and $R^{2.2}$ may be any substituent of $R^2$ described herein, including in any aspect, embodiment, example, FIGURE, or claim. In embodiments, the compound has the formula:

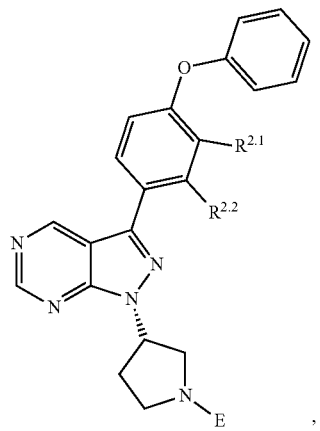

wherein E is as described herein. $R^{2.1}$ and $R^{2.2}$ are each $R^1$ at a fixed position on the attached ring. $R^{2.1}$ and $R^{2.2}$ may be any substituent of $R^2$ described herein, including in any aspect, embodiment, example, FIGURE, or claim.

In embodiments, the compound has the formula:

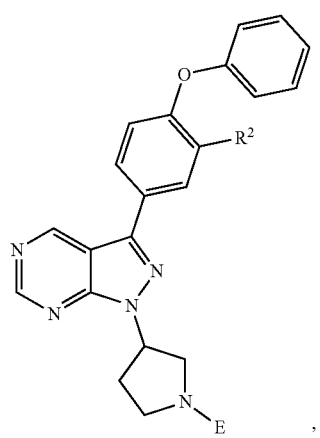

wherein $R^2$ and E are as described herein. In embodiments, the compound has the formula:

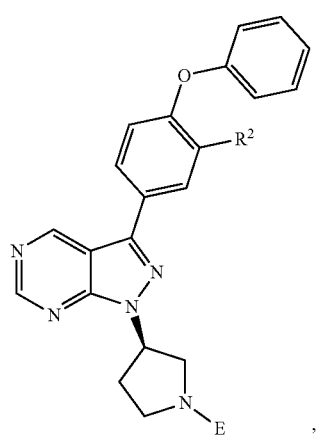

wherein $R^2$ and E are as described herein. In embodiments, the compound has the formula:

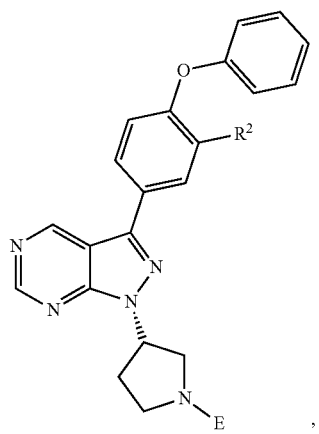

wherein $R^2$ and E are as described herein.

In embodiments, the compound has the formula:

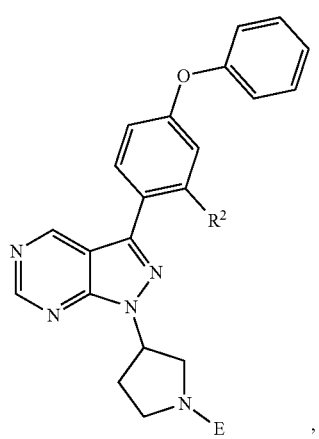

Wherein $R^2$ and E are as described herein. In embodiments, the compound has the formula:

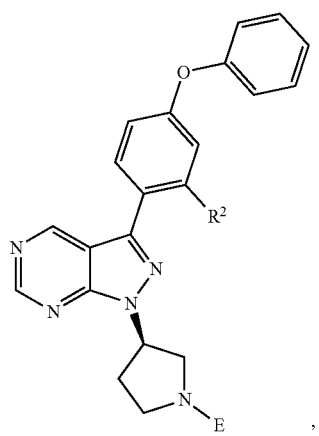

wherein $R^2$ and E are as described herein. In embodiments, the compound has the formula:

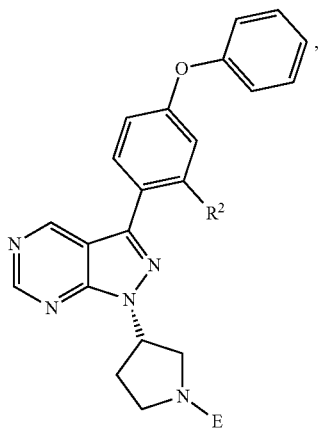

wherein R² and E are as described herein.

In embodiments, the compound has the formula:

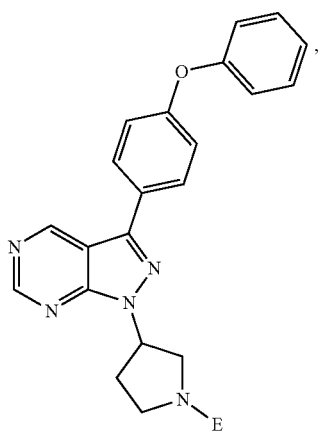

wherein E is as described herein. In embodiments, the compound has the formula:

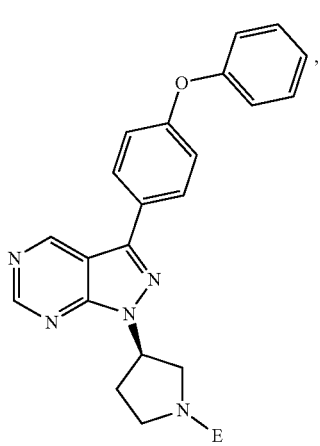

wherein E is as described herein. In embodiments, the compound has the formula:

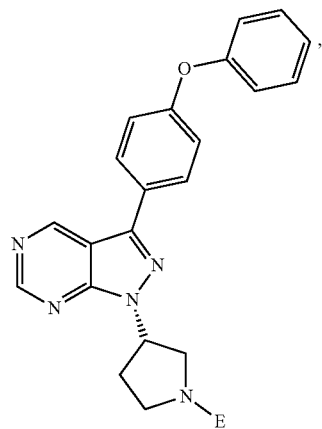

wherein E is as described herein.

In embodiments, the compound has the formula:

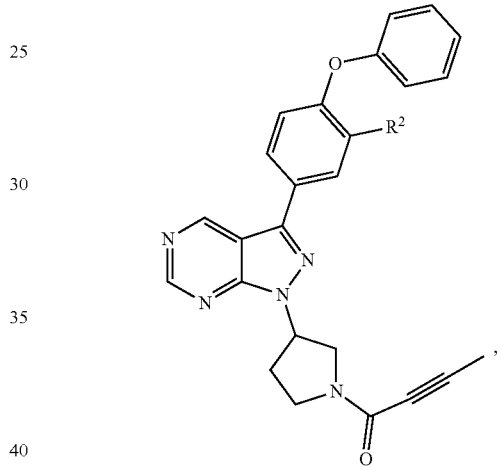

wherein R² and E are as described herein. In embodiments, the compound has the formula:

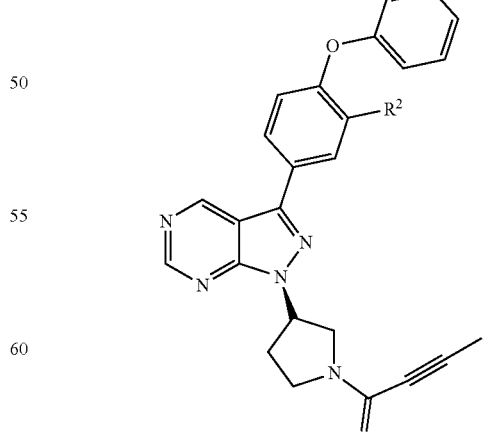

wherein R² and E are as described herein. In embodiments, the compound has the formula:

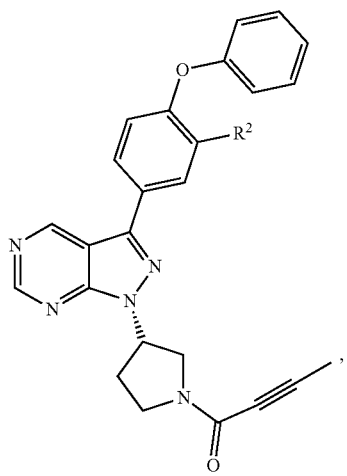

wherein R² and E are as described herein.
In embodiments, the compound has the formula:

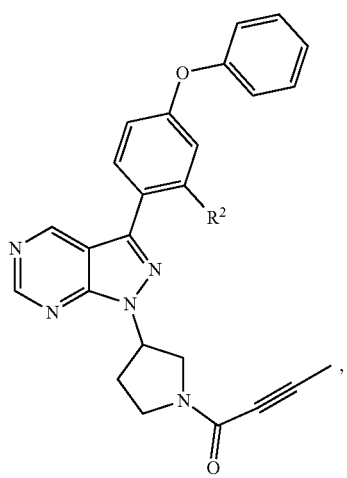

wherein R² and E are as described herein. In embodiments, the compound has the formula:

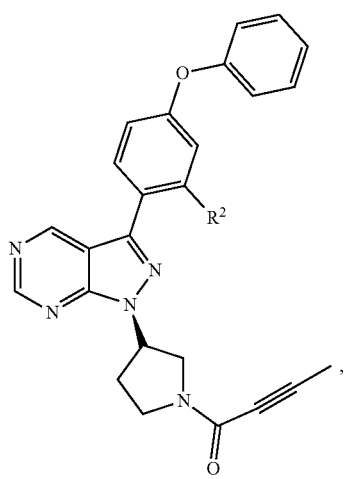

wherein R² and E are as described herein. In embodiments, the compound has the formula:

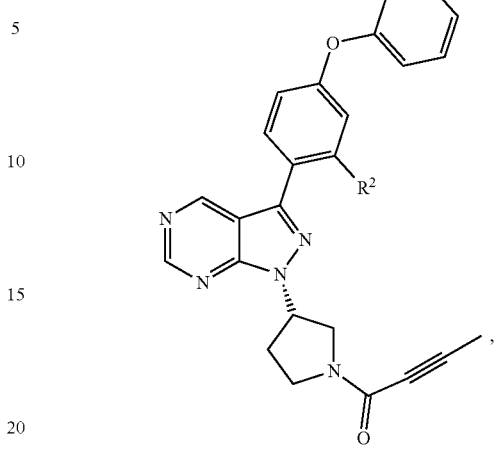

wherein R² and E are as described herein.
In embodiments, the compound has the formula:

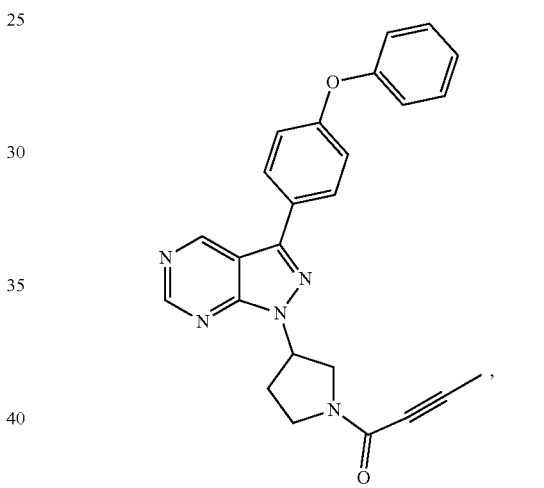

wherein E is as described herein. In embodiments, the compound has the formula:

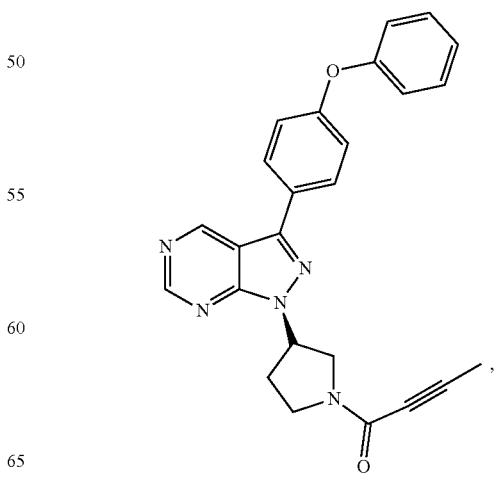

wherein E is as described herein. In embodiments, the compound has the formula:

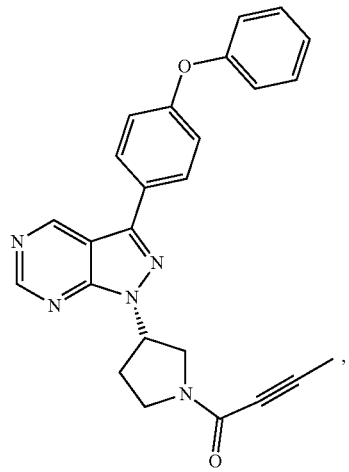

wherein E is as described herein.
In embodiments, the compound has the formula:

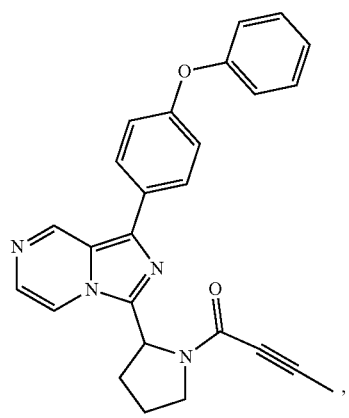

wherein E is as described herein. In embodiments, the compound has the formula:

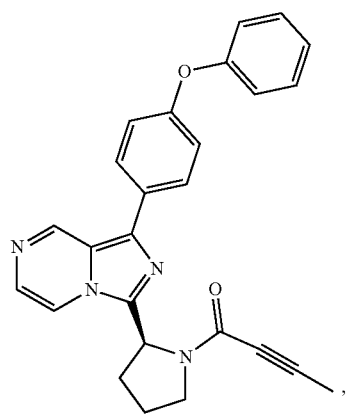

wherein E is as described herein. In embodiments, the compound has the formula:

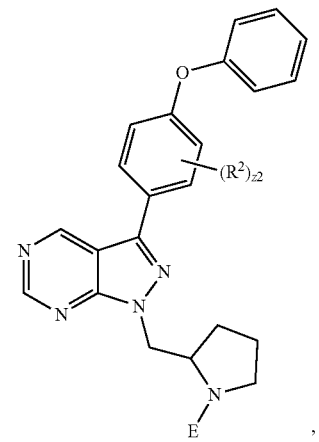

wherein E is as described herein.
In embodiments, the compound has the formula:

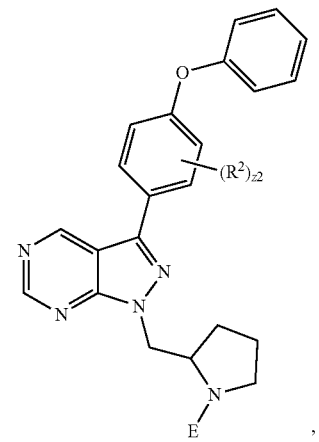

wherein $R^2$, z2, and E are as described herein. In embodiments, the compound has the formula:

wherein $R^2$, z2, and E are as described herein. In embodiments, the compound has the formula:

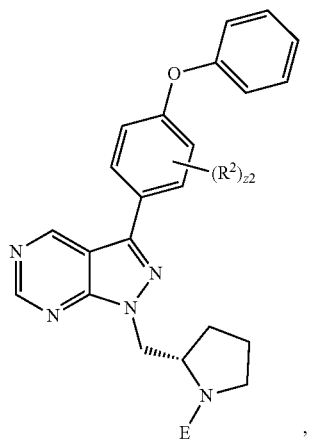

wherein $R^2$, z2, and E are as described herein.

In embodiments, the compound has the formula:

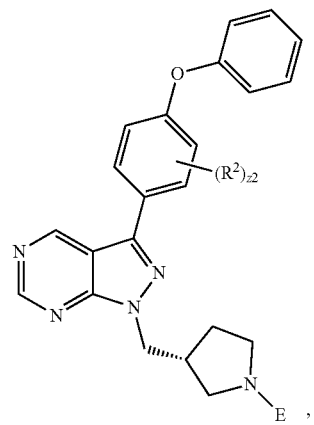

wherein $R^2$, z2, and E are as described herein.

In embodiments, the compound has the formula:

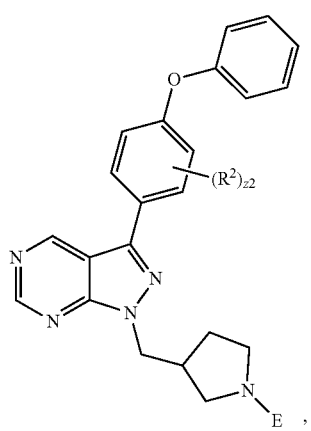

wherein $R^2$, z2, and E are as described herein. In embodiments, the compound has the formula:

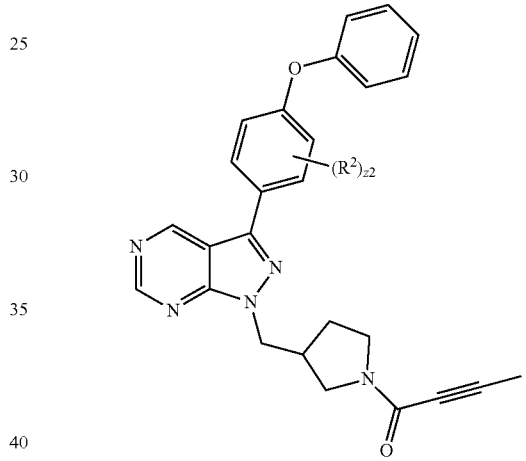

wherein $R^2$ and z2 are as described herein. In embodiments, the compound has the formula:

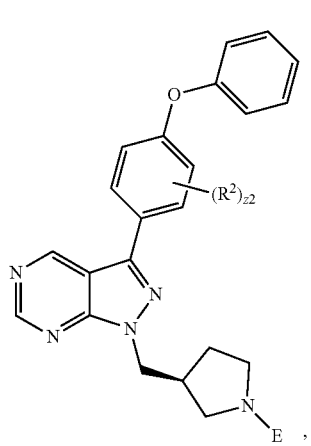

wherein $R^2$, z2, and E are as described herein. In embodiments, the compound has the formula:

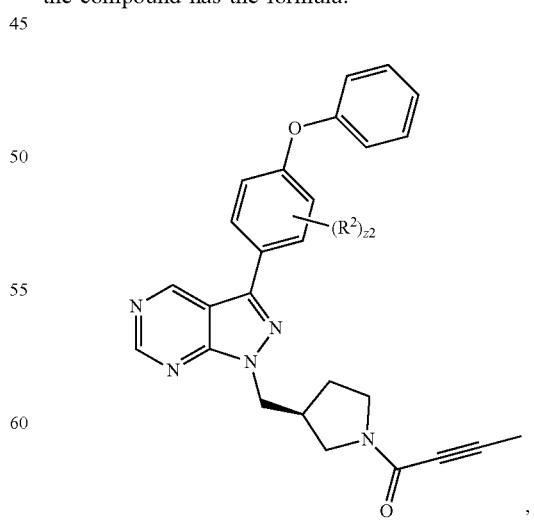

wherein $R^2$ and z2 are as described herein. In embodiments, the compound has the formula:

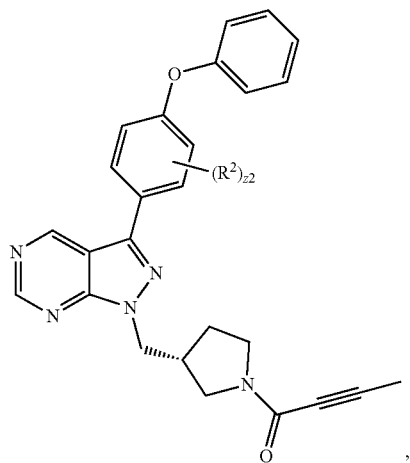
wherein R² and z2 are as described herein.
In embodiments, the compound has the formula:
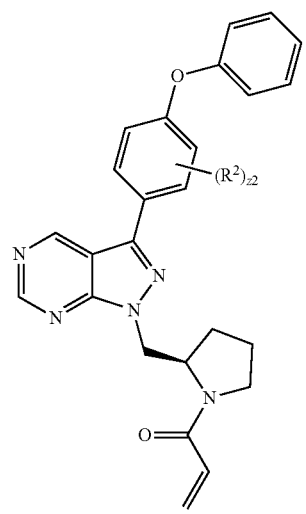
wherein R² and z2 are as described herein. In embodiments, the compound has the formula:
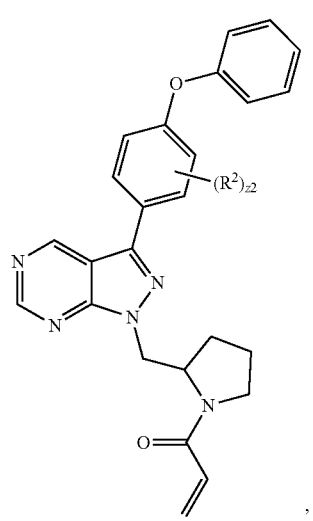
wherein R² and z2 are as described herein. In embodiments, the compound has the formula:
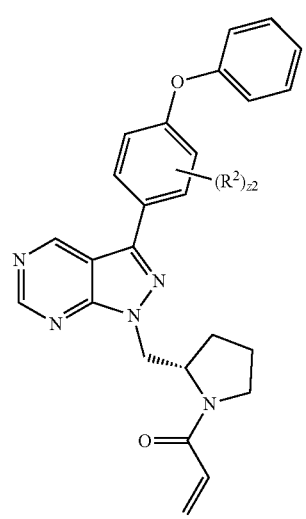
wherein R² and z2 are as described herein.

In embodiments, the compound has the formula:

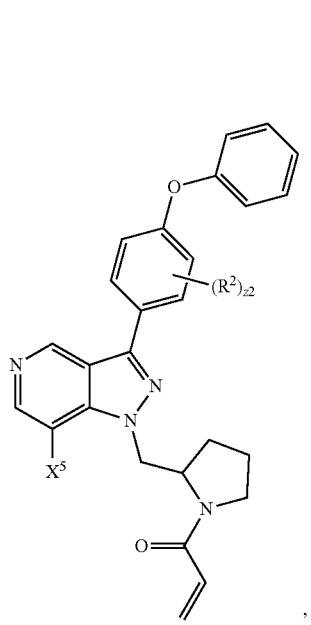

wherein $X^5$, $R^2$ and z2 are as described herein. In embodiments, the compound has the formula:

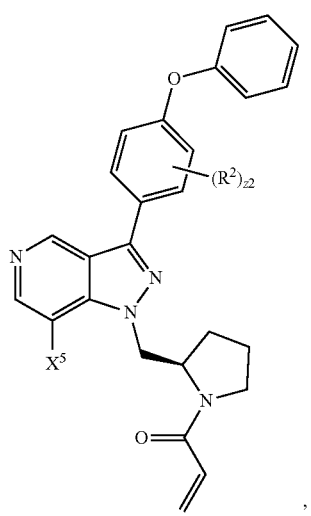

wherein $X^5$, $R^2$ and z2 are as described herein. In embodiments, the compound has the formula:

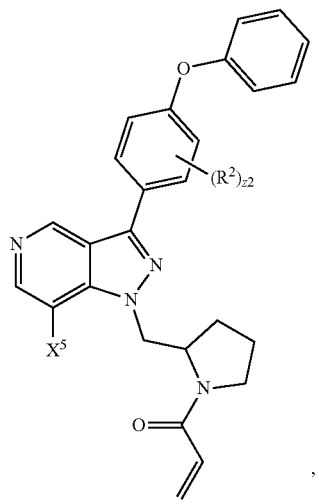

wherein $X^5$, $R^2$ and z2 are as described herein.

In embodiments, the compound has the formula:

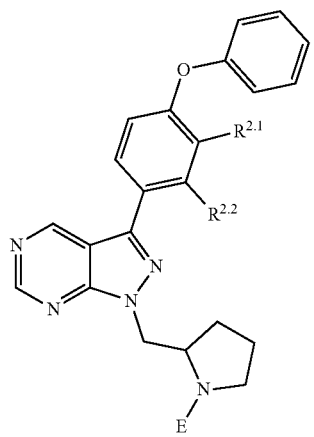

wherein E is as described herein. $R^{2.1}$ and $R^{2.2}$ are each $R^1$ at a fixed position on the attached ring. $R^{2.1}$ and $R^{2.2}$ may be any substituent of $R^2$ described herein, including in any aspect, embodiment, example, FIGURE, or claim. In embodiments, the compound has the formula:

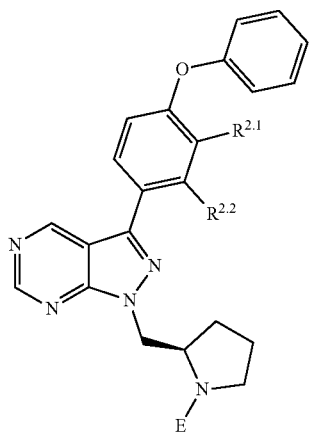

wherein E is as described herein. $R^{2.1}$ and $R^{2.2}$ are each $R^1$ at a fixed position on the attached ring. $R^{2.1}$ and $R^{2.2}$ may be any substituent of $R^2$ described herein, including in any aspect, embodiment, example, FIGURE, or claim. In embodiments, the compound has the formula:

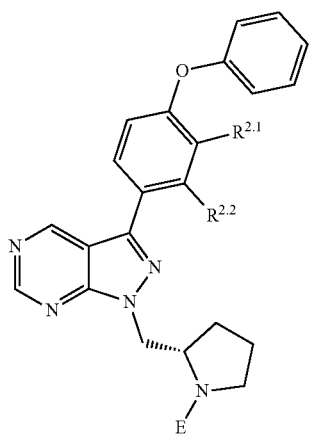

, wherein E is as described herein. $R^{2.1}$ and $R^{2.2}$ are each $R^1$ at a fixed position on the attached ring. $R^{2.1}$ and $R^{2.2}$ may be any substituent of $R^2$ described herein, including in any aspect, embodiment, example, FIGURE, or claim.

In embodiments, the compound has the formula:

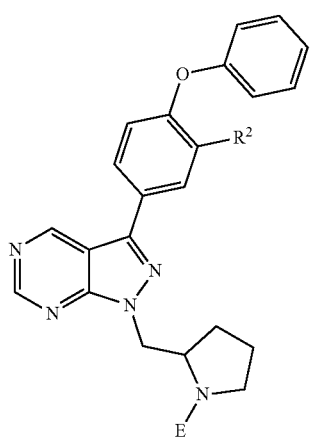

, wherein $R^2$ and E are as described herein. In embodiments, the compound has the formula:

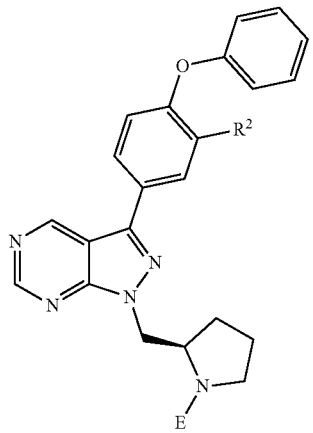

, wherein $R^2$ and E are as described herein. In embodiments, the compound has the formula:

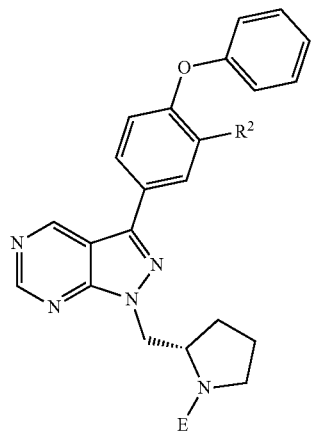
wherein R² and E are as described herein.
In embodiments, the compound has the formula:
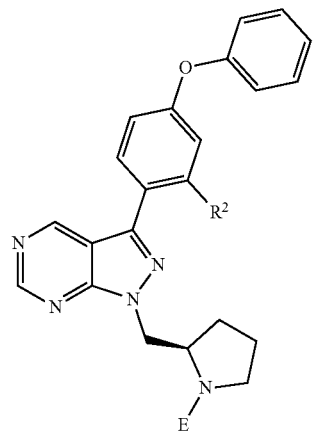
wherein R² and E are as described herein. In embodiments, the compound has the formula:
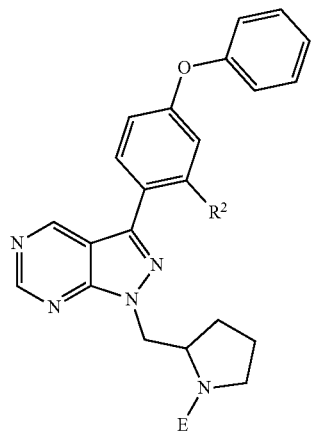
wherein R² and E are as described herein. In embodiments, the compound has the formula:
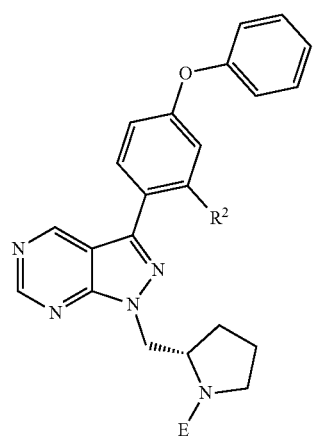
wherein R² and E are as described herein.

In embodiments, the compound has the formula:
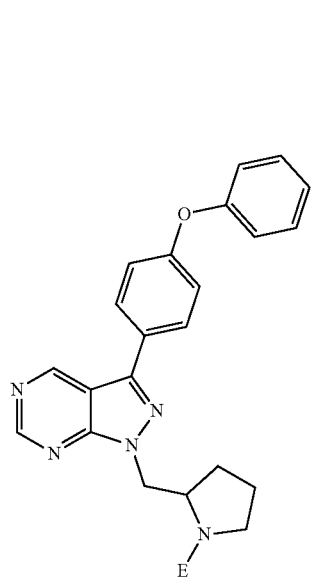
wherein E is as described herein. In embodiments, the compound has the formula:
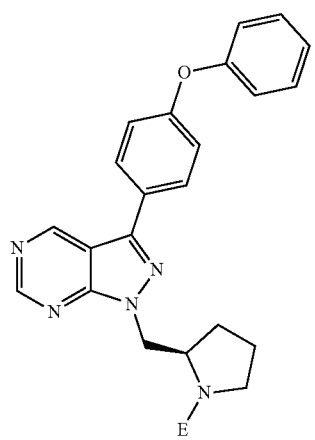
wherein E is as described herein. In embodiments, the compound has the formula:
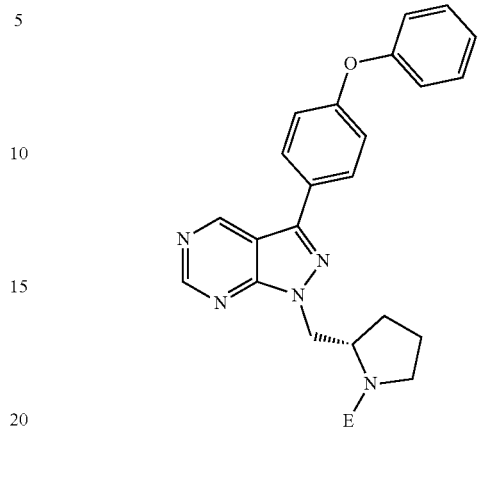
wherein E is as described herein.
In embodiments, the compound has the formula:
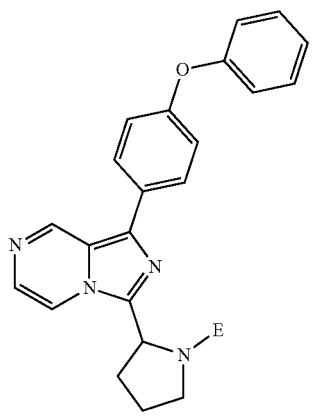
wherein E is as described herein. In embodiments, the compound has the formula:

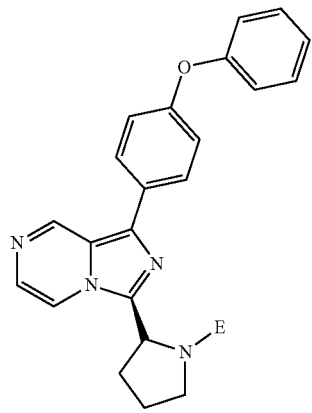
, wherein E is as described herein. In embodiments, the compound has the formula:

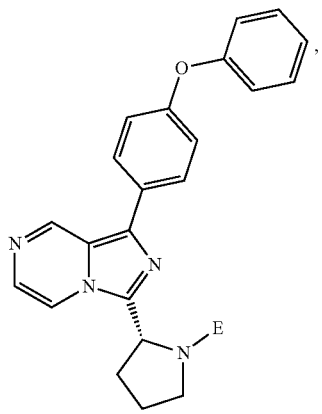
, wherein E is as described herein.

In embodiments, the compound has the formula:

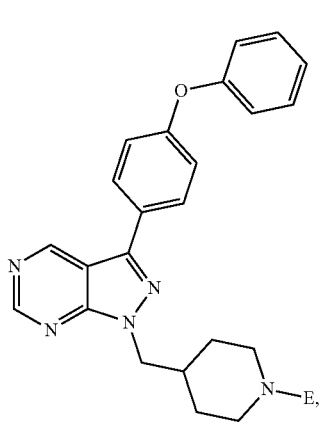
, wherein E is as described herein.

In embodiments, the compound has the formula:

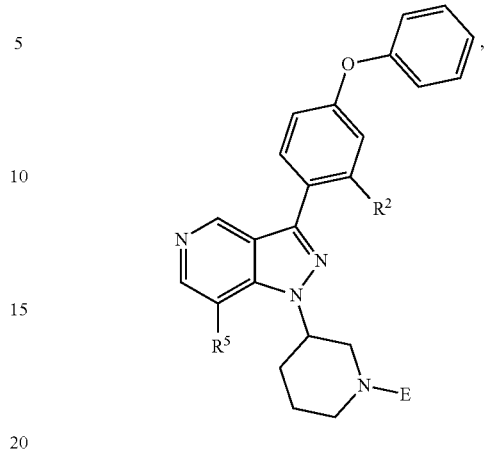
, wherein $R^2$, $R^5$, and E are as described herein. In embodiments, the compound has the formula:

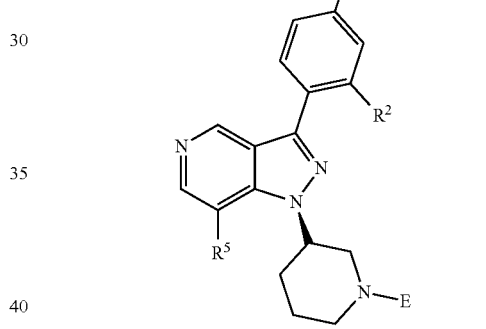
, wherein $R^2$, $R^5$, and E are a described herein. In embodiments, the compound has the formula:

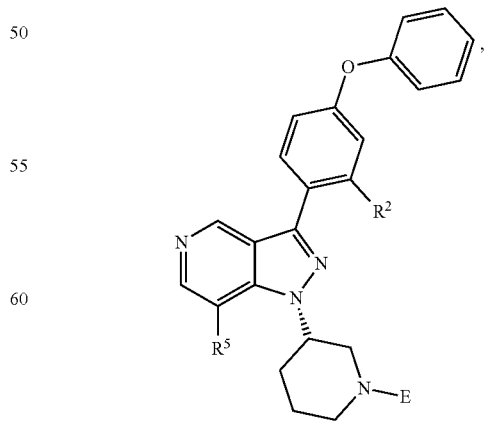
, wherein $R^2$, $R^5$, and E are as described herein.

In embodiments, the compound has the formula:

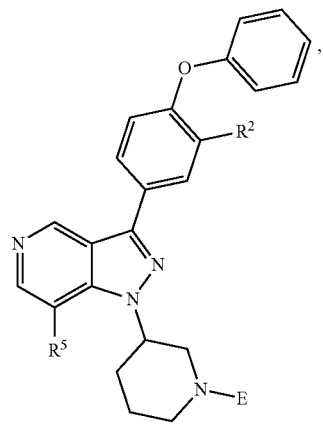

wherein $R^2$, $R^5$, and E are as described herein. In embodiments, the compound has the formula:

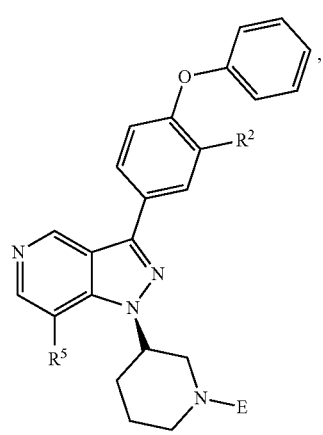

wherein $R^2$, $R^5$, and E are as described herein. In embodiments, the compound has the formula:

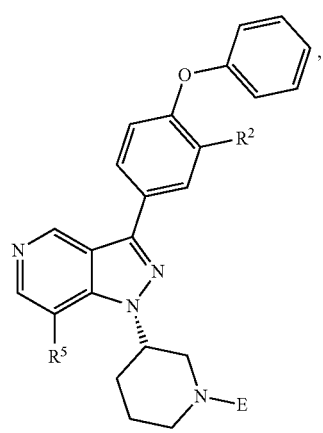

wherein $R^2$, $R^5$, and E are as described herein.

In embodiments, the compound has the formula:

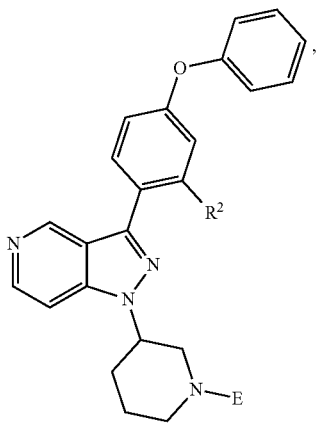

wherein $R^2$ and E are as described herein. In embodiments, the compound has the formula:

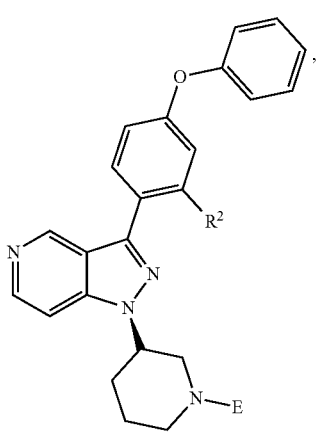

wherein $R^2$ and E are as described herein. In embodiments, the compound has the formula:

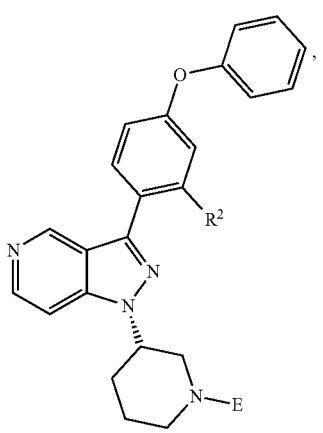

$R^2$ and E are as described herein.

In embodiments, the compound has the formula:

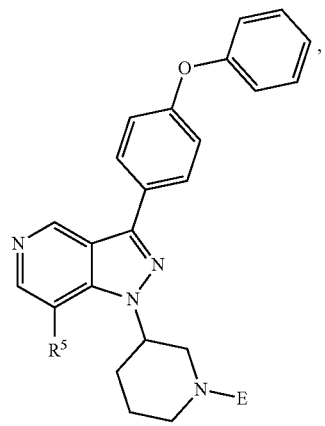

wherein $R^5$ and E are as described herein. In embodiments, the compound has the formula:

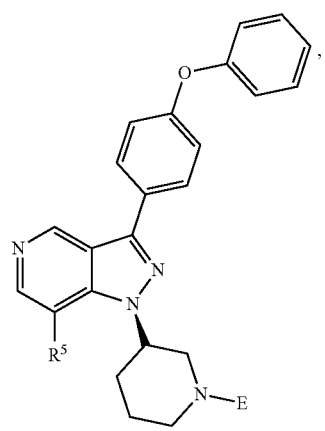

wherein $R^5$ and E are as described herein. In embodiments, the compound has the formula:

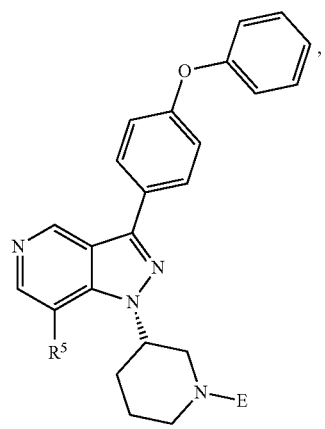

wherein $R^5$ and E are as described herein.

In embodiments, the compound has the formula:

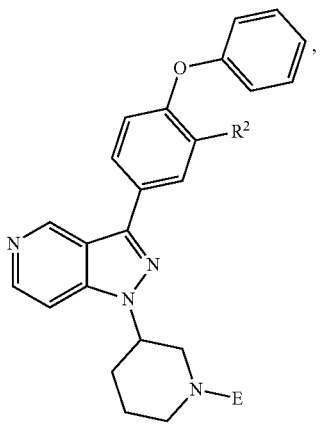

wherein $R^2$ and E are as described herein. In embodiments, the compound has the formula:

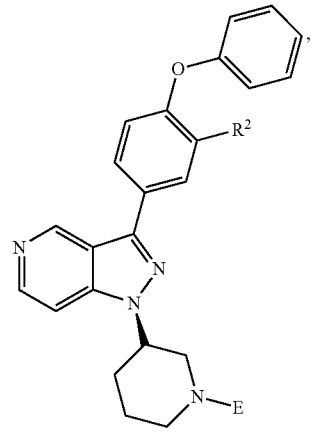

wherein $R^2$ and E are as described herein. In embodiments, the compound has the formula:

wherein $R^2$ and E are as described herein.

In embodiments, the compound has the formula:

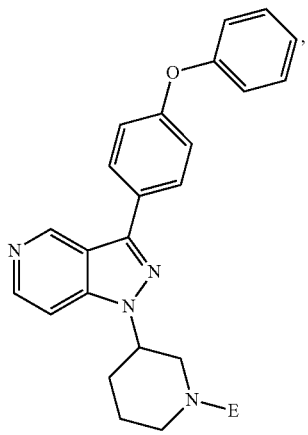

wherein $R^2$, $R^5$, and E are as described herein. In embodiments, the compound has the formula:

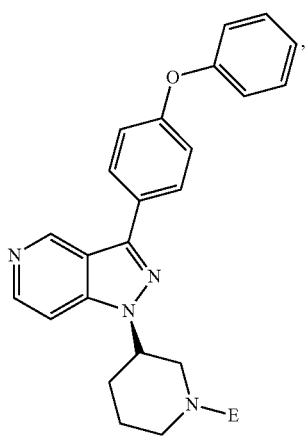

wherein $R^2$, $R^5$, and E are as described herein. In embodiments, the compound has the formula:

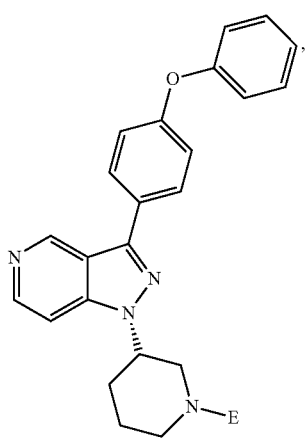

wherein $R^2$, R, and E are as described herein.

In embodiments, the compound has the formula:

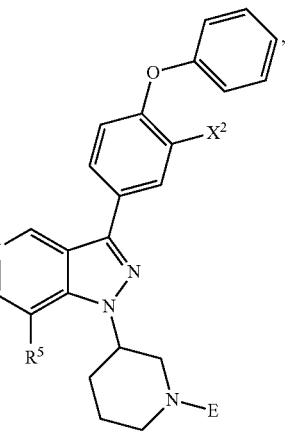

wherein $X^2$, $R^5$, and E are as described herein. In embodiments, the compound has the formula:

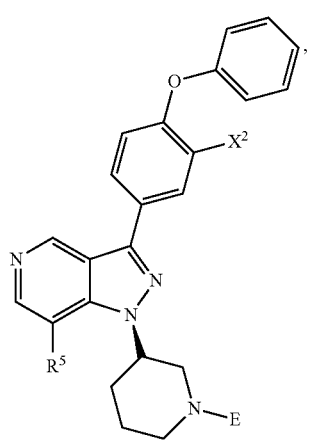

wherein $X^2$, $R^5$, and E are as described herein. In embodiments, the compound has the formula:

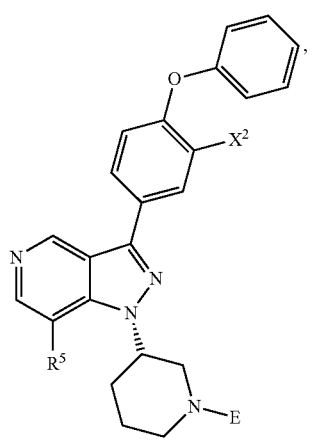

wherein $X^2$, $R^5$, and E are as described herein.

In embodiments, the compound has the formula:

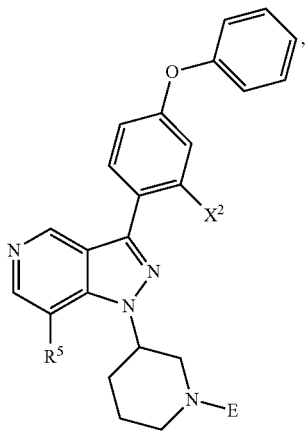

wherein $X^2$, $R^5$, and E are as described herein. In embodiments, the compound has the formula:

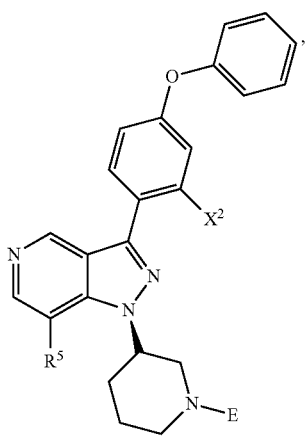

wherein $X^2$, $R^5$, and E are as described herein. In embodiments, the compound has the formula:

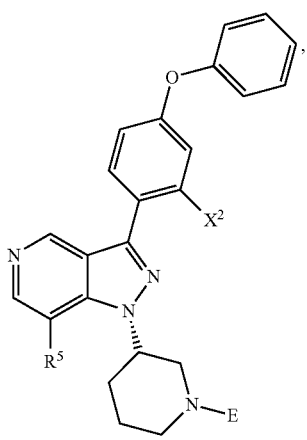

wherein $X^2$, $R^5$, and E are as described herein.

In embodiments, the compound has the formula:

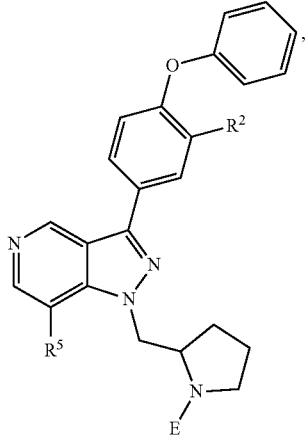

wherein $R^2$, $R^5$, and E are as described herein. In embodiments, the compound has the formula:

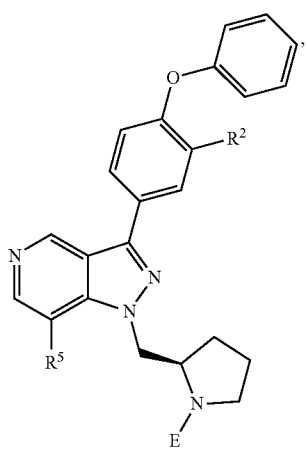

wherein $R^2$, $R^5$, and E are as described herein. In embodiments, the compound has the formula:

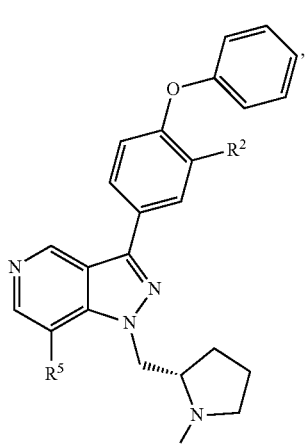

wherein $R^2$, $R^5$, and E are as described herein.

In embodiments, the compound has the formula:

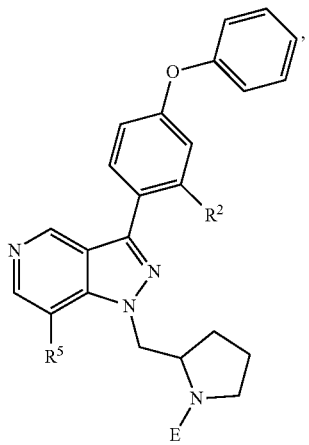

wherein $R^2$, $R^5$, and E are as described herein. In embodiments, the compound has the formula:

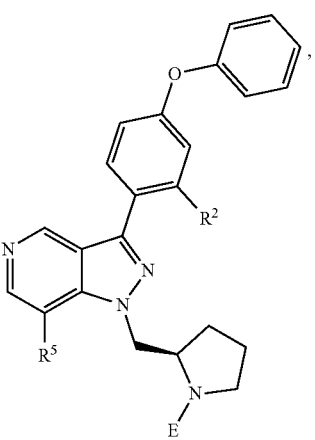

wherein $R^2$, $R^5$, and E are as described herein. In embodiments, the compound has the formula:

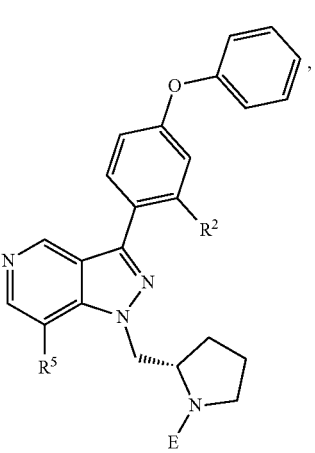

wherein $R^2$, $R^5$, and E are as described herein.

In embodiments, the compound has the formula:

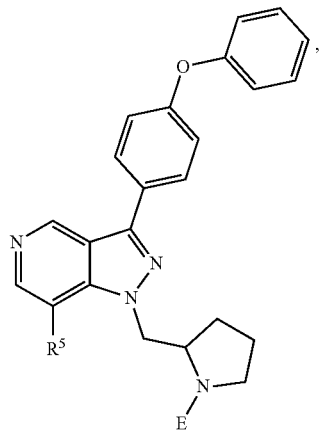

wherein $R^5$ and E are as described herein. In embodiments, the compound has the formula:

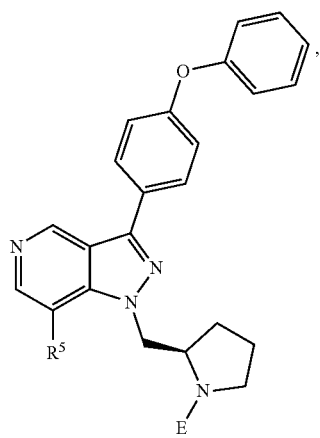

wherein $R^5$ and E are as described herein. In embodiments, the compound has the formula:

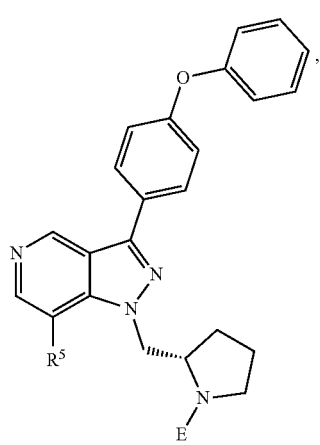

wherein $R^5$ and E are as described herein.

In embodiments, the compound has the formula:

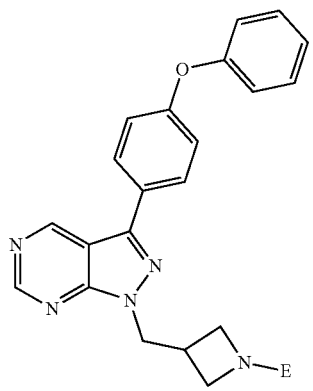 or wherein E is as described herein.

In embodiments, the compound has the formula:

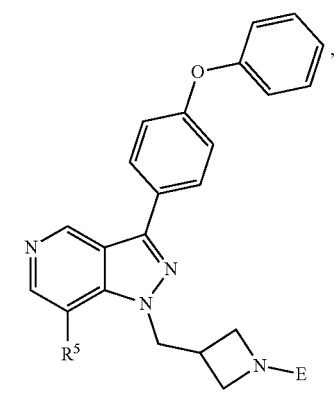

wherein R⁵ and E are as described herein.

In embodiments, the compound has the formula:

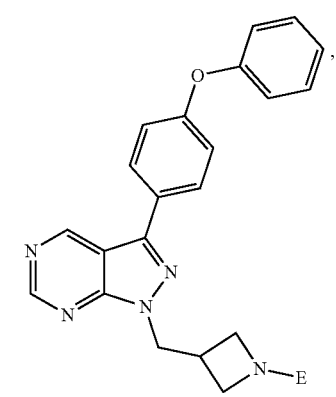

wherein E is as described herein.

In embodiments, the compound has the formula:

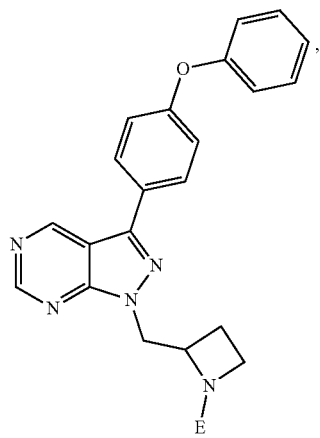

wherein E is as described herein.

In embodiments, the compound has the formula:

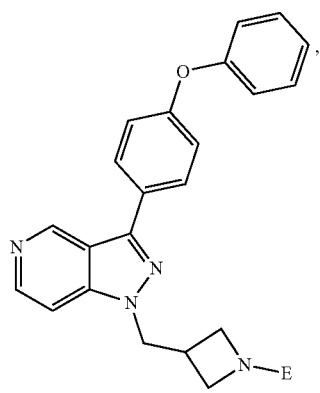

wherein E is as described herein.

In embodiments, the compound has the formula:

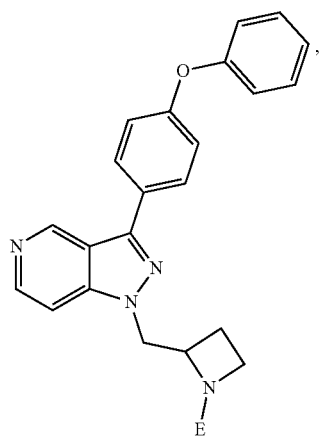

wherein E is as described herein.

In embodiments, the compound has the formula:
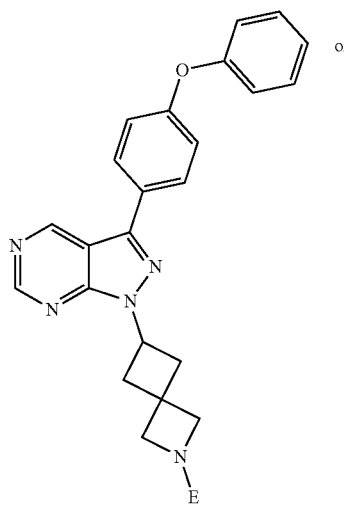
or
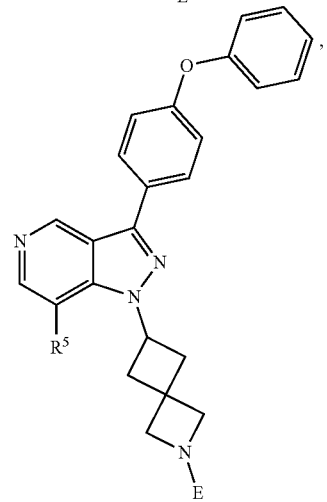
wherein R⁵ and E are as described herein.
In embodiments, the compound has the formula:
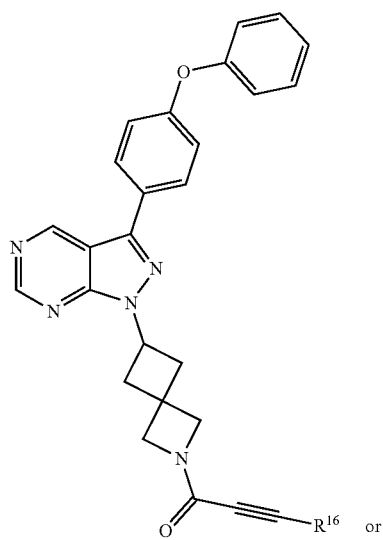
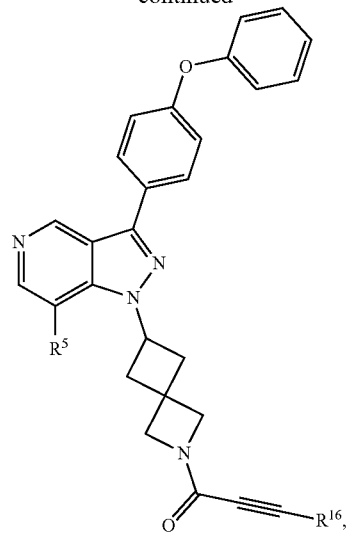
wherein R⁵ and R¹⁶ are as described herein.
In embodiments, the compound has the formula:
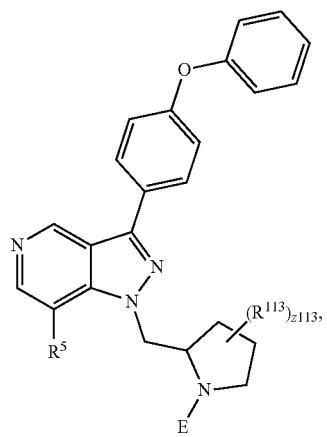
wherein R⁵, R¹¹³, and E are as described herein. The symbol z113 is an integer from 0 to 7. In embodiments, the compound has the formula:
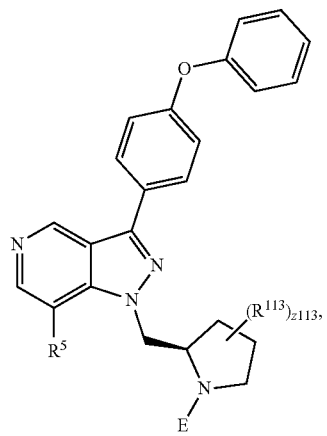

wherein $R^5$, $R^{113}$, and E are as described herein. The symbol z113 is an integer from 0 to 7. In embodiments, the compound has the formula:

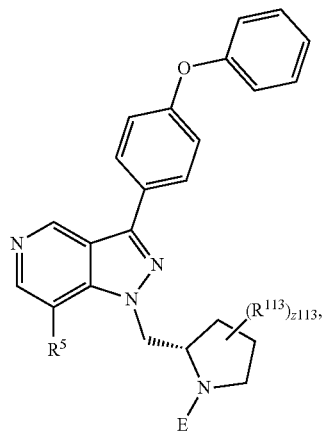

wherein $R^5$, $R^{113}$, and E are as described herein. The symbol z113 is an integer from 0 to 7.

In embodiments, the compound has the formula:

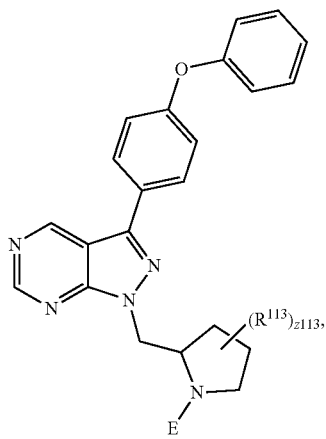

wherein $R^{113}$ and E are as described herein. The symbol z113 is an integer from 0 to 7. In embodiments, the compound has the formula:

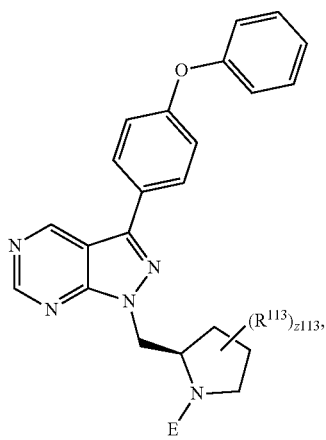

wherein $R^{113}$ and E are as described herein. The symbol z113 is an integer from 0 to 7. In embodiments, the compound has the formula:

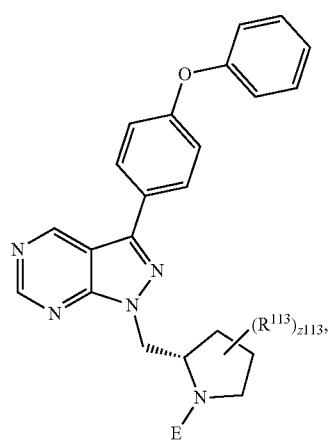

wherein $R^{113}$ and E are as described herein. The symbol z113 is an integer from 0 to 7.

In embodiments, the compound has the formula:

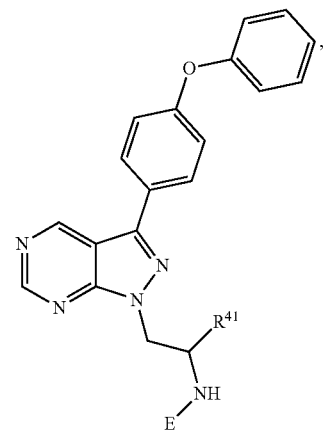

wherein $R^{41}$ and E are as described herein.

In embodiments, the compound has the formula:

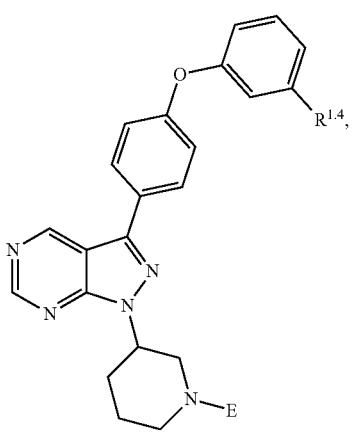

wherein E is as described herein. $R^{1.4}$ is an $R^1$ at a fixed position on the attached ring. $R^{1.4}$ may be any substituent of $R^1$ described herein, including in any aspect, embodiment, example, FIGURE, or claim. In embodiments, the compound has the formula:

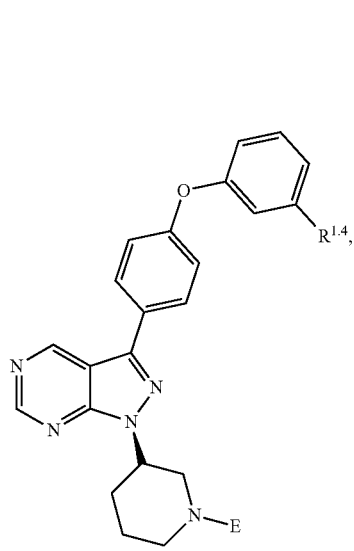

wherein E is as described herein. $R^{1.4}$ is an $R^1$ at a fixed position on the attached ring. $R^{1.4}$ may be any substituent of $R^1$ described herein, including in any aspect, embodiment, example, FIGURE, or claim. In embodiments, the compound has the formula:

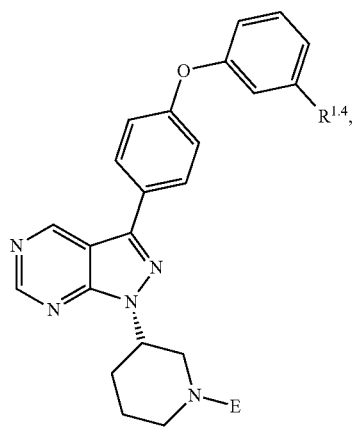

wherein E is as described herein. $R^{1.4}$ is an $R^1$ at a fixed position on the attached ring. $R^{1.4}$ may be any substituent of $R^1$ described herein, including in any aspect, embodiment, example, FIGURE, or claim.

In embodiments, the compound has the formula:

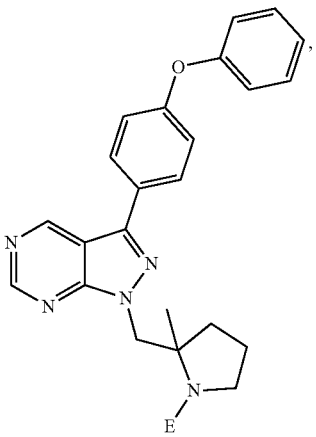

is as described herein.

In embodiments, the compound has the formula:

wherein $R^{113}$ and E are as described herein. The symbol z113 is an integer from 0 to 7. In embodiments, z113 is 0. In embodiments, z13 is 1. In embodiments, z113 is 2. In embodiments, z113 is 3. In embodiments, z113 is 4. In embodiments, z113 is 5. In embodiments, z113 is 6. In embodiments, z113 is 7. $R^{1.4}$ is an $R^1$ at a fixed position on the attached ring. $R^{1.4}$ may be any substituent of $R^1$ described herein, including in any aspect, embodiment, example, FIGURE, or claim. In embodiments, the compound has the formula:

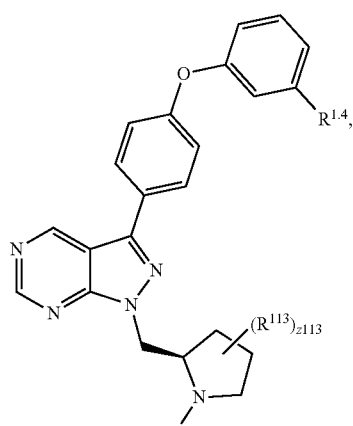

wherein $R^{113}$ and E areas described herein. The symbol z113 is an integer from 0 to 7. $R^{1.4}$ is an $R^1$ at a fixed position on the attached ring. $R^{1.4}$ may be any substituent of $R^1$ described herein, including in any aspect embodiment, example, FIGURE, or claim. In embodiments, the compound has the formula:

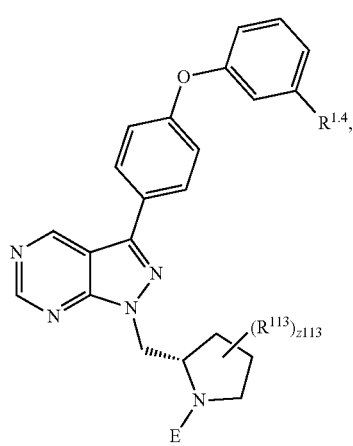

wherein $R^{113}$ and E are as described herein. The symbol z113 is an integer from 0 to 7. $R^{1.4}$ is an $R^1$ at a fixed position on the attached ring. $R^{1.4}$ may be any substituent of $R^1$ described herein, including in any aspect, embodiment, example, FIGURE, or claim.

In embodiments, the compound has the formula:

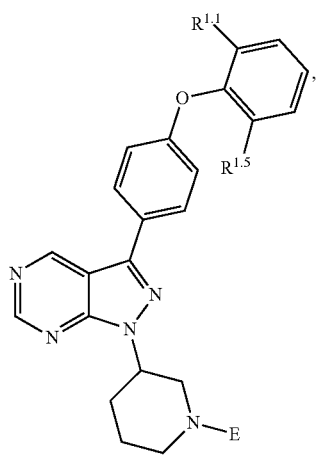

wherein E is as described herein. $R^{1.1}$ and $R^{1.5}$ are each $R^1$ at a fixed position on the attached ring. $R^{1.1}$ and $R^{1.5}$ may be independently any substituent of $R^1$ described herein, including in any aspect, embodiment, example, FIGURE, or claim. In embodiments, the compound has the formula:

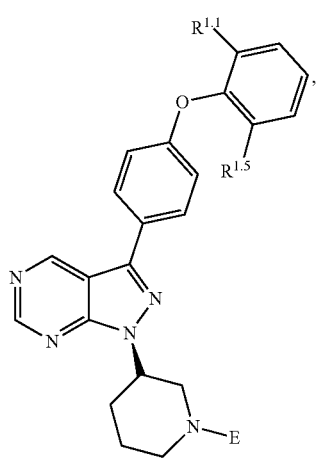

wherein E is as described herein. $R^{1.1}$ and $R^{1.5}$ are each $R^1$ at a fixed position on the attached ring. $R^{1.1}$ and $R^{1.5}$ may be independently any substituent of $R^1$ described herein, including in any aspect, embodiment, example, FIGURE, or claim. In embodiments, the compound has the formula:

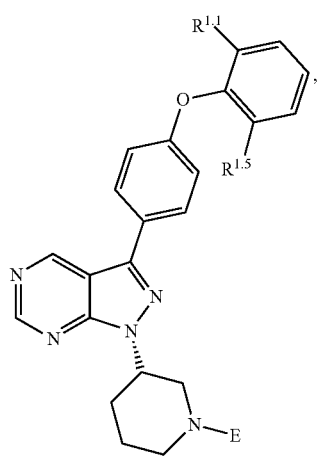

wherein E is as described herein. $R^{1.1}$ and $R^{1.5}$ are each $R^1$ at a fixed position on the attached ring. $R^{1.1}$ and $R^{1.5}$ may be independently any substituent of $R^1$ described herein, including in any aspect, embodiment, example, FIGURE, or claim.

In embodiments, the compound has the formula:

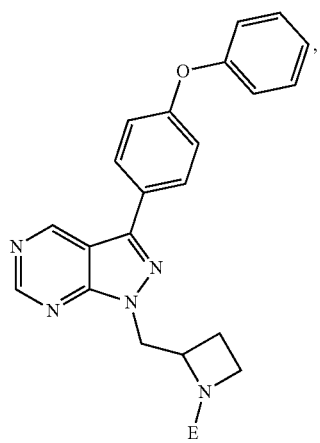

wherein E is as described herein. In embodiments, the compound has the formula:

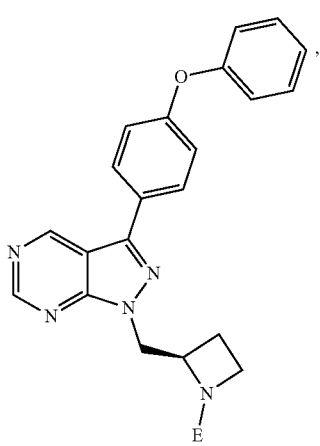

wherein E is as described herein. In embodiments, the compound has the formula:

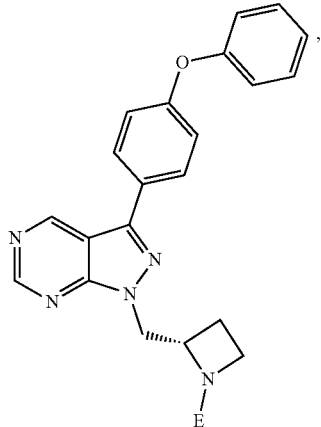

wherein E is as described herein.

In embodiments, the compound has the formula:

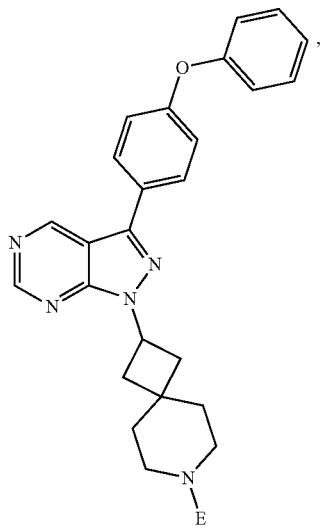

wherein E is as described herein.

In embodiments, the compound has the formula:

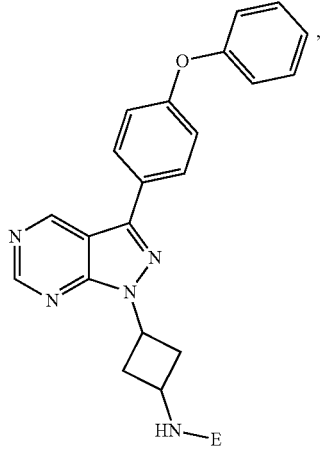

wherein E is as described herein.

313
In embodiments, the compound has the formula:
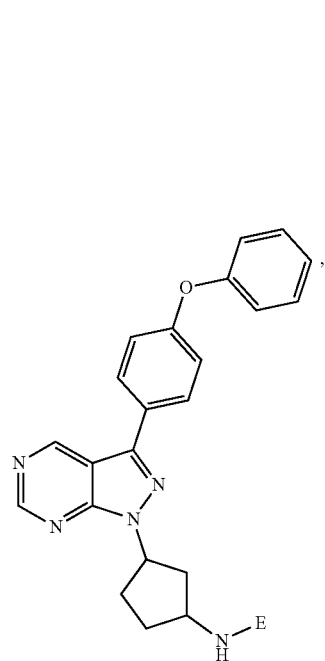
wherein E is as described herein.
In embodiments, the compound has the formula:
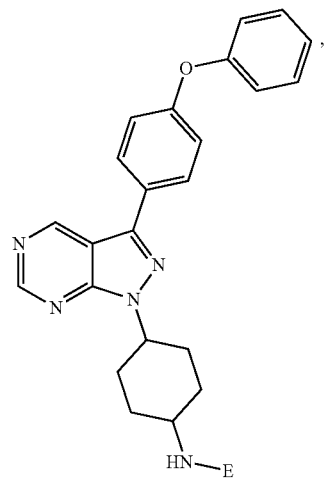
wherein E is as described herein.
314
In embodiments, the compound has the formula:
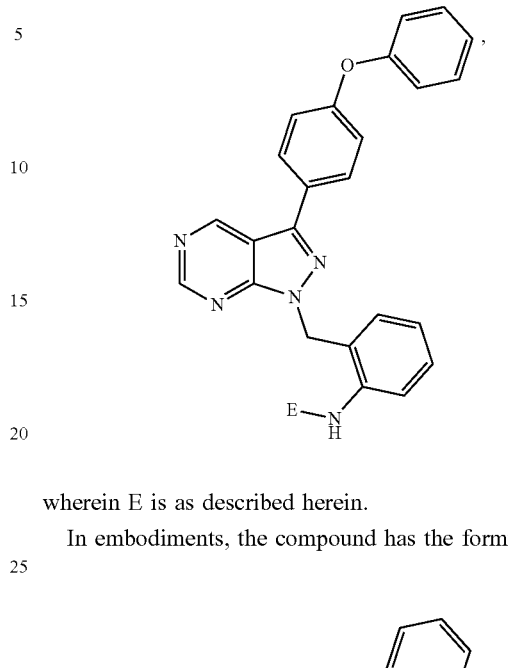
wherein E is as described herein.
In embodiments, the compound has the formula:
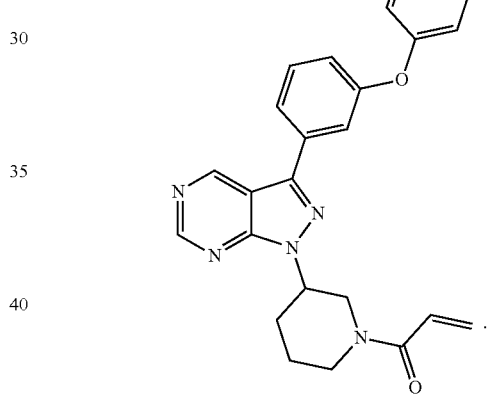
In embodiments, the compound has the formula:
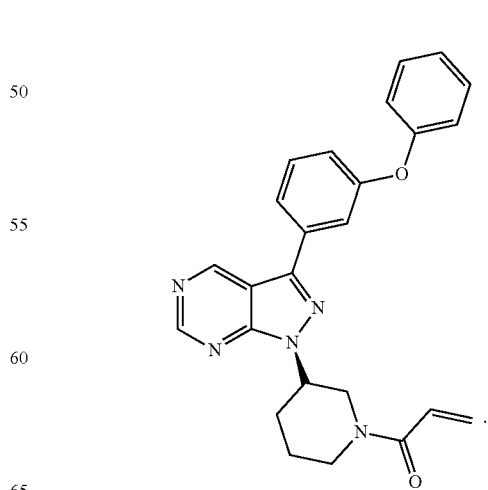

In embodiments, the compound has the formula:
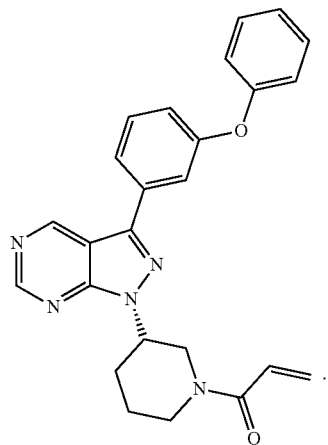
In embodiments, the compound has the formula:
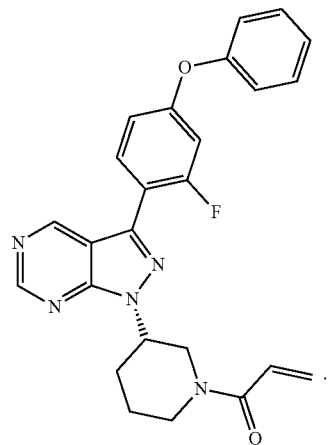
In embodiments, the compound has the formula:
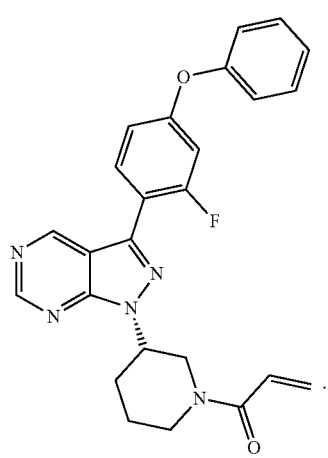
In embodiments, the compound has the formula:
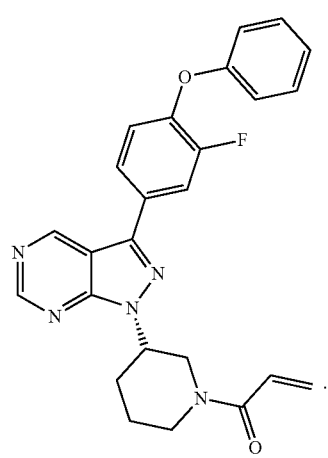
In embodiments, the compound has the formula:
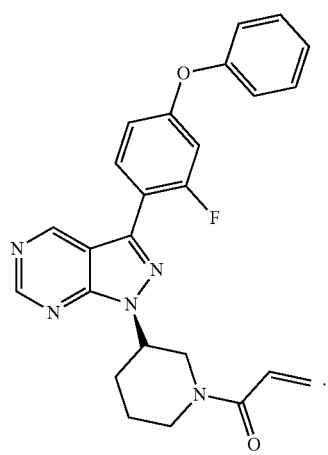
In embodiments, the compound has the formula:
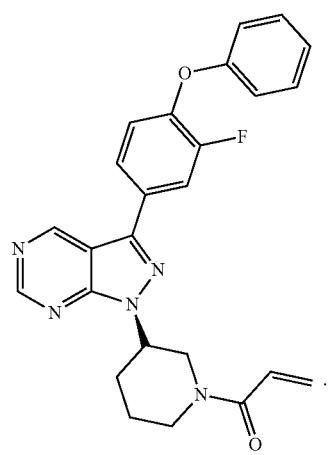

317
In embodiments, the compound has the formula:
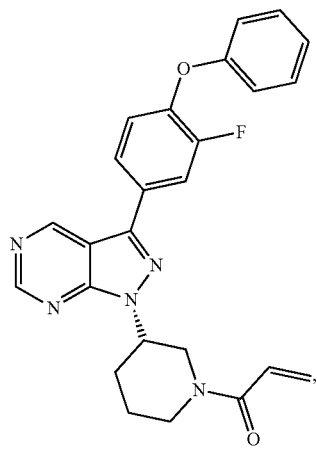
In embodiments, the compound has the formula:
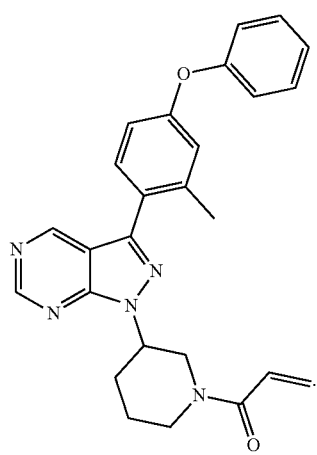 [SMILES: C=CC(=O)N1CCCC(n2nc(-c3ccc(Oc4ccccc4)cc3C)c3cncnc32)C1]
In embodiments, the compound has the formula:
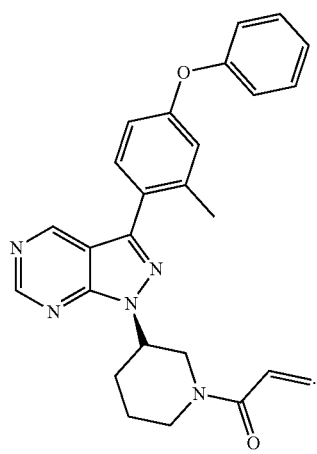
318
In embodiments, the compound has the formula:
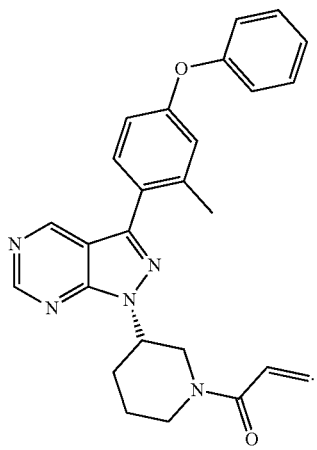
In embodiments, the compound has the formula:
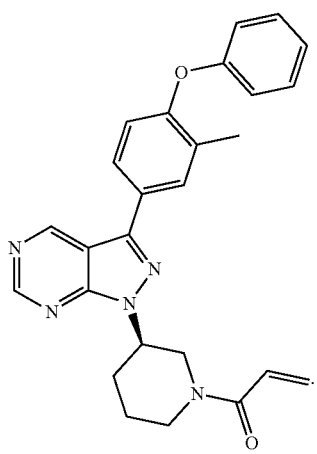
In embodiments, the compound has the formula:

In embodiments, the compound has the formula:
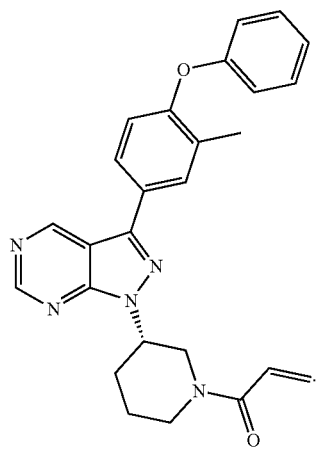
In embodiments, the compound has the formula:
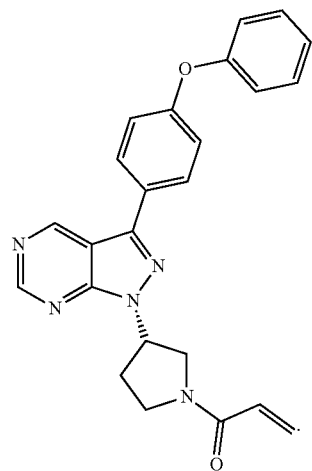
In embodiments, the compound has the formula:
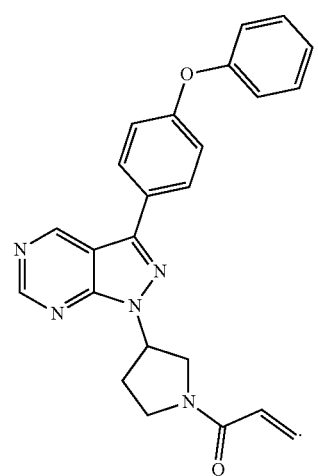
In embodiments, the compound has the formula:
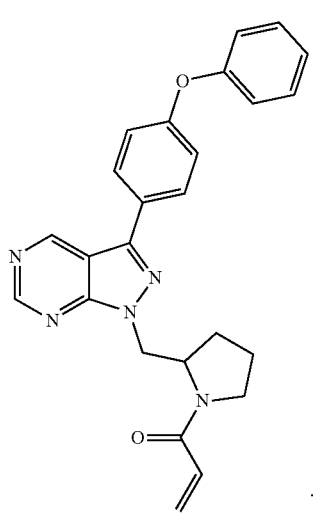
In embodiments, the compound has the formula:
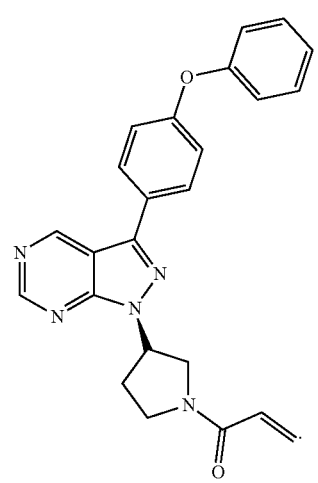
In embodiments, the compound has the formula:
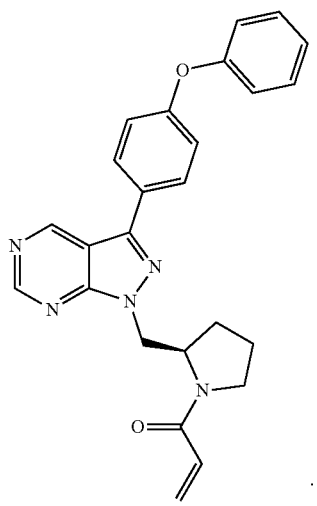

In embodiments, the compound has the formula:
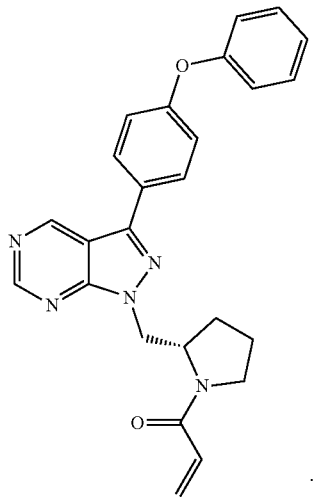
In embodiments, the compound has the formula:
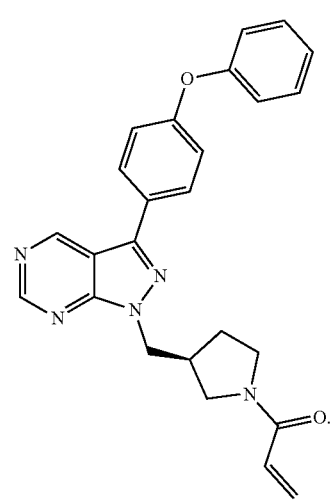
In embodiments, the compound has the formula:
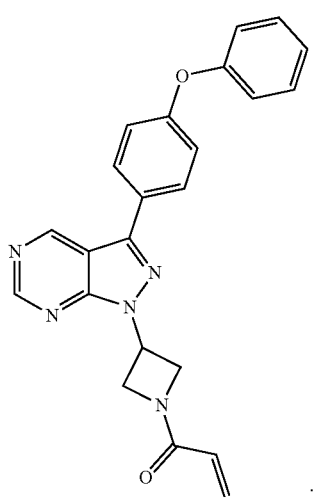 [SMILES: C=CC(=O)N1CC(n2nc(-c3ccc(Oc4ccccc4)cc3)c3cncnc32)C1]
In embodiments, the compound has the formula:
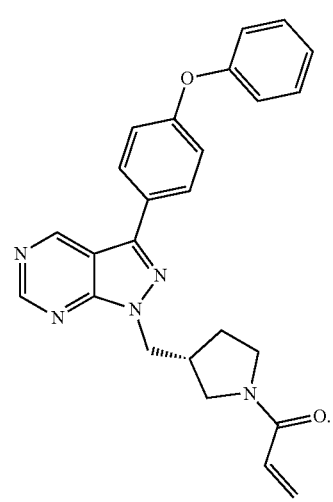 [SMILES: C=CC(=O)N1CCC(Cn2nc(-c3ccc(Oc4ccccc4)cc3)c3cncnc32)C1]
In embodiments, the compound has the formula:
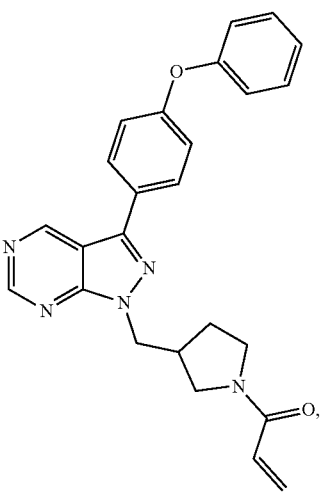
In embodiments, the compound has the formula:
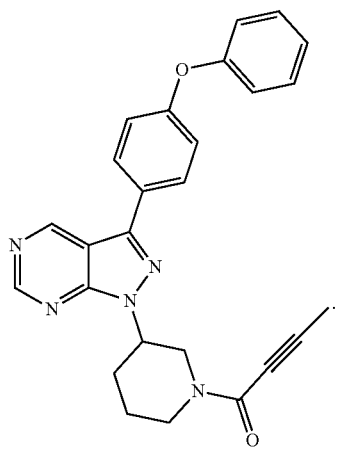 [SMILES: CC#CC(=O)N1CCCC(n2nc(-c3ccc(Oc4ccccc4)cc3)c3cncnc32)C1]

323
In embodiments, the compound has the formula:
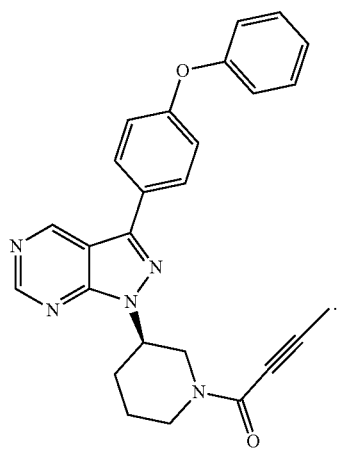 [SMILES: CC#CC(=O)N1CCC[C@@H](n2nc(-c3ccc(Oc4ccccc4)cc3)c3cncnc32)C1]
In embodiments, the compound has the formula:
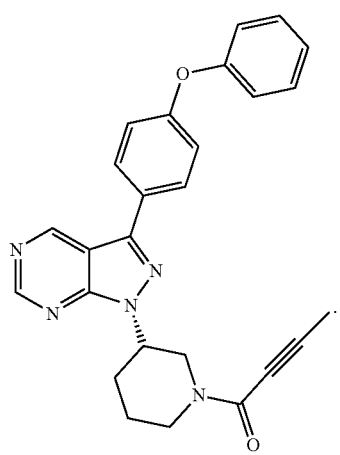
In embodiments, the compound has the formula:
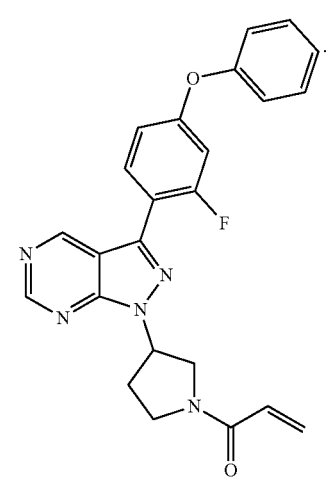 [SMILES: C=CC(=O)N1CCC(n2nc(-c3ccc(Oc4ccccc4)cc3F)c3cncnc32)C1]
324
In embodiments, the compound has the formula;
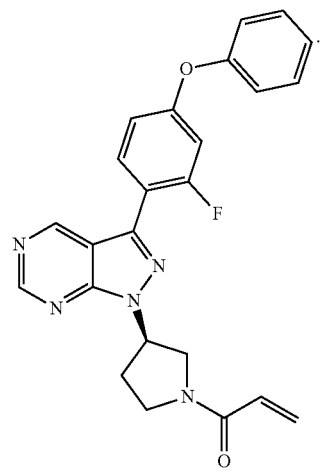 [SMILES: C=CC(=O)N1CC[C@@H](n2nc(-c3ccc(Oc4ccccc4)cc3F)c3cncnc32)C1]
In embodiments, the compound has the formula:
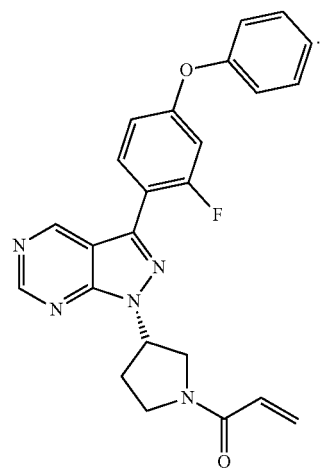
In embodiments, the compound has the formula:
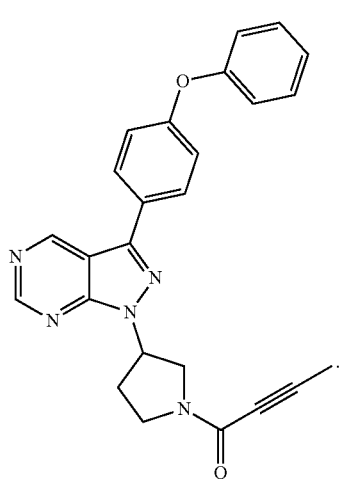 [SMILES: CC#CC(=O)N1CCC(n2nc(-c3ccc(Oc4ccccc4)cc3)c3cncnc32)C1]

In embodiments, the compound has the formula:
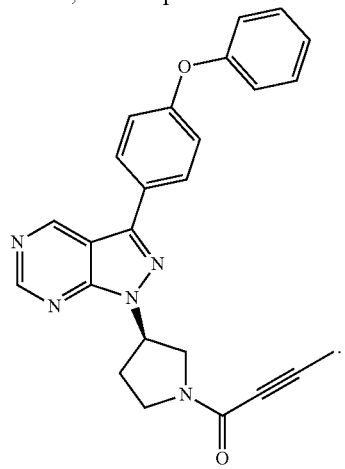
In embodiments, the compound has the formula:
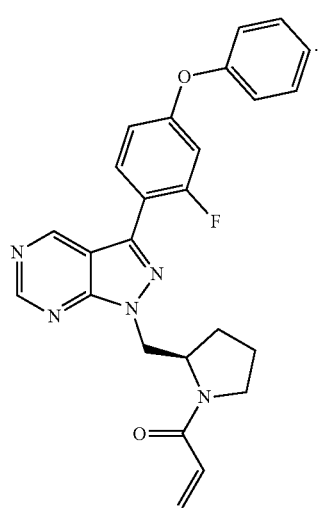
In embodiments, the compound has the formula:
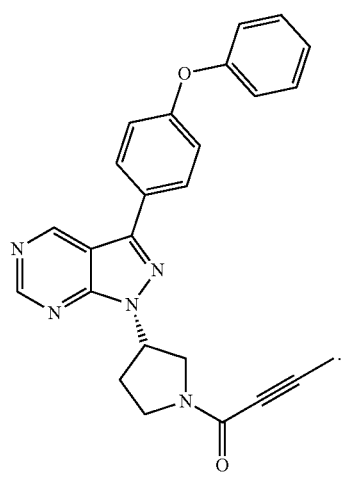
In embodiments, the compound has the formula:
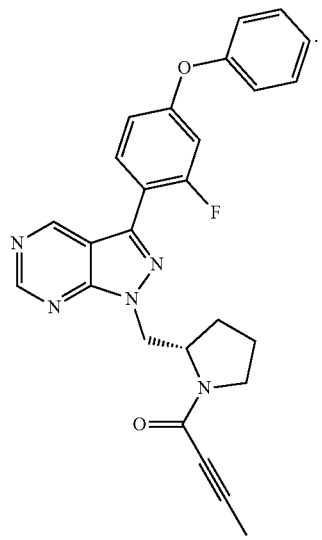
In embodiments, the compound has the formula:
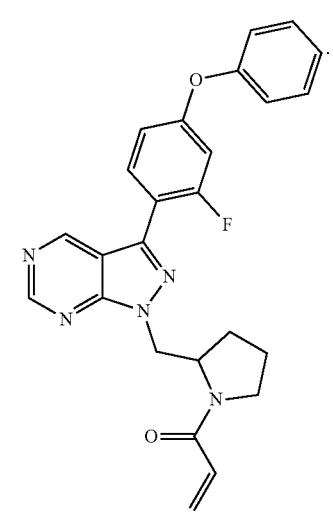
In embodiments, the compound has the formula:
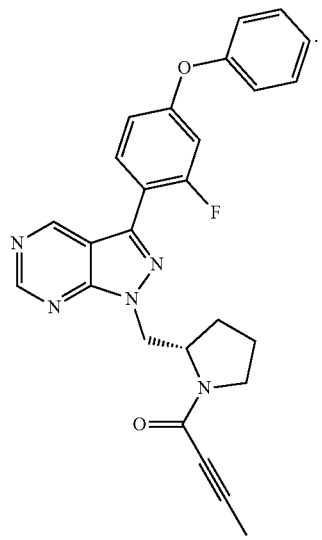

In embodiments, the compound has the formula:
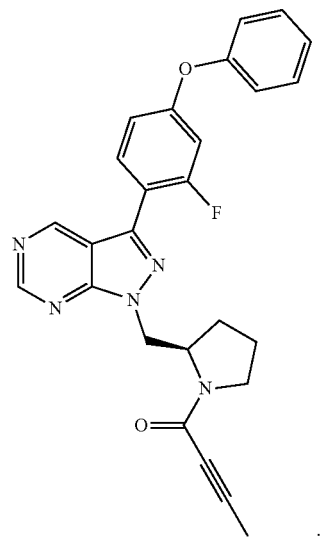 [SMILES: CC#CC(=O)N1CCC[C@@H]1Cn1nc(-c2ccc(Oc3ccccc3)cc2F)c2cncnc21 ; "."]
In embodiments, the compound has the formula:
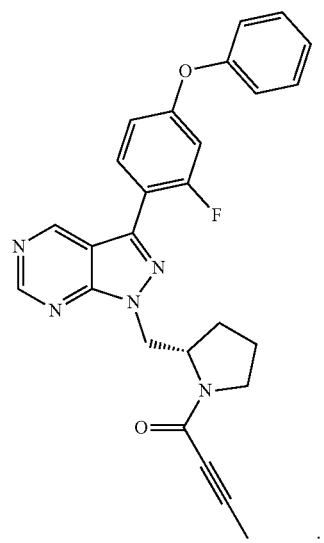
In embodiments, the compound has the formula:
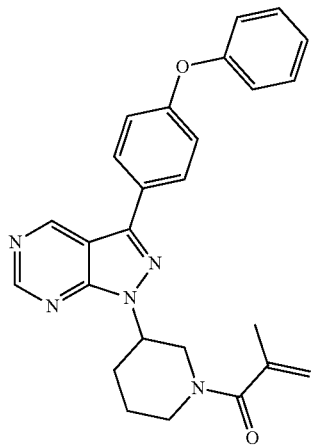 [SMILES: C=C(C)C(=O)N1CCCC(n2nc(-c3ccc(Oc4ccccc4)cc3)c3cncnc32)C1]
In embodiments, the compound has the formula:
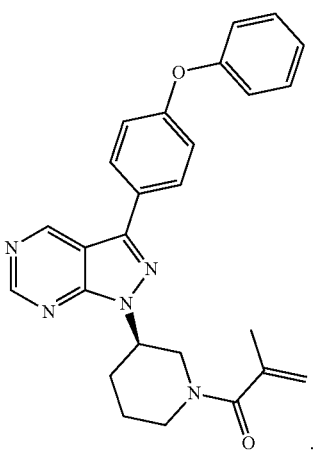 [SMILES: C=C(C)C(=O)N1CCC[C@@H](n2nc(-c3ccc(Oc4ccccc4)cc3)c3cncnc32)C1 ; "."]
In embodiments, the compound has the formula:
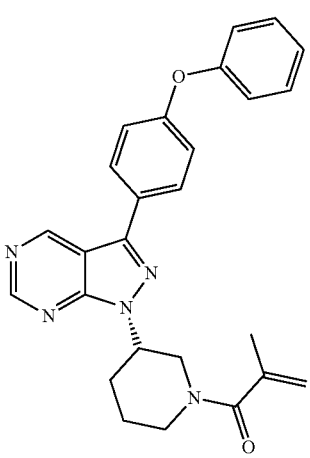

In embodiments, the compound has the formula:
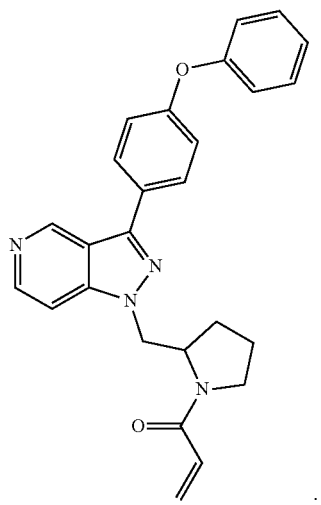 [SMILES: C=CC(=O)N1CCCC1Cn1nc(-c2ccc(Oc3ccccc3)cc2)c2cnccc21 ; "."]
In embodiments, the compound has the formula:
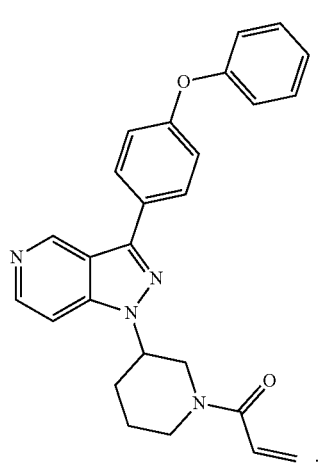
In embodiments, the compound has the formula:
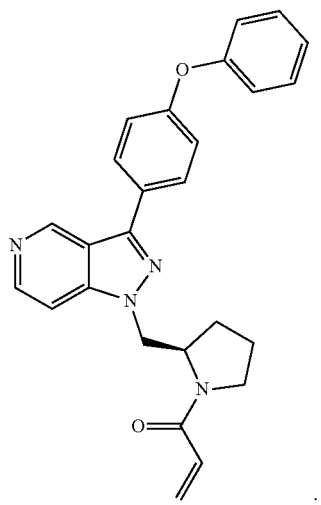 [SMILES: C=CC(=O)N1CCC[C@@H]1Cn1nc(-c2ccc(Oc3ccccc3)cc2)c2cnccc21 ; "."]
In embodiments, the compound has the formula:
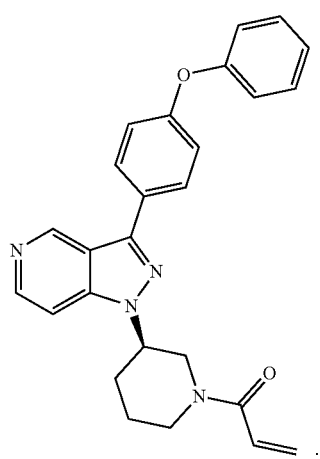 [SMILES: C=CC(=O)N1CCC[C@@H](n2nc(-c3ccc(Oc4ccccc4)cc3)c3cnccc32)C1 ; "."]
In embodiments, the compound has the formula:
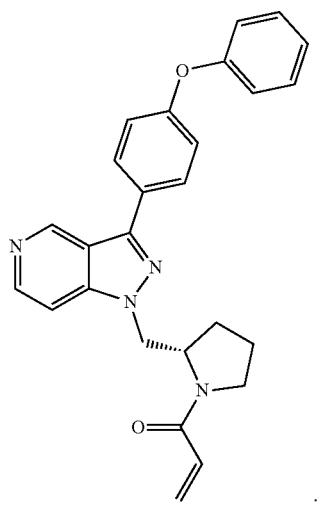
In embodiments, the compound has the formula:
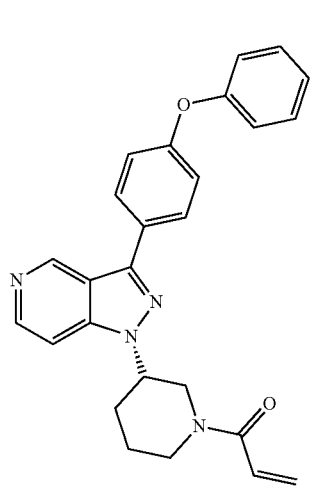

In embodiments, the compound has the formula:
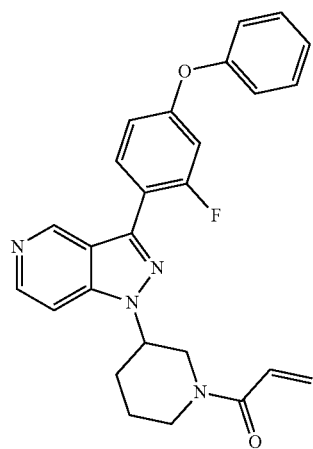
In embodiments, the compound has the formula:
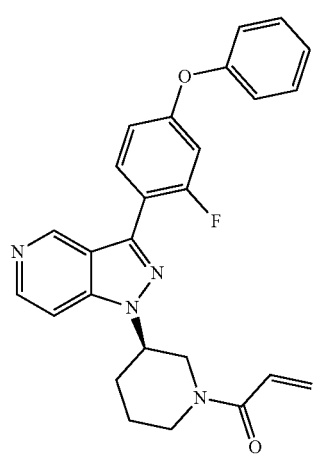
In embodiments, the compound has the formula:
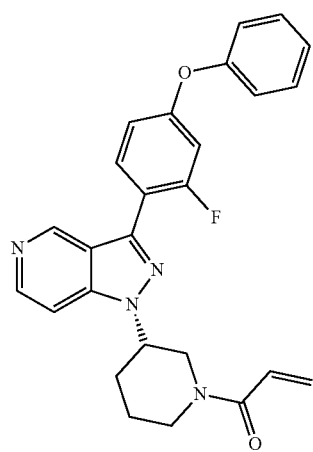
In embodiments, the compound has the formula:
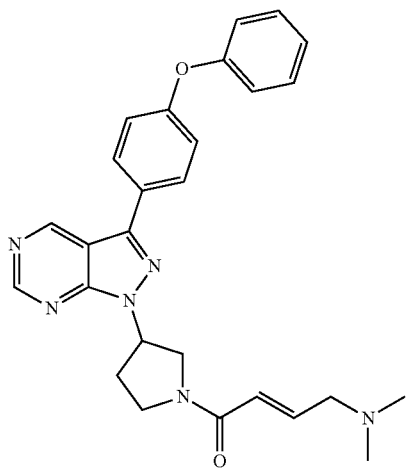
In embodiments, the compound has the formula:
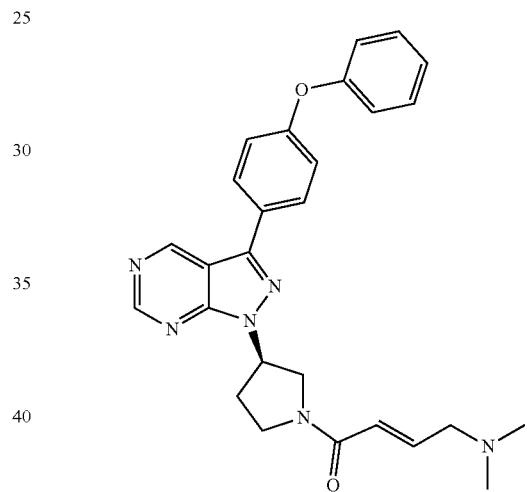
In embodiments, the compound has the formula:
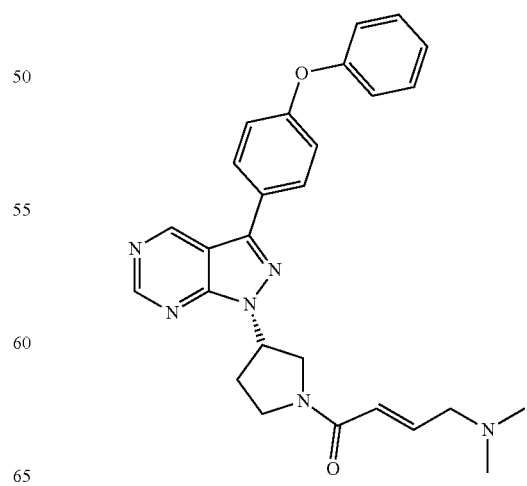

In embodiments, the compound has the formula:
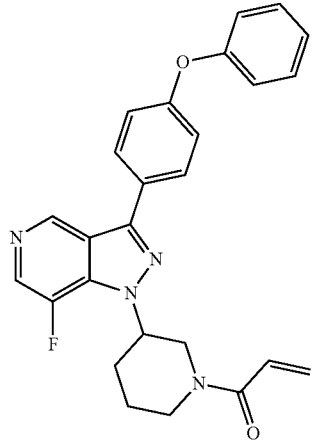
In embodiments, the compound has the formula:
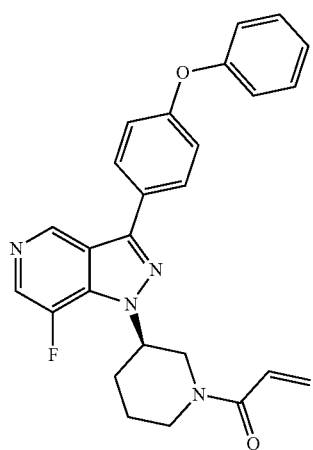
In embodiments, the compound has the formula:
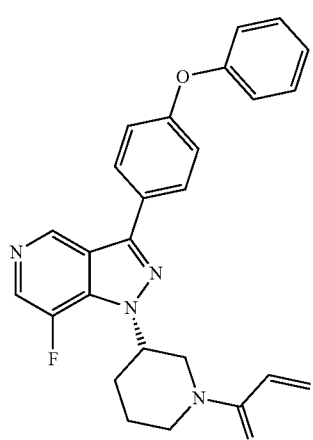
In embodiments, the compound has the formula:
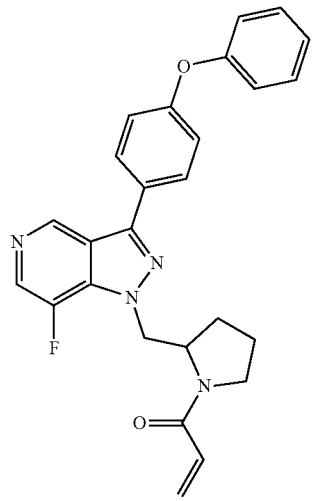
In embodiments, the compound has the formula:
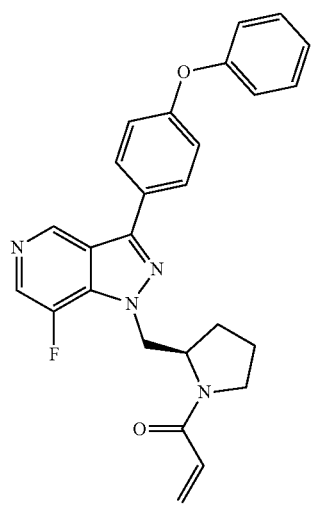
In embodiments, the compound has the formula:
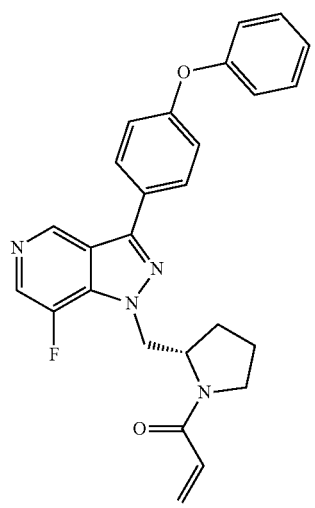

In embodiments, the compound has the formula:
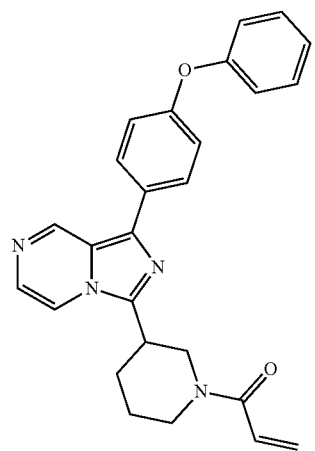
In embodiments, the compound has the formula:
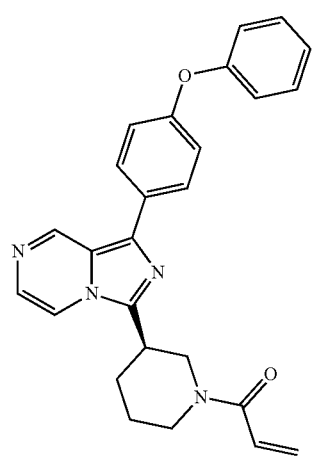
In embodiments, the compound has the formula:
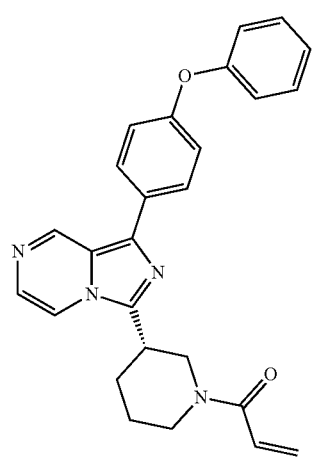
In embodiments, the compound has the formula:
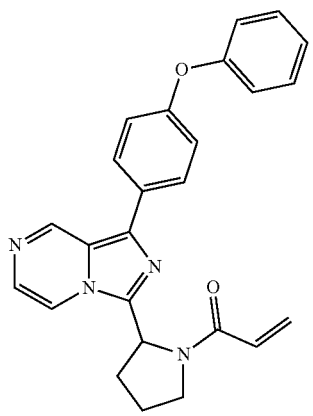
In embodiments, the compound has the formula:
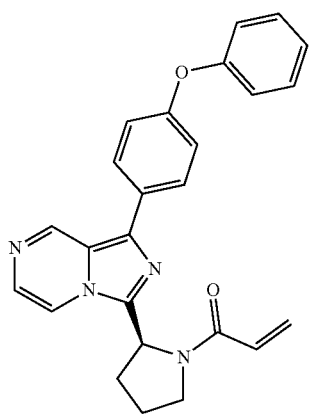
In embodiments, the compound has the formula:
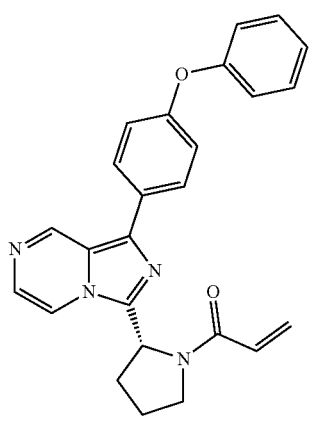

In embodiments, the compound has the formula:
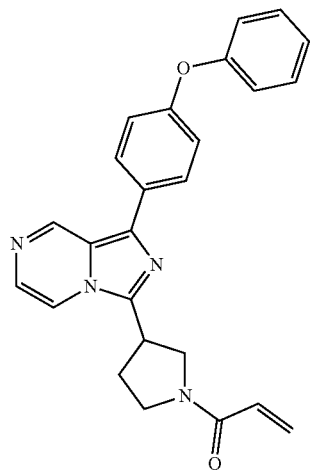
In embodiments, the compound has the formula:
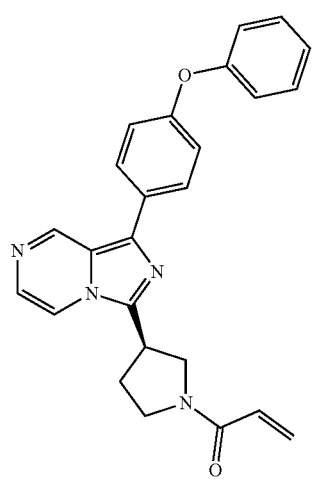
In embodiments, the compound has the formula:
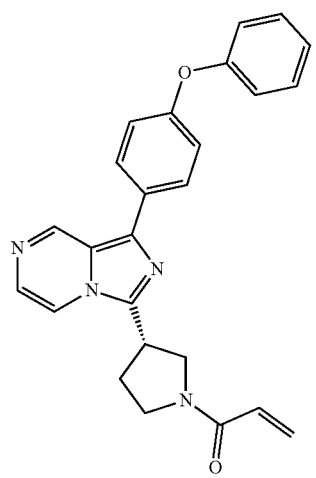
In embodiments, the compound has the formula:
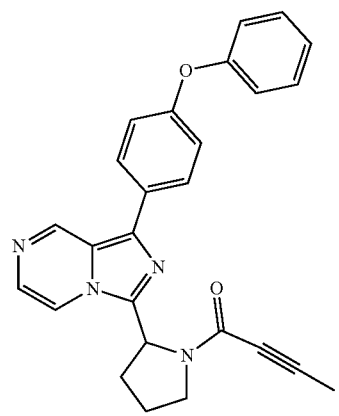
In embodiments, the compound has the formula:
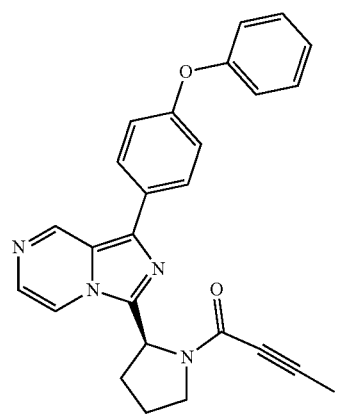
In embodiments, the compound has the formula:
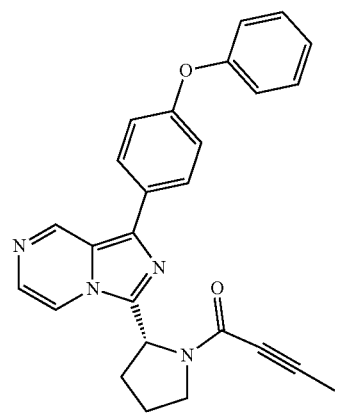

339
In embodiments, the compound has the formula:
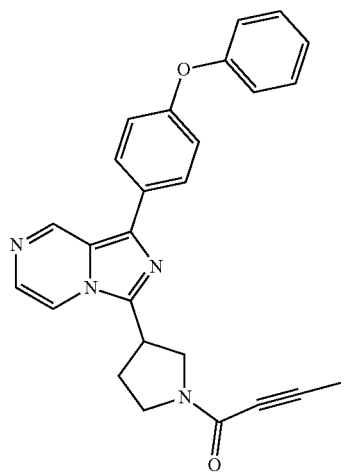
In embodiments, the compound has the formula:
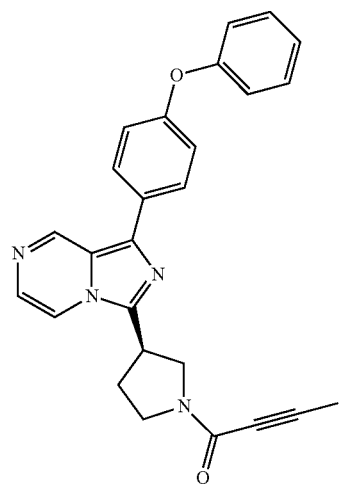
340
In embodiments, the compound has the formula:
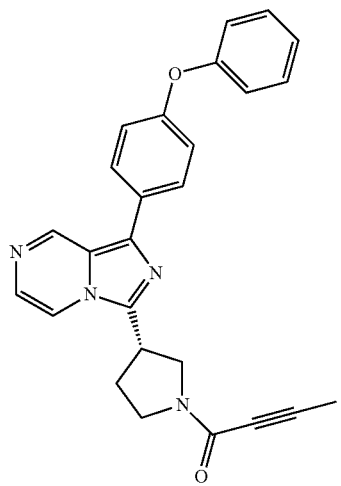
In embodiments, the compound has the formula:
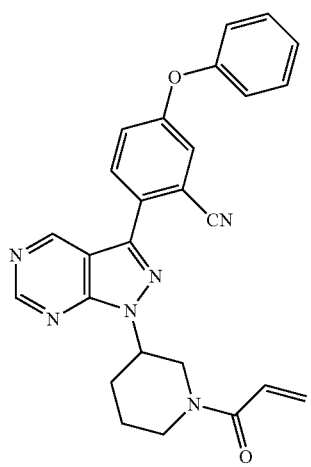
In embodiments, the compound has the formula:
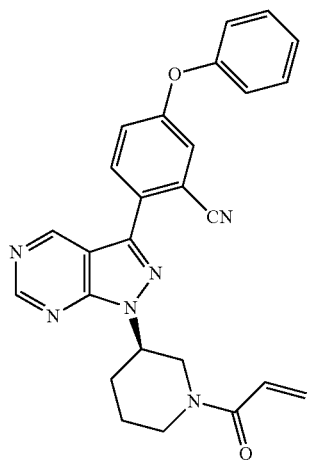

In embodiments, the compound has the formula:
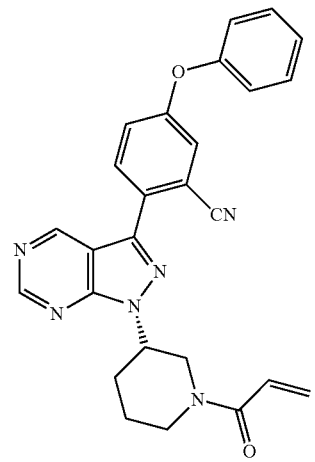
In embodiments, the compound has the formula:
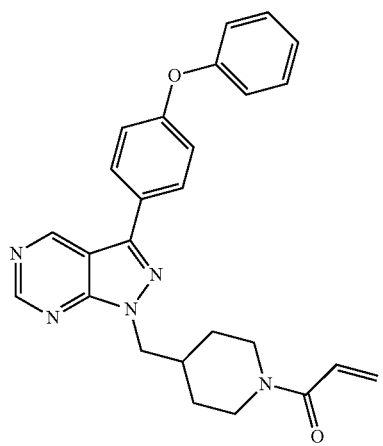
In embodiments, the compound has the formula:
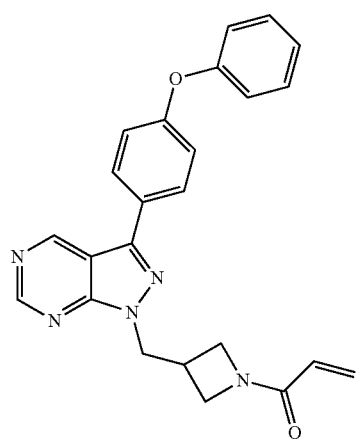
In embodiments, the compound has the formula:
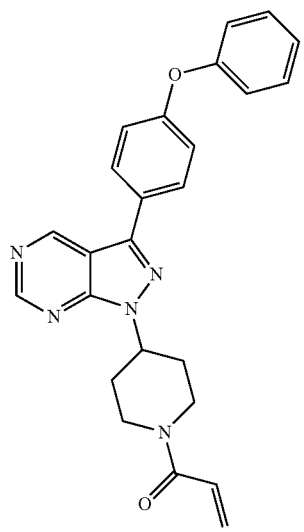
In embodiments, the compound has the formula:
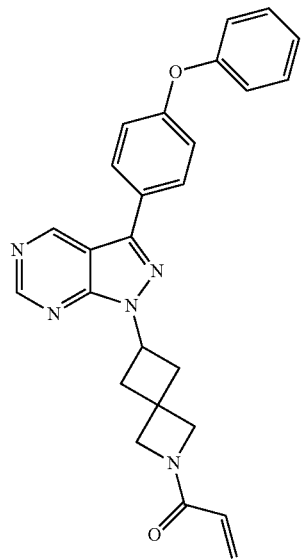

In embodiments, the compound has the formula:
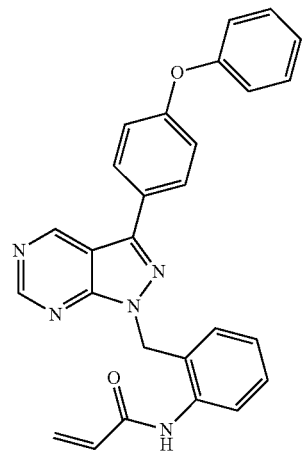
In embodiments, the compound has the formula:
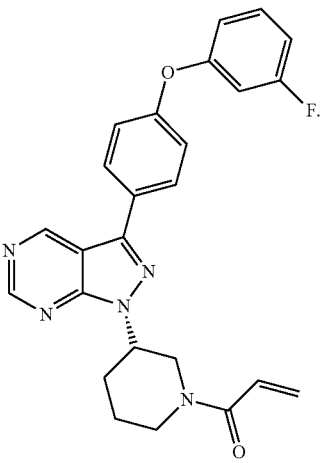
In embodiments, the compound has the formula:
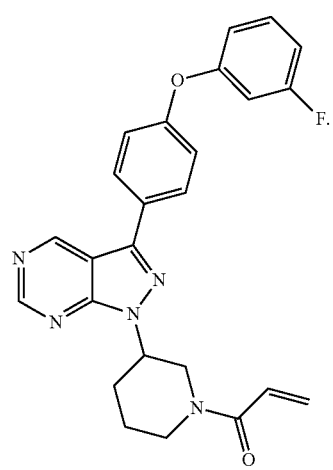 [SMILES: C=CC(=O)N1CCCC(n2nc(-c3ccc(Oc4cccc(F)c4)cc3)c3cncnc32)C1]
In embodiments, the compound has the formula:
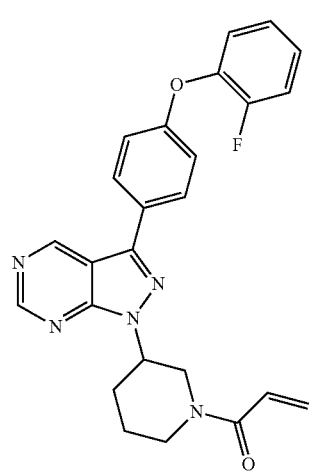
In embodiments, the compound has the formula:
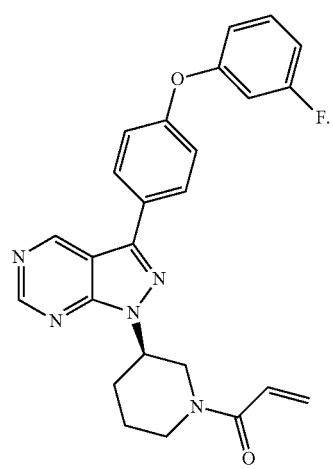 [SMILES: C=CC(=O)N1CCC[C@@H](n2nc(-c3ccc(Oc4cccc(F)c4)cc3)c3cncnc32)C1]
In embodiments, the compound has the formula:
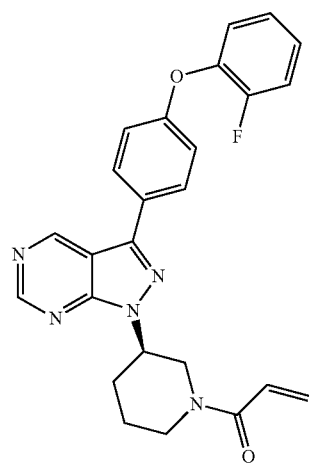

In embodiments, the compound has the formula:
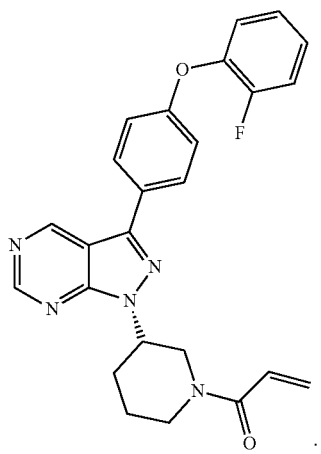
In embodiments, the compound has the formula:
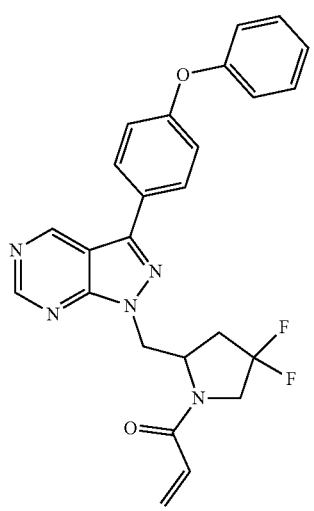
In embodiments, the compound has the formula:
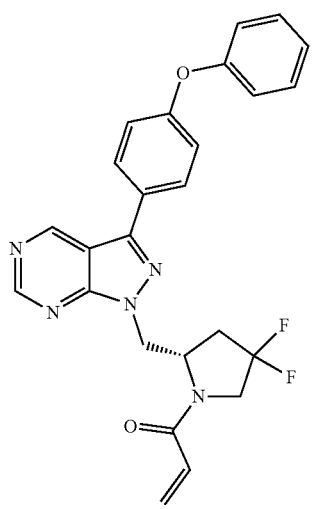
In embodiments, the compound has the formula:
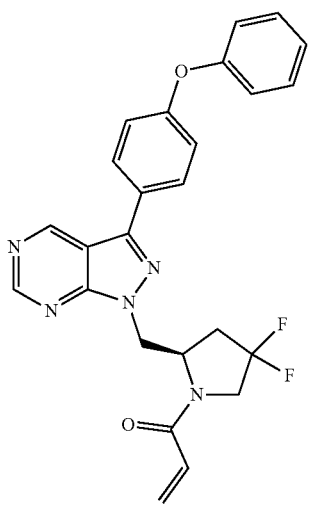
In embodiments, the compound has the formula:
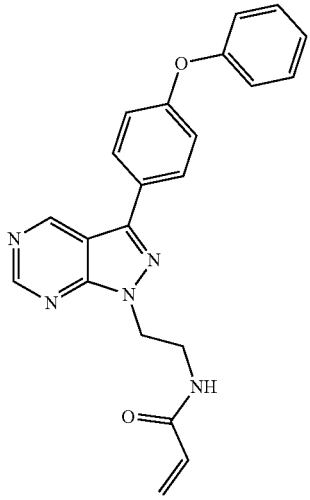

In embodiments, the compound has the formula:
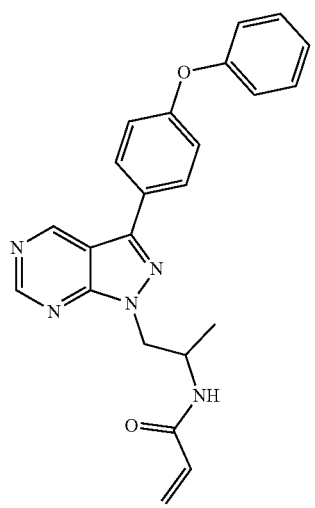
In embodiments, the compound has the formula:
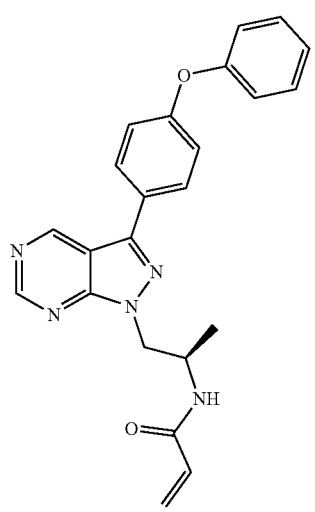
In embodiments, the compound has the formula:
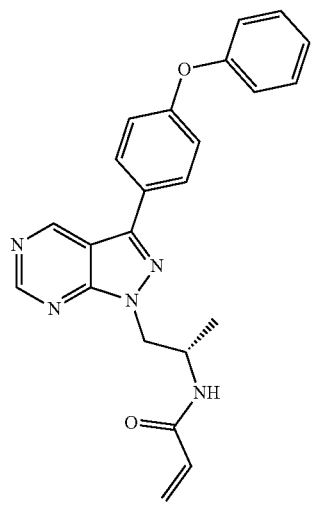
In embodiments, the compound has the formula:
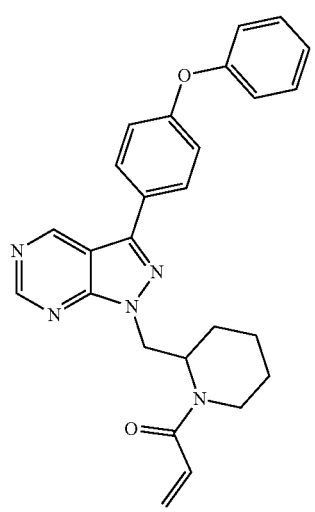

In embodiments, the compound has the formula:
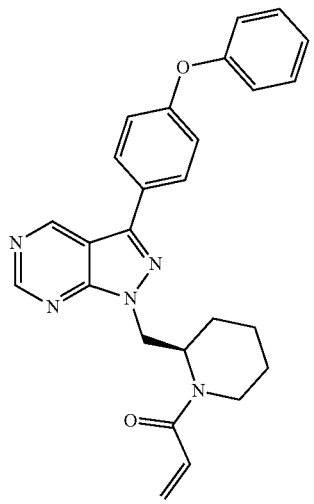
In embodiments, the compound has the formula:
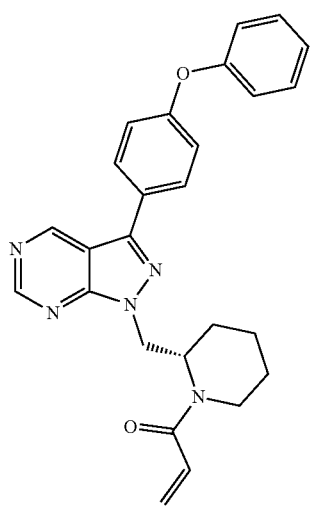
In embodiments, the compound has the formula:
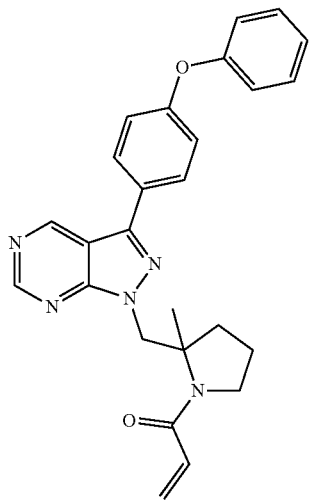
In embodiments, the compound has the formula:
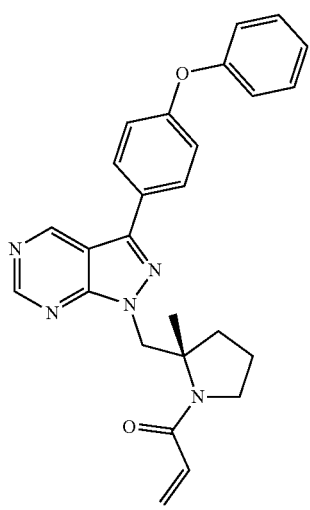

351
In embodiments, the compound has the formula:
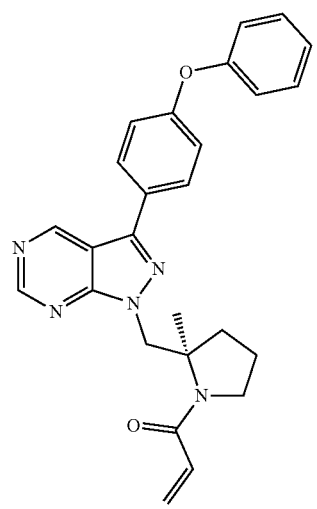
In embodiments, the compound has the formula:
352
In embodiments, the compound has the formula:
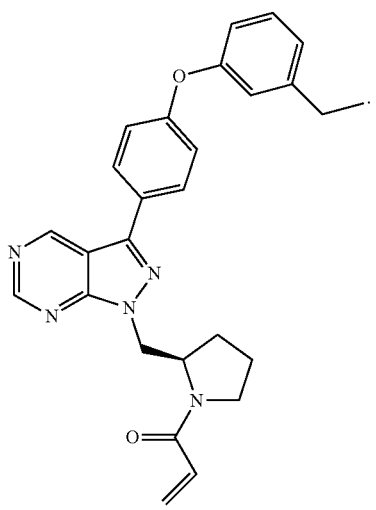 [SMILES: C=CC(=O)N1CCC[C@@H]1Cn1nc(-c2ccc(Oc3cccc(CC)c3)cc2)c2cncnc21]
In embodiments, the compound has the formula:

In embodiments, the compound has the formula:
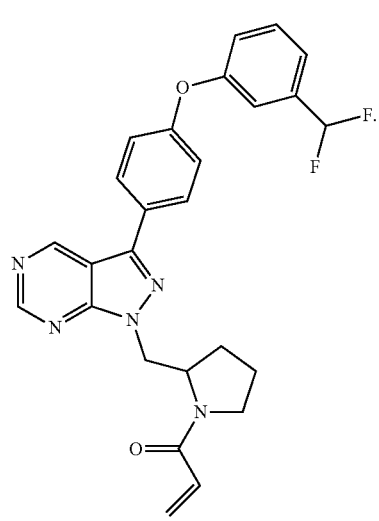 [SMILES: C=CC(=O)N1CCCC1Cn1nc(-c2ccc(Oc3cccc(C(F)F)c3)cc2)c2cncnc21]
In embodiments, the compound has the formula:
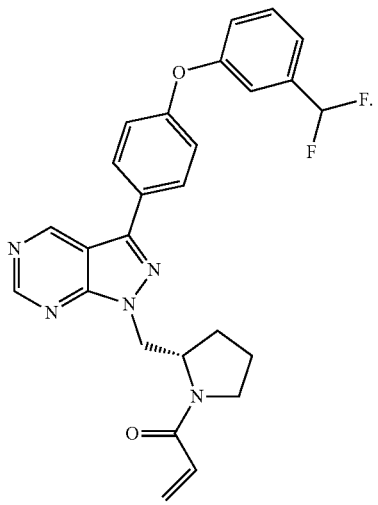
In embodiments, the compound has the formula:
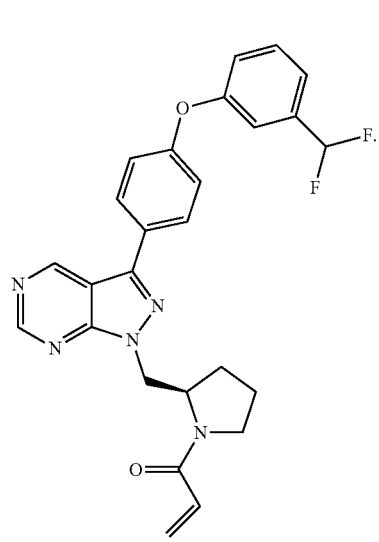 [SMILES: C=CC(=O)N1CCC[C@@H]1Cn1nc(-c2ccc(Oc3cccc(C(F)F)c3)cc2)c2cncnc21]
In embodiments, the compound has the formula:
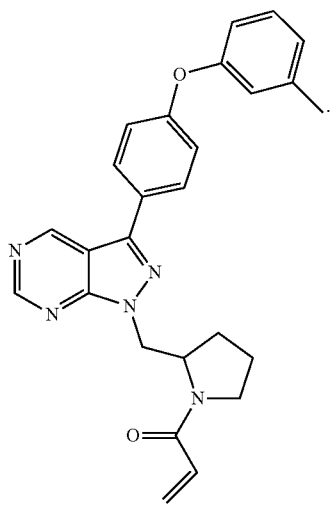 [SMILES: C=CC(=O)N1CCCC1Cn1nc(-c2ccc(Oc3cccc(C)c3)cc2)c2cncnc21]

In embodiments, the compound has the formula:
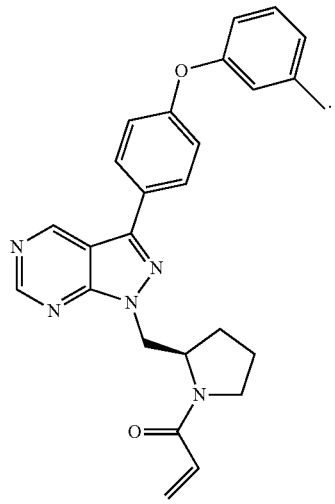 [SMILES: C=CC(=O)N1CCC[C@@H]1Cn1nc(-c2ccc(Oc3cccc(C)c3)cc2)c2cncnc21]
In embodiments, the compound has the formula:
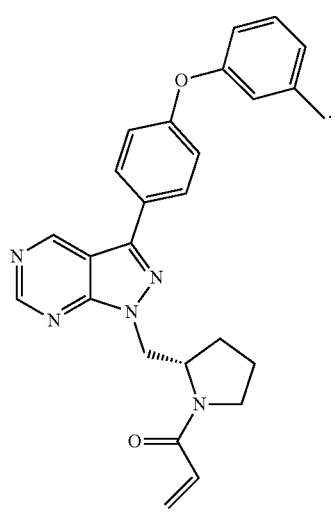 [SMILES: C=CC(=O)N1CCC[C@H]1Cn1nc(-c2ccc(Oc3cccc(C)c3)cc2)c2cncnc21]
In embodiments, the compound has the formula:
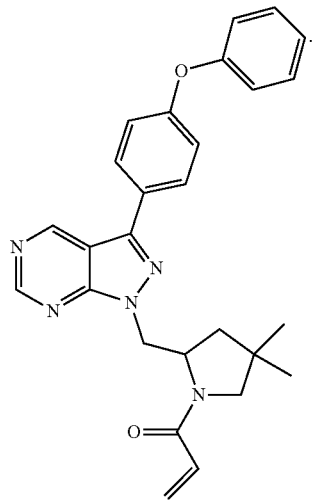
In embodiments, the compound has the formula:
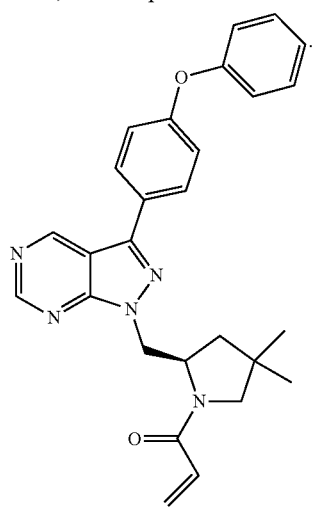
In embodiments, the compound has the formula:
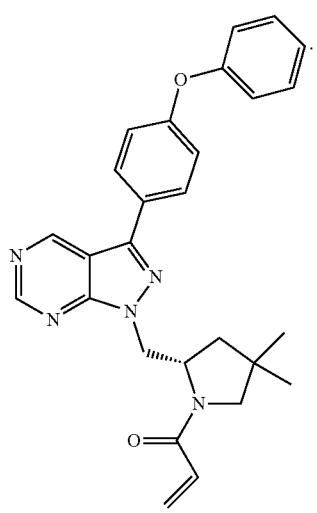 [SMILES: C=CC(=O)N1CC(C)(C)C[C@H]1Cn1nc(-c2ccc(Oc3ccccc3)cc2)c2cncnc21]

In embodiments, the compound has the formula:
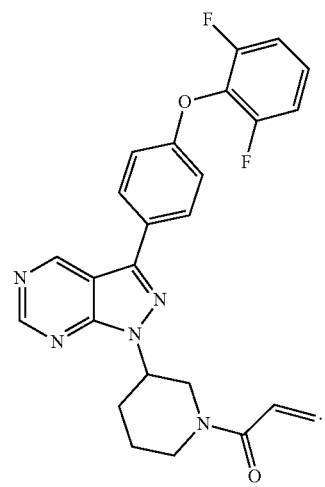
In embodiments, the compound has the formula:
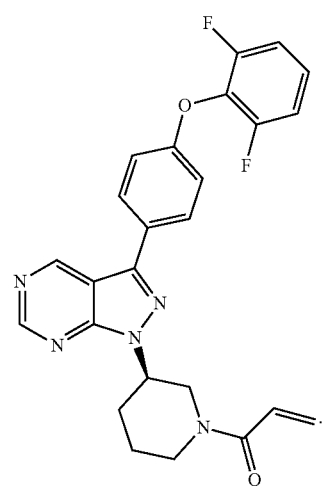
In embodiments, the compound has the formula:
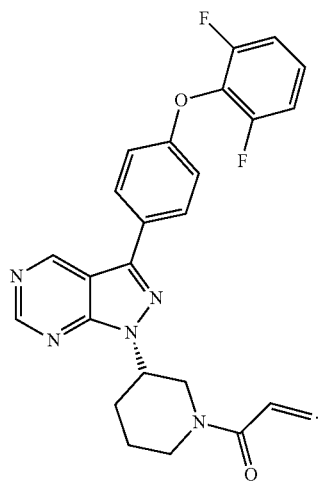 [SMILES: C=CC(=O)N1CCCC(n2nc(-c3ccc(Oc4c(F)cccc4F)cc3)c3cncnc32)C1]
In embodiments, the compound has the formula:
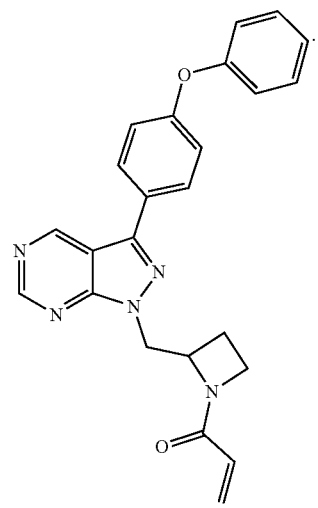 [SMILES: C=CC(=O)N1CCC1Cn1nc(-c2ccc(Oc3ccccc3)cc2)c2cncnc21]

In embodiments, the compound has the formula:
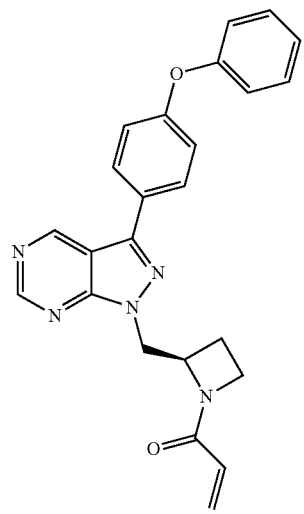
In embodiments, the compound has the formula:
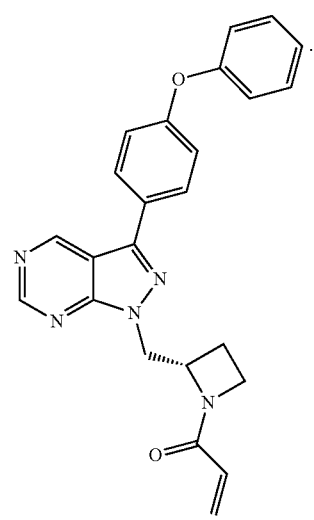
In embodiments, the compound has the formula:
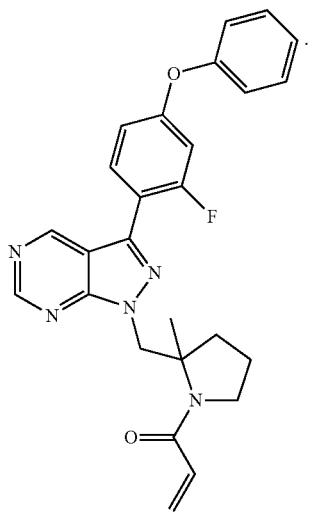 [SMILES: C=CC(=O)N1CCCC1(C)Cn1nc(-c2ccc(Oc3ccccc3)cc2F)c2cncnc21]
In embodiments, the compound has the formula:
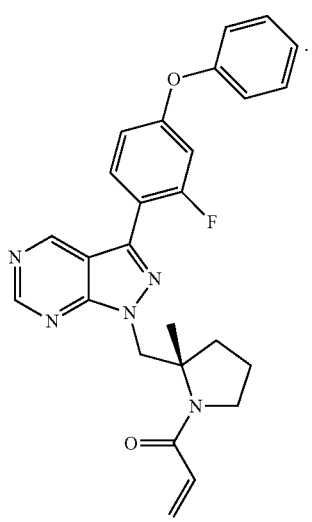 [SMILES: C=CC(=O)N1CCC[C@@]1(C)Cn1nc(-c2ccc(Oc3ccccc3)cc2F)c2cncnc21]

361
In embodiments, the compound has the formula:
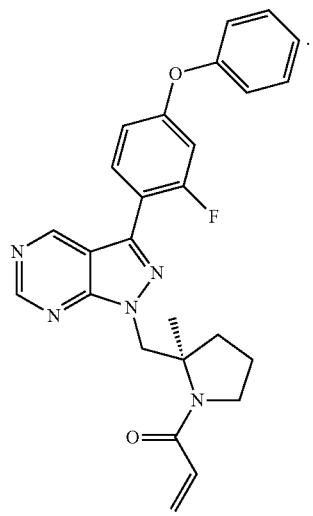 [SMILES: C=CC(=O)N1CCC[C@]1(C)Cn1nc(-c2ccc(Oc3ccccc3)cc2F)c2cncnc21]
In embodiments, the compound has the formula:
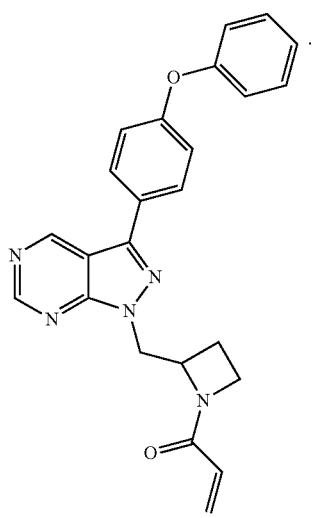
362
In embodiments, the compound has the formula:
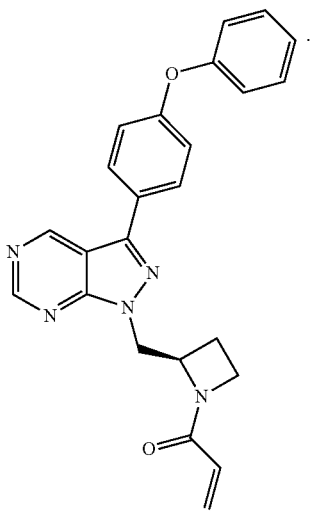 [SMILES: C=CC(=O)N1CC[C@@H]1Cn1nc(-c2ccc(Oc3ccccc3)cc2)c2cncnc21]
In embodiments, the compound has the formula:
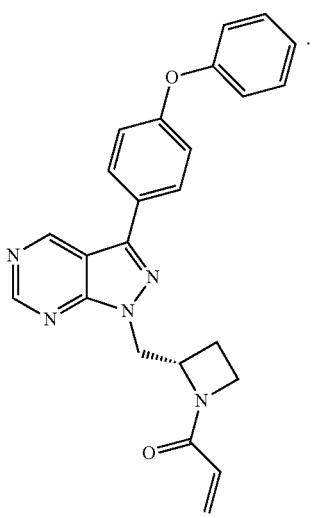 [SMILES: C=CC(=O)N1CC[C@H]1Cn1nc(-c2ccc(Oc3ccccc3)cc2)c2cncnc21]

363
In embodiments, the compound has the formula:
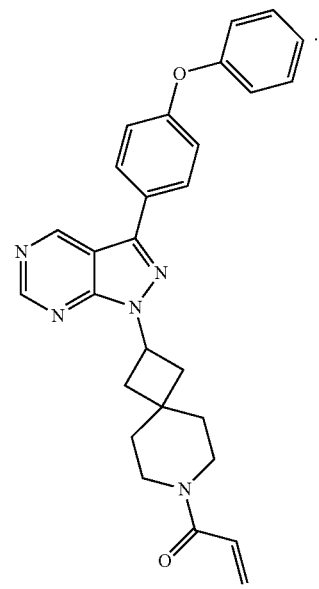 [SMILES: C=CC(=O)N1CCC2(CC1)CC(n1nc(-c3ccc(Oc4ccccc4)cc3)c3cncnc31)C2]
In embodiments, the compound has the formula:
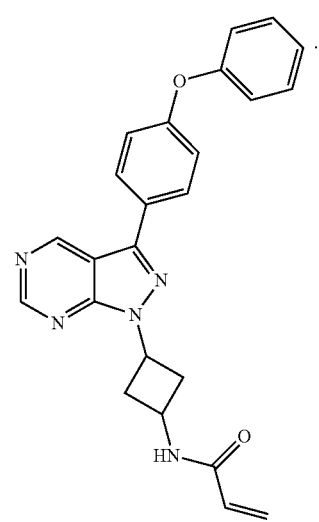 [SMILES: C=CC(=O)NC1CC(n2nc(-c3ccc(Oc4ccccc4)cc3)c3cncnc32)C1]
364
In embodiments, the compound has the formula:
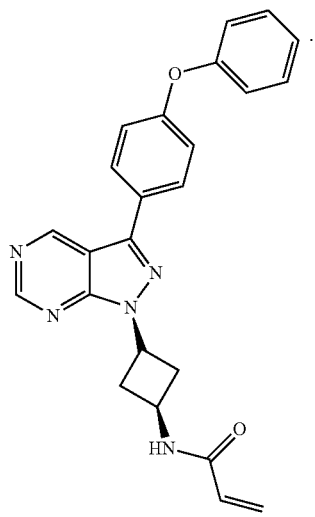
In embodiments, the compound has the formula:
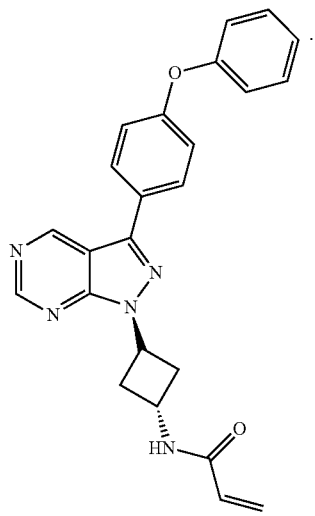

In embodiments, the compound has the formula:
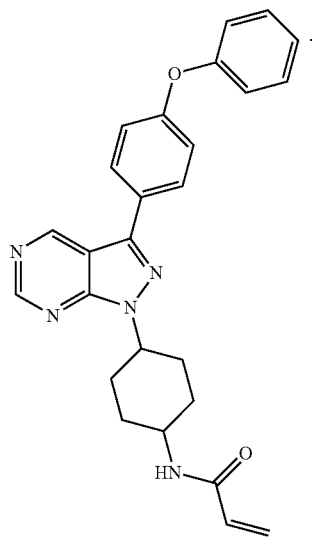 [SMILES: C=CC(=O)NC1CCC(n2nc(-c3ccc(Oc4ccccc4)cc3)c3cncnc32)CC1]
In embodiments, the compound has the formula:
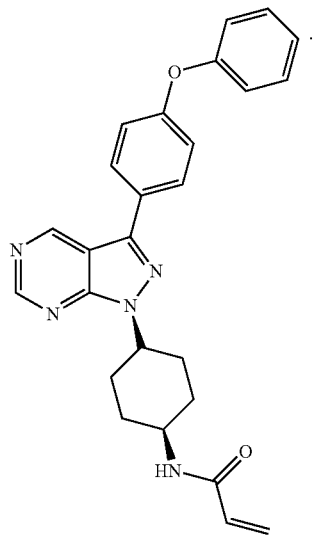
In embodiments, the compound has the formula:
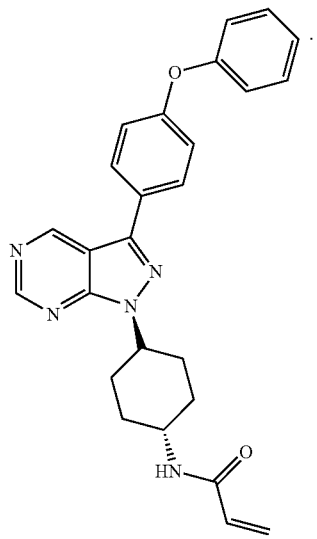
In embodiments, the compound has the formula:
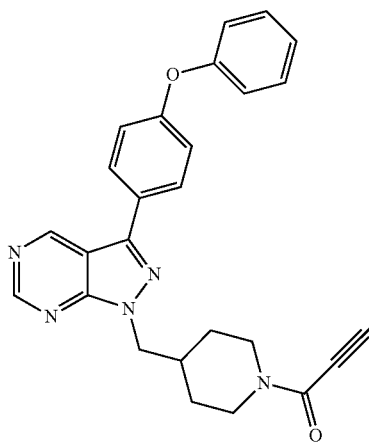
In embodiments, the compound has the formula:
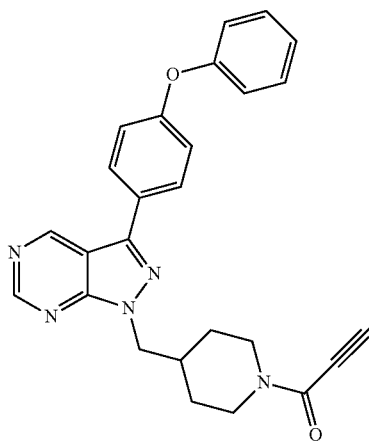

In embodiments, the compound has the formula:
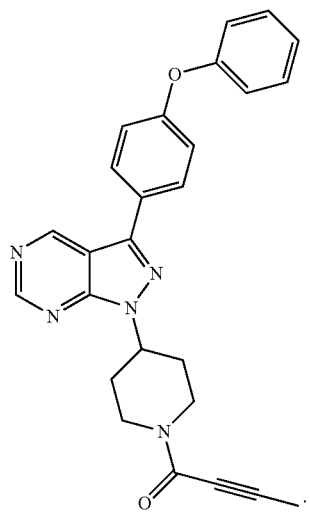 [SMILES: CC#CC(=O)N1CCC(n2nc(-c3ccc(Oc4ccccc4)cc3)c3cncnc32)CC1]
In embodiments, the compound has the formula:
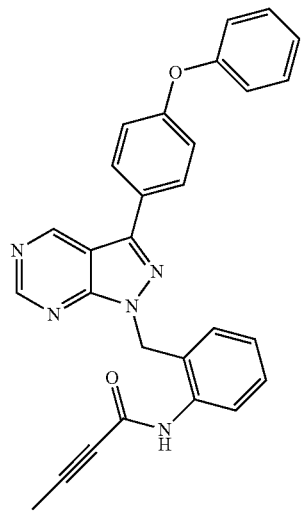
In embodiments, the compound has the formula:
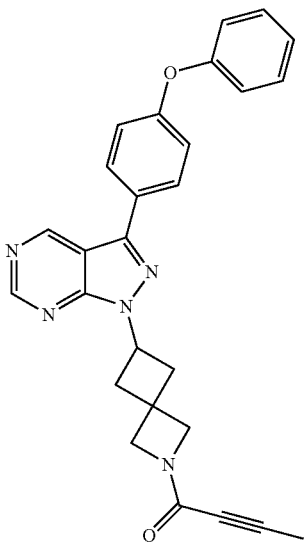 [SMILES: CC#CC(=O)N1CC2(CC(n3nc(-c4ccc(Oc5ccccc5)cc4)c4cncnc43)C2)C1]
In embodiments, the compound has the formula:
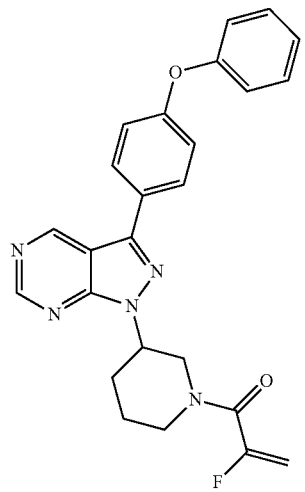

In embodiments, the compound has the formula:
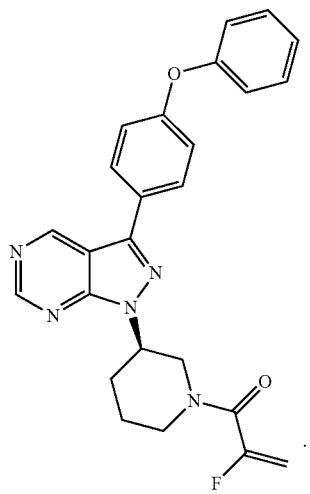 [SMILES: C=C(F)C(=O)N1CCC[C@@H](n2nc(-c3ccc(Oc4ccccc4)cc3)c3cncnc32)C1]
In embodiments, the compound has the formula:
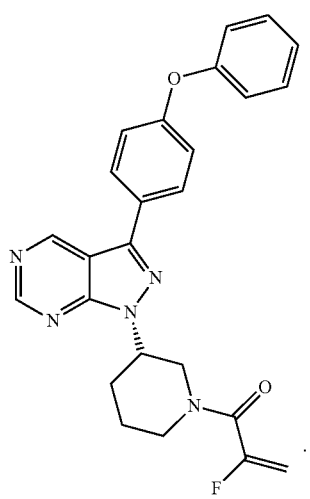
In embodiments, the compound has the formula:
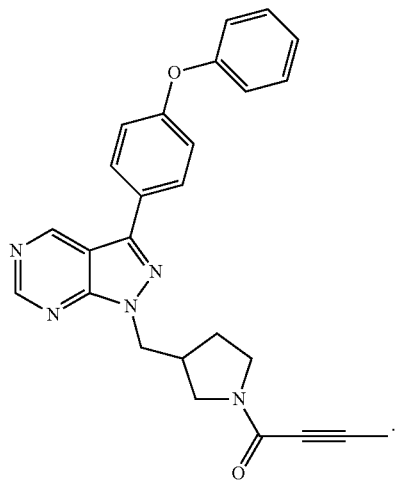 [SMILES: CC#CC(=O)N1CCC(Cn2nc(-c3ccc(Oc4ccccc4)cc3)c3cncnc32)C1]
In embodiments, the compound has the formula:
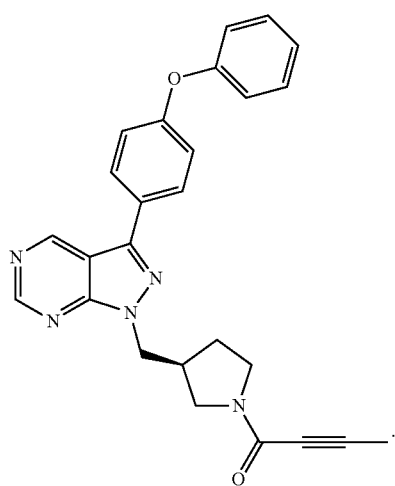 [SMILES: CC#CC(=O)N1CC[C@H](Cn2nc(-c3ccc(Oc4ccccc4)cc3)c3cncnc32)C1]

In embodiments, the compound has the formula:
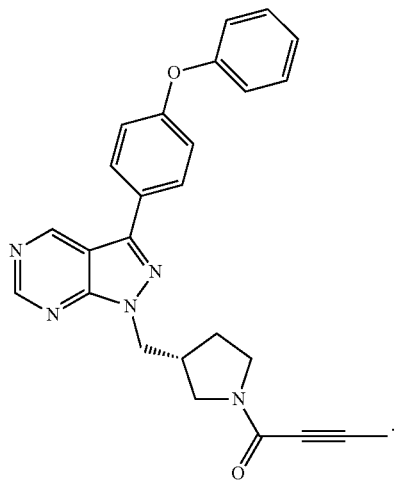 [SMILES: CC#CC(=O)N1CC[C@@H](Cn2nc(-c3ccc(Oc4ccccc4)cc3)c3cncnc32)C1]
In embodiments, the compound has the formula:
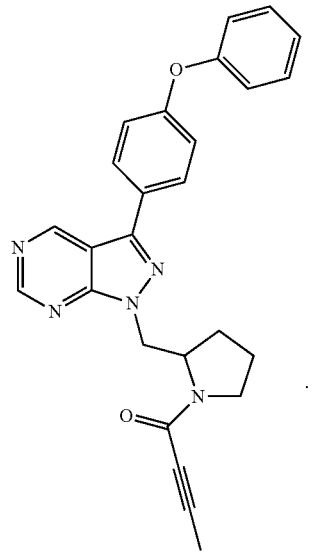 [SMILES: CC#CC(=O)N1CCCC1Cn1nc(-c2ccc(Oc3ccccc3)cc2)c2cncnc21]
In embodiments, the compound has the formula:
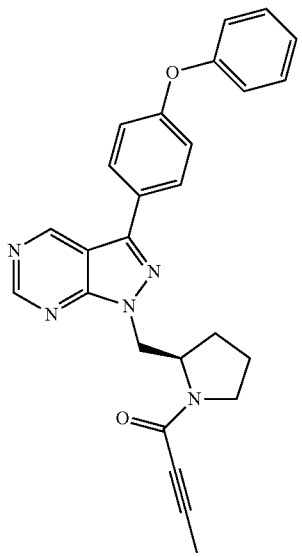
In embodiments, the compound has the formula:
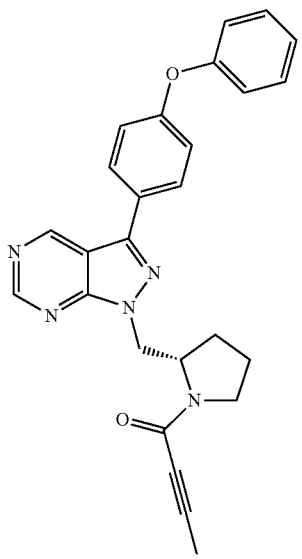

In embodiments, the compound has the formula:
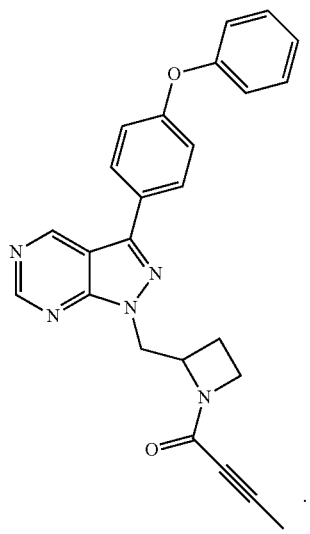 [SMILES: CC#CC(=O)N1CCC1Cn1nc(-c2ccc(Oc3ccccc3)cc2)c2cncnc21]
In embodiments, the compound has the formula:
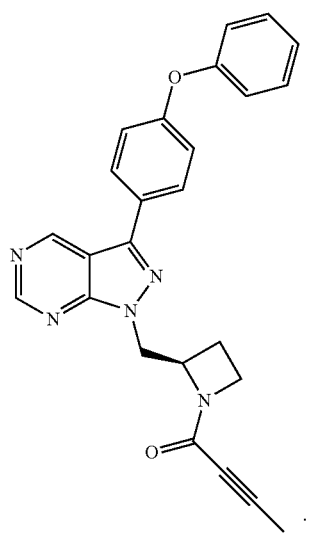 [SMILES: CC#CC(=O)N1CC[C@@H]1Cn1nc(-c2ccc(Oc3ccccc3)cc2)c2cncnc21]
In embodiments, the compound has the formula:
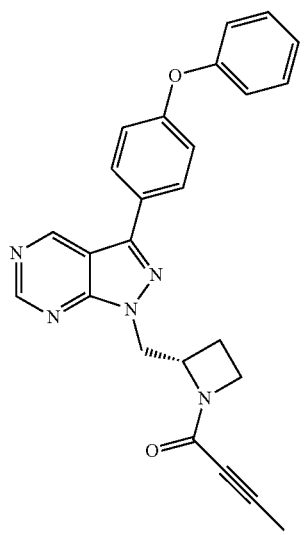
In embodiments, the compound has the formula:
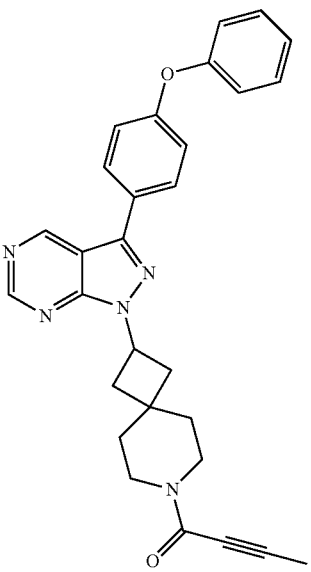

In embodiments, the compound has the formula:
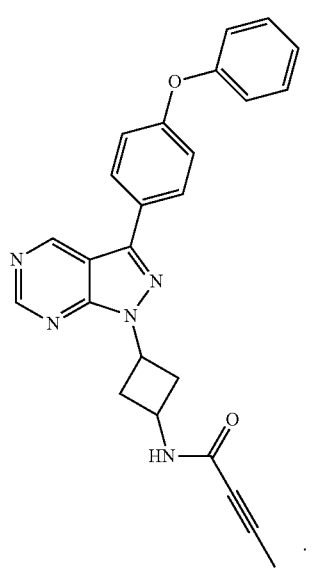 [SMILES: CC#CC(=O)NC1CC(n2nc(-c3ccc(Oc4ccccc4)cc3)c3cncnc32)C1]
In embodiments, the compound has the formula:
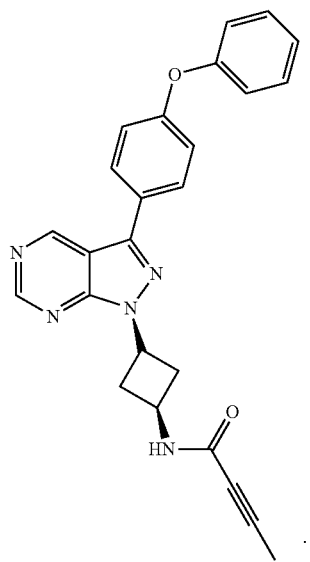
In embodiments, the compound has the formula:
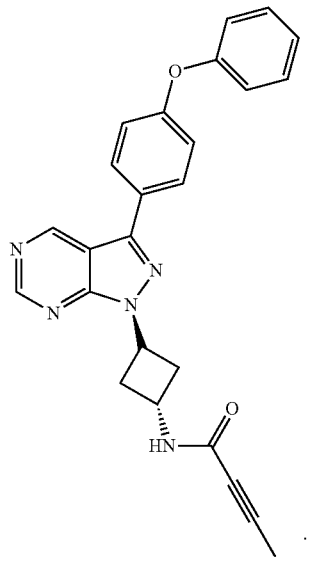
In embodiments, the compound has the formula:
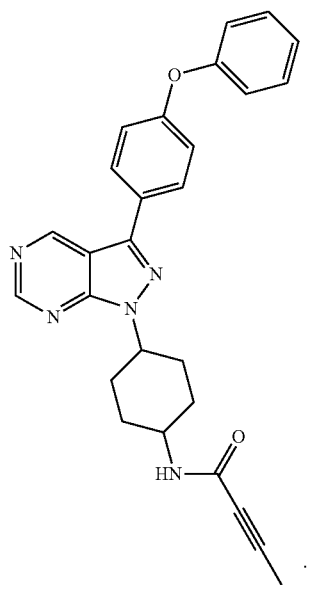 [SMILES: CC#CC(=O)NC1CCC(n2nc(-c3ccc(Oc4ccccc4)cc3)c3cncnc32)CC1]

377
In embodiments, the compound has the formula:
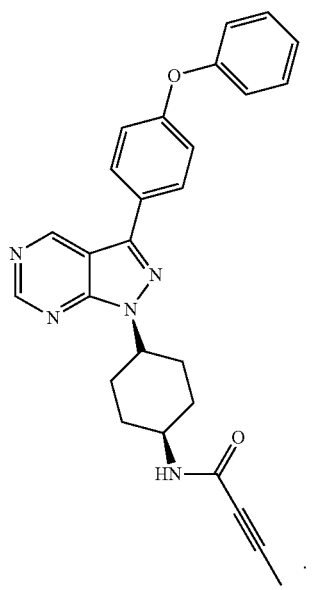
In embodiments, the compound has the formula:
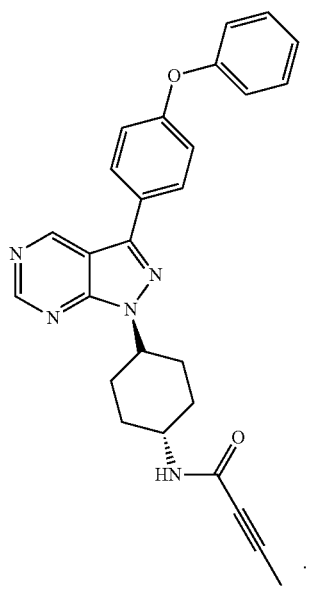
378
In embodiments, the compound has the formula:
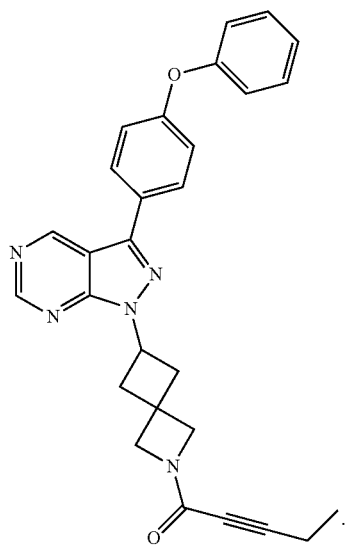 [SMILES: CCC#CC(=O)N1CC2(CC(n3nc(-c4ccc(Oc5ccccc5)cc4)c4cncnc43)C2)C1]
In embodiments, the compound has the formula:
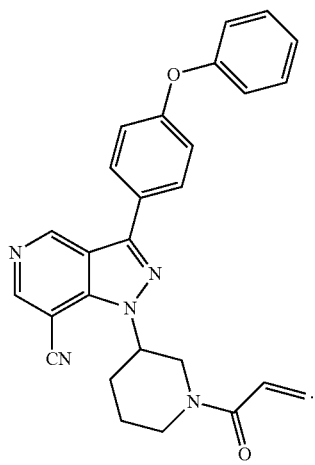 [SMILES: C=CC(=O)N1CCCC(n2nc(-c3ccc(Oc4ccccc4)cc3)c3cncc(C#N)c32)C1]

In embodiments, the compound has the formula:
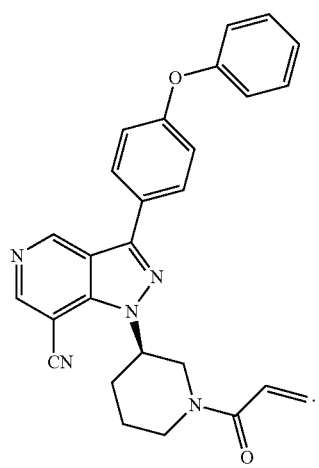 [SMILES: C=CC(=O)N1CCC[C@@H](n2nc(-c3ccc(Oc4ccccc4)cc3)c3cncc(C#N)c32)C1]
In embodiments, the compound has the formula:
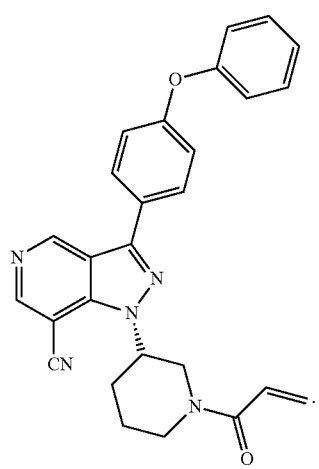
In embodiments, the compound has the formula:
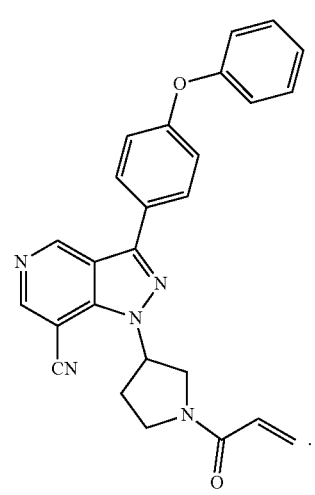 [SMILES: C=CC(=O)N1CCC(n2nc(-c3ccc(Oc4ccccc4)cc3)c3cncc(C#N)c32)C1]
In embodiments, the compound has the formula:
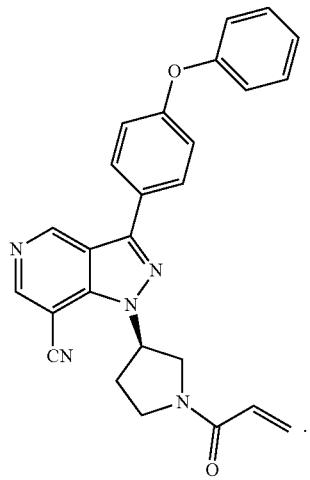 [SMILES: C=CC(=O)N1CC[C@@H](n2nc(-c3ccc(Oc4ccccc4)cc3)c3cncc(C#N)c32)C1]
In embodiments, the compound has the formula:
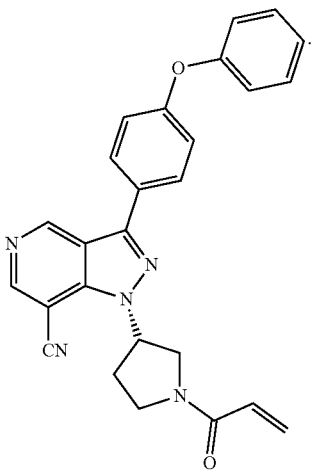
In embodiments, the compound has the formula:
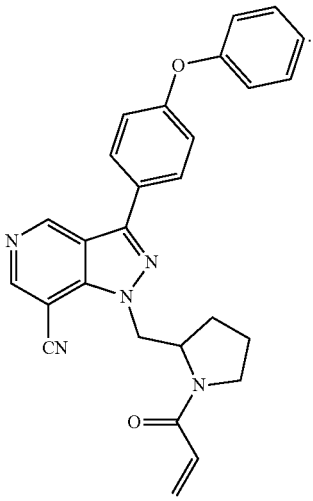

In embodiments, the compound has the formula:
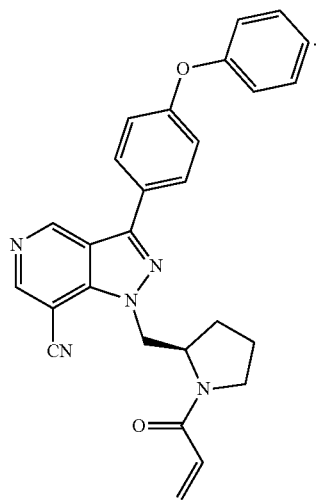
In embodiments, the compound has the formula:
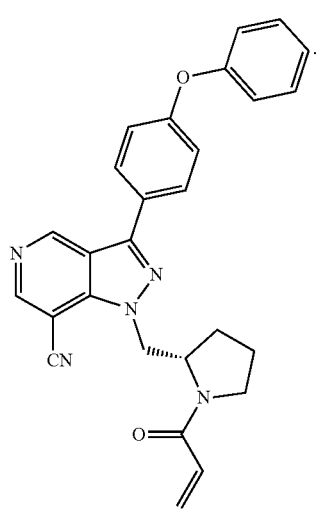
In embodiments, the compound has the formula:
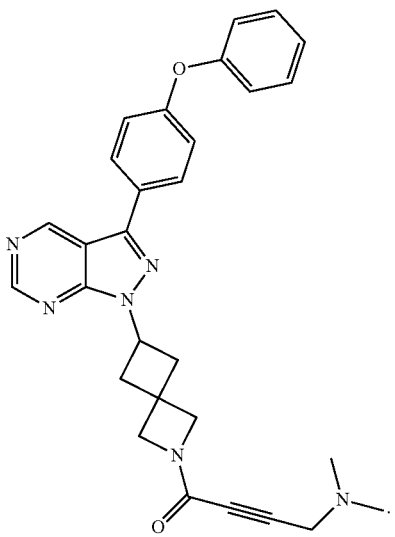 [SMILES: CN(C)CC#CC(=O)N1CC2(CC(n3nc(-c4ccc(Oc5ccccc5)cc4)c4cncnc43)C2)C1]
In embodiments, the compound has the formula:
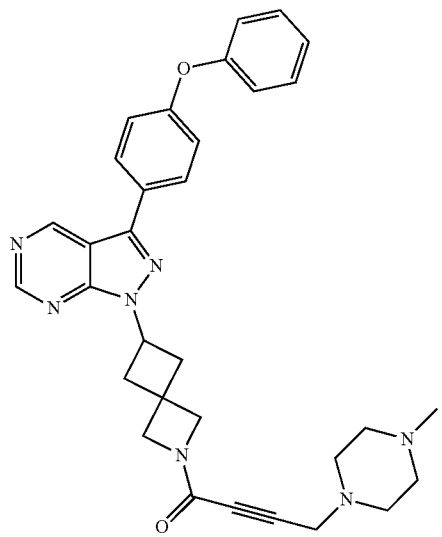 [SMILES: CN1CCN(CC#CC(=O)N2CC3(CC(n4nc(-c5ccc(Oc6ccccc6)cc5)c5cncnc54)C3)C2)CC1]

383
In embodiments, the compound has the formula:
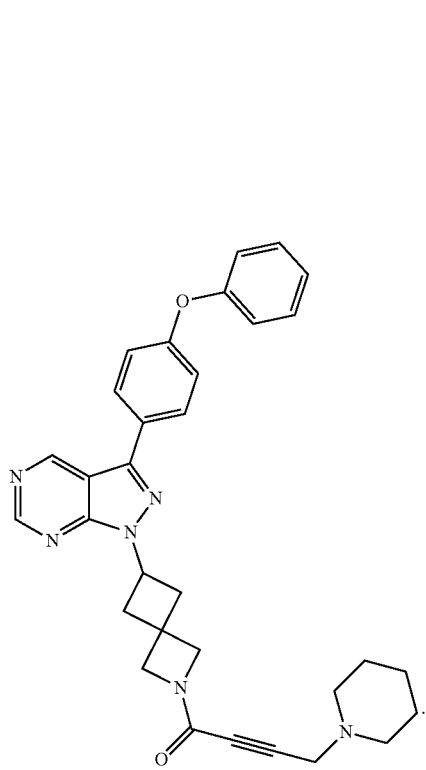 [SMILES: O=C(C#CCN1CCCCC1)N1CC2(CC(n3nc(-c4ccc(Oc5ccccc5)cc4)c4cncnc43)C2)C1]
In embodiments, the compound has the formula:
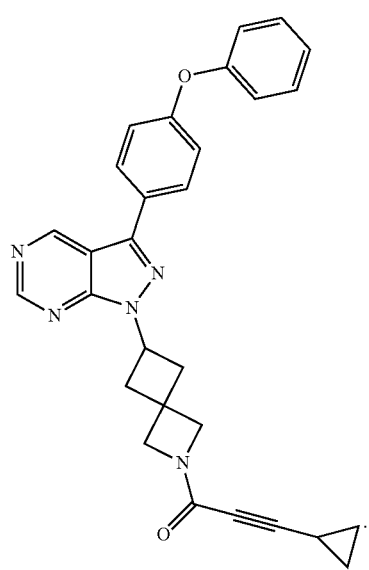 [SMILES: O=C(C#CC1CC1)N1CC2(CC(n3nc(-c4ccc(Oc5ccccc5)cc4)c4cncnc43)C2)C1]
384
In embodiments, the compound has the formula:
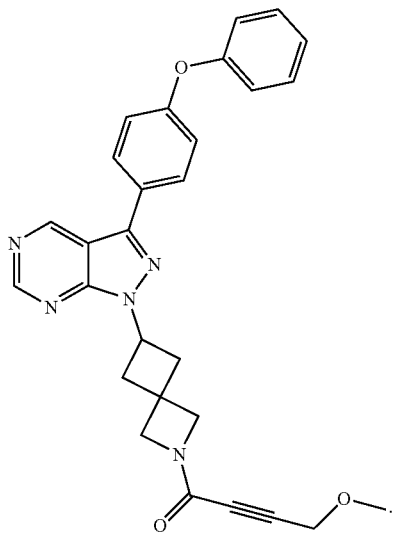 [SMILES: COCC#CC(=O)N1CC2(CC(n3nc(-c4ccc(Oc5ccccc5)cc4)c4cncnc43)C2)C1]
In embodiments, the compound has the formula:
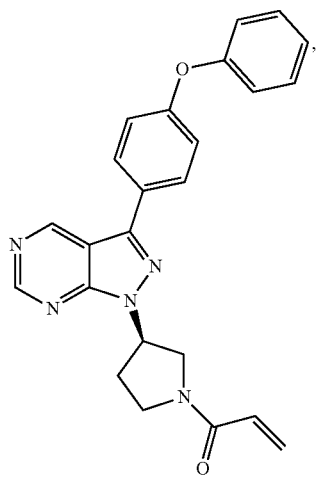
In embodiments, the compound has the formula:
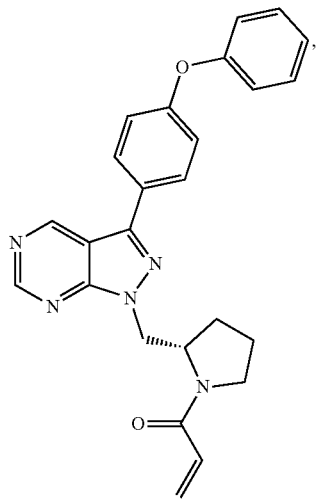

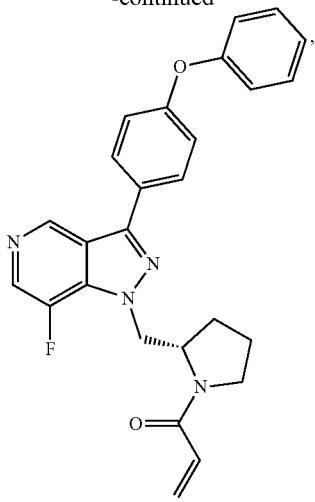

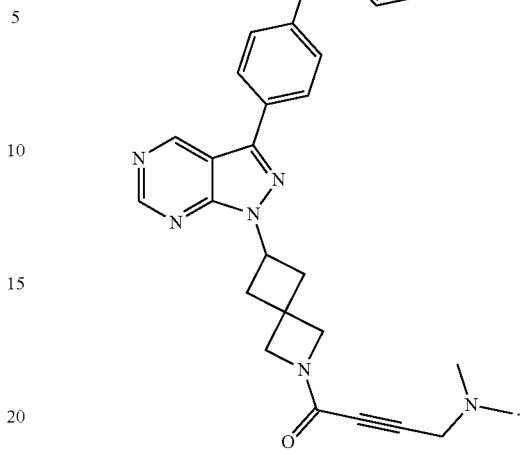

In some embodiments, a compound as described herein may include multiple instances of $R^1$ or $R^2$, and/or other variables. In such embodiments, each variable may optional be different and be appropriately labeled to distinguish each group for greater clarity. For example, where each $R^1$ and/or $R^2$, is different, they may be referred to, for example, as $R^{1.1}$, $R^{1.2}$, $R^{1.3}$, $R^{1.4}$, $R^{1.5}$, $R^{2.1}$, $R^{2.2}$, $R^{2.3}$, or $R^{2.4}$, respectively, wherein the definition of $R^1$ is assumed by $R^{1.1}$, $R^{1.2}$, $R^{1.3}$, $R^{1.4}$, $R^{1.5}$; and/or $R^2$ is assumed by $R^{2.1}$, $R^{2.2}$, $R^{2.3}$, $R^{2.4}$. The variables used within a definition of $R^1$ and/or $R^2$, and/or other variables that appear at multiple instances and are different may similarly be appropriately labeled to distinguish each group for greater clarity. In some embodiments, the compound is a compound described herein (e.g., in an aspect, embodiment, example, claim, table, scheme, drawing, or FIGURE).

In embodiments, unless otherwise indicated, a compound described herein is a racemic mixture of all stereoisomers. In embodiments, unless otherwise indicated, a compound described herein is a racemic mixture of all enantiomers. In embodiments, unless otherwise indicated, a compound described herein is a racemic mixture of two opposite stereoisomers. In embodiments, unless otherwise indicated, a compound described herein is a racemic mixture of two opposite enantiomers. In embodiments, unless otherwise indicated, a compound described herein is a single stereoisomer. In embodiments, unless otherwise indicated, a compound described herein is a single enantiomer. In embodiments, the compound is a compound described herein (e.g., in an aspect, embodiment, example, FIGURE, table, scheme, or claim).

III. Pharmaceutical Compositions

In an aspect is provided a pharmaceutical composition including a compound described herein, or pharmaceutically acceptable salt thereof, and a pharmaceutically acceptable excipient.

In embodiments of the pharmaceutical compositions, the compound, or pharmaceutically acceptable salt thereof, is included in a therapeutically effective amount.

In embodiments of the pharmaceutical compositions, the pharmaceutical composition includes a second agent (e.g. therapeutic agent). In embodiments of the pharmaceutical compositions, the pharmaceutical composition includes a second agent (e.g. therapeutic agent) in a therapeutically effective amount. In embodiments of the pharmaceutical compositions, the second agent is an agent for treating cancer. In embodiments, the second agent is an anti-cancer agent. In embodiments, the second agent is a chemotherapeutic. In embodiments, the second agent is an anti-inflammatory agent.

IV. Methods of Treatment

In an aspect is provided a method of treating cancer including administering to a subject in need thereof an effective amount of a compound described herein.

In an aspect is provided a method of treating an inflammatory disease including administering to a subject in need thereof an effective amount of a compound described herein. In embodiments, the disease is multiple sclerosis. In embodiments, inflammatory disease includes encephalitis. In embodiments, inflammatory disease includes Alzheimer's disease associated encephalitis (i.e. inflammation in the brain tissue associated with Alzheimer's disease). In embodiments, inflammatory disease includes Parkinson's disease associated encephalitis (i.e. inflammation in the brain tissue associated with Parkinson's disease).

In an aspect is provided a method of treating a disease associated with Bruton's Tyrosine Kinase activity including administering to a subject in need thereof an effective amount of a compound described herein. In embodiments, the disease is associated with aberrant Bruton's Tyrosine Kinase activity. In embodiments, the disease is associated with aberrant microglial activity. For example, diseases with aberrant microglial activity may be found in Graeber et al. (FEBS Letters, Volume 585, Issue 23, 1 Dec. 2011, Pages 3798-3805), Dheen et al. (Curr Med Chem. 2007; 14(11): 1189-97), and Reus et al. (Neuroscience. 2015 Aug. 6; 300:141-54) which are incorporated by reference in their entirety for all purposes. In embodiments, the disease is a psychiatric disorder or a neurological disorder. In embodiments, the disease is autism, Rett syndrome, Fragile X syndrome, myocardial infarction, glaucoma, tuberous sclerosis, neuropathic pain, anxiety, chronic neurodegeneration, depression, epilepsy, HIV-associated dementia, or neuroinflammation.

In an aspect is provided a method of treating stroke including administering to a subject in need thereof an effective amount of a compound described herein.

In an aspect is provided a method of treating an autoimmune disease (e.g., brain autoimmune disease, neurological autoimmune disease, autoimmune disease in the CNS, brain, cerebrospinal fluid, eyes, or spinal cord) including administering to a subject in need thereof an effective amount of a compound described herein. In embodiments, the disease is multiple sclerosis. In embodiments, the disease is encephalitis. In embodiments, the disease is Guillain-Barre syndrome. In embodiments, the disease is neuromyelitis optica. In embodiments, the disease is myelitis. In embodiments, the disease is optic neuritis. In embodiments, the disease is a paraneoplastic neurological disorder (e.g., paraneoplastic opsoclonus-myoclonus). In embodiments, the disease is a chronic autoimmune neuropathy (e.g., chronic inflammatory demyelinating neuropathy, multifocal motor neuropathy, or IgM anti-myelin-associated glycoprotein neuropathy). In embodiments, the disease is stiff-person syndrome. In embodiments, the disease is an inflammatory myopathy (e.g., polymyositis, dermatomyositis, or inclusion body myositis). In embodiments, the disease is myasthenia gravis.

In embodiments, the cancer is a hematological cancer. In embodiments, the cancer is a blood cancer. In embodiments, the cancer is a metastatic cancer. In embodiments, the cancer is a blood cancer that has metastasized to the brain. In embodiments, the cancer is a brain cancer due to metastasis of another cancer (e.g., blood cancer). In embodiments, the cancer is leukemia. In embodiments, the cancer is a B-cell associated cancer (e.g., in the CNS, brain, cerebrospinal fluid, eyes, or spinal cord). In embodiments, the cancer is lymphoma (e.g., in the CNS, brain, cerebrospinal fluid, eyes, or spinal cord). In embodiments, the cancer is diffuse large B-cell lymphoma. In embodiments, the cancer is multiple myeloma. In embodiments, the cancer is mantle cell lymphoma (e.g., in the CNS, brain, cerebrospinal fluid, eyes, or spinal cord). In embodiments, the cancer is chronic lymphocytic leukemia (e.g., in the CNS, brain, cerebrospinal fluid, eyes, or spinal cord). In embodiments, the cancer is Waldenstrom's macroglubulinemia (e.g., in the CNS, brain, cerebrospinal fluid, eyes, or spinal cord). In embodiments, the cancer is non-Hodgkin's lymphoma (e.g., in the CNS, brain, cerebrospinal fluid, eyes, or spinal cord). In embodiments, the cancer is follicular lymphoma. In embodiments, the cancer is Burkitt's lymphoma. In embodiments, the cancer is splenic marginal zone lymphoma. In embodiments, the cancer is mucosa-associated lymphoid tissue lymphoma. In embodiments, the cancer is Hodgkin lymphoma. In embodiments, the cancer is a primary central nervous system lymphoma (e.g., diffuse large B-cell lymphoma). In embodiments, the cancer is astrocytoma, atypical teratoid rhaboid tumor, chondrosarcoma, choroid plexus, craniopharyngioma, ependymoma, germ cell tumor, glioblastoma, glioma, hemangioma, juvenile pilocytic astrocytoma, lipoma, lymphoma, medulloblastoma, meningioma, neurofibroma, neuronal tumor, mixed neuronal-glial tumor, oligoastrocytoma, oligodendroglioma, pineal tumor, pituitary tumor, or schwannoma. In embodiments, the disease is HIV-associated central nervous system lymphoma.

In embodiments, the method includes administering a second agent (e.g. therapeutic agent). In embodiments, the method includes administering a second agent (e.g. therapeutic agent) in a therapeutically effective amount. In embodiments, the second agent is an agent for treating cancer. In embodiments, the second agent is an anti-cancer agent. In embodiments, the second agent is a chemotherapeutic. In embodiments, the second agent is an anti-inflammatory agent.

V. Methods of Inhibiting

In an aspect is provided a method of inhibiting Bruton's Tyrosine Kinase activity including contacting the Bruton's Tyrosine Kinase with a compound described herein. In embodiments, the Bruton's Tyrosine Kinase is a human Bruton's Tyrosine Kinase. In embodiments, the Bruton's Tyrosine Kinase is in the central nervous system. In embodiments, the Bruton's Tyrosine Kinase is in the brain. In embodiments, the Bruton's Tyrosine Kinase is in the spine. In embodiments, the Bruton's Tyrosine Kinase is in the spinal cord. In embodiments, the method is performed in vitro. In embodiments, the Bruton's Tyrosine Kinase is within a cell or a subject (e.g. human, or cancer subject).

In embodiments, the inhibition is competitive inhibition. In embodiments, the inhibition is irreversible. In embodiments, the inhibition is reversible. In embodiments, the compound covalently binds to the Bruton's Tyrosine Kinase.

Where the compound covalently binds to the Bruton's Tyrosine Kinase a Bruton's Tyrosine Kinase protein (e.g., human Bruton's Tyrosine Kinase) covalently bonded to a Bruton's Tyrosine Kinase inhibitor is formed (also referred to herein as a "BTK-compound adduct"), as described below. In embodiments, the resulting covalent bond is reversible. Where the resulting covalent bond is reversible, the bonding reverses upon denaturation of the protein. Thus, in embodiments, the reversibility of a covalent bond between the compound and the Bruton's Tyrosine Kinase upon denaturation of the Bruton's Tyrosine Kinase avoids or decreases autoimmune response in a subject subsequent to administration of the compound (relative to irreversibility). Moreover, in embodiments, the reversibility of a covalent bond between the compound and the Bruton's Tyrosine Kinase upon denaturation of the Bruton's Tyrosine Kinase avoids or decreases the toxicity (e.g. liver toxicity) of the compound in a subject (relative to irreversibility).

VI. Bruton's Tyrosine Kinase Protein

In an aspect is provided a Bruton's tyrosine kinase protein covalently bonded to a compound described herein (e.g., Bruton's Tyrosine Kinase inhibitor, Bruton's Tyrosine Kinase antagonist, compound described herein, or a portion of a compound described herein).

In an embodiment, the Bruton's tyrosine kinase protein is covalently bonded (e.g., reversibly or irreversibly) to a portion of a compound described herein (e.g., portion of a Bruton's tyrosine kinase inhibitor or portion of a compound described herein).

In embodiments, the compound is bonded to a cysteine residue of the Bruton's tyrosine kinase protein. In embodiments, the compound is covalently bonded to a cysteine residue of the Bruton's tyrosine kinase protein. In embodiments, the compound is reversibly covalently bonded to a cysteine residue of the Bruton's tyrosine kinase protein. In embodiments, the compound is irreversibly covalently bonded to a cysteine residue of the Bruton's tyrosine kinase protein. In embodiments, the compound is bonded (e.g., covalently, irreversibly covalently, or reversibly covalently) to an aspartate residue of the Bruton's tyrosine kinase protein. In embodiments, the compound is bonded (e.g., covalently, irreversibly covalently, or reversibly covalently) to an glutamate residue of the Bruton's tyrosine kinase protein. In embodiments, the compound is bonded (e.g., covalently, irreversibly covalently, or reversibly covalently) to an arginine residue of the Bruton's tyrosine kinase protein. In embodiments, the compound is bonded (e.g., covalently, irreversibly covalently, or reversibly covalently) to a lysine residue of the Bruton's tyrosine kinase protein. In embodiments, the compound is bonded (e.g., covalently, irreversibly covalently, or reversibly covalently) to a tyrosine residue of the Bruton's tyrosine kinase protein.

In an embodiment, the Bruton's tyrosine kinase protein is covalently bonded (e.g., reversibly or irreversibly) to a portion of a compound described herein (e.g., portion of a Bruton's Tyrosine Kinase inhibitor, portion of a Bruton's Tyrosine Kinase antagonist, or portion of a compound described herein).

In embodiments, the Bruton's tyrosine kinase protein is in the central nervous system of a subject. In embodiments, the Bruton's tyrosine kinase protein is in the brain of a subject.

In an aspect is provided a Bruton's Tyrosine Kinase protein (e.g., human BTK) covalently bonded to a Bruton's Tyrosine Kinase inhibitor (e.g., Bruton's Tyrosine Kinase antagonist, compound described herein, or a portion of a compound described herein).

In embodiments, the Bruton's Tyrosine Kinase protein (e.g., human Bruton's Tyrosine Kinase) is covalently bonded to a Bruton's Tyrosine Kinase inhibitor (e.g., Bruton's Tyrosine Kinase antagonist, compound described herein, or a portion of a compound described herein). In embodiments, the Bruton's Tyrosine Kinase protein (e.g., human Bruton's Tyrosine Kinase) is irreversibly covalently bonded to a Bruton's Tyrosine Kinase inhibitor (e.g., Bruton's Tyrosine Kinase antagonist, compound described herein, or a portion of a compound described herein). In embodiments, the Bruton's Tyrosine Kinase protein (e.g., human Bruton's Tyrosine Kinase) is reversibly covalently bonded to a Bruton's Tyrosine Kinase inhibitor (e.g., Bruton's Tyrosine Kinase antagonist, compound described herein, or a portion of a compound described herein). In embodiments, the Bruton's Tyrosine Kinase protein (e.g., human Bruton's Tyrosine Kinase) is covalently bonded to a portion of a Bruton's Tyrosine Kinase inhibitor (e.g., Bruton's Tyrosine Kinase antagonist or compound described herein). In embodiments, the Bruton's Tyrosine Kinase protein (e.g., human Bruton's Tyrosine Kinase) is irreversibly covalently bonded to a portion of a Bruton's Tyrosine Kinase inhibitor (e.g., Bruton's Tyrosine Kinase antagonist or compound described herein). In embodiments, the Bruton's Tyrosine Kinase protein (e.g., human Bruton's Tyrosine Kinase) is reversibly covalently bonded to a portion of a Bruton's Tyrosine Kinase inhibitor (e.g., Bruton's Tyrosine Kinase antagonist or compound described herein). In embodiments, the Bruton's Tyrosine Kinase inhibitor (e.g., Bruton's Tyrosine Kinase antagonist or compound described herein) is bonded to a cysteine residue (e.g., Cys481 of human BTK or cysteine corresponding to Cys481 of human BTK) of the Bruton's Tyrosine Kinase protein (e.g., human Bruton's Tyrosine Kinase). In embodiments, the portion of a Bruton's Tyrosine Kinase inhibitor (e.g., Bruton's Tyrosine Kinase antagonist or compound described herein) is bonded to a cysteine residue (e.g., Cys481 of human BTK or cysteine corresponding to Cys481 of human BTK) of the Bruton's Tyrosine Kinase protein (e.g., human Bruton's Tyrosine Kinase).

In embodiments, the Bruton's Tyrosine Kinase inhibitor (e.g., Bruton's Tyrosine Kinase antagonist or compound described herein) is bonded to cysteine 481 of the Bruton's Tyrosine Kinase protein (e.g., human Bruton's Tyrosine Kinase). In embodiments, the Bruton's Tyrosine Kinase inhibitor (e.g., Bruton's Tyrosine Kinase antagonist or compound described herein) is bonded to cysteine 481 of the Bruton's Tyrosine Kinase protein (e.g., human Bruton's Tyrosine Kinase) corresponding to RefSeq (protein) NP_000052. In embodiments, the Bruton's Tyrosine Kinase inhibitor (e.g., Bruton's Tyrosine Kinase antagonist or compound described herein) interacts (e.g., contacts) with hydrophobic groups (e.g., in the active site) of the Bruton's Tyrosine Kinase protein (e.g., human Bruton's Tyrosine Kinase) corresponding to RefSeq (protein) NP_000052. In embodiments, the Bruton's Tyrosine Kinase inhibitor (e.g., Bruton's Tyrosine Kinase antagonist or compound described herein) interacts (e.g., contacts) with the active site of the Bruton's Tyrosine Kinase protein (e.g., human Bruton's Tyrosine Kinase). In embodiments, the Bruton's Tyrosine Kinase inhibitor (e.g., Bruton's Tyrosine Kinase antagonist or compound described herein) interacts (e.g., contacts) with the active site of the Bruton's Tyrosine Kinase protein (e.g., human Bruton's Tyrosine Kinase) corresponding to RefSeq (protein) NP_000052.

In embodiments, the Bruton's Tyrosine Kinase inhibitor (e.g., Bruton's Tyrosine Kinase antagonist or compound described herein) is bonded to the amino acid corresponding to cysteine 481 of the Bruton's Tyrosine Kinase protein (e.g., human Bruton's Tyrosine Kinase). In embodiments, the Bruton's Tyrosine Kinase inhibitor (e.g., Bruton's Tyrosine Kinase antagonist or compound described herein) is bonded to the amino acid corresponding to cysteine 481 of the Bruton's Tyrosine Kinase protein (e.g., human Bruton's Tyrosine Kinase) corresponding to RefSeq (protein) NP_000052. In embodiments, the Bruton's Tyrosine Kinase inhibitor (e.g., Bruton's Tyrosine Kinase antagonist or compound described herein) interacts (e.g., contacts) with the amino acids corresponding to the active site of the Bruton's Tyrosine Kinase protein (e.g., human Bruton's Tyrosine Kinase). In embodiments, the Bruton's Tyrosine Kinase inhibitor (e.g., Bruton's Tyrosine Kinase antagonist or compound described herein) interacts (e.g., contacts) with the amino acids corresponding to the active site of the Bruton's Tyrosine Kinase protein (e.g., human Bruton's Tyrosine Kinase) corresponding to RefSeq (protein) NP_000052.

In embodiments, a portion of the Bruton's Tyrosine Kinase inhibitor (e.g., Bruton's Tyrosine Kinase antagonist or compound described herein) is bonded to cysteine 481 of the Bruton's Tyrosine Kinase protein (e.g., human Bruton's Tyrosine Kinase). In embodiments, a portion of the Bruton's Tyrosine Kinase inhibitor (e.g., Bruton's Tyrosine Kinase antagonist or compound described herein) is bonded to cysteine 481 of the Bruton's Tyrosine Kinase protein (e.g., human Bruton's Tyrosine Kinase) corresponding to RefSeq (protein) NP_000052.

In embodiments, a portion of the Bruton's Tyrosine Kinase inhibitor (e.g., Bruton's Tyrosine Kinase antagonist or compound described herein) is bonded to the amino acid corresponding to cysteine 481 of the Bruton's Tyrosine Kinase protein (e.g., human Bruton's Tyrosine Kinase). In embodiments, a portion of the Bruton's Tyrosine Kinase inhibitor (e.g., Bruton's Tyrosine Kinase antagonist or compound described herein) is bonded to the amino acid corresponding to cysteine 481 of the Bruton's Tyrosine Kinase protein (e.g., human Bruton's Tyrosine Kinase) corresponding to RefSeq (protein) NP_000052. In embodiments, a portion of the Bruton's Tyrosine Kinase inhibitor (e.g., Bruton's Tyrosine Kinase antagonist or compound described herein) interacts (e.g., contacts) with the amino acids corresponding to the active site of the Bruton's Tyrosine Kinase protein (e.g., human Bruton's Tyrosine Kinase). In embodiments, a portion of the Bruton's Tyrosine Kinase inhibitor (e.g., Bruton's Tyrosine Kinase antagonist or compound described herein) interacts (e.g., contacts) with the amino acids corresponding to the active site of the Bruton's Tyrosine Kinase protein (e.g., human Bruton's Tyrosine Kinase) corresponding to RefSeq (protein) NP_000052.

In an aspect is provided a Bruton's Tyrosine Kinase protein (e.g., human Bruton's Tyrosine Kinase) covalently bonded to a compound described herein, or a portion of a compound described herein.

In embodiments, the Bruton's Tyrosine Kinase protein (e.g., human Bruton's Tyrosine Kinase) is covalently bonded to a compound described herein. In embodiments, the Bruton's Tyrosine Kinase protein (e.g., human Bruton's Tyrosine Kinase) is irreversibly covalently bonded to a compound described herein. In embodiments, the Bruton's Tyrosine Kinase protein (e.g., human Bruton's Tyrosine Kinase) is reversibly covalently bonded to a compound described herein. In embodiments, the Bruton's Tyrosine Kinase protein (e.g., human Bruton's Tyrosine Kinase) is covalently bonded to a portion of a compound described herein. In embodiments, the Bruton's Tyrosine Kinase protein (e.g., human Bruton's Tyrosine Kinase) is irreversibly covalently bonded to a portion of a compound described herein. In embodiments, the Bruton's Tyrosine Kinase protein (e.g., human Bruton's Tyrosine Kinase) is reversibly covalently bonded to a portion of a compound described herein. In embodiments, the compound is bonded to a cysteine residue of the Bruton's Tyrosine Kinase protein (e.g., human Bruton's Tyrosine Kinase). In embodiments, the portion of a compound is bonded to a cysteine residue of the Bruton's Tyrosine Kinase protein (e.g., human Bruton's Tyrosine Kinase).

In embodiments, the Bruton's Tyrosine Kinase protein covalently bonded to a compound described herein is the product of a reaction between the Bruton's Tyrosine Kinase protein and a compound described herein. It will be understood that the covalently bonded Bruton's Tyrosine Kinase protein and Bruton's Tyrosine Kinase inhibitor (e.g., compound described herein) are the remnants of the reactant Bruton's Tyrosine Kinase protein and Bruton's Tyrosine Kinase inhibitor or compound, wherein each reactant now participates in the covalent bond between the Bruton's Tyrosine Kinase protein and Bruton's Tyrosine Kinase inhibitor or compound. In embodiments of the covalently bonded Bruton's Tyrosine Kinase protein and compound described herein, the remnant of the E substitutent is a linker including a covalent bond between the Bruton's Tyrosine Kinase protein and the remainder of the compound described herein. It will be understood by a person of ordinary skill in the art that when a Bruton's Tyrosine Kinase protein is covalently bonded to a Bruton's Tyrosine Kinase inhibitor (e.g., compound described herein), the Bruton's Tyrosine Kinase inhibitor (e.g., compound described herein) forms a remnant of the pre-reacted Bruton's Tyrosine Kinase inhibitor (e.g., compound described herein) wherein a bond connects the remnant of the Bruton's Tyrosine Kinase inhibitor (e.g., compound described herein) to the remnant of the Bruton's Tyrosine Kinase protein (e.g., cysteine sulfur, sulfur of amino acid corresponding to cysteine 481 of human Bruton's Tyrosine Kinase, sulfur of cysteine 481 of human Bruton's Tyrosine Kinase). The remnant of the Bruton's Tyrosine Kinase inhibitor (compound described herein) may also be called a portion of the Bruton's Tyrosine Kinase inhibitor. In embodiments, the remnant of the E substituent is a linker selected from a bond, —S(O)$_2$—, —NH—, —O—, —S—, —C(O)—, —C(O)NH—, —NHC(O)—, —NHC(O)NH—, —NHC(O)NH—, —C(O)O—, —OC(O)—, —CH$_2$NH—, substituted (e.g., substituted with a substituent group, a size-limited substituent group, or lower substituent group) or unsubstituted alkylene (e.g., C$_1$-C$_8$, C$_1$-C$_6$, C$_1$-C$_4$, or C$_1$-C$_2$), substituted (e.g., substituted with a substituent group, a size-limited substituent group, or lower substituent group) or unsubstituted heteroalkylene (e.g., 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkylene (e.g., C$_3$-C$_8$, C$_3$-C$_6$, C$_4$-C$_6$, or C$_5$-C$_6$), substituted (e.g., substituted with a substituent group, a size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted arylene (e.g., $C_6$-$C_{10}$ or phenyl), or substituted (e.g., substituted with a substituent group, a size-limited substituent group, or lower substituent group) or unsubstituted heteroarylene (e.g., 5 to 10 membered, 5 to 9 membered, or 5 to 6 membered).

As a non-limiting example, the Bruton's Tyrosine Kinase protein covalently bonded to a compound described herein may have the formula:

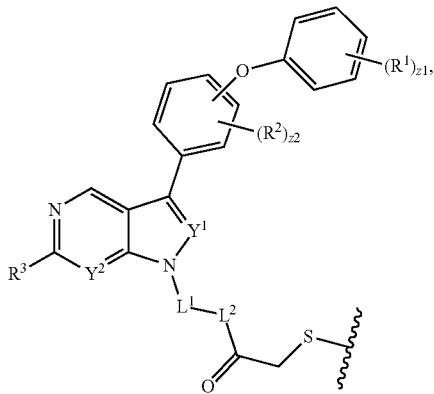

wherein S is the sulfur of a Bruton's Tyrosine Kinase protein cysteine (e.g., corresponding to cysteine 481 of human Bruton's Tyrosine Kinase), which is bonded to the remainder of the Bruton's Tyrosine Kinase protein and wherein $R^1$, z1, $R^2$, z2, $R^3$, $Y^2$, $Y^1$, $L^1$, and $L^2$ are as described herein. As a non-limiting example, the Bruton's Tyrosine Kinase protein covalently bonded to a compound described herein may have the formula:

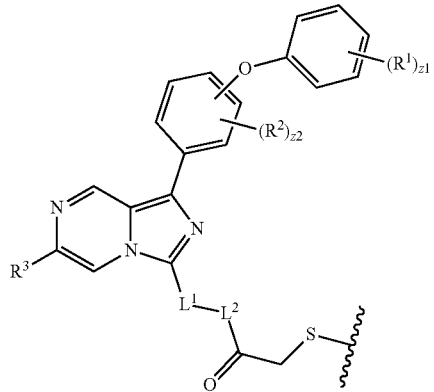

wherein S is the sulfur of a Bruton's Tyrosine Kinase protein cysteine (e.g., corresponding to cysteine 481 of human Bruton's Tyrosine Kinase), which is bonded to the remainder of the Bruton's Tyrosine Kinase protein and wherein $R^1$, z1, $R^2$, z2, $R^3$, $L^1$, and $L^2$ are as described herein. As a non-limiting example, the Bruton's Tyrosine Kinase protein covalently bonded to a compound described herein may have the formula

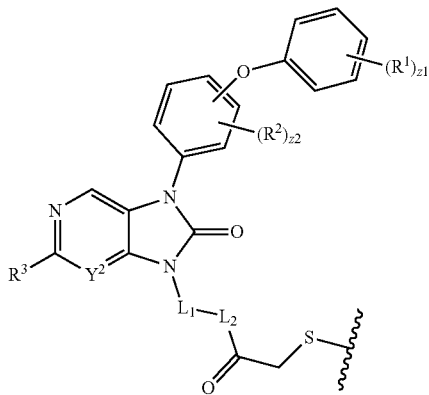

wherein S is the sulfur of a Bruton's Tyrosine Kinase protein cysteine (e.g., corresponding to cysteine 481 of human Bruton's Tyrosine Kinase), which is bonded to the remainder of the Bruton's Tyrosine Kinase protein and wherein $R^1$, z1, $R^2$, z2, $R^3$, $Y^2$, $L^1$, and $L^2$ are as described herein.

As a non-limiting example, the Bruton's Tyrosine Kinase protein covalently bonded to a compound described herein may have the formula:

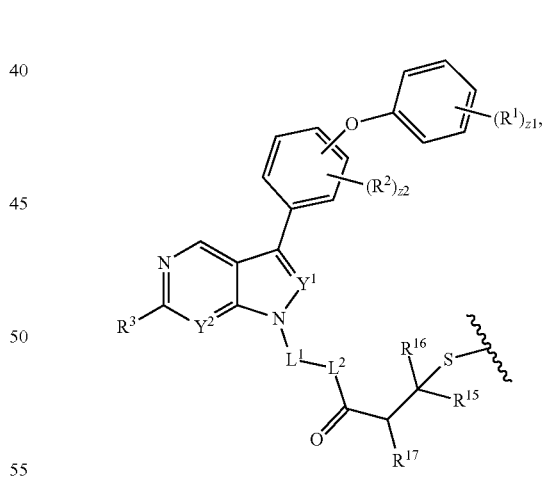

wherein S is the sulfur of a Bruton's Tyrosine Kinase protein cysteine (e.g., corresponding to cysteine 481 of human Bruton's Tyrosine Kinase), which is bonded to the remainder of the Bruton's Tyrosine Kinase protein and wherein $R^1$, $R^{15}$, $R^{16}$, $R^{17}$, z1, $R^2$, z2, $R^3$, $Y^2$, $L^1$, and $L^2$ are as described herein. As a non-limiting example, the Bruton's Tyrosine Kinase protein covalently bonded to a compound described herein may have the formula:

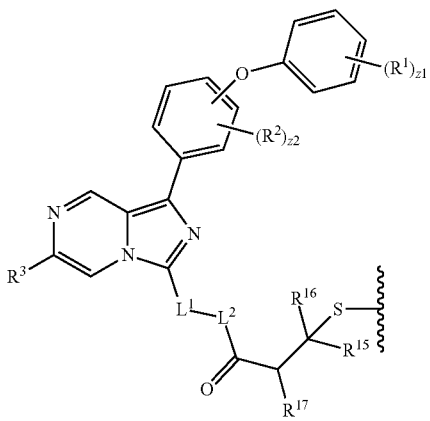

wherein S is the sulfur of a Bruton's Tyrosine Kinase protein cysteine (e.g., corresponding to cysteine 481 of human Bruton's Tyrosine Kinase), which is bonded to the remainder of the Bruton's Tyrosine Kinase protein and wherein $R^1$, $R^5$, $R^{16}$, $R^{17}$, z1, $R^2$, z2, $R^3$, $Y^2$, $L^1$, and $L^2$ are as described herein. As a non-limiting example, the Bruton's Tyrosine Kinase protein covalently bonded to a compound described herein may have the formula:

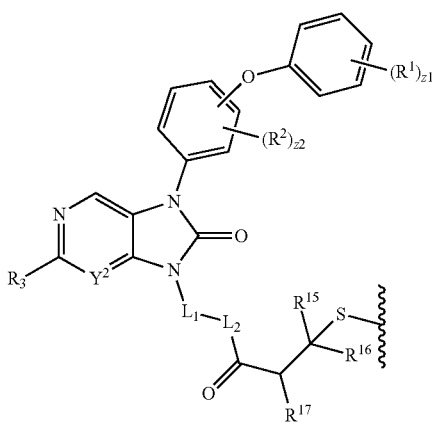

wherein S is the sulfur of a Bruton's Tyrosine Kinase protein cysteine (e.g., corresponding to cysteine 481 of human Bruton's Tyrosine Kinase), which is bonded to the remainder of the Bruton's Tyrosine Kinase protein and wherein $R^1$, $R^{15}$, $R^{16}$, $R^{17}$, z1, $R^2$, z2, $R^3$, $Y^2$, $L^1$, and $L^2$ are as described herein.

As a non-limiting example, the Bruton's Tyrosine Kinase protein covalently bonded to a compound described herein may have the formula:

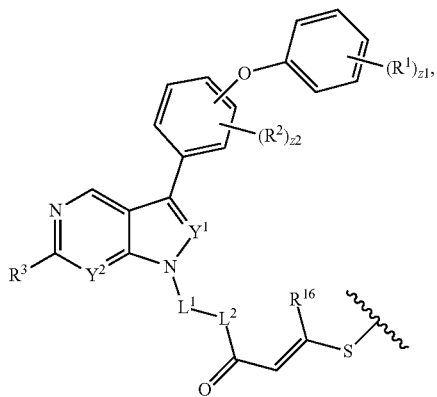

wherein S is the sulfur of a Bruton's Tyrosine Kinase protein cysteine (e.g., corresponding to cysteine 481 of human Bruton's Tyrosine Kinase), which is bonded to the remainder of the Bruton's Tyrosine Kinase protein and wherein $R^1$, $R^{15}$, $R^{16}$, $R^{17}$, z1, $R^2$, z2, $R^3$, $Y^2$, $L^1$, and $L^2$ are as described herein. As a non-limiting example, the Bruton's Tyrosine Kinase protein covalently bonded to a compound described herein may have the formula:

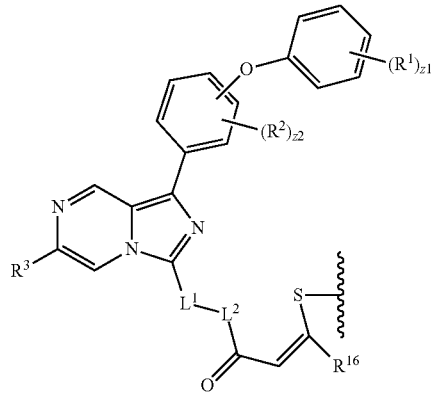

wherein S is the sulfur of a Bruton's Tyrosine Kinase protein cysteine (e.g., corresponding to cysteine 481 of human Bruton's Tyrosine Kinase), which is bonded to the remainder of the Bruton's Tyrosine Kinase protein and wherein $R^1$, $R^{15}$, $R^{16}$, $R^{17}$, z1, $R^2$, z2, $R^3$, $Y^2$, $L^1$, and $L^2$ are as described herein. As a non-limiting example, the Bruton's Tyrosine Kinase protein covalently bonded to a compound described herein may have the formula:

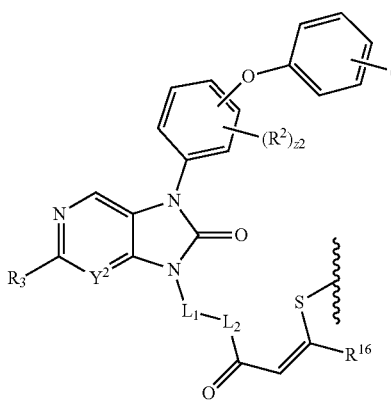

wherein S is the sulfur of a Bruton's Tyrosine Kinase protein cysteine (e.g., corresponding to cysteine 481 of human Bruton's Tyrosine Kinase), which is bonded to the remainder of the Bruton's Tyrosine Kinase protein and wherein $R^1$, $R^{15}$, $R^{16}$, z1, $R^2$, z2, $R^3$, $Y^2$, $L^1$, and $L^2$ are as described herein.

As a non-limiting example, the Bruton's Tyrosine Kinase protein covalently bonded to a compound described herein may have the formula:

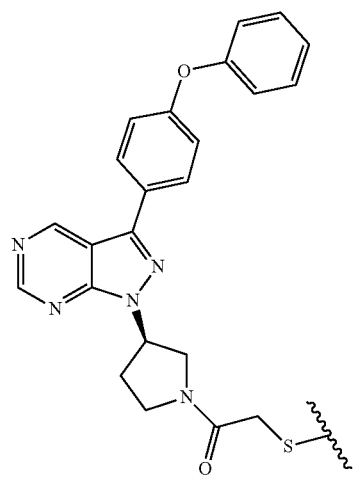

wherein S is the sulfur of a Bruton's Tyrosine Kinase protein cysteine (e.g., corresponding to cysteine 481 of human Bruton's Tyrosine Kinase), which is bonded to the remainder of the Bruton's Tyrosine Kinase protein.

As a non-limiting example, the Bruton's Tyrosine Kinase protein covalently bonded to a compound described herein may have the formula:

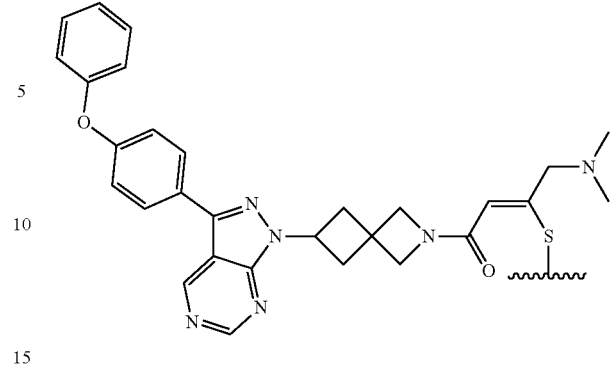

wherein S is the sulfur of a Bruton's Tyrosine Kinase protein cysteine (e.g., corresponding to cysteine 481 of human Bruton's Tyrosine Kinase), which is bonded to the remainder of the Bruton's Tyrosine Kinase protein.

As a non-limiting example, the Bruton's Tyrosine Kinase protein covalently bonded to a compound described herein may have the formula:

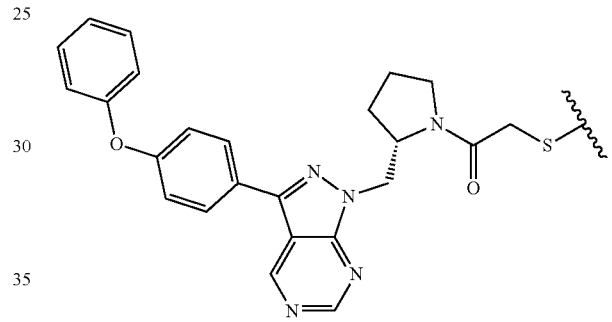

wherein S is the sulfur of a Bruton's Tyrosine Kinase protein cysteine (e.g., corresponding to cysteine 481 of human Bruton's Tyrosine Kinase), which is bonded to the remainder of the Bruton's Tyrosine Kinase protein.

As a non-limiting example, the Bruton's Tyrosine Kinase protein covalently bonded to a compound described herein may have the formula:

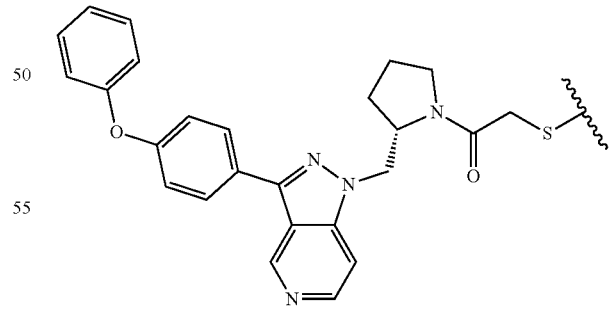

wherein S is the sulfur of a Bruton's Tyrosine Kinase protein cysteine (e.g., corresponding to cysteine 481 of human Bruton's Tyrosine Kinase), which is bonded to the remainder of the Bruton's Tyrosine Kinase protein. In embodiments, the Bruton's Tyrosine Kinase is in vitro. In embodiments, the Bruton's Tyrosine Kinase is within a cell or a subject (e.g. human, or cancer subject).

VII. EMBODIMENTS

Embodiment 1

A compound having the formula:

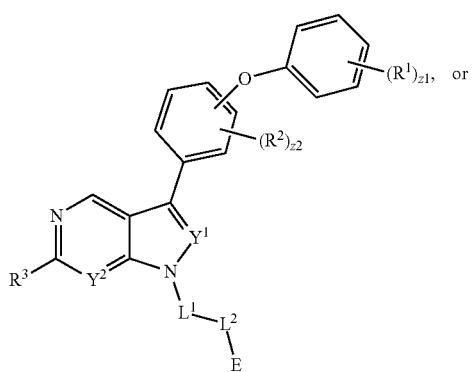

(I)

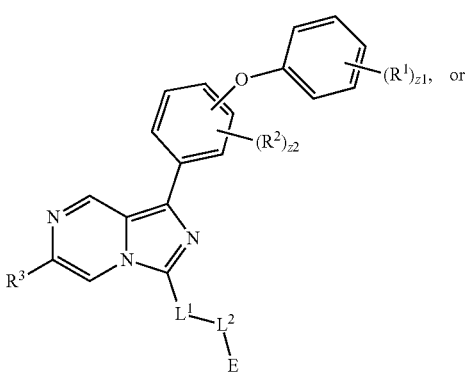

(II)

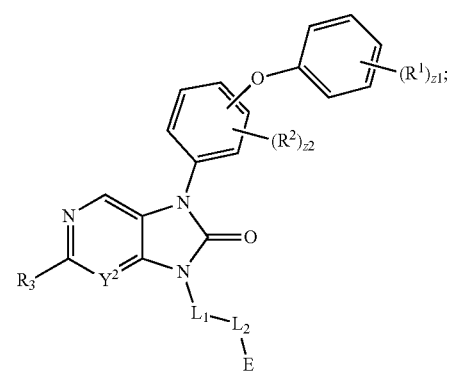

(III); wherein, $R^1$ is independently halogen, $-CX^1_3$, $-CHX^1_2$, $-CH_2X^1$, $-OCX^1_3$, $-OCH_2X^1$, $-OCHX^1_2$, $-CN$, $-SO_{n1}R^{1D}$, $-SO_{v1}NR^{1A}R^{1B}$, $-NHC(O)NR^{1A}R^{1B}$, $-N(O)_{m1}$, $-NR^{1A}R^{1B}$, $-C(O)R^{1C}$, $-C(O)-OR^{1C}$, $-C(O)NR^{1A}R^{1B}$, $-OR^{1D}$, $-NR^{1A}SO_2R^{1D}$, $-NR^{1A}C(O)R^{1C}$, $-NR^{1A}C(O)OR^{1C}$, $-NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl; z1 is an integer from 0 to 5; $R^2$ is independently halogen, $-CX^2_3$, $-CHX^2_2$, $-CH_2X^2$, $-OCX^2_3$, $-OCH_2X^2$, $-OCHX^2_2$, $-CN$, $-SO_{n2}R^{2D}$, $-SO_{v2}NR^{2A}R^{2B}$, $-NHC(O)NR^{2A}R^{2B}$, $-N(O)_{m2}$, $-NR^{2A}R^{2B}$, $-C(O)R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2}OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl; z2 is an integer from 0 to 4; 3 is hydrogen or $-NH_2$; $Y^1$ is N or $C(R^4)$; $R^4$ is hydrogen, halogen, $-CX^4_3$, $-CHX^4_2$, $-CH_2X^4$, $-OCX^4_3$, $-OCH_2X^4$, $-OCHX^4_2$, $-CN$, $-SO_{n4}R^{4D}$, $-SO_{v4}NR^{4A}R^{4B}$, $-NHC(O)NR^{4A}R^{4B}$, $-N(O)_{m4}$, $-NR^{4A}R^{4B}$, $-C(O)R^{4C}$, $-C(O)-OR^{4C}$, $-C(O)NR^{4A}R^{4B}$, $-OR^{4D}$, $-NR^{4A}SO_2R^{4D}$, $-NR^{4A}C(O)R^{4C}$, $-NR^{4A}C(O)OR^{4C}$, $-NR^{4A}OR^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $Y^2$ is N or $C(R^5)$; $R^5$ is hydrogen, halogen, $-CX^5_3$, $-CHX^5_2$, $-CH_2X^5$, $-OCX^5_3$, $-OCH_2X^5$, $-OCHX^5_2$, $-CN$, $-SO_{n5}R^{5D}$, $-SO_{v5}NR^{5A}R^{5B}$, $-NHC(O)NR^{5A}R^{5B}$, $-N(O)_{m5}$, $-NR^{5A}R^{5B}$, $-C(O)R^{5C}$, $-C(O)-OR^{5C}$, $-C(O)NR^{5A}R^{5B}$, $-OR^{5D}$, $-NR^{5A}SO_2R^{5D}$, $-NR^{5A}C(O)R^{5C}$, $-NR^{5A}C(O)OR^{5C}$, $-NR^{5A}OR^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; L, is a bond, $-S(O)_2-$, $-S(O)_2$-Ph-, $-NR-$, $-O-$, $-S-$, $-C(O)-$, $-C(O)NR^6-$, $-NR^6C(O)-$, $-NR^6C(O)NH-$, $-NHC(O)NR^6-$, $-C(O)O-$, $-OC(O)-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $R^6$ is hydrogen, halogen, $-CX^6_3$, $-CHX^6_2$, $-CH_2X^6$, $-OCX^6_3$, $-OCH_2X^6$, $-OCHX^6_2$, $-CN$, $-SO_{n6}R^{6D}$, $-SO_{v6}NR^{6A}R^{6B}$, $-NHC(O)NR^{6A}R^{6B}$, $-N(O)_{m6}$, $-NR^{6A}R^{6B}$, $-C(O)R^{6C}$, $-C(O)-OR^{6C}$, $-C(O)NR^{6A}R^{6B}$, $-OR^{6D}$, $-NR^{6A}SO_2R^{6D}$, $-NR^{6A}C(O)R^{6C}$, $-NR^{6A}C(O)OR^{6C}$, $-NR^{6A}OR^{6C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $L^2$ is a bond, $-S(O)_2-$, $-S(O)_2$-Ph-, $-NR^7-$, $-O-$, $-S-$, $-C(O)-$, $-C(O)NR^7-$, $-NR^7C(O)-$, $-NR^7C(O)NH-$, $-NHC(O)NR^7-$, $-C(O)O-$, $-OC(O)-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $R^7$ is hydrogen, halogen, $-CX^7_3$, $-CHX^7_2$, $-CH_2X^7$, $-OCX^7_3$, $-OCH_2X^7$, $-OCHX^7_2$, $-CN$, $-SO_{n7}R^{7D}$, $-SO_{v7}NR^{7A}R^{7B}$, $-NHC(O)NR^{7A}R^{7B}$, $-N(O)_{m7}$, $-NR^{7A}R^{7B}$, $-C(O)R^{7C}$, $-C(O)-OR^{7C}$, $-C(O)NR^{7A}R^{7B}$, $-OR^{7D}$, $-NR^{7A}SO_2R^{7D}$, $-NR^{7A}C(O)R^{7C}$, $-NR^{7A}C(O)OR^{7C}$, $-NR^{7A}OR^{7C}$, substituted or unsubstituted alkyl, substituted or unsubstituted heteroalkyl, substituted or unsubstituted cycloalkyl, substituted or unsubstituted heterocycloalkyl, substituted or unsubstituted heterocycloalkyl, substituted or unsubstituted aryl, or substituted or unsubstituted heteroaryl; E is an electrophilic moiety; each $R^{1A}$, $R^{1B}$, $R^{1C}$, $R^{1D}$, $R^{2A}$, $R^{2B}$, $R^{2C}$, $R^{2D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, and $R^{7D}$ is independently hydrogen, —$CX_3$, —CN, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{4A}$ and $R^{4B}$ substituents bonded to the same nitrogen atom may optionally be joined to form a substituted or unsubstituted heterocycloalkyl or substituted or unsubstituted heteroaryl; $R^{5A}$ and $R^{5B}$ substituents bonded to the same nitrogen atom may optionally be joined to form a substituted or unsubstituted heterocycloalkyl or substituted or unsubstituted heteroaryl; $R^{6A}$ and $R^{6B}$ substituents bonded to the same nitrogen atom may optionally be joined to form a substituted or unsubstituted heterocycloalkyl or substituted or unsubstituted heteroaryl; $R^{7A}$ and $R^{7B}$ substituents bonded to the same nitrogen atom may optionally be joined to form a substituted or unsubstituted heterocycloalkyl or substituted or unsubstituted heteroaryl; each X, $X^1$, $X^2$, $X^4$, $X^5$, $X^6$, and $X^7$ is independently —F, —Cl, —Br, or —I; n1, n2, n4, n5, n6, and n7 are independently an integer from 0 to 4; and m1, m2, m4, m5, m6, m7, v1, v2, v4, v5, v6, and v7, are independently an integer from 1 to 2.

Embodiment 2

The compound of embodiment 1 having the formula:

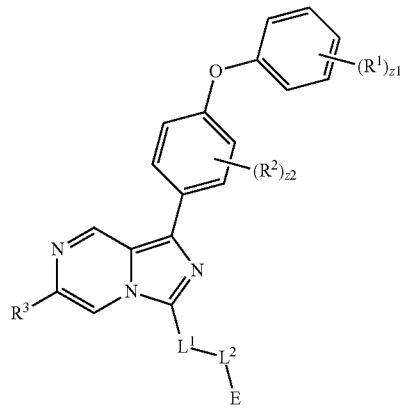

(IIA)

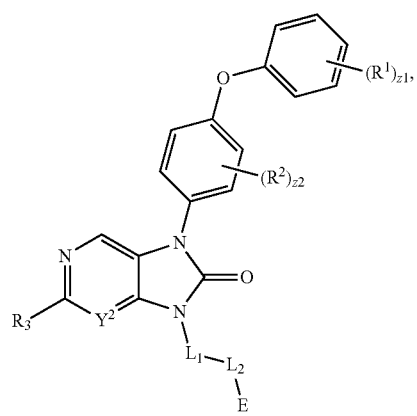

(IIIA)

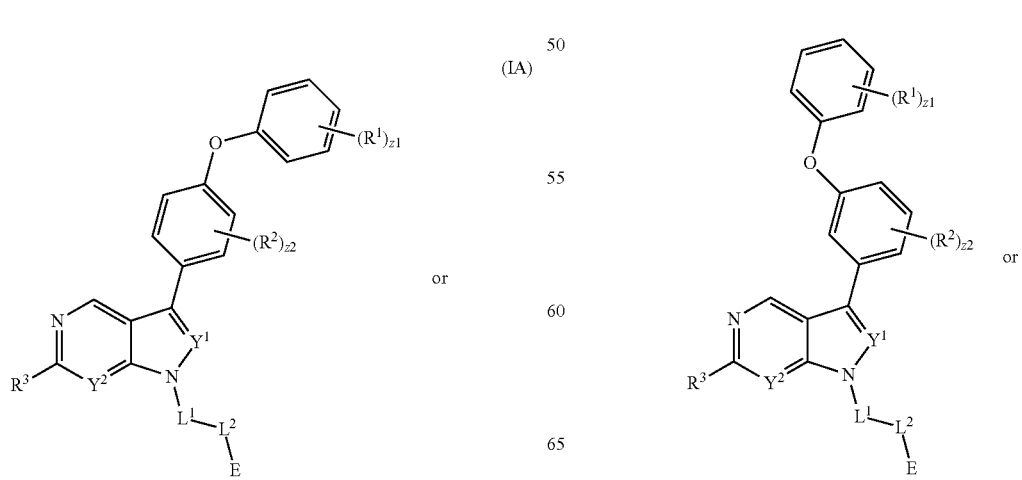

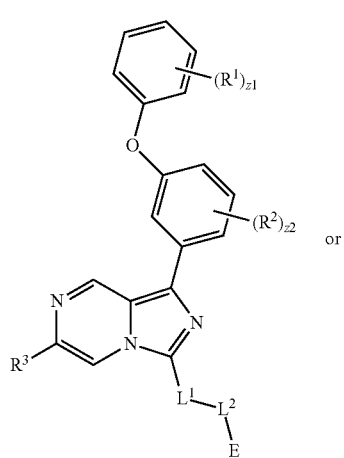
(IIB)
or
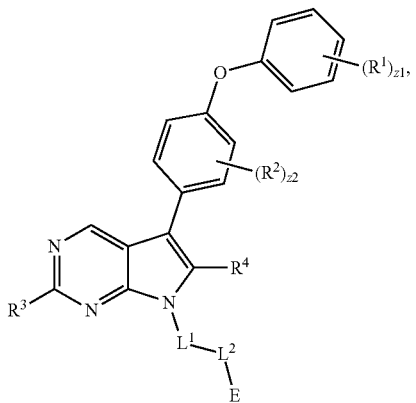
(ID)
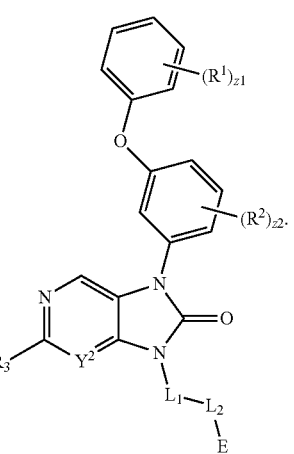
(IIIB)
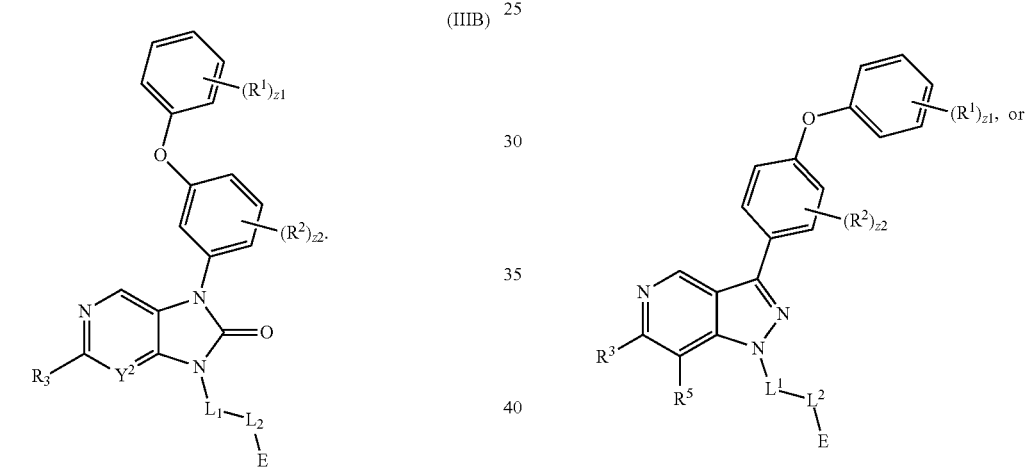
(IE)
Embodiment 3
The compound of embodiment 1 having the formula:
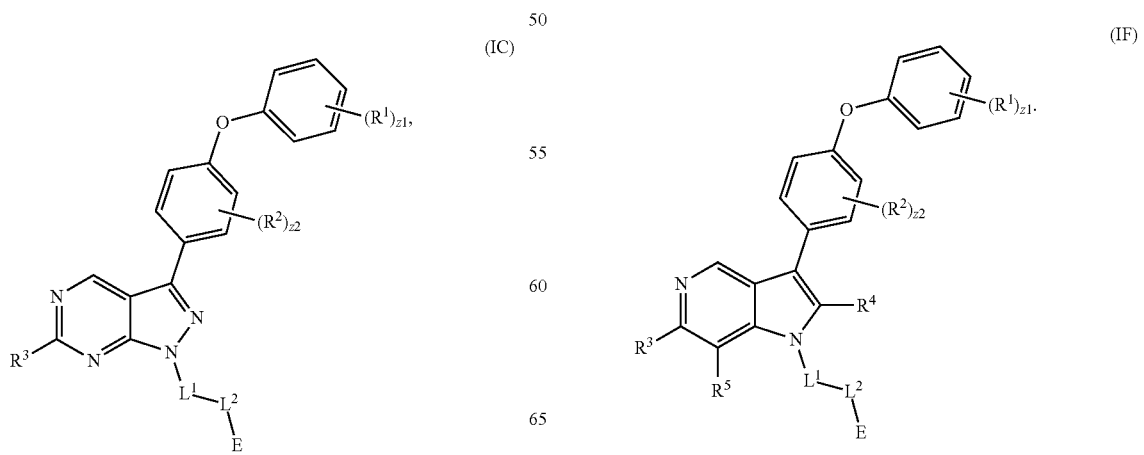
(IC) (IF)

Embodiment 4

The compound of embodiment 1 having the formula:

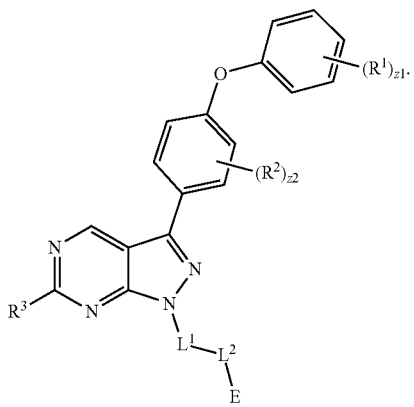

(IC)

Embodiment 5

The compound of one of embodiments 1 to 4, wherein $R^3$ is hydrogen.

Embodiment 6

The compound of one of embodiments 1 to 4, wherein $R^3$ is —$NH_2$.

Embodiment 7

The compound of one of embodiments 1 to 6, wherein $R^1$ is independently
halogen, —$CX_3$, —CN, —OH, —$NH_2$, —COOH, —$CONH_2$, —$NO_2$, —SH, —$OCX^1{}_3$, —$OCHX^1{}_2$, —$CHX_2$, —$CH_2X^1$, substituted or unsubstituted $C_1$-$C_8$ alkyl, or substituted or unsubstituted 2 to 8 membered heteroalkyl; two adjacent $R^1$ substituents may optionally be joined to form a substituted or unsubstituted $C_3$-$C_8$ cycloalkyl, substituted or unsubstituted 3 to 8 membered heterocycloalkyl, substituted or unsubstituted phenyl, or substituted or unsubstituted 5 to 6 membered heteroaryl.

Embodiment 8

The compound of one of embodiments 1 to 6, wherein $R^1$ is independently halogen, —$CX^1{}_3$, —CN, unsubstituted $C_1$-$C_4$ alkyl, or unsubstituted 2 to 4 membered heteroalkyl.

Embodiment 9

The compound of one of embodiments 1 to 6, wherein $R^1$ is independently halogen, —$CX^{13}$, —CN, unsubstituted methyl, unsubstituted ethyl, unsubstituted methoxy, or unsubstituted ethoxy.

Embodiment 10

The compound of one of embodiments 1 to 9, wherein z1 is 0.

Embodiment 11

The compound of one of embodiments 1 to 9, wherein z1 is 1.

Embodiment 12

The compound of one of embodiments 1 to 11, wherein $R^2$ is independently
halogen, —$CX^2{}_3$, —CN, —OH, —$NH_2$, —COOH, —$CONH_2$, —$NO_2$, —SH, —$OCX^2{}_3$, —$OCHX^2{}_2$, —$CHX^2{}_2$, —$CH_2X^2$, substituted or unsubstituted $C_1$-$C_8$ alkyl, or substituted or unsubstituted 2 to 8 membered heteroalkyl; two adjacent $R^2$ substituents may optionally be joined to form a substituted or unsubstituted $C_3$-$C_8$ cycloalkyl, substituted or unsubstituted 3 to 8 membered heterocycloalkyl, substituted or unsubstituted phenyl, or substituted or unsubstituted 5 to 6 membered heteroaryl.

Embodiment 13

The compound of one of embodiments 1 to 11, wherein $R^2$ is independently halogen, —$CX^2{}_3$, —CN, unsubstituted $C_1$-$C_4$ alkyl, or unsubstituted 2 to 4 membered heteroalkyl.

Embodiment 14

The compound of one of embodiments 1 to 11, wherein $R^2$ is independently halogen, —$CX^2{}_3$, —CN, unsubstituted methyl, unsubstituted ethyl, unsubstituted methoxy, or unsubstituted ethoxy.

Embodiment 15

The compound of one of embodiments 1 to 14, wherein z2 is 0.

Embodiment 16

The compound of one of embodiments 1 to 14, wherein z2 is 1.

Embodiment 17

The compound of one of embodiments 1 to 16, wherein $L^1$ is a bond, —$S(O)_2$—, —$S(O)_2$-Ph-, substituted or unsubstituted $C_1$-$C_8$ alkylene, substituted or unsubstituted 2 to 8 membered heteroalkylene, substituted or unsubstituted $C_3$-$C_8$ cycloalkylene, substituted or unsubstituted 3 to 8 membered heterocycloalkylene, substituted or unsubstituted phenylene, or substituted or unsubstituted 5 to 6 membered heteroarylene.

Embodiment 18

The compound of one of embodiments 1 to 16, wherein $L^1$ is a bond.

Embodiment 19

The compound of one of embodiments 1 to 16, wherein $L^1$ is a substituted or unsubstituted $C_1$-$C_6$ alkylene, substituted or unsubstituted 2 to 6 membered heteroalkylene, substituted or unsubstituted $C_3$-$C_6$ cycloalkylene, substituted or unsubstituted 3 to 6 membered heterocycloalkylene, substituted or unsubstituted phenylene, or substituted or unsubstituted 5 to 6 membered heteroarylene.

Embodiment 20

The compound of one of embodiments 1 to 16, wherein $L^1$ is an unsubstituted $C_1$-$C_6$ alkylene, unsubstituted 2 to 6 membered heteroalkylene, or unsubstituted $C_3$-$C_6$ cycloalkylene.

Embodiment 21

The compound of one of embodiments 1 to 16, wherein $L^1$ is an unsubstituted methylene.

Embodiment 22

The compound of one of embodiments 1 to 21, wherein $L^2$ is —$NR^7$— or substituted or unsubstituted heterocycloalkylene comprising a ring nitrogen bonded directly to E.

Embodiment 23

The compound of one of embodiments 1 to 21, wherein $L^2$ is —$NR^7$— or substituted or unsubstituted spirocyclic heterocycloalkylene comprising a ring nitrogen bonded directly to E.

Embodiment 24

The compound of one of embodiments 1 to 21, wherein $L^2$ is —$NR^7$—.

Embodiment 25

The compound of embodiment 24, wherein $R^7$ is hydrogen, substituted or unsubstituted $C_1$-$C_6$ alkyl, or substituted or unsubstituted 2 to 6 membered heteroalkyl.

Embodiment 26

The compound of embodiment 24, wherein $R^7$ is hydrogen or unsubstituted $C_1$-$C_3$ alkyl.

Embodiment 27

The compound of embodiment 24, wherein $R^7$ is hydrogen.

Embodiment 28

The compound of one of embodiments 1 to 21, wherein $L^2$ is substituted or unsubstituted heterocycloalkylene.

Embodiment 29

The compound of one of embodiments 1 to 21, wherein $L^2$ is substituted or unsubstituted piperidinylene or substituted or unsubstituted pyrrolindinylene.

Embodiment 30

The compound of one of embodiments 1 to 21, wherein $L^2$ is unsubstituted piperidinylene or unsubstituted pyrrolindinylene.

Embodiment 31

The compound of one of embodiments 1 to 30, wherein E is a covalent cysteine modifier moiety.

Embodiment 32

The compound of one of embodiments 1 to 30, wherein E is:

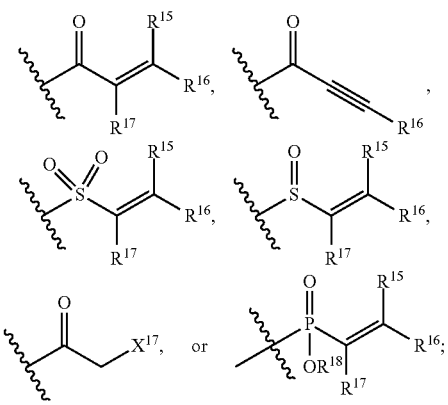

$R^{15}$ is independently hydrogen, halogen, $CX^{15}_3$, —$CHX^{15}_2$, —$CH_2X^{15}$, —CN, —$SO_{n15}R^{1D}$, —$SO_{v15}NR^{15A}R^{15B}$, —$NHNR^{15A}R^{15B}$, —$ONR^{15A}R^{15B}$, —NHC=(O)$NHNR^{15A}R^{15B}$, —NHC(O)$NR^{15A}R^{15B}$, —$N(O)_{m15}$, —$NR^{15A}R^{15B}$, —$C(O)R_{15C}$, —C(O)—$OR^{15C}$, —C(O)$NR^{15A}R^{15B}$, —$OR^{15D}$, —$NR^{15A}SO_2R^{15D}$, —$NR^{15A}C(O)R^{15C}$, —$NR^{15A}C(O)OR^{15C}$, —$NR^{15A}OR^{15C}$, —$OCX^{15}_3$, —$OCHX^{15}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^{16}$ is independently hydrogen, halogen, $CX^{16}_3$, —$CHX^{16}_2$, —$CH_2X^{16}$, —CN, —$SO_{n16}R^{6D}$, —$SO_{v16}NR^{16A}R^{16B}$, —$NHNR^{16A}R^{16B}$, —$ONR^{16A}R^{16B}$, —NHC=(O)$NHNR^{16A}R^{16B}$, —NHC(O)$NR^{16A}R^{16B}$, —$N(O)_{m16}$, —$NR^{16A}R^{16B}$, —$C(O)R^{16C}$, —C(O)—$OR^{16C}$, —C(O)$NR^{16A}R^{16B}$, —$OR^{16D}$, —$NR^{16A}SO_2R^{16D}$, —$NR^{16A}C(O)R^{16C}$, —$NR^{16A}C(O)OR^{16C}$, —$NR^{16A}OR^{16C}$, —$OCX^{16}_3$, —$OCHX^{16}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^{17}$ is independently hydrogen, halogen, $CX^{17}_3$, —$CHX^{17}_2$, —$CH_2X^{17}$, —CN, —$SO_{n17}R^{17D}$, —$SO_{v17}NR^{17A}R^{17B}$, —$NHNR^{17A}R^{17B}$, —$ONR^{17A}R^{17B}$, —NHC=(O)$NHNR^{17A}R^{17B}$, —NHC(O)$NR^{17A}R^{17B}$, —$N(O)_{m17}$, —$NR^{17A}R^{17B}$, —$C(O)R^{17C}$, —C(O)—$OR^{17C}$, —C(O)$NR^{17A}R^{17B}$, —$OR^{17D}$, —$NR^{17A}SO_2R^{17D}$, —$NR^{17A}C(O)R^{17C}$, —$NR^{17A}C(O)OR^{17C}$, —$NR^{17A}OR^{17C}$, —$OCX^{17}_3$, —$OCHX^{17}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^{18}$ is independently hydrogen, —$CX^{18}_3$, —$CHX^{18}_2$, —$CH_2X^{18}$, —$C(O)R^{18C}$, —$C(O)OR^{18C}$, —$C(O)NR^{18A}R^{18B}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^{15A}$, $R^{15B}$, $R^{15C}$, $R^{15D}$, $R^{16A}$, $R^{16B}$, $R^{16C}$, $R^{16D}$, $R^{17A}$, $R^{17B}$, $R^{17C}$, $R^{17D}$, $R^{18A}$, $R^{18B}$, $R^{18C}$, $R^{18D}$ are independently hydrogen, $-CX_3$, $-CN$, $-COOH$, $-CONH_2$, $-CHX_2$, $-CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{15A}$ and $R^{15B}$ substituents bonded to the same nitrogen atom may optionally be joined to form a substituted or unsubstituted heterocycloalkyl or substituted or unsubstituted heteroaryl; $R^{16A}$ and $R^{16B}$ substituents bonded to the same nitrogen atom may optionally be joined to form a substituted or unsubstituted heterocycloalkyl or substituted or unsubstituted heteroaryl; $R^{17A}$ and $R^{17B}$ substituents bonded to the same nitrogen atom may optionally be joined to form a substituted or unsubstituted heterocycloalkyl or substituted or unsubstituted heteroaryl; $R^{18A}$ and $R^{18B}$ substituents bonded to the same nitrogen atom may optionally be joined to form a substituted or unsubstituted heterocycloalkyl or substituted or unsubstituted heteroaryl; each X, $X^{15}$, $X^{16}$, $X^{17}$ and $X^{18}$ is independently $-F$, $-Cl$, $-Br$, or $-I$; n15, n16, n17, v15, v16, and v17, are independently an integer from 0 to 4; and m15, m16, and m17 are independently and integer from 1 to 2.

Embodiment 33

The compound of embodiment 32, wherein $R^{15}$, $R^{16}$, $R^{17}$, and $R^{18}$ are hydrogen.

Embodiment 34

The compound of embodiment 32, wherein E is:

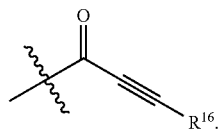

Embodiment 35

The compound of embodiment 34, wherein $R^{16}$ is hydrogen, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 36

The compound of one of embodiments 32 to 33, wherein E is:

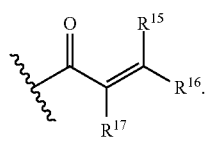

Embodiment 37

The compound of embodiment 36, wherein $R^{15}$ is hydrogen; $R^{16}$ is hydrogen, $-CH_3$, $-CH_2NR^{16A}R^{16B}$, or

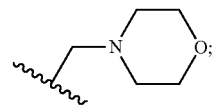 [SMILES: *CN1CCOCC1]

$R^{17}$ is hydrogen; and $R^{16A}$ and $R^{16B}$ are independently hydrogen or unsubstituted alkyl.

Embodiment 38

The compound of embodiment 37, wherein $R^{6A}$ and $R^{6B}$ are independently unsubstituted methyl.

Embodiment 39

The compound of embodiment 36, wherein $R^{15}$ is hydrogen; $R^{16}$ is hydrogen; $R^{17}$ is hydrogen, $-CH_3$, $-CH_2NR^{17A}R^{17B}$, or

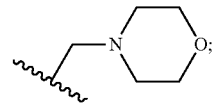

and $R^{17A}$ and $R^{17B}$ are independently hydrogen or unsubstituted alkyl.

Embodiment 40

The compound of embodiment 39, wherein $R^{17A}$ and $R^{17B}$ are independently unsubstituted methyl.

Embodiment 41

The compound of embodiment 36, wherein $R^1$ is hydrogen, $-CH_3$, $-CH_2NR^{15A}R^{15B}$,

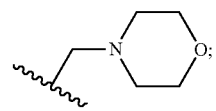 [SMILES: *CN1CCOCC1]

$R^{16}$ is hydrogen; $R^{17}$ is hydrogen; and $R^{15A}$ and $R^{15B}$ are independently hydrogen or unsubstituted alkyl.

Embodiment 42

The compound of embodiment 41, wherein $R^{15A}$ and $R^{15B}$ are independently unsubstituted methyl.

Embodiment 43

The compound of one of embodiments 1 to 42, wherein $R^4$ is hydrogen, substituted or unsubstituted $C_1$-$C_8$ alkyl, or substituted or unsubstituted 2 to 8 membered heteroalkyl.

Embodiment 44

The compound of one of embodiments 1 to 43, wherein $R^5$ is hydrogen, substituted or unsubstituted $C_1$-$C_8$ alkyl, or substituted or unsubstituted 2 to 8 membered heteroalkyl.

Embodiment 45
The compound of embodiment 1, wherein the compound has the formula:
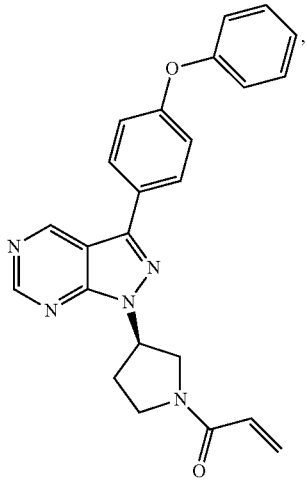
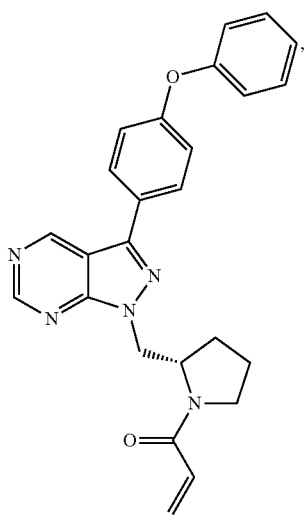
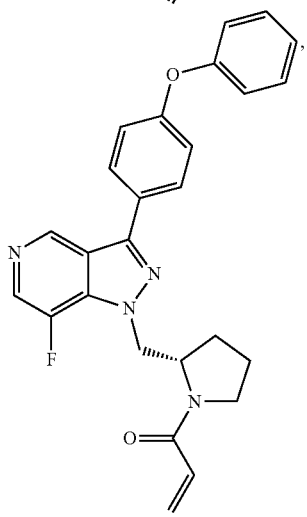
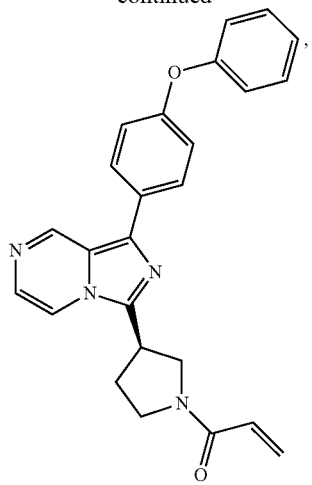
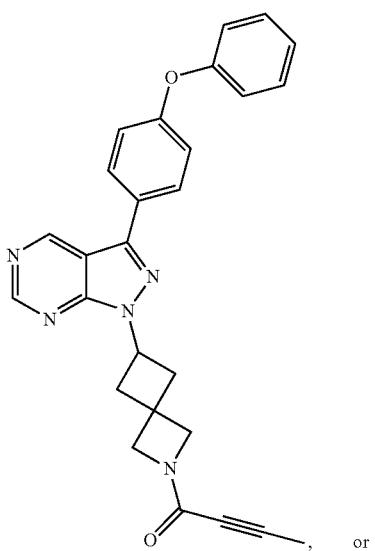
, or
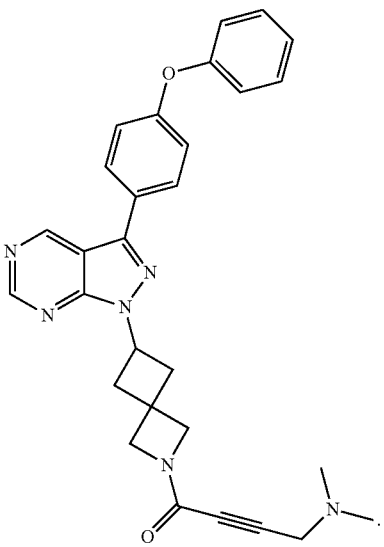

Embodiment 46

The compound of one of embodiments 1 to 45, wherein the compound is capable of entering the central nervous system of a patient following administration outside of the central nervous system.

Embodiment 47

A pharmaceutical composition comprising the compound of any one of embodiments 1 to 46 and a pharmaceutically acceptable excipient.

Embodiment 48

A method of inhibiting Bruton's tyrosine kinase activity, said method comprising: contacting the Bruton's tyrosine kinase with an effective amount of a compound of one of embodiments 1 to 46.

Embodiment 49

A method of treating cancer, said method comprising administering to a subject in need thereof an effective amount of a compound of one of embodiments 1 to 46.

Embodiment 50

A Bruton's tyrosine kinase protein covalently bonded to a compound of one of embodiments 1 to 46.

Embodiment 51

The Bruton's tyrosine kinase protein of embodiment 50, wherein the compound is bonded to a cysteine residue of the protein.

Embodiment 52

The Bruton's tyrosine kinase protein of embodiment 50, covalently bonded to a portion of a compound of one of embodiments 1 to 46.

Embodiment 53

The Bruton's tyrosine kinase protein of embodiment 50, irreversibly covalently bonded to a portion of a compound of one of embodiments 1 to 46.

Embodiment 54

The Bruton's tyrosine kinase protein of one of embodiments 50 to 53, wherein the Bruton's tyrosine kinase protein is in the central nervous system of a subject.

Embodiment 55

The Bruton's tyrosine kinase protein of one of embodiments 50 to 53, wherein the Bruton's tyrosine kinase protein is in the brain of a subject.

Embodiment 56

A method of treating an inflammatory disease, said method comprising administering to a subject in need thereof an effective amount of a compound of one of embodiments 1 to 46.

Embodiment 57

The method of embodiment 56, wherein the inflammatory disease is multiple sclerosis, encephalitis, Alzheimer's disease associated encephalitis, or Parkinson's disease associated encephalitis.

Embodiment 58

A method of treating a disease associated with aberrant Bruton's Tyrosine Kinase activity including administering to a subject in need thereof an effective amount of a compound of one of embodiments 1 to 46.

Embodiment 59

The method of embodiment 58, wherein the disease is a psychiatric disorder or a neurological disorder.

Embodiment 60

The method of embodiment 58, wherein the disease is autism, Rett syndrome, Fragile X syndrome, myocardial infarction, glaucoma, tuberous sclerosis, neuropathic pain, anxiety, chronic neurodegeneration, depression, epilepsy, HIV-associated dementia, or neuroinflammation.

Embodiment 61

A method of treating stroke including administering to a subject in need thereof an effective amount of a compound of one of embodiments 1 to 46.

Embodiment 62

A method of treating an autoimmune disease, said method comprising administering to a subject in need thereof an effective amount of a compound of one of embodiments 1 to 46.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

Example A. General Synthetic Methods for Preparing Compounds

Scheme 1: Method A

415
-continued

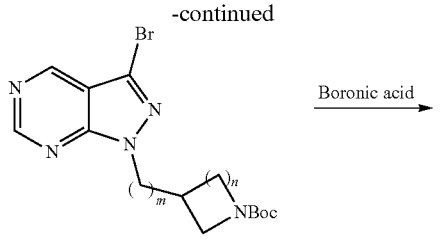

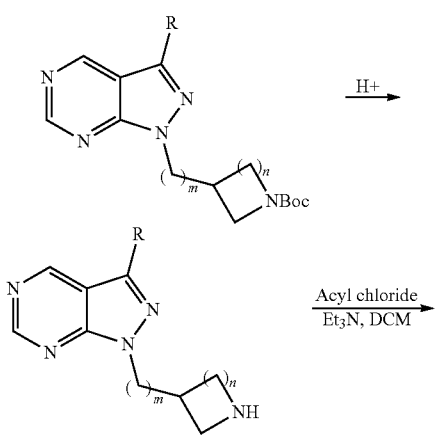

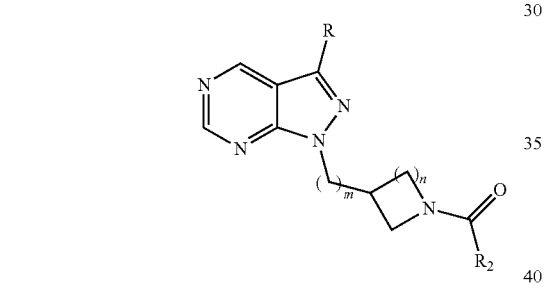

Example 1: (R)-1-(3-(3-(4-phenoxyphenyl)-1H-pyrazolo[3,4-d]pyrimidin-1-yl)piperidin-1-yl)prop-2-en-1-one; (compound A9)

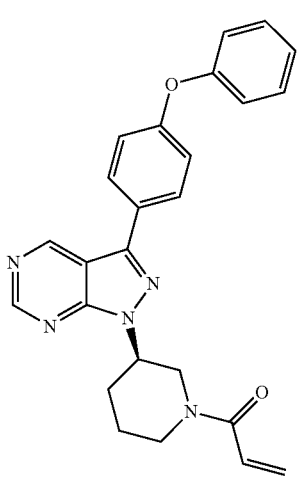 [SMILES: C=CC(=O)N1CCC[C@@H](n2nc(-c3ccc(Oc4ccccc4)cc3)c3cncnc32)C1]

416

Step 1: tert-butyl (R)-3-(3-bromo-1H-pyrazolo[3,4-d]pyrimidin-1-yl)piperidine-1-carboxylate

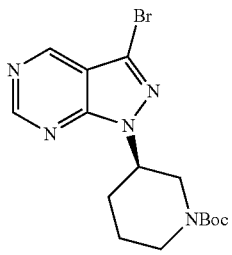 [SMILES: CC(C)(C)OC(=O)N1CCC[C@@H](n2nc(Br)c3cncnc32)C1]

DIAD (0.9 mL, 4.5 mmol) was added to a solution of TPP (1186 mg, 4.5 mmol) and tert-butyl (3S)-3-hydroxypiperidine-1-carboxylate (910 mg, 4.5 mmol) in THF (10 mL). After 5 min, 3-bromo-1H-pyrazolo[3,4-d]pyrimidine (300 mg, 1.5 mmol) was added. After 4 h, the reaction mixture was concentrated. The residue was dissolved in ethyl acetate (10 mL) and hexane was added with stirring until a precipitate formed. The precipitate was removed by filtration and the filtrate was concentrated. The concentrate was purified by silica gel chromatography (0-60% Hex:EtOAc) to afford the title compound (528 mg, 1.38 mmol, 92% yield).

Step 2: tert-butyl (R)-3-(3-(4-phenoxyphenyl)-1H-pyrazolo[3,4-d]pyrimidin-1-yl)piperidine-1-carboxylate

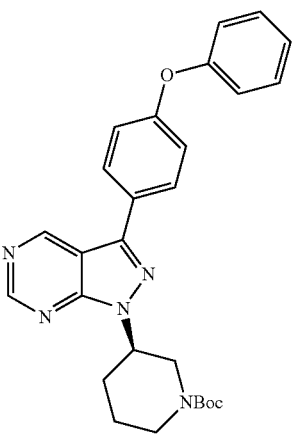 [SMILES: CC(C)(C)OC(=O)N1CCC[C@@H](n2nc(-c3ccc(Oc4ccccc4)cc3)c3cncnc32)C1]

A mixture of tert-butyl (3R)-3-(3-bromopyrazolo[3,4-d]pyrimidin-1-yl)piperidine-1-carboxylate (200 mg, 0.52 mmol), (4-phenoxyphenyl)boronic acid (146 mg, 0.68 mmol) and $K_2CO_3$ (217 mg, 1.6 mmol) in toluene (6 mL)/water (1 mL) was degassed. Pd(dppf)Cl$_2$ (38.28 mg, 0.0500 mmol) was then added and the mixture was degassed again. The mixture was stirred at 90° C. overnight. The solvent was evaporated and the crude residue was purified via normal phase chromatography (0-80% Hex:EtOAc) to afford the title compound (208 mg, 0.44 mmol, 84% yield), which was used for the next step.

Step 3: (R)-3-(4-phenoxyphenyl)-1-(piperidin-3-yl)-1H-pyrazolo[3,4-d]pyrimidine

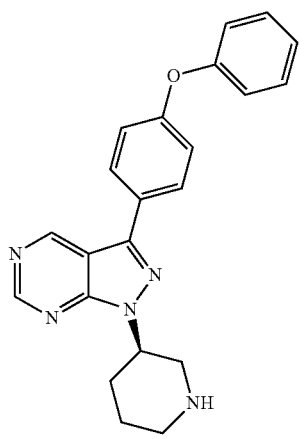

tert-Butyl (3R)-3-[3-(4-phenoxyphenyl)pyrazolo[3,4-d]pyrimidin-1-yl]piperidine-1-carboxylate (60 mg, 0.13 mmol) was dissolved in DCM (2 mL). TFA (0.29 mL, 3.82 mmol) was added and the mixture was stirred at room temperature for 30 min. The solvent was evaporated and the crude residue was used for the next step without purification. Assuming 100% yield.

Step 4: (R)-1-(3-(3-(4-phenoxyphenyl)-1H-pyrazolo[3,4-d]pyrimidin-1-yl)piperidin-1-yl)prop-2-en-1-one

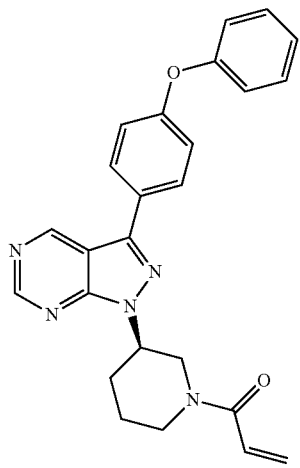 [SMILES: C=CC(=O)N1CCC[C@@H](n2nc(-c3ccc(Oc4ccccc4)cc3)c3cncnc32)C1]

3-(4-Phenoxyphenyl)-1-[(3R)-3-piperidyl]pyrazolo[3,4-d]pyrimidine (47 mg, 0.13 mmol) was dissolved in THF (3 mL) and a sat. aq. sol. of K₂CO₃ (2 ml). Acryloyl Chloride (10.28 uL, 0.1300 mmol) was added and the mixture was stirred at room temperature for 15 min. The organic layer was evaporated and the crude residue was purified by normal phase chromatography (10-80% Hex:EtOAc) to afford the title compound (20 mg, 0.05 mmol, 36% yield). MS: m/z 426.2 [M+H]⁺.

The following compounds were prepared by Scheme 1: Method A

Example 2: (S)-1-(3-(3-(4-phenoxyphenyl)-1H-pyrazolo[3,4-d]pyrimidin-1-yl)pyrrolidin-1-yl)prop-2-en-1-one; (compound A12)

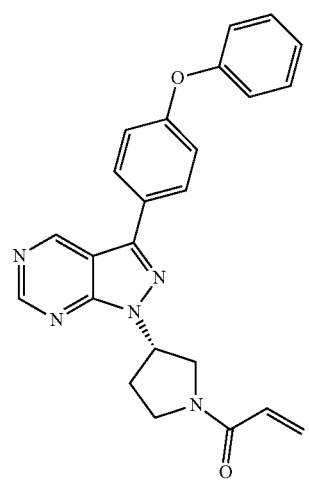 [SMILES: C=CC(=O)N1CC[C@H](n2nc(-c3ccc(Oc4ccccc4)cc3)c3cncnc32)C1]

MS: m/z 412.3 [M+H]⁺.

Example 3: 1-(3-(3-(4-phenoxyphenyl)-1H-pyrazolo[3,4-d]pyrimidin-1-yl)azetidin-1-yl)prop-2-en-1-one; (compound A13)

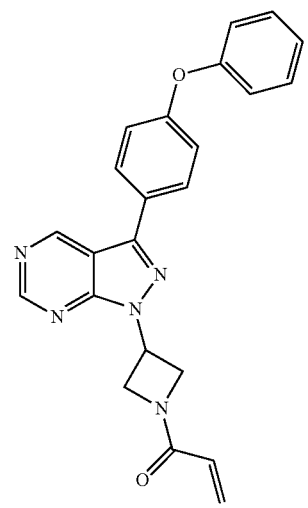 [SMILES: C=CC(=O)N1CC(n2nc(-c3ccc(Oc4ccccc4)cc3)c3cncnc32)C1]

MS: m/z 398.1 [M+H]⁺.

Example 6: (R)-1-(3-(3-(3-phenoxyphenyl)-1H-pyrazolo[3,4-d]pyrimidin-1-yl)piperidin-1-yl)prop-2-en-1-one; (compound A1)

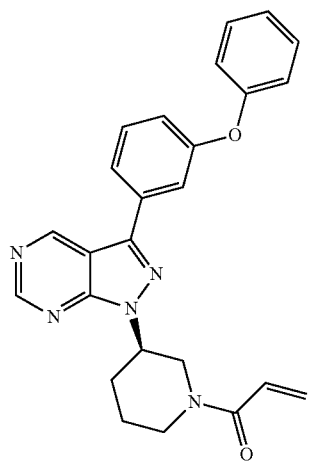 [SMILES: C=CC(=O)N1CCC[C@@H](n2nc(-c3cccc(Oc4ccccc4)c3)c3cncnc32)C1]

MS: m/z 425.6 [M+H]+.

Example 7: (R)-1-(3-(3-(2-fluoro-4-phenoxyphenyl)-1H-pyrazolo[3,4-d]pyrimidin-1-yl)piperidin-1-yl)prop-2-en-1-one; (compound A2)

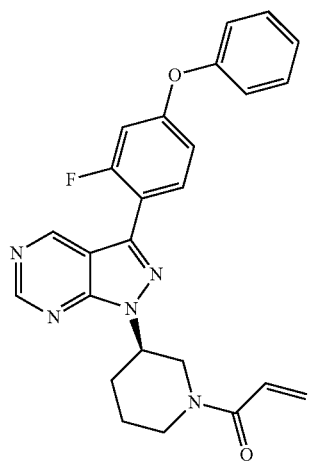 [SMILES: C=CC(=O)N1CCC[C@@H](n2nc(-c3ccc(Oc4ccccc4)cc3F)c3cncnc32)C1]

MS: m/z 443.7 [M+H]+.

Example 8: (R)-1-(3-(3-(3-fluoro-4-phenoxyphenyl)-1H-pyrazolo[3,4-d]pyrimidin-1-yl)piperidin-1-yl)prop-2-en-1-one; (compound A3)

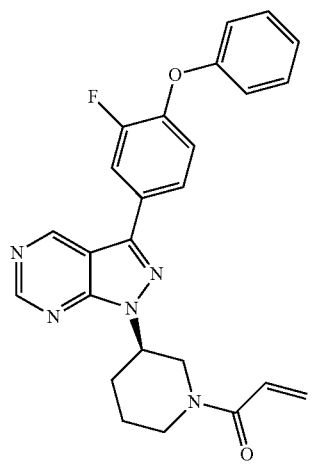 [SMILES: C=CC(=O)N1CCC[C@@H](n2nc(-c3ccc(Oc4ccccc4)c(F)c3)c3cncnc32)C1]

MS: m/z 443.6 [M+H]+.

Example 9: (R)-1-(3-(3-(2-methyl-4-phenoxyphenyl)-1H-pyrazolo[3,4-d]pyrimidin-1-yl)piperidin-1-yl)prop-2-en-1-one; (compound A4)

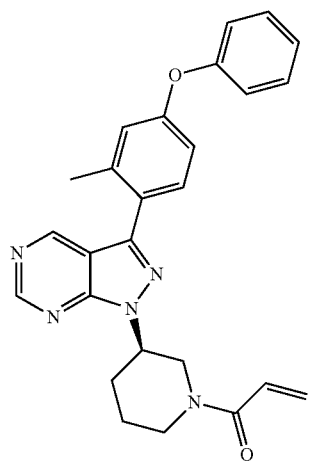 [SMILES: C=CC(=O)N1CCC[C@@H](n2nc(-c3ccc(Oc4ccccc4)cc3C)c3cncnc32)C1]

MS: m/z 439.6 [M+H]+.

Example 10: (R)-1-(3-(3-(3-methyl-4-phenoxyphenyl)-1H-pyrazolo[3,4-d]pyrimidin-1-yl)piperidin-1-yl)prop-2-en-1-one; (compound A5)

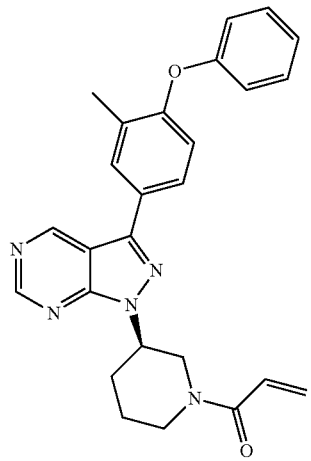 [SMILES: C=CC(=O)N1CCC[C@@H](n2nc(-c3ccc(Oc4ccccc4)c(C)c3)c3cncnc32)C1]

MS: m/z 440.0 [M+H]+.

Example 11: (R)-1-(3-(3-(4-phenoxyphenyl)-1H-pyrazolo[3,4-d]pyrimidin-1-yl)pyrrolidin-1-yl)prop-2-en-1-one; (compound A6)

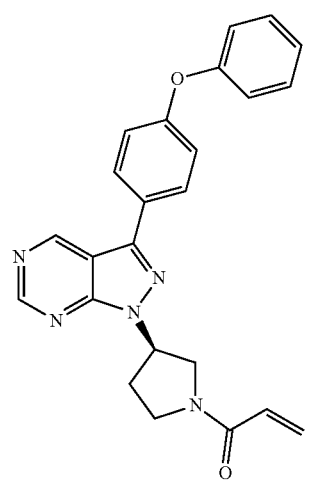 [SMILES: C=CC(=O)N1CC[C@@H](n2nc(-c3ccc(Oc4ccccc4)cc3)c3cncnc32)C1]

MS: m/z 412.1 [M+H]+.

Example 12: (R)-1-(2-((3-(4-phenoxyphenyl)-1H-pyrazolo[3,4-d]pyrimidin-1-yl)methyl)pyrrolidin-1-yl)prop-2-en-1-one; (compound A7)

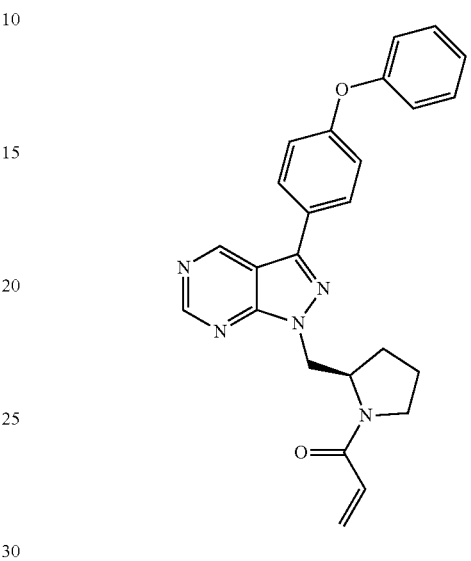

MS: m/z 425.9 [M+H]+.

Example 13: (S)-1-(2-((3-(4-phenoxyphenyl)-1H-pyrazolo[3,4-d]pyrimidin-1-yl)methyl)pyrrolidin-1-yl)prop-2-en-1-one; (compound A8)

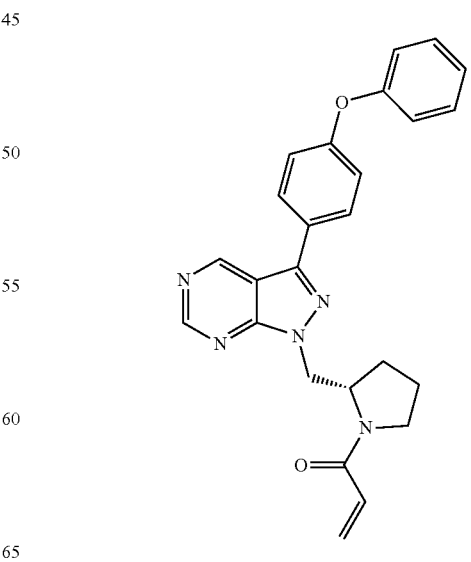

MS: m/z 426.1 [M+H]+.

Example 14: (R)-1-(3-((3-(4-phenoxyphenyl)-1H-pyrazolo[34-d]pyrimidin-1-yl)methyl)pyrrolidin-1-yl)prop-2-en-1-one; (compound A14)

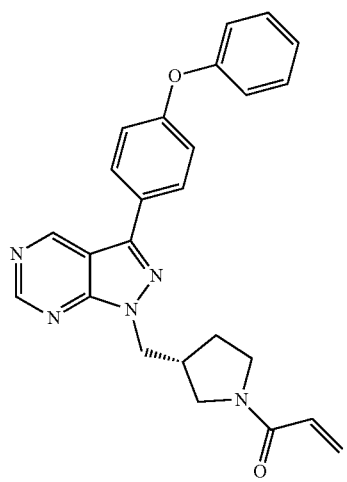 [SMILES: C=CC(=O)N1CC[C@@H](Cn2nc(-c3ccc(Oc4ccccc4)cc3)c3cncnc32)C1]

MS: m/z 425.9 [M+H]⁺.

Example 15: (S)-1-(3-((3-(4-phenoxyphenyl)-1H-pyrazolo[3,4-d]pyrimidin-1-yl)methyl)pyrrolidin-1-yl)prop-2-en-1-one; (compound A15)

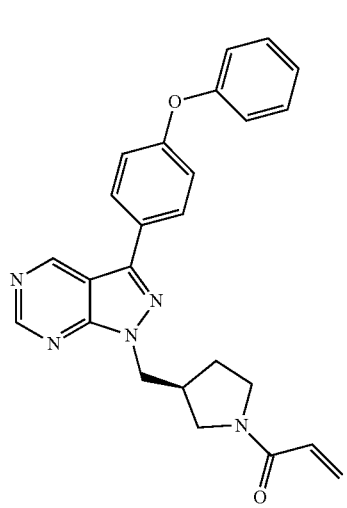 [SMILES: C=CC(=O)N1CC[C@H](Cn2nc(-c3ccc(Oc4ccccc4)cc3)c3cncnc32)C1]

MS: m/z 425.9 [M+H]⁺.

Example 16: (R)-1-(3-(3-(2-fluoro-4-phenoxyphenyl)-1H-pyrazolo[3,4-d]pyrimidin-1-yl)pyrrolidin-1-yl)prop-2-en-1-one; (compound A17)

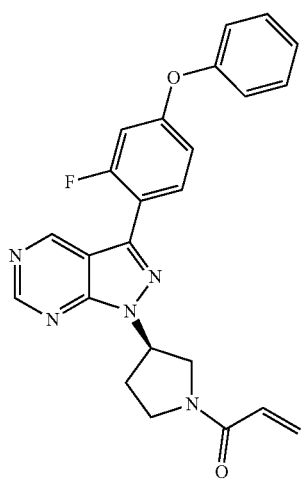 [SMILES: C=CC(=O)N1CC[C@@H](n2nc(-c3ccc(Oc4ccccc4)cc3F)c3cncnc32)C1]

MS: m/z 430.1 [M+H]₊.

Example 17: (S)-1-(2-((3-(2-fluoro-4-phenoxyphenyl)-1H-pyrazolo[3,4-d]pyrimidin-1-yl)methyl)pyrrolidin-1-yl)prop-2-en-1-one; (compound A19)

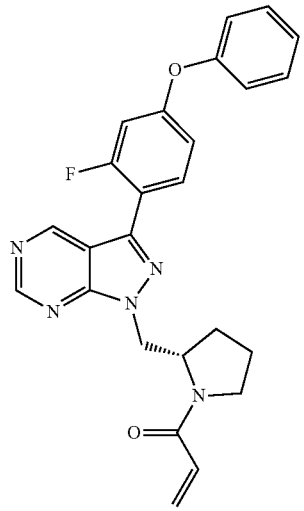 [SMILES: C=CC(=O)N1CCC[C@H]1Cn1nc(-c2ccc(Oc3ccccc3)cc2F)c2cncnc21]

MS: m/z 443.9 [M+H]⁺.

Scheme 2: Method B

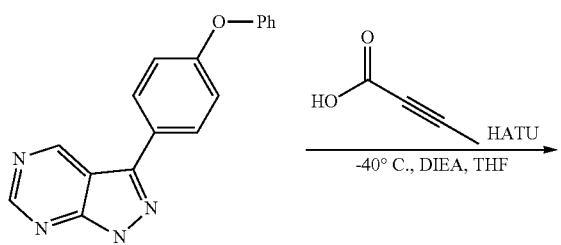

The following compounds were prepared by Scheme 2: Method B

Example 19: (R)-1-(3-(3-(4-phenoxyphenyl)-1H-pyrazolo[3,4-d]pyrimidin-1-yl)pyrrolidin-1-yl)but-2-yn-1-one; (compound A18)

but-2-ynoic acid (44 mg, 0.52 mmol) and HATU (201 mg, 0.53 mmol) in DMF (5 mL) was added DIPEA (129 mg, 1 mmol). The resulted mixture was stirred at room temperature for 2 h, then quenched with of water (10 mL). The reaction was extracted with EtOAc (25 mL×2), washed with brine (25 mL×3), dried over $Na_2SO_4$, filtered and concentrated to afford crude product. Further purification by normal phase chromatography (DCM: MeOH=0-10%) provided the title compound (110 mg, 57%) as a yellow solid. MS: m/z 438.1 $[M+H]^+$.

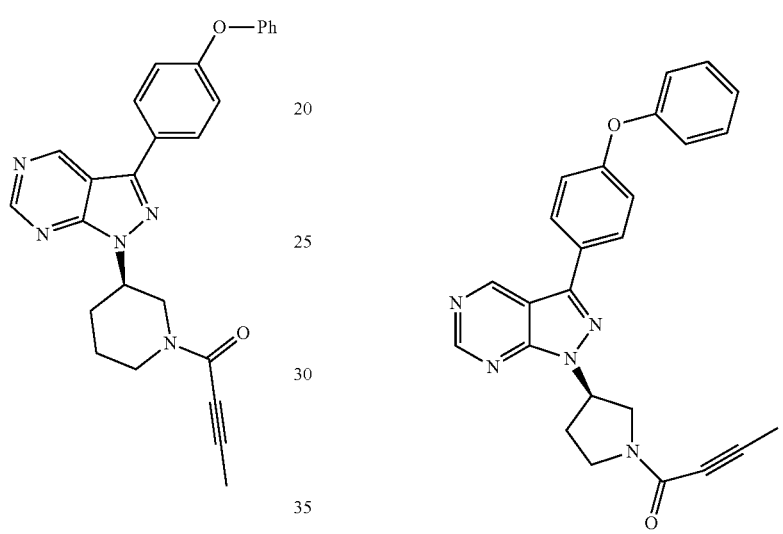

Example 18: (R)-1-(3-(3-(4-phenoxyphenyl)-1H-pyrazolo[3,4-d]pyrimidin-1-yl)piperidin-1-yl)but-2-yn-1-one; (compound A16)

MS: m/z 424.1 $[M+H]^+$.

Example 20: (S)-1-(2-((3-(2-fluoro-4-phenoxyphenyl)-1H-pyrazolo[3,4-d]pyrimidin-1-yl)methyl)pyrrolidin-1-yl)but-2-yn-1-one; (compound A20)

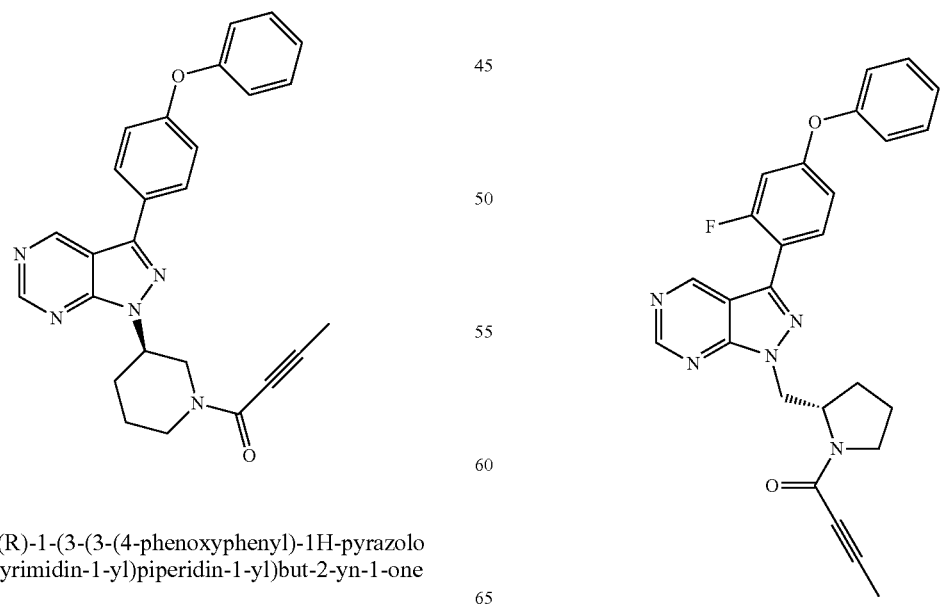

Step 1: (R)-1-(3-(3-(4-phenoxyphenyl)-1H-pyrazolo[3,4-d]pyrimidin-1-yl)piperidin-1-yl)but-2-yn-1-one To a solution of (R)-3-(4-phenoxyphenyl)-1-(piperidin-3-yl)-1H-pyrazolo[3,4-d]pyrimidine (180 mg, 0.44 mmol), MS: m/z 456.2 $[M+H]^+$.

Example 21: (R)-2-methyl-1-(3-(3-(4-phenoxyphenyl)-1H-pyrazolo[3,4-d]pyrimidin-1-yl)piperidin-1-yl)prop-2-en-1-one; (compound A21)

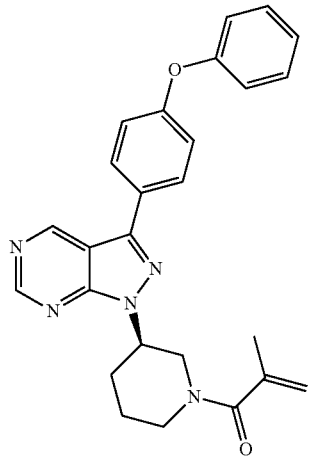 [SMILES: C=C(C)C(=O)N1CCC[C@@H](n2nc(-c3ccc(Oc4ccccc4)cc3)c3cncnc32)C1]

MS: m/z 440.1 [M+H]$^+$.

Scheme 3: Method C

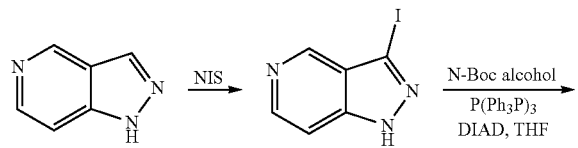

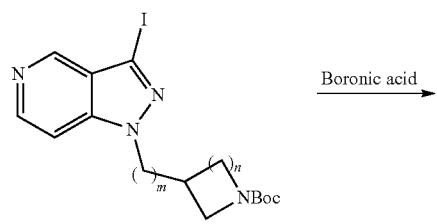

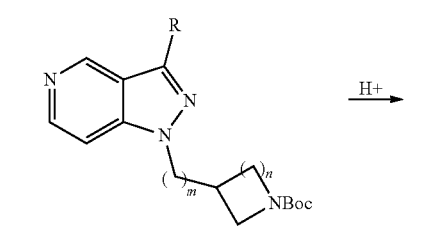

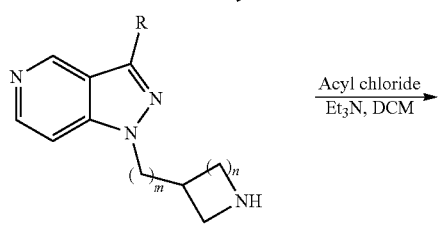

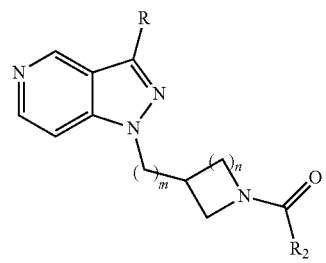

Step 1: 3-iodo-1H-pyrazolo[4,3-c]pyridine

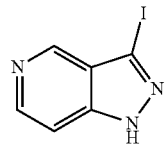

1H-Pyrazolo[4,3-c]pyridine (833 mg, 7 mmol) was dissolved in DMF (10 mL) and NIS (1.89 g, 8.4 mmol) was added. The reaction mixture was stirred for 3 h at 80° C., then quenched with H$_2$O and extracted with EtOAc. The organic phase was washed with brine and dried over anhydrous Na$_2$SO$_4$, filtered and then concentrated to afford 3-iodo-1H-pyrazolo[4,3-c]pyridine (1.4 g). The crude material was used without further purification.

The following compounds were prepared in a similar manner to Scheme 1: Method A

Example 22: (S)-1-(2-((3-(4-phenoxyphenyl)-1H-pyrazolo[4,3-c]pyridin-1-yl)methyl)pyrrolidin-1-yl)prop-2-en-1-one; (compound A22)

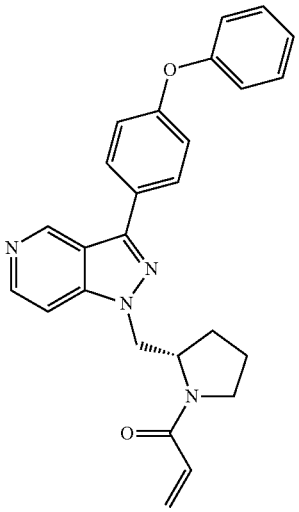 [SMILES: C=CC(=O)N1CCC[C@H]1Cn1nc(-c2ccc(Oc3ccccc3)cc2)c2cnccc21]

MS: m/z 424.9 [M+H]$^+$.

429

Example 23: (R)-1-(3-(3-(4-phenoxyphenyl)-H-pyrazolo[4,3-c]pyridin-1-yl)piperidin-1-yl)prop-2-en-1-one; (compound A23)

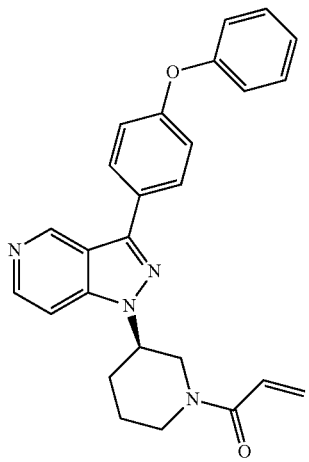 [SMILES: C=CC(=O)N1CCC[C@@H](n2nc(-c3ccc(Oc4ccccc4)cc3)c3cnccc32)C1]

MS: m/z 425.2 [M+H]⁺.

Example 24: (R)-1-(3-(3-(2-fluoro-4-phenoxyphenyl)-1H-pyrazolo[4,3-c]pyridin-1-yl)piperidin-1-yl)prop-2-en-1-one; (compound A24)

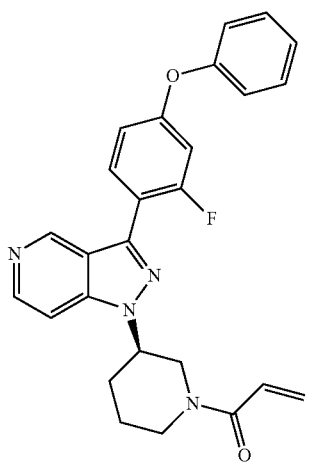 [SMILES: C=CC(=O)N1CCC[C@@H](n2nc(-c3ccc(Oc4ccccc4)cc3F)c3cnccc32)C1]

MS: m/z 443.2 [M+H]⁺.

430

Scheme 4: Method D

Example 25: (R,E)-4-(dimethylamino)-1-(3-(3-(4-phenoxyphenyl)-1H-pyrazolo[4,3-c]pyridin-1-yl)pyrrolidin-1-yl)but-2-en-1-one; (compound A25)

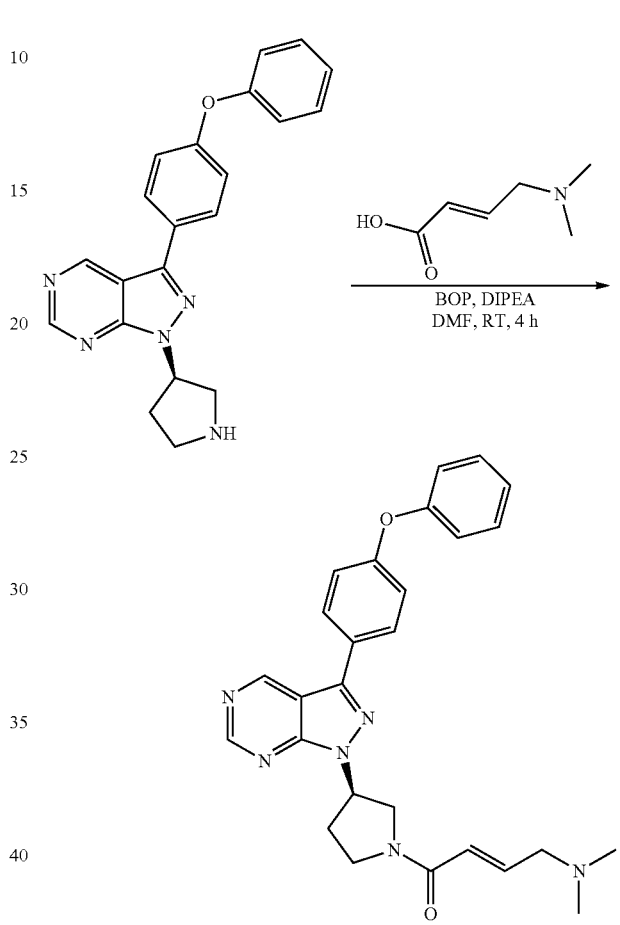

Step 1: DIPEA (144 mg, 1.12 mmol) was added to a stirred solution of (R)-3-(4-phenoxyphenyl)-1-(pyrrolidin-3-yl)-1H-pyrazolo[3,4-d]pyrimidine (220 mg, 0.56 mmol), (E)-4-(dimethylamino)but-2-enoic acid (87 mg, 0.67 mmol) and BOP (296 mg, 0.67 mmol) in DMF (6 mL) at 0° C. The mixture was stirred at room temperature for 4 h., then washed with brine (2×25 mL), dried over Na₂SO₄ and then concentrated. The crude residue was purified by flash column chromatography with MeOH/DCM to afford (R,E)-4-(dimethylamino)-1-(3-(3-(4-phenoxyphenyl)-1H-pyrazolo[4,3-c]pyridin-1-yl)pyrrolidin-1-yl)but-2-en-1-one (51 mg, 16%) as a white solid. MS: m/z 469.2 [M+H]+.

Scheme 5: Method E

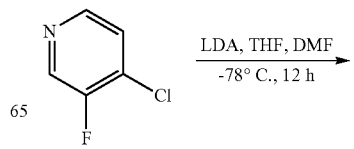

Step 1: 4-chloro-5-fluoronicotinaldehyde

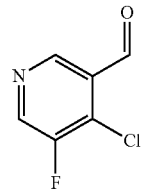

To a diluted solution of LDA (2.0 M in THF, 13.7 mL, 27.4 mmol) in THF (20 mL) at −78° C. under Ar was added 4-chloro-3-fluoropyridine (3 g, 22.8 mmol) in anhydrous THF (5 mL). The resulting mixture was stirred at −78° C. for 2.5 hours, then DMF (2.028 g, 27.4 mmol) was added and the reaction was warmed to room temperature, quenched with sat. NH$_4$Cl, and extracted with EtOAc (3×100 mL). The combined extracts were dried over anhydrous Na$_2$SO$_4$, filtered and concentrated. The residue was purified by combi-flash (0-30%, EtOAc in Petroleum ether) to afford 4-chloro-5-fluoronicotinaldehyde (460 mg, 12%) as an off-white solid.

Step 2: 7-fluoro-1H-pyrazolo[4,3-c]pyridine

To a stirred solution of 4-chloro-5-fluoronicotinaldehyde (460 mg, 2.9 mmol) in DME (2.5 mL) in a sealed tube was added hydrazine hydrate (0.577 g, 11.532 mmol). The resulted mixture was stirred at 120° C. for overnight, then diluted with water and extracted with EtOAc. The organic phase was washed with brine, dried over anhydrous Na$_2$SO$_4$, filtered and concentrated to afford 7-fluoro-1H-pyrazolo[4,3-c]pyridine (334 mg, 85%) as a yellow solid.

Step 3: 7-fluoro-3-iodo-1H-pyrazolo[4,3-c]pyridine

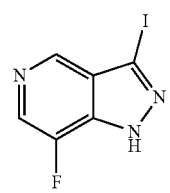

To a stirred solution of 7-fluoro-1H-pyrazolo[4,3-c]pyridine (334 mg, 2.4 mmol) in DMF (4 mL) were added I$_2$ (512 g, 4.9 mmol) and K$_2$CO$_3$ (678 mg, 4.9 mmol). The resulted mixture was stirred at 65° C. for 13 h, then diluted with water and extracted with EtOAc. The organic phase was washed with brine, dried over anhydrous Na$_2$SO$_4$, filtered and concentrated to afford 7-fluoro-3-iodo-1H-pyrazolo[4,3-c]pyridine (400 mg, 62%) as a yellow solid. The following compounds were prepared in a similar manner to Scheme 1: Method A

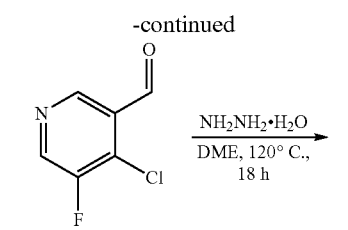
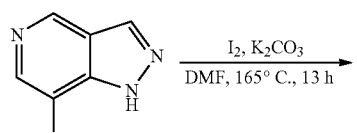
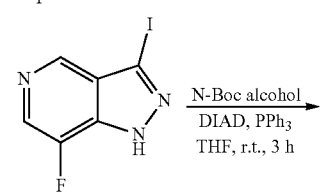
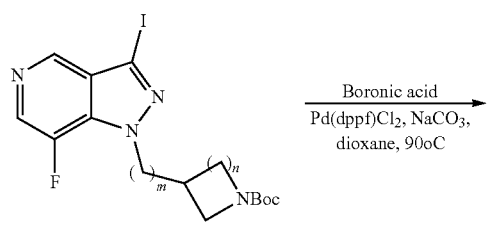
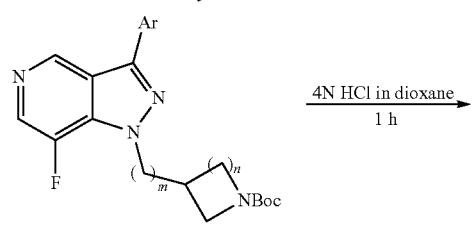
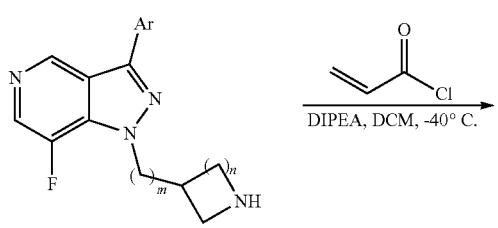
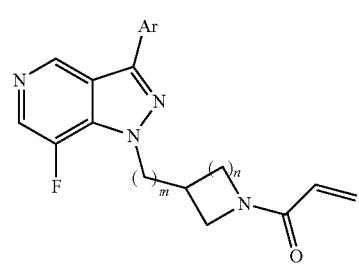

Example 26: (R)-1-(3-(7-fluoro-3-(4-phenoxyphenyl)-1H-pyrazolo[4,3-c]pyridin-1-yl)piperidin-1-yl)prop-2-en-1-one; (compound A26)
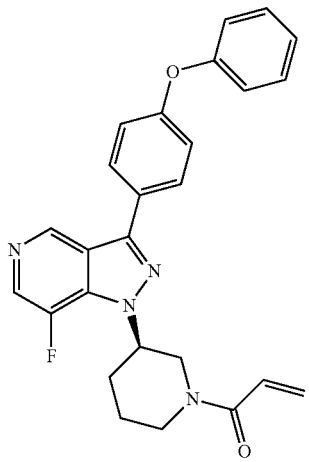 [SMILES: C=CC(=O)N1CCC[C@@H](n2nc(-c3ccc(Oc4ccccc4)cc3)c3cncc(F)c32)C1]
MS: m/z 443.1 [M+H]+.
Example 27: (S)-1-(2-((7-fluoro-3-(4-phenoxyphenyl)-1H-pyrazolo[4,3-c]pyridin-1-yl)methyl)pyrrolidin-1-yl)prop-2-en-1-one; (compound A27)
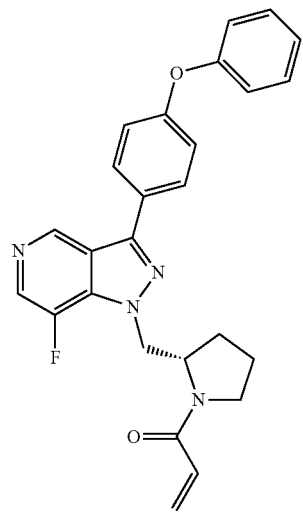 [SMILES: C=CC(=O)N1CCC[C@H]1Cn1nc(-c2ccc(Oc3ccccc3)cc2)c2cncc(F)c21]
MS: m/z 443.1 [M+H]+.
Scheme 6: Method F
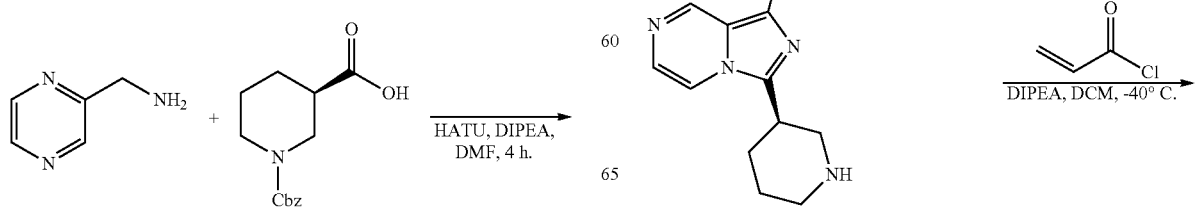
-continued
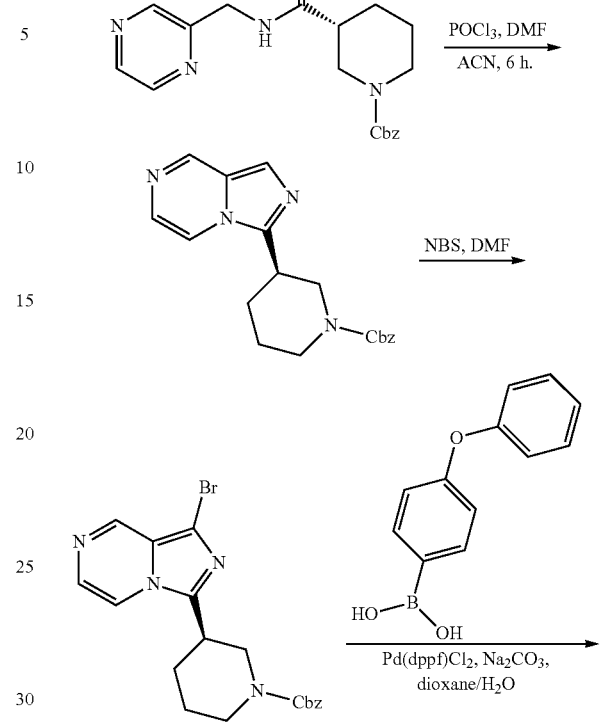

-continued

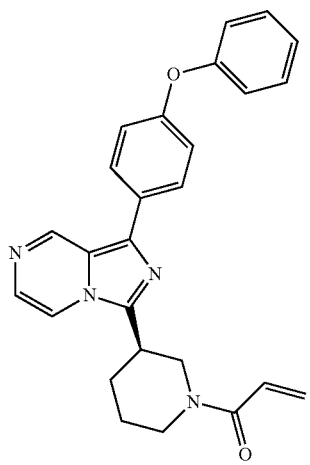 [SMILES: C=CC(=O)N1CCC[C@@H](c2nc(-c3ccc(Oc4ccccc4)cc3)c3cnccn23)C1]

Example 28: (R)-1-(3-(1-(4-phenoxyphenyl)imidazo[1,5-a]pyrazin-3-yl)piperidin-1-yl)prop-2-en-1-one; (compound A28)

Step 1: Benzyl (R)-3-((pyrazin-2-ylmethy)carbamoyl)piperidine-1-carboxylate

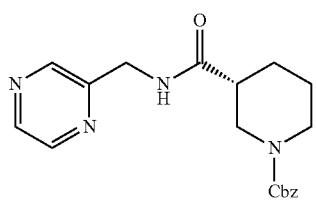 [SMILES: O=C(NCc1cnccn1)[C@@H]1CCCN(C(=O)OCc2ccccc2)C1]

To a mixture of pyrazin-2-ylmethanamine (500 mg, 4.58 mmol), (R)-1-((benzyloxy)carbonyl)piperidine-3-carboxylic acid (1.2 g, 4.6 mmol) and HATU (2.01 g, 5.5 mmol) in DMF (10 mL) was added DIPEA (1.2 g, 9.2 mmol). The mixture was stirred for 4 h at room temperature and then diluted with water (40 mL) and extracted with EtOAc (30 mL×3). The combined organic layer was washed with brine (50 mL), dried over anhydrous $Na_2SO_4$, filtered and concentrated to afford benzyl (R)-3-((pyrazin-2-ylmethyl)carbamoyl)piperidine-1-carboxylate (2.1 g, crude).

Step 2: Benzyl (R)-3-(imidazo[1,5-a]pyrazin-3-yl)piperidine-1-carboxylate

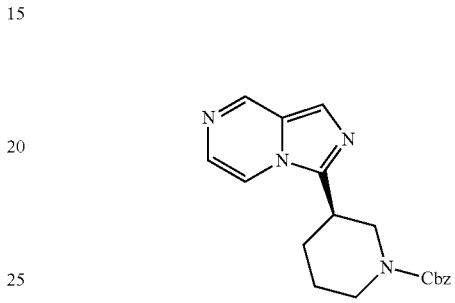

To a solution of (R)-3-((pyrazin-2-ylmethyl)carbamoyl)piperidine-1-carboxylate (2.1 g, 5.9 mmol) in ACN (40 mL) was added $POCl_3$ (2 mL) and DMF (2 mL) slowly at 0° C. The reaction stirred at room temperature for 2 h before cooling to 0° C. and poured slowly to a mixture of crushed ice and aq. $NH_4OH$ (100 mL). The resultant mixture was extracted with EtOAc (80 mL×3), washed with brine (100 mL), dried over anhydrous $Na_2SO_4$, filtered and concentrated to afford benzyl (R)-3-(imidazo[1,5-a]pyrazin-3-yl)piperidine-1-carboxylate (1.99 g, crude).

Step 3: Benzyl (R)-3-(1-bromoimidazo[1,5-a]pyrazin-3-yl)piperidine-1-carboxylate

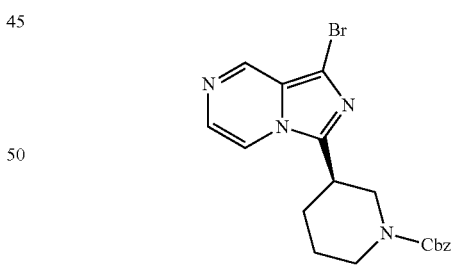

Benzyl (R)-3-(imidazo[1,5-a]pyrazin-3-yl)piperidine-1-carboxylate (1.99 g, 5.9 mmol) was dissolved in DMF (12 mL) and cooled to 0° C. NBS (1.054 g, 5.92 mmol) dissolved in 3 mL of DMF was added slowly and stirred for 1 h at room temperature. The reaction mixture was quenched with sat. $NaHCO_3$ (50 mL) and extracted with EtOAc (50 mL×3). The combined organic phase was washed with brine (80 mL) and dried over anhydrous $Na_2SO_4$, filtered and concentrated to afford benzyl (R)-3-(1-bromoimidazo[1,5-a]pyrazin-3-yl)piperidine-1-carboxylate (2.01 g, crude).

Step 4: Benzyl (R)-3-(1-(4-phenoxyphenyl)imidazo[1,5-a]pyrazin-3-yl)piperidine-1-carboxylate

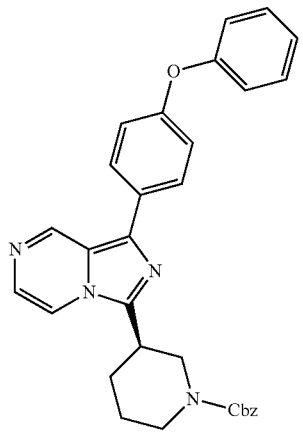 [SMILES: O=C(OCc1ccccc1)N1CCC[C@@H](c2nc(-c3ccc(Oc4ccccc4)cc3)c3cnccn23)C1]

Pd(dppf)Cl₂ (178 mmg, 0.243 mmol) was added to a degassed mixture of benzyl (R)-3-(1-bromoimidazo[1,5-a]pyrazin-3-yl)piperidine-1-carboxylate (2.01 g, 4.86 mmol), (4-phenoxyphenyl)boronic acid (1.25 g, 5.83 mmol) and Na₂CO₃ (1.03 g, 9.72 mmol) in dioxane (18 mL)/water (6 mL) under an N2 atmosphere. The mixture was stirred at 90° C. for 4 h, after LC/MS showed the reaction completed, the solvent was evaporated and the crude residue was purified by normal phase chromatography (Hex:EtOAc=0-80%) to afford benzyl (R)-3-(1-(4-phenoxyphenyl)imidazo[1,5-a]pyrazin-3-yl)piperidine-1-carboxylate (1.136 g, 47%).

Step 5: (R)-1-(4-phenoxyphenyl)-3-(piperidin-3-yl)imidazo[1,5-a]pyrazine

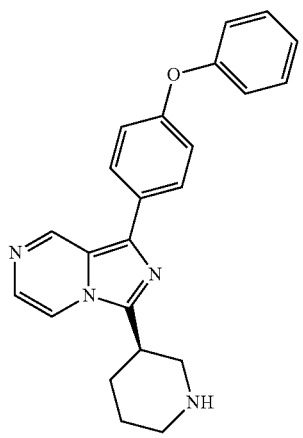 [SMILES: c1ccc(Oc2ccc(-c3nc([C@@H]4CCCNC4)n4ccncc34)cc2)cc1]

To a stirred solution of benzyl (R)-3-(1-(4-phenoxyphenyl)imidazo[1,5-a]pyrazin-3-yl)piperidine-1-carboxylate (504 mg, 1 mmol) in methanol (14 mL) was added Pd/C (100 mg) and ammonium formate (630 g, 10 mmol). The solution was stirred at 60° C. for 3 h, filtered, and the filtrate was concentrated, then water (30 mL) was added and then extracted with EtOAc. The organic layer was dried over anhydrous Na₂SO₄, filtered and concentrated to afford (R)-1-(4-phenoxyphenyl)-3-(piperidin-3-yl)imidazo[1,5-a]pyrazine as a yellow solid (330 mg, crude).

Step 6: (R)-1-(3-(1-(4-phenoxyphenyl)imidazo[1,5-a]pyrazin-3-yl)piperidin-1-yl)prop-2-en-1-one

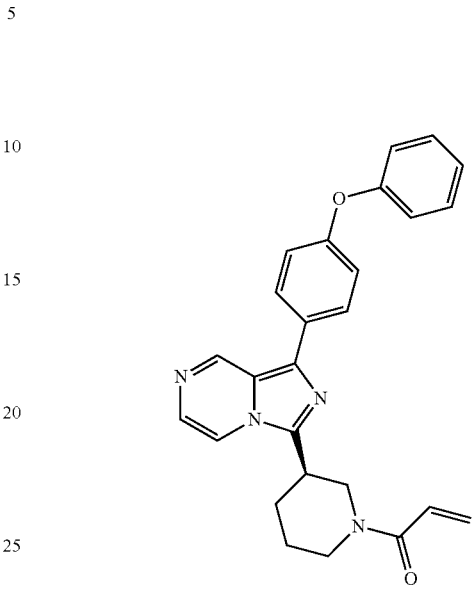

To a solution of (R)-1-(4-phenoxyphenyl)-3-(piperidin-3-yl)imidazo[1,5-a]pyrazine as a yellow solid (190 mg, 0.514 mmol) and DIPEA (133 mg, 1.028 mmol) in DCM (10 mL) at −40° C. was slowly added acryloyl chloride (46 mg, 0.514 mmol). The resulted mixture was stirred at −40° C. for 10 min then the solvent was evaporated and the crude residue was purified by normal phase chromatography (DCM:MeOH=0-10%) to afford (R)-1-(3-(1-(4-phenoxyphenyl)imidazo[1,5-a]pyrazin-3-yl)piperidin-1-yl)prop-2-en-1-one (15 mg, 5%) as a white solid. MS: m/z 424.9 [M+H].

The following compounds were prepared Scheme 6: Method F

Example 29: (S)-1-(2-(1-(4-phenoxyphenyl)imidazo[1,5-a]pyrazin-3-yl)pyrrolidin-1-yl)prop-2-en-1-one; (compound A29)

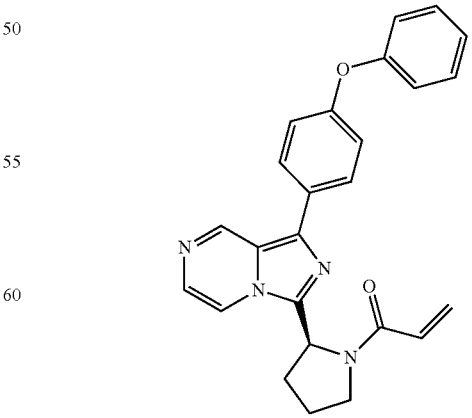

MS: m/z 411.1 [M+H]⁺.

Example 30: (R)-1-(3-(1-(4-phenoxyphenyl)imidazo[1,5-a]pyrazin-3-yl)pyrrolidin-1-yl)prop-2-en-1-one; (compound A30)

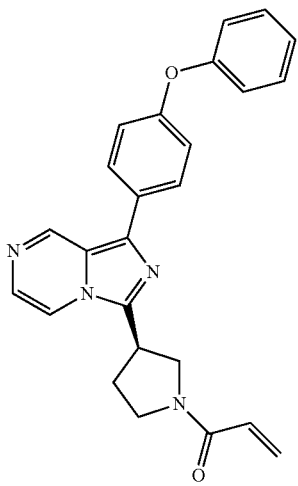 [SMILES: C=CC(=O)N1CC[C@@H](c2nc(-c3ccc(Oc4ccccc4)cc3)c3cnccn23)C1]

MS: m/z 411.2 [M+H]⁺.

The following compounds were prepared Scheme 6: Method F and Scheme 2: Method B

Example 31: (S)-1-(2-(1-(4-phenoxyphenyl)imidazo[1,5-a]pyrazin-3-yl)pyrrolidin-1-yl)but-2-yn-1-one; (compound A31)

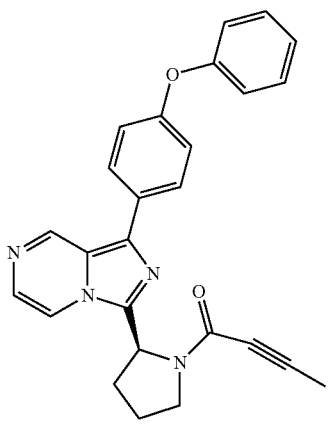 [SMILES: CC#CC(=O)N1CCC[C@H]1c1nc(-c2ccc(Oc3ccccc3)cc2)c2cnccn12]

MS: m/z 422.9 [M+H].

Example 32: (R)-1-(3-(1-(4-phenoxyphenyl)imidazo[1,5-a]pyrazin-3-yl)pyrrolidin-1-yl)but-2-yn-1-one; (compound A32)

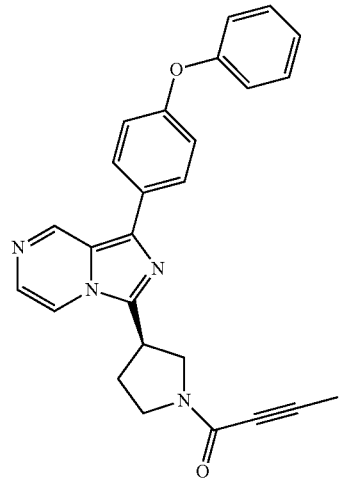 [SMILES: CC#CC(=O)N1CC[C@@H](c2nc(-c3ccc(Oc4ccccc4)cc3)c3cnccn23)C1]

MS: m/z 423.1 [M+H]₊.

Example 33: (R)-2-(1-(1-acryloylpiperidin-3-yl)-H-pyrazolo[3,4-d]pyrimidin-3-yl)-5-phenoxybenzonitrile; (compound A33)

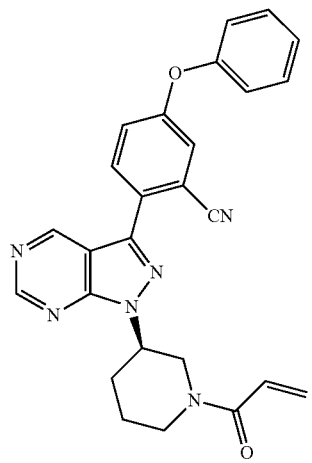 [SMILES: C=CC(=O)N1CCC[C@@H](n2nc(-c3ccc(Oc4ccccc4)cc3C#N)c3cncnc32)C1]

Step 1: 2-nitro-5-phenoxybenzonitrile

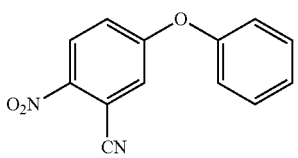

To a slurry of NaH (2.6 g, 65.7 mmol) in THF (3.0 mL) were added 5-fluoro-2-nitrobenzonitrile (9.1 g, 54.8 mmol) and phenol (5.16 g, 54.8 mmol). The reaction vial was capped and the reaction mixture was stirred at RT for 50 min. Water (50 mL) and EtOAc (150 mL) were added. The layers were separated, and the aqueous layer was extracted with EtOAc (2×150 mL). The combined organic layers were washed with brine (3 mL) and then concentrated under a stream of nitrogen at 50° C. to afford 2-nitro-5-phenoxybenzonitrile (10.0 g, 76%) as a yellow solid.

Step 2: 2-amino-5-phenoxybenzonitrile

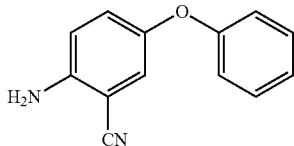 [SMILES: N#Cc1cc(Oc2ccccc2)ccc1[N+](=O)[O-]]

To mixture of 2-nitro-5-phenoxybenzonitrile (10.0 g, 41.7 mmol) and Fe powder (9.32 g, 166.8 mmol) in AcOH (150 mL) and EtOH (150 mL) was heated to 50° C. for 2 h, the reaction mixture was cooled to room temperature and diluted by EA (250 mL), filtered through celite and then the filtrate was washed with sat. NaHCO$_3$ (250 mL×3). The organic layers was dried over Na$_2$SO$_4$, filtered and concentrated to afford the crude product. Further purification by column chromatography (SiO$_2$, 200-300 m, eluted by PE/EtOAc=5/1) provided 2-amino-5-phenoxybenzonitrile (8.1 g, 93%) as a yellow solid.

Step 3: 2-bromo-5-phenoxybenzonitrile

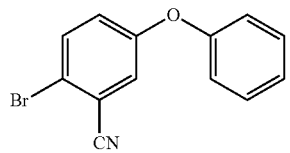 [SMILES: N#Cc1cc(Oc2ccccc2)ccc1Br]

To a slurry of CuBr$_2$ (10.2 g, 45.7 mmol) and tert-butyl nitrite (6.8 mL, 57.4 mmol) in CH$_3$CN (50.0 mL) at 0° C. was added a solution of 2-amino-5-(phenyloxy)benzonitrile (8.0 g, 38.1 mmol) in CH$_3$CN (100 mL). The ice bath was removed, and the reaction was stirred at RT for 10 min. 6 M aq. HCl (50 mL), brine (50 mL), and EtOAc (100 mL) were added. The layers were separated, and the aqueous layer was extracted with EtOAc (200×2 mL). The combined organic layers were washed with 6 M aq. HCl (50 mL) and brine (2 mL), and concentrated to give the crude product. Further purification via flash column chromatography (0-20% EtOAc/hexanes) afforded 2-bromo-5-phenoxybenzonitrile (4.5 g, 42%) as a yellow solid.

Step 4: (2-cyano-4-phenoxyphenyl)boronic Acid

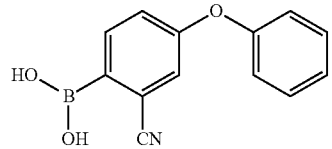 [SMILES: N#Cc1cc(Oc2ccccc2)ccc1B(O)O]

2-Bromo-5-fluorobenzonitrile (2.0 g, 7.4 mmol) and triisopropyl borate (2.4 mL, 11.0 mmol) were dissolved in a mixture of toluene (48 mL) and tetrahydrofuran (12 mL), and the solution was cooled in a dry ice/acetone bath. A solution of n-BuLi in hexanes (2.5M, 4.5 mL, 11.0 mmol) was added drop-wise over 1 hour, and the reaction was then allowed to warm to room temperature with stirring over 18 hours. The mixture was cooled in an ice bath and treated with a 2N aq. HCl solution until the pH reached 1, then allowed to warm to room temperature, at which time the layers were separated, and the aq. layer was extracted twice with EtOAc. The combined organic layers were washed twice with water, once with saturated NaCl, dried over MgSO$_4$ and concentrated to afford (2-cyano-4-phenoxyphenyl)boronic acid (1.1 g, 62%).

Example 33 was provided in a similar manner to Scheme 1: Method A. MS: m/z 451.1 [M+H]$^+$.

The following compounds were prepared by Scheme 1: Method A

Example 34: 1-(4-((3-(4-phenoxyphenyl)-1H-pyrazolo[3,4-d]pyrimidin-1-yl)methyl)piperidin-1-yl)prop-2-en-1-one; (compound A34)

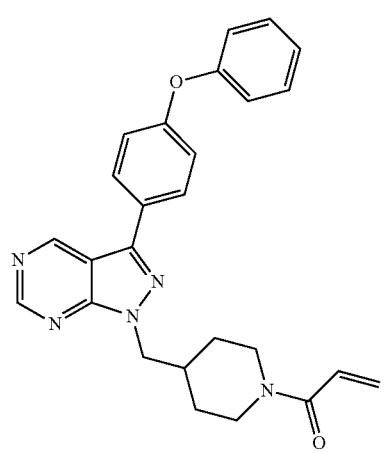 [SMILES: C=CC(=O)N1CCC(Cn2nc(-c3ccc(Oc4ccccc4)cc3)c3cncnc32)CC1]

MS: m/z 440.0 [M+H]$^+$.

Example 35: 1-(3-((3-(4-phenoxyphenyl)-1H-pyrazolo[3,4-d]pyrimidin-1-yl)methyl)azetidin-1-yl)prop-2-en-1-one; (compound A35)

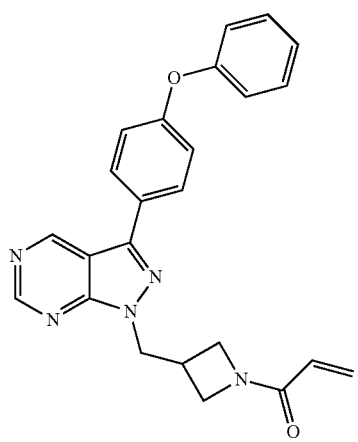 [SMILES: C=CC(=O)N1CC(Cn2nc(-c3ccc(Oc4ccccc4)cc3)c3cncnc32)C1]

MS: m/z 412.2 [M+H]+.

Example 36: 1-(4-(3-(4-phenoxyphenyl)-1H-pyrazolo[3,4-d]pyrimidin-1-yl)piperidin-1-yl)prop-2-en-1-one; (compound A36)

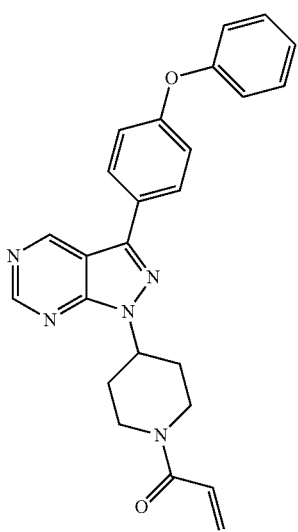 [SMILES: C=CC(=O)N1CCC(n2nc(-c3ccc(Oc4ccccc4)cc3)c3cncnc32)CC1]

MS: m/z 426.2 [M+H]+.

Example 37: 1-(6-(3-(4-phenoxyphenyl)-1H-pyrazolo[3,4-d]pyrimidin-1-yl)-2-azaspiro[3.3]heptan-2-yl)prop-2-en-1-one; (compound A37)

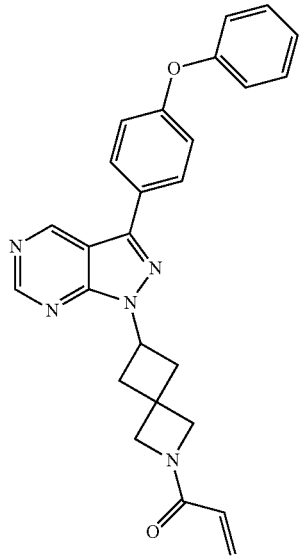 [SMILES: C=CC(=O)N1CC2(CC(n3nc(-c4ccc(Oc5ccccc5)cc4)c4cncnc43)C2)C1]

MS: m/z 438.1 [M+H]+.

Example 38: N-(2-((3-(4-phenoxyphenyl)-1H-pyrazolo[3,4-d]pyrimidin-1-yl)methyl)phenyl)acrylamide; (compound A38)

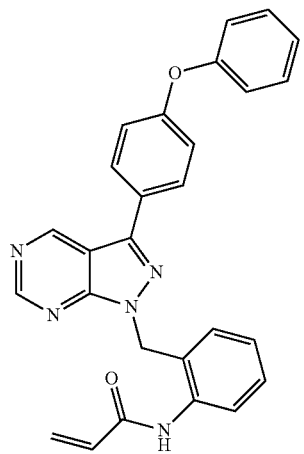 [SMILES: C=CC(=O)Nc1ccccc1Cn1nc(-c2ccc(Oc3ccccc3)cc2)c2cncnc21]

MS: m/z 448.1 [M+H]+.

Example 39: (R)-1-(3-(3-(4-(3-fluorophenoxy)phenyl)-1H-pyrazolo[3,4-d]pyrimidin-1-yl)piperidin-1-yl)prop-2-en-1-one; (compound A39)

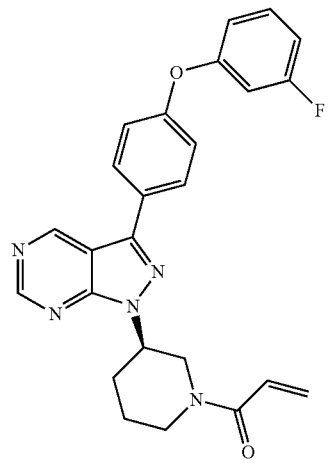 [SMILES: C=CC(=O)N1CCC[C@@H](n2nc(-c3ccc(Oc4cccc(F)c4)cc3)c3cncnc32)C1]

MS: m/z 444.1 [M+H]+.

Example 40: (R)-1-(3-(3-(4-(2-fluorophenoxy)phenyl)-1H-pyrazolo[3,4-d]pyrimidin-1-yl)piperidin-1-yl)prop-2-en-1-one; (compound A40)

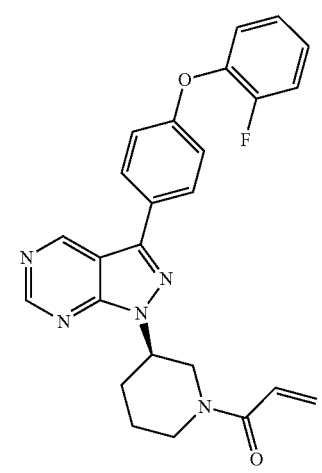 [SMILES: C=CC(=O)N1CCC[C@@H](n2nc(-c3ccc(Oc4ccccc4F)cc3)c3cncnc32)C1]

MS: m/z 444.2 [M+H]+.

Example 41: (S)-1-(4,4-difluoro-2-((3-(4-phenoxyphenyl)-1H-pyrazolo[3,4-d]pyrimidin-1-yl)methyl)pyrrolidin-1-yl)prop-2-en-1-one; (compound A41)

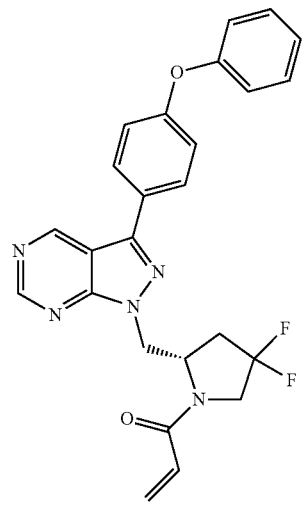 [SMILES: C=CC(=O)N1CC(F)(F)C[C@H]1Cn1nc(-c2ccc(Oc3ccccc3)cc2)c2cncnc21]

MS: m/z 462.3 [M+H]+.

Example 42: N-(2-(3-(4-phenoxyphenyl)-1H-pyrazolo[3,4-d]pyrimidin-1-yl)ethyl)acrylamide; (compound A42)

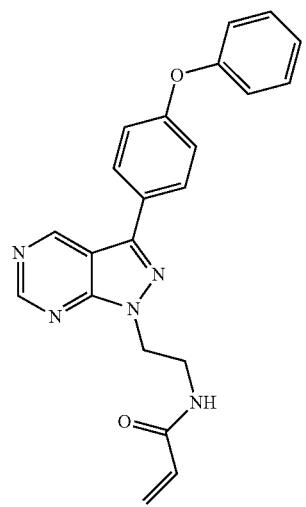 [SMILES: C=CC(=O)NCCn1nc(-c2ccc(Oc3ccccc3)cc2)c2cncnc21]

MS: m/z 396.0 [M+H]+.

Example 43: (S)—N-(1-(3-(4-phenoxyphenyl)-1H-pyrazolo[3,4-d]pyrimidin-1-yl)propan-2-yl)acrylamide; (compound A43)

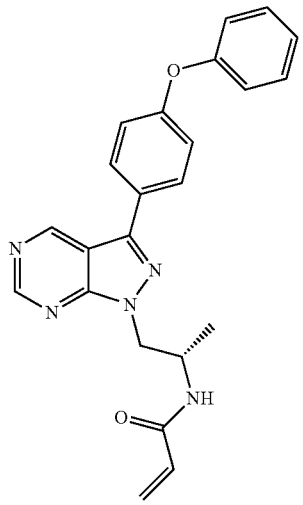 [SMILES: C=CC(=O)N[C@@H](C)Cn1nc(-c2ccc(Oc3ccccc3)cc2)c2cncnc21]

MS: m/z 400.0 [M+H]$^+$.

Example 44: (S)-1-(2-((3-(4-phenoxyphenyl)-1H-pyrazolo[3,4-d]pyrimidin-1-yl)methyl)piperidin-1-yl)prop-2-en-1-one; (compound A44)

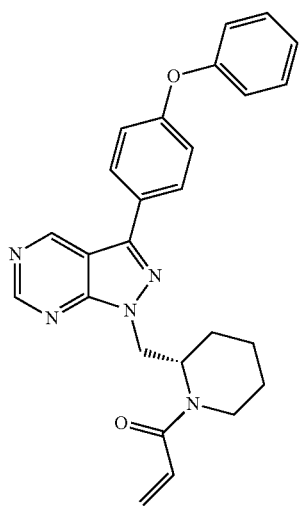 [SMILES: C=CC(=O)N1CCCC[C@H]1Cn1nc(-c2ccc(Oc3ccccc3)cc2)c2cncnc21]

MS: m/z 439.9 [M+H]$^+$.

Example 45: (S)-1-(2-methyl-2-((3-(4-phenoxyphenyl)-1H-pyrazolo[3,4-d]pyrimidin-1-yl)methyl)pyrrolidin-1-yl)prop-2-en-1-one; (compound A45)

MS: m/z 440.3 [M+H]$^+$.

Example 46: (S)-1-(2-((3-(4-(3-ethylphenoxy)phenyl)-1H-pyrazolo[3,4-d]pyrimidin-1-yl)methyl)pyrrolidin-1-yl)prop-2-en-1-one; (compound A46)

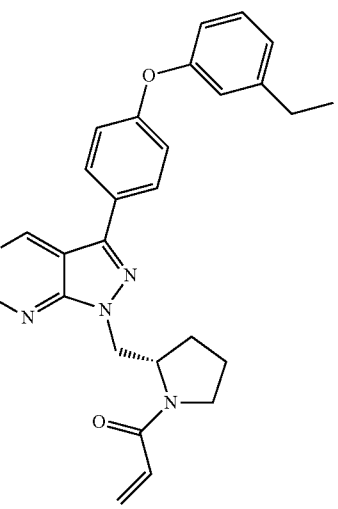

MS: m/z 453.8 [M+H]$^+$.

Example 47: (S)-1-(2-((3-(4-(3-(difluoromethyl) phenoxy)phenyl)-1H-pyrazolo[3,4-d]pyrimidin-1-yl) methyl)pyrrolidin-1-yl)prop-2-en-1-one; (compound A47)

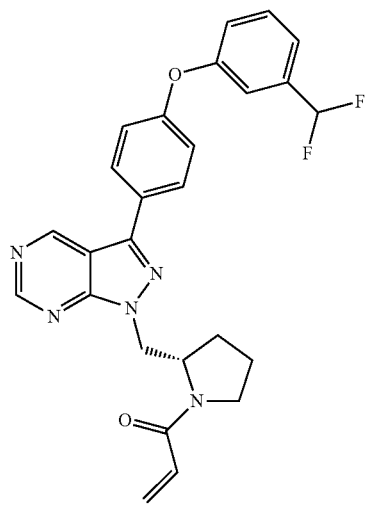 [SMILES: C=CC(=O)N1CCC[C@H]1Cn1nc(-c2ccc(Oc3cccc(C(F)F)c3)cc2)c2cncnc21]

MS: m/z 476.3 [M+H]$^+$.

Example 48: (S)-1-(2-((3-(4-(m-tolyloxy)phenyl)- 1H-pyrazolo[3,4-d]pyrimidin-1-yl)methyl)pyrrolidin-1-yl)prop-2-en-1-one; (compound A48)

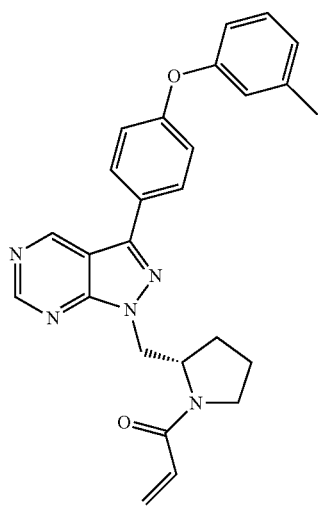 [SMILES: C=CC(=O)N1CCC[C@H]1Cn1nc(-c2ccc(Oc3cccc(C)c3)cc2)c2cncnc21]

MS: m/z 440.0 [M+H]$_+$.

Example 49: (S)-1-(4,4-dimethyl-2-((3-(4-phenoxyphenyl)-1H-pyrazolo[3,4-d]pyrimidin-1-yl)methyl) pyrrolidin-1-yl)prop-2-en-1-one; (compound A49)

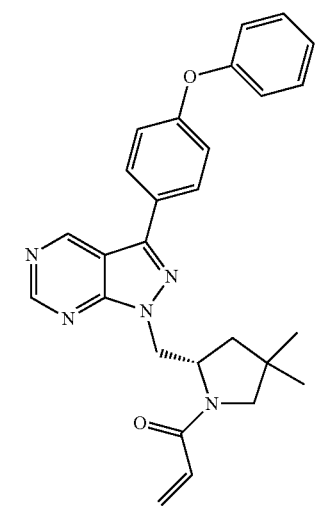 [SMILES: C=CC(=O)N1CC(C)(C)C[C@H]1Cn1nc(-c2ccc(Oc3ccccc3)cc2)c2cncnc21]

MS: m/z 454.2 [M+H]$^+$.

Example 50: (R)-1-(3-(3-(4-(2,6-difluorophenoxy) phenyl)-1H-pyrazolo[3,4-d]pyrimidin-1-yl)piperidin-1-yl)prop-2-en-1-one; (compound A50)

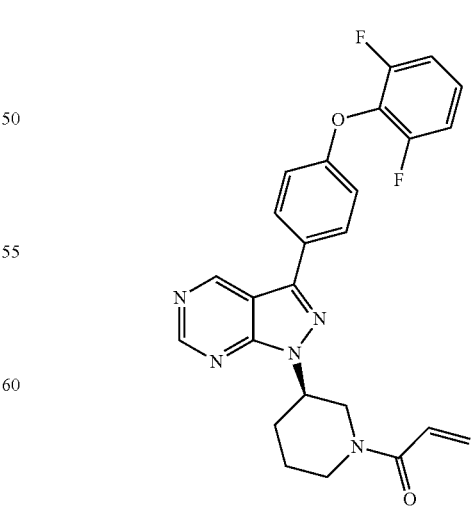

MS: m/z 462.1 [M+H]$^+$.

Example 51: (S)-1-(2-((3-(4-phenoxyphenyl)-1H-pyrazolo[3,4-d]pyrimidin-1-yl)methyl)azetidin-1-yl)prop-2-en-1-one; (compound A51)

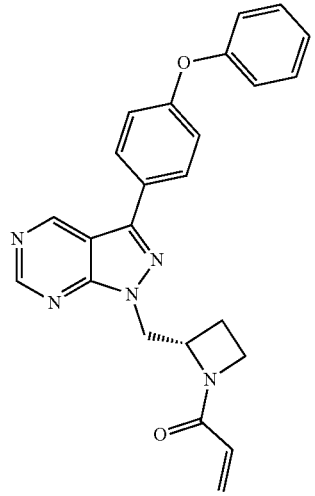 [SMILES: C=CC(=O)N1CC[C@H]1Cn1nc(-c2ccc(Oc3ccccc3)cc2)c2cncnc21]

MS: m/z 412.2 [M+H]⁺.

Example 52: (S)-1-(2-((3-(2-fluoro-4-phenoxyphenyl)-1H-pyrazolo[3,4-d]pyrimidin-1-yl)methyl)-2-methylpyrrolidin-1-yl)prop-2-en-1-one; (compound A52)

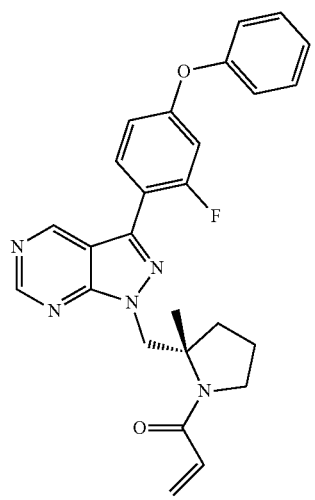 [SMILES: C=CC(=O)N1CCC[C@@]1(C)Cn1nc(-c2ccc(Oc3ccccc3)cc2F)c2cncnc21]

MS: m/z 458.1 [M+H]⁺.

Example 53: (R)-1-(2-((3-(4-phenoxyphenyl)-1H-pyrazolo[3,4-d]pyrimidin-1-yl)methyl)azetidin-1-yl)prop-2-en-1-one; (compound A53)

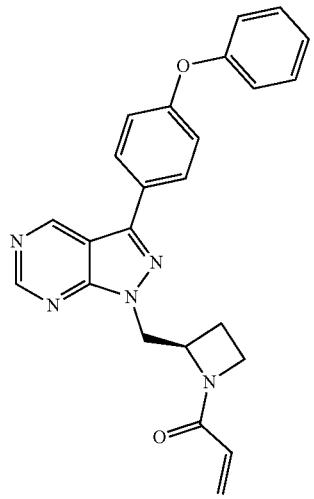 [SMILES: C=CC(=O)N1CC[C@@H]1Cn1nc(-c2ccc(Oc3ccccc3)cc2)c2cncnc21]

MS: m/z 411.9 [M+H]⁺.

Example 54: 1-(2-(3-(4-phenoxyphenyl)-1H-pyrazolo[3,4-d]pyrimidin-1-yl)-7-azaspiro[3.5]nonan-7-yl)prop-2-en-1-one; (compound A54)

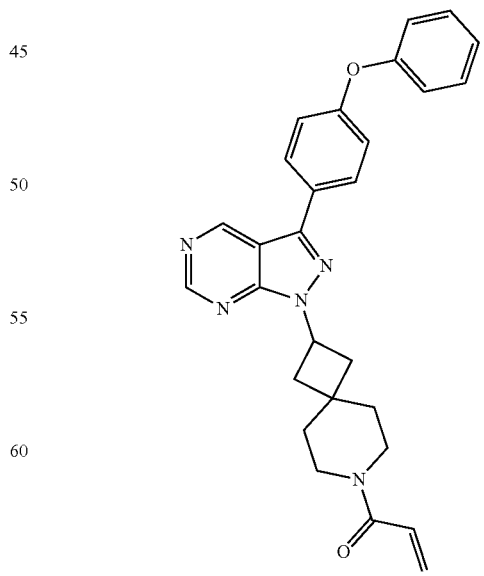

MS: m/z 466.3 [M+H]⁺.

Example 55: N-((1r,3r)-3-(3-(4-phenoxyphenyl)-1H-pyrazolo[3,4-d]pyrimidin-1-yl)cyclobutyl)acrylamide; (compound A55)

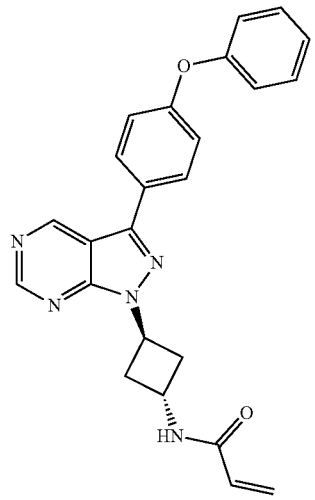 [SMILES: C=CC(=O)N[C@H]1C[C@H](n2nc(-c3ccc(Oc4ccccc4)cc3)c3cncnc32)C1]

MS: m/z 411.8 [M+H]+.

Example 56: N-((1r,4r)-4-(3-(4-phenoxyphenyl)-1H-pyrazolo[3,4-d]pyrimidin-1-yl)cyclohexyl)acrylamide; (compound A56)

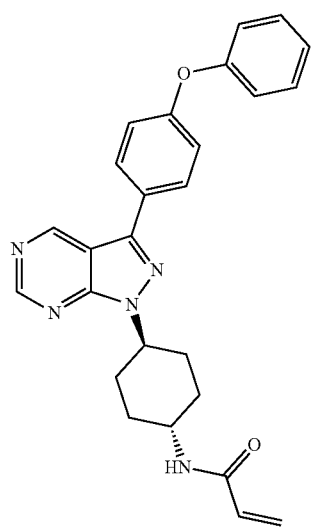 [SMILES: C=CC(=O)N[C@H]1CC[C@H](n2nc(-c3ccc(Oc4ccccc4)cc3)c3cncnc32)CC1]

MS: m/z 440.3 [M+H]+.

The following compounds were prepared by Scheme 1: Method A and Scheme 2: Method B Example 57: 1-(4-((3-(4-phenoxyphenyl)-1H-pyrazolo[3,4-d]pyrimidin-1-yl)methyl)piperidin-1-yl)but-2-yn-1-one; (compound A57)

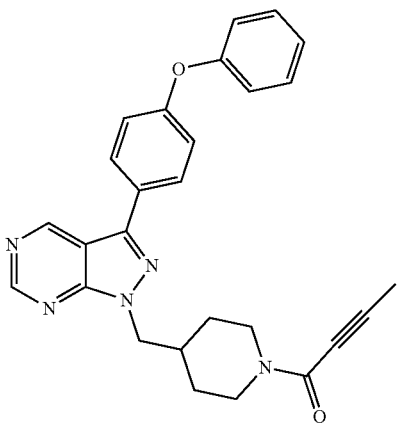 [SMILES: CC#CC(=O)N1CCC(Cn2nc(-c3ccc(Oc4ccccc4)cc3)c3cncnc32)CC1]

MS: m/z 451.9 [M+H]+.

Example 58: 1-(3-((3-(4-phenoxyphenyl)-1H-pyrazolo[3,4-d]pyrimidin-1-yl)methyl)azetidin-1-yl)but-2-yn-1-one; (compound A58)

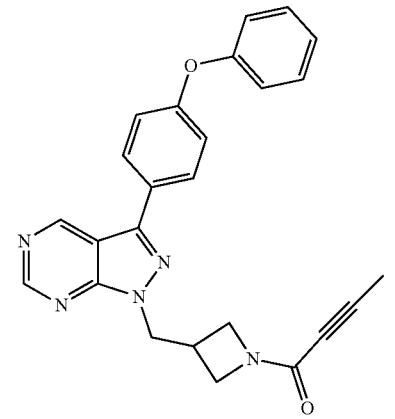 [SMILES: CC#CC(=O)N1CC(Cn2nc(-c3ccc(Oc4ccccc4)cc3)c3cncnc32)C1]

MS: m/z 424.1 [M+H]+.

Example 59: 1-(4-(3-(4-phenoxyphenyl)-1H-pyrazolo[3,4-d]pyrimidin-1-yl)piperidin-1-yl)but-2-yn-1-one; (compound A59)

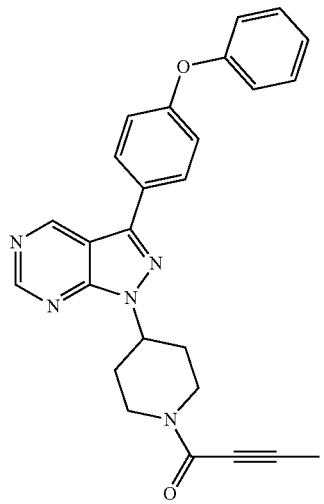 [SMILES: CC#CC(=O)N1CCC(n2nc(-c3ccc(Oc4ccccc4)cc3)c3cncnc32)CC1]

MS: m/z 438.1 [M+H]+.

Example 60: 1-(6-(3-(4-phenoxyphenyl)-1H-pyrazolo[3,4-d]pyrimidin-1-yl)-2-azaspiro[3.3]heptan-2-yl)but-2-yn-1-one; (compound A60)

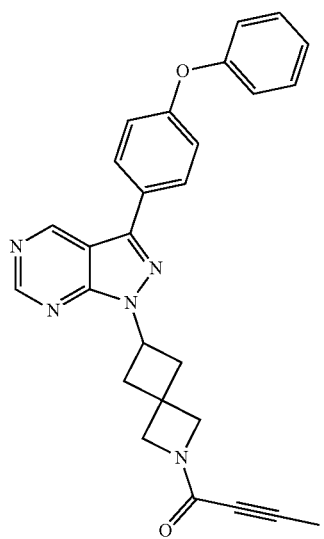 [SMILES: CC#CC(=O)N1CC2(CC(n3nc(-c4ccc(Oc5ccccc5)cc4)c4cncnc43)C2)C1]

MS: m/z 450.1 [M+H]+.

Example 61: N-(2-((3-(4-phenoxyphenyl)-1H-pyrazolo[3,4-d]pyrimidin-1-yl)methyl)phenyl)but-2-ynamide; (compound A61)

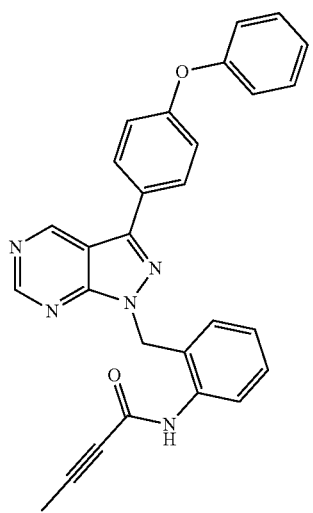 [SMILES: CC#CC(=O)Nc1ccccc1Cn1nc(-c2ccc(Oc3ccccc3)cc2)c2cncnc21]

MS: m/z 460.3 [M+H]+.

Example 62: (R)-2-fluoro-1-(3-(3-(4-phenoxyphenyl)-1H-pyrazolo[3,4-d]pyrimidin-1-yl)piperidin-1-yl)prop-2-en-1-one; (compound A62)

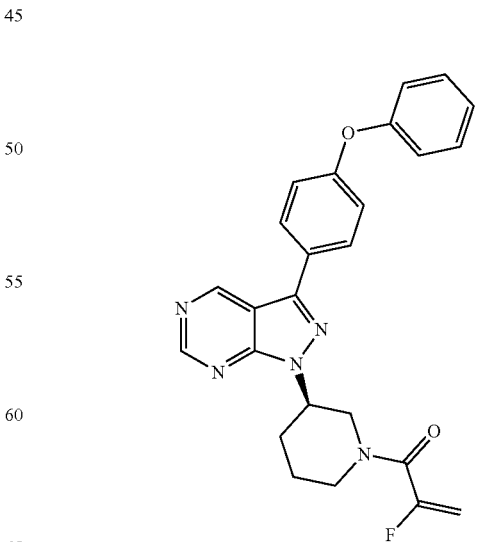

MS: m/z 444.3 [M+H]+.

Example 63: (R)-1-(3-((3-(4-phenoxyphenyl)-1H-pyrazolo[3,4-d]pyrimidin-1-yl)methyl)pyrrolidin-1-yl)but-2-yn-1-one; (compound A63)

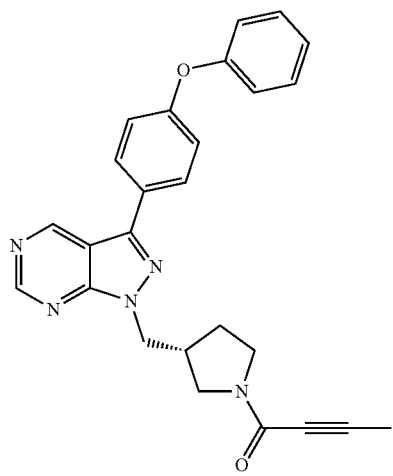 [SMILES: CC#CC(=O)N1CC[C@@H](Cn2nc(-c3ccc(Oc4ccccc4)cc3)c3cncnc32)C1]

MS: m/z 437.9 [M+H]$^+$.

Example 64: (S)-1-(3-((3-(4-phenoxyphenyl)-1H-pyrazolo[3,4-d]pyrimidin-1-yl)methyl)pyrrolidin-1-yl)but-2-yn-1-one; (compound A64)

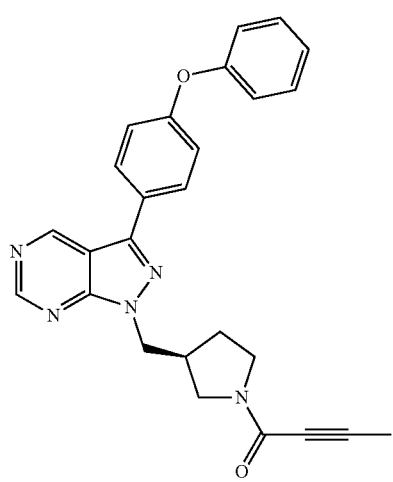 [SMILES: CC#CC(=O)N1CC[C@H](Cn2nc(-c3ccc(Oc4ccccc4)cc3)c3cncnc32)C1]

MS: m/z 437.9 [M+H]$^+$.

Example 65: (R)-1-(2-((3-(4-phenoxyphenyl)-1H-pyrazolo[3,4-d]pyrimidin-1-yl)methyl)pyrrolidin-1-yl)but-2-yn-1-one; (compound A65)

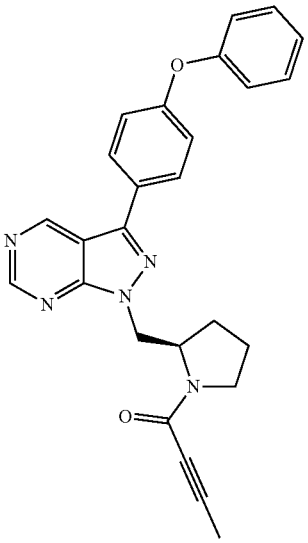 [SMILES: CC#CC(=O)N1CCC[C@@H]1Cn1nc(-c2ccc(Oc3ccccc3)cc2)c2cncnc21]

MS: m/z 437.9 [M+H]$^+$.

Example 66: (S)-1-(2-((3-(4-phenoxyphenyl)-1H-pyrazolo[3,4-d]pyrimidin-1-yl)methyl)azetidin-1-yl)but-2-yn-1-one; (compound A66)

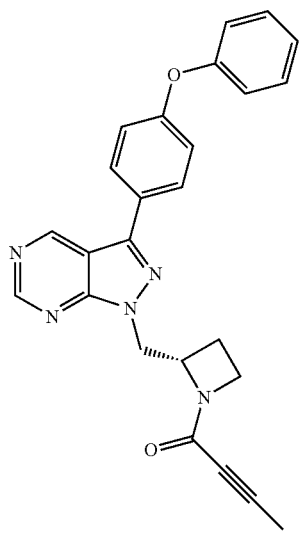 [SMILES: CC#CC(=O)N1CC[C@H]1Cn1nc(-c2ccc(Oc3ccccc3)cc2)c2cncnc21]

MS: m/z 423.9 [M+H]$^+$.

Example 67: (R)-1-(2-((3-(4-phenoxyphenyl)-1H-pyrazolo[3,4-d]pyrimidin-1-yl)methyl)azetidin-1-yl)but-2-yn-1-one; (compound A67)

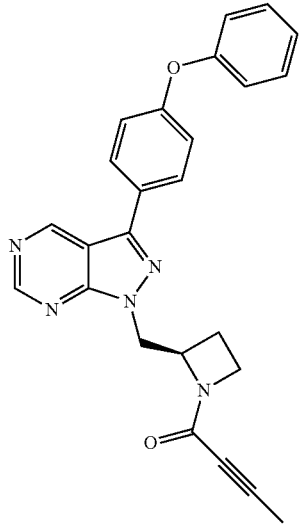 [SMILES: CC#CC(=O)N1CC[C@@H]1Cn1nc(-c2ccc(Oc3ccccc3)cc2)c2cncnc21]

MS: m/z 423.9 [M+H]+.

Example 68: 1-(2-(3-(4-phenoxyphenyl)-1H-pyrazolo[3,4-d]pyrimidin-1-yl)-7-azaspiro[3.5]nonan-7-yl)but-2-yn-1-one; (compound A68)

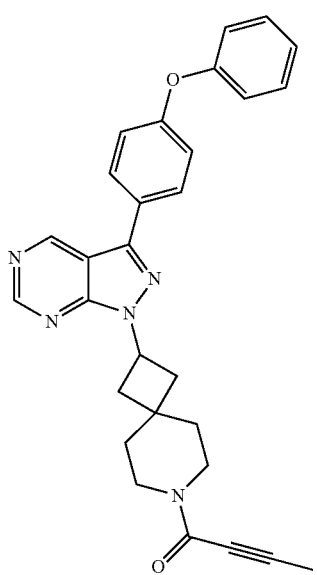 [SMILES: CC#CC(=O)N1CCC2(CC1)CC(n1nc(-c3ccc(Oc4ccccc4)cc3)c3cncnc31)C2]

MS: m/z 478.2 [M+H]+.

Example 69: N-((1r,3r)-3-(3-(4-phenoxyphenyl)-1H-pyrazolo[3,4-d]pyrimidin-1-yl)cyclobutyl)but-2-ynamide; (compound A69)

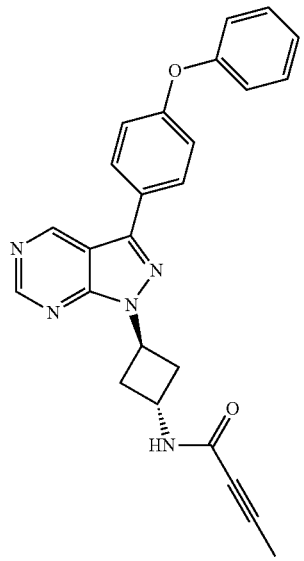 [SMILES: CC#CC(=O)N[C@H]1C[C@H](n2nc(-c3ccc(Oc4ccccc4)cc3)c3cncnc32)C1]

MS: m/z 424.3 [M+H]+.

Example 70: N-((1r,4r)-4-(3-(4-phenoxyphenyl)-1H-pyrazolo[3,4-d]pyrimidin-1-yl)cyclohexyl)but-2-ynamide; (compound A70)

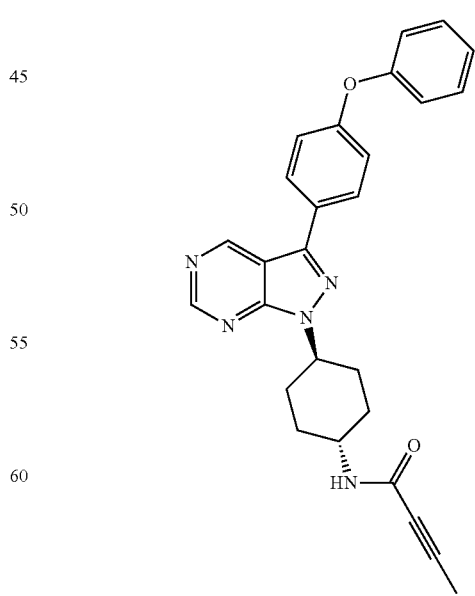

MS: m/z 452.3 [M+H]+.

Example 71: 1-(6-(3-(4-phenoxyphenyl)-1H-pyrazolo[3,4-d]pyrimidin-1-yl)-2-azaspiro[3.3]heptan-2-yl)pent-2-yn-1-one; (compound A71)
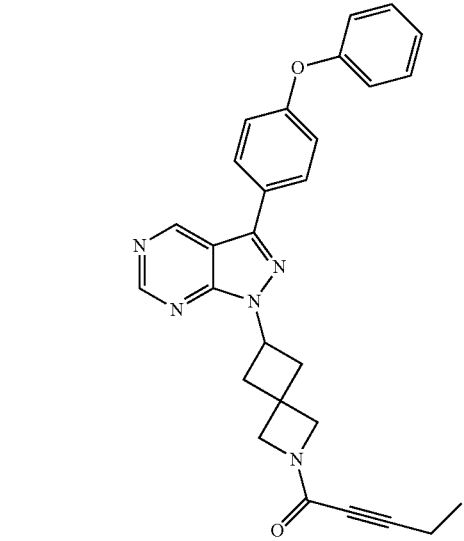 [SMILES: CCC#CC(=O)N1CC2(CC(n3nc(-c4ccc(Oc5ccccc5)cc4)c4cncnc43)C2)C1]
MS: m/z 452.3 [M+H]⁺.
Scheme 7: Method G
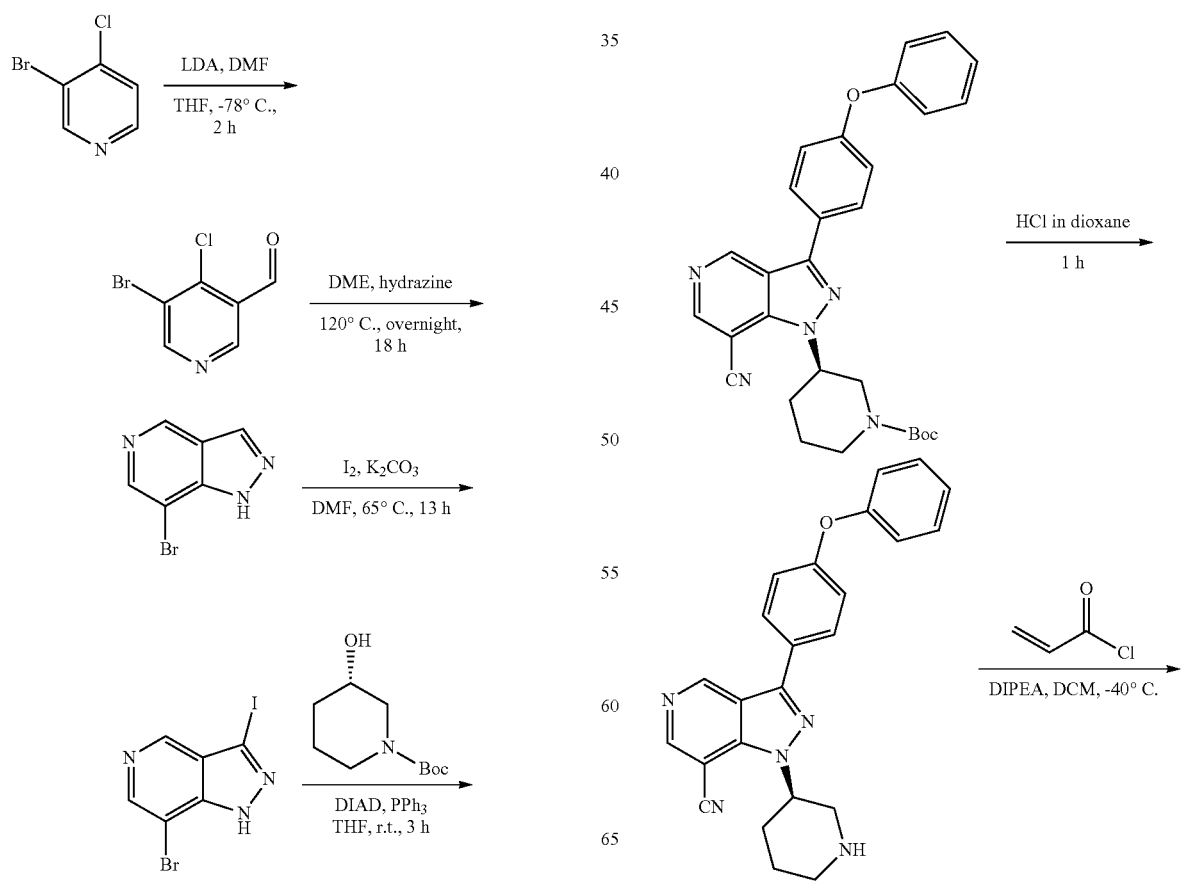
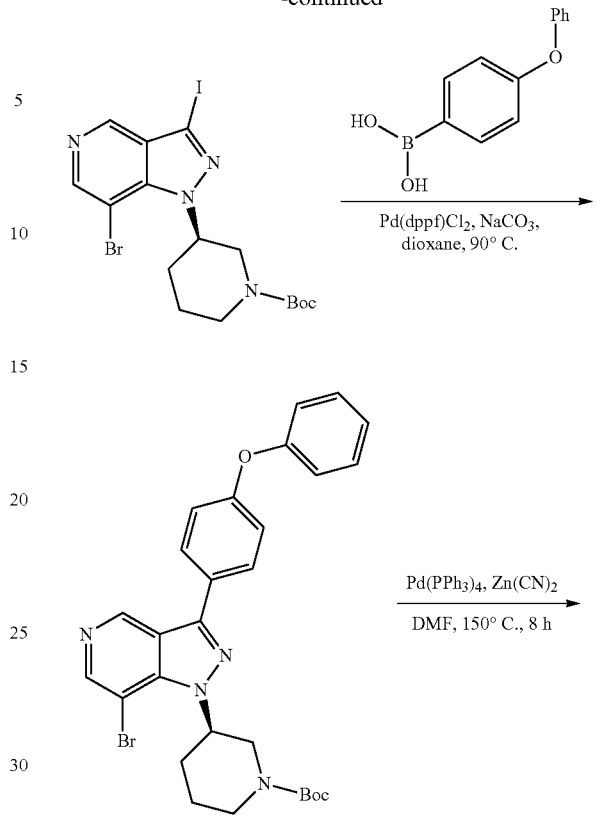

463
-continued

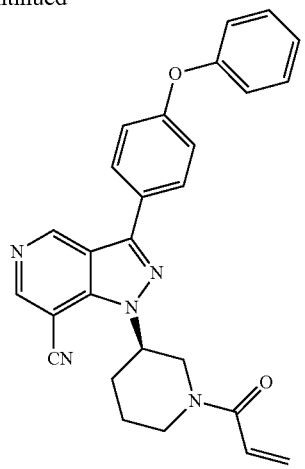

Example 72: (R)-1-(1-acryloylpiperidin-3-yl)-3-(4-phenoxyphenyl)-1H-pyrazolo[4,3-c]pyridine-7-carbonitrile; (compound A72)

Step 1: 5-Bromo-4-chloronicotinaldehyde

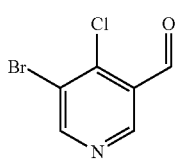

To a solution of LDA (2.0 M in THF, 34.55 mL, 69.1 mmol) and THF (20 mL) was added 3-bromo-4-chloropyridine (11 g, 57.6 mmol) in anhydrous THF (5 mL) at −78° C. under Ar. The resulting mixture was stirred at −78° C. for 2.5 hours. DMF (5.4 mL, 69.1 mmol) was added and the reaction was warmed to room temperature. The reaction was quenched with sat. NH$_4$Cl, and extracted with EtOAc (3×100 mL). The combined extracts were dried over anhydrous Na$_2$SO$_4$, filtered and concentrated. The residue was purified by combiflash (0-30%, EtOAc in Petroleum ether) to afford 5-bromo-4-chloronicotinaldehyde (8.2 g, 66%) as a pale yellow solid.

Step 2: 7-Bromo-1H-pyrazolo[4,3-c]pyridine

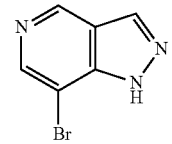

To a stirred solution of 5-bromo-4-chloronicotinaldehyde (1 g, 4.54 mmol) in DME (5 mL) was added hydrazine hydrate (1.135 g, 18.14 mmol). The resulted mixture was stirred at 120° C. overnight in a sealed tube. Water was added to dilute the mixture and then extracted with EtOAc. The organic phase was washed with brine, dried over anhydrous Na$_2$SO$_4$, filtered and concentrated to afford 7-bromo-1H-pyrazolo[4,3-c]pyridine (670 mg, 74%) as a yellow solid.

Step 3: 7-Bromo-3-iodo-1H-pyrazolo[4,3-c]pyridine

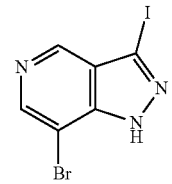 [SMILES: Brc1cncc2c(I)n[nH]c12]

To a stirred solution of 7-bromo-1H-pyrazolo[4,3-c]pyridine (670 mg, 3.4 mmol) in DMF (6 mL) was added I2 (710 mg, 6.8 mmol) and K$_2$CO$_3$ (940 mg, 6.8 mmol). The resulted mixture was stirred at 65° C. for 13 h. Water was added to dilute the mixture and then extracted with EtOAc. The organic phase was washed with brine, dried over anhydrous Na$_2$SO$_4$, filtered and concentrated to afford 7-bromo-3-iodo-1H-pyrazolo[4,3-c]pyridine (960 mg, 88%) as a yellow solid.

Step 4: tert-Butyl (R)-3-(7-bromo-3-iodo-1H-pyrazolo[4,3-c]pyridin-1-yl)piperidine-1-carboxylate

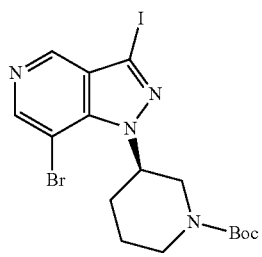 [SMILES: CC(C)(C)OC(=O)N1CCC[C@@H](n2nc(I)c3cncc(Br)c32)C1]

DIAD (461 mg, 2.28 mmol) was added to a mixture of TPP (598 mg, 2.28 mmol), 7-bromo-3-iodo-1H-pyrazolo[4,3-c]pyridine (246 mg, 0.76 mmol) and tert-butyl (S)-3-hydroxypiperidine-1-carboxylate (458 mg, 2.28 mmol) in THF (7 mL). After stirring for 4 h at room temperature, the mixture was concentrated to give a residue which was precipitated in EtOAc (10 mL) and hexane, the formed solid was removed by filtration and the filtrate was concentrated to give a residue, which was purified by normal phase silica gel chromatography (Hex:EtOAc=0-60%) to afford tert-butyl (R)-3-(7-bromo-3-iodo-1H-pyrazolo[4,3-c]pyridin-1-yl)piperidine-1-carboxylate (472 mg, 99%).

Step 5:tert-Butyl(R)-3-(7-bromo-3-(4-phenoxyphenyl)-1H-pyrazolo[4,3-c]pyridin-1-yl)piperidine-1-carboxylate

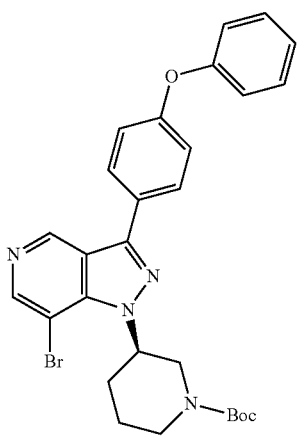 [SMILES: CC(C)(C)OC(=O)N1CCC[C@@H](n2nc(-c3ccc(Oc4ccccc4)cc3)c3cncc(Br)c32)C1]

Pd(dppf)Cl$_2$ (34 mg, 0.0468 mmol) was added to a degassed mixture of tert-butyl (R)-3-(7-bromo-3-iodo-1H-pyrazolo[4,3-c]pyridin-1-yl)piperidine-1-carboxylate (472 mg, 0.933 mmol), (4-phenoxyphenyl)boronic acid (152 mg, 0.71 mmol) and Na$_2$CO$_3$ (198 mg, 0.868 mmol) in dioxane (9 mL)/water (3 mL) under N$_2$ protection. The mixture was stirred at 90° C. for 4 h, then the mixture was concentrated to give a crude residue which was purified by normal phase chromatography (Hex:EtOAc=0-80%) to afford tert-butyl (R)-3-(7-bromo-3-(4-phenoxyphenyl)-1H-pyrazolo[4,3-c]pyridin-1-yl)piperidine-1-carboxylate (196 mg, 38%) as a brown solid.

Step 6: tert-Butyl (R)-3-(7-cyano-3-(4-phenoxyphenyl)-1H-pyrazolo[4,3-c]pyridin-1-yl)piperidine-1-carboxylate

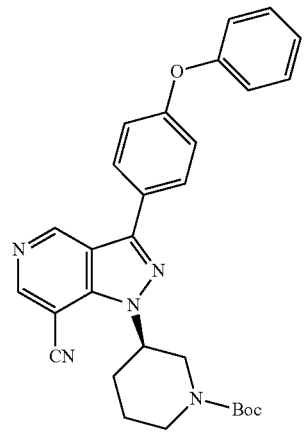 [SMILES: CC(C)(C)OC(=O)N1CCC[C@@H](n2nc(-c3ccc(Oc4ccccc4)cc3)c3cncc(C#N)c32)C1]

A mixture of tert-butyl (R)-3-(7-bromo-3-(4-phenoxyphenyl)-1H-pyrazolo[4,3-c]pyridin-1-yl)piperidine-1-carboxylate (196 mg, 0.357 mmol), Zn(CN)$_2$ (84 mg, 0.714 mmol) and DMF (3 mL) was stirred at 150° C. for 8 h under Ar. The mixture was filtered and the filtrate was diluted with EtOAc, washed with water and brine and then dried over anhydrous Na$_2$SO$_4$, filtered and concentrated to give a crude residue, which was purified by normal phase chromatography (Hex:EtOAc=0-80%) to afford tert-butyl (R)-3-(7-cyano-3-(4-phenoxyphenyl)-1H-pyrazolo[4,3-c]pyridin-1-yl)piperidine-1-carboxylate (69 mg, 39%) as a white solid.

Step 7: (R)-3-(4-Phenoxyphenyl)-1-(piperidin-3-yl)-1H-pyrazolo[4,3-c]pyridine-7-carbonitrile hydrochloride

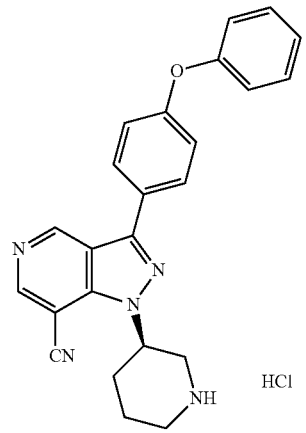 [SMILES: N#Cc1cncc2c(-c3ccc(Oc4ccccc4)cc3)nn([C@@H]3CCCNC3)c12 ; Cl]

A solution of tert-butyl (R)-3-(7-cyano-3-(4-phenoxyplienyl)-1H-pyrazolo[4,3-c]pyridin-1-yl)piperidine-1-carboxylate (69 mg, 0.139 mmol) in HC/dioxane (4 M, 4 mL) was stirred at 25° C. for 3 h. The mixture was concentrated to give a residue, in which hydrochloric acid (1N, 10 mL) was added, and then extracted with EtOAc. The aqueous phase was concentrated to afford (R)-3-(4-phenoxyphenyl)-1-(piperidin-3-yl)-1H-pyrazolo[4,3-c]pyridine-7-carbonitrile hydrochloride (68 mg, 99%) as a yellow solid.

Step 8: (R)-1-(1-Acryloylpiperidin-3-yl)-3-(4-phenoxyphenyl)-1H-pyrazolo[4,3-c]pyridine-7-carbonitrile Example 74: (S)-1-((1-Acryloylpyrrolidin-2-yl)methyl)-3-(4-phenoxyphenyl)-1H-pyrazolo[4,3-c]pyridine-7-carbonitrile; (compound A74)

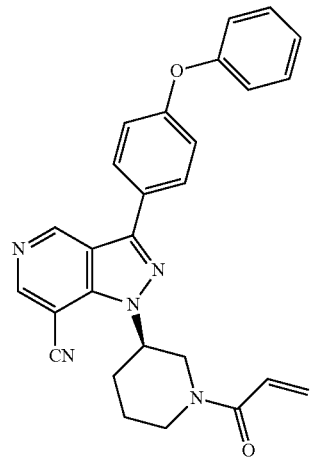 [SMILES: C=CC(=O)N1CCC[C@@H](n2nc(-c3ccc(Oc4ccccc4)cc3)c3cncc(C#N)c32)C1]

To a solution of (R)-3-(4-phenoxyphenyl)-1-(piperidin-3-yl)-1H-pyrazolo[4,3-c]pyridine-7-carbonitrile hydrochloride (69 mg, 0.16 mmol) and DIPEA (41 mg, 0.32 mmol) in DCM (5 mL) at −40° C. was slowly added a solution of acryloyl chloride (15 mg, 0.16 mmol). The resulted mixture was stirred at −40° C. for 5 min. Then the mixture was extracted with EtOAc, dried over Na$_2$SO$_4$ and then filtered. The filtrate was evaporated and the crude residue was purified by normal phase chromatography (DCM:MeOH=0-20%) to afford (R)-1-(1-Acryloylpiperidin-3-yl)-3-(4-phenoxyphenyl)-1H-pyrazolo[4,3-c]pyridine-7-carbonitrile (20 mg, 25%) as a white solid. MS: m/z 450.3 [M+H]+.

The following compounds were prepared by Scheme 7: Method G.

Example 73: (R)-1-(1-acryloylpyrrolidin-3-yl)-3-(4-phenoxyphenyl)-1H-pyrazolo[4,3-c]pyridine-7-carbonitrile; (compound A73)

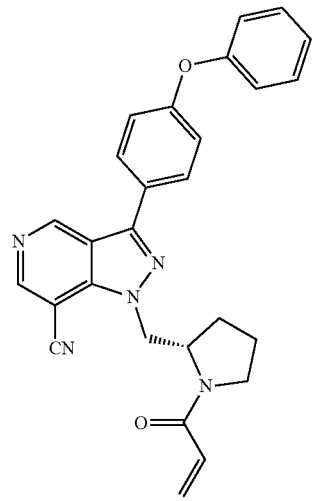

MS: m/z 450.3 [M+H]+.

Scheme 8: Method H

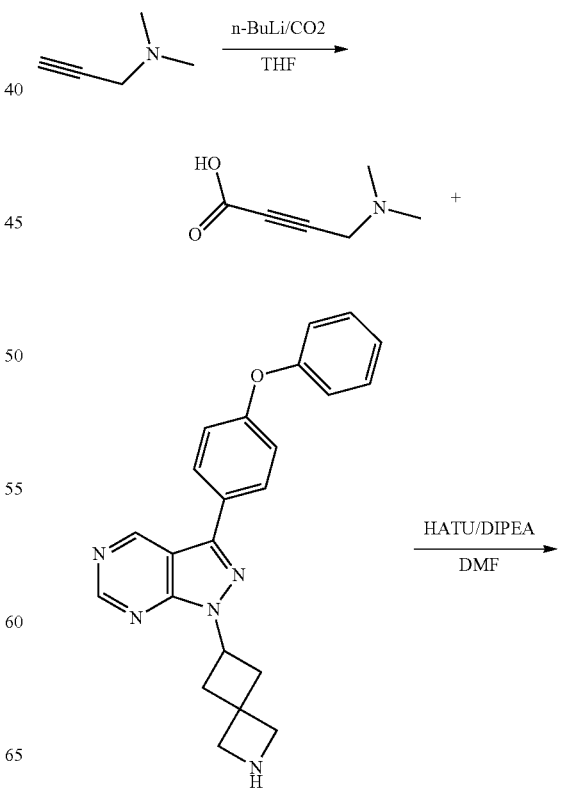

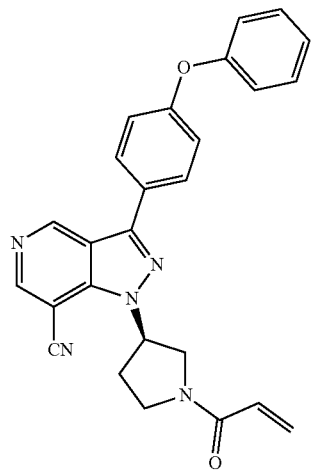 [SMILES: C=CC(=O)N1CC[C@@H](n2nc(-c3ccc(Oc4ccccc4)cc3)c3cncc(C#N)c32)C1]

MS: m/z 436.3 [M+H]+.

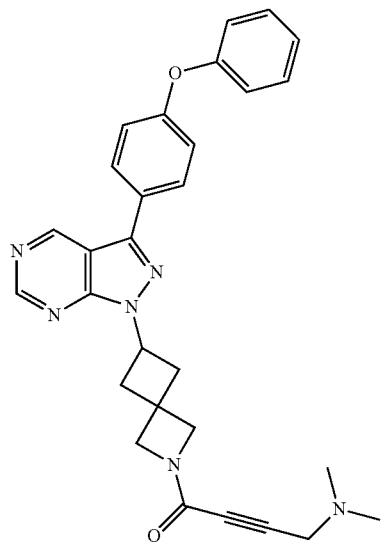

Example 75: 4-(dimethylamino)-1-(6-(3-(4-phenoxyphenyl)-1H-pyrazolo[3,4-d]pyrimidin-1-yl)-2-azaspiro[3.3]heptan-2-yl)but-2-yn-1-one; (compound A75)

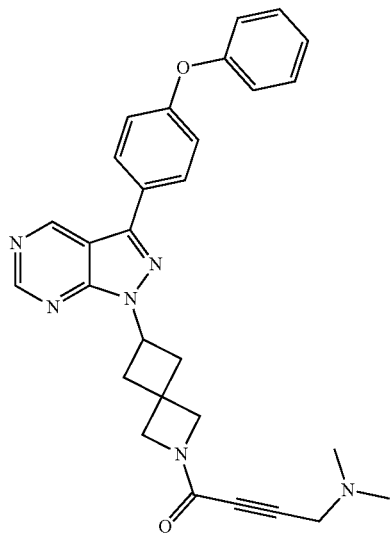 [SMILES: CN(C)CC#CC(=O)N1CC2(CC(n3nc(-c4ccc(Oc5ccccc5)cc4)c4cncnc43)C2)C1]

Step 1: 4-(Dimethylamino)but-2-ynoic Acid

n-BuLi in hexane (2.5M, 24.06 mmol, 9.62 mL) was slowly added to a solution of N,N-dimethylprop-2-yn-1-amine (24.06 mmol, 2.59 mL) in dry THF (10 mL) at −78° C. The mixture was stirred for 1 h at −78° C., then crushed $CO_2$ (241 mmol, 10.59 g) was added in one portion and the reaction mixture was stirred for an additional 10 min. The resulting solution was poured into water and washed with ethyl acetate. The aqueous layer was evaporated in to give the crude amino acid. It was dissolved in methanol, and the insoluble salts were removed via filtration. The filtrate was evaporated to afford 4-(dimethylamino)but-2-ynoic acid (1.5 g, 50%).

Step 2: 4-(Dimethylamino)-1-(6-(3-(4-phenoxyphenyl)-1H-pyrazolo[3,4-d]pyrimidin-1-yl)-2-azaspiro[3.3]heptan-2-yl)but-2-yn-1-one To solution of 3-(4-phenoxyphenyl)-1-(2-azaspiro[3.3]heptan-6-yl)-1H-pyrazolo[3,4-d]pyrimidine (150 mg, 0.4 mmol) (Scheme 1: Method A), 4-(dimethylamino)but-2-ynoic acid (51 mg, 0.4 mmol) and HATU (152 mg, 0.4 mmol) in DMF (50 mL) was added DIPEA (129 mg, 1 mmol). The resulted mixture was stirred at room temperature for 2 h, then 10 mL of water was added. The mixture was extracted with EtOAc (15 mL×2), washed with brine (15 mL×3), dried over $Na_2SO_4$, filtered and concentrated to give a residue which was purified by prep-TLC to afford 4-(dimethylamino)-1-(6-(3-(4-phenoxyphenyl)-H-pyrazolo[3,4-d]pyrimidin-1-yl)-2-azaspiro[3.3]heptan-2-yl)but-2-yn-1-one (16 mg, 8%) as a white solid. MS: m/z 493.2 [M+H]⁺.

The following compounds were prepared by Scheme 8: Method H.

Example 76: 4-(4-Methylpiperazin-1-yl)-1-(6-(3-(4-phenoxyphenyl)-1H-pyrazolo[3,4-d]pyrimidin-1-yl)-2-azaspiro[3.3]heptan-2-yl)but-2-yn-1-one; (compound A76)

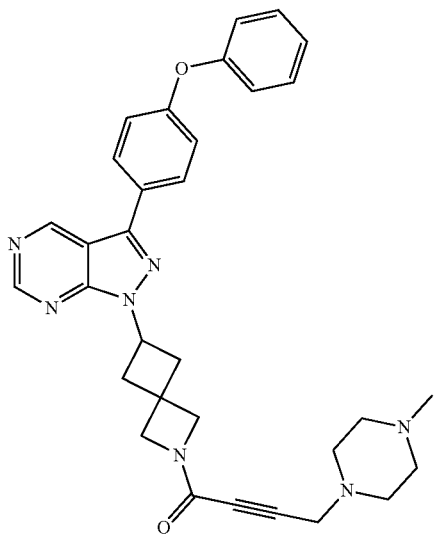 [SMILES: CN1CCN(CC#CC(=O)N2CC3(CC(n4nc(-c5ccc(Oc6ccccc6)cc5)c5cncnc54)C3)C2)CC1]

MS: m/z 548.3 [M+H]+.

Example 77: 1-(6-(3-(4-Phenoxyphenyl)-1H-pyrazolo[3,4-d]pyrimidin-1-yl)-2-azaspiro[3.3]heptan-2-yl)-4-(piperidin-1-yl)but-2-yn-1-one; (compound A77)

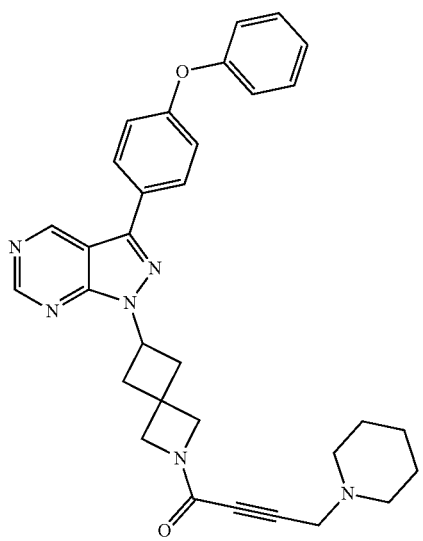 [SMILES: O=C(C#CCN1CCCCC1)N1CC2(CC(n3nc(-c4ccc(Oc5ccccc5)cc4)c4cncnc43)C2)C1]

MS: m/z 532.7 [M+H]+.

Example 78: 3-Cyclopropyl-1-(6-(3-(4-phenoxyphenyl)-1H-pyrazolo[3,4-d]pyrimidin-1-yl)-2-azaspiro[3.3]heptan-2-yl)prop-2-yn-1-one; (compound A78)

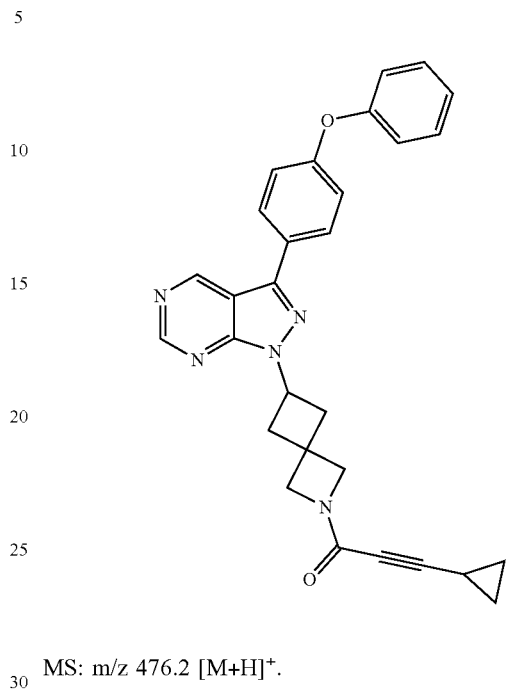

MS: m/z 476.2 [M+H]+.

Example 79: 4-Methoxy-1-(6-(3-(4-phenoxyphenyl)-1H-pyrazolo[3,4-d]pyrimidin-1-yl)-2-azaspiro[3.3]heptan-2-yl)but-2-yn-1-one; (compound A79)

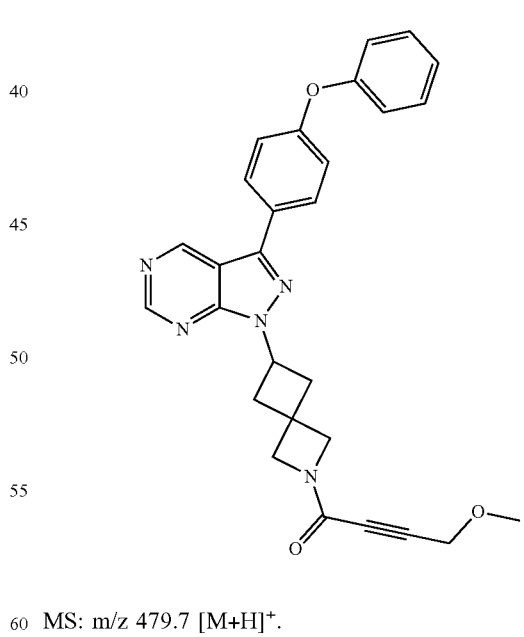

MS: m/z 479.7 [M+H]+.

Example B: Characterization of Compounds (e.g., BTK Inhibitor, BTK Antagonist, BTK Modulator)

Note the key for the assay results: A=<100 nM; B=100-500 nM; C=>500 nM.

| Compound | Assay Result |
|---|---|
| Compound: A1<br>ITK IC50 (nM) C<br>BTK IC50 (nM) A<br>JAK3 IC50 (nM) C<br>TXK IC50 (nM) B | |
| Compound: A2<br>ITK IC50 (nM) C<br>BTK IC50 (nM) A<br>JAK3 IC50 (nM) B<br>TXK IC50 (nM) A | |
| Compound: A3<br>ITK IC50 (nM) C<br>BTK IC50 (nM) A<br>JAK3 IC50 (nM) C<br>TXK IC50 (nM) A | |
| Compound: A4<br>ITK IC50 (nM) C<br>BTK IC50 (nM) A<br>JAK3 IC50 (nM) C<br>TXK IC50 (nM) A | |
| Compound: A5<br>ITK IC50 (nM) C<br>BTK IC50 (nM) A<br>JAK3 IC50 (nM) C<br>TXK IC50 (nM) B | |
| Compound: A6<br>ITK IC50 (nM) C<br>BTK IC50 (nM) A<br>JAK3 IC50 (nM) C<br>TXK IC50 (nM) A | |

-continued

| Compound | Assay Result |
|---|---|
| 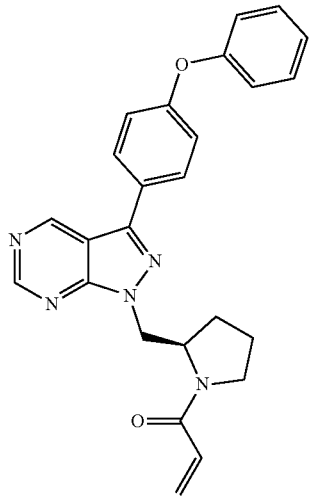 [SMILES: C=CC(=O)N1CCC[C@@H]1Cn1nc(-c2ccc(Oc3ccccc3)cc2)c2cncnc21] | Compound: A7<br>ITK IC50 (nM) C<br>BTK IC50 (nM) A<br>JAK3 IC50 (nM) C<br>TXK IC50 (nM) B |
| 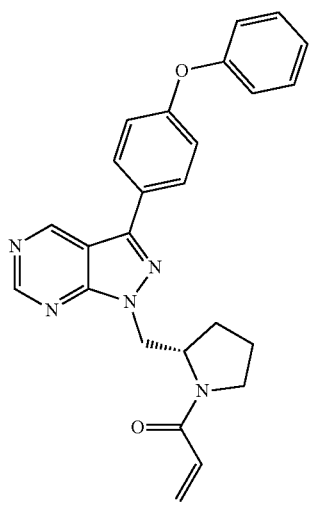 [SMILES: C=CC(=O)N1CCC[C@H]1Cn1nc(-c2ccc(Oc3ccccc3)cc2)c2cncnc21] | Compound: A8<br>ITK IC50 (nM) C<br>BTK IC50 (nM) A<br>JAK3 IC50 (nM) C<br>TXK IC50 (nM) A |
| 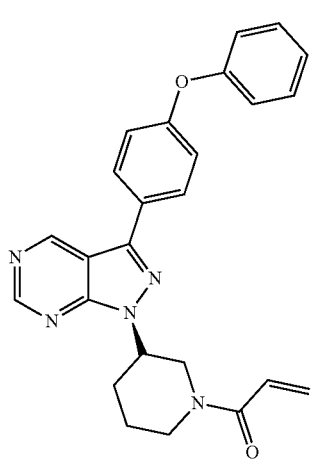 | Compound: A9<br>ITK IC50 (nM) C<br>BTK IC50 (nM) A<br>JAK3 IC50 (nM) C<br>TXK IC50 (nM) A |

-continued

| Compound | Assay Result |
|---|---|
| 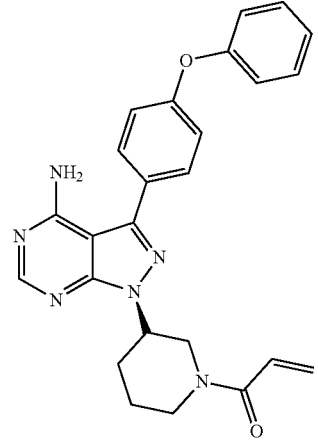 | Compound: A10<br>ITK IC50 (nM) A<br>BTK IC50 (nM) A<br>JAK3 IC50 (nM) A<br>RLK IC50 (nM) A<br>EGFR (nM) A<br>TEC (nM) A |
| 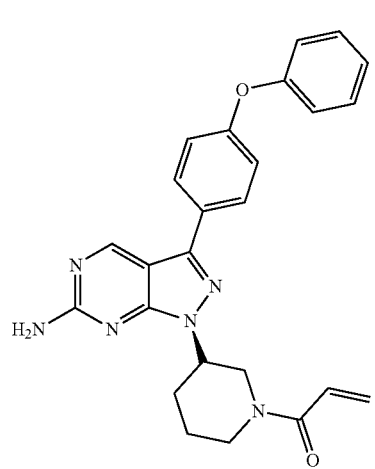 | Compound: A11<br>ITK IC50 (nM) C<br>BTK IC50 (nM) A<br>JAK3 IC50 (nM) C<br>RLK IC50 (nM) B |
| 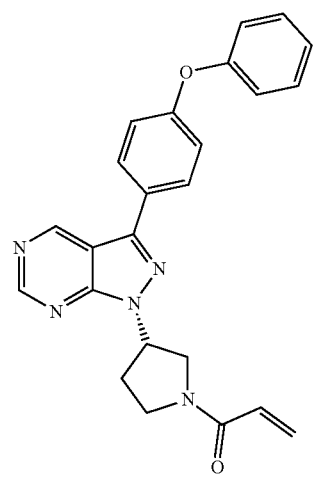 | Compound: A12<br>ITK IC50 (nM) C<br>BTK IC50 (nM) A<br>JAK3 IC50 (nM) C<br>TXK IC50 (nM) B |

477
-continued

| Compound | Assay Result |
|---|---|
| 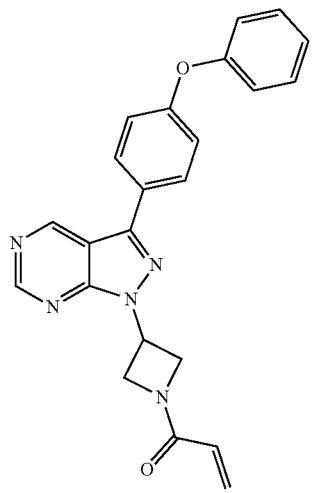 [SMILES: C=CC(=O)N1CC(n2nc(-c3ccc(Oc4ccccc4)cc3)c3cncnc32)C1] | Compound: A13<br>ITK IC50 (nM)  C<br>BTK IC50 (nM)  B<br>JAK3 IC50 (nM)  C<br>TXK IC50 (nM)  B |
| 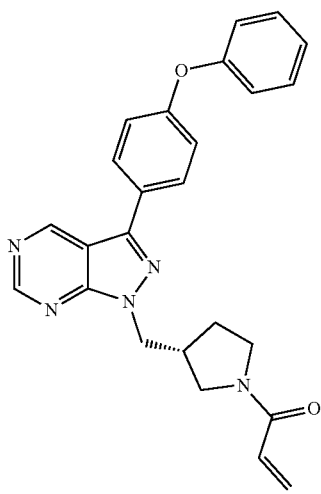 [SMILES: C=CC(=O)N1CC[C@@H](Cn2nc(-c3ccc(Oc4ccccc4)cc3)c3cncnc32)C1] | Compound: A14<br>ITK IC50 (nM)  C<br>BTK IC50 (nM)  B<br>JAK3 IC50 (nM)  C<br>TXK IC50 (nM)  B |
| 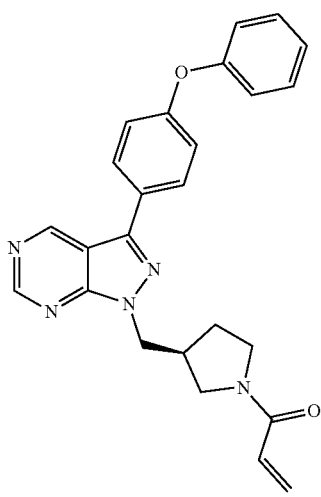 [SMILES: C=CC(=O)N1CC[C@H](Cn2nc(-c3ccc(Oc4ccccc4)cc3)c3cncnc32)C1] | Compound: A15<br>ITK IC50 (nM)  C<br>BTK IC50 (nM)  A<br>JAK3 IC50 (nM)  C<br>TXK IC50 (nM)  B |

478
-continued

| Compound | Assay Result |
|---|---|
| 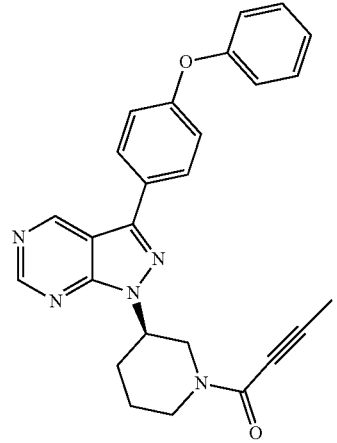 [SMILES: CC#CC(=O)N1CCC[C@@H](n2nc(-c3ccc(Oc4ccccc4)cc3)c3cncnc32)C1] | Compound: A16<br>ITK IC50 (nM)  C<br>BTK IC50 (nM)  C<br>JAK3 IC50 (nM)  C<br>TXK IC50 (nM)  C |
| 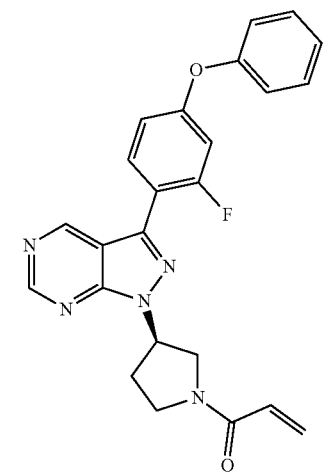 [SMILES: C=CC(=O)N1CC[C@@H](n2nc(-c3ccc(Oc4ccccc4)cc3F)c3cncnc32)C1] | Compound: A17<br>ITK IC50 (nM)  C<br>BTK IC50 (nM)  A<br>JAK3 IC50 (nM)  C<br>TXK IC50 (nM)  A |
| 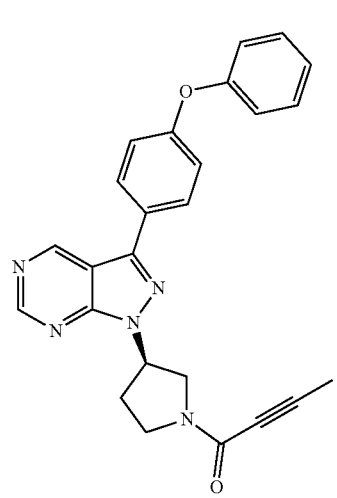 [SMILES: CC#CC(=O)N1CC[C@@H](n2nc(-c3ccc(Oc4ccccc4)cc3)c3cncnc32)C1] | Compound: A18<br>ITK IC50 (nM)  C<br>BTK IC50 (nM)  B<br>JAK3 IC50 (nM)  C<br>TXK IC50 (nM)  C |

-continued

| Compound | Assay Result |
|---|---|
| 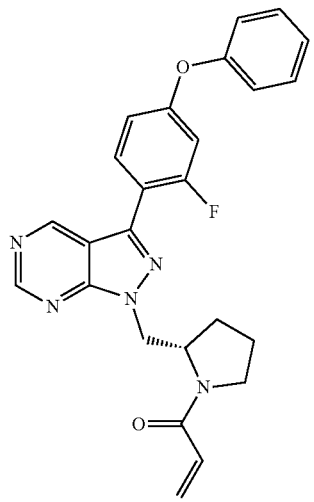 [SMILES: C=CC(=O)N1CCC[C@H]1Cn1nc(-c2ccc(Oc3ccccc3)cc2F)c2cncnc21] | Compound: A19<br>ITK IC50 (nM) C<br>BTK IC50 (nM) A<br>JAK3 IC50 (nM) C<br>TXK IC50 (nM) A |
| 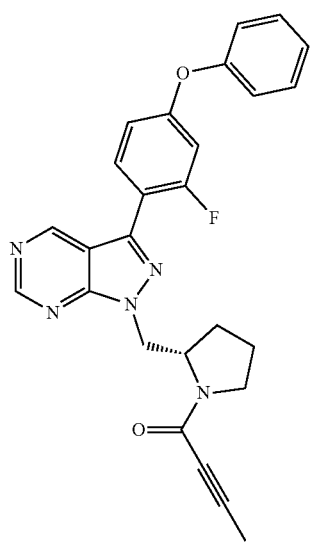 [SMILES: CC#CC(=O)N1CCC[C@H]1Cn1nc(-c2ccc(Oc3ccccc3)cc2F)c2cncnc21] | Compound: A20<br>ITK IC50 (nM) C<br>BTK IC50 (nM) A<br>JAK3 IC50 (nM) C<br>TXK IC50 (nM) C |
| 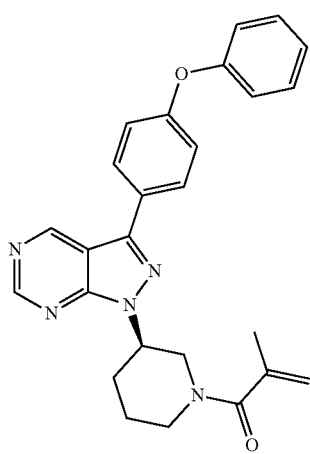 [SMILES: C=C(C)C(=O)N1CCC[C@@H](n2nc(-c3ccc(Oc4ccccc4)cc3)c3cncnc32)C1] | Compound: A21<br>ITK IC50 (nM) C<br>BTK IC50 (nM) C<br>JAK3 IC50 (nM) C<br>TXK IC50 (nM) C |

-continued

| Compound | Assay Result |
|---|---|
| 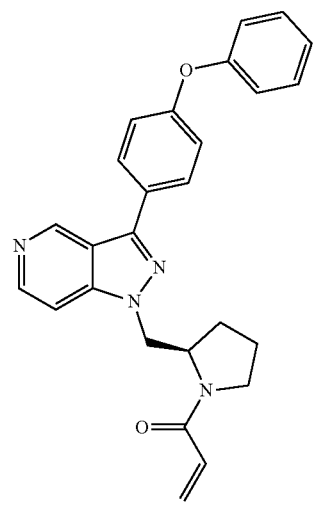 [SMILES: C=CC(=O)N1CCC[C@@H]1Cn1nc(-c2ccc(Oc3ccccc3)cc2)c2cnccc21] | Compound: A22<br>ITK IC50 (nM) C<br>BTK IC50 (nM) A<br>JAK3 IC50 (nM) C<br>TXK IC50 (nM) A |
| 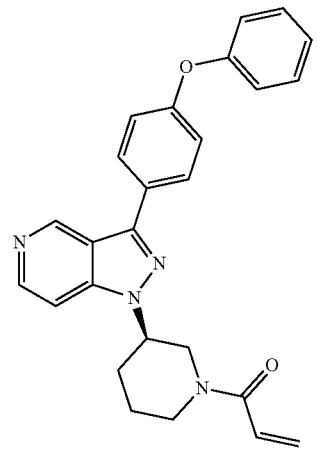 [SMILES: C=CC(=O)N1CCC[C@@H](n2nc(-c3ccc(Oc4ccccc4)cc3)c3cnccc32)C1] | Compound: A23<br>ITK IC50 (nM) C<br>BTK IC50 (nM) A<br>JAK3 IC50 (nM) C<br>TXK IC50 (nM) A |
| 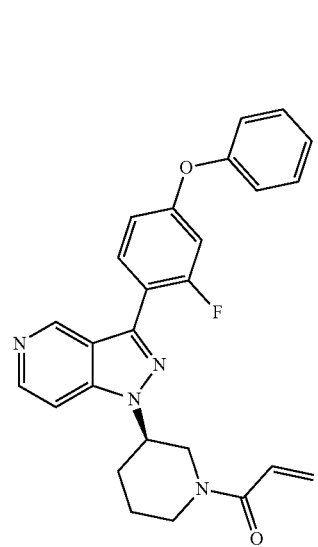 [SMILES: C=CC(=O)N1CCC[C@@H](n2nc(-c3ccc(Oc4ccccc4)cc3F)c3cnccc32)C1] | Compound: A24<br>ITK IC50 (nM) C<br>BTK IC50 (nM) A<br>JAK3 IC50 (nM) C<br>TXK IC50 (nM) A |

-continued

| Compound | Assay Result |
|---|---|
| 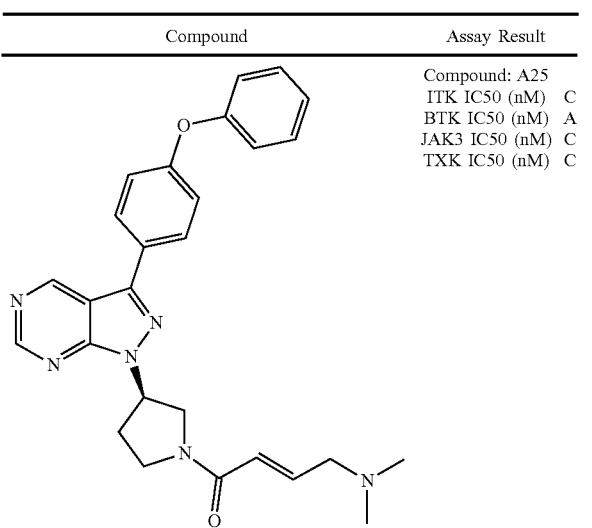 | Compound: A25<br>ITK IC50 (nM) C<br>BTK IC50 (nM) A<br>JAK3 IC50 (nM) C<br>TXK IC50 (nM) C |
| 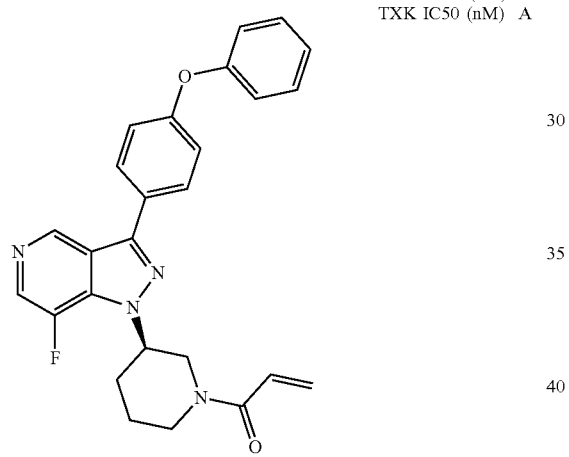 | Compound: A26<br>ITK IC50 (nM) C<br>BTK IC50 (nM) A<br>JAK3 IC50 (nM) C<br>TXK IC50 (nM) A |
| 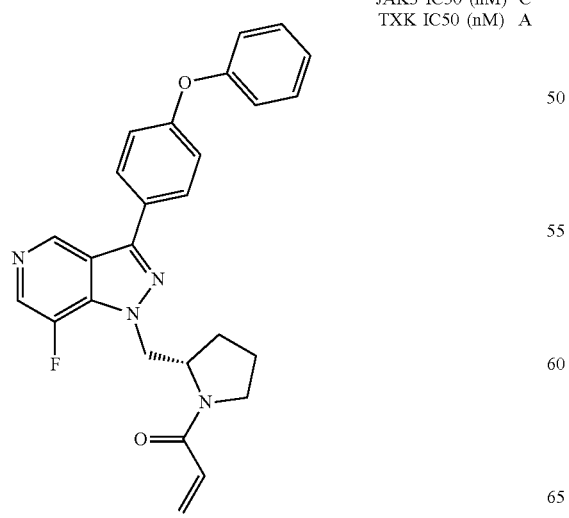 | Compound: A27<br>ITK IC50 (nM) C<br>BTK IC50 (nM) A<br>JAK3 IC50 (nM) C<br>TXK IC50 (nM) A |

-continued

| Compound | Assay Result |
|---|---|
| 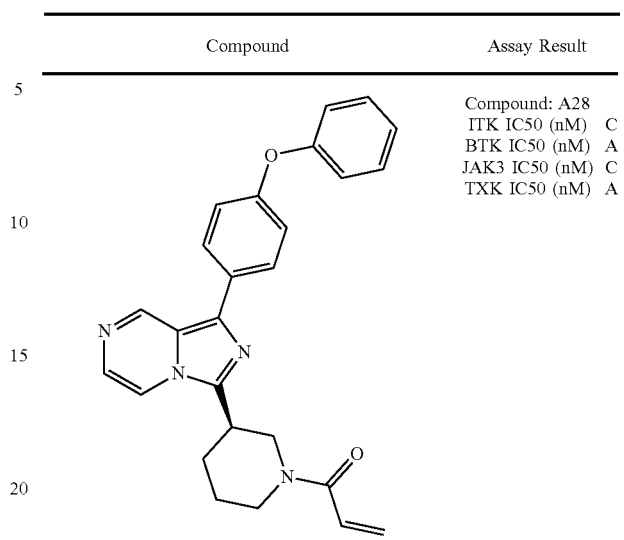 | Compound: A28<br>ITK IC50 (nM) C<br>BTK IC50 (nM) A<br>JAK3 IC50 (nM) C<br>TXK IC50 (nM) A |
| 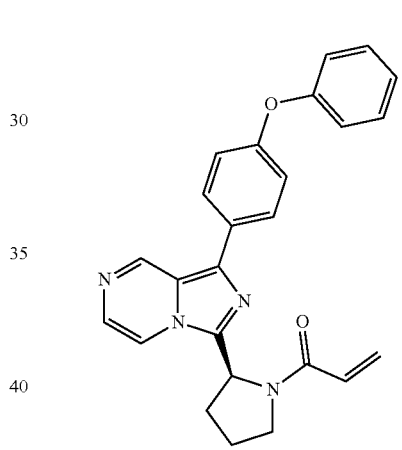 | Compound: A29<br>ITK IC50 (nM) C<br>BTK IC50 (nM) A<br>JAK3 IC50 (nM) C<br>TXK IC50 (nM) B |
| 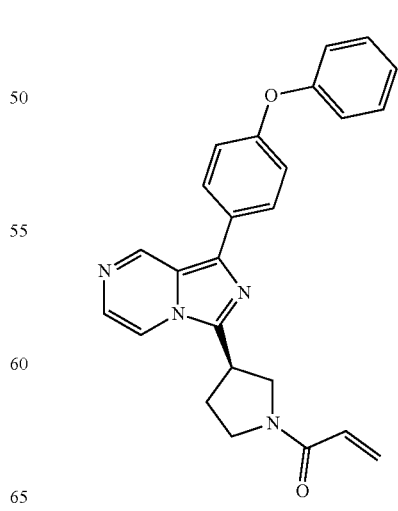 | Compound: A30<br>ITK IC50 (nM) C<br>BTK IC50 (nM) A<br>JAK3 IC50 (nM) C<br>TXK IC50 (nM) A |

| Compound | Assay Result |
|---|---|
| 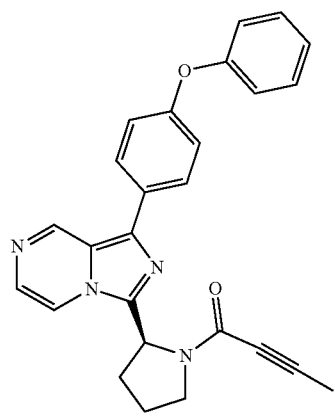 [SMILES: CC#CC(=O)N1CCC[C@H]1c1nc(-c2ccc(Oc3ccccc3)cc2)c2cnccn12] | Compound: A31<br>ITK IC50 (nM) C<br>BTK IC50 (nM) C<br>JAK3 IC50 (nM) C<br>TXK IC50 (nM) C |
| 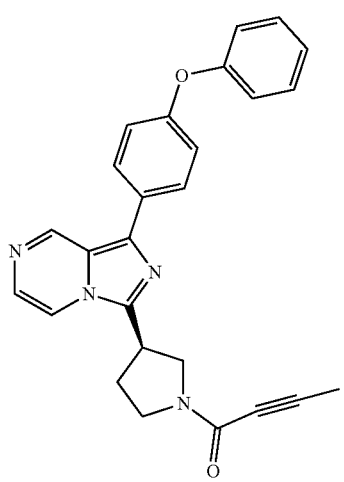 [SMILES: CC#CC(=O)N1CC[C@@H](c2nc(-c3ccc(Oc4ccccc4)cc3)c3cnccn23)C1] | Compound: A32<br>ITK IC50 (nM) C<br>BTK IC50 (nM) A<br>JAK3 IC50 (nM) C<br>TXK IC50 (nM) B |
| 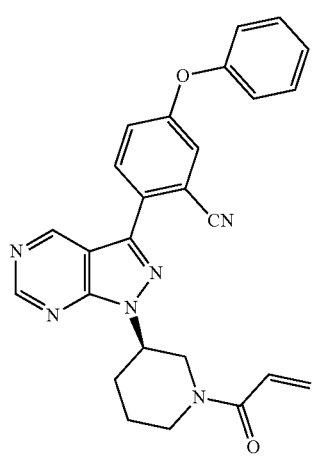 [SMILES: C=CC(=O)N1CCC[C@@H](n2nc(-c3ccc(Oc4ccccc4)cc3C#N)c3cncnc32)C1] | Compound: A33<br>ITK IC50 (nM) C<br>BTK IC50 (nM) B<br>JAK3 IC50 (nM) C<br>TXK IC50 (nM) C |

| Compound | Assay Result |
|---|---|
| 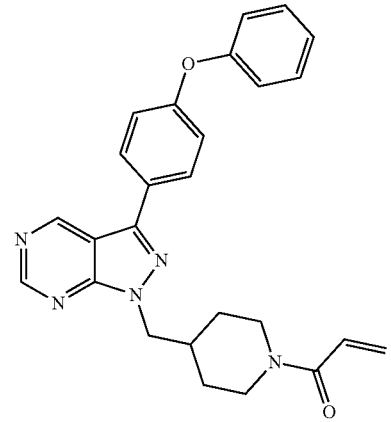 [SMILES: C=CC(=O)N1CCC(Cn2nc(-c3ccc(Oc4ccccc4)cc3)c3cncnc32)CC1] | Compound: A34<br>ITK IC50 (nM) C<br>BTK IC50 (nM) A<br>JAK3 IC50 (nM) C<br>TXK IC50 (nM) C |
| 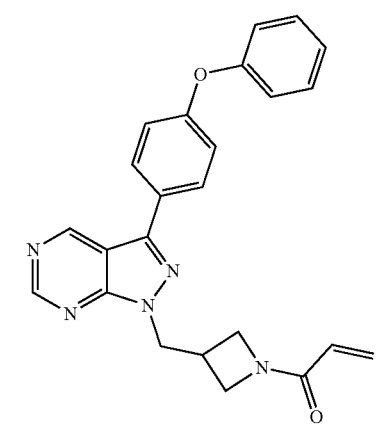 [SMILES: C=CC(=O)N1CC(Cn2nc(-c3ccc(Oc4ccccc4)cc3)c3cncnc32)C1] | Compound: A35<br>ITK IC50 (nM) C<br>BTK IC50 (nM) A<br>JAK3 IC50 (nM) C<br>TXK IC50 (nM) B |
| 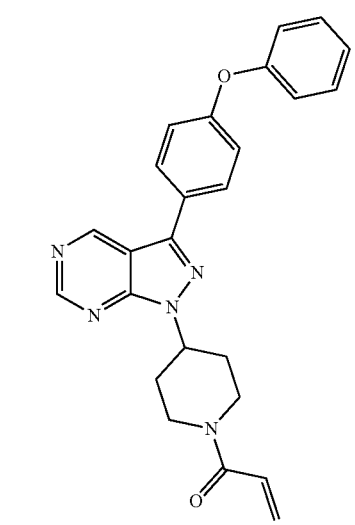 [SMILES: C=CC(=O)N1CCC(n2nc(-c3ccc(Oc4ccccc4)cc3)c3cncnc32)CC1] | Compound: A36<br>ITK IC50 (nM) C<br>BTK IC50 (nM) B<br>JAK3 IC50 (nM) C<br>TXK IC50 (nM) B |

485
-continued

| Compound | Assay Result |
|---|---|
| 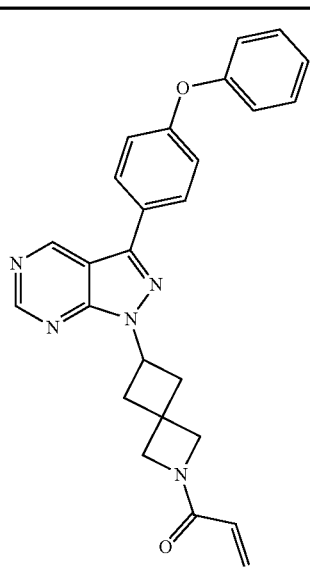 | Compound: A37<br>ITK IC50 (nM)  C<br>BTK IC50 (nM)  A<br>JAK3 IC50 (nM)  C<br>TXK IC50 (nM)  B |
| 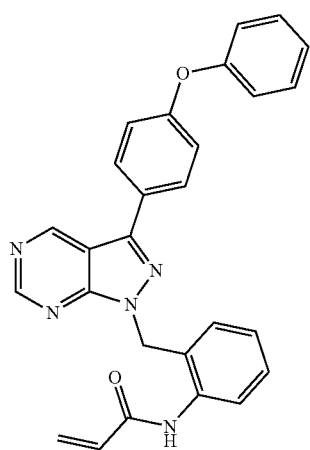 [SMILES: C=CC(=O)Nc1ccccc1Cn1nc(-c2ccc(Oc3ccccc3)cc2)c2cncnc21] | Compound: A38<br>ITK IC50 (nM)  C<br>BTK IC50 (nM)  A<br>JAK3 IC50 (nM)  C<br>TXK IC50 (nM)  A |
| 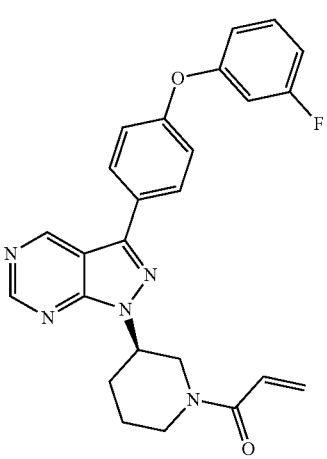 [SMILES: C=CC(=O)N1CCC[C@@H](n2nc(-c3ccc(Oc4cccc(F)c4)cc3)c3cncnc32)C1] | Compound: A39<br>ITK IC50 (nM)  C<br>BTK IC50 (nM)  A<br>JAK3 IC50 (nM)  C<br>TXK IC50 (nM)  A |

486
-continued

| Compound | Assay Result |
|---|---|
| 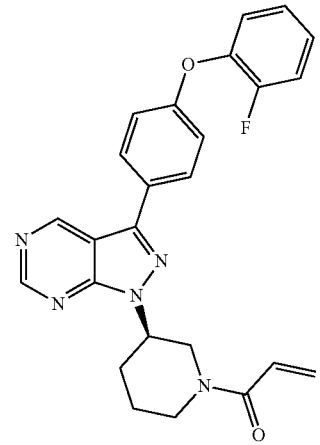 [SMILES: C=CC(=O)N1CCC[C@@H](n2nc(-c3ccc(Oc4ccccc4F)cc3)c3cncnc32)C1] | Compound: A40<br>ITK IC50 (nM)  C<br>BTK IC50 (nM)  A<br>JAK3 IC50 (nM)  C<br>TXK IC50 (nM)  A |
| 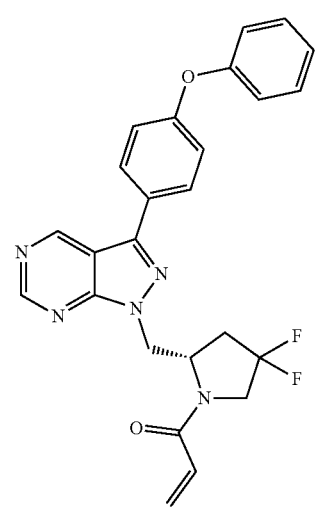 [SMILES: C=CC(=O)N1CC(F)(F)C[C@H]1Cn1nc(-c2ccc(Oc3ccccc3)cc2)c2cncnc21] | Compound: A41<br>ITK IC50 (nM)  C<br>BTK IC50 (nM)  A<br>JAK3 IC50 (nM)  C<br>TXK IC50 (nM)  A |
| 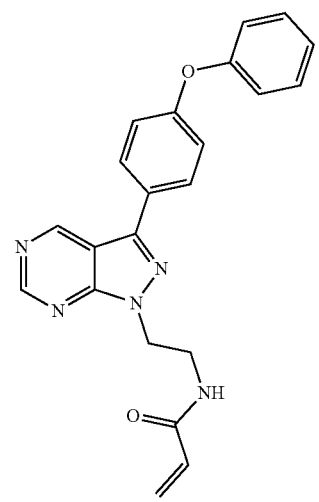 [SMILES: C=CC(=O)NCCn1nc(-c2ccc(Oc3ccccc3)cc2)c2cncnc21] | Compound: A42<br>ITK IC50 (nM)  C<br>BTK IC50 (nM)  B<br>JAK3 IC50 (nM)  C<br>TXK IC50 (nM)  C |

487
-continued

| Compound | Assay Result |
|---|---|
| 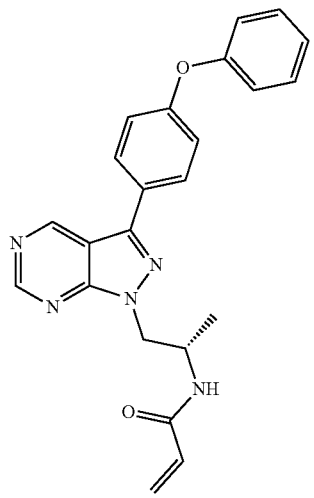 [SMILES: C=CC(=O)N[C@@H](C)Cn1nc(-c2ccc(Oc3ccccc3)cc2)c2cncnc21] | Compound: A43<br>ITK IC50 (nM)  C<br>BTK IC50 (nM)  A<br>JAK3 IC50 (nM)  C<br>TXK IC50 (nM)  B |
| 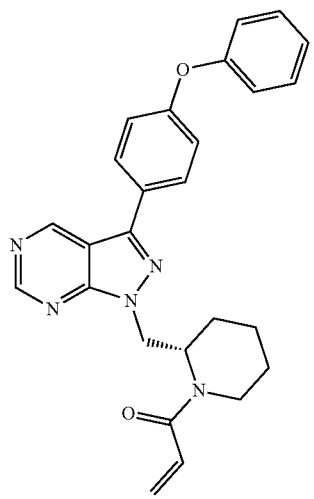 [SMILES: C=CC(=O)N1CCCC[C@H]1Cn1nc(-c2ccc(Oc3ccccc3)cc2)c2cncnc21] | Compound: A44<br>ITK IC50 (nM)  C<br>BTK IC50 (nM)  A<br>JAK3 IC50 (nM)  C<br>TXK IC50 (nM)  B |
| 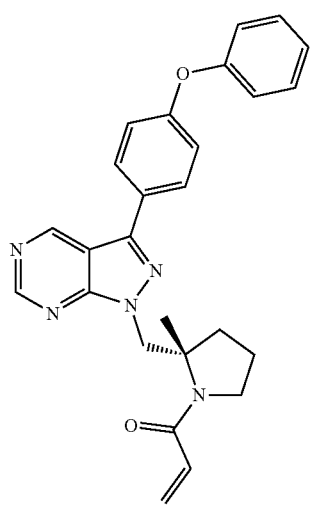 [SMILES: C=CC(=O)N1CCC[C@@]1(C)Cn1nc(-c2ccc(Oc3ccccc3)cc2)c2cncnc21] | Compound: A45<br>ITK IC50 (nM)  C<br>BTK IC50 (nM)  A<br>JAK3 IC50 (nM)  C<br>TXK IC50 (nM)  A |

488
-continued

| Compound | Assay Result |
|---|---|
| 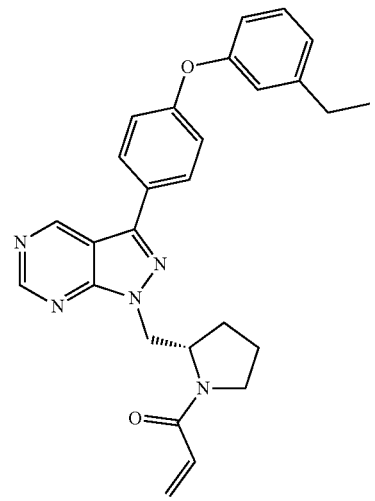 [SMILES: C=CC(=O)N1CCC[C@H]1Cn1nc(-c2ccc(Oc3cccc(CC)c3)cc2)c2cncnc21] | Compound: A46<br>ITK IC50 (nM)  C<br>BTK IC50 (nM)  A<br>JAK3 IC50 (nM)  C<br>TXK IC50 (nM)  A |
| 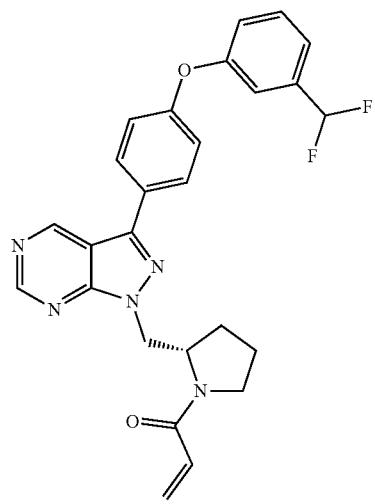 [SMILES: C=CC(=O)N1CCC[C@H]1Cn1nc(-c2ccc(Oc3cccc(C(F)F)c3)cc2)c2cncnc21] | Compound: A47<br>ITK IC50 (nM)  C<br>BTK IC50 (nM)  A<br>JAK3 IC50 (nM)  C<br>TXK IC50 (nM)  A |
| 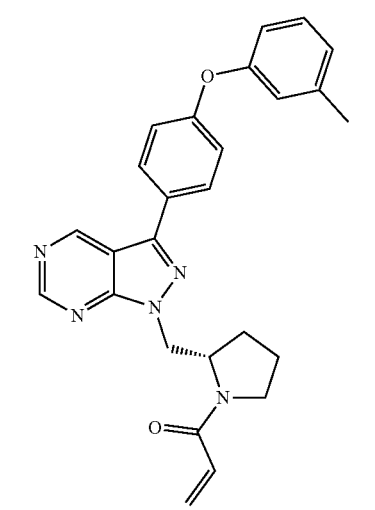 [SMILES: C=CC(=O)N1CCC[C@H]1Cn1nc(-c2ccc(Oc3cccc(C)c3)cc2)c2cncnc21] | Compound: A48<br>ITK IC50 (nM)  C<br>BTK IC50 (nM)  A<br>JAK3 IC50 (nM)  C<br>TXK IC50 (nM)  A |

| Compound | Assay Result |
|---|---|
| 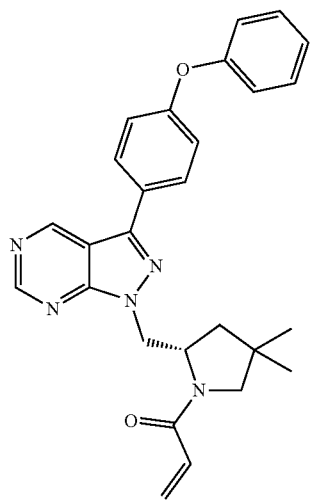 [SMILES: C=CC(=O)N1CC(C)(C)C[C@H]1Cn1nc(-c2ccc(Oc3ccccc3)cc2)c2cncnc21] | Compound: A49<br>ITK IC50 (nM) C<br>BTK IC50 (nM) A<br>JAK3 IC50 (nM) C<br>TXK IC50 (nM) A |
| 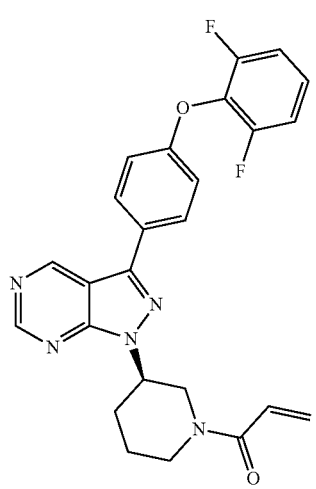 [SMILES: C=CC(=O)N1CCC[C@@H](n2nc(-c3ccc(Oc4c(F)cccc4F)cc3)c3cncnc32)C1] | Compound: A50<br>ITK IC50 (nM) C<br>BTK IC50 (nM) A<br>JAK3 IC50 (nM) C<br>TXK IC50 (nM) B |
| 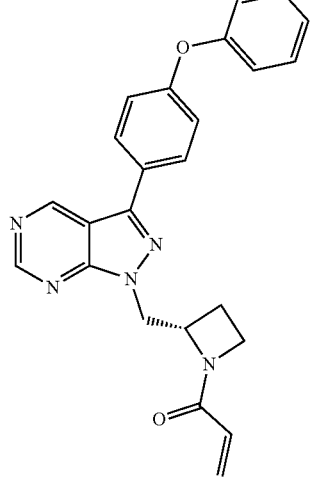 | Compound: A51<br>ITK IC50 (nM) C<br>BTK IC50 (nM) A<br>JAK3 IC50 (nM) C<br>TXK IC50 (nM) A |

| Compound | Assay Result |
|---|---|
| 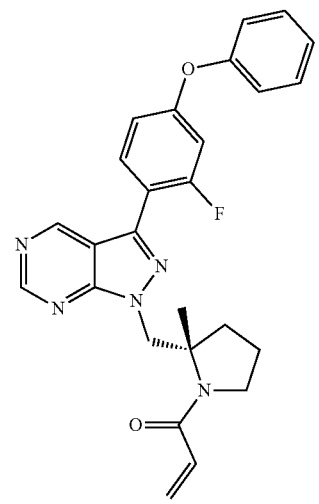 [SMILES: C=CC(=O)N1CCC[C@@]1(C)Cn1nc(-c2ccc(Oc3ccccc3)cc2F)c2cncnc21] | Compound: A52<br>ITK IC50 (nM) C<br>BTK IC50 (nM) A<br>JAK3 IC50 (nM) C<br>TXK IC50 (nM) A |
| 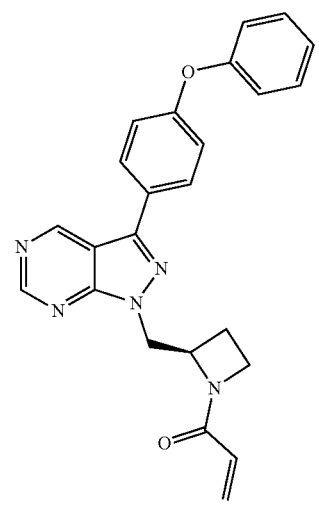 [SMILES: C=CC(=O)N1CC[C@@H]1Cn1nc(-c2ccc(Oc3ccccc3)cc2)c2cncnc21] | Compound: A53<br>ITK IC50 (nM) C<br>BTK IC50 (nM) A<br>JAK3 IC50 (nM) C<br>TXK IC50 (nM) A |
| 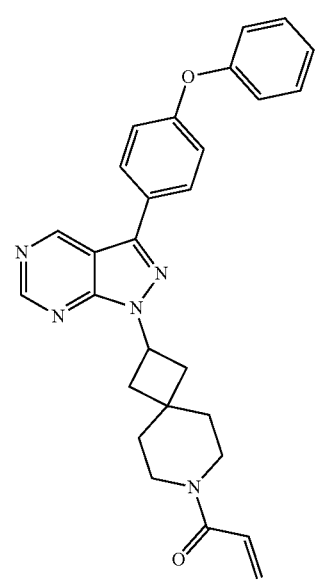 [SMILES: C=CC(=O)N1CCC2(CC1)CC(n1nc(-c3ccc(Oc4ccccc4)cc3)c3cncnc31)C2] | Compound: A54<br>ITK IC50 (nM) C<br>BTK IC50 (nM) C<br>JAK3 IC50 (nM) C<br>TXK IC50 (nM) C |

491
-continued

| Compound | Assay Result |
|---|---|
| 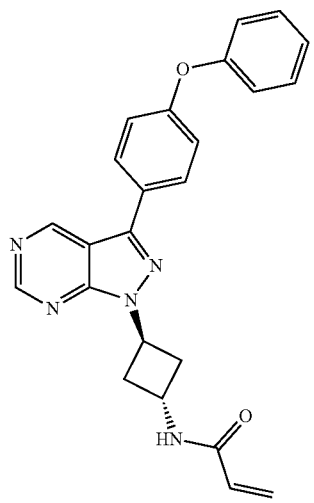 [SMILES: C=CC(=O)N[C@H]1C[C@H](n2nc(-c3ccc(Oc4ccccc4)cc3)c3cncnc32)C1] | Compound: A55<br>ITK IC50 (nM) C<br>BTK IC50 (nM) B<br>JAK3 IC50 (nM) C<br>TXK IC50 (nM) C |
| 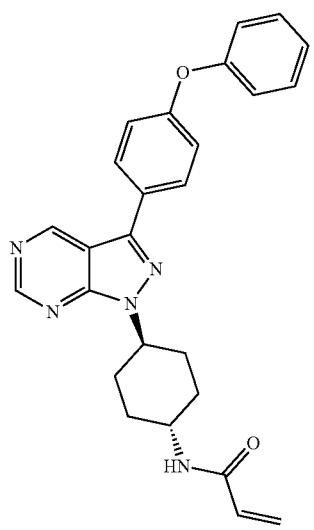 [SMILES: C=CC(=O)N[C@H]1CC[C@H](n2nc(-c3ccc(Oc4ccccc4)cc3)c3cncnc32)CC1] | Compound: A56<br>ITK IC50 (nM) C<br>BTK IC50 (nM) C<br>JAK3 IC50 (nM) C<br>TXK IC50 (nM) C |
| 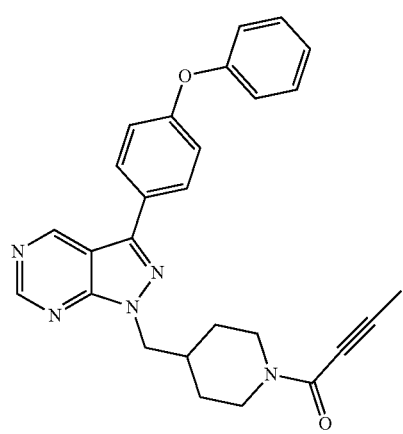 [SMILES: CC#CC(=O)N1CCC(Cn2nc(-c3ccc(Oc4ccccc4)cc3)c3cncnc32)CC1] | Compound: A57<br>ITK IC50 (nM) C<br>BTK IC50 (nM) C<br>JAK3 IC50 (nM) C<br>TXK IC50 (nM) C |

492
-continued

| Compound | Assay Result |
|---|---|
| 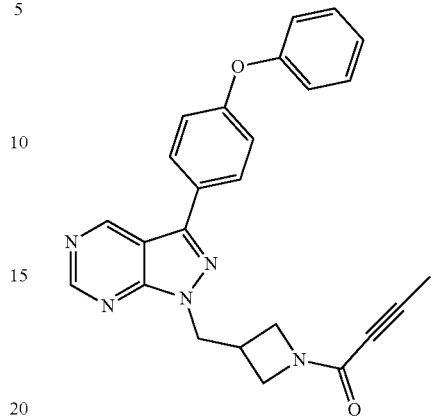 | Compound: A58<br>ITK IC50 (nM) C<br>BTK IC50 (nM) C<br>JAK3 IC50 (nM) C<br>TXK IC50 (nM) C |
| 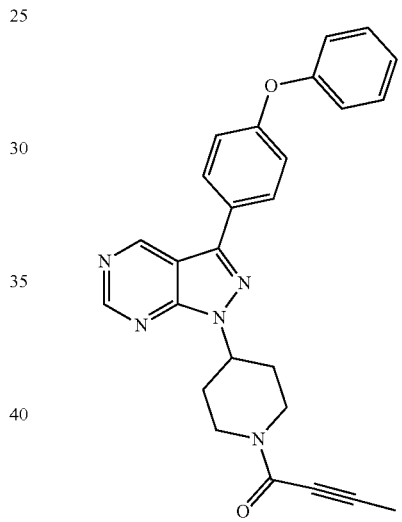 | Compound: A59<br>ITK IC50 (nM) C<br>BTK IC50 (nM) B<br>JAK3 IC50 (nM) C<br>TXK IC50 (nM) C |
| 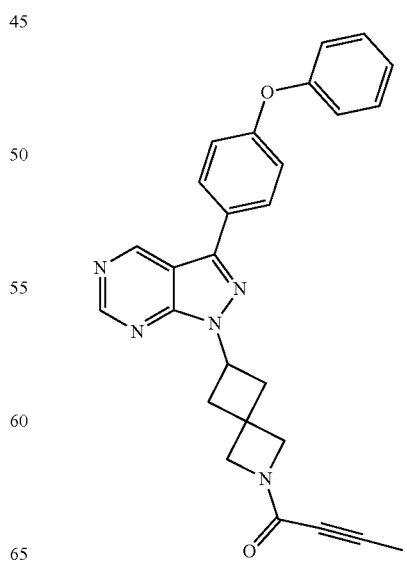 | Compound: A60<br>ITK IC50 (nM) C<br>BTK IC50 (nM) A<br>JAK3 IC50 (nM) C<br>TXK IC50 (nM) A |

| Compound | Assay Result |
|---|---|
| 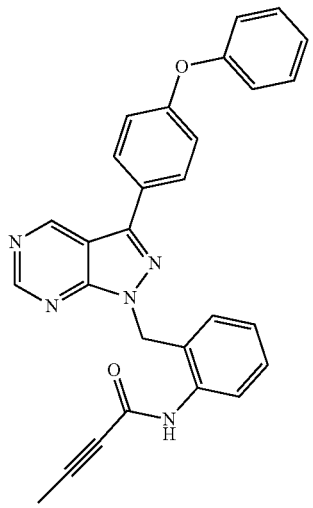 [SMILES: CC#CC(=O)Nc1ccccc1Cn1nc(-c2ccc(Oc3ccccc3)cc2)c2cncnc21] | Compound: A61<br>ITK IC50 (nM) C<br>BTK IC50 (nM) C<br>JAK3 IC50 (nM) C<br>TXK IC50 (nM) A |
| 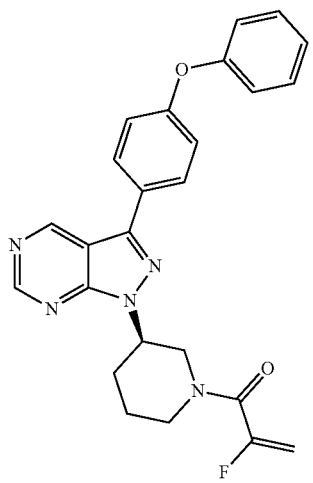 [SMILES: C=C(F)C(=O)N1CCC[C@@H](n2nc(-c3ccc(Oc4ccccc4)cc3)c3cncnc32)C1] | Compound: A62<br>ITK IC50 (nM) C<br>BTK IC50 (nM) B<br>JAK3 IC50 (nM) C<br>TXK IC50 (nM) B |
| 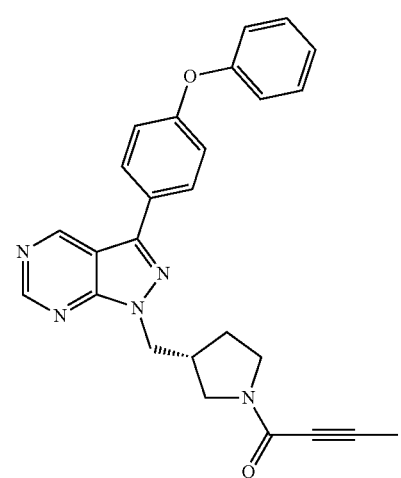 [SMILES: CC#CC(=O)N1CC[C@@H](Cn2nc(-c3ccc(Oc4ccccc4)cc3)c3cncnc32)C1] | Compound: A63<br>ITK IC50 (nM) C<br>BTK IC50 (nM) B<br>JAK3 IC50 (nM) C<br>TXK IC50 (nM) C |

| Compound | Assay Result |
|---|---|
| 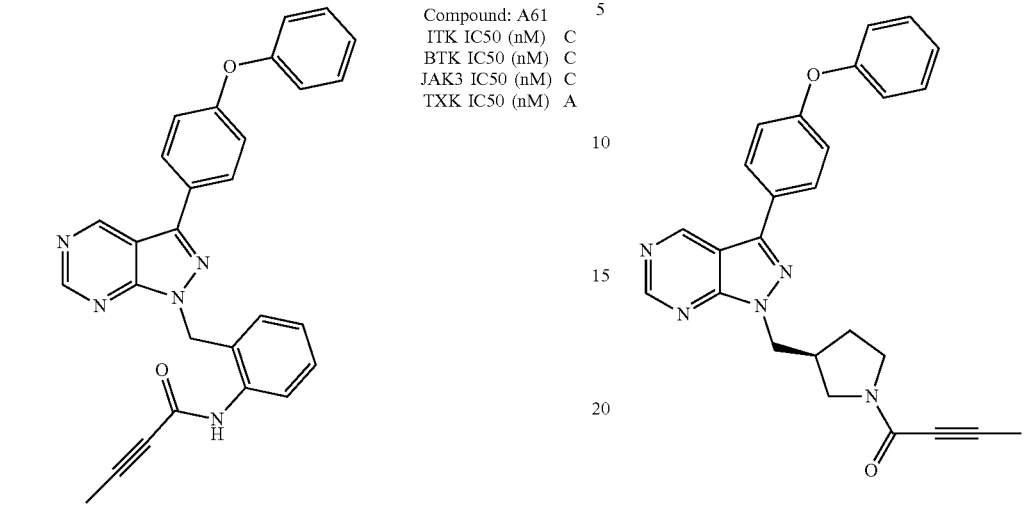 | Compound: A64<br>ITK IC50 (nM) C<br>BTK IC50 (nM) A<br>JAK3 IC50 (nM) C<br>TXK IC50 (nM) B |
| 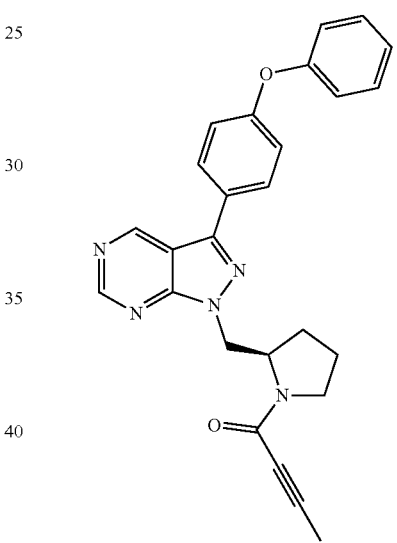 | Compound: A65<br>ITK IC50 (nM) C<br>BTK IC50 (nM) B<br>JAK3 IC50 (nM) C<br>TXK IC50 (nM) C |
| 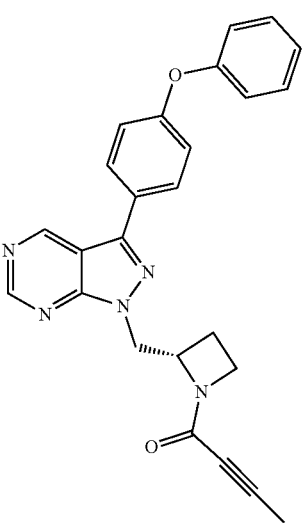 [SMILES: CC#CC(=O)N1CC[C@H]1Cn1nc(-c2ccc(Oc3ccccc3)cc2)c2cncnc21] | Compound: A66<br>ITK IC50 (nM) C<br>BTK IC50 (nM) B<br>JAK3 IC50 (nM) C<br>TXK IC50 (nM) C |

-continued

| Compound | Assay Result |
|---|---|
| 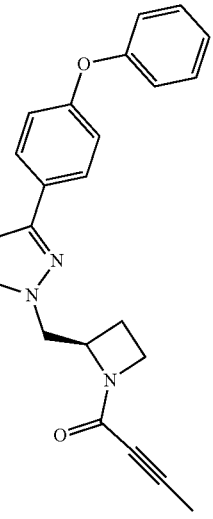 | Compound: A67<br>ITK IC50 (nM)  C<br>BTK IC50 (nM)  B<br>JAK3 IC50 (nM)  C<br>TXK IC50 (nM)  C |
| 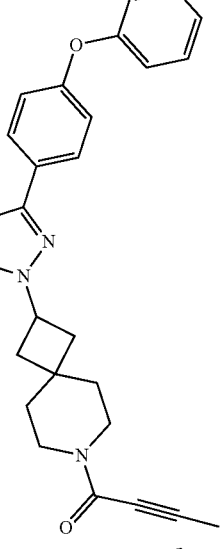 | Compound: A68<br>ITK IC50 (nM)  C<br>BTK IC50 (nM)  C<br>JAK3 IC50 (nM)  C<br>TXK IC50 (nM)  C |
| 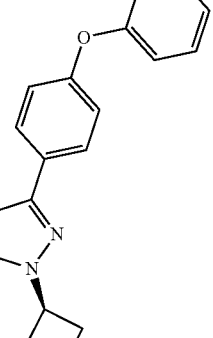 | Compound: A69<br>ITK IC50 (nM)  C<br>BTK IC50 (nM)  A<br>JAK3 IC50 (nM)  C<br>TXK IC50 (nM)  C |

-continued

| Compound | Assay Result |
|---|---|
| 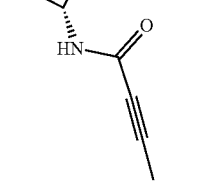 | Compound: A70<br>ITK IC50 (nM)  C<br>BTK IC50 (nM)  C<br>JAK3 IC50 (nM)  C<br>TXK IC50 (nM)  C |
| 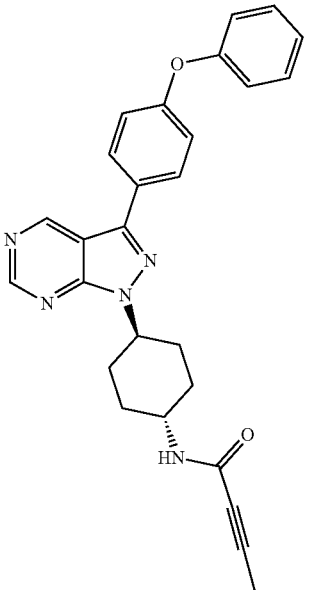 [SMILES: CC#CC(=O)N[C@H]1CC[C@H](n2nc(-c3ccc(Oc4ccccc4)cc3)c3cncnc32)CC1] | Compound: A71<br>ITK IC50 (nM)  C<br>BTK IC50 (nM)  B<br>JAK3 IC50 (nM)  C<br>TXK IC50 (nM)  B |
| 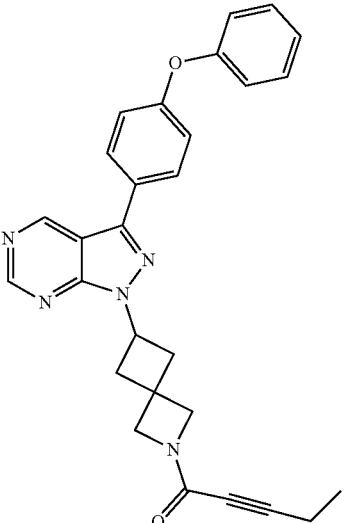 [SMILES: CCC#CC(=O)N1CC2(CC(n3nc(-c4ccc(Oc5ccccc5)cc4)c4cncnc43)C2)C1] | Compound: A72<br>ITK IC50 (nM)  C<br>BTK IC50 (nM)  A<br>JAK3 IC50 (nM)  C<br>TXK IC50 (nM)  A |

497
-continued

| Compound | Assay Result |
|---|---|
| 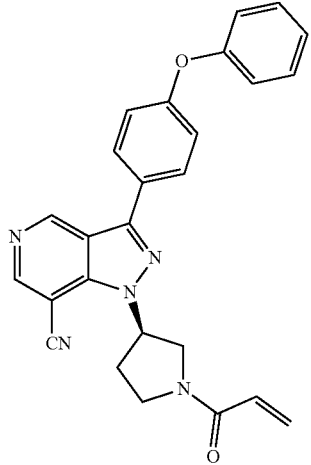 [SMILES: C=CC(=O)N1CC[C@@H](n2nc(-c3ccc(Oc4ccccc4)cc3)c3cncc(C#N)c32)C1] | Compound: A73<br>ITK IC50 (nM)  C<br>BTK IC50 (nM)  A<br>JAK3 IC50 (nM)  C<br>TXK IC50 (nM)  A |
| 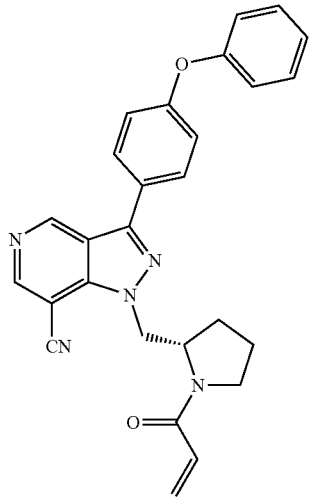 [SMILES: C=CC(=O)N1CCC[C@H]1Cn1nc(-c2ccc(Oc3ccccc3)cc2)c2cncc(C#N)c21] | Compound: A74<br>ITK IC50 (nM)  C<br>BTK IC50 (nM)  A<br>JAK3 IC50 (nM)  C<br>TXK IC50 (nM)  C |
| 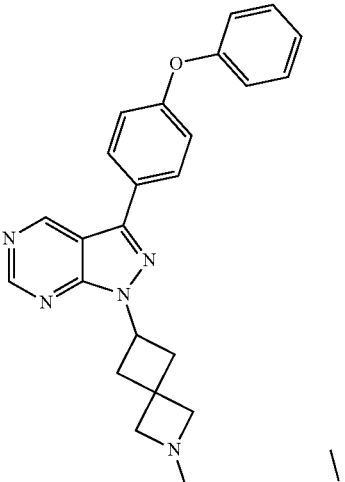 | Compound: A75<br>ITK IC50 (nM)  B<br>BTK IC50 (nM)  A<br>JAK3 IC50 (nM)  B<br>TXK IC50 (nM)  A |

498
-continued

| Compound | Assay Result |
|---|---|
| 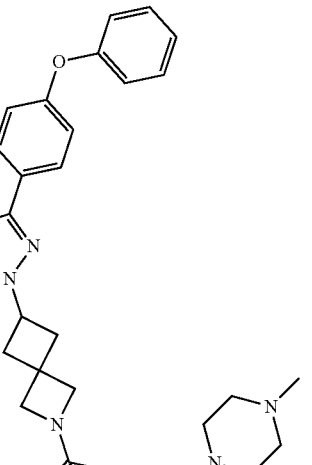 | Compound: A76<br>ITK IC50 (nM)  C<br>BTK IC50 (nM)  A<br>JAK3 IC50 (nM)  C<br>TXK IC50 (nM)  A |
| 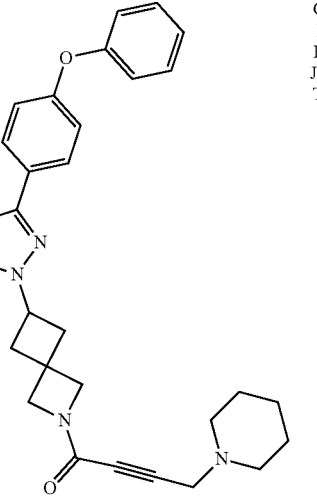 | Compound: A77<br>ITK IC50 (nM)  C<br>BTK IC50 (nM)  A<br>JAK3 IC50 (nM)  C<br>TXK IC50 (nM)  A |
| 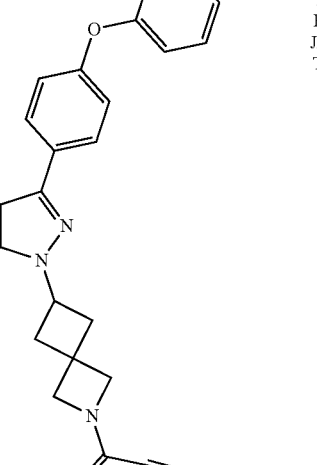 | Compound: A78<br>ITK IC50 (nM)  C<br>BTK IC50 (nM)  B<br>JAK3 IC50 (nM)  C<br>TXK IC50 (nM)  C |

| Compound | Assay Result |
|---|---|
| 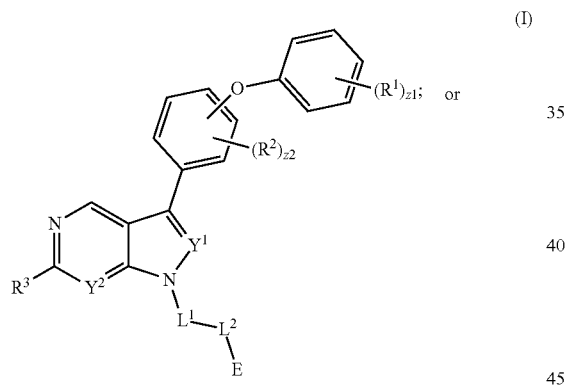 | Compound: A79<br>ITK IC50 (nM) C<br>BTK IC50 (nM) A<br>JAK3 IC50 (nM) C<br>TXK IC50 (nM) A |

A = <100 nM; B = 100-500 nM; C = >500 nM

What is claimed is:

1. A compound having the formula:

(I)

wherein, $R^1$ is independently halogen, —$CX^1_3$, —$CHX^1_2$, —$CH_2X^1$, —$OCX^1_3$, —$OCH_2X^1$, —$OCHX^1_2$, —CN, —$SO_{n1}R^{1D}$, —$SO_{v1}$ $NR^{1A}R^{1B}$, —NHC(O)$NR^{1A}R^{1B}$, —N(O)$_{m1}$, —$NR^{1A}R^{1B}$, —C(O)$R^{1C}$, —C(O)—$OR^{1C}$, —C(O)$NR^{1A}R^{1B}$, —$OR^{1D}$, —$NR^{1A}SO_2R^{1D}$, —$NR^{1A}$C(O)$R^{1C}$, —$NR^{1A}$C(O)$OR^{1C}$, —$NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl;

z1 is an integer from 0 to 5;

$R^2$ is independently halogen, —$CX^2_3$, —$CHX^2_2$, —$CH_2X^2$, —$OCX^2_3$, —$OCH_2X^2$, —$OCHX^2_2$, —CN, —$SO_{n2}R^{2D}$, —$SO_{v2}$ $NR^{2A}R^{2B}$, —NHC(O)$NR^{2A}R^{2B}$, —N(O)$_{m2}$, —$NR^{2A}R^{2B}$, —C(O)$R^{2C}$, —C(O)—$OR^{2C}$, —C(O)$NR^{2A}R^{2B}$, —$OR^{2D}$, —$NR^{2A}SO_2R^{2D}$, —$NR^{2A}AC(O)R^{2C}$, —$NR^{2A}C(O)OR^{2C}$, —$NR^{2A}OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl;

z2 is an integer from 0 to 4;

$R^3$ is hydrogen or —$NH_2$;

$Y^1$ is N;

$Y^2$ is N;

$L^1$ is a bond, —$S(O)_2$—, —$S(O)_2$-Ph-, —NR—, —O—, —S—, —C(O)—, —C(O)NR—, —$NR_6$C(O)—, —$NR^6$C(O)NH—, —NHC(O)NR—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^6$ is hydrogen, halogen, —$CX^6_3$, —$CHX^6_2$, —$CH_2X^6$, —$OCX^6_3$, —$OCH_2X^6$, —$OCHX^6_2$, —CN, —$S_{n6}R^{6D}$, —$SO_{v6}$ $NR^{6A}R^{6B}$, —NHC(O)$NR^{6A}R^{6B}$, —N(O)$_{m6}$, —$NR^{6A}R^{6B}$, —C(O)$R^{6C}$, —C(O)—$OR^{6C}$, —C(O)$NR^{6A}R^{6B}$, —$OR^{6D}$, —$NR^{6A}SO_2R^{6D}$, —$N^{6A}C(O)R^{6C}$, —$N^{6A}C(O)OR^{6C}$, —$NR^{6A}OR^{6C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^2$ is a bond, —$S(O)_2$—, —$S(O)_2$-Ph-, —$NR^{7A}$—, —O—, —S—, —C(O)—, —C(O)$NR^{7A}$—, —$NR^7$C(O)—, —$NR^7$C(O)NH—, —NHC(O)NR—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^7$ is hydrogen, halogen, —$CX^7_3$, —$CHX^7_2$, —$CH_2X^7$, —$OCX^7_3$, —$OCH_2X^7$, —$OCHX^7_2$, —CN, —$SO_{n7}R^{7D}$, —$SO_{v7}$ $NR^{7A}R^{7B}$, —NHC(O)$NR^{7A}R^{7B}$, —N(O)$_{m7}$, —$NR^{7A}R^{7B}$, —C(O)$R^{7C}$, —C(O)—$OR^{7C}$, —C(O)$NR^{7A}R^{7B}$, —$OR^{7D}$, —$NR^{7A}SO_2^{7D}$, —$NR^{7A}C(O)R^{7C}$, —$NR^{7A}C(O)OR^{7C}$, —$NR^{7A}OR^{7C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

E is:

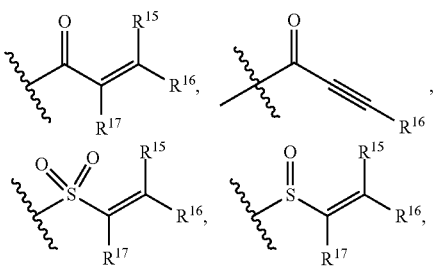

-continued

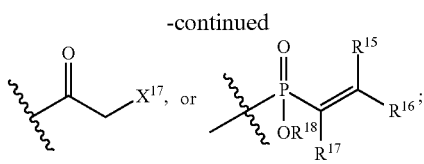

$R^{15}$ is independently hydrogen, halogen, $CX^{15}_3$, $-CHX^{15}_2$, $-CH_2X^{15}$, $-CN$, $-SO_{n15}R^{15D}$, $-SO_{v15}NR^{15A}R^{15B}$, $-NHNR^{15A}R^{15B}$, $-ONR^{15A}R^{15B}$, $-NHC=(O)NHNR^{15A}R^{15B}$, $-NHC(O)NR^{15A}R^{15B}$, $-N(O)_{m15}$, $-NR^{15A}R^{15B}$, $-C(O)R^{15C}$, $-C(O)-OR^{15C}$, $-C(O)NR^{15A}R^{15B}$, $-OR^{15D}$, $-NR^{15A}SO_2R^{15D}$, $-NR^{15A}C(O)R^{15C}$, $-NR^{15A}C(O)OR^{15C}$, $-NR^{15A}OR^{15C}$, $-OCX^{15}_3$, $-OCHX^{15}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^{16}$ is independently hydrogen, halogen, $CX^{16}_3$, $-CHX^{16}_2$, $-CH_2X^{16}$, $-CN$, $-SO_{n16}R^{16D}$, $-SO_{v16}NR^{16A}R^{16B}$, $-NHNR^{16A}R^{16B}$, $-ONR^{16A}R^{16B}$, $-NHC=(O)NHNR^{16A}R^{16B}$, $-NHC(O)NR^{16A}R^{16B}$, $-N(O)_{m16}$, $-NR^{16A}R^{16B}$, $-C(O)R^{16C}$, $-C(O)-OR^{16C}$, $-C(O)NR^{16A}R^{16B}$, $-OR^{16D}$, $-NR^{16A}SO_2R^{16D}$, $-NR^{16A}C(O)R^{16C}$, $-NR^{16A}C(O)OR^{16C}$, $-NR^{16A}OR^{16C}$, $-OCX^{16}_3$, $-OCHX^{16}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^{17}$ is independently hydrogen, halogen, $CX^{17}_3$, $-CHX^{17}_2$, $-CH_2X^{17}$, $-CN$, $-SO_{n17}R^{17D}$, $-SO_{v17}NR^{17A}R^{17B}$, $-NHNR^{17A}R^{17B}$, $-ONR^{17A}R^{17B}$, $-NHC=(O)NHNR^{17A}R^{17B}$, $-NHC(O)NR^{17A}R^{17B}$, $-N(O)_{m17}$, $-NR^{17A}R^{17B}$, $-C(O)R^{17C}$, $-C(O)-OR^{17C}$, $-C(O)NR^{17A}R^{17B}$, $-OR^{17D}$, $-NR^{17A}SO_2R^{17D}$, $-NR^{17A}C(O)R^{17C}$, $-NR^{17A}C(O)OR^{17C}$, $-NR^{17A}OR^{17C}$, $-OCX^{17}_3$, $-OCHX^{17}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^8$ is independently hydrogen, $-CX^{18}_3$, $-CHX^{18}_2$, $-CH_2X^{18}$, $-C(O)R^{18C}$, $-C(O)OR^{18C}$, $-C(O)NR^{18A}R^{18B}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

Each $R^{1A}$, $R^{1B}$, $R^{1C}$, $R^{1D}$, $R^{2A}$, $R^{2B}$, $R^{2C}$, $R^{2D}$, $R^{6A}$, $R^{6B}$, $R^{6C}$, $R^{6D}$, $R^{7A}$, $R^{7B}$, $R^{7C}$, $R^{7D}$, $R^{15A}$, $R^{15B}$, $R^{15C}$, $R^{15D}$, $R^{16A}$, $R^{16B}$, $R^{16C}$, $R^{16D}$, $R^{17A}$, $R^{17B}$, $R^{17C}$, $R^{17D}$, $R^{18A}$, $R^{18B}$, and $R^{18C}$ is independently hydrogen, $-CX_3$, $-CN$, $-COOH$, $-CONH_2$, $-CHX_2$, $-CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{6A}$ and $R^{6B}$ substituents bond the same nitrogen atom may optionally be joined to form a substituted or unsubstituted heterocycloalkyl or substituted or unsubstituted heteroaryl; $R^{7A}$ and $R^{7B}$ substituents bonded to the same nitrogen atom may optionally be joined form a substituted or unsubstituted heterocycloalkyl or substituted or unsubstituted heteroaryl; $R^{15A}$ and $R^{15B}$ substituents bonded to the same nitrogen atom may optionally be joined to form a substituted or unsubstituted heterocycloalkyl or substituted or unsubstituted heteroaryl; $R^{16A}$ and $R^{16B}$ substituents bonded to the same nitrogen atom may optionally be joined to form a substituted or unsubstituted heterocycloalkyl or substituted or unsubstituted heteroaryl; $R^{17A}$ and $R^{17B}$ substituents bonded to the same nitrogen atom may optionally be joined to form a substituted or unsubstituted heterocycloalkyl or substituted or unsubstituted heteroaryl; $R^{18A}$ and $R^{18B}$ substituents bonded to the same nitrogen atom may optionally be joined to form a substituted or unsubstituted heterocycloalkyl or substituted or unsubstituted heteroaryl;

each X, $X^1$, $X^2$, $X^6$, $X^7$, $X^{15}$, $X^{16}$, $X^{17}$, and $X^{18}$ is independently $-F$, $-Cl$, $-Br$, or $-I$;

n1, n2, n6, n7, n15, n16, and n17 are independently an integer from 0 to 4; and m1, m2, m6, m7, m15, m16, m17, v1, v2, v6, v7, v15, v16, and v17 are independently an integer from 1 to 2.

2. The compound of claim 1 having the formula:

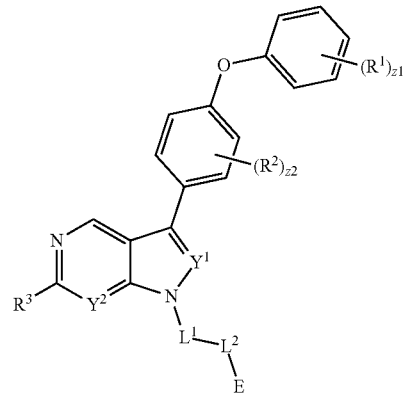

(IA)

or

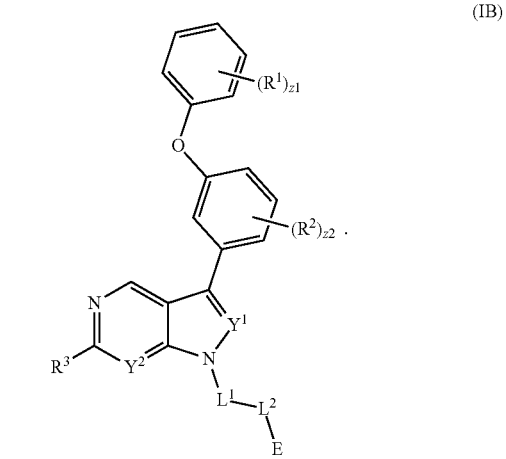

(IB)

3. The compound of claim 1 having the formula:

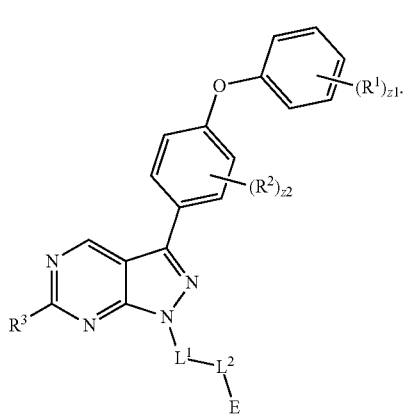

(IC)

4. The compound of claim 1, wherein $R^3$ is hydrogen.

5. The compound of claim 1, wherein $R^3$ is —$NH_2$.

6. The compound of claim 1, wherein $R^1$ is independently halogen, —$CX^1_3$, —CN, —OH, —$NH_2$, —COOH, —$CONH_2$, —$NO_2$, —SH, —$OCX^1_3$, —$OCHX^1_2$, —$CHX^1_2$, —$CH_2X^1$, substituted or unsubstituted $C_1$-$C_8$ alkyl, or substituted or unsubstituted 2 to 8 membered heteroalkyl; two adjacent $R^1$ substituents may optionally be joined to form a substituted or unsubstituted $C_3$-$C_8$ cycloalkyl, substituted or unsubstituted 3 to 8 membered heterocycloalkyl, substituted or unsubstituted phenyl, or substituted or unsubstituted 5 to 6 membered heteroaryl.

7. The compound of claim 1, wherein z1 is 0, 1 or 2.

8. The compound of claim 1, wherein $R^2$ is independently halogen, —$CX^2_3$, —CN, —OH, —$NH_2$, —COOH, —$CONH_2$, —$N_2$, —SH, —$OCX^2_3$, —$OCHX^2_2$, —$CHX^2_2$, —$CH_2X^2$, substituted or unsubstituted $C_1$-$C_8$ alkyl, or substituted or unsubstituted 2 to 8 membered heteroalkyl; two adjacent $R^2$ substituents may optionally be joined to form a substituted or unsubstituted $C_3$-$C_8$ cycloalkyl, substituted or unsubstituted 3 to 8 membered heterocycloalkyl, substituted or unsubstituted phenyl, or substituted or unsubstituted 5 to 6 membered heteroaryl.

9. The compound of claim 1, wherein z2 is 0, 1 or 2.

10. The compound of claim 1, wherein $L^1$ is a bond, —$S(O)_2$—, —$S(O)_2$-Ph-, substituted or unsubstituted $C_1$-$C_8$ alkylene, substituted or unsubstituted 2 to 8 membered heteroalkylene, substituted or unsubstituted $C_3$-$C_8$ cycloalkylene, substituted or unsubstituted 3 to 8 membered heterocycloalkylene, substituted or unsubstituted phenylene, or substituted or unsubstituted 5 to 6 membered heteroarylene.

11. The compound of claim 1, wherein $L^1$ is a bond.

12. The compound of claim 1, wherein $L^1$ is an unsubstituted methylene.

13. The compound of claim 1, wherein $L^2$ is —$NR^{7A}$— or substituted or unsubstituted heterocycloalkylene comprising a ring nitrogen bonded directly to E.

14. The compound of claim 1, wherein $L^2$ is —$NR^{7A}$—.

15. The compound of claim 14, wherein $R^7$ is hydrogen, substituted or unsubstituted $C_1$-$C_6$ alkyl, or substituted or unsubstituted 2 to 6 membered heteroalkyl.

16. The compound of claim 1, wherein $L^2$ is substituted or unsubstituted heterocycloalkylene.

17. The compound of claim 1, wherein $L^2$ is substituted or unsubstituted azepanylene, substituted or unsubstituted piperidinylene, or substituted or unsubstituted pyrrolidinylene.

18. The compound of claim 1, wherein E is:

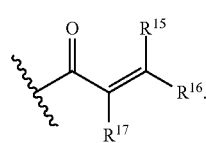

19. The compound of claim 1, wherein $R^{15}$, $R^{16}$, $R^{17}$, and $R^{18}$ are hydrogen.

20. The compound of claim 1, wherein $R^1$ is independently halogen.

21. The compound of claim 1, wherein $R^2$ is independently halogen.

22. The compound of claim 1, wherein the compound has the formula:

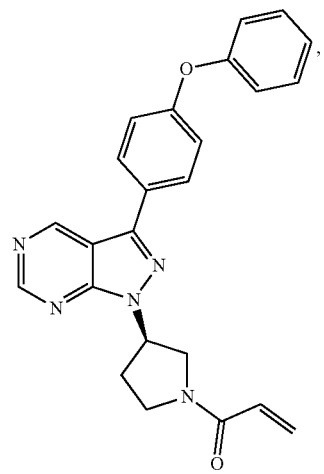

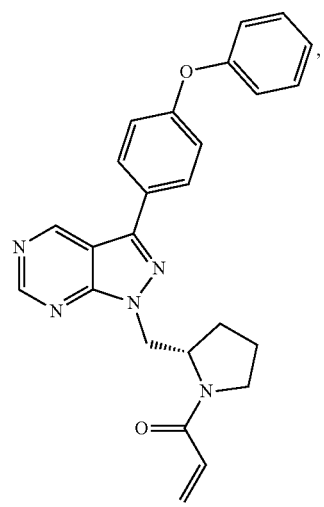

-continued

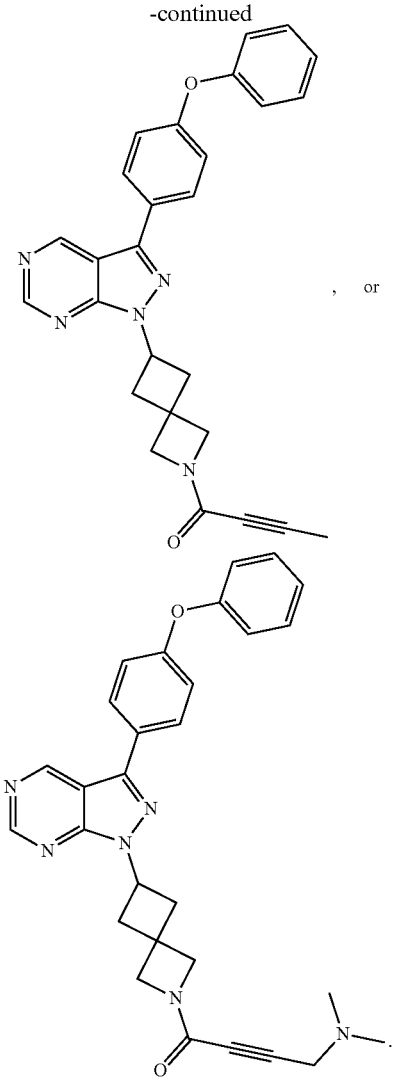

, or

23. The compound of claim 1, wherein the compound is capable of entering the central nervous system of a patient following administration outside of the central nervous system.

24. A pharmaceutical composition comprising the compound of claim 1 and a pharmaceutically acceptable excipient.

25. A method of treating a lymphoma or multiple sclerosise, said method comprising administering to a subject in need thereof an effective amount of a compound of claim 1.

26. A Bruton's tyrosine kinase protein covalently bonded to a compound of claim 1.

27. The compound of claim 1, wherein -$L^1$-$L^2$-E is:

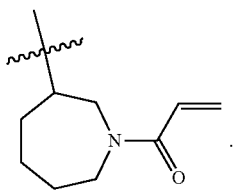 [SMILES: *C1CCCCN(C(=O)C=C)C1]

28. The method of claim 25, wherein the lymphoma is diffuse large B-cell lymphoma, Hodgkin lymphoma, chronic lymphocytic leukemia, or follicular lymphoma.

* * * * *

UNITED STATES PATENT AND TRADEMARK OFFICE
CERTIFICATE OF CORRECTION

PATENT NO. : 10,870,652 B2  
APPLICATION NO. : 16/083409  
DATED : December 22, 2020  
INVENTOR(S) : Ryan Hudson et al.

Page 1 of 1

It is certified that error appears in the above-identified patent and that said Letters Patent is hereby corrected as shown below:

On the Title Page

In Column 1, Item (73), delete "CORVUS PHARMACEUTICALS, INC., Burlingame, CA (US)" and insert -- ANGEL PHARMACEUTICAL CO., LTD., Jiaxing City (CN) --, therefor.

Signed and Sealed this  
Fifteenth Day of March, 2022

Drew Hirshfeld  
*Performing the Functions and Duties of the  
Under Secretary of Commerce for Intellectual Property and  
Director of the United States Patent and Trademark Office*